United States Patent [19]
Hinuma et al.

[11] Patent Number: 6,114,139
[45] Date of Patent: Sep. 5, 2000

[54] G-PROTEIN COUPLED RECEPTOR PROTEIN AND A DNA ENCODING THE RECEPTOR

[75] Inventors: Shuji Hinuma, Tsukuba; Masaki Hosoya, Tsuchiura; Ryo Fujii, Tsukuba; Tetsuya Ohtaki, Tsukuba; Shoji Fukusumi, Tsukuba; Kazuhiro Ohgi, Tsukuba, all of Japan

[73] Assignee: Takeda Chemical Industries, Ltd., Osaka, Japan

[21] Appl. No.: 08/513,974

[22] PCT Filed: Aug. 10, 1995

[86] PCT No.: PCT/JP95/01599

§ 371 Date: Sep. 14, 1995

§ 102(e) Date: Sep. 14, 1995

[87] PCT Pub. No.: WO96/05302

PCT Pub. Date: Feb. 22, 1996

[30] Foreign Application Priority Data

| Aug. 11, 1994 | [JP] | Japan | 6-189272 |
| Aug. 11, 1994 | [JP] | Japan | 6-189273 |
| Aug. 11, 1994 | [JP] | Japan | 6-189274 |
| Sep. 30, 1994 | [JP] | Japan | 6-236356 |
| Sep. 30, 1994 | [JP] | Japan | 6-236357 |
| Nov. 2, 1994 | [JP] | Japan | 6-270017 |
| Dec. 28, 1994 | [JP] | Japan | 6-326611 |
| Jan. 20, 1995 | [JP] | Japan | 7-007177 |
| Mar. 16, 1995 | [JP] | Japan | 7-057186 |
| Apr. 19, 1995 | [JP] | Japan | 7-093989 |

[51] Int. Cl.$^7$ .......................... C12N 15/12; C12N 15/63; C12N 5/10; C07K 14/705

[52] U.S. Cl. ................... 435/69.1; 530/350; 536/23.5; 435/325; 435/320.1

[58] Field of Search .......... 536/23.5; 435/69.1, 435/325, 320.1; 530/350

[56] References Cited

U.S. PATENT DOCUMENTS 5,508,164 4/1996 Kausch et al. ...................... 435/6

FOREIGN PATENT DOCUMENTS

| 0 578 62 A2 | 6/1993 | European Pat. Off. .......... C12Q 1/68 |
| WO 92/01810 | 2/1992 | WIPO .............................. C12Q 1/00 |
| 9303137 | 2/1993 | WIPO . |
| WO 94/05695 | 3/1994 | WIPO . |
| WO 95/10538 | 4/1995 | WIPO . |

OTHER PUBLICATIONS

Marchese et al. (Oct. 1994) Genomics 23 : 609–618.
Marchese et al. (Sep. 1995) Genomics 29 : 335–344.
Probst, et al., *DNA and Cell Biology*, vol. 11, No. 1, p. 1–20, 1992.
Okamoto, et al., *J. Biological Chemistry*, vol. 267, No. 12, pp. 8342–8346, 1992.
Libert, et al., *Science*, vol. 244, pp. 569–572, 1989.
Webb, et al., *FEBS Letters*, vol. 324(2), pp. 219–225, 1993.
Lustig, et al., *Proc. Natl. Acad. Sci. USA*, vol. 90, pp. 5113–5117, 1993.
Rice, et al., *Am. J. Respir. Cell. Mol. Biol.*, vol. 12, pp. 27–32, 1995.
Parr, et al., *Proc. Natl. Acad. Sci. USA*, vol. 91, pp. 3275–3279, 1994.
Valera, et al., *Nature*, vol. 371.6, pp. 516–519, 1994.
Erb et al., *J. Biol. Chem.*, vol. 270(9), pp. 4185–4188, 1995.
Abbracchio et al., *Pharmac. Ther.*, vol. 64, pp. 445–475, 1994.
Dubyak, et al., *Am. Phys. Soc.*, pp. C577–C606, 1993.
Burnstock et al., *Circulation Research*, vol. 58(3), pp. 319–330, 1986.
Welch, S.K. et al. (1995) Biochem. Biophys. Res. Comm. 209: 606–613.
Watson et al. (1994) The G–Protein Linked Receptor Facts Book, Academic Press, San Diego, pp. 2–6.
Bowie et al. (1990) Science 247 : 1306–1310.

*Primary Examiner*—Stephen Walsh
*Assistant Examiner*—Michael D. Pak
*Attorney, Agent, or Firm*—David G. Conlin; David S. Resnick; Dike, Bronstein, Roberts & Cushman, LLP

[57] ABSTRACT

DNA primers effective in screening G protein coupled receptor protein-encoding DNA fragments are provided. The primers which are complementary to nucleotide sequences that are in community with (homologous to) the nucleotide sequences encoding amino acid sequences corresponding to or near the first membrane-spanning domain or the sixth membrane-spanning domain each of known various G protein coupled receptor proteins were designed and synthesized. Methods of amplifying G protein coupled receptor protein-encoding DNAs using the above DNA primers, and novel target G protein coupled receptor protein-encoding DNAs are also provided. Screening of DNA libraries can be efficiently carried out. Human pituitary gland or amygdala-derived and mouse pancreas-derived G protein coupled receptor proteins, etc. or salts thereof, partial peptides thereof, DNAs coding for the above G protein coupled receptor proteins, processes for producing the above G protein coupled receptor proteins, methods of determining ligands for the above G protein coupled receptor proteins, methods of screening compounds that inhibit the binding between the ligand and the G protein coupled receptor proteins or screening kits therefor, compounds or salts thereof obtained by the above screening method or the screening kit, pharmaceutical compositions containing the above compounds or salts thereof, and antibodies against the above protein coupled receptor proteins or partial peptides thereof are provided.

6 Claims, 81 Drawing Sheets

FIGURE 1

OLIGODEOXYNUCLEOTIDE SEQUENCE FOR 5' SIDE PRIMER

```
Primer HS-1        CGTGGCCATCCTGGGCAACACCCTG
                      G C GG         CT
                                     G
                                     T
```

| | |
|---|---|
| HTRHR | CCTGGGCATTGTAGGCAACATCATGGT |
| HUMRANTES | CATTGGCCTGGTTGGAAACATCCTGGT |
| HSBLR1A | CCTGGGCGTGATCGGCAACGTCCTGGT |
| HUMSOMAT | GGTGGGGCTGGTGGGCAACGCCCTGGT |
| RNU02083 | AGTGGGCCTCTTCGGAAACTTCCTGGT |
| U00442 | GGTGGGCTTAGTGGGCAATTCCCTGGT |
| HUMNMBR | CGTGGGCTTGCTGGGCAACATCATGCT |
| HSHM4 | GGTGACCATCATCGGCAACATCCTGGT |
| RATAADRE01 | CTTTGCCATCGTGGGCAACATCTTGGT |
| HUMSSTR3X | GGTGGGCCTGCTGGGTAACTCGCTGGT |
| HUMC5AAR | GGTGGGAGTGCTGGGCAATGCCCTGGT |
| HUMRDC1A | CATCGGCATGATTGCCAACTCCGTGGT |
| HUMOPIODRE | CGTGGCGGTGCTCGGCAACCTCGTGGT |
| RATA2BAR | GCTGGCAGTGGCGGGCAACGTGCTGGT |

FIGURE 2

OLIGODEOXYNUCLEOTIDE SEQUENCE FOR 3' SIDE PRIMER

```
Complementary Sequence      TTTGCCATCTGCTGGATGCCCCACAAC
to Primer HS-2                 C        C     TTT C
                                        G         G
                                        T         T HUMSGIR             TTTGCCCTCTGCTGGTTCCCTCTCAAC
        HUMBOMB3S           TTTGCCCTCTGCTGGTTGCCAAATCAC
        S46950              TTTGCCCTCTGCTGGCTGCCCCTACAC
        MUSGPCR             TTTGCCCTCGTCTGGTGCCCTCTCAAC
        S43387              TTTGCCCTTTTATGGATGCCCTACAGG
        RATNEURA            TTTGCCATCTGCTGGCTGCCCTATCAC
        RATA1ARA            TTTGCCCTCAGCTGGCTGCCGCTGCAT
        HUMOPIODRE          TTTGCCATCTGCTGGCTGCCCTATCAC
        HUMNEKAR            TTTGCCATCTGCTGGCTGCCCTACCAC
        RATADENREC          TTTGCCTTGTGCTGGCTGCCTTTGTCC
        HUMSRI1A            TTTGTCATCTGCTGGATGCCTTTCTAC
        S8637154            TTTGCTATCTGCTGGCTGCCCTATCAT
        RNCGPCR             TTTGCCGCCTGCTGGATGCCTTTTACC
        HUMSSTR4Z           TTTGTGCTCTGCTGGATGCCTTTCTAC
        RATGNRHA            TTTGCACACTGGTCGAAGCCAGACAAA
```

FIGURE 3

OLIGODEOXYNUCLEOTIDE SEQUENCE FOR 5' SIDE PRIMER

```
Primer 3A            CTGACCGCTCTIACIACTGACCGATAC
                        T T     GG GT    A C
                                              G Primer 3B            CTGACCGCTCTIACIACTGACCGATAT
                        T T     GG GT    A C
                                              G L11064               CTCACCATGATGAGCGTGGACCGCTAC
L11065               TTGACCATGATGGAGTGTGACCGCTAC
D16349               CTCTGCACCATGAGCGTGGACCGCTAC
X69676               CTGATGCTCGTGAGTATCGACCGCTAC
M35328               CTTACGGCACTGTCAGCTGACAGGTAC
M73482               CTCACTGCCCTCAGCGCCGACAGGTAC
M73481               CTCACGGCGCTCTCGGCAGACAGATAC
L08893               TTAACAATTCTCAGCGCTGACAGATAC
X62933               ATGACCGCCATCGCCGCTGACAGGTAC
X62934               ATGACAACTGTGGCCTTTGACAGATAC
J05189               ATGACAGCCATTGCAGTGGACAGGTAT
M60786               CTCTGCGCTCTCAGTGTGGACAGGTAC
L04672               CTCACCTGCCTCAGCATTGACCGCTAC
X61496               TTGCTGGCTATCACTGTGGACCGCTAC
X59249               TTGCTGGCCATTGCTGTAGACCGATAC
L09249               CTCACCTGCCTCAGCATTGACCGCTAC
P30731               CTGACAGCTATCGCAGTGGACCGCCAC
M31210               CTCCTCGCCATCGCCATTGAGCGCTAT
U03642               CTCACCGGCCTCAGCTTCGACCGCTAC
```

FIGURE 4

OLIGODEOXYNUCLEOTIDE SEQUENCE FOR 5' SIDE PRIMER

Primer 3C          CTCGCCGCTATIAGCATGGACCGITAC
                     G   CC  G T       T Primer 3D          CTCGCCGCTATIAGCATGGACCGITAT
                     G   CC  G T       T L32840             ATTACCTGCATGAGTGTCGATAGGTAC
X64052             CTCACGTGTCTCAGCATCGATCGCTAC
M90065             CTCACGTGTCTCAGCATCGATCGCTAC
M91464             CTCACGTGTCTCAGCATTGATCGATAC
M88096             CTGGTAGCCATCTCTCTGGAGAGATAT
M99418             CTCGTGGCCATAGCCCTGGAGCGATAC
L04473             CTCGTGGCCATCGCACTGGAGCGGTAC
M73969             CTGGCCTGCATCAGTGTGGACCGTTAC
X65858             TTGGCCTGCATCAGTGTGGACCGTTAC
S46665             CTGGCTACCATTAGTGCCGACCGTTTC
M60626             ATCGCCCTCATTGCTCTGGACCGCTGT

FIGURE 5

OLIGODEOXYNUCLEOTIDE SEQUENCE FOR 3' SIDE PRIMER

```
Complementary Sequence    TTTACCITCTGTTGGICGCCCTACCACATC
to Primer 6A                 GT          TC   T T Complementary Sequence    TTCACCITCTGTTGGICGCCCTACCACATC
to Primer 6B                 GT          TC   T T L11064              TTCGTGGTGTGCTGGGCGCCCATCCACATC
       L11065              TTCATCATCTGTTGGACCCCCATTCACATC
       D16349              TTTATCGTCTGCTGGACCCCCATCCACATC
       X69676              TTTGTGCTGTGTTGGGTGCCTTTCCAGATC
       M35328              TTTGCCTTCTGCTGGCTCCCCAACCATGTC
       M73482              TTCATCTTCTGTTGGTTTCCAAACCACATC
       M73481              TTCGCCTTCTGCTGGCTCCCCAATCATGTC
       L08893              TTTGCCCTCTGCTGGTTGCCAAATCACCTC
       X62933              TTTGCCATCTGCTGGCTGCCCTACCACCTC
       X62934              TTCGCCATCTGCTGGCTGCCCTTCCACATC
       J05189              TTTGCCATCTGCTGGCTGCCCTATCACGTG
       M60786              TTCGCCCTGTGCTGGTTCCCTCTTCACTTA
       L04672              TTTGTCATCTGCTGGCTGCCCTACCACGTG
       X61496              TTTGCCGCCTGCTGGATGCCTTTTACCCTC
       X59249              TTTGCCTTGTGCTGGCTGCCTTTGTCCATC
       L09249              TTTGCCATCTGCTGGCTGCCCTACCACGTG
       P30731              TTTGCCCTCTGCTGGTTCCCTCTCAACTGC
       M31210              TTCATCGCCTGCTGGGCACCGCTCTTCATC
       U03642              TTTGCCCTGTGCTGGATGCCCTACCACCTG
```

FIGURE 6

OLIGODEOXYNUCLEOTIDE SEQUENCE FOR 3' SIDE PRIMER

```
Complementary Sequence    TTTTTCITTTGCTGGITTCCCTACCACATG
to Primer 6C                   CC T  G C            T T
```

```
L32840        TTCATCATTTGCTGGCTTCCCTTCCATGTT
X64052        TTCTTCTTTTCCTGGGTTCCCCACCAAATA
M90065        TTCTTCTTTTCCTGGGTTCCCCACCAAATA
M91464        TTTTTCTTTTCCTGGATTCCCCACCAAATA
M88096        TTCTTCCTGTGCTGGATGCCCATCTTCAGC
M99418        TTCTTCCTGTGTTGGCTGCCAGTGTACAGC
L04473        TTTTTCTGTGTTGGTTGCCAGTTTATAGT
M73969        TTCCTGCTTTGCTGGCTGCCCTACAACCTG
X65858        TTCCTGCTTTGCTGGCTGCCCTACAACCTG
S46665        TTCTTTATCTTCTGGCTGCCCTATCAGGTG
M60626        TTTTTCTCTGCTGGTCCCCATATCAGGTG
```

FIGURE 7

OLIGODEOXYNUCLEOTIDE SEQUENCE FOR 5' SIDE PRIMER

```
Primer T2A          GTCACCAACITGTTCATCCTCAICCTG
                     C          AC         GT  T
                                               A
```

| | |
|---|---|
| HUMGALAREC | ACCACCAACCTGTTCATCCTCAACCTG |
| RATADRA1B | CCCACCAACTACTTTATCGTCAACCTG |
| HUMADRB1 | ACCACCAACCTGTTCATCCTCAACCTG |
| RABIL8RSB | GTCACCGACGTCTACCTGCTGAACCTG |
| HUMOPIODRE | GTCACCAACTCCTTCCTCGTGAACCTG |
| BTSKR | GTGACCAACTACTTCATCGTCAACCTG |
| HUMSRI2A | ATCACCAACATTTACATCCTCAACCTG |
| HUMSSTR3Y | GTCACCAACGTCTACATCCTCAACCTG |
| HUMGARE | GTCACCAACGCCTTCCTCCTCTCACTG |
| HUMCCKAR | GTCACCAACATCTTCCTCCTCTCCCTG |
| HUMSHTR | CCCTCCAACTACCTGATCGTGTCCCTG |
| HUMD1B | ATGACCAACGTCTTCATCGTGTCTCTG |
| HUM5HT1E | CCTGCCAACTACCTAATCTGTTCTCTG |
| HUMD4C | CCCACCAACTCCTTCATCGTGAGCCTG |
| MMSERO | GCCACCAACTATTCCTGATGTCACTT |
| RATADRA1A | GTCACCAACTATTTCATCGTGAACCTG |
| S57565 | CTGACCAATTGCTTCATTGTGTCCCTG |

FIGURE 8

COMPLEMENTARY OLIGODEOXYNUCLEOTIDE SEQUENCE TO 3' SIDE PRIMER

```
Complementary Sequence     AACCCCITCITCTATTGCTTTITCICT
to Primer T7A                    T T         C C    C G G HUMGALAREC                 AATCCTATCATTTATGCATTTCTCTCT
RATA1ADREC                 AACCCCATCGTCTATGCCTTCCGGATC
PIGA2R                     AATCCTCTCTTTATGGCTTTCTGGGG
RAT5HTRTC                  AACCCTATCATCTACCCGCTCTTTATG
S58541                     AACCCCATCATTTATGCCTTTAATGCT
HUMGRPR                    AACCCCTTTGCCCTCTACCTGCTGAGC
MUSGRPBOM                  AACCCCTTTGCTCTTTATCTGCTGAGC
RRVT1AIIR                  AACCCTCTGTTCTACGGCTTTCTGGGG
HUMADRB1                   AACCCCATCATCTACTGCCGCAGCCCC
HSHM4                      AACCCCGTGTGCTATGCTCTGTGCAAC
HUMGARE                    AACCCCCTGGTCTACTGCTTCATGCAC
RATCCKAR                   AACCCCATCATCTATTGCTTCATGAAC
S59749                     AATCCCATGCTCTACACCTTCGCTGGC
HUMSST28A                  AACCCCGTCCTCTACGGCTTCCTCTCG
RNGPROCR                   AACCCCATCCTCTACGGCTTCCTCTCC
MUSSSRI1A                  AACCCCATACTCTACGGCTTCCTGTCG
HUMA1AADR                  AACCCGCTCATCTACCCCTGTTCCAGC
S66181                     AACCCGGTTCTCTACGCCTTCCTGGAC
HUMSSTR3Y                  AACCCCATCCTTTATGGCTTCCTCTCC
```

FIGURE 9

OLIGODEOXYNUCLEOTIDE SEQUENCE FOR 5' SIDE PRIMER

```
Primer TM1-A2        TGITGGTTATIGGIGTTGTIGGIAA
                        CC GC    C     G MUSBB2R              TGGTGGTGGTGGTGGTGGTGGGCAA
BTSKR                TGGTGCTGGTGGCTGTGATGGGCAA
BOVEETBR             TGTTCGTGCTGGGCATCATCGGAAA
HUMNEUYREC           TGATCATTCTTGGTGTCTCTGGAAA
MMSUBKREC            TGGTGCTGGTGGCTGTAACAGGCAA
HUMPGE2R             TGTTCATCTTCGGGGTGGTGGGCAA
HUMPIR               TGTTCGTGGCCGGTGTGGTGGGCAA
HSU11053             TGTTCGTCGTGGGCTTGGTGGGCAA
RRMC3RA              TGGTGATCCTGGCTGTGGTGAGGAA
HUMMR                TGGTTATCCTGGCCGTGGTCAGGAA
MUSGRPBOM            TCATCGTGATAGGTCTTATTGGCAA
RATCHOLREC           TCTTTCTGATGAGTGTTGGCGGAAA
RATCCKAR             TATTCCTTCTCAGTGTGCGGGGGAA
```

FIGURE 10

COMPLEMENTARY OLIGODEOXYNUCLEOTIDE SEQUENCE TO 3' SIDE PRIMER

```
Complementary Sequence    GCCATIACCITGGACAGATACCGAT
to Primer TM3-B2              A    T A       C G   A G HUMCCKR         GCCATCGCACTGGAGCGGTACAG
    HUMCCKBGR       GCCATCGCACTGGAGCGGTACAG
    MMGMC5R         GCCATTGCGGTGGACAGGTACA
    HUMV2R          GCCATGACGCTGGACCGCCACCG
    RATNEURA        GCCATTGCAGTGGACAGGTA
    DOGGSTRN        GCCATCGCCCTGGAGCGATACAG
    RAT5HT5A        GCAATAGCTTTGGACCGCTACTGGT
    MUSALP2ADA      GCCATTAGTCTGGACCGCTACTGGT
    HUMADORA1X      GCAATTGCTGTGGACCGCTACC
    HUMOPIODRE      GCCATCGCGGTGGACAGATACA
    MUSGRPBOM       GCACTGTCAGCTGACAGGTACAAA
    RATCCKAR        GCCATCTCTCTGGAGAGATATGG
    HSTRHREC        GCCTTTACCATTGAGAGGTACATA
```

FIGURE 11

OLIGODEOXYNUCLEOTIDE SEQUENCE FOR 5' SIDE PRIMER

```
Primer TM3-C2        CATGGCCGTGGAGAGITACITGGC
                       TT   C      C     T  A HUMNK3R              CATTGCGGTGGACAGGTATATGGC
HSMRNAOXY            CATGTCCCTGGACCGCTGCCTGGC
S68242               CATATCGCTGGAGAGATACGGAGC
CFGPCR4              CATCGCTCTGGACAGGTACTGGGC
MMSUBPREC                 TGGCCTTTGACAGATACATGGC
HUMOPIODRE           CATCGCGGTGGACAGATACATGGC
HUMGALAREC              ATGTCCGTGGACCGCTACGTGGC
HSS31G               CATTGCCCTGGACAGGTACTGGGC
HUMARB3A             CCTGGCCGTGGACCGCTACCTGGC
HUMHPR               CATGGCCGTGGAGCGCTGCCTGGC
RATCCKAR             CATCTCTCTGGAGAGATATGGCGC
```

FIGURE 12

COMPLEMENTARY OLIGODEOXYNUCLEOTIDE SEQUENCE TO 3' SIDE PRIMER

```
Complementary Sequence    TTTGCCITCTGCTGGATCCCCAAC
to Primer TM6-E2             C      G     C G   TT HUMNEKAR           TTTGCCATCTGCTGGCTGCCCTAC
       HUMSUBPRA          TTCGCCATCTGCTGGCTGCCCTTC
       RATSKR             TTTGCCATCTGCTGGCTGCCCTAC
       MUSGRPBOM          TTTGCCTTCTGCTGGCTCCCCAAC
       HUMOPIODRE         TTTGCCATCTGCTGGCTGCCCTA
       HUMA2XXX           TTTGCCCTCTGCTGGCTGCCCCT
       HUMADRBR           TTCACCCTCTGCTGGCTGCCCTTC
       CFGPCR8            TTCGCCCTCTGTGGCTGCCCCT
       HUMETSR            TTTGCCCTCTGCTGGCTTCCCCT
       MMNPY1CDS          TTCGCCGTCTGCTGGCTGCCCCT
       HSMRNAOXY          TTCATCGTGTGCTGGACGCCTTTC
       RATCCKAR           TTCTTCCTGTGCTGGATGCCCATC
```

FIGURE 13

OLIGODEOXYNUCLEOTIDE SEQUENCE FOR 5' SIDE PRIMER

Primer TM2F18         ARYYTIGCIITIGCNGAY

| | |
|---|---|
| HUMTSHX | AACCTGGCCTTTGCGGAT |
| HUMNEKAR | AATCTGGCGCTGGCTGAC |
| HUMFMLP | AACCTGGCCGTGGCTGAC |
| HUMINTLEU8 | AACCTAGCCTTGGCCGAC |
| HUMA1AADR | AACCTGGCCGTGGCCGAC |
| HUMIL8RA | AACCTGGCCTTGGCCGAC |
| HSDD2 | AGCCTCGCAGTGGCCGAC |
| HUMANTIR | AATTTAGCACTGGCTGAC |
| HUMSOMAT | AACCTGGCCGTAGCCGAC |
| HUMEL4REC | AGCTTGGCTGTGGCTGAT |
| HSTRHREC | AGCCTGGCAGTAGCTGAT |
| HSU07882 | AACCTGGCCTTAGCCGAT |

( R = A or G, Y = C or T, N = A, C, G or T, and
  I = Inosine )

FIGURE 14

COMPLEMENTARY OLIGODEOXYNUCLEOTIDE SEQUENCE TO 3' SIDE PRIMER

Complementary Sequence    TTYNYNNTNTGYTGGITICCI
to Primer TM6R21

| | |
|---|---|
| HSBAR | TTCACCCTCTGCTGGCTGCCC |
| HUMNEKAR | TTTGCCATCTGCTGGCTGCCC |
| HUMETN1R | TTTGCTCTTTGCTGGTTCCCT |
| HUMHISH2R | TTCATCATCTGCTGGTTTCCC |
| HUMA1AADR | TTCGTGCTCTGCTGGTTCCCT |
| HUMIL8RA | TTCCTGCTTTGCTGGCTGCCC |
| HUMNMBR | TTCATCTTCTGTTGGTTTCCT |
| HUMNKIRX | TTCGCCATCTGCTGGCTGCCC |
| HUMSUBPRA | TTCGCCATCTGCTGGCTGCCC |
| HUM5HT1DA | TTTATCATCTGCTGGCTGCCC |
| HUMPFPR2A | TTCTTCATCTGTTGGTTTCCC |
| HSDD2 | TTCATCATCTGCTGGCTGCCC |
| HUMNEUYREC | TTTGCAGTCTGCTGGCTCCCT |
| HUM2XXX | TTTGCCCTCTGCTGGCTGCCC |
| HUMBK2A | TTCATCATCTGCTGGCTGCCC |
| HUMFMLPX | TTCTTCATCTGTTGGTTTCCC |
| HUMSSTR3X | TTCGTGCTCTGCTGGATGCCC |
| HUMCCKR | TTTTTTCTGTGTTGGTTGCCA |
| HSNEURA | TTTGTGGTCTGCTGGCTGCCC |

( Y = C or T, N = A, C, G or T, and I = Inosine )

FIGURE 15

OLIGODEOXYNUCLEOTIDE SEQUENCE FOR 5' SIDE PRIMER

```
Primer S3A       GCCTGITIAIGATGAGTGTGGAIAGIT
                    C   G C     TC        C HUMGALAREC       CCCTGGCCGCGATGTCCGTGGACCGCT
S70057           GCCTCGTGGCCATCGCACTGGAGCGGT
S67127           ACCTCTGCGCTCTTAGTGTTGACAGGT
S44866           GTCTATGTGCTCTGAGTATTGACAGAT
HUMC5AAR         TCCTGGCCACCATCAGCGCCGACCGCT
HUMANTIR         TACTCACGTGTCTCAGCATTGATCGAT
HUMBK2A          TCCTGATGCTGGTGAGCATCGACCGCT
HSNEURA          ACGTGGCCAGCCTGAGTGTGGAGCGCT
HUMGRPR          CACTCACGGCGCTCTCGGCAGACAGAT
HUMFSRS          GCCTGACAGTCATGAGCGTGGACCGCT
HUMIL8RA         TGTTGGCCTGCATCAGTGTGGACCGTT
HUMNEKAR         CCATGACCGCCATTGCTGCCGACAGGT
```

FIGURE 16

COMPLEMENTARY OLIGODEOXYNUCLEOTIDE SEQUENCE TO 3' SIDE PRIMER

```
Complementary Sequence      TGGITICCCTACCACITIATCAICATC
to Primer S6A                  T  T    GG    GT HUMGALAREC             TGGCTGCCGCACCACATCATCCATCTC
     S70057                 TGGTTGCCAGTTTATAGTGCCAACACG
     S67127                 TGGTTCCCTCTTCATTTAAGCCGTATA
     S44866                 TGGCTTCCCCTTCACCTCAGCAGGATT
     HUMC5AAR               TGGTTGCCCTACCAGGTGACGGGGATA
     HUMANTIR               TGGATTCCCCACCAAATATTCACTTTT
     HUMBK2A                TGGCTGCCCTTCCAGATCAGCACCTTC
     HSNEURA                TGGACTCCGTTCCTCTATGACTTCTAC
     HUMGRPR                TGGCTCCCCAATCATGTCATCTACCTG
     HUMFSRS                TGGCTGCCCTTCTTCACCGTCAACATC
     HUMIL8RA               TGGCTGCCCTACAACCTGGTCCTGCTG
     HUMNEKAR               TGGCTGCCCTACCACCTCTACTTCATC
```

FIGURE 18

```
                    10        20        30        40        50
A58-T7-2   GTCGGGCATGGTGGGCAACCCCCTGGTCATCTTCGTGATCCTTCGCTACGC
X:         ::::: ::::::::::::::::::::::::::::::::::::::::::::::
HUMSOMAT   GTGGGGCTGGTGGGCAACGCCCTGGTCATCTTCGTGATCCTTCGCTACGC
                   285       295       305       315       325
                    60        70        80        90       100

A58-T7-2   CAAGATGAAGACGGCTACCAACATCTACCTGCTCAACCTGGCCGTAGCCG
           ::::::::::::::::::::::::::::::::::::::::::::::::::
HUMSOMAT   CAAGATGAAGACGGCTACCAACATCTACCTGCTCAACCTGGCCGTAGCCG
                   335       345       355       365       375
                   110       120       130       140       150

A58-T7-2   ACGAGCTCTTCATGCTGAGCCTGCCCTTCGGGCTGTGCCCCATCCGCCCTG
           ::::::::::::::::::::::::::::::::::::::::::::::::::
HUMSOMAT   ACGAGCTCTTCATGCTGAGCCTGCCCTTCGGGCTGTGCCCCATCCGCCCTG
                   385       395       405       415       425
                   160       170       180       190       200

A58-T7-2   CGCCACTGGCCCTTCGGGCCGTCCGGGCTGTGCCGGGCTGTCAGCGTCGA
           ::::::::::::::::::::::::::::::::::::::::::::::::::
HUMSOMAT   CGCCACTGGCCCTTCGGGCCGTCCGGGCTGTGCCGGGCTGTCAGCGTCGA
                   435       445       455       465       475
                   210       220       230       240

A58-T7-2   CGGCCTCAACATGTTCACCAGCGTCTTCTGTCTCACCGTGCTCAGCGT
           :::::::::::::::::::::::::::::::::::::::::::::::X
HUMSOMAT   CGGCCTCAACATGTTCACCAGCGTCTTCTGTCTCACCGTGCTCAGCGT
                   485       495       505       515
```

FIGURE 19

```
                        10         20         30         40         50
A58-SP6     CAGTGTCCACACCCGGCCTGTGGTCGGCAGTCTTCGTGGTCTACACTTTCCT
            X::: :::::::::::::::::::::::::::::::::::::::::::::::
HUMSOMATA   CAGTGGCCACACCCGGCCTGTCGGCAGTCTTCGTGGTCTACACTTTCCT
                        706        716        726        736       746
                         60         70         80         90        100

A58-SP6     GCTGGGCTTCCTGCTGTCCGTGCTGGCCTGTGCCTGTGCCTGTGCTACCTGCTCA
            ::::::::::::::::::::::::::::::::::::::::::::::::::::
HUMSOMATA   GCTGGGCTTCCTGCTGTCCGTGCTGGCCTGTGCCTGTGCCTGTGCTACCTGCTCA
                        756        766        776        786       796
                        110        120        130        140       150

A58-SP6     TCGTGGGCAAGATGCGCGCCCGTGTCCCTGCGGCTGGCTGGCAGCAGCGC
            ::::::::::::::::::::::::::::::::::::::::::::::::::
HUMSOMATA   TCGTGGGCAAGATGCGCGCCCGTGTCCCTGCGGCTGGCTGGCAGCAGCGC
                        806        816        826        836       846
                        160        170        180        190       200

A58-SP6     AGGCGCTCGGAGAAGAAATCACCAGCTGGTGCTGATGTCGTGGTCGT
            :::::::::::::::::::::::::::::::::::::::::::::::
HUMSOMATA   AGGCGCTCGGAGAAGAAATCACCAGCTGGTGCTGATGTCGTGGTCGT
                        856        866        876        886       896
                        210        220

A58-SP6     CTTTGCCCTCTGCTGGTTGCCTCTCCAC
            ::::: ::::::: ::::: :: :::X
HUMSOMATA   CTTTGTCTCTGCTGGATGCCTTTCTAC
                        906        916
```

FIGURE 20

```
            10         20         30         40         50
57-A-2      GTGGGCATGCTGGGCAACCTCCTGGAAGGCAGTCGCCGAGGTGGCCGGTT
            X:::   :::::: ::   : ::::::::::::::::::::::::::::
HUMDRD5A    GTGGCGCTGCTGGTCATGC-CCTGGAAGGCAGTCGCCGAGGTGGCCGGTT
            424        434        444        454
            60         70         80         90         100
57-A-2      ACTGGCCCTTTGGAGCGTTCTGCGACGTCTGGGTGGCCTTCGACATCATG
            ::::::::::::::::::::::::::::::::::::::::::::::::::
HUMDRD5A    ACTGGCCCTTTGGAGCGTTCTGCGACGTCTGGGTGGCCTTCGACATCATG
            464        474        484        494        504
            110        120        130        140        150
57-A-2      TGCTCCACTGCCTCCATCCTGAACCTGTGCGTCATCAGCGTGGACCGCTA
            ::::::::::::::::::::::::::::::::::::::::::::::::::
HUMDRD5A    TGCTCCACTGCCTCCATCCTGAACCTGTGCGTCATCAGCGTGGACCGCTA
            514        524        534        544        554
            160        170        180        190        200
57-A-2      CTGGGCCATCTCCAGGCCCTTCCGCTACAAGCGCAAGATGACTCAGCGCA
            ::::::::::::::::::::::::::::::::::::::::::::::::::
HUMDRD5A    CTGGGCCATCTCCAGGCCCTTCCGCTACAAGCGCAAGATGACTCAGCGCA
            564        574        584        594        604
            210        220        230        240        250
57-A-2      TGGCCTTGGTCATGGTCGGCCTGGCATGGACCTTGTCCATCCTCATCTCC
            ::::::::::::::::::::::::::::::::::::::::::::::::::
HUMDRD5A    TGGCCTTGGTCATGGTCGGCCTGGCATGGACCTTGTCCATCCTCATCTCC
            614        624        634        644        654
            260        270        280        290        300
57-A-2      TTCATTCCGGTCCAGGTCAACTGGGACAGGGACCAGGCGGGCTCTTGGGG
            :::::::::::::::::  :::::::: ::::::::::::::  :::::::
HUMDRD5A    TTCATTCCGGTCCAGCTCAACTGGCACAGGGACCAGGCGGCCTCTTGGGG
            664        674        684        694        704
            310
57-A-2      GGGGCTGGACCTGCCAAA
            :::::::::::::::::X
HUMDRD5A    CGGGCTGGACCTGCCAAA
            714        724
```

FIGURE 21

```
              10        20        30        40        50
B54     GTGGGCATCGTGGGCAACATCCTGGTCATATTCGTGATCCTACGCTATGC
        X::::  ::  ::: :::     :::::::::::::::::::::::::
RNU04738 GTGGGCCTGGTAGGAAACGCCCTGGTCATATTCGTGATCCTACGCTATGC
              233       243       253       263       273
               60        70        80        90       100

B54     CAAAATGAAGACAGCCACCAACATCTACCTGCTCAACCTGGCCGTCGCTG
        ::::::::::::::::  ::::::::::::::::::::::::::::::
RNU04738 CAAAATGAAGACAGCCACCAACATCTACCTGCTCAACCTGGCCGTCGCTG
              283       293       303       313       323
              110       120       130       140       150

B54     ATGAGCTCTTCATGCTCTCAGTGTGCCATTTGTGGCCTCGGCGGCCCCTG
        ::::::::::::::::::::::::::::::::::::::::::::::::
RNU04738 ATGAGCTCTTCATGCTCTCAGTGTGCCATTTGTGGCCTCGGCGGCCCCTG
              333       343       353       363       373
              160       170       180

B54     CGCCACTGGCCGTTCGGGGCGGTGTGCCGC
        ::::::::::::::::::::::::::::X
RNU04738 CGCCACTGGCCGTTCGGGGCGGTGTGCCGC
              383       393       403
```

FIGURE 22

```
                 9              18             27             36             45             54
5' GTG GGC ATG GTG GGC AAC GTC CTG CTG GTG ATC GCG CGG GTG CGC CGG
   Val Gly Met Val Gly Asn Val Leu Leu Val Ile Ala Arg Val Arg Arg
                63             72             81             90             99            108
   CTG CAC AAC GTG ACG AAC TTC CTC ATC GGC AAC CTG GCC TTG TCC GAC GTG CTC
   Leu His Asn Val Thr Asn Phe Leu Ile Gly Asn Leu Ala Leu Ser Asp Val Leu
                117            126            135            144            153            162
   ATG TGC ACC GCC TGC GTG CCG CCG CTG ACG CTG GCC TAT GCC TTC TTC GAG CCA CGC GGC
   Met Cys Thr Ala Cys Val Pro Leu Thr Leu Ala Tyr Ala Phe Phe Glu Pro Arg Gly
                171            180            189            198            207            216
   TGG GTG TTC GGC GGC CTG GGC TGC CAC CTG GTC TTC TTC CAG CCG GTC ACC
   Trp Val Phe Gly Gly Gly Leu Cys His Leu Val Phe Phe Gln Pro Val Thr
                225            234            243            252            261            270
   GTC TAT GTG TCG GTG TTC ACG TTC ACC ACC ATC GAA GTG GAC CGG TAC GTC GGT
   Val Tyr Val Ser Val Phe Thr Phe Thr Thr Ile Glu Val Asp Arg Tyr Val Gly
                279            288            297
   GCT GGT GCA CCC GCT GAG GCG GGG CAT 3'
   Ala Gly Ala Pro Ala Glu Ala Gly His
```

FIGURE 23

```
5'
GGC CTG CTG GTC ACC TAC CTG CCT CTG GTC ATC CTC TCT TAC
         9       18       27       36       45       54
Gly Leu Leu Val Thr Tyr Leu Pro Leu Val Ile Leu Ser Tyr

GTC CGG GTG TCA GTG AAG CTC CGC AAC CCG GTG TGC GTG ACC CAG
         63       72       81       90       99      108
Val Arg Val Ser Val Lys Leu Arg Asn Pro Val Cys Val Thr Gln

AGC CAG GCC GAC TGG GAC CGC GCT CGG CGG ACC TTC TTG CTG GTG
        117      126      135      144      153      162
Ser Gln Ala Asp Trp Asp Arg Ala Arg Arg Thr Phe Cys Leu Leu Val

GTG GTC GTG GTG TTT GCC ATC TGC TGG TTG CCT TAC TAC 3'
        171      180      189      198
Val Val Val Val Phe Ala Ile Cys Trp Leu Pro Tyr Tyr
```

FIGURE 26

```
                  10         20         30         40         50
p19P2       1 VGMVGNVLLV LVIARVRRLH NVTNFLIGNL ALSDVLMCTA CVPLTLAYAF  50
S12863      1 LGVSGNLALI IIILKQKEMR NVTNILIVNL SFSDLLVAVM CLPFTFVYTL  50

60         70         80         90        100
p19p2      51 EPRGWVFGGG LCHLVFFLQP VTVYVSVFTL TTIEVDRYVG AGAPAEAGH  100
S12863     51 MDH-WVFGET MCKLNPFVQC VSITVSIFSL VLIAVERHQL IINPRGWRPN 100

110        120        130        140        150
p19P2     101                                                       150
S12863    101 NRHAYIGITV IWVLAVASSL PFVIYQILTD EPFQNVSLAA FKDKYVCFDK 150

160        170        180        190        200
p19P2     151       GLLLV TYLLPLLVIL LS-------Y VRSVKLRNPV VPVCVTQSQA 200
S12863    151 FPSDSHRLSY TTLLLVLQYF GPLCFIFICY FKIYIRLKRR NNMMDKIRDS 200

210        220        230        240        250
p19P2     201 DWDRARRRRT FCLLVVVVVV FAICWLPYY.  .........  .........  250
S12863    201 KYRSSETKRI NVMLLSIVVA FAVCWLPLT.  .........  .........  250
```

FIGURE 27

```
GTG GGC ATG GTG GGC AAC ATC CTG CTG GTG CTG GTG ATC GCG CGG GTG      48
Val Gly Met Val Gly Asn Ile Leu Leu Val Leu Val Ile Ala Arg Val
 1               5                  10                  15
CGC CGG CTG TAC AAC GTG ACG AAT TTC CTC ATC GGC AAC CTG GCC TTG      96
Arg Arg Leu Tyr Asn Val Thr Asn Phe Leu Ile Gly Asn Leu Ala Leu
             20                  25                  30
TCC GAC GTG CTC ATG TGC ACC GCC TGC GTG CCG CTC ACG CTG GCC TAT     144
Ser Asp Val Leu Met Cys Thr Ala Cys Val Pro Leu Thr Leu Ala Tyr
         35                  40                  45
GCC TTC GAG CCA CGC GGC TGG GTG TTC GGC GGC GGC CTG TGC CAC CTG     192
Ala Phe Glu Pro Arg Gly Trp Val Phe Gly Gly Gly Leu Cys His Leu
     50                  55                  60
GTC TTC TTC CTG CAG GCG GTC ACC GTC TAT GTG TCG GTG TTC ACG CTC     240
Val Phe Phe Leu Gln Ala Val Thr Val Tyr Val Ser Val Phe Thr Leu
 65                  70                  75                  80
ACC ACC ATC GCA GTG GAC CGC TAC GTC GTG CTG GTG CAC CCG CTG AGG     288
Thr Thr Ile Ala Val Asp Arg Tyr Val Val Leu Val His Pro Leu Arg
                 85                  90                  95
CGG CGC ATC TCG CTG CGC CTC AGC GCC TAC GCT GTG CTG GCC ATC TGG     336
Arg Arg Ile Ser Leu Arg Leu Ser Ala Tyr Ala Val Leu Ala Ile Trp
             100                 105                 110
GTG CTG TCC GCG GTG CTG GCG CTG CCC GCC GCC GTG CAC ACC TAT CAC     384
Val Leu Ser Ala Val Leu Ala Leu Pro Ala Ala Val His Thr Tyr His
         115                 120                 125
GTG GAG CTC AAG CCG CAC GAC GTG CGC CTC TGC GAG GAG TTC TGG GGC     432
Val Glu Leu Lys Pro His Asp Val Arg Leu Cys Glu Glu Phe Trp Gly
     130                 135                 140
TCC CAG GAG CGC CAG CGC CAG CTC TAC GCC TGG GGG CTG CTG CTG GTC     480
Ser Gln Glu Arg Gln Arg Gln Leu Tyr Ala Trp Gly Leu Leu Leu Val
145                 150                 155                 160
ACC TAC CTG CTC CCT CTG CTG GTC ATC CTC CTG TCT TAC GCC CGG GTG     528
Thr Tyr Leu Leu Pro Leu Leu Val Ile Leu Leu Ser Tyr Ala Arg Val
                 165                 170                 175
TCA GTG AAG CTC CGC AAC CGC GTG GTG CCG GGC CGC GTG ACC CAG AGC     576
Ser Val Lys Leu Arg Asn Arg Val Val Pro Gly Arg Val Thr Gln Ser
             180                 185                 190
CAG GCC GAC TGG GAC CGC GCT CGG CGC CGG CGC ACC TTC TGC TTG CTG     624
Gln Ala Asp Trp Asp Arg Ala Arg Arg Arg Arg Thr Phe Cys Leu Leu
         195                 200                 205

GTG GTG GTC GTG GTG GTG TTC ACC CTC TGC TGG CTG CCC TTC TTC         669
Val Val Val Val Val Val Phe Thr Leu Cys Trp Leu Pro Phe Phe
         210                 215                 220
```

FIGURE 29

```
5'
     10              19              28              37              46              55
    GTG GGC ATG CTG GGC AAC GCC CTG GTC TGT CAT ATC TTC AAG AAC CAG CGA
                                    Val Cys His Ile Phe Lys Asn Gln Arg 64              73              82              91              100             109
    ATG CAC TCG GCC ACC AGC CTC TTC ATC GTC AAC CTG GCA GTT GCC GAC ATA ATG
    Met His Ser Ala Thr Ser Leu Phe Ile Val Asn Leu Ala Val Ala Asp Ile Met 118             127             136             145             154             163
    ATC ACG CTC AAC ACC CCC TTC ACT TTG GTT CGC TTT GTG AAC AGC ACA TGG
    Ile Thr Leu Asn Thr Pro Phe Thr Leu Val Arg Phe Val Asn Ser Thr Trp 172             181             190             199             208             217
    ATA TTT GGG AAG GGC ATG TGC CAT GTC AGC CGC TTT GCC CAG TAC TGC TCA CTG
    Ile Phe Gly Lys Gly Met Cys His Val Ser Arg Phe Ala Gln Tyr Cys Ser Leu 226             235
    CAC GTC TCA GCA CTG ACA  3'
    His Val Ser Ala Leu Thr
```

FIGURE 30

```
                 9                  18             27             36             45              54
5' GAG CCA GCT GAC CTC TTC TGG AAG AAC CTG GAC TTG CCC ACC TTC ATC CTG CTC
   Glu Pro Ala Asp Leu Phe Trp Lys Asn Leu Asp Leu Pro Thr Phe Ile Leu Leu 63                 72             81             90             99              108
   AAC ATC CTG CCC CTC ATC ATC TCT GTG GCC TAC GTT CGT GTG ACC AAG AAA
   Asn Ile Leu Pro Leu Ile Ile Ser Val Ala Tyr Val Arg Val Thr Lys Lys 117                126            135            144            153             162
   CTG TGG CTG TGT AAT ATG ATT GTC GAT GTG ACC ACA GAG CAG TAC TTT GCC CTG
   Leu Trp Leu Cys Asn Met Ile Val Asp Val Thr Thr Glu Gln Tyr Phe Ala Leu 171                180            189            198            207             216
   CGG CCC AAA AAG AAG ATG TTG ATG CTG GTG GTA GTC CTC TTT
   Arg Pro Lys Lys Lys Thr Ile Lys Met Leu Met Leu Val Val Val Leu Phe 225                234
   GCC CTC TGC TGG TTG CCT CTC GAC 3'
   Ala Leu Cys Trp Leu Pro Leu Asp
```

FIGURE 33

```
              10         20         30         40         50
p63A2    1 VCHVIFKNQR MHSATSLFIV NLAVADIMIT LLNTPFTLVR FVNSTWIFGK  50
P30731   1 VCHVIFKNQR MHSATSLFIV NLAVADIMIT LLNTPFTLVR FVNSTWVFGK  50

60         70         80         90        100
p63A2   51 GMCHVSRFAQ YCSLHVSALT                                  100
P30731  51 GMCHVSRFAQ YCSLHVSALT LTAIAVDRHQ VIMHPLKPRI SITKGVIYIA 100

110        120        130        140        150
p63A2  101                                            EP ADLFWKNLDL 150
P30731 101 VIWVMATFFS LPHAICQKLF TFKYSEDIVR SLCLPDFPEP ADLFWKYLDL 150

160        170        180        190        200
p63A2  151 PTFILLNILP LLIISVAYVR VTKKLWLCNM IVDVTTEQYF ALRPKKKKTI 200
P30731 151 ATFILLYLLP LFIISVAYAR VAKKLWLCNT IGDVTTEQYL ALRRKKKTTV 200

210        220        230        240        250
p63A2  201 KMLMLVVVL. .......... .......... .......... ..........  250
P30731 201 KMLVLVVVL. .......... .......... .......... ..........  250
```

FIGURE 34A

| | |
|---|---:|
| CATCGTCAAG CAGATGAAGA TCATCCACGA GGATGGCTAC TCCGAGGGCC AGCAGAAATT | 60 |
| CTGCCCCTTC TTCCCGCGAG TGCTTTCCCG CTCTCCAAAC CCCACTCCCA GGTGGCC | 117 |

```
ATG GCC TCA TCG ACC ACT CGG GGC CCC AGG GTT TCT GAC TTA TTT TCT    165
Met Ala Ser Ser Thr Thr Arg Gly Pro Arg Val Ser Asp Leu Phe Ser
 1               5                  10                  15

GGG CTG CCG CCG GCG GTC ACA ACT CCC GCC AAC CAG AGC GCA GAG GCC    213
Gly Leu Pro Pro Ala Val Thr Thr Pro Ala Asn Gln Ser Ala Glu Ala
             20                  25                  30

TCG GCG GGC AAC GGG TCG GTG GCT GGC GCG GAC GCT CCA GCC GTC ACG    261
Ser Ala Gly Asn Gly Ser Val Ala Gly Ala Asp Ala Pro Ala Val Thr
             35                  40                  45

CCC TTC CAG AGC CTG CAG CTG GTG CAT CAG CTG AAG GGG CTG ATC GTG    309
Pro Phe Gln Ser Leu Gln Leu Val His Gln Leu Lys Gly Leu Ile Val
     50                  55                  60

CTG CTC TAC AGC GTC GTG GTG GTC GTG GGG CTG GTG GGC AAC TGC CTG    357
Leu Leu Tyr Ser Val Val Val Val Val Gly Leu Val Gly Asn Cys Leu
 65                  70                  75                  80

CTG GTG CTG GTG ATC GCG CGG GTG CGC CGG CTG CAC AAC GTG ACG AAC    405
Leu Val Leu Val Ile Ala Arg Val Arg Arg Leu His Asn Val Thr Asn
                 85                  90                  95

TTC CTC ATC GGC AAC CTG GCC TTG TCC GAC GTG CTC ATG TGC ACC GCC    453
Phe Leu Ile Gly Asn Leu Ala Leu Ser Asp Val Leu Met Cys Thr Ala
                 100                 105                 110

TGC GTG CCG CTC ACG CTG GCC TAT GCC TTC GAG CCA CGC GGC TGG GTG    501
Cys Val Pro Leu Thr Leu Ala Tyr Ala Phe Glu Pro Arg Gly Trp Val
             115                 120                 125

TTC GGC GGC GGC CTG TGC CAC CTG GTC TTC TTC CTG CAG CCG GTC ACC    549
Phe Gly Gly Gly Leu Cys His Leu Val Phe Phe Leu Gln Pro Val Thr
         130                 135                 140

GTC TAT GTG TCG GTG TTC ACG CTC ACC ACC ATC GCA GTG GAC CGC TAC    597
Val Tyr Val Ser Val Phe Thr Leu Thr Thr Ile Ala Val Asp Arg Tyr
 145                 150                 155                 160
```

FIGURE 34B

| | |
|---|---|
| GTC GTG CTG GTG CAC CCG CTG AGG CGG CGC ATC TCG CTG CGC CTC AGC<br>Val Val Leu Val His Pro Leu Arg Arg Arg Ile Ser Leu Arg Leu Ser<br>              165                      170                  175 | 645 |
| GCC TAC GCT GTG CTG GCC ATC TGG GCG CTG TCC GCG GTG CTG GCG CTG<br>Ala Tyr Ala Val Leu Ala Ile Trp Ala Leu Ser Ala Val Leu Ala Leu<br>              180                      185                  190 | 693 |
| CCC GCC GCC GTG CAC ACC TAT CAC GTG GAG CTC AAG CCG CAC GAC GTG<br>Pro Ala Ala Val His Thr Tyr His Val Glu Leu Lys Pro His Asp Val<br>              195                      200                  205 | 741 |
| CGC CTC TGC GAG GAG TTC TGG GGC TCC CAG GAG CGC CAG CGC CAG CTC<br>Arg Leu Cys Glu Glu Phe Trp Gly Ser Gln Glu Arg Gln Arg Gln Leu<br>    210                      215                      220 | 789 |
| TAC GCC TGG GGG CTG CTG CTG GTC ACC TAC CTG CTC CCT CTG CTG GTC<br>Tyr Ala Trp Gly Leu Leu Leu Val Thr Tyr Leu Leu Pro Leu Leu Val<br>225                      230                      235                  240 | 837 |
| ATC CTC CTG TCT TAC GTC CGG GTG TCA GTG AAG CTC CGC AAC CGC GTG<br>Ile Leu Leu Ser Tyr Val Arg Val Ser Val Lys Leu Arg Asn Arg Val<br>              245                      250                  255 | 885 |
| GTG CCG GGC TGC GTG ACC CAG AGC CAG GCC GAC TGG GAC CGC GCT CGG<br>Val Pro Gly Cys Val Thr Gln Ser Gln Ala Asp Trp Asp Arg Ala Arg<br>              260                      265                  270 | 933 |
| CGC CGG CGC ACC TTC TGC TTG CTG GTG GTG GTC GTG GTG GTG TTC GCC<br>Arg Arg Arg Thr Phe Cys Leu Leu Val Val Val Val Val Val Phe Ala<br>              275                      280                  285 | 981 |
| GTC TGC TGG CTG CCG CTG CAC GTC TTC AAC CTG CTG CGG GAC CTC GAC<br>Val Cys Trp Leu Pro Leu His Val Phe Asn Leu Leu Arg Asp Leu Asp<br>              290                      295                  300 | 1029 |
| CCC CAC GCC ATC GAC CCT TAC GCC TTT GGG CTG GTG CAG CTG CTC TGC<br>Pro His Ala Ile Asp Pro Tyr Ala Phe Gly Leu Val Gln Leu Leu Cys<br>305                      310                      315                  320 | 1077 |
| CAC TGG CTC GCC ATG AGT TCG GCC TGC TAC AAC CCC TTC ATC TAC GCC<br>His Trp Leu Ala Met Ser Ser Ala Cys Tyr Asn Pro Phe Ile Tyr Ala<br>              325                      330                  335 | 1125 |

FIGURE 34C

| | |
|---|---|
| TGG CTG CAC GAC AGC TTC CGC GAG GAG CTG CGC AAA CTG TTG GTC GCT<br>Trp Leu His Asp Ser Phe Arg Glu Glu Leu Arg Lys Leu Leu Val Ala<br>340                       345                 350 | 1173 |
| TGG CCC CGC AAG ATA GCC CCC CAT GGC CAG AAT ATG ACC GTC AGC GTG<br>Trp Pro Arg Lys Ile Ala Pro His Gly Gln Asn Met Thr Val Ser Val<br>      355                   360                 365 | 1221 |
| GTC ATC TGATGCCACT TAGCCAGGCC TTGGTCAAGG AGCTCCACTT CAACTGGCCT<br>Val Ile<br>    370 | 1277 |
| CCTAGGGCAC CACTCGAGGT CAATCTGGTG CTTATTCTCA GCACCAGAGC TAGC | 1331 |

FIGURE 37

| | |
|---|---|
| GTG GGC CTG GTG GGC AAC ATC CTG GCT TCC TGG CAC AAG CGT GGA GGT<br>Val Gly Leu Val Gly Asn Ile Leu Ala Ser Trp His Lys Arg Gly Gly<br>　1　　　　　　　5　　　　　　　　　10　　　　　　　　15 | 48 |
| CGC CGT GCT GCT TGG GTA GTG TGT GGA GTC GTG TGG CTG GCT GTG ACA<br>Arg Arg Ala Ala Trp Val Val Cys Gly Val Val Trp Leu Ala Val Thr<br>　　　　　　　20　　　　　　　　25　　　　　　　　30 | 96 |
| GCC CAG TGC CTG CCC ACG GCA GTC TTT GCT GCC ACA GGC ATC CAG CGC<br>Ala Gln Cys Leu Pro Thr Ala Val Phe Ala Ala Thr Gly Ile Gln Arg<br>　　　　　35　　　　　　　　40　　　　　　　　45 | 144 |
| AAC CGC ACT GTG TGC TAC GAC CTG AGC CCA CCC ATC CTG TCT ACT CGC<br>Asn Arg Thr Val Cys Tyr Asp Leu Ser Pro Pro Ile Leu Ser Thr Arg<br>　　50　　　　　　　　55　　　　　　　　60 | 192 |
| TAC CTG CCC TAT GGT ATG GCC CTC ACG GTC ATC GGC TTC TTG CTG CCC<br>Tyr Leu Pro Tyr Gly Met Ala Leu Thr Val Ile Gly Phe Leu Leu Pro<br>65　　　　　　　　70　　　　　　　　75　　　　　　　　80 | 240 |
| TTC ATA GCC TTA CTG GCT TGT TAT TGT CGC ATG GCC CGC CGC CTG TGT<br>Phe Ile Ala Leu Leu Ala Cys Tyr Cys Arg Met Ala Arg Arg Leu Cys<br>　　　　　　　85　　　　　　　　90　　　　　　　　95 | 288 |
| CGC CAG GAT GGC CCA GCA GGT CCT GTG GCC CAA GAG CGG CGC AGC AAG<br>Arg Gln Asp Gly Pro Ala Gly Pro Val Ala Gln Glu Arg Arg Ser Lys<br>　　　　　100　　　　　　　　105　　　　　　　110 | 336 |
| GCG GCT CGT ATG GCT GTG GTG GTG GCA GCT GTC TTT GCC CTC TGC TGG<br>Ala Ala Arg Met Ala Val Val Val Ala Ala Val Phe Ala Leu Cys Trp<br>　　　　　115　　　　　　　　120　　　　　　　125 | 384 |
| CTG CCT CTC TAC<br>Leu Pro Leu Tyr<br>　130 | 396 |

FIGURE 39

```
                10         20         30         40         50
p3H2-17    1 VGLVGNILAS WHKRGGRRAA WVVCGVVWLA VTAQCLPTAV FAATGIQRN-   50
p34996     1 RYTGVVHPLK SLGRLKKKNA VYVSSLVWAL VVAVIAPILF YSGTGVRRN-   50
A46226     1 RYLAVVHPTR SARWRTAPVA RTVSAAVWVA SAVVVLPVVV F--SGVPRG-   50
JN0605     1 RYVAVVHPLR AATYRRPSVA KLINLGVWLA SLLVTLPIAI FADTRPARGG   50
S28787     1 RYLAIVHATN SQKPRKLLAE KVVYVGVWLP AVLLTIPDLI FADIKEVDE-   50

60         70         80         90        100
p3H2-17   51 RTV-CYDL-- SPPILSTRYL PYGMALTVIG FLLPFIALLA CYCRMARRLC  100
p34996    51 KTITCYDT-- TADEYLRSYF VYSMCTTVFM FCIPFIVILG CYGLIVKALI  100
A46226    51 MST-CHMQWP EPAAAWRAGF IIY--TAALG FFGPLLVICL CYLLIVVKVR  100
JN0605    51 QAVACNLQWP HPAWSAVFVV YTF----LLG FLLPVLAIGL CYLLIVGKVR  100
S28787    51 RYI-CDRF-- YPSDLWLVVF QFQ--HIVVG LLLPGIVILS CYCIIISKLS  100

110        120        130        140        150
p3H2-17  101 RQDGPA-GPV AQE-RRS--K AARMAVVVAA VFALCWLPLY ..........  150
p34996   101 YKDLDN-SPL ----RR---K SIYLVIIVLT VFAVSYLPFH ..........  150
A46226   101 SAGRRVWAPS CQRRRRSERR VTRMVVAVVA LFVLCWMPFY ..........  150
JN0605   101 AVALRA---G WQQRRRSEKK ITRLVLMVVV VFVLCWMPFY ..........  150
S28787   101 HSKG------ YQKR-----K ALKTTVILIL TFFACWLPYY ..........  150
```

FIGURE 40

| | |
|---|---|
| GTG GGC CTG GTG GGC AAC TTC CTG GCC GCG ATG TCT GTG GAT CGC TAC<br>Val Gly Leu Val Gly Asn Phe Leu Ala Ala Met Ser Val Asp Arg Tyr<br>　1　　　　　　　5　　　　　　　　　　10　　　　　　　　15 | 48 |
| GTG GCC ATT GTG CAC TCG CGG CGC TCC TCC TCC CTC AGG GTG TCC CGC<br>Val Ala Ile Val His Ser Arg Arg Ser Ser Ser Leu Arg Val Ser Arg<br>　　　　　　20　　　　　　　　　25　　　　　　　　30 | 96 |
| AAC GCA CTG CTG GGC GTG GGC TTC ATC TGG GCG CTG TCC ATC GCC ATG<br>Asn Ala Leu Leu Gly Val Gly Phe Ile Trp Ala Leu Ser Ile Ala Met<br>　　　　35　　　　　　　　　40　　　　　　　　45 | 144 |
| GCC TCG CCG GTG GCC TAC CAC CAG CGT CTT TTC CAT CGG GAC AGC AAC<br>Ala Ser Pro Val Ala Tyr His Gln Arg Leu Phe His Arg Asp Ser Asn<br>　　50　　　　　　　　　55　　　　　　　　60 | 192 |
| CAG ACC TTC TGC TGG GAG CAG TGG CCC AAC AAG CTC CAC AAG AAG GCT<br>Gln Thr Phe Cys Trp Glu Gln Trp Pro Asn Lys Leu His Lys Lys Ala<br>65　　　　　　　　70　　　　　　　　　75　　　　　　　　80 | 240 |
| TAC GTG GTG TGC ACT TTC GTC TTT GGG TAC CTT CTG CCC TTA CTG CTC<br>Tyr Val Val Cys Thr Phe Val Phe Gly Tyr Leu Leu Pro Leu Leu Leu<br>　　　　　　85　　　　　　　　　90　　　　　　　　95 | 288 |
| ATC TGC TTT TGC TAT GCC AAG GTC CTT AAT CAT CTG CAT AAA AAG CTG<br>Ile Cys Phe Cys Tyr Ala Lys Val Leu Asn His Leu His Lys Lys Leu<br>　　　　　100　　　　　　　　　105　　　　　　　110 | 336 |
| AAA AAC ATG TCA AAA AAG TCT GAA GCA TCC AAG AAA AAG ACT GCA CAG<br>Lys Asn Met Ser Lys Lys Ser Glu Ala Ser Lys Lys Lys Thr Ala Gln<br>　　　　115　　　　　　　　　120　　　　　　　　125 | 384 |
| ACC GTC CTG GTG GTC GTT GTA GTA TTT GCC CTC TGC TGG CTG CCT TTC<br>Thr Val Leu Val Val Val Val Val Phe Ala Leu Cys Trp Leu Pro Phe<br>　　130　　　　　　　　　135　　　　　　　140 | 432 |
| TAC<br>Tyr<br>145 | 435 |

FIGURE 42

```
                   10          20          30          40          50
p3H2-34     1  VGLVGNFLAA  MSVDRYVAIV  HSRRSSSLRV  SRNALLGVGF  IWALSIAMAS   50
JN0605      1  MFTSVFCLTV  LSVDRYVAVV  HPLRAATYRR  PSVAKLINLG  VWLASLLVTL   50
B41795      1  QFTSIFCLTV  MSIDRYLAVV  HPIKSAKWRR  PRTAKMITMA  VWGVSLLVIL   50
A39297      1  MFTSIYCLTV  LSVDRYVAVV  HPIKAARYRR  PTVAKVVNLG  VWVLSLLVIL   50

60          70          80          90         100
p3H2-34    51  PVA-YHQRLF  HRDSNQTFCW  EQWPNKLHK-  -KAYVVCTFV  FGYLLPLLLI  100
JN0605     51  PIAIFADTRP  ARGGQAVACN  LQWPHPAWS-  -AVFVVYTFL  LGFLLPVLAI  100
B41795     51  PIMIYAGLRS  NQWGRSS-CT  INWPGESGAW  YTGFIIYTFI  LGFLVPLTII  100
A39297     51  PIVVFSRTAA  NSDGTVA-CN  MLMPEPAQRW  LVGFVLYTFL  MGFLLPVGAI  100

110         120         130         140         150
p3H2-34   101  CFCY----AK  VLNHLHKKLK  NMSKKSEASK  KKTAQTVLVV  VVVFALCWLP  150
JN0605    101  GLCYLLIVGK  MRAVALRAGW  QQRRRSE---  KKITRLVLMV  VVVFVLCWMP  150
B41795    101  CLCYLFIIIK  VKSSGIRVGS  SKRKKSE---  KKVTRMVSIV  VAVFIFCWLP  150
A39297    101  CLCYVLIIAK  MRMVALKAGW  QQRKRSE---  RKITLMVMMV  VMVFVICWMP  150

```
                 10              19          28          37          46              55
5' GTG GGC ATG GTG GGC AAC GTC CTG GTG CTC TGG TTC TTC GGC TTC TCC ATC AAG
   Val Gly Met Val Gly Asn Val Leu Val Leu Trp Phe Phe Gly Phe Ser Ile Lys 64              73          82          91          100             109
   AGG ACC CCC TTC TCC GTC TAC TTC CTG CAC CTG GCC AGC GCC GAC GGC GCC TAC
   Arg Thr Pro Phe Ser Val Tyr Phe Leu His Leu Ala Ser Ala Asp Gly Ala Tyr 118             127         136         145         154             163
   CTC TTC AGC AAG GCC GTG TTC TCC CTG CTG AAC GCC GGC GGC TTC CTG GGC ACC
   Leu Phe Ser Lys Ala Val Phe Ser Leu Leu Asn Ala Gly Gly Phe Leu Gly Thr 172             181         190         199         208             217
   TTC GCC CAC TAT GTG CGC AGC CTG GCC CGG GTG CTG GGG CTC TGC GCC TTC GTG
   Phe Ala His Tyr Val Arg Ser Leu Ala Arg Val Leu Gly Leu Cys Ala Phe Val 226             235         244         253         262
   GCG GGC GTG AGC CTC CTG CCG GCC GTG AGC ATG GAG CGC TGC GCG TCT G 3'
   Ala Gly Val Ser Leu Leu Pro Ala Val Ser Met Glu Arg Cys Ala Ser
```

FIGURE 45

```
             10         20         30         40         50
pMD4    1 VGMVGNVLVL WFFGFSIKRT PFSVYFLHLA SADGAYLFSK AVFSLLNAGG  50
A35639  1 CGLVGNGLVL WFFGFSIKRT PFSIYFLHLA SADGIYLFSK AVIALLNMGT  50

60         70         80         90        100
pMD4   51 FLGTFAHYVR SWARVLGLCA FVAGVSLLPA VSMERCAS.. ..........  100
A35639 51 FLGSFPDYVR RVSRIVGLCT FFAGVSLLPA ISIERCVS.. ..........  100
```

FIGURE 51

```
              10         20         30         40         50
pMJ10   1 LLTLHPVNSQ KHRTSHWASR VVLGVALSAT AFSVPYLVFR ETYDDR-K-G  50
B42009  1 ICVLHPVWAQ NHRTVSLAMK VIVGPWILAL VLTLPVFLFL TTVTIP-N-G  50
JC2014  1 VCVLHPVITQ NHRTVSLAKK VIIGPWVMAL LLTLPVIIRV TTVPGK-T-G  50
A46520  1 ICVLHPVWAQ NHRNVSLAKK VIVGPWICAL LLTLPVIIRV TTLSHPRAPG  50
A46525  1 LLVFKPILCQ KVRGTGLAWM ACGVAWVLAL LLTIPSFVYR EAYKDFYS-E  50
S28787  1 LAIVHATNSQ KPRKLLAEKV VYVGVWLPAV LLTIPDLIFA DI-KEV-D-E  50

60         70         80         90        100
pMJ10  51 RVTCRNWYAV STDWESKEMQ TVRQWIHATC FISRFILGFL LPFLVIGFCY 100
B42009 51 DIYCTFWFAS AGG-TPEERL KVAITMLIAR GIIRFVIGFS LPMSIVAICY 100
JC2014 51 TVACTFWFSP WTN-DPKERI KVAVAMLTVR GIIRFIIGFS APMSIVAVSY 100
A46520 51 KMACTFDWSP WTE-DPALKL KVAISMFMVR GIIRFIIGFS TPMSIVAVCY 100
A46525 51 HTVCGIWYGG GS--FPKEKA VA------- -ILRLMVGFV LPLLTLNICY 100
S28787 51 RYICDRFYP- SDLA-----L VWFQFQH-- ----IVVGLL LPGIVILSCY 100

110        120        130        140        150
pMJ10  101 ERVARKMKER GLFKSSKPFK VTMTAVI--- ---------- ---------- 150
B42009 101 GLIAAKIHKK GMIKSSRPLR VLTAVVA--- ---------- ---------- 150
JC2014 101 GLIATKIHKQ GLIKSSRPLR VLSFVAA--- ---------- ---------- 150
A46520 101 GLIATKIHRQ GLIKSSRPLR VLSFVAA--- ---------- ---------- 150
A46525 101 TFLLLRTWSR KATRSTKTLK VVMAVVI--- ---------- ---------- 150
S28787 101 CIWISWLSHS KGYQKRKALK TTVILIL--- ---------- ---------- 150
```

FIGURE 46A

```
CAAAGCAACA GGTGCAACCT CAAGGCACTG AAAGCAAGGG GACGCAGCTC ACAAGGGCCA      60

AGGGATTGAA CCCATAACCG CTCAGAAGAT TCTCCGCCTG CCGAGAGCTG CGGAGGAGTC     120

CCACCCGTCC AGCTTGCTGA CTGCGAGCAG TGAGAGTCGC CTAGACCCGT ACCTCTGTGT     180

TCTGGAGCCT GCCGCCCCCG CACGGGAAAG GCTTAGCTCG GGACTTGCAG CACCGCCTCC     240

TCTTTAGCCA GGCCAGGCAC GAGGATAGTG TGATCGGGCA CAGCCAGGGT CGCTCTTCCA     300

GGCTTTCTTG CGGGTTGCGG GAGGTACTAG TTGGAGACGC GCGCGCTCGC TCTCGCCGCT     360

CTGTCCTGGG CCACTCCGTG ATCCTAAGGC TACCTCCAGA GCCAGTTTTC CCTGGCTGGC     420

ACAACTCTCC AGGGCGCTCC GGTCCGTTGC ACAGCGCCCC AAGGGGGTAC CCAGTAAGTG     480
```

```
ATG GAA CTG GCT ATG GTG AAC CTC AGT GAA GGG AAT GGG AGC GAC CCA      528
Met Glu Leu Ala Met Val Asn Leu Ser Glu Gly Asn Gly Ser Asp Pro
 1               5                  10                  15

GAG CCG CCA GCC CCG GAG TCC AGG CCG CTC TTC GGC ATT GGC GTG GAG      576
Glu Pro Pro Ala Pro Glu Ser Arg Pro Leu Phe Gly Ile Gly Val Glu
             20                  25                  30

AAC TTC ATT ACG CTG GTA GTG TTT GGC CTG ATT TTC GCG ATG GGC GTG      624
Asn Phe Ile Thr Leu Val Val Phe Gly Leu Ile Phe Ala Met Gly Val
         35                  40                  45

CTG GGC AAC AGC CTG GTG ATC ACC GTG CTG GCG CGC AGC AAA CCA GGC      672
Leu Gly Asn Ser Leu Val Ile Thr Val Leu Ala Arg Ser Lys Pro Gly
     50                  55                  60

AAC CCC CGC AGC ACC ACC AAC CTG TTT ATC CTC AAT CTG AGC ATC GCA      720
Asn Pro Arg Ser Thr Thr Asn Leu Phe Ile Leu Asn Leu Ser Ile Ala
 65                  70                  75                  80

GAC CTG GCC TAC CTG CTC TTC TGC ATC CCT TTT CAG GCC ACC GTG TAT      768
Asp Leu Ala Tyr Leu Leu Phe Cys Ile Pro Phe Gln Ala Thr Val Tyr
             85                  90                  95

GCA CTG CCC ACC TGG GTG CTG GGC GCC TTC ATC TGC AAG TTT ATA CAC      816
Ala Leu Pro Thr Trp Val Leu Gly Ala Phe Ile Cys Lys Phe Ile His
            100                 105                 110
```

FIGURE 46B

```
TAC TTC TTC ACC GTG TCC ATG CTG GTG AGC ATC TTC ACC CTG GCC GCG        864
Tyr Phe Phe Thr Val Ser Met Leu Val Ser Ile Phe Thr Leu Ala Ala
        115                 120                 125

ATG TCT GTG GAT CGC TAC GTG GCC ATT GTG CAC TCG CGG CGC TCC TCC        912
Met Ser Val Asp Arg Tyr Val Ala Ile Val His Ser Arg Arg Ser Ser
        130                 135                 140

TCC CTC AGG GTG TCC CGC AAC GCA CTG CTG GGC GTG GGC TTC ATC TGG        960
Ser Leu Arg Val Ser Arg Asn Ala Leu Leu Gly Val Gly Phe Ile Trp
145                 150                 155                 160

GCG CTG TCC ATC GCC ATG GCC TCG CCG GTG GCC TAC CAC CAG CGT CTT       1008
Ala Leu Ser Ile Ala Met Ala Ser Pro Val Ala Tyr His Gln Arg Leu
                165                 170                 175

TTC CAT CGG GAC AGC AAC CAG ACC TTC TGC TGG GAG CAG TGG CCC AAC       1056
Phe His Arg Asp Ser Asn Gln Thr Phe Cys Trp Glu Gln Trp Pro Asn
            180                 185                 190

AAG CTC CAC AAG AAG GCT TAC GTG GTG TGC ACT TTC GTC TTT GGG TAC       1104
Lys Leu His Lys Lys Ala Tyr Val Val Cys Thr Phe Val Phe Gly Tyr
        195                 200                 205

CTT CTG CCC TTA CTG CTC ATC TGC TTT TGC TAT GCC AAG GTC CTT AAT       1152
Leu Leu Pro Leu Leu Leu Ile Cys Phe Cys Tyr Ala Lys Val Leu Asn
    210                 215                 220

CAT CTG CAT AAA AAG CTG AAA AAC ATG TCA AAA AAG TCT GAA GCA TCC       1200
His Leu His Lys Lys Leu Lys Asn Met Ser Lys Lys Ser Glu Ala Ser
225                 230                 235                 240

AAG AAA AAG ACT GCA CAG ACC GTC CTG GTG GTC GTT GTA GTA TTT GGC       1248
Lys Lys Lys Thr Ala Gln Thr Val Leu Val Val Val Val Val Phe Gly
                245                 250                 255

ATA TCC TGG CTG CCC CAT CAT GTC GTC CAC CTC TGG GCT GAG TTT GGA       1296
Ile Ser Trp Leu Pro His His Val Val His Leu Trp Ala Glu Phe Gly
            260                 265                 270

GCC TTC CCA CTG ACG CCA GCT TCC TTC TTC TTC AGA ATC ACC GCC CAT       1344
Ala Phe Pro Leu Thr Pro Ala Ser Phe Phe Phe Arg Ile Thr Ala His
        275                 280                 285
```

FIGURE 46C

```
TGC CTG GCA TAC AGC AAC TCC TCA GTG AAC CCC ATC ATA TAT GCC TTT     1392
Cys Leu Ala Tyr Ser Asn Ser Ser Val Asn Pro Ile Ile Tyr Ala Phe
    290                 295                 300

CTC TCA GAA AAC TTC CGG AAG GCG TAC AAG CAA GTG TTC AAG TGT CAT     1440
Leu Ser Glu Asn Phe Arg Lys Ala Tyr Lys Gln Val Phe Lys Cys His
305                 310                 315                 320

GTT TGC GAT GAA TCT CCA CGC AGT GAA ACT AAG GAA AAC AAG AGC CGG     1488
Val Cys Asp Glu Ser Pro Arg Ser Glu Thr Lys Glu Asn Lys Ser Arg
                325                 330                 335

ATG GAC ACC CCG CCA TCC ACC AAC TGC ACC CAC GTG TGAAGGTTTG          1534
Met Asp Thr Pro Pro Ser Thr Asn Cys Thr His Val
                340                 345

CGGGAGCCTC CCGACTTCCA GCTCCCATGT GTGTTAGAGA GAGGAGGGCG GAGCGAATTA   1594

TCAAGTAACA TGG                                                      1607
```

Figure 48

```
                    10         20         30         40         50
MOUSEGALRECE   1  MELAMVNLSE GNGSDPEPPA PESRPLFGIG VENFITLVVF GLIFAMGVLG  50
HUMGALAMI      1  MELAVGNLSE GNASCPEPPA PEPGPLFGIG VENFVTLVVF GLIFALGVLG  50

60         70         80         90        100
MOUSEGALRECE  51  NSLVITVLAR SKPGKPRSTT NLFILNLSIA DLAYLLFCIP FOATVYALPT 100
HUMGALAMI     51  NSLVITVLAR SKPGKPRSTT NLFILNLSIA DLAYLLFCIP FOATVYALPT 100

110        120        130        140        150
MOUSEGALRECE 101  WVLGAFICKF IHYFFTVSML VSIFTLAAMS VDRYVAIVHS RRSSSLRVSR 150
HUMGALAMI    101  WVLGAFICKF IHYFFTVSML VSIFTLAAMS VDRYVAIVHS RRSSSLRVSR 150

160        170        180        190        200
MOUSEGALRECE 151  NALLGVGFIW ALSIAMASPV AYHQRLFH-R DSNQTFCWEQ WPNKLHKKAY 200
HUMGALAMI    151  NALLGVGCIW ALSIAMASPV AYHQGLFHPR ASNQTFCWEQ WPDPRHKKAY 200

210        220        230        240        250
MOUSEGALRECE 201  VVCTFVFGYL LPLLLICFCY AKVLNHLHKK LKNMSKKSEA SKKKTAQTVL 250
HUMGALAMI    201  VVCTFVFGYL LPLLLICFCY AKVLNHLHKK LKNMSKKSEA SKKKTAQTVL 250

260        270        280        290        300
MOUSEGALRECE 251  VVVVVFGISW LPHHVVHLWA EFGAFPLTPA SFFFRITAHC LAYSNSSVNP 300
HUMGALAMI    251  VVVVVFGISW LPHHIIHLWA EFGVFPLTPA SFLFRITAHC LAYSNSSVNP 300

310        320        330        340        350
MOUSEGALRECE 301  IIYAFLSENF RKAYKQVFKC HVCDESPRSE TKENKSRMDT PPSTNCTHVX 350
HUMGALAMI    301  IIYAFLSENF RKAYKQVFKC HIRKDSHLSD TKENKSRIDT PPSTNCTHVX 350

360        370        380        390        400
MOUSEGALRECE 351  ---------- ---------- ---------- ---------- ---------- 400
HUMGALAMI    351  X--------- ---------- ---------- ---------- ---------- 400
```

FIGURE 49

```
CTCGCGGCTC TGGGTATGGA TCGGTAT CTT CTC ACC CTT CAC CCA GTG TGG        51
                                Leu Leu Thr Leu His Pro Val Trp
                                 1               5

TCC CAA AAG CAC CGA ACC TCA CAC TGG GCT TCC AGA GTC GTT CTG GGA      99
Ser Gln Lys His Arg Thr Ser His Trp Ala Ser Arg Val Val Leu Gly
         10              15                  20

GTC TGG CTC TCT GCC ACT GCC TTC AGC GTG CCC TAT TTG GTT TTC AGG      147
Val Trp Leu Ser Ala Thr Ala Phe Ser Val Pro Tyr Leu Val Phe Arg
 25              30                  35                  40

GAG ACA TAT GAT GAC CGT AAA GGA AGA GTG ACC TGC AGA AAT AAC TAC      195
Glu Thr Tyr Asp Asp Arg Lys Gly Arg Val Thr Cys Arg Asn Asn Tyr
                 45                  50                  55

GCT GTG TCC ACT GAC TGG GAA AGC AAA GAG ATG CAA ACA GTA AGA CAA      243
Ala Val Ser Thr Asp Trp Glu Ser Lys Glu Met Gln Thr Val Arg Gln
                 60                  65                  70

TGG ATT CAT GCC ACC TGT TTC ATC AGC CGC TTC ATA CTG GGC TTC CTT      291
Trp Ile His Ala Thr Cys Phe Ile Ser Arg Phe Ile Leu Gly Phe Leu
             75                  80                  85

CTG CCT TTC TTA GTC ATT GGC TTT TGT TAT GAA AGA GTA GCC CGC AAG      339
Leu Pro Phe Leu Val Ile Gly Phe Cys Tyr Glu Arg Val Ala Arg Lys
             90                  95                 100

ATG AAA GAG AGG GGC CTC TTT AAA TCC AGC AAA CCC TTC AAA GTC ACG      387
Met Lys Glu Arg Gly Leu Phe Lys Ser Ser Lys Pro Phe Lys Val Thr
105             110                 115                 120

ATG ACT GCT GTT ATC TCTTTTTTCT GTCCTGGCTT CCCTACCACA TG              434
Met Thr Ala Val Ile
                125
```

FIGURE 52

```
CTGACTGCTC TGGGGACTGA CCGGTAT TTC AAG ATT GTG AAG CCC CTT TCC          51
                                Phe Lys Ile Val Lys Pro Leu Ser
                                 1               5

ACG TCC TTC ATC CAG TCT GTG AAC TAC AGC AAA CTC GTC TCG CTG GTG        99
Thr Ser Phe Ile Gln Ser Val Asn Tyr Ser Lys Leu Val Ser Leu Val
        10              15              20

GTC TGG TTG CTC ATG CTC CTC CTC GCC GTC CCC AAC GTC ATT CTC ACC       147
Val Trp Leu Leu Met Leu Leu Leu Ala Val Pro Asn Val Ile Leu Thr
 25              30              35                          40

AAC CAG AGA GTT AAG GAC GTG ACG CAG ATA AAA TGC ATG GAA CTT AAA       195
Asn Gln Arg Val Lys Asp Val Thr Gln Ile Lys Cys Met Glu Leu Lys
                 45              50              55

AAC GAA CTG GGC CGC CAG TGG CAC AAG GCG TCA AAC TAC ATC TTT GTG       243
Asn Glu Leu Gly Arg Gln Trp His Lys Ala Ser Asn Tyr Ile Phe Val
             60              65              70

GGC ATT TTC TGG CTT GTG TTC CTT TTG CTA ATC ATT TTC TAC ACT GCT       291
Gly Ile Phe Trp Leu Val Phe Leu Leu Leu Ile Ile Phe Tyr Thr Ala
         75              80              85

ATC ACC AGG AAA ATC TTT AAG TCC CAC CTG AAA TCC AGA AAG AAT TCC       339
Ile Thr Arg Lys Ile Phe Lys Ser His Leu Lys Ser Arg Lys Asn Ser
         90              95              100

ATC TCG GTC AAA AAG AAA TCT AGC CGC AAC ATC TTC AGC ATC GTG           384
Ile Ser Val Lys Lys Lys Ser Ser Arg Asn Ile Phe Ser Ile Val
105              110              115

TTTATCCTCT GTTGGCCCCC CTACCACATC                                      414
```

FIGURE 54

```
              10         20         30         40         50
pMH28   1  FKIVKPLSTS FIQSVNYSKL VSLVVWLLML LLAVPNVILT NQRVKDVTQI  50
p35343  1  LAIVHATST- LIQKRHLVKF VCIAMWLLSV ILALPILILR NPVKVNLSTL  50
A41795  1  VAVVHPIKAA RYRRPTVAKV VNLGVWVLSL LVILPIVVFS RTAANSDGTV  50
A47457  1  VAVVHPLRAA TYRRPSVAKL INLGVWLASL LVTLPIAIFA DTRPARGGQ-  50

60         70         80         90        100
pMH28   51 KCME-LKNEL GRQWHKASNY IFVGIF-WLV FLLLIIFYTA IT-RKIFKSH 100
P35343  51 VCYEDVGNNT SRL--RVVLR ILPQTFGFLV PLLIMLFCYG FTLRTLFKAH 100
A41795  51 ACNM-LMPEP AQRWLVGFV- LYTFLMGFLL PVGAICLCYV LIIAKMRMVA 100
A47457  51 AVAC-NLQWP HPAWSAVFV- VYTFLLGFLL PVLAIGLCYL LIVGKMRAVA 100

110        120        130        140        150
pMH28   101 LKSRKNSI-S VKKKSSRNIF S--IV---   ----------  --------- 150
P35343  101 MG----QKHR AMR----VIF AVVLV---   ----------  --------- 150
A41795  101 LKAGWQQRKR SERKITLMVM MVVMV---   ----------  --------- 150
A47457  101 LRAGWQQRRR SEKKITRLVL MVVVV---   ----------  --------- 150
```

FIGURE 55

| | | | | | | | | | | | | | | | | |
|---|---|---|---|---|---|---|---|---|---|---|---|---|---|---|---|---|

<u>GCCACCAACG TGTTCATCCT GTGTCTG</u> GTG GAC CTG CTG GCT GCC CTG ACC     51
                                                   Val Asp Leu Leu Ala Ala Leu Thr
                                                     1                 5

CTC ATG CCT CTG GCC ATG CTC TCC AGC TCC GCC CTC TTT GAC CAC GCC     99
Leu Met Pro Leu Ala Met Leu Ser Ser Ser Ala Leu Phe Asp His Ala
     10                   15                         20

CTC TTT GGG GAG GTG GCC TGC CGC CTC TAC TTG TTC CTG AGC GTC TGC     147
Leu Phe Gly Glu Val Ala Cys Arg Leu Tyr Leu Phe Leu Ser Val Cys
     25                   30                         35                         40

TTT GTC AGC CTG GCC ATC CTC TCG GTG TCC GCC ATC AAT GTG GAG CGC     195
Phe Val Ser Leu Ala Ile Leu Ser Val Ser Ala Ile Asn Val Glu Arg
                      45                         50                          55

TAC TAT TAT GTG GTC CAC CCC ATG CGC TAT GAG GTG CGC ATG AAA CTG     243
Tyr Tyr Tyr Val Val His Pro Met Arg Tyr Glu Val Arg Met Lys Leu
                  60                         65                         70

GGG CTG GTG GCC TCT GTG CTG GTG GGC GTG TGG GTG AAG GCC CTG GCC     291
Gly Leu Val Ala Ser Val Leu Val Gly Val Trp Val Lys Ala Leu Ala
                  75                         80                         85

ATG GCT TCT GTG CCA GTG TTG GGA AGG GTG TCC TGG GAG GAA GGC CCT     339
Met Ala Ser Val Pro Val Leu Gly Arg Val Ser Trp Glu Glu Gly Pro
     90                   95                         100

CCC AGT GTC CCC CCA GGC TGT TCA CTC CAA TGG AGC CAC AGT GCC TAC     387
Pro Ser Val Pro Pro Gly Cys Ser Leu Gln Trp Ser His Ser Ala Tyr
 105                   110                         115                         120

TGC CAG CTT TTC GTG GTG GTC TTC GCC GTC CTC TAC TTC CTG CTG CCC     435
Cys Gln Leu Phe Val Val Val Phe Ala Val Leu Tyr Phe Leu Leu Pro
                          125                         130                         135

CTG CTC CTC ATC CTT GTG GTC TAC TGC AGC ATG TTC CGG GTG GCT CGT     483
Leu Leu Leu Ile Leu Val Val Tyr Cys Ser Met Phe Arg Val Ala Arg
                        140                         145                         150

GTG GCT GCC ATG CAG CAC GGG CCG CTG CCC ACG TGG ATG GAG ACG CCC     531
Val Ala Ala Met Gln His Gly Pro Leu Pro Thr Trp Met Glu Thr Pro
                155                         160                         165

FIGURE 56

| | |
|---|---|
| CGG CAA CGC TCC GAG TCT CTC AGC AGC CGC TCC ACT ATG GTC ACC AGC<br>Arg Gln Arg Ser Glu Ser Leu Ser Ser Arg Ser Thr Met Val Thr Ser<br>    170                           175                       180 | 579 |
| TCG GGG GCC CCG CAG ACC ACC CCT CAC CGG ACG TTT GGC GGA GGG AAG<br>Ser Gly Ala Pro Gln Thr Thr Pro His Arg Thr Phe Gly Gly Gly Lys<br>185                     190                      195                   200 | 627 |
| GCA GCA GTG GTC CTC CTG GCT GTG GGA GGA CAG TTC CTG CTC TGT TGG<br>Ala Ala Val Val Leu Leu Ala Val Gly Gly Gln Phe Leu Leu Cys Trp<br>                     205                     210                    215 | 675 |
| TTG CCC TAC TTC TCC TTC CAC CTC TAT GTG GCC CTG AGC GCT CAG CCC<br>Leu Pro Tyr Phe Ser Phe His Leu Tyr Val Ala Leu Ser Ala Gln Pro<br>        220                      225                    230 | 723 |
| ATT GCA GCG GGG CAG GTG GAG AAC GTG GTG ACC TGG ATT GGC TAC TTC<br>Ile Ala Ala Gly Gln Val Glu Asn Val Val Thr Trp Ile Gly Tyr Phe<br>        235                      240                    245 | 771 |
| TGC TTC ACC TCC AACCCTCTCC TCTATTCCTT CCTCCCT<br>Cys Phe Thr Ser<br>    250 | 810 |

FIGURE 60

```
            10         20         30         40         50
p19P2   1 VGMVGNVLLV LVIARVRRLH NVTNFLIGNL ALSDVLMCTA CVPLTLAYAF 50
S12863  1 LGVSGNLALI IIILKQKEMR NVTNILIVNL SFSDLLVAVM CLPFTFVYTL 50

60         70         80         90        100
p19P2  51 EPRGWVFGGG LCHLVFFLQP VTVYSVFTL TTIAVDRYVV LVHPLRRRI- 100
S12863 51 MDH-WVFGET MCKLNPFVQC VSITVSIFSL VLIAVERHQL IINPRGWRPN 100

110        120        130        140        150
p19P2 101 ---------- ---------- ---------- ---------- ---------- 150
S12863 101 NRHAYIGITV IWVLAVASSL PFVIYQILTD EPFQNVSLAA FKDKYVCFDK 150

160        170        180        190        200
p19P2 151 -----GLLLV IYLLPLLVIL LS-------Y VRVSVKLRNR VVPGCVTQSQ 200
S12863 151 FPSDSHRLSY TTLLLVLQYF GPLCFIFICY FKIYIRLKRR NNMMDKIRDS 200

210        220        230        240        250
p19P2 201 ADWDRARRRR TFCLVVVVV VFAICWLPYY ---------- ---------- 250
S12863 201 KYRSSETKRI NVMLLSIVVA -FAVCWLPLT ---------- ---------- 250
```

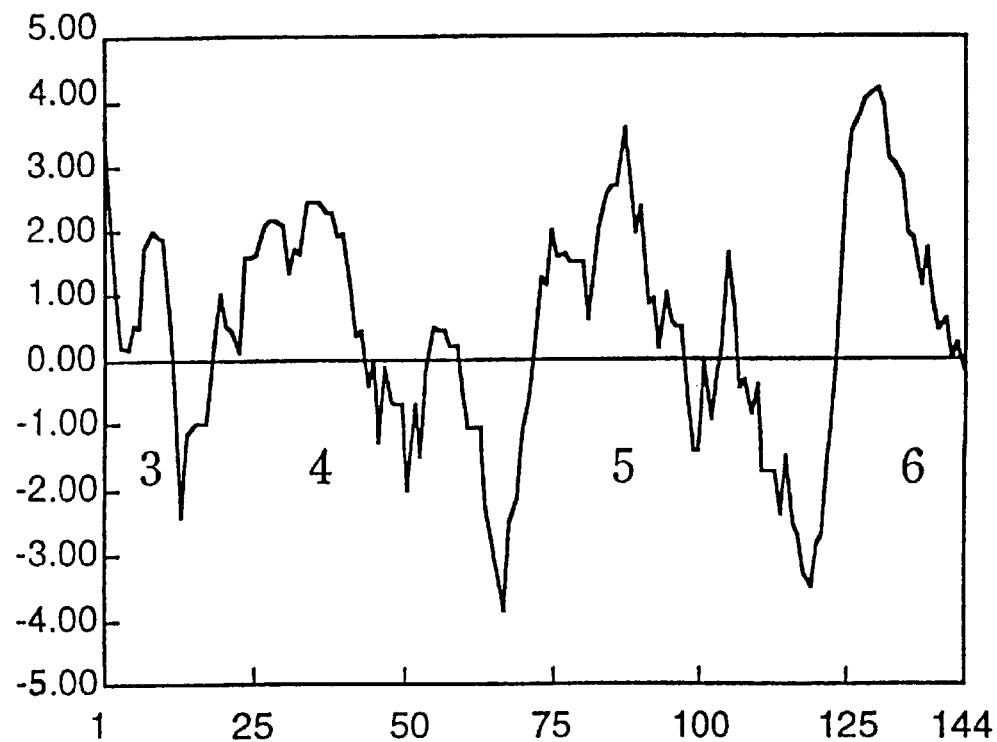

```
                  10         20         30         40         50
p19P2          1  VGMVGNVLLV LVIARVRRLH NVTNFLIGNL ALSDVLMCTA CVPLTLAYAF  50
pG3-2/pG1-10   1  VGMVGNILLV LVIARVRRLY NVTNFLIGNL ALSDVLMCTA CVPLTLAYAF  50

60         70         80         90         100
p19P2         51  EPRGWVFGGG LCHLVFFLQP VTVYVSVFTL TTIAVDRYVV LVHPLRRRI-  100
pG3-2/pG1-10  51  EPRGWVFGGG LCHLVFFLQA VTVYVSVFTL TTIAVDRYVV LVHPLRRRIS  100

110        120        130        140        150
p19P2        101  ---------- ---------- ---------- ---------- ----------  150
pG3-2/pG1-10 101  LRLSAYAVLA IWVLSAVLAL PAAVHTYHVE LKPHDVRLCE EFWGSQERQR  150

160        170        180        190        200
p19P2        151  -----GLLLV TYLLPLLVIL LSYVRVSVKL RNRVVPGCVT QSQADWDRAR  200
pG3-2/pG1-10 151  QLYAWGLLLV TYLLPLLVIL LSYARVSVKL RNRVVPGRVT QSQADWDRAR  200

210        220        230        240        250
p19P2        201  RRRTFCLLVV VVVVFAICWL PYY------- ---------- ----------  250
pG3-2/pG1-10 201  RRRTFCLLVV VVVVFTLCWL PFF------- ---------- ----------  250
```

FIGURE 62

| | | | | | | | | | | | | | | | |
|---|---|---|---|---|---|---|---|---|---|---|---|---|---|---|---|
| CTG | TGT | GTC | ATC | GCG | GTG | GAT | AGG | TAC | GTG | GTT | CTG | GTG | CAC | CCG | CTA | 48
| Leu | Cys | Val | Ile | Ala | Val | Asp | Arg | Tyr | Val | Val | Leu | Val | His | Pro | Leu |
| 1 | | | | 5 | | | | | 10 | | | | | 15 | | |

CGT CGG CGC ATT TCA CTG AGG CTC AGC GCC TAC GCG GTG CTG GGC ATC    96
Arg Arg Arg Ile Ser Leu Arg Leu Ser Ala Tyr Ala Val Leu Gly Ile
            20              25              30

TGG GCT CTA TCT GCA GTG CTG GCG CTG CCG GCC GCG GTG CAC ACC TAC   144
Trp Ala Leu Ser Ala Val Leu Ala Leu Pro Ala Ala Val His Thr Tyr
        35              40              45

CAT GTG GAG CTC AAG CCC CAC GAC GTG AGC CTC TGC GAG GAG TTC TGG   192
His Val Glu Leu Lys Pro His Asp Val Ser Leu Cys Glu Glu Phe Trp
    50              55              60

GGC TCG CAG GAG CGC CAA CGC CAG ATC TAC GCC TGG GGG CTG CTT CTG   240
Gly Ser Gln Glu Arg Gln Arg Gln Ile Tyr Ala Trp Gly Leu Leu Leu
65              70              75              80

GGC ACC TAT TTG CTC CCC CTG CTG GCC ATC CTC CTG TCT TAC GTA CGG   288
Gly Thr Tyr Leu Leu Pro Leu Leu Ala Ile Leu Leu Ser Tyr Val Arg
                85              90              95

GTG TCA GTG AAG CTG AGG AAC CGC GTG GTG CCT GGC AGC GTG ACC CAG   336
Val Ser Val Lys Leu Arg Asn Arg Val Val Pro Gly Ser Val Thr Gln
            100             105             110

AGT CAA GCT GAC TGG GAC CGA GCG CGT CGC CGC CGC ACT TTC TGT CTG   384
Ser Gln Ala Asp Trp Asp Arg Ala Arg Arg Arg Arg Thr Phe Cys Leu
        115             120             125

CTG GTG GTG GTG GTG GTA GTG TTC ACG CTC TGC TGG CTG CCC TTC TAC   432
Leu Val Val Val Val Val Val Phe Thr Leu Cys Trp Leu Pro Phe Tyr
    130             135             140

```
                     10         20         30         40         50
p19P2       1  VGMVGNVLLV LVIARVRRLH NVTNFLIGNL ALSDVLMCTA CVPLTLAYAF  50
pG3-2/pG1-10 1 VGMVGNILLV LVIARVRRLY NVTNFLIGNL ALSDVLMCTA CVPLTLAYAF  50
p5S38      -79 ---------- ---------- ---------- ---------- ----------  -30

60         70         80         90        100
p19P2       51 EPRGWVFGGG LCHLVFFLQP VTVYVSVFTL TTIAVDRYVV LVHPLRRRI-  100
pG3-2/pG1-10 51 EPRGWVFGGG LCHLVFFLQA VTVYVSVFTL TTIAVDRYVV LVHPLRRRIS 100
p5S38      -29 ---------- ---------- --------L CVIAVDRYVV LVHPLRRRIS  21

110        120        130        140        150
P19P2      101 ---------- ---------- ---------- ---------- ----------  150
PG3-2/PG1-10 101 LRLSAYAVLA IWVLSAVLAL PAAVHTYHVE LKPHDVRLCE EFWGSQERQR 150
P5S38       22 LRLSAYAVLG IWALSAVLAL PAAVHTYHVE LKPHDVSLCE EFWGSQERQR  71

160        170        180        190        200
P19P2      151 -----GLLLV TYLLPLLVIL LSYVRVSVKL RNRVVPGCVT QSQADWDRAR 200
PG3-2/PG1-10 151 QLYAWGLLLV TYLLPLLVIL LSYARVSVKL RNRVVPGRVT QSQADWDRAR 200
P5S38       72 QIYAWGLLLG TYLLPLLAIL LSYVRVSVKL RNRVVPGSVT QSQADWDRAR 121

210        220        230        240        250
P19P2      201 RRRTFCLLVV VVVVFAICWL PYY------- ---------- ----------  250
PG3-2/PG1-10 201 RRRTFCLLVV VVVVFTLCWL PFF------- ---------- ----------  250
P5S38      122 RRRTFCLLVV VVVVFTLCWL PFY------- ---------- ----------  250
```

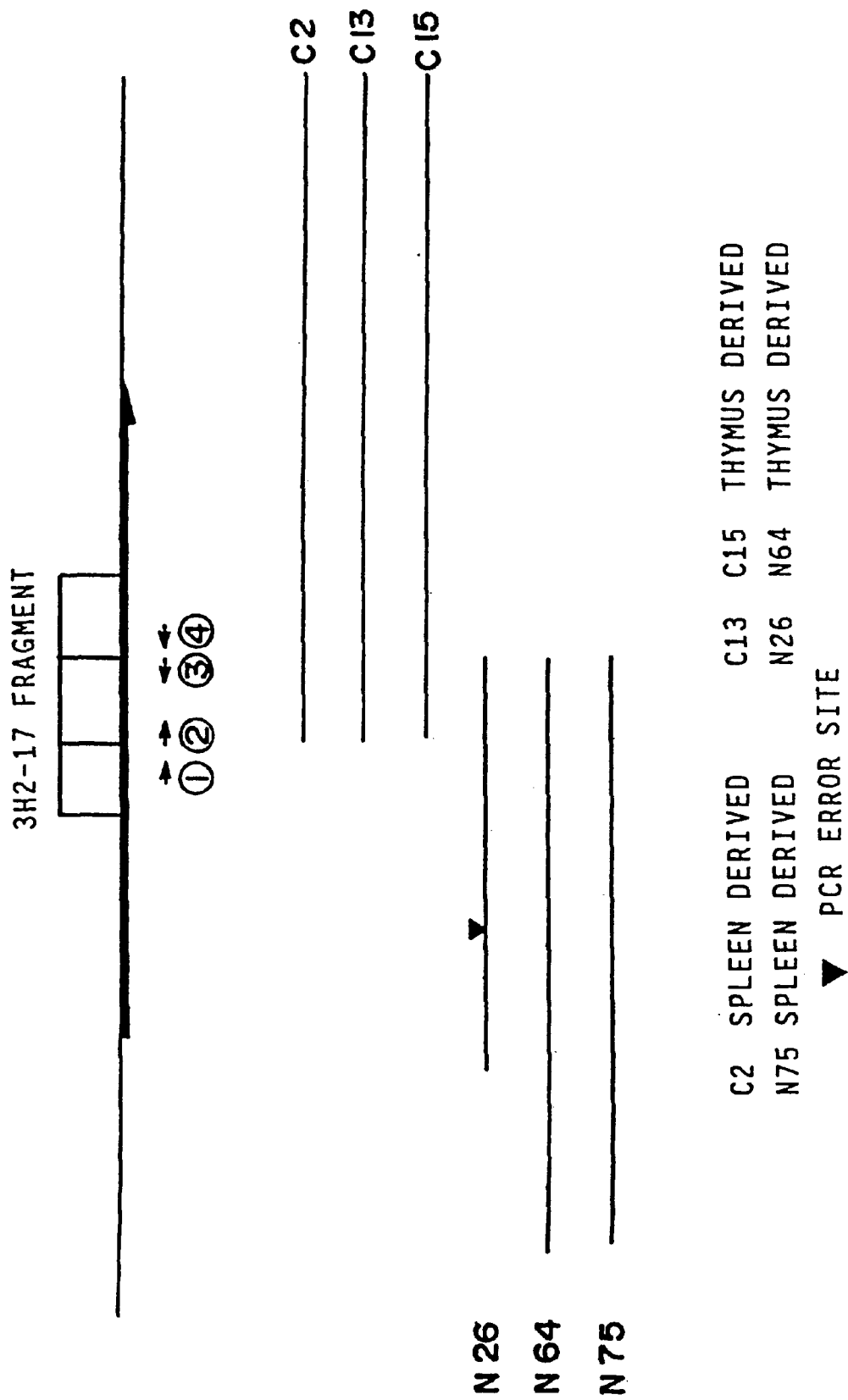

FIGURE 69A

```
GAGCATAGGA AAGGCTGACA GGCAGTT ATG GAG CAG GAC AAT GGC ACC ATC              51
                               Met Glu Gln Asp Asn Gly Thr Ile
                                 1               5

CAG GCT CCA GGC TTG CCG CCC ACC ACC TGC GTC TAC CGT GAG GAT TTC            99
Gln Ala Pro Gly Leu Pro Pro Thr Thr Cys Val Tyr Arg Glu Asp Phe
        10              15                  20

AAG CGA CTG CTG CTA ACC CCG GTA TAC TCG GTG GTG CTG GTG GTC GGC           147
Lys Arg Leu Leu Leu Thr Pro Val Tyr Ser Val Val Leu Val Val Gly
 25                  30                  35                  40

CTG CCA CTG AAC ATC TGC GTC ATT GCC CAG ATC TGC GCA TCC CGC CGG           195
Leu Pro Leu Asn Ile Cys Val Ile Ala Gln Ile Cys Ala Ser Arg Arg
                 45                  50                  55

ACC CTG ACC CGT TCC GCT GTG TAC ACC CTG AAC CTG GCA CTG GCG GAC           243
Thr Leu Thr Arg Ser Ala Val Tyr Thr Leu Asn Leu Ala Leu Ala Asp
             60                  65                  70

CTG ATG TAT GCC TGT TCA CTA CCC CTA CTT ATC TAT AAC TAC GCC AGA           291
Leu Met Tyr Ala Cys Ser Leu Pro Leu Leu Ile Tyr Asn Tyr Ala Arg
             75                  80                  85

GGG GAC CAC TGG CCC TTC GGA GAC CTC GCC TGC CGC TTT GTA CGC TTC           339
Gly Asp His Trp Pro Phe Gly Asp Leu Ala Cys Arg Phe Val Arg Phe
         90                  95                 100

CTC TTC TAT GCC AAT CTA CAT GGC AGC ATC CTG TTC CTC ACC TGC ATT           387
Leu Phe Tyr Ala Asn Leu His Gly Ser Ile Leu Phe Leu Thr Cys Ile
105                 110                 115                 120

AGC TTC CAG CGC TAC CTG GGC ATC TGC CAC CCC CTG GCT TCC TGG CAC           435
Ser Phe Gln Arg Tyr Leu Gly Ile Cys His Pro Leu Ala Ser Trp His
                125                 130                 135

AAG CGT GGA GGT CGC CGT GCT GCT TGG GTA GTG TGT GGA GTC GTG TGG           483
Lys Arg Gly Gly Arg Arg Ala Ala Trp Val Val Cys Gly Val Val Trp
            140                 145                 150

CTG GCT GTG ACA GCC CAG TGC CTG CCC ACG GCA GTC TTT GCT GCC ACA           531
Leu Ala Val Thr Ala Gln Cys Leu Pro Thr Ala Val Phe Ala Ala Thr
            155                 160                 165
```

FIGURE 69B

```
GGC ATC CAG CGC AAC CGC ACT GTG TGC TAC GAC CTG AGC CCA CCC ATC       579
Gly Ile Gln Arg Asn Arg Thr Val Cys Tyr Asp Leu Ser Pro Pro Ile
    170             175                 180

CTG TCT ACT CGC TAC CTG CCC TAT GGT ATG GCC CTC ACG GTC ATC GGC       627
Leu Ser Thr Arg Tyr Leu Pro Tyr Gly Met Ala Leu Thr Val Ile Gly
185             190                 195                     200

TTC TTG CTG CCC TTC ATA GCC TTA CTG GCT TGT TAT TGT CGC ATG GCC       675
Phe Leu Leu Pro Phe Ile Ala Leu Leu Ala Cys Tyr Cys Arg Met Ala
                205             210                 215

CGC CGC CTG TGT CGC CAG GAT GGC CCA GCA GGT CCT GTG GCC CAA GAG       723
Arg Arg Leu Cys Arg Gln Asp Gly Pro Ala Gly Pro Val Ala Gln Glu
            220                 225                 230

CGG CGC AGC AAG GCG GCT CGT ATG GCT GTG GTG GTG GCA GCT GTC TTT       771
Arg Arg Ser Lys Ala Ala Arg Met Ala Val Val Val Ala Ala Val Phe
                235                 240                 245

GCC ATC AGC TTC CTG CCT TTC CAC ATC ACC AAG ACA GCC TAC TTG GCT       819
Ala Ile Ser Phe Leu Pro Phe His Ile Thr Lys Thr Ala Tyr Leu Ala
        250                 255                 260

GTG CGC TCC ACG CCC GGT GTC TCT TGC CCT GTG CTG GAG ACC TTC GCT       867
Val Arg Ser Thr Pro Gly Val Ser Cys Pro Val Leu Glu Thr Phe Ala
265             270                 275                     280

GCT GCC TAC AAA GGC ACT CGG CCC TTC GCC AGT GTC AAC AGT GTT CTG       915
Ala Ala Tyr Lys Gly Thr Arg Pro Phe Ala Ser Val Asn Ser Val Leu
                285                 290                 295

GAC CCC ATT CTC TTC TAC TTC ACA CAA CAG AAG TTC CGG CGG CAA CCC       963
Asp Pro Ile Leu Phe Tyr Phe Thr Gln Gln Lys Phe Arg Arg Gln Pro
            300                 305                 310

CAC GAT CTC TTA CAG AGG CTC ACA GCC AAG TGG CAG AGG CAG AGA GTC      1011
His Asp Leu Leu Gln Arg Leu Thr Ala Lys Trp Gln Arg Gln Arg Val
        315                 320                 325

TGAGGCCCC                                                            1020
```

FIGURE 71

```
                          10         20         30         40         50
75+13, CODING   1  MEQD------ --NGTIQAPG LPP------- -TT-CVYR-E DFKRLLLTP- 50
P2UR_MOUSE      1  MAADLEPWNS TINGTWEGDE LGY------- ---KCRFN-E DFKYVLL-P- 50
P2YR_CHICK      1  MTEALISAAL --NGT-Q-PE LLAGGWAAGN ATTKCSLTKT GFQFYYL-PT 50

60         70         80         90        100
75+13, CODING  51  V-YSVVLVVG -LPLNICVIA QI--CASRRT LTR-SAVYTL NLALADLMYA 100
P2UR_MOUSE     51  VSYGVVCVLG -LCLNVVALY -IFLC-RLKT WNA-STTYMF HLAVSDSLYA 100
P2YR_CHICK     51  V-YILVFITG FLG-NSVAIW M-F-VFHMRP WSGIS-VYMF NLALADFLYV 100

110        120        130        140        150
75+13, CODING 101  CSLPLLIYNY ARG-DHWPFG DLACRFVRFL FYANLHGSIL FLTCISFQRY 150
P2UR_MOUSE    101  ASLPLLVYYY ARG-DHWPFS TVLCKLVRFL FYTNLYCSIL FLTCISVHRC 150
P2YR_CHICK    101  LTLPALIFYY FNKTC-WIFG DVMCKLQRFI FHVNLYGSIL FLTCISVHRY 150

160        170        180        190        200
75+13, CODING 151  LGICHPLASW HKRGGR-RAA WVVCGVVWLA VTAQCL-PTA VFAA-TGIQR 200
P2UR_MOUSE    151  LGVLRPLHSL --RWGRARYA RRVAAVVWVL VLA-CQAPVL YFVT-TSVRG 200
P2YR_CHICK    151  TGVVHPLKSL G-RLKKKN-A VYVSSLVWAL WVAVIA-PIL -FYSGTGVRR 200

210        220        230        240        250
75+13, CODING 201  NRT-VCYDLS PPI-L-STRY LPYGMALIVI GFLLPFIALL ACYCRMARRL 250
P2UR_MOUSE    201  TR-ITCHDTS ARE-LFSHFV A-YSSVMLGL LFAVPFSVIL VCYVLMARRL 250
P2YR_CHICK    201  NKTITCYDTT ADEYLRSYFV --YSMCTTVF MFCIPFIVIL GCYGLIVKAL 250

260        270        280        290        300
75+13, CODING 251  CRQDGPA-GP VAQERRSKAA --RMAVVWAA VFAISFLPFH ITKTAYLAVR 300
P2UR_MOUSE    251  -LK--PAYGT TGGLPRAKRK SVRTIALVLA VFALCFLPFH VTRTLYYSFR 300
P2YR_CHICK    251  IYKD-LDNSP ---L-RRK-- SIYLVIIVLT VFAVSYLPFH VMKTLNLRAR 300

310        320        330        340        350
75+13, CODING 301  STP---GVSC PVLETFAAAY KGTRPFASVN SVLDPILFYF TQQKFRRQPH 350
P2UR_MOUSE    301  SLD----LSC HTLNAINMAY KITRPLASAN SCLDPVLYFL AGQRLVRFAR 350
P2YR_CHICK    301  -LDFQTPQMC AFNDKVYATY QVTRGLASLN SCVDPILYFL AGDTFRRRLS 350

360        370        380        390        400
75+13, CODING 351  DLLQRLTAKW QRQRV*---- ---------- ---------- ---------- 400
P2UR_MOUSE    351  DAKPPTEPTP SPQARRKLGL HRPNRTVRKD LSVSSDDSRR TESTPAGSET 400
P2YR_CHICK    351  RATRKSSRRS EPNVQSKSEE MTLNILTEYK QNGDTSL--- ---------- 400

410        420        430        440        450
75+13, CODING 401  ---------- ---------- ---------- ---------- ---------- 450
P2UR_MOUSE    401  KDIRL----- ---------- ---------- ---------- ---------- 450
P2YR_CHICK    401  ---------- ---------- ---------- ---------- ---------- 450
```

FIGURE 72

```
            9           18          27          36          45          54
5' GCC ACC AAC GTG TTC ATC CTG TCA CTG GCC GAT GTG CTG GTG ACA GCC ATC TGC
   --- --- --- --- --- --- --- --- --- --- --- --- --- --- --- --- --- ---
                                       Ala Asp Val Leu Val Thr Ala Ile Cys 63          72          81          90          99         108
   CTG CCG GCC AGT CTG CTG GTA GAC ATC ACG GAA TCC TGG CTC TTT GGC CAT GCC
   --- --- --- --- --- --- --- --- --- --- --- --- --- --- --- --- --- ---
   Leu Pro Ala Ser Leu Leu Val Asp Ile Thr Glu Ser Trp Leu Phe Gly His Ala 117         126         135         144         153         162
   CTC TGC AAG GTC ATC CCC TAT CTA CAG GCC GTG TCC GTG TCA GTG GTC GTG CTG
   --- --- --- --- --- --- --- --- --- --- --- --- --- --- --- --- --- ---
   Leu Cys Lys Val Ile Pro Tyr Leu Gln Ala Val Ser Val Ser Val Val Val Leu 171         180         189         198         207         216
   ACT CTC AGC TCC ATC GCC CTG GAC CGC TGG TAC GCC ATC TGC CAC CCG CTG TTG
   --- --- --- --- --- --- --- --- --- --- --- --- --- --- --- --- --- ---
   Thr Leu Ser Ser Ile Ala Leu Asp Arg Trp Tyr Ala Ile Cys His Pro Leu Leu 225         234         243         252         261         270
   TTC AAG AGC ACT GCC CGG CGC GCC CGC GGC TCC ATC CTC GGC ATC TGG GCG GTG
   --- --- --- --- --- --- --- --- --- --- --- --- --- --- --- --- --- ---
   Phe Lys Ser Thr Ala Arg Arg Ala Arg Gly Ser Ile Leu Gly Ile Trp Ala Val 279         288         297         306         315         324
   TCG CTG GCT GTC ATG GTG CCT CAG GCT GCT GTC ATG GAG TGT AGC AGC GTG CTG
   --- --- --- --- --- --- --- --- --- --- --- --- --- --- --- --- --- ---
   Ser Leu Ala Val Met Val Pro Gln Ala Ala Val Met Glu Cys Ser Ser Val Leu 333         342         351         360         369         378
   CCC GAG CTG GCC AAC CGC ACC CGC CTC CTG TCT GTC TGT GAT GAG CGC TGG GCA
   --- --- --- --- --- --- --- --- --- --- --- --- --- --- --- --- --- ---
   Pro Glu Leu Ala Asn Arg Thr Arg Leu Leu Ser Val Cys Asp Glu Arg Trp Ala 387         396         405         414         423         432
   GAC GAC CTG TAC CCC AAG ATC TAC CAC AGC TGC TTC TTC ATT GTC ACC TAC CTG
   --- --- --- --- --- --- --- --- --- --- --- --- --- --- --- --- --- ---
   Asp Asp Leu Tyr Pro Lys Ile Tyr His Ser Cys Phe Phe Ile Val Thr Tyr Leu 441         450         459         468         477         486
   GCC CCA CTG GGC CTC ATG GCC ATG GCC TAT TTC CAG ATC TTC CGC AAG CTC TGG
   --- --- --- --- --- --- --- --- --- --- --- --- --- --- --- --- --- ---
   Ala Pro Leu Gly Leu Met Ala Met Ala Tyr Phe Gln Ile Phe Arg Lys Leu Trp 495         504         513         522         531         540
   GGC CGC CAG ATC CCC GGC ACC ACC TCG GCC CTG GTG CGC AAC TGG AAG CGG CCC
```

FIGURE 73

```
    ---  ---  ---  ---  ---  ---  ---  ---  ---  ---  ---  ---  ---  ---  ---  ---
    Gly  Arg  Gln  Ile  Pro  Gly  Thr  Thr  Ser  Ala  Leu  Val  Arg  Asn  Trp  Lys  Arg  Pro 549            558            567            576            585            594
    TCA  GAC  CAG  CTG  GAC  GAC  CAG  GGC  CAG  GGC  CTG  AGC  TCA  GAG  CCC  CAG  CCC  CGG
    ---  ---  ---  ---  ---  ---  ---  ---  ---  ---  ---  ---  ---  ---  ---  ---  ---  ---
    Ser  Asp  Gln  Leu  Asp  Asp  Gln  Gly  Gln  Gly  Leu  Ser  Ser  Glu  Pro  Gln  Pro  Arg 603            612            621            630            639            648
    GCC  CGC  GCC  TTC  CTG  GCC  GAG  GTG  AAA  CAG  ATG  CGA  GCC  CGG  AGG  AAG  ACG  GCC
    ---  ---  ---  ---  ---  ---  ---  ---  ---  ---  ---  ---  ---  ---  ---  ---  ---  ---
    Ala  Arg  Ala  Phe  Leu  Ala  Glu  Val  Lys  Gln  Met  Arg  Ala  Arg  Arg  Lys  Thr  Ala 657            666            675            684            693            702
    AAG  ATG  CTG  ATG  GTG  GTG  CTG  CTG  GTC  TTC  GCC  CTC  TGC  TAC  CTG  CCC  ATC  AGT
    ---  ---  ---  ---  ---  ---  ---  ---  ---  ---  ---  ---  ---  ---  ---  ---  ---  ---
    Lys  Met  Leu  Met  Val  Val  Leu  Leu  Val  Phe  Ala  Leu  Cys  Tyr  Leu  Pro  Ile  Ser 711            720            729            738            747            756
    GTC  CTC  AAC  GTC  CTC  AAG  AGG  GTC  TTC  GGG  ATG  TTC  CGC  CAA  GCC  AGC  GAC  CGA
    ---  ---  ---  ---  ---  ---  ---  ---  ---  ---  ---  ---  ---  ---  ---  ---  ---  ---
    Val  Leu  Asn  Val  Leu  Lys  Arg  Val  Phe  Gly  Met  Phe  Arg  Gln  Ala  Ser  Asp  Arg 765            774            783            792            801            810
    GAG  GCC  ATC  TAC  GCC  TGC  TTC  ACC  TTC  TCC  CAC  TGG  CTG  GTG  TAC  GCC  AAC  AGC
    ---  ---  ---  ---  ---  ---  ---  ---  ---  ---  ---  ---  ---  ---  ---  ---  ---  ---
    Glu  Ala  Ile  Tyr  Ala  Cys  Phe  Thr  Phe  Ser  His  Trp  Leu  Val  Tyr  Ala  Asn  Ser 819            828            837
    GCC  GCC  AAT  CCC  CTC  CTC  TAC  TCC  TTC  CTC  CCT  3'
    ---  ---
    Ala  Ala
```

FIGURE 74
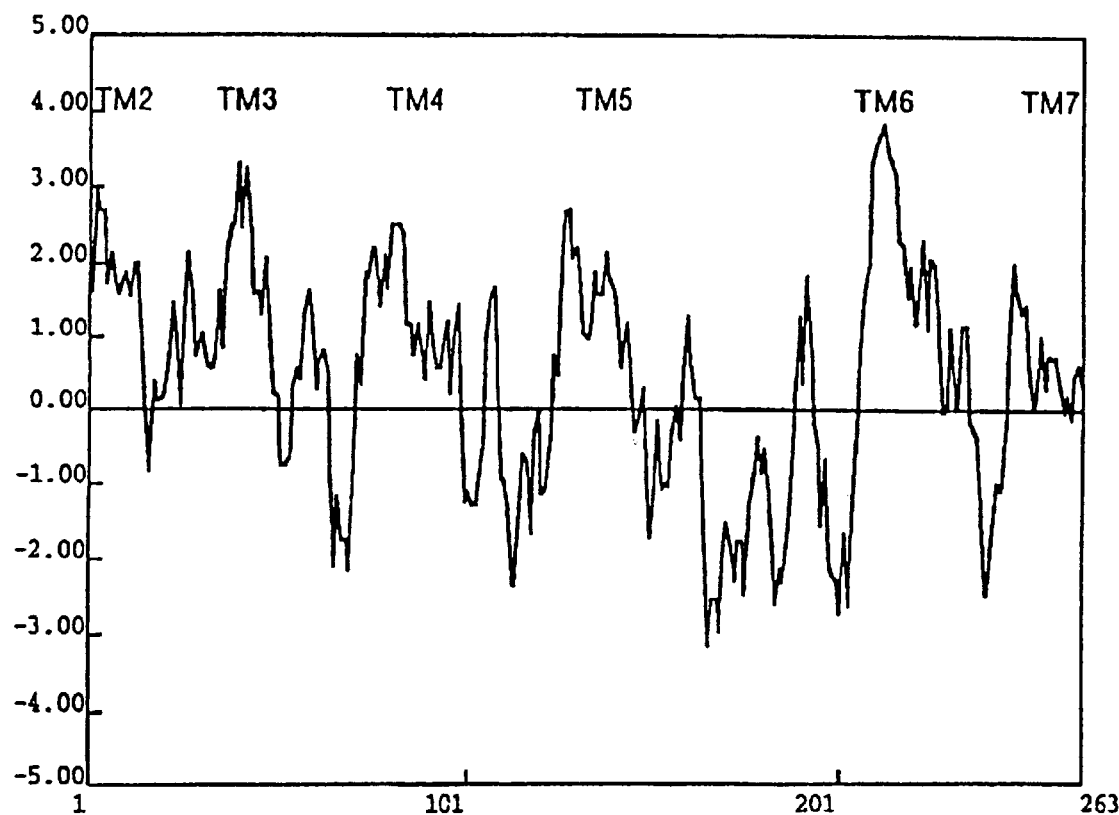
10 μM ATP
FIGURE 75
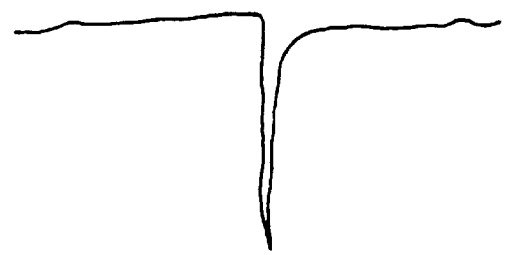
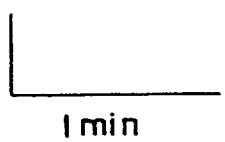

FIGURE 76

```
                       10         20         30         40         50
h3H2-17 (5-3)   1                                                           50
p3H2-17  (5' )  1  GTGGGCCTGG TGGGCAACAT CCTGGCTTCC TGGCACAAGC GTGGAGGTCG   50

60         70         80         90        100
h3H2-17 (5-3)  51                                               TGACAACCC  100
p3H2-17  (5' ) 51  CCGTGCTGCT TGGGTAGTGT GTGGAGTCGT GTGGCTGGCT GTGACAGCCC  100

110        120        130        140        150
h3H2-17 (5-3) 101  AGTGCCTGCC CACAGCCATC TTCGCTGCCA CAGGCATCCA GCGTAACCGC  150
p3H2-17  (5' )101  AGTGCCTGCC CACGGCAGTC TTTGCTGCCA CAGGCATCCA GCGCAACCGC  150

160        170        180        190        200
h3H2-17       151  ACTGTCTGCT ATGACCTCAG CCCGCCTGCC CTGGCCACCC ACTATATGCC  200
p3H2-17  (5' )151  ACTGTGTGCT ACGACCTGAG CCCACCCATC CTGTCTACTC GCTACCTGCC  200

210        220        230        240        250
h3H2-17 (5-3) 201  CTATGGCATG GCTCTCACTG TCATCGGCTT CCTGCTGCCC TTTGCTGCCC  250
p3H2-17  (5' )201  CTATGGTATG GCCCTCACGG TCATCGGCTT CTTGCTGCCC TTCATAGCCT  250

260        270        280        290        300
h3H2-17 (5-3) 251  TGCTGGCCTG CTACTGTCTC CTGGCCTGCC GCC-------- ----------  300
p3H2-17  (5' )251  TACTGGCTTG TTATTGTCGC ATGGCCCGCC GCCTGTGTCG CCAGGATGGC  300

310        320        330        340        350
h3H2-17 (5-3) 301  ---------- ---------- ---------- ---------- ----------  350
p3H2-17  (5' )301  CCAGCAGGTC CTGTGGCCCA AGAGCGGCGC AGCAAGGCGG CTCGTATGGC  350

360        370        380        390        400
h3H2-17 (5-3) 351  ---------- ---------- ---------- ---------- ----------  400
P3H2-17  (5' )351  TGTGGTGGTG GCAGCTGTCT TTGCCCTCTG CTGGCTGCCT CTCTAC----  400
```

FIGURE 77A

| | |
|---|---|
| TGACTCCCTG AACATAGGAA ACCCACCTGG GCAGCC ATG GAA TGG GAC AAT GGC<br>Met Glu Trp Asp Asn Gly<br>1 5 | 54 |
| ACA GGC CAG GCT CTG GGC TTG CCA CCC ACC ACC TGT GTC TAC CGC GAG<br>Thr Gly Gln Ala Leu Gly Leu Pro Pro Thr Thr Cys Val Tyr Arg Glu<br>10 15 20 | 102 |
| AAC TTC AAG CAA CTG CTG CTG CCA CCT GTG TAT TCG GCG GTG CTG GCG<br>Asn Phe Lys Gln Leu Leu Leu Pro Pro Val Tyr Ser Ala Val Leu Ala<br>25 30 35 | 150 |
| GCT GGC CTG CCG CTG AAC ATC TGT GTC ATT ACC CAG ATC TGC ACG TCC<br>Ala Gly Leu Pro Leu Asn Ile Cys Val Ile Thr Gln Ile Cys Thr Ser<br>40 45 50 | 198 |
| CGC CGG GCC CTG ACC CGC ACG GCC GTG TAC ACC CTA AAC CTT GCT CTG<br>Arg Arg Ala Leu Thr Arg Thr Ala Val Tyr Thr Leu Asn Leu Ala Leu<br>55 60 65 70 | 246 |
| GCT GAC CTG CTA TAT GCC TGC TCC CTG CCC CTG CTC ATC TAC AAC TAT<br>Ala Asp Leu Leu Tyr Ala Cys Ser Leu Pro Leu Leu Ile Tyr Asn Tyr<br>75 80 85 | 294 |
| GCC CAA GGT GAT CAC TGG CCC TTT GGC GAC TTC GCC TGC CGC CTG GTC<br>Ala Gln Gly Asp His Trp Pro Phe Gly Asp Phe Ala Cys Arg Leu Val<br>90 95 100 | 342 |
| CGC TTC CTC TTC TAT GCC AAC CTG CAC GGC AGC ATC CTC TTC CTC ACC<br>Arg Phe Leu Phe Tyr Ala Asn Leu His Gly Ser Ile Leu Phe Leu Thr<br>105 110 115 | 390 |
| TGC ATC AGC TTC CAG CGC TAC CTG GGC ATC TGC CAC CCG CTG GCC CCC<br>Cys Ile Ser Phe Gln Arg Tyr Leu Gly Ile Cys His Pro Leu Ala Pro<br>120 125 130 | 438 |
| TGG CAC AAA CGT GGG GGC CGC CGG GCT GCC TGG CTA GTG TGT GTA ACC<br>Trp His Lys Arg Gly Gly Arg Arg Ala Ala Trp Leu Val Cys Val Thr<br>135 140 145 150 | 486 |
| GTG TGG CTG GCC GTG ACA ACC CAG TGC CTG CCC ACA GCC ATC TTC GCT<br>Val Trp Leu Ala Val Thr Thr Gln Cys Leu Pro Thr Ala Ile Phe Ala<br>155 160 165 | 534 |

FIGURE 77B

```
GCC ACA GGC ATC CAG CGT AAC CGC ACT GTC TGC TAT GAC CTC AGC CCG        582
Ala Thr Gly Ile Gln Arg Asn Arg Thr Val Cys Tyr Asp Leu Ser Pro
            170                 175                 180

CCT GCC CTG GCC ACC CAC TAT ATG CCC TAT GGC ATG GCT CTC ACT GTC        630
Pro Ala Leu Ala Thr His Tyr Met Pro Tyr Gly Met Ala Leu Thr Val
            185                 190                 195

ATC GGC TTC CTG CTG CCC TTT GCT GCC CTG CTG GCC TGC TAC TGT CTC        678
Ile Gly Phe Leu Leu Pro Phe Ala Ala Leu Leu Ala Cys Tyr Cys Leu
            200                 205                 210

CTG GCC TGC CGC CTG TGC CGC CAG GAT GGC CCG GCA GAG CCT GTG GCC        726
Leu Ala Cys Arg Leu Cys Arg Gln Asp Gly Pro Ala Glu Pro Val Ala
215                 220                 225                 230

CAG GAG CGG CGT GGC AAG GCG GCC CGC ATG GCC GTG GTG GTG GCT GCT        774
Gln Glu Arg Arg Gly Lys Ala Ala Arg Met Ala Val Val Val Ala Ala
                235                 240                 245

GCC TTT GCC ATC AGC TTC CTG CCT TTT CAC ATC ACC AAG ACA GCC TAC        822
Ala Phe Ala Ile Ser Phe Leu Pro Phe His Ile Thr Lys Thr Ala Tyr
            250                 255                 260

CTG GCA GTG GGC TCG ACG CCG GGC GTC CCC TGC ACT GTA TTG GAG GCC        870
Leu Ala Val Gly Ser Thr Pro Gly Val Pro Cys Thr Val Leu Glu Ala
            265                 270                 275

TTT GCA GCG GCC TAC AAA GGC ACG CGG CCG TTT GCC AGT GCC AAC AGC        918
Phe Ala Ala Ala Tyr Lys Gly Thr Arg Pro Phe Ala Ser Ala Asn Ser
            280                 285                 290

GTG CTG GAC CCC ATC CTC TTC TAC TTC ACC CAG AAG AAG TTC CGC CGG        966
Val Leu Asp Pro Ile Leu Phe Tyr Phe Thr Gln Lys Lys Phe Arg Arg
295                 300                 305                 310

CGA CCA CAT GAG CTC CTA CAG AAA CTC ACA GCC AAA TGG CAG AGG CAG       1014
Arg Pro His Glu Leu Leu Gln Lys Leu Thr Ala Lys Trp Gln Arg Gln
            315                 320                 325

GGT CGC TGA                                                           1023
Gly Arg
```

FIGURE 79

```
                     10          20          30          40          50
human prino.  1  MEWDNGTGQA  LGLPPTTCVY  RENFKCLLLP  PVYSAVLAAG  LPLNICVITQ   50
mouseFULL3H2  1  MEQDNGTIQA  PGLPPTTCVY  REDFKRLLLT  PVYSVVLVVG  LPLNICVIAQ   50

60          70          80          90         100
human prino. 51  ICTSRRALTR  TAVYTLNLAL  ADLLYACSLP  LLIYNYACGD  HWPFGDFACR  100
mouseFULL3H2 51  ICASRRTLTR  SAVYTLNLAL  ADLMYACSLP  LLIYNYARGD  HWPFGDLACR  100

110         120         130         140         150
human prino. 101 LVRFLFYANL  HGSILFLTCI  SFQRYLGICH  PLAPWHKRGG  RRAAWLVCVT  150
mouseFULL3H2 101 FVRFLFYANL  HGSILFLTCI  SFORYLGICH  PLASWHKRGG  RRAAWVVCGV  150

160         170         180         190         200
human PRINO  151 VWLAVTTQCL  PTAIFAATGI  QRNRTVCYDL  SPPALATHYM  PYGMALTVIG  200
mouseFULL 3H2 151 VWLAVTAQCL  PTAVFAATGI  QRNRTVCYDL  SPPILSTRYL  PYGMALTVIG  200

210         220         230         240         250
human prino. 201 FLLPFAALLA  CYCLLACRLC  RQDGPAEPVA  QERRGKAARM  AVVVAAAFAI  250
mouseFULL3H2 201 FLLPFIALLA  CYCRMARRLC  RQDGPAGPVA  QERRSKAARM  AVVVAAVFAI  250

260         270         280         290         300
human prino. 251 SFLPFHITKT  AYLAVGSTPG  VPCTVLEAFA  AAYKGTRPFA  SANSVLDPIL  300
mouseFULL    251 SFLPFHITKT  AYLAVRSTPG  VSCPVLETFA  AAYKGTRPFA  SVNSVLDPIL  300

310         320         330         340         350
human prino. 301 FYFTQKKFRR  RPHELLQKLT  AKWQROGR*   ----------  ----------  350
mouseFULL3H2 301 FYFTQQKFRR  QPHDLLQRLT  AKWQRQRV*   ----------  ----------  350
```

G-PROTEIN COUPLED RECEPTOR PROTEIN AND A DNA ENCODING THE RECEPTOR

FIELD OF THE INVENTION

The present invention relates to novel DNAs which are useful as DNA primers for a polymerase chain reaction (PCR); methods for amplifying DNAs each coding for a G protein coupled receptor protein via PCR techniques using said DNA; screening methods for DNAs each encoding a G protein coupled receptor protein via PCR techniques using said DNA; G protein coupled receptor protein-encoding DNAs obtained by said screening method; G protein coupled receptor proteins which are encoded by the DNA obtained via said screening method, peptide fragments or segments thereof, and modified peptide derivatives thereof; etc.

The present invention also relates to novel G protein coupled receptor proteins; novel G protein coupled receptor protein-encoding DNAs; processes for producing said G protein coupled receptor protein; use of said receptor protein and said protein-encoding DNA; etc.

The present invention also relates to novel human amygdaloid nucleus-derived G protein coupled receptor proteins; novel DNAs each coding for said G protein coupled receptor protein; processes for producing said G protein coupled receptor protein; use of said receptor protein and said protein-encoding DNA; etc.

The present invention also relates to novel mouse pancreatic β cell line MIN6-derived G protein coupled receptor proteins; novel DNAs each coding for said G protein coupled receptor protein; processes for producing said G protein coupled receptor protein; use of said receptor protein and said protein-encoding DNA; etc. Further, the present invention relates to novel human-derived G protein coupled receptor proteins (human prinoceptors); novel DNAs each coding for said G protein coupled receptor protein; processes for producing said G protein coupled receptor protein; use of said receptor protein and said protein-encoding DNA; etc.

BACKGROUND OF THE INVENTION

A variety of hormones, neurotransmitters and the like control, regulate or adjust the functions of living bodies via specific receptors located in cell membranes. Many of these receptors mediate the transmission of intracellular signals via activation of guanine nucleotide-binding proteins (hereinafter, sometimes referred to as G proteins) with which the receptor is coupled and possess the common (homologous) structure, i.e. seven transmembranes (membrane-spanning regions (domains)). Therefore, such receptors are generically referred to as G protein coupled receptors or seven transmembrane (membrane-spanning) receptors.

G protein coupled receptor proteins have a very important role as targets for molecules such as hormones, neurotransmitters and physiologically active substances, which molecules control, regulate or adjust the functions of living bodies. Each molecule has its own receptor protein which is specific thereto, whereby the specificities of individual physiologically active substances, including specific target cells and organs, specific pharmacological actions, specific action strength, action time, etc., are decided. Accordingly, it has been believed that, if G protein coupled receptor genes or cDNA can be cloned, those will be helpful not only for the clarification of structure, function, physiological action, etc.
of the G protein coupled receptor but also for the development of pharmaceuticals by investigating the substances which act on the receptor. Until now, only several G protein coupled receptor genes or cDNAs have been cloned but it is believed that there are many unknown G protein coupled receptor genes which have not been recognized yet.

The characteristic feature of the G protein coupled receptor proteins which have been known up to now is that seven clusters of hydrophobic amino acid residues are located in the primary structure and pass through (span) the cell membrane at each region thereof. It has been known that such a structure is common among all of the known G protein coupled receptor proteins and further that the amino acid sequences corresponding to the area where the protein passes through the membrane (membrane-spanning region or transmembrane region) and the amino acid sequences near the membrane-spanning region are often highly conserved among the receptors.

When an unknown protein has such a structure, it is strongly suggested that said protein is within a category of the G protein coupled receptor proteins. In addition, some amino acid residue alinements are common (homologous) and, by taking it as a characteristic feature, it is further strongly suggested that said protein is a G protein coupled receptor protein.

Libert, F, et al. (Science, 244:569–571; 1989) reported a method for cloning novel receptor genes by means of a polymerase chain reaction (hereinafter, sometimes referred to as PCR or a PCR technique) for a synthetic DNA primer which was synthesized based upon the information of common amino acid sequences obtained from a comparison among known G protein coupled receptor proteins. Libert, F. et al. used a, pair of synthetic DNA primers corresponding to the portions of the third and the sixth membrane-spanning regions. However, in general, the design of primers used for the PCR regulates the molecular species of DNAs which are to be amplified. In addition, when a similarity (homology) in the amino acid sequence level is used as a basis, the use of different codons affects on the binding (hybridization) of the primer thereby resulting in a decrease in the amplifying efficiency.

Accordingly, although various novel receptor protein DNAs have been obtained using said DNA primers, it is not possible to succeed in amplifying DNAs for all receptor proteins in the prior art.

Further, the amino acid sequence which is common to from the first to the seventh membrane-spanning regions among 74 G protein coupled receptor proteins was reported by William C. Probst, et al. (DNA and Cell Biology, Vol. 11, No. 1, 1992, pp. 1–20). In this report, however, there is no suggestion for a method in which DNA coding for a novel G protein coupled receptor protein is screened by means of PCR using DNA primers which are complementary to the DNA coding for those amino acid sequences.

It would be desirable to develop DNA primers for PCR techniques which allow selective and efficient screenings of DNAs coding for the areas (regions) more nearer the full length of novel G protein coupled receptor proteins by utilizing the common (homologous) sequence(s) of the G protein coupled receptor protein or the DNA coding therefor.

It would also be desirable to develop synthetic DNA primers corresponding to the portions of the third and the sixth membrane-spanning regions, said primer being useful in screening for DNA coding for G protein coupled receptor proteins in more selective and efficient manner as compared with a series of the synthetic DNA primers corresponding to the sequences of the third to the sixth membrane-spanning regions as reported by Libert, F. et al.

G protein coupled receptor proteins are important for investigating substances which control the function of living organisms and proceeding developments thereof as pharmaceuticals. Finding and development of candidate compounds for new pharmaceuticals can be efficiently proceeded by using G protein coupled receptor proteins and by conducting receptor binding experiments and evaluating experiments on agonists/antagonists using intracellular information transmittance systems as indexes. Especially when the presence of a novel G protein coupled receptor protein can be clarified, the presence of a substance having a specific action thereon can be suggested.

If a novel DNA which codes for a novel G protein coupled receptor protein can be efficiently screened and isolated, it will now be possible to proceed with the isolation of DNA having an entire coding region, the construction of an expression system therefor and the screening of an acting ligand.

A hypothalamo-hypophysial system is one of the passages for controlling, regulating or adjusting the functions of organisms relying upon interactions of hormones and neurotransmitters with G protein coupled receptors. In the hypothalamo-hypophysial system, the secretion of pituitary hormones from the pituitary body (hypophysis) is regulated by hypothalamic hormones (hypophysiotropic releasing factors), and the functions of target cells and organs are controlled by pituitary hormones released into the blood. Functions; which are important for the living body are regulated through this system, such as maintenance of homeostasis and control of development and growth of a genital system and an individual organism. Representative examples of the hypothalamic hormones include TRH, LH-RH, CRF, GRF, somatostatin, galanin, etc. Representative examples of the pituitary hormones include TSH, ACTH, FSH, LH, prolactin, growth hormone, oxytocin, vasopressin, etc. In particular, the secretion of pituitary hormones is regulated according to a positive feedback mechanism or a negative feedback mechanism relied on the hypothalamic hormones and peripheral hormones secreted from the target endocrine glands. A variety of receptor proteins present in the pituitary gland play a major role for regulating the hypothalamo-hypophysial system.

It has been widely known that these hormones, factors and receptors are widely distributed in the brain instead of existing only locally in the hypothalamo-hypophysial system. This fact suggests that the substances which are called "hypothalamic hormones" are working as neurotransmitters or neuroregulators in the central nervous system. It is further considered that these substances are similarly distributed even in the peripheral tissues to play the role of important functions. The pancreas plays an important role of carrying out the carbohydrate metabolism by secreting not only a digestive fluid but also glucagon and insulin. Insulin is secreted from the β cells and its secretion is promoted chiefly by glucose. It has, however, been known that a variety of receptors exist in the β cells, and the secretion of insulin is controlled by various factors such as peptide hormones (galanin, somatostatin, gastric inhibitory polypeptide, glucagon, amylin, etc.), sugars (mannose, etc.), amino acids, and neurotransmitters in addition to glucose.

It has thus been known that in the pituitary gland and in the pancreas are present receptor proteins for many hormones and neurotransmitters, said receptor proteins; playing important roles for regulating the functions. As for the galanin and amylin, however, there has not yet been reported any discovery concerning the structure of their receptor protein cDNAs. It is not known whether there exist any unknown receptor proteins or receptor protein subtypes.

For substances regulating the functions of the pituitary gland and pancreas, there exist receptor proteins specific to said substance on the surfaces of various functional cells of the pituitary gland and pancreas. The pituitary gland and the pancreas are associations of a plurality of functional cells, and the actions of the individual substances are defined by the distributions of their target receptor proteins among the functional cells. Accordingly, a substance, in many cases, exhibits an extensive variety of actions. To comprehend such complex systems, it is necessary to clarify the relations between the acting substances and the specific receptor proteins. It is further necessary to efficiently screen for receptor protein agonists and antagonists capable of regulating the pituitary gland and pancreas, to clarify the structures of genes of receptor proteins from the standpoint of investigating and developing pharmaceuticals, and further to express them in a suitable expression system.

By utilizing the fact that a G protein coupled receptor protein exhibits homology in part of the structure thereof at the amino acid sequence level, an experiment of looking at DNAs coding for novel receptor proteins relying upon a polymerase chain reaction (hereinafter simply referred to as "PCR") has recently been made.

In the central nervous system, many receptor proteins such as dopamine receptor protein, LH-RH receptor protein, neurotensin receptor protein, opioid receptor protein, CRF receptor protein, CRF receptor protein, somatostatin receptor protein, galanin receptor protein, TRH receptor protein, etc. are G protein coupled receptor proteins, and it has been clarified that ligands to these receptors exert a variety of effects in the central nervous system.

In the immune system, an α- or a β-chemokine receptor protein, an MIPIα receptor protein, an IL-8 receptor protein, a C5a receptor protein, etc. have been known as such G protein coupled receptor proteins, and are working as receptor proteins responsive to immunoregulating substances to play important roles for regulating the functions of the living body. There is, for example, an IL-6 receptor protein that acts both in the above-mentioned central nervous system and in the immune system. IL-6 is both a β-cell differentiating factor and a biologically active factor related to the proliferation and differentiation of nerve cells.

It has been widely known that these hormones, factors and receptor proteins are usually widely distributed up to the peripheral tissues instead of existing only locally in the central nervous system and in the immune system and are producing important functions, respectively. Agonists and antagonists for these receptor proteins are now being developed as various useful pharmaceuticals.

For substances regulating the functions of the central nervous system and the immune system, there exist receptor proteins specific to said substance on the surfaces of various functional cells of the central nervous system and the immune system. The central nervous system and the immune system are associations of a plurality of functional cells, and the actions of the individual substances are defined by the distributions of their target receptor proteins among the functional cells. Accordingly, a substance, in many cases, exhibits an extensive variety of actions. Moreover, there is an example wherein many factors play a part in a physiological phenomenon. To comprehend such complex systems, it is necessary to clarify relations between the acting substances and the specific receptor proteins.

As discussed herein above, the G protein coupled receptor protein is present on the cell surface of living body cells and organs and has a very important role as a target for molecules such as hormones, neurotransmitters and physiologically active substances, which molecules control, regulate or adjust the functions of living body cells and organs.

SUMMARY OF THE INVENTION

One object of the present invention is to provide novel DNAs which are useful as DNA primers for a polymerase chain reaction; methods for amplifying a DNA coding for a G protein coupled receptor protein using said DNA; screening methods for the DNA coding for a G protein coupled receptor protein using said DNA; DNAs obtained by said screening method; and G protein coupled receptor proteins encoded by the DNA obtained by said screening method, peptide fragments or segments thereof, modified peptide derivatives thereof or salts thereof.

Another object of the present invention is to provide processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising an effective amount of the inhibitory compound; antibodies against said receptor protein; immunoassays using said receptor protein or said antibody and use of said receptor protein and encoding DNA.

Yet another object of the present invention is to provide novel G protein coupled receptor proteins which are expressed in pituitary glands or pancreatic β cells; DNAs comprising a DNA coding for said G protein coupled receptor protein; processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising the inhibitory compound; antibodies against said receptor protein; immunoassays using said receptor protein or said antibody and use of said receptor protein and encoding DNA.

Still another object of the present invention is to provide novel human amygdaloid nucleus-derived G protein coupled receptor proteins; DNAs comprising a DNA coding for said G protein coupled receptor protein; processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising the inhibitory compound; antibodies against said receptor protein; immunoassays using said receptor protein or said antibody and use of said receptor protein and encoding DNA.

Yet another object of the present invention is to provide novel mouse pancreatic β cell line MIN6-derived G protein coupled receptor proteins; DNAs comprising a DNA coding for said G protein coupled receptor protein; processes for producing said receptor protein; transformants capable of expressing said receptor protein; cell membrane fractions obtained from said transformant; methods for determining a ligand to the receptor protein; screening methods for a compound or a salt thereof capable of inhibiting the binding of the ligand with the receptor protein; kits for said screening method, pharmaceutical compositions comprising the inhibitory compound; antibodies against said receptor protein; immunoassays using said receptor protein or said antibody and use of said receptor protein and encoding DNA.

The present inventors have succeeded in synthesizing novel DNA primers based upon the similarity (homology) with the base sequences coding for the first membrane-spanning region or the sixth membrane-spanning region each of known G protein coupled receptor proteins. It is to be particularly noted that there has been no report of a DNA primer pair which has been synthesized paying attention to the similarity with the base sequence coding for the first and the sixth membrane-spanning region of the known G protein coupled receptor protein.

Next the present inventors have succeeded in synthesizing other novel DNA primers based upon the similarity (homology) with the base sequences coding for the third or the sixth membrane-spanning region each of known G protein coupled receptor proteins. They have also unexpectedly succeeded in efficiently amplifying DNAs (DNA fragments) coding for G protein coupled receptor proteins by means of PCR using those DNA primers.

They have further succeeded in synthesizing novel DNA primers based upon the similarity (homology) with the base sequences coding for the second or the seventh membrane-spanning region each of known G protein coupled receptor proteins; upon the similarity (homology) with the base sequences coding for first or the third membrane-spanning region each of known G protein coupled receptor proteins; and upon the similarity (homology) with the base sequences coding for the second or the sixth membrane-spanning region each of known G protein coupled receptor proteins. They have furthermore and unexpectedly succeeded in efficiently amplifying DNAs (DNA fragments) coding for G protein coupled receptor proteins by conducting PCR using those DNA primers.

Moreover, the present inventors have succeeded in efficiently cloning full-length DNA coding for said G protein coupled receptor protein via using amplified DNAs (DNA fragments) coding for said G protein coupled receptor protein. Thus, they have found that novel DNA coding for novel G protein coupled receptor proteins can be isolated, characterized or prepared via conducting amplifications and analyses of various DNA using said DNA primers.

To be more specific, the present inventors have selected amino acid sequences which are each common to the portion corresponding to or near the first and the sixth membrane-spanning region of the known individual G protein coupled receptor proteins and have designed the DNA primer (SEQ ID NO: 1) coding for the amino acid sequence common (homologous) to the first membrane-spanning region and the DNA primer (SEQ ID NO: 2) which is complementary to the nucleotide sequence coding for the amino acid sequence common (homologous) to the area near the sixth membrane-spanning region. Those DNA primers have a different nucleotide sequence as compared with reported DNA primers (e.g. a set of synthetic DNA primers corresponding to the third and the sixth membrane-spanning regions (SEQ ID NO: 60 and SEQ ID NO: 61) as reported by Libert, F. et al.) and such instant primers are novel and unique.

Especially for an object of conducting an efficient elongation reaction in the PCR, the 3'-terminal region of the instant primers contains the nucleotide sequence which is common (homologous) among many receptor proteins. Even in other areas, the similarity (homology) at the nucleotide sequence level (base sequence level) is utilized for setting the mixed base (nucleotide) parts wherein their nucleotide sequences (base sequences) are matched for as many nucleotides (bases) as possible among many DNA for the receptor proteins. Then the present inventors have amplified cDNA derived from human brain amygdala, human pituitary gland and rat brain, found the amplified products as shown in FIG. 17 and, from those products, obtained the G protein coupled receptor protein cDNAs having the sequence as shown in FIG. 18, FIG. 19, FIG. 20, FIG. 21, FIG. 22, FIG. 23, FIG. 27, FIG. 29, FIG. 34, FIG. 37, FIG. 40, FIG. 43 or FIG. 46. Among them, the G protein coupled receptor protein cDNAs having the sequence as shown in FIG. 22, FIG. 23, FIG. 27, FIG. 29, FIG. 34, FIG. 37, FIG. 40, FIG. 43 or FIG. 46 are novel.

Further, the present inventors have selected the amino acid sequences common (homologous) to the third and the sixth membrane-spanning region each of the known G protein coupled receptor proteins and designed the DNA primers; coding for the amino acid sequence common (homologous) to the third membrane-spanning region (SEQ ID NO: 3; SEQ ID NO: 5, SEQ ID NO: 6 and SEQ ID NO: 7) and the DNA primers which are complementary to the nucleotide sequence coding for the amino acid sequence common (homologous) to the portion near the sixth membrane-spanning region (SEQ ID NO: 4, SEQ ID NO: 8 and SEQ ID NO: 9). Again, those DNA primers have different base sequences from those of the DNA primers previously reported (e.g., a set of synthetic DNA primers corresponding to the sequence of the third and the sixth membrane-spanning regions (SEQ ID NO: 60 and SEQ ID NO: 61) as reported by Libert, F. et al.) and such instant primers are novel and unique. The present inventors amplified cDNA derived from the smooth muscles of gastric pylorus of rabbits using said DNA primer and obtained G protein coupled receptor protein cDNA having the sequence of FIG. 49 or FIG. 52. Those cDNAs are novel.

Still further, the present inventors have selected the amino acid sequences common (homologous) to the second and the seventh membrane-spanning region each of the known G protein coupled receptor proteins and designed the DNA primer coding for the amino acid sequence common (homologous) to the second membrane-spanning region (SEQ ID NO: 10) and the DNA primer which is complementary to the base sequence coding for the amino acid sequence common (homologous) to the portions near the seventh membrane-spanning region (SEQ ID NO: 11). Those DNA primers have different base sequences from those of DNA primers previously reported (e.g., a set of synthetic DNA primers corresponding to the part of the third and the sixth membrane-spanning regions (SEQ ID NO: 60 and SEQ ID NO: 61) as reported by Libert, F. et al) and such instant primers are novel and unique. The present inventors amplified cDNA derived from the smooth muscles of gastric pylorus of rabbits using said DNA primer and obtained G protein coupled receptor protein cDNAs having each the sequence of FIG. 55, FIG. 56, FIG. 72, or FIG. 73. Those cDNAs are novel.

Furthermore, the present inventors have selected the amino acid sequences common (homologous) to the first and the third membrane-spanning region each of the known G protein coupled receptor proteins and designed the DNA primer coding for the amino acid sequence common (homologous) to the first membrane-spanning region (SEQ ID NO: 12) and the DNA primer which is complementary to the base sequence coding for the amino acid sequence common (homologous) to the portions near the third membrane-spanning region (SEQ ID NO: 13). Still further, the present inventors have selected the amino acid sequences common (homologous) to the third and the sixth membrane-spanning region each of the known G protein coupled receptor proteins and designed the DNA primers coding for the amino acid sequence common (homologous) to the third membrane-spanning region (SEQ ID NO: 10 and SEQ ID NO: 18) and the DNA primers which are complementary to the base sequence coding for the amino acid sequence common (homologous) to the parts near the sixth membrane-spanning region (SEQ ID NO: 15 and SEQ ID NO: 19). Further, the present inventors have selected the amino acid sequences common (homologous) to the second and the sixth membrane-spanning region each of the known G protein coupled receptor proteins and designed the DNA primer coding for the amino acid sequence common (homologous) to the second membrane-spanning region (SEQ ID NO: 16) and the DNA primer which is complementary to the base sequence coding for the amino acid sequence common (homologous) to the parts, near the sixth membrane-spanning region (SEQ ID NO: 17). Those DNA primers have different base sequences from those of DNA primers previously reported (e.g., a set of synthetic DNA primers corresponding to the part of the third and the sixth membrane-spanning regions (SEQ ID NO: 60 and SEQ ID NO: 61) as reported by Libert, F. et al) and such instant primers are novel and unique.

Still another object of the present invention is to provide a G protein coupled receptor protein expressed in the pituitary gland and pancreatic β cells, a DNA comprising a DNA coding for said protein, a process for producing said protein, and use of said protein and DNA.

In order to achieve the above-mentioned aims, the present inventors have made extensive investigations. As a result, the present inventors have succeeded in amplifying cDNA derived from the human pituitary gland and the mouse pancreatic β-cell strain, MIN 6, with a synthetic DNA primer for efficiently isolating G protein coupled receptor protein-encoding DNA, and have forwarded the analysis. Thus, the present inventors have succeeded in isolating novel human and mouse-derived G protein coupled receptor protein-encoding cDNAs, in determining the partial structure thereof, and have considered that these cDNA sequences are preserved very well in the human and in the mouse, and are coding for novel receptor proteins for the same ligand. Based upon the above knowledge, the present inventors have discovered that these DNAs make it possible to obtain a cDNA having a full length open reading frame (ORF) of the receptor protein, hence, to produce the receptor protein. The inventors have further discovered that the above-mentioned receptor protein obtained when the G protein coupled receptor protein-encoding cDNA is expressed by a suitable means permits screening for a ligand to the receptor protein from the living body or from natural or non-natural compounds under guidance of data obtainable in receptor coupling tests or measurements of intracellular second messengers, etc. and further allows screening for a compound that inhibits the binding of the ligand and the receptor protein.

In one embodiment, the present inventors have carried out PCR amplification of novel human pituitary gland-derived cDNA fragments as shown in FIGS. 22 and 23, and have subcloned them to obtain a plasmid vector (p19P2). From analysis of the partial sequence, it has been clarified that the cDNA has been encoded a novel receptor protein. The synthetic DNA primers used for amplifying the cDNA are corresponding to seven hydrophobic clusters that exist in the known G protein coupled receptor proteins in common, i.e., corresponding to the first and sixth membrane-spanning regions among the membrane-spanning domains. The nucleotide sequence (SEQ ID NO: 29) has been determined from the primer region at the 5' side (first membrane-spanning domain side) and has been translated into an amino acid sequence (SEQ ID NO: 24) [FIG. 22]. As a result, the second and third membrane-spanning domains have been confirmed on the hydrophobicity plotting [FIG. 58]. Similarly, the nucleotide sequence (SEQ ID NO: 30) has been determined from the primer region at the 3' side (sixth membrane-spanning domain side) and has been translated into an amino acid sequence (SEQ ID NO: 25) [FIG. 23]. As a result, the presence of the sixth and fifth membrane-spanning domains has been confirmed on the hydrophobicity plots [FIG. 59]. The size of the amplified cDNA is about 700 bp which is nearly comparable with the number of bases between the first membrane-spanning domain and the sixth membrane-spanning domain of the known G protein coupled receptor protein.

G protein coupled receptor proteins exert common property to some extent at an amino acid sequence level, and are forming one protein family. Therefore, data base retrieval has been carried out based upon the amino acid sequence of the subject novel receptor protein (protein encoded by cDNA included in p19P2). As a result, a high homology has been exhibited as compared with the known G protein coupled receptor protein (rat neuropeptide Y receptor protein encoded by S12863) that is shown in FIG. 60. This fact tells that the novel receptor protein of the present invention belongs to the G protein coupled receptor protein family. Moreover, the data base has been retrieved using, as a template, the amino acid sequence encoded by the DNA of the invention. It exhibits high homology to the amino acid sequences of the known G protein coupled receptor proteins, mouse-derived ligand unknown RP-23 (B40470), human-derived ligand unknown K-opioid receptor protein (P30098) and human-derived NK-2 receptor protein (JQ1059). However, none of them are in perfect agreement, from which it is learned that a novel receptor protein had been encoded. The aforementioned abbreviations in parentheses are reference numbers that are assigned when they are registered as data to NBRF-PIR/Swiss-PROT and are, usually, each called "Accession Number".

Next, by using the novel G protein coupled receptor protein-encoding cDNA fragment (p19P2) of the present invention, a cDNA having a full-length open reading frame of the receptor protein of the present invention has been obtained from human pituitary gland cDNA libraries. The nucleotide sequence analysis of a plasmid (phGR3) carrying the cDNA having a full length open reading frame of the receptor protein shows that the nucleotide sequence of a coding region of this receptor protein is represented by SEQ ID NO: 31, and the amino acid sequence deduced therefrom is represented by SEQ ID NO: 26 [FIG. 34]. Based upon the amino acid sequence, hydrophobicity plotting has been carried out. The results are shown in FIG. 36. From the hydrophobicity plotting, it has been clarified that the receptor protein of the present invention possessed seven hydrophobic domains. That is, it has been confirmed that the receptor protein encoded by the cDNA obtained according to the present invention is a seven transmembrane (membrane-spanning) G protein coupled receptor protein. An expression of mRNA for receptor genes encoded by the cDNA of the present invention has been checked by northern blotting techniques at a mRNA level, and it has been confirmed that the receptor gene has been expressed in the human pituitary gland [FIG. 35].

The present inventors have further succeeded in PCR amplification of a mouse pancreatic β cell strain, MIN6 derived cDNA fragment, and cloning of pG3-2 and pG1-10. Then, based on the nucleotide sequence of cDNA included in these two plasmid vectors, the nucleotide sequence shown in FIG. 27 has been derived. It was learned from the nucleotide sequence that the cDNA encodes a novel receptor protein. Upon translating the nucleotide sequence into an amino acid sequence, the presence of the third, fourth, fifth and sixth membrane-spanning domains has been confirmed on the hydrophobicity plots [FIG. 28]. The size of the amplified cDNA is about 400 bp which is nearly comparable with t-he number of bases between the third membrane-spanning domain and the sixth membrane-spanning domain of the known G protein coupled receptor protein. The amino acid sequence has been compared with amino acid sequences [FIGS. 22 and 23] encoded by the G protein coupled receptor protein cDNA included in p19P2 cloned from the human pituitary gland. As a result, homology is more than 95% [FIG. 61]. From this fact, it was estimated that the protein encoded by the cDNA included in pG3-2 is a mouse type G protein coupled receptor protein relative to the human-derived one encoded by the cDNA included in p19P2.

The present inventors have further amplified a mouse pancreatic β-cell strain, MIN6-derived cDNA fragment by the PCR followed by subcloning into a plasmid vector to obtain a clone (p5S38) having a nucleotide sequence as shown in FIG. 62. From the nucleotide sequence (SEQ ID NO: 33), it has been clarified that the cDNA encodes a novel receptor protein. Upon translating the nucleotide sequence into an amino acid sequence (SEQ ID NO: 28), the presence of the third, fourth, fifth and sixth membrane-spanning domains has been confirmed on the hydrophobicity plots [FIG. 64]. The size of the amplified DNA is about 400 bp that is nearly comparable with the known G protein coupled receptor protein. The amino acid sequence has been compared with amino acid sequences [FIGS. 22 and 23] encoded by the G protein coupled receptor protein cDNA included in p19P2 cloned from the human pituitary gland and with amino acid sequences of proteins encoded by pG3-2 and pG1-10 derived from the mouse pancreatic β-cell strain. As a result, homology is more than 95% to them [FIG. 63]. This fact suggests that the protein encoded by the human-derived pituitary gland-derived p19P2, the proteins encoded by the mouse pancreatic β-cell strain-derived pG3-2 and pG1-10, and the protein encoded by the mouse pancreatic β-cell strain-derived p5S38, pertain to a receptor family that recognizes the same ligand.

Another object of the present invention is to provide a novel human amygdaloid nucleus-derived protein coupled receptor protein, a DNA containing a DNA coding for said G protein coupled receptor protein, a process for producing said G protein coupled receptor protein, and use of said protein and DNA.

The present inventors have synthesized DNA primers for efficiently isolating a DNA coding for G protein coupled receptor proteins, amplified an amygdaloid nucleus-derived cDNA with the above primer, and have analyzed it.

As a result, the present inventors have succeeded in isolating, from the human amygdaloid nucleus, a cDNA coding for a novel G protein coupled receptor protein and have determined its partial structure. The nucleotide sequence of the isolated cDNA is preserved very well as compared with that of the mouse glucocorticoid-induced receptor (hereinafter sometimes referred to as "GIR") and is considered to be encoding a receptor protein to the same ligand (Molecular Endocrinology 5:1331–1338, 1991). It is reputed that, in the mouse, the GIR is a receptor which is induced by glucocorticoid and expressed in T-cells and is working as a receptor to immunoregulating factors in the immune system on the T-cells. The present inventors have succeeded in the isolation of this human type GIR from the human amygdaloid nucleus. Accordingly, it is suggested that the isolated GIR is expressed even in the human central nervous system to carry out some function. From these facts, it is considered that the receptor protein is strongly expressed in the human brain and in the immune system and is also functioning therein. These characterized DNAs allow one to obtain a cDNA having a full length open reading frame of the receptor and production of the receptor proteins. The receptor proteins expressed by a suitable means, furthermore, permit screening for a ligand to the receptor proteins from the living body or from natural and non-natural compounds depending on indications obtainable in receptor protein-binding experiments, measurements of intracellular second messengers, etc. It further allows one to screen for compounds capable of inhibiting the binding between the ligand and the receptor protein.

To be more specific, the present inventors have amplified, as a novel human amygdaloid nucleus-derived cDNA, one species, as shown in FIGS. 29 and 30, by PCR, cloned it, and clarified from the analysis of a partial sequence thereof that a novel receptor protein is encoded. The synthetic DNA primers used for amplifying the cDNA are corresponding to seven hydrophobic clusters that exist in the G protein coupled receptor proteins in common, i.e., corresponding to the first and sixth membrane-spanning regions among the membrane-spanning domains. The nucleotide sequence has been determined from the primer region at the 5' side (first membrane-spanning domain side) and has been translated into an amino acid sequence. As a result, the second and third membrane-spanning domains have been confirmed on the hydrophobicity plotting [FIG. 31]. Similarly, the nucleotide sequence has been determined from the primer region at the 3' side (sixth membrane-spanning domain side) and has been translated into an amino acid sequence . As a result, the presence of the fifth and fourth membrane-spanning domains has been confirmed on the hydrophobicity plots [FIG. 32]. The size of the amplified cDNA is about 700 bp which is nearly comparable with the number of bases of the known G protein coupled receptor protein.

The inventors have further retrieved the data base based on, as a template, the nucleotide sequence of the isolated DNA and observed high homology to the DNA that codes for mouse-derived glucocorticoid-induced receptor protein which is a widely known G protein coupled receptor protein [FIG. 33]. This result strongly suggests that the DNA of the present invention is encoding a human-type receptor protein of GIR.

Yet another object of the present invention is to provide a novel mouse pancreatic β-cell strain, MIN6-derived protein coupled receptor protein, a DNA containing a DNA coding for said G protein coupled receptor protein, a process for producing said G protein coupled receptor protein and use of said protein and DNA. The present inventors have synthesized DNA primers for efficiently isolating a DNA coding for G protein coupled receptor proteins, amplified a mouse pancreatic β-cell strain, MIN6-derived cDNA with the above primer, and have analyzed it.

As a result, the present inventors have succeeded in isolating a mouse-derived cDNA coding for a novel G protein coupled receptor protein and have determined its partial structure. The isolated cDNA is homologous to known G protein coupled receptors at the nucleotide sequence level and at the amino acid sequence level and is considered to be encoding a novel receptor protein which is expressed in the mouse pancreas and is also functioning therein. These characterized DNAs allow one to obtain a cDNA having a full length open reading frame of the receptor and production of the receptor proteins. Human-derived cDNAs may be cloned by using, as a probe, said mouse-derived cDNA. The receptor proteins expressed by a suitable means, furthermore, permit screening for a ligand to the receptor protein from the living body or from natural and non-natural compounds relying on indications obtainable in receptor protein-binding experiments, measurements of intracellular second messengers, etc. It further allows one to screen for compounds capable of inhibiting the binding of the ligand with the receptor protein.

To be more specific, the present inventors, have amplified, as a novel mouse pancreatic β-cell strain, MIN6-derived cDNA, p3H2-17, as shown in FIG. 37, by PCR, cloned it, and clarified from the analysis of a partial sequence thereof that a novel receptor protein is encoded. The nucleotide sequence has been translated into an amino acid sequence. As a result, the presence of the third, fourth, fifth and sixth membrane-spanning domains has been confirmed on the hydrophobicity plots [FIG. 38]. The size of the amplified cDNA is about 400 bp which is nearly comparable with that of the known G protein coupled receptor protein.

The inventors have retrieved the data base based on, as a template, the nucleotide sequence of the isolated DNA and observed 30% homology to chicken ATP receptor (P34996), 25% homology to human somatostatin receptor subtype 3 (A46226), 27% homology to human somatostatin receptor subtype 4 (JN0605), and 28% homology to bovine neuropeptide Y receptor (S28787), respectively (FIG. 39), which are known G protein coupled receptor proteins. The aforementioned abbreviations in parentheses are reference numbers that are assigned when they are registered as data to NBRF-PIR/Swiss-PROT and are, usually, each called "Accession Number".

An expression of receptor genes encoded by the cDNA fragment included in p3H2-17 of the present invention has been checked by northern blotting techniques at a mRNA level, and it has been confirmed that the receptor gene has been intensely expressed in the mouse thymus and spleen. It has beer also confirmed that the receptor gene has been expressed ir the mouse brain and pancreas (FIG. 65).

Next, by utilizing the information on the nucleotide sequence of the fragment included in p3H2-17, cDNA encoding a full-length open reading frame of the mouse pancreatic β-cell strain, MIN6-derived G protein coupled receptor protein of the present invention has been obtained from mouse thymic and spleenic poly(A)⁺RNA by 5'RACE (5' rapid amplification of cDNA ends) techniques (Frohman M. A. et al., Proc. Natl. Acad. Sci. USA, 85:8998–9002 (1988); Belyavsky A. et al., Nucleic Acids Res., 17:2919–2932 (1989); Edwards J. B. D. M. et al., Nucleic Acids Res., 19:5227–5232 (1991)) and 3'RACE (3' rapid amplification of cDNA ends) techniques (Frohman M. A. et al., Proc. Natl. Acad. Sci. USA, 85:8998–9002 (1988); Belyavsky A. et al., Nucleic Acids Res., 17:2919–2932 (1989)).

The plasmid (pMAH2-17) carrying cDNA encoding a full-length open reading frame of the receptor protein of the present invention has been subjected to sequencing analysis. As a result, the nucleotide sequence of the region coding for the receptor protein is represented by SEQ ID NO: 41 and the amino acid sequence deduced therefrom is represented by SEQ ID NO: 39 (FIG. 69). Based on the amino acid sequence, hydrophobicity plotting has been carried out. The results are shown in FIG. 70.

It has been clarified from the hydrophobicity plotting that the mouse pancreatic β-cell strain, MIN6-derived receptor protein of the present invention has seven hydrophobic domains. Thus, it has been confirmed that the receptor protein encoded by the cDNA included in pMAH2-17 according to the present invention is a seven transmembrane G protein coupled receptor protein.

Data base retrieval has been carried out based on the full-length amino acid sequence encoded by the cDNA included in pMAH2-17, and it has been observed that the amino acid sequence has 44.0% homology to mouse $P_{2U}$purinoceptor (P35383) and 38.1% homology to chicken $P_{2Y}$purinoceptor (P34996), respectively (FIG. 71), which are known G protein coupled receptor proteins. The aforementioned abbreviations in parentheses are reference numbers that are assigned when they are registered as data to NBRF-PIF/Swiss-PROT and are, usually, each called "Accession Number". Since the receptor protein encoded by pMAH2-17 is highly homologous to prinoceptors, it is considered that there are strong possibility of a subtype within prinoceptor families. Therefore, the present inventors have carried out an electrophysiological analysis of the receptor gene in Xenopus oocytes and found significant inward currents elicited by Xenopus oocytes carrying the subject receptor gene in response to ATP stimulation (FIG. 75). As a result, it has been determined that the receptor encoded by pMAH2-17 is one of the subtypes within prinoceptor families. It has been discussed and expected that there are a variety of subtypes among purinoceptors (Pharmac. Ther., Vol. 64, pp. 445–475 (1994).

All data are supporting that the mouse pancreatic β-cell strain, MIN6-derived receptor protein of the present invention (e.g., SEQ ID NO: 38 and SEQ ID NO: 39, or proteins encoded by pMAH2-17) is a novel purinoceptor subtype which is clearly distinct from chicken $P_{2y1}$purinoceptor (FEBS LETTERS, Vol. 324(2), 219–225 (1993)); mouse $P_{2y2}$or $P_{2u}$purinoceptor (Proc. Natl. Acad. Sci. USA, Vol. 90, pp. 5113–5117 (1993)); rat $P_{2u}$ or $P_{2y2}$purinoceptor (Am. J. Respir. Cell Mol. Biol., Vol. 12, pp. 27–32 (1995)); human $P_{2u}$ or $P_{2y2}$purinoceptor (Proc. Natl. Acad. Sci. USA, Vol. 91, pp. 3275–3279 (1994)); and rat $P_{2x}$purinoceptor (Nature, Vol. 371.6, pp. 516–519 (1994)).

It is also strongly suggested that agonists and/or antagonists related to the receptor encoded by pMAH2-17 would be useful in therapeutic or prophylactic treatment of diseases or syndromes in connection with purine ligand compounds. It is expected that the agonists of the receptor encoded by pMAH2-17 are useful as an immunomodulator or an antitumor agent, in addition they are useful in therapeutically or prophylactically treating hypertension, diabetes, cystic fibrosis, etc. It is still expected that the antagonists of the receptor encoded by pMAH2-17 are useful as hypotensive agents, analgesics, agents for therapeutically or prophylactically treating incontinence of urine, etc.

Another object of the present invention is to provide a novel human-derived protein coupled receptor protein of prinoceptor type, a DNA containing a DNA coding for said G protein coupled receptor protein, a process for producing said G protein coupled receptor protein, and use of said protein and DNA. The present inventors have synthesized DNA primers for efficiently isolating a DNA coding for prinoceptor type G protein coupled receptor proteins on the basis of the nucleotide sequence of mouse purinoceptor, amplified a human-derived cDNA with the above primer, and have analyzed it.

As a result, the present inventors have succeeded in isolating a human-derived cDNA coding for a novel G protein coupled receptor protein and have determined its full-length structure [FIG. 77]. The isolated cDNA is homologous to mouse G protein coupled receptor (purinoceptor) at the nucleotide sequence level and at the amino acid sequence level (87% homology; FIG. 79) and is considered to be encoding a novel purinoceptor protein. The receptor proteins expressed by a suitable means, furthermore, permit screening for a ligand to the receptor protein from the living body or from natural and non-natural compounds relying on indications obtainable in receptor protein-binding experiments, etc. It further allows one to screen for compounds capable of inhibiting the binding of the ligand with the receptor protein.

It is also strongly suggested that agonists and/or antagonists related to the human receptor encoded by phAH2-17 would be useful in therapeutic or prophylactic treatment of diseases or syndromes in connection with purine ligand compounds. It is expected that the agonists of the human receptor are useful as an immunomodulator or an antitumor agent, in addition they are useful in therapeutically or prophylactically treating hypertension, diabetes, cystic fibrosis, etc. It is still expected that the antagonists of the human receptor are useful as hypotensive agents, analgesics, agents for therapeutically or prophylactically treating incontinence of urine, etc.

Accordingly, one aspect of the present invention is (1) DNAs comprising a nucleotide sequence represented by a SEQ ID NO selected from the group consisting of SEQ ID NO: 1 to SEQ ID NO: 19;

(2) DNAs according to the above (1) comprising a nucleotide sequence represented by a SEQ ID NO selected from the group consisting of SEQ ID NO: 1 to SEQ ID NO: 9;

(3) DNAs according to the above (1) comprising a nucleotide sequence represented by SEQ ID NO: 1 or SEQ ID NO: 2;

(4) DNAs according to the above (1) wherein the DNA is a primer for polymerase chain reaction in order to amplify a DNA coding for a G protein coupled receptor protein;

(5) a method for amplifying a DNA coding for a G protein coupled receptor protein by polymerase chain reaction techniques, which comprises:

(i) carrying out a polymerase chain reaction in the presence of a mixture of

① a DNA coding for G protein coupled receptor protein, said DNA being capable of acting as a template, ② at least one DNA primer selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO:: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19; or (ii) carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13;

(6) a method for screening a DNA library for a DNA coding for a G protein coupled receptor protein, which comprises:

(i) carrying out a polymerase chain reaction in the presence of a mixture of

① said DNA library,

② at least one DNA primer selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, to amplify selectively a template DNA coding for G protein coupled receptor protein, contained in the DNA library; or (ii) carrying out a polymerase chain reaction in the presence of a mixture of ① said DNA library ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13, to amplify selectively a DNA coding for G protein coupled receptor protein, contained in the DNA library;

(7) a DNA coding for a G protein coupled receptor protein, which is obtained by a method according to the above (5) or (6); and (8) G protein coupled receptor proteins encoded by a DNA according to the above (7), their peptide segments or fragments and salts thereof.

Another specific aspect of the invention is:

(9) a method for amplifying a DNA coding for G protein coupled receptor protein (e.g. a region corresponding to from the first to sixth membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19;

(10) a method for amplifying a DNA coding for G protein coupled receptor protein (e.g. a region corresponding to from the first to seventh membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 11;

(11) a method for amplifying a DNA coding for G protein coupled receptor protein (e.g. a region corresponding to from the third to sixth membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19;

(12) a method for amplifying a DNA coding for G protein coupled receptor protein (e.g. a region corresponding to from the third to seventh membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and ③ at least one DNA primer selected from the group consisting of DNA primers comprising a nucleotide sequence represented by SEQ ID NO: 11;

(13) a method for amplifying a DNA coding for G protein coupled receptor protein (e.g. a region corresponding to from the second to sixth membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a templates, ② at least one DNA primer selected from the group consisting of DNA primers comprising a nucleotide sequence represented by SEQ ID NO: 10 and DNA primers comprising a nucleotide sequence represented by SEQ ID NO: 16, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19;

(14) a method for amplifying a DNA coding for G protein coupled receptor protein (e.g. a region corresponding to from the second to seventh membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 10 and DNA primers comprising a nucleotide sequence represented by SEQ ID NO: 16, and ③ at least one DNA primer selected from the group consisting of DNA primers comprising a nucleotide sequence represented by SEQ ID NO: 11;

(15) a method for amplifying a DNA coding for G protein coupled receptor protein (e.g. a region corresponding to from the first to third membrane-spanning domains of G protein coupled receptor proteins or other domains thereof) by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13;

(16) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 1, and ③ at least one DNA primer selected from the group consisting of DNA primers comprising a nucleotide sequence represented by SEQ ID NO: 2;

(17) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 3, and ③ at least one DNA primer selected from the group consisting of DNA primers comprising a nucleotide sequence represented by SEQ ID NO: 4;

(18) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 6, and ③ at least one DNA primer selected from the group consisting of DNA primers comprising a nucleotide sequence represented by SEQ ID NO: 8;

(19) a method for amplifying a DNA coding for G protein coupled receptor protein by polymerase chain reaction techniques, which comprises carrying out a polymerase chain reaction in the presence of a mixture of ① a DNA coding for G protein coupled receptor protein, said DNA being capable of acting as a template, ② at least one DNA primer selected from the group consisting of DNA primers comprising a nucleotide sequence represented by SEQ ID NO: 10, and ③ at least one DNA primer selected from the group consisting of DNA primers comprising a nucleotide sequence represented by SEQ ID NO: 11;

(20) a method for amplifying DNA coding for a G protein coupled receptor protein which comprises (i) carrying out a polymerase chain reaction in the presence of a mixture of ① a DNA coding for G protein coupled receptor protein, said DNA being capable of acting as a template, ② at least one DNA primer which is capable of binding with the 3'-side nucleotide sequence of the −chain (minus chain) of the template DNA coding for G protein coupled receptor protein to allow the extension of the +chain (plus chain) in the 5'→3' direction, said DNA primer being selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 12, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ③ at least one DNA primer which is capable of binding with the 3'-side nucleotide sequence of the +chain (plus chain) of the template DNA coding for G protein coupled receptor protein to allow the extension of the −chain (minus chain) in the 5'→3' direction, said DNA primer being selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, or (ii) carrying out a polymerase chain reaction in the presence of a mixture of ① a DNA coding for G protein coupled receptor protein, said DNA being capable of acting as a template, ② at least one DNA primer which is capable of binding with the 3'-side nucleotide sequence of the −chain (minus chain) of the template DNA coding for G protein coupled receptor protein to allow the extension of the +chain (plus chain) in the 5'→3' direction, said DNA primer being selected from the group consisting of DNA primers comprising a nucleotide sequence represented by SEQ ID NO: 1 and DNA primers comprising a nucleotide sequence represented by SEQ ID NO: 12, and ③ at least one DNA primer which is capable of binding with the 3'-side nucleotide sequence of the +chain (plus chain) of the template DNA coding for G protein coupled receptor protein to allow the extension of the −chain (minus chain) in the 5'→3' direction, said DNA primer being selected from the group consisting of DNA primers comprising a nucleotide sequence represented by SEQ ID NO: 13;

(21) a method for screening DNA libraries for a DNA coding for G protein coupled receptor protein (e.g. from the first to sixth membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, to amplify selectively a template DNA coding for G protein coupled receptor protein (e.g. from the first to sixth membrane-spanning domains or other domains of G protein coupled receptor protein), contained in the DNA library;

(22) a method for screening DNA libraries for a DNA coding for G protein coupled receptor protein (e.g. from the first to seventh membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 11, to amplify selectively a template DNA coding for G protein coupled receptor protein (e.g. from the first to seventh membrane-spanning domains or other domains of G protein coupled receptor protein), contained in the DNA library;

(23) a method for screening DNA libraries for a DNA coding for G protein coupled receptor protein (e.g. from the third to sixth membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, to amplify selectively a template DNA coding for G protein coupled receptor protein (e.g. from the third to sixth membrane-spanning domains or other domains of G protein coupled receptor protein), contained in the DNA library;

(24) a method for screening DNA libraries for a DNA coding for G protein coupled receptor protein (e.g. from the third to seventh membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 14 and DNA primers comprising a nucleotide sequence represented by SEQ ID NO: 18, and ③ at least one DNA primer selected from the group consisting of DNA primers comprising a nucleotide sequence represented by SEQ ID NO: 11, to amplify selectively a template DNA coding for G protein coupled receptor protein (e.g. from the third to seventh membrane-spanning domains or other domains of G protein coupled receptor protein), contained in the DNA library;

(25) a method for screening DNA libraries for a DNA coding for G protein coupled receptor protein (e.g. from the second to sixth membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 10 and DNA primers comprising a nucleotide sequence represented by SEQ ID NO: 16, and ③ at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19, to amplify selectively a template DNA coding for G protein coupled receptor protein (e.g. from the second to sixth membrane-spanning domains or other domains of G protein coupled receptor protein), contained in the DNA library;

(26) a method for screening DNA libraries for a DNA coding for G protein coupled receptor protein (e.g. from the second to seventh membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 10 and DNA primers comprising a nucleotide sequence represented by SEQ ID NO: 16, and ③ at least one DNA primer selected from the group consisting of DNA primers comprising a nucleotide sequence represented by SEQ ID NO: 11, to amplify selectively a template DNA coding for G protein coupled receptor protein (e.g. from the second to seventh membrane-spanning domains or other domains of G protein coupled receptor protein), contained in the DNA library;

(27) a method for screening DNA libraries for a DNA coding for G protein coupled receptor protein (e.g. from the first to third membrane-spanning domains or other domains of G protein coupled receptor protein), which comprises carrying out a polymerase chain reaction in the presence of a mixture of ① said DNA library, ② at least one DNA primer selected from the group consisting of DNA primers comprising a nucleotide sequence represented by SEQ ID NO: 1 and DNA primers comprising a nucleotide sequence represented by SEQ ID NO: 12, and ③ at least one DNA primer selected from the group consisting of DNA primers comprising a nucleotide sequence represented by SEQ ID NO: 13, to amplify selectively a template DNA coding for G protein coupled receptor protein (e.g. from the first to third membrane-spanning domains or other domains of G protein coupled receptor protein), contained in the DNA library;

(28) a method for screening DNA libraries for a DNA coding for G protein coupled receptor protein, which comprises carrying out a polymerase chain reaction in the presence of a mixture of ① said DNA library, ② at least one DNA primer selected from the group consisting of DNA primers comprising a nucleotide sequence represented by SEQ ID NO: 1, and ③ at least one DNA primer selected from the group consisting of DNA primers comprising a nucleotide sequence represented by SEQ ID NO: 2, to amplify selectively the template DNA coding for G protein coupled receptor protein, contained in the DNA library;

(29) a method for screening DNA libraries to detect a DNA coding for G protein coupled receptor protein, which comprises carrying out a polymerase chain reaction in the presence of a mixture of ① said DNA library, ② at least one DNA primer selected from the group consisting of DNA primers comprising a nucleotide sequence represented by SEQ ID NO: 3, and ③ at least one DNA primer selected from the group consisting of DNA primers comprising a nucleotide sequence represented by SEQ ID NO: 4, to amplify selectively a template DNA coding for G protein coupled receptor protein, contained in the DNA library;

(30) a method for screening DNA libraries for a DNA coding for G protein coupled receptor protein, which comprises carrying out a polymerase chain reaction in the presence of a mixture of ① said DNA library, ② at least one DNA primer selected from the group consisting of DNA primers comprising a nucleotide sequence represented by SEQ ID NO: 6, and ③ at least one DNA primer selected from the group consisting of DNA primers comprising a nucleotide sequence represented by SEQ ID NO: 8, to amplify selectively a template DNA coding for G protein coupled receptor protein, contained in the DNA library;

(31) a method for screening DNA libraries for a DNA coding for G protein coupled receptor protein, which comprises carrying out a polymerase chain reaction in the presence of a mixture of ① said DNA library, ② at least one DNA primer selected from the group consisting of DNA primers comprising a nucleotide sequence represented by SEQ ID NO: 10, and ③ at least one DNA primer selected from the group consisting of DNA primers comprising a nucleotide sequence represented by SEQ ID NO: 11, to amplify selectively a template DNA coding for G protein coupled receptor protein, contained in the DNA library; and

(32) a method for screening DNA libraries according to any of the above (6), and (21) to (31) wherein said DNA library is derived from an origin selected from the group consisting of human tissues and human cells. Examples of such human tissues include adrenal, umbilical cord, brain, tongue, liver, lymph gland, lung, thymus, placenta, peritoneum, retina, spleen, heart, smooth muscle, intestine, vessel, bone, kidney, skin, fetus, mammary gland, ovary, testis, pituitary gland, pancreas, submandibular gland, spine, prostate gland, stomach, thyroid gland, trachea (windpipe), skeletal muscle, uterus, adipose tissue, urinary bladder, cornea, olfactory bulb, bone marrow, amnion, etc. Examples of such human cells include nerve cells, epithelial cells, endothelial cells, leukocytes, lymphocytes, gliacytes, fibroblasts, keratinized cells, osteoblasts, osteoclasts, astrocytes, melanocytes, various carcinomas, various sarcomas, various cells derived from the above-mentioned human tissues.

Yet another aspect of the present invention is a degenerate deoxynucleotide which has an oligonucleotide sequence to which a SEQ ID NO selected from the group consisting of SEQ ID NO: 1 to SEQ ID NO: 19 is assigned.

Another aspect of the present invention is

(33) a G protein coupled receptor protein comprising an amino acid sequence selected from the group consisting of amino acid sequences represented by SEQ ID NO: 24 and/or SEQ ID NO: 25 and substantial equivalents to the amino acid sequence represented by SEQ ID NO: 24 or SEQ ID NO: 25; or a salt thereof;

(34) a G protein coupled receptor protein according to the above (33) comprising an amino acid sequence selected from the group consisting of an amino acid sequence represented by SEQ ID NO: 26 and substantial equivalents to the amino acid sequence represented by SEQ ID NO: 26; or a salt thereof;

(35) a G protein coupled receptor protein comprising an amino acid sequence selected from the group consisting of an amino acid sequence represented by SEQ ID NO: 27 and substantial equivalents to the amino acid sequence represented by SEQ ID NO: 27; or a salt thereof;

(36) a G protein coupled receptor protein comprising an amino acid sequence selected from the group consisting of an amino acid sequence represented by SEQ ID NO: 28 and substantial equivalents to the amino acid sequence represented by SEQ ID NO: 28; or a salt thereof;

(37) a G protein coupled receptor protein comprising an amino acid sequence selected from the group consisting of amino acid sequences represented by SEQ ID NO: 34 and/or SEQ ID NO: 35 and substantial equivalents to the amino acid sequence represented by SEQ ID NO: 34 or SEQ ID NO: 35; or a salt thereof;

(38) a G protein coupled receptor protein comprising an amino acid sequence selected from the group consisting of an amino acid sequence represented by SEQ ID NO: 38 and substantial equivalents to the amino acid sequence represented by SEQ ID NO: 38; or a salt thereof;

(39) a G protein coupled receptor protein according to the above (38) comprising an amino acid sequence selected from the group consisting of an amino acid sequence represented by SEQ ID NO: 39 and substantial equivalents to the amino acid sequence represented by SEQ ID NO: 39; or a salt thereof;

(40) a G protein coupled receptor protein comprising an amino acid sequence represented by SEQ ID NO: 56 and substantial equivalents to the amino acid sequence represented by SEQ ID NO: 56; or a salt thereof;

(41) a peptide segment or fragment of a G protein coupled receptor protein according to any of the above (33) to (40), a modified derivative thereof or a salt thereof;

(42) a DNA which comprises a nucleotide sequence coding for a G protein coupled receptor protein of the above (33);

(43) a DNA which comprises a nucleotide sequence coding for a G protein coupled receptor protein of the above (34);

(44) a DNA which comprises a nucleotide sequence coding for a G protein coupled receptor protein of the above (35);

(45) a DNA which comprises a nucleotide sequence coding for a G protein coupled receptor protein of the above (36);

(46) a DNA which comprises a nucleotide sequence coding for a G protein coupled receptor protein of the above (37);

(47) a DNA which comprises a nucleotide sequence coding for a G protein coupled receptor protein of the above (38);

(48) a DNA which comprises a nucleotide sequence coding for a G protein coupled receptor protein of the above (39);

(49) a DNA which comprises a nucleotide sequence coding for a G protein coupled receptor protein of the above (40);

(50) a DNA of the above (42) comprising a nucleotide sequence represented by SEQ ID NO: 29 and/or SEQ ID NO: 30;

(51) a DNA of the above (43) comprising a nucleotide sequence represented by SEQ ID NO: 31;

(52) a DNA of the above (44) comprising a nucleotide sequence represented by SEQ ID NO: 32;

(53) a DNA of the above (45) comprising a nucleotide sequence represented by SEQ ID NO: 33;

(54) a DNA of the above (46) comprising a nucleotide sequence represented by SEQ ID NO: 36 and/or SEQ ID NO: 37;

(55) a DNA of the above (47) comprising a nucleotide sequence represented by SEQ ID NO: 40;

(56) a DNA of the above (48) comprising a nucleotide sequence represented by SEQ ID NO: 41;

(57) a DNA of the above (49) comprising a nucleotide sequence represented by SEQ ID NO: 57;

(58) a vector comprising a DNA according to any of the above (42) to (57);

(59) a transformant (including a transfectant) carrying a vector of the above (58);

(60) a process for producing a G protein coupled receptor protein or a salt thereof according to any of the above (33) to (40), which comprises culturing a transformant of the above (59) to express said G protein coupled receptor protein on the membrane of the transformant;

(61) a method for determining a ligand to a G protein coupled receptor protein according to any of the above (33) to (40), which comprises contacting (i) at least one component selected from the group consisting of G protein coupled receptor proteins or salts thereof according to any of the above (33) to (40), peptide fragments or segments or salts thereof according to the above (41), and mixtures thereof, with (ii) at least one compound to be tested;

(62) a screening method for a compound capable of inhibiting the binding of a G protein coupled receptor protein according to any of the above (33) to (40) with a ligand, which comprises carrying out a comparison between:

(i) at least one case where said ligand is contacted with at least one component selected from the group consisting of G protein coupled receptor proteins or salts thereof according to any of the above (33) to (40), peptide fragments or segments or salts thereof according to the above (41), and mixtures thereof, and (ii) at least one case where said ligand together with a compound to be tested is contacted with at least one component selected from the group consisting of G protein coupled receptor proteins or salts thereof according to any of the above (33) to (40), peptide fragments or segments or salts thereof according to the above (41), and mixtures thereof;

(63) a kit for the screening of one or more compounds capable of inhibiting the binding of a G protein coupled receptor protein according to any of the above (33) to (40), with a ligand, which comprises at least one component selected from the group consisting of G protein coupled receptor proteins or salts thereof according to any of the above (33) to (40), peptide fragments or segments or salts thereof according to the above (41), and mixtures thereof; and

(64) an antibody against at least one component selected from the group consisting of G protein coupled receptor proteins or salts thereof according to any of the above (33) to (40), peptide fragments or segments or salts thereof according to the above (41), and mixtures thereof.

Yet another aspect of the present invention is

(65) a G protein coupled receptor protein according to the above (33) comprising (i) an amino acid sequence selected from the group consisting of an amino acid sequence represented by SEQ ID NO: 24, amino acid sequences wherein one or more amino acid residues (preferably from 2 to 30 amino acid residues, more preferably from 2 to 10 amino acid residues) are deleted from the amino acid sequence of SEQ ID NO: 24, amino acid sequences wherein one or more amino acid residues (preferably from 2 to 30 amino acid residues, more preferably from 2 to 10 amino acid residues) are added to the amino acid sequence of SEQ ID NO: 24, and amino acid sequences wherein one or more amino acid residues (preferably from 2 to 30 amino acid residues, more preferably from 2 to 10 amino acid residues) in the amino acid sequence of SEQ ID NO: 24 are substituted with one or more other amino acid residues, or/and (ii) an amino acid sequence selected from the group consisting of an amino acid sequence represented by SEQ ID NO: 25, amino acid sequences wherein one or more amino acid residues (preferably from 2 to 30 amino acid residues, more preferably from 2 to 10 amino acid residues) are deleted from the amino acid sequence of SEQ ID NO: 25, amino acid sequences wherein one or more amino acid residues (preferably from 2 to 30 amino acid residues, more preferably from 2 to 10 amino acid residues) are added to the amino acid sequence of SEQ ID NO: 25, and amino acid sequences wherein one or more amino acid residues (preferably from 2 to 30 amino acid residues, more preferably from 2 to 10 amino acid residues) in the amino acid sequence of SEQ ID NO: 25 are substituted with one or more other amino acid residues, or a salt thereof;

(66) a G protein coupled receptor protein according to the above (34) comprising an amino acid sequence selected from the group consisting of an amino acid sequence represented by SEQ ID NO: 26, amino acid sequences wherein one or more amino acid residues (preferably from 2 to 30 amino acid residues, more preferably from 2 to 10 amino acid residues) are deleted from the amino acid sequence of SEQ ID NO: 26, amino acid sequences wherein one or more amino acid residue; (preferably from 2 to 30 amino acid residues, more preferably from 2 to 10 amino acid residues) are added to the amino acid sequence of SEQ ID NO: 26, and amino acid sequences wherein one or more amino acid residues (preferably from 2 to 30 amino acid residues, more preferably from 2 to 10 amino acid residues) in the amino acid sequence of SEQ ID NO: 26 are substituted with one or more other amino acid residues, or a salt thereof;

(67) a G protein coupled receptor protein according to the above (35) comprising an amino acid sequence selected from the group consisting of an amino acid sequence represented by SEQ ID NO: 27, amino acid sequences wherein one or more amino acid residues (preferably from 2 to 30 amino acid residues, more preferably from 2 to 10 amino acid residues) are deleted from the amino acid sequence of SEQ ID NO: 27, amino acid sequences wherein one or more amino acid residues (preferably from 2 to 30 amino acid residues, more preferably from 2 to 10 amino acid residues) are added to the amino acid sequence of SEQ ID NO: 27, and amino acid sequences wherein one or more amino acid residues (preferably from 2 to 30 amino acid residues, more preferably from 2 to 10 amino acid residues) in the amino acid sequence of SEQ ID NO: 27 are substituted with one or more other amino acid residues, or a salt thereof;

(68) a G protein coupled receptor protein according to the above (36) comprising an amino acid sequence selected from the group consisting of an amino acid sequence represented by SEQ ID NO: 28, amino acid sequences wherein one or more amino acid residues (preferably from 2 to 30 amino acid residues, more preferably from 2 to 10 amino acid residues) are deleted from the amino acid sequence of SEQ ID NO: 28, amino acid sequences wherein one or more amino acid residues; (preferably from 2 to 30 amino acid residues, more preferably from 2 to 10 amino acid residues) are added to the amino acid sequence of SEQ ID NO: 28, and amino acid sequences wherein one or more amino acid residues (preferably from 2 to 30 amino acid residues, more preferably from 2 to 10 amino acid residues) in the amino acid sequence of SEQ ID NO: 28 are substituted with one or more other amino acid residues, or a salt thereof;

(69) a G protein coupled receptor protein according to the above (37) comprising (i) an amino acid sequence selected from the group consisting of an amino acid sequence represented by SEQ ID NO: 34, amino acid sequences wherein one or more amino acid residues (preferably from 2 to 30 amino acid residues, more preferably from 2 to 10 amino acid residues) are deleted from the amino acid sequence of SEQ ID NO: 34, amino acid sequences wherein one or more amino acid residues (preferably from 2 to 30 amino acid residues, more preferably from 2 to 10 amino acid residues) are added to the amino acid sequence of SEQ ID NO: 34, and amino acid sequences wherein one or more amino acid residues (preferably from 2 to 30 amino acid residues, more preferably from 2 to 10 amino acid residues) in the amino acid sequence of SEQ ID NO: 34 are substituted with one or more other amino acid residues, or/and (ii) an amino acid sequence selected from the group consisting of an amino acid sequence represented by SEQ ID NO: 35, amino acid sequences wherein one or more amino acid residues (preferably from 2 to 30 amino acid residues, more preferably from 2 to 10 amino acid residues) are deleted from the amino acid sequence of SEQ ID NO: 35, amino acid sequences wherein one or more amino acid residues (preferably from 2 to 30 amino acid residues, more preferably from 2 to 10 amino acid residues) are added to the amino acid sequence of SEQ ID NO: 35, and amino acid sequences wherein one or more amino acid residues (preferably from 2 to 30 amino acid residues, more preferably from 2 to 10 amino acid residues) in the amino acid sequence of SEQ ID NO: 35 are substituted with one or more other amino acid residues, or a salt thereof;

(70) a G protein coupled receptor protein according to the above (38) comprising an amino acid sequence selected from the group consisting of an amino acid sequence represented by SEQ ID NO: 38, amino acid sequences wherein one or more amino acid residues (preferably from 2 to 30 amino acid residues, more preferably from 2 to 10 amino acid residues) are deleted from the amino acid sequence of SEQ ID NO: 38, amino acid sequences wherein one or more amino acid residues (preferably from 2 to 30 amino acid residues, more preferably from 2 to 10 amino acid residues) are added to the amino acid sequence of SEQ ID NO: 38, and amino acid sequences wherein one or more amino acid residues (preferably from 2 to 30 amino acid residues, more preferably from 2 to 10 amino acid residues) in the amino acid sequence of SEQ ID NO: 38 are substituted with one or more other amino acid residues, or a salt thereof;

(71) a G protein coupled receptor protein according to the above (39) comprising an amino acid sequence selected from the group consisting of an amino acid sequence represented by SEQ ID NO: 39, amino acid sequences wherein one or more amino acid residues (preferably from 2 to 30 amino acid residues, more preferably from 2 to 10 amino acid residues) are deleted from the amino acid sequence of SEQ ID NO: 39, amino acid sequences wherein one or more amino acid residues (preferably from 2 to 30 amino acid residues, more preferably from 2 to 10 amino acid residues) are added to the amino acid sequence of SEQ ID NO: 39, and amino acid sequences wherein one or more amino acid residues (preferably from 2 to 30 amino acid residues, more preferably from 2 to 10 amino acid residues) in the amino acid sequence of SEQ ID NO: 39 are substituted with one or more other amino acid residues, or a salt thereof;

(72) a G protein coupled receptor protein according to the above (40) comprising an amino acid sequence selected from the group consisting of an amino acid sequence represented by SEQ ID NO: 56, amino acid sequences wherein one or more amino acid residues (preferably from 2 to 30 amino acid residues, more preferably from 2 to 10 amino acid residues) are deleted from the amino acid sequence of SEQ ID NO: 56, amino acid sequences wherein one or more amino acid residues (preferably from 2 to 30 amino acid residues, more preferably from 2 to 10 amino acid residues) are added to the amino acid sequence of SEQ ID NO: 56, and amino acid sequences wherein one or more amino acid residues (preferably from 2 to 30 amino acid residues, more preferably from 2 to 10 amino acid residues) in the amino acid sequence of SEQ ID NO: 56 are substituted with one or more other amino acid residues, or a salt thereof;

(73) a method for determining a ligand according to the above (61) wherein said ligand is selected from the group consisting of angiotensin, bombesin, canavinoid, cholecystokinin, glutamine, serotonin, melatonin, neuropeptide Y, opioid, purine, vasopressin, oxytocin, VIP (vasoactive intestinal and related peptides), somatostatin, dopamine, motilin, amylin, bradykinin, CGRP (calcitonin gene related peptides), adrenomedullin, leukotriene, pancreastatin, prostaglandin, thromboxanes, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptides and galanin;

(74) a method for the screening of a compound or a salt thereof capable of inhibiting the binding of a ligand with a G protein coupled receptor protein according to any of the above (33) to (40), which comprises measuring amounts of a labeled ligand bound to the said G protein coupled receptor protein in at least two cases:

(i) where the labeled ligand is contacted with at least one component selected from the group consisting of G protein coupled receptor proteins or salts thereof according to any of the above (33) to (40), peptide fragments or segments or salts thereof according to the above (41), and mixtures thereof, and (ii) where the labeled ligand together with a compound to be tested is contacted with at least one component elected from the group consisting of G protein coupled receptor proteins or salts thereof according to any of the above (33) to (40), peptide fragments or segments or salts thereof according to the above (41), and mixtures thereof, and comparing the measured amounts of the labeled ligand;

(75) a method for the screening of a compound or a salt thereof capable of inhibiting the binding of a ligand with a G protein coupled receptor protein according to any of the above (33) to (40), which comprises measuring amounts of a labeled ligand bound to a cell comprising the said G protein coupled receptor protein in at least two cases:

(i) where the labeled ligand is contacted with the said cell, and (ii) where the labeled ligand together with a compound to be tested is contacted with the said cell, and comparing the measured amounts of the labeled ligand;

(76) a method for the screening of a compound or a salt thereof capable of inhibiting the binding of a ligand with a G protein coupled receptor protein according to any of the above (33) to (40), which comprises measuring amounts of a labeled ligand bound to a membrane fraction of a cell comprising the said G protein coupled receptor protein in at least two cases:

(i) where the labeled ligand is contacted with the said membrane fraction, and (ii) where the labeled ligand together with a compound to be tested is contacted with the membrane fraction, and comparing the measured amounts of the labeled ligand;

(77) a method for the screening of a compound or a salt thereof capable of inhibiting the binding of a ligand with a G protein coupled receptor protein according to any of the above (33) to (40), which comprises measuring amounts of a labeled ligand bound to said G protein coupled receptor protein in at least two cases:

(i) where the labeled ligand is contacted with a G protein coupled receptor protein according to any of the above (33) to (40) which is expressed on the membrane of a transformant according to the above (59) during incubation of the transformant, and (ii) where the labeled ligand together with a compound to be tested is contacted with the G protein coupled receptor protein according to any of the above (33) to (40) which is expressed on the membrane of a transformant according to the above (59) during incubation of the transformant, and comparing the measured amounts of the labeled ligand;

(78) a method for the screening of a compound or a salt thereof capable of inhibiting the binding of a ligand with a G protein coupled receptor protein according to any of the above (33) to (40), which comprises measuring G protein coupled receptor protein-mediated cell-stimulating activities in at least two cases:

(i) where a compound capable of activating the G protein coupled receptor protein according to any of the above (33) to (40) is contacted with a cell comprising the said G protein coupled receptor protein, and (ii) where the compound capable of activating the G protein together with a compound to be tested is contacted with the cell comprising the said G protein coupled receptor protein, and comparing the measured cell-stimulating activities;

(79) a method for the screening of a compound or a salt thereof capable of inhibiting the binding of a ligand with a G protein coupled receptor protein according to any of the above (33) to (40), which comprises measuring G protein coupled receptor protein-mediated cell-stimulating activities in at least two cases:

(i) where a compound capable of activating the G protein coupled receptor protein according to any of the above (33) to (40) is contacted with a G protein coupled receptor protein according to any of the above (33) to (40) which is expressed on the membrane of a transformant according to the above (59) during incubation of the transformant, and (ii) where the compound capable of activating the G protein together with a compound to be tested is contacted with the G protein coupled receptor protein according to any of the above (33) to (40) which is expressed on the membrane of a transformant according to the above (59) during incubation of the transformant, and comparing the measured cell-stimulating activities;

(80) a method according to the above (78) or (79) wherein said compound capable of activating the G protein coupled receptor protein according to any of the above (33) to (40) is selected from the group consisting of angiotensin, bombesin, canavinoid, cholecystokinin, glutamine, serotonin, melatonin, neuropeptide Y, opioid, purine, vasopressin, oxytocin, VIP (vasoactive intestinal and related peptides), somatostatin, dopamine, motilin, amylin, bradykinin, CGRP (calcitonin gene related peptides), adrenomedullin, leukotriene, pancreastatin, prostaglandin, thromboxane, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptides and galanin;

(81) a compound which is determined through a method according to any of the above (62) and (74) to (80) or a salt thereof;

(82) a pharmaceutical composition comprising an effective amount of a compound according to the above (81) or a salt thereof;

(83) a screening kit according to the above (63), comprising a cell comprising a G protein coupled receptor protein according to any of the above (33) to (40);

(84) a screening kit according to the above (63), comprising a membrane fraction derived from a cell comprising a G protein coupled receptor protein according to any of the above (33) to (40);

(85) a screening kit according to the above (63), comprising a cell of the (59) or (109) mentioned herein below;

(86) a screening kit according to the above (63), comprising a membrane fraction derived from a cell of the (59) or (109);

(87) a compound which is determined by means of a screening kit according to any of the above (63) and (83) to (86) or a salt thereof;

(88) a pharmaceutical composition comprising an effective amount of a compound according to the above (87) or a salt thereof; and

(89) a method for measuring at least one component selected from the group consisting of G protein coupled receptor proteins or salts thereof according to any of the above (33) to (40), peptide fragments or segments or salts thereof according to the above (41), and mixtures thereof, which comprises contacting an antibody according to the above (64) with the component selected from the group consisting of G protein coupled receptor proteins or salts thereof according to any of the above (33) to (40), peptide segments or salts thereof according to the above (41), and mixtures thereof.

Still another aspect of the present invention is

(90) a ligand to a G protein coupled receptor protein according to any of the above (33) to (40), which is determined through the following step of:

contacting (i) at least one component selected from the group consisting of G protein coupled receptor proteins or salts thereof according to any of the above (33) to (40), peptide fragments or segments or salts thereof according to the above (41), and mixtures thereof, with (ii) at least one compound to be examined; and

(91) a compound capable of inhibiting the binding of a G protein coupled receptor protein according to any of the above (33) to (40) with a ligand, which is determined through carrying out a comparison between:

(i) at least one case where said ligand is contacted with at least one component selected from the group consisting of G protein coupled receptor proteins or salts thereof according to any of the above (33) to (40), peptide fragments or segments or salts thereof according to the above (41), and mixtures thereof, and (ii) at least one case where said ligand together with a compound to be tested is contacted with at least one component selected from the group consisting of G protein coupled receptor proteins or salts thereof according to any of the above (33) to (40), peptide fragments or segments or salts thereof according to the above (41), and mixtures thereof.

Another aspect of the present invention is

(92) a recombinant G protein coupled receptor protein and a salt thereof which is obtained by the expression of a DNA according to any of the above (42) to (57), or a modified or fragmented derivative thereof;

(93) a method for amplifying a DNA coding for G protein coupled receptor protein by polymerase chain reaction techniques, which comprises carrying out a polymerase chain reaction in the presence of a mixture of (1) a DNA coding for G protein coupled receptor protein, said DNA being capable of acting as a template, and (2) at least one DNA primer selected from tie group consisting of DNA primers comprising either SEQ ID NO: 1 or SEQ ID NO: 2; and

(94) a method for screening DNA libraries for a DNA coding for G protein coupled receptor protein, which comprises carrying out a polymerase chain reaction in the presence of a mixture of (1) said DNA library, and (2) at least one DNA primer selected from the group consisting of DNA primers comprising either SEQ ID NO: 1 or SEQ ID NO: 2, to amplify selectively the DNA coding for G protein coupled receptor protein, contained in the DNA library.

Yet another aspect of the present invention is

(95) a monoclonal antibody against at least one component selected from the group consisting of G protein coupled receptor proteins or salts thereof according to any of the above (33) to (40), peptide fragments or segments or salts thereof according to the above (41), and mixtures thereof;

(96) a preparation of purified polyclonal antibodies against at least one component selected from the group consisting of G protein coupled receptor proteins or salts thereof according to any of the above (33) to (40), peptide fragments or segments or salts thereof according to the above (41), and mixtures thereof;

(97) an immunoassay for detecting a G protein coupled receptor protein which comprising (i) incubating a sample to be tested with an antibody according to the above (64) to allow formation of an antigen-antibody complex; and (ii) detecting an antigen-antibody complex formed in step (i); and

(98) an immunoassay for detecting antibodies against a G protein coupled receptor protein which comprising (i) incubating a sample to be tested with al least one component selected from the group consisting of G protein coupled receptor proteins or salts thereof according to any of the above (33) to (40), peptide fragments or segments or salts thereof according to the above (41), and mixtures thereof to allow formation of an antigen-antibody complex; and (ii) detecting an antigen-antibody complex formed in step (a).

Still another aspect of the present invention is

(99) an antisense DNA or RNA which comprises a nucleotide sequence complementary to at least a portion of a DNA according to any of the above (42) to (57), said antisense DNA or RNA being hybridizable to said DNA according to any of the above (42) to (57);

(100) an antisense DNA or RNA according to the above (99) wherein said antisense DNA or RNA comprises the 5' end hairpin loop, 5' end 6-base-pair repeat, 5' end untranslated region, protein translation initiation site or codon, ORF translation initiation site or codon, 3'-untranslated region, 3' end palindrome region, or 3' end hairpin loop of a G protein coupled receptor protein DNA according to any of the above (42) to (57);

(101) an antisense DNA or RNA according to the above (99) in a pharmaceutically acceptable carrier;

(102) an antisense DNA or RNA according to the above (99) comprising from 2 to 50 nucleotides;

(103) a method for modulating the activity of a G protein coupled receptor protein comprising contacting cells expressing the G protein coupled receptor protein with an antisense DNA or RNA according to the above (99);

(104) a method for producing an antibody against a G protein coupled receptor protein according to any of the above (33) to (40), which comprises administering to an individual at least one component selected from the group consisting of G protein coupled receptor proteins or salts thereof according to any of the above (33) to (40), peptide fragments or segments or salts thereof according to the above (41), and mixtures thereof; and (105) a method for producing a hybridoma which produces a monoclonal antibody against a G protein coupled receptor protein according to any of the above (33) to (40), which comprises (i) immunizing an individual with at least one component selected from the group consisting of G protein coupled receptor proteins or salts thereof according to any of the above (33) to (40), peptide fragments or segments or salts thereof according to the above (41), and mixtures thereof;

(ii) immortalizing antibody producing cells, from the immunized individual;

(iii) selecting an immortal cell which produces antibodies reactive with the G protein coupled receptor protein; and (iv) growing said immortal cell.

Yet another aspect of the present invention is (106) a PCR screening kit for a DNA (or nucleotide sequence) coding for G protein coupled receptor protein in a DNA library which comprises (i) ① at least one DNA primer selected from the group consisting of DNA primers comprising a nucleotide sequence represented by SEQ ID NO: 1, DNA primers comprising a nucleotide sequence represented by SEQ ID NO: 3, DNA primers comprising a nucleotide sequence represented by SEQ ID NO: 5, DNA primers comprising a nucleotide sequence represented by SEQ ID NO: 6, DNA primers comprising a nucleotide sequence represented by SEQ ID NO: 7, DNA primers comprising a nucleotide sequence represented by SEQ ID NO: 10, DNA primers comprising a nucleotide sequence represented by SEQ ID NO: 14, DNA primers comprising a nucleotide sequence represented by SEQ ID NO: 16 and DNA primers comprising a nucleotide sequence represented by SEQ ID NO: 18, and ② at least one DNA primer selected from the group consisting of DNA primers comprising a nucleotide sequence represented by SEQ ID NO: 2, DNA primers comprising a nucleotide sequence represented by SEQ ID NO: 4, DNA primers comprising a nucleotide sequence represented by SEQ ID NO: 8, DNA primers comprising a nucleotide sequence represented by SEQ ID NO: 9, DNA primers comprising a nucleotide sequence represented by SEQ ID NO: 11, DNA primers comprising a nucleotide sequence represented by SEQ ID NO: 15, DNA primers comprising a nucleotide sequence represented by SEQ ID NO: 17 and DNA primers comprising a nucleotide sequence represented by SEQ ID NO: 19; or (ii) ① at least one DNA primer selected from the group consisting of DNA primers comprising a nucleotide sequence represented by SEQ ID NO: 1 and DNA primers comprising a nucleotide sequence represented by SEQ ID NO: 12, and ② at least one DNA primer selected from the group consisting of DNA primers comprising a nucleotide sequence represented by SEQ ID NO: 13;

(107) a vector comprising the DNA according to the above (7);

(108) an expression system comprising an open reading frame (ORF) of DNA derived from a G protein coupled receptor protein DNA according to any of the above (7) and (42) to (57), wherein the ORF is operably linked to a control sequence compatible with a desired host cell;

(109) a transformant (including a transfectant) carrying a vector of the above (107) or an expression system of the above (108);

(110) a process for producing a G protein coupled receptor protein or a salt thereof, which comprises culturing the transformant of the above (109) to express said G protein coupled receptor protein on the membrane of the transformant;

(111) a method for expressing a polypeptide of G protein coupled receptor protein, comprising:

(a) providing a transformant of the above (59) or (109); and (b) incubating the transformant under conditions which allow expression of the polypeptide of G protein coupled receptor protein;

(112) a method for preparing a transformant according to the above (59) or (109), comprising:

(a) providing a host cell capable of transformation;

(b) providing a vector according to the above (58) or (107) or an expression system according to the above (108); and (c) incubating (a) with (b) under conditions which allow transformation of the host cell with the vector or the expression system;

(113) a pharmaceutical composition according to the above (82) or (88), comprising an effective amount of a compound according to the above (81) or (87) or a pharmaceutically acceptable salt thereof in admixture with a pharmaceutically acceptable carrier, excipient or diluent;

(114) the pharmaceutical composition according to the above (82) or (88), for inhibiting the binding of a C protein coupled receptor protein according to the present invention with a ligand;

(115) a method for inhibiting the binding of a G protein coupled receptor protein according to the present invention with a ligand in a medium which comprises contacting an effective amount of a compound according to the above (81) or (87) or a salt thereof with said medium;

(116) a method for modulating the activity of a G protein coupled receptor protein comprising contacting cells expressing the G protein coupled receptor protein with a an effective amount of a compound according to the above (81) or (87) or a salt thereof;

(117) the ligand according to the above (93) being labeled with a detectable reporter;

(118) the antibody according to the above (64) wherein the antibody is labeled with a detectable reporter;

(119) a pharmaceutical composition for controlling an expression of G protein coupled receptor protein, which comprises an effective amount of the antisense DNA according to the above (99), and (120) a culture product produced by a transformant according to the above (59) or (109).

Yet another aspect of the present invention is (121) a DNA according to the above (1) wherein the DNA is an oligonucleotide having from 8 to 60 base residues;

(122) a DNA according to the above (1) wherein the DNA is synthetic;

(123) a DNA (or nucleotide sequence) coding for a G protein coupled receptor protein or a fragment thereof, which is obtained through the method according to any of the above (5) to (32);

(124) a DNA (or nucleotide sequence) according to the above (123), wherein said G protein coupled receptor protein is selected from the group consisting of angiotensin receptor, bombesin receptor, canavinoid receptor, cholecystokinin receptor, glutamine receptor, serotonin receptor, melatonin receptor, neuropeptide Y receptor, opioid receptor, purine receptor, vasopressin receptor, oxytocin receptor, VIP receptor (vasoactive intestinal and related peptide receptor), somatostatin receptor, dopamine receptor, motilin receptor, amylin receptor, bradykinin receptor, CGRP receptor (calcitonin gene related peptide receptor), adrenomedullin receptor, leukotriene receptor, pancreastatin receptor, prostaglandin receptor, thromboxane receptor, adenosine receptor, adrenaline receptor, α- and β-chemokine receptor including IL-8, GROα, GROβ, GROγ, NAP-2, ENA-78, PF4, IP10, GCP-2, MCP-1, HC14, MCP-3, I-309, MIP1α, MIP-1β, and RANTES receptors, endothelin receptor, enterogastrin receptor, histamine receptor, neurotensin receptor, TRH receptor, pancreatic polypeptide receptor, and galanin receptor; and (125) a culture product produced by a transformant according to the above (59) or (109).

As used herein the term "substantial equivalent(s)" means that the activity of the protein, e.g., nature of the ligand binding activity, and physical characteristics are substantially the same. Substitutions, deletions or insertions of amino acids often do not produce radical changes in the physical and chemical characteristics of a polypeptide, in which case polypeptides containing the substitution, deletion, or insertion would be considered to be substantially equivalent to polypeptides lacking the substitution, deletion, or insertion. Substantially equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine, The positively charged (basic) amino acids include arginine, lysine and histidine. The negatively charged (acidic) amino acids include aspartic acid and glutamic acid.

BRIEF DESCRIPTION OF THE DRAWINGS

FIG. 1 depicts the community (homology) of the sequence of 5' side synthetic DNA primers (HS-1) having a nucleotide sequence represented by SEQ ID NO: 1 with the nucleotide sequence each of other G protein coupled receptor protein-encoding cDNAs and genes (SEQ ID NOS: 62–75).

FIG. 2 depicts the community (homology) of the sequence which is complementary to 3' side synthetic DNA primers (HS-2) having a nucleotide sequence represented by SEQ ID NO: 2 with the nucleotide sequence each of other G protein coupled receptor protein-encoding cDNAs and genes (SEQ ID NOS: 76–91).

FIG. 3 depicts the community (homology) of the sequence of 5' side synthetic DNA primers (3A) having a nucleotide sequence represented by SEQ ID NO: 5 or 5' side synthetic DNA primers (3B) having a nucleotide sequence represented by SEQ ID NO: 6 relative to the nucleotide sequence each of other G protein coupled receptor protein-encoding cDNAs and genes (SEQ ID NOS: 92–110).

FIG. 4 depicts the community (homology) of the sequence of 5' side synthetic DNA primers (3C) having a nucleotide sequence represented by SEQ ID NO: 7 or 5' side synthetic DNA primers (3D) having a nucleotide sequence represented by SEQ ID NO: 3 relative to the nucleotide sequence each of other G protein coupled receptor protein-encoding cDNAs and genes (SEQ ID NOS: 111–121).

FIG. 5 depicts the community (homology) of the sequence (6A) which is complementary to 3' side synthetic DNA primers having a nucleotide sequence represented by SEQ ID NO: 8 or the nucleotide sequence (6B) which is complementary to 3' side synthetic DNA primers having a nucleotide sequence represented by SEQ ID NO: 9 relative to the nucleotide sequence each of other G protein coupled receptor protein-encoding cDNAs and genes (SEQ ID NOS: 122–142).

FIG. 6 depicts the community (homology) of the sequence (6C) which is complementary to 3' side synthetic DNA primers having a nucleotide sequence represented by SEQ ID NO: 4 relative to the nucleotide sequence each of other G protein coupled receptor protein-encoding cDNAs and genes (SEQ ID NOS: 143–154).

FIG. 7 depicts the community (homology) of the sequence of 5' side synthetic DNA primers (T2A) having a nucleotide sequence represented by SEQ ID NO: 10 with the nucleotide sequence each of other G protein coupled receptor protein-encoding cDNAs and genes (SEQ ID NOS: 155–171).

FIG. 8 depicts the community (homology) of the sequence which is complementary to 3' side synthetic DNA primers (T7A) having a nucleotide sequence represented by SEQ ID NO: 11 relative to the nucleotide sequence each of other G protein coupled receptor protein-encoding cDNAs and genes (SEQ ID NOS: 172–191).

FIG. 9 depicts the community (homology) of the sequence of 5' side synthetic DNA primers (TM1-A2) having a nucleotide sequence represented by SEQ ID NO: 12 relative to the nucleotide sequence each of other G protein coupled receptor protein-encoding cDNAs and genes (SEQ ID NOS: 192–204).

FIG. 10 depicts the community (homology) of the sequence which is complementary to 3' side synthetic DNA primers (TM3-B2) having a nucleotide sequence represented by SEQ ID NO: 13 relative to the nucleotide sequence each of other G protein coupled receptor protein-encoding cDNAs and genes (SEQ ID NOS: 205–218).

FIG. 11 depicts the community (homology) of the sequence of 5' side synthetic DNA primers (TM3-C2) having a nucleotide sequence represented by SEQ ID NO: 14 relative to the nucleotide sequence each of other G protein coupled receptor protein-encoding cDNAs and genes (SEQ ID NOS: 219–229).

FIG. 12 depicts the community (homology) of the sequence which is complementary to 3' side synthetic DNA primers (TM6-E2) having a nucleotide sequence represented by SEQ ID NO: 15 relative to the nucleotide sequence each of other G protein coupled receptor protein-encoding cDNAs and genes (SEQ ID NOS: 230–242).

FIG. 13 depicts the community (homology) of the sequence of 5' side synthetic DNA primers (TM2F18) having a nucleotide sequence represented by SEQ ID NO: 16 relative to the nucleotide sequence each of other G protein coupled receptor protein-encoding cDNAs and genes (SEQ ID NOS: 243–254).

FIG. 14 depicts the community (homology) of the sequence which is complementary to 3' side synthetic DNA primers (TM6R21) having a nucleotide sequence represented by SEQ ID NO: 17 relative to the nucleotide sequence each of other G protein coupled receptor protein-encoding cDNAs and genes (SEQ ID NOS: 255–274).

FIG. 15 depicts the community (homology) of the sequence of 5' side synthetic DNA primers (S3A) having a nucleotide sequence represented by SEQ ID NO: 18 relative to the nucleotide sequence each of other G protein coupled receptor protein-encoding cDNAs and genes (SEQ ID NOS: 275–286).

FIG. 16 depicts the community (homology) of the sequence which is complementary to 3' side synthetic DNA primers (S6A) having a nucleotide sequence represented by SEQ ID NO: 19 relative to the nucleotide sequence each of other G protein coupled receptor protein-encoding cDNAs and genes (SEQ ID NOS: 287–299).

FIG. 18 shows the nucleotide sequence determined by sequencing of clone A58 (SEQ ID NO: 300) with a T7 primer wherein the clone A58 is obtained by amplifying human brain amygdala-derived cDNA by PCR under mild conditions and subcloning it to TM pCR™II (HUMSOMAT: SEQ ID NO: 301).

FIG. 19 shows the nucleotide sequence determined by sequencing of clone A58 with an SP6 primer (SEQ ID NO: 302) (HUMSOMATA: SEQ ID NO: 303).

FIG. 20 shows the nucleotide sequence determined by sequencing of clone 57-A-2 (SEQ ID NO: 304) by using a -21M13 primer wherein the clone 57-A-2 is obtained by amplifying human brain amygdala-derived cDNA by PCR under severe conditions and subcloning it to Pcr™II (HUMDRDSA: SEQ ID NO: 305).

FIG. 21 shows the nucleotide sequence determined by sequencing of clone B54 with a T7 primer wherein the clone B54 (SEQ ID NO: 306) is obtained by amplifying rat whole brain-derived cDNA by PCR under mild conditions and subcloning it to Pcr™II (RNU04738: SEQ ID NO: 307).

FIG. 22 illustrates the nucleotide sequence (SEQ ID NO: 308) of the human pituitary gland-derived G protein coupled receptor protein cDNA fragment included in the cDNA clone p19P2 isolated by PCR using a human pituitary gland-derived cDNA and the amino acid sequence (SEQ ID NO: 309) encoded thereby, wherein the primer used for sequencing is -21M13, and the underlined part corresponds to the synthetic primer.

FIG. 23 illustrates the nucleotide sequence (SEQ ID NO: 310) of the human pituitary gland-derived G protein coupled receptor protein cDNA fragment included in the cDNA clone p19P2 isolated by PCR using a human pituitary gland-derived cDNA and the amino acid sequence (SEQ ID NO: 311) encoded thereby, wherein the primer used for sequencing is M13RV-N (Takara, Japan), and the underlined part corresponds to the synthetic primer.

FIG. 26 shows the partial amino acid sequence (p19P2) (SEQ ID NO: 312) of the protein encoded by the human pituitary gland-derived G protein coupled receptor protein cDNA fragment included in p19P2, as shown in FIGS. 22 and 23, relative to the known G protein coupled receptor protein, S12863 (SEQ ID NO: 313), wherein reverse amino acid residues are in agreement, the 1st to 99th amino acid residues of the p19P2 sequence correspond to the 1st to 99th amino acid residues in FIG. 22, and the 156th to 230th amino acid residues thereof correspond to the 1st to 68th amino acid residues in FIG. 23.

FIG. 27 is the nucleotide sequence (SEQ ID NO: 314) of the MIN6-derived G protein coupled receptor protein cDNA fragment derived based upon the nucleotide sequences of the MIN6-derived G protein coupled receptor protein cDNA fragments each included in the cDNA clones, pG3-2 and pG1-10, isolated by PCR using a MIN6-derived cDNA and the amino acid sequence encoded (SEQ ID NO: 315) thereby, wherein the underlined parts corresponds to the synthetic primers.

FIG. 29 is the partial nucleotide sequence (SEQ ID NO: 316) of the novel receptor protein cDNA clone, p63A2, obtained from the human amygdaloid nucleus by PCR amplification and the amino acid sequence (SEQ ID NO: 317) encoded thereby, wherein the underlined part corresponds to the synthetic primer.

FIG. 30 is the partial nucleotide sequence (SEQ ID NO: 318) of the novel receptor protein cDNA clone, p63A2, obtained from the human amygdaloid nucleus by PCR amplification and the amino acid sequence (SEQ ID NO: 319) encoded thereby, wherein the underlined part corresponds to the synthetic primer.

FIG. 33 is the partial amino acid sequence (p63A2) (SEQ ID NO: 320) of the protein encoded by the novel receptor protein cDNA fragment included in p63A2, relative to the partial amino acid sequence of the G protein coupled receptor protein (P30731) (SEQ ID NO: 321) expressed and induced by a mouse T cell-derived glucocorticoid, wherein reverse amino acid residues are in agreement.

FIGS. 34A, 34B and 34C are the whole nucleotide sequence (SEQ ID NO: 322) of the the human pituitary gland-derived G protein coupled receptor protein cDNA, included in the cDNA clone, phGR3, isolated from the human-derived cDNA library by plaque hybridization using an DNA insert in the p19P2 as a probe, and the amino acid sequence (SEQ ID NO: 323) encoded thereby.

FIG. 37 is the partial nucleotide sequence (SEQ ID NO: 324) of the novel receptor protein cDNA clone, p3H2-17, obtained from mouse pancreatic β-cell strain, MIN6, by PCR amplification and the amino acid sequence (SEQ ID NO: 325) encoded thereby, wherein the underlined part corresponds to the synthetic primer used for the PCR amplification.

FIG. 39 is the partial amino acid sequence encoded by the novel receptor protein cDNA included in p3H2-17 (SEQ ID NO: 326), relative to the partial amino acid sequence each of chicken ATP receptor protein (P34996) (SEQ ID NO: 327), human somatostatin receptor subtype 3 protein (A46226) (SEQ ID NO: 328), human somatostatin receptor subtype 4 protein (JN0605) (SEQ ID NO: 329) and bovine neuropeptide Y receptor protein (S28787) (SEQ ID NO: 330), wherein reverse amino acid residues are in agreement.

FIG. 40 is the partial nucleotide sequence (SEQ ID NO: 331) of the novel receptor protein cDNA clone, p3H2-34, obtained from mouse pancreatic β-cell strain, MIN6, by PCR amplification and the amino acid sequence (SEQ ID NO: 332) encoded thereby, wherein the underlined parts correspond to the synthetic primers used for the PCR amplification.

FIG. 42 is the partial amino acid sequences encoded by the novel receptor protein cDNA included in p3H2-34 (SEQ ID NO: 333), relative to the partial amino acid sequence each of human somatostatin receptor subtype 4 protein (JN0605) (SEQ ID NO: 334), human somatostatin receptor subtype 2 protein (B41795) (SEQ ID NO: 335) and rat-derived ligand unknown receptor protein (A39297) (SEQ ID NO: 336), wherein reverse amino acid residues are in agreement.

FIG. 43 is the nucleotide sequence (SEQ ID NO: 337) of the rabbit gastropyrolic part smooth muscle-derived G protein coupled receptor protein cDNA fragment included in the novel receptor protein cDNA clone, pMD4, obtained from rabbit gastropyrolic part smooth muscles by PCR amplification, and the amino acid sequence (SEQ ID NO: 338) encoded thereby, wherein the underlined parts correspond to the synthetic primers used for the PCR amplification.

FIG. 45 is the partial amino acid sequence (pMD4) (SEQ ID NO: 339) of the protein encoded by the rabbit gastropyrolic part smooth muscle-derived G protein coupled receptor protein cDNA fragment included in pMD4 as shown in FIG. 43, relative to the known G protein coupled receptor protein, rat ligand unknown receptor protein (A35639) (SEQ ID NO: 340), wherein reverse amino acid residues are in agreement, the 1st to 88th amino acid residues of the pMD4 sequence correspond to the 1st to 88th amino acid residues in FIG. 43.

FIGS. 46A, 46B and 46C shows the nucleotide sequence (SEQ ID NO: 341) of the mouse-derived galanin receptor protein cDNA clone, pMGR20, which has been cloned with, as a probe, the cDNA insert in p3H2-34 and the amino acid sequence encoded thereby (SEQ ID NO: 342).

FIG. 48 is the amino acid sequence (MOUSEGALRECE) (SEQ ID NO: 343) of the mouse-derived galanin receptor protein encoded by pMGR20, relative to the amino acid sequence (HUMAGALAMI) (SEQ ID NO: 344) of the human-derived galanin receptor protein, wherein reverse amino acid residues are in agreement.

FIG. 49 is the nucleotide sequence (SEQ ID NO: 345) of the rabbit gastropyrolic part smooth muscle-derived G protein coupled receptor protein cDNA fragment included in the novel receptor protein cDNA clone, pMJ10, obtained from rabbit gastropyrolic part smooth muscles by PCR amplification and the amino acid sequence encoded thereby (SEQ ID NO: 346), wherein the underlined parts corresponds to the synthetic primers used for the PCR amplification.

FIG. 51 is the partial amino acid sequence (pMJ10) (SEQ ID NO: 347) of the protein encoded by the rabbit gastropyrolic part smooth muscle-derived G protein coupled receptor protein cDNA fragment included in pMJ10 shown in FIG. 49, relative to human ligand unknown receptor protein (B42009) (SEQ ID NO: 348), human N-formylpeptide receptor protein (JC2014) (SEQ ID NO: 349), rabbit N-formylpeptide receptor protein (A46520) (SEQ ID NO: 350), mouse C5a anaphylatoxin receptor protein (A46525) (SEQ ID NO: 351) and bovine neuropeptide Y receptor protein (,28787) (SEQ ID NO: 352) which are known G protein coupled receptor proteins, wherein reverse amino acid residues are in agreement, and the 1st to 125th amino acid residues of pMJ10 correspond to the 1st to 125th amino acid residues in FIG. 49.

FIG. 52 is the nucleotide sequence (SEQ ID NO: 353) of the rabbit gastropyrolic part smooth muscle-derived G protein coupled receptor protein cDNA fragment included in the novel receptor protein cDNA clone, pMH28, obtained from rabbit gastropyrolic part smooth muscles by PCR amplification and the amino acid sequence encoded thereby (SEQ ID NO: 354), wherein the underlined parts correspond to the synthetic primers used for the PCR amplification.

FIG. 54 is the partial amino acid sequence (pMH28) (SEQ ID NO: 355) of the protein encoded by the rabbit gastropyrolic part smooth muscle-derived G protein coupled receptor protein cDNA fragment included in pMH28 shown in FIG. 52, relative to mouse IL-8 receptor protein (P35343) (SEQ ID NO: 356), human somatostatin receptor protein 1 (A41795) (SEQ ID NO: 357) and human somatostatin receptor protein 4 (A47457) (SEQ ID NO: 358) which are known G protein coupled receptor proteins, wherein reverse amino acid residues are in agreement, and the 1st to 119th amino acid residues of pMH28 correspond to the 1st to 119th amino acid residues in FIG. 52.

FIG. 55 is the nucleotide sequence (SEQ ID NO: 359) of the rabbit gastropyrolic part smooth muscle-derived G protein coupled receptor protein cDNA fragment included in the novel receptor protein cDNA clone, pMN7, obtained from rabbit gastropyrolic part smooth muscles by PCR amplification and the amino acid sequence encoded thereby (SEQ ID NO: 360), wherein the underlined 5'-end nucleotide sequence part corresponds to the synthetic primer used for the PCR amplification.

FIG. 56 is the nucleotide sequence (SEQ ID NO: 359) of the rabbit gastropyrolic part smooth muscle-derived G protein coupled receptor protein cDNA fragment included in the novel receptor protein cDNA clone, pMN7, obtained from rabbit gastropyrolic part smooth muscles by PCR amplification and the amino acid sequence encoded thereby (SEQ ID NO: 360), wherein the underlined 3'-end nucleotide sequence part corresponds to the synthetic primer used for the PCR amplification.

FIG. 60 shows the partial amino acid sequence (p19P2) (SEQ ID NO: 361) of the protein encoded by the human pituitary gland-derived G protein coupled receptor protein cDNA fragment included in p19P2, as shown in FIGS. 22 and 23, relative to the known G protein coupled receptor protein, S12863 (SEQ ID NO: 362), wherein reverse amino acid residues are in agreement, the 1st to 99th amino acid residues of the p19P2 sequence correspond to the 1st to 99th amino acid residues in FIG. 22, and the 156th to 230th amino acid residues thereof correspond to the 1st to 68th amino acid residues in FIG. 23.

FIG. 61 is the partial amino acid sequence (pG3-2/pG1-10) (SEQ ID NO: 363) of the MIN6-derived G protein coupled receptor protein, as shown in FIG. 27, relative to the partial amino acid sequence (p19P2) (SEQ ID NO: 364) of the protein encoded by p19P2, as shown in FIGS. 22 and 23, wherein reverse amino acid residues are in agreement, the 1st to 99th amino acid residues of the p19P2 sequence correspond to the 1st to 99th amino acid residues in FIG. 22, the 156th to 223rd amino acid residues thereof correspond to the 1st to 68th amino acid residues in FIG. 23, and the 1st to 223rd amino acid residues of the pG3-2/pG1-10 sequence correspond to the 1st to 223rd amino acid residues in FIG. 27.

FIG. 62 is the nucleotide sequence (SEQ ID NO: 365) of the MIN6-derived G protein coupled receptor protein cDNA fragment included in the cDNA clone, p5S38, isolated by PCR using a MIN6-derived cDNA and the amino acid sequence (SEQ ID NO: 366) encoded thereby, wherein the underlined parts corresponds to the synthetic primers.

FIG. 63 is the partial amino acid sequence (p5S38) (SEQ ID NO: 369) of the MIN6-derived G protein coupled receptor protein, as shown in FIG. 62, relative to the partial amino acid sequence (p19P2) (SEQ ID NO: 367) of the G protein coupled receptor protein encoded by p19P2, as shown in FIGS. 22 and 23, as well as the partial amino acid sequence (SEQ ID NO: 368) of the G protein coupled receptor protein encoded by the nucleotide sequence derived from the nucleotide sequence of the cDNA fragment included in pG3-2 and pG1-10, as shown in FIG. 27, wherein reverse amino acid residues are in agreement, the 1st to 144th amino acid residues of the p5S38 sequence correspond to the 1st to 144th amino acid residues in FIG. 62, the 1st to 99th amino acid residues of the p19P2 sequence correspond to the 1st to 99th amino acid residues in FIG. 22, the 156th to 223rd amino acid residues thereof correspond to the 1st to 68th amino acid residues in FIG. 23, and the 1st to 223rd amino acid residues of the pG3-2/pG1-10 sequence correspond to the 1st to 223rd amino acid residues in FIG. 27.

FIG. 64 is the partial hydrophobicity plotting profile of the protein encoded by the MIN6-derived G protein coupled receptor protein cDNA fragment included in p5S38, prepared based upon the amino acid sequence shown in FIG. 62.

Lane 1 indicates the size marker 6 (Wako Pure Chemical, Japan).

Lane 2 indicates the internal control which is the thymus-derived PCR product obtained by PCR amplification using the primer having SEQ ID NO: 20 and the primer having SEQ ID NO: 22 with Taq polymerase.

Lane 3 indicates the negative control which is the PCR product obtained by Ex Taq polymerase PCR amplification of thymus cDNA prior to addition of anchors.

Lane 4 indicates the negative control which is the PCR product obtained by Taq polymerase PCR amplification of thymus cDNA prior to addition of anchors.

Lane 5 indicates the PCR product obtained by 5'RACE of thymus poly(A)⁺RNA with Pfu polymerase.

Lane 6 indicates the PCR product obtained by 5'RACE of thymus poly(A)⁺RNA with Vent polymerase.

Lane 7 indicates the PCR product obtained by 5'RACE of thymus poly(A)⁺RNA with Ex Tag polymerase.

Lane 8 indicates the PCR product obtained by 5'RACE of thymus poly(A)⁺RNA with Tag polymerase.

Lane 9 indicates the size marker 5 (Wako Pure Chemical, Japan).

Lane 10 indicates the internal control which is the spleen-derived PCR product obtained by PCR amplification using the primer having SEQ ID NO: 20 and the primer having SEQ ID NO: 22 with Tag polymerase.

Lane 11 indicates the negative control which is the PCR product obtained by Ex Tag polymerase PCR amplification of spleen cDNA prior to addition of anchors.

Lane 12 indicates the negative control which is the PCR product obtained by Tag polymerase PCR amplification of spleen cDNA prior to addition of anchors.

Lane 13 indicates the PCR product obtained by 5'RACE of poly(A)⁺RNA with Pfu polymerase.

Lane 14 indicates the PCR product obtained by 5'RACE of spleen poly(A)⁺RNA with Vent polymerase.

Lane 15 indicates the PCR product obtained by 5'RACE of spleen poly(A)⁺RNA with Ex Tag polymerase.

Lane 16 indicates the PCR product obtained by 5'RACE of spleen poly(A)⁺RNA with Tag polymerase.

Lane 17 indicates the size marker 5 (Wako Pure Chemical, Japan).

Each blacked triangle indicates the band recovered.

Figure 67:
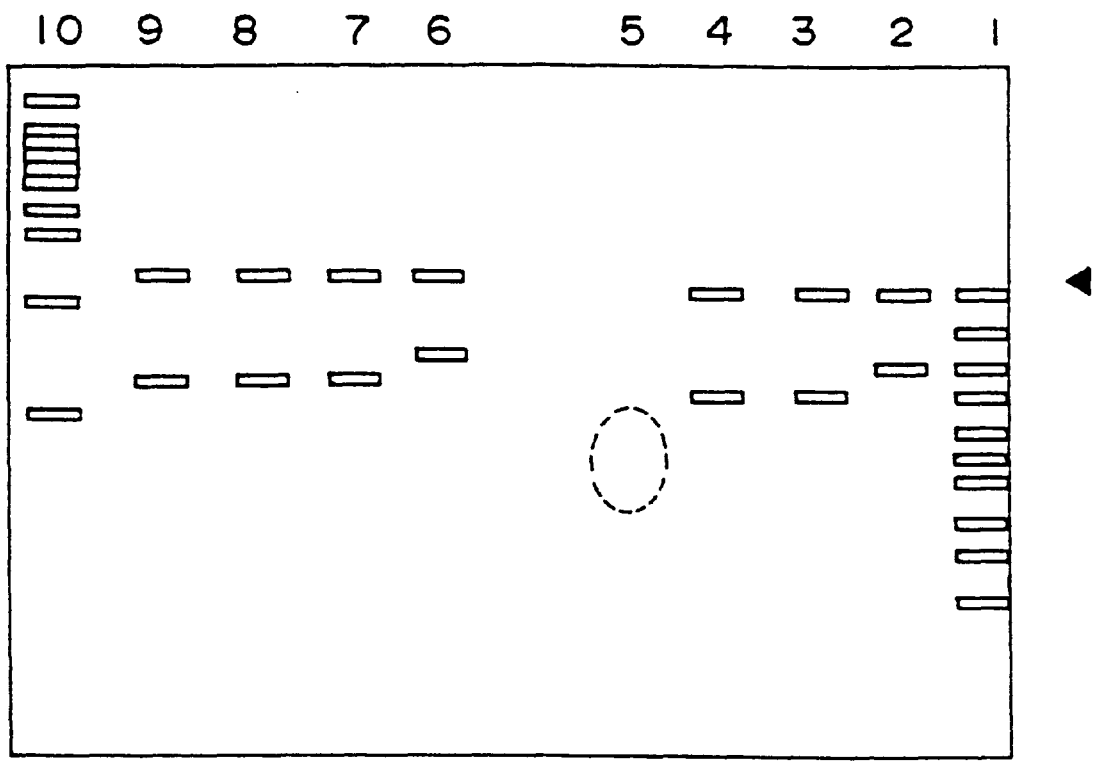

FIG. 67 shows the agarose gel electrophoresis analysis profile of the PCR products obtained by 3'RACE PCR of the receptor gene included in p3H2-17 using mouse thymus and spleen poly(A)+RNA.

Lane 1 indicates the size marker 5 (Wako Pure Chemical, Japan).

Lane 2 indicates the PCR product obtained by 3'RACE of spleen poly(A)+RNA with Taq polymerase.

Lane 3 indicates the PCR product obtained by 3'RACE of spleen poly(A)+RNA with Ex Taq polymerase.

Lane 4 indicates the PCR product obtained by 3'RACE of spleen poly(A)+RNA with Vent polymerase.

Lane 5 indicates the PCR product obtained by 3'RACE of spleen poly(A)+RNA with Pfu polymerase.

Lane 6 indicates the PCR product obtained by 3'RACE of thymus poly(A)+RNA with Taq polymerase.

Lane 7 indicates the PCR product obtained by 3'RACE of thymus poly(A +RNA with Ex Taq polymerase.

Lane 8 indicates the PCR product obtained by 3'RACE of thymus poly(A)+RNA with Vent polymerase.

Lane 9 indicates the PCR product obtained by 3'RACE of thymus poly(A)+RNA with Pfu polymerase.

Lane 10 indicates the size marker 6 (Wako Pure Chemical, Japan).

Each blacked triangle indicates the band recovered.

FIG. 68 depicts the model of the RACE products of the receptor protein cDNA fragment included in p3H2-17 obtained by 5'RACE and 3'RACE. Open squares represent regions which have already been isolated and included in p3H2-17. Small arrows, ①, ②, ③ and ④, indicate the positions and directions of the primers designed in Working Example 19. The big arrow shows a predicted full-length open reading frame of the receptor protein held by p3H2-17. Numbers at both ends, N26, N64, N75, C2, C13 and C15, indicate clone numbers of the RACE products obtained. Among these RACE products, N26, N64 and N75 are inserted into pCR™II vector and C2, C13 and C15 are inserted into the SmaI site of pUC18. The solid triangle indicates the PCR error position which has been clarified through sequencing.

FIGS. 69A and 69B are the nucleotide sequence (SEQ ID NO: 370) of the open reading frame and neighboring regions thereof of mouse G protein coupled receptor protein cDNA included in the cDNA clone pMAH2-17 obtained from mouse spleen and thymus poly(A) RNA by RACE techniques based on the nucleotide sequence of the cDNA fragment included in p3H2-17 and the amino acid sequence (SEQ ID NO: 371) encoded thereby.

Figure 70:
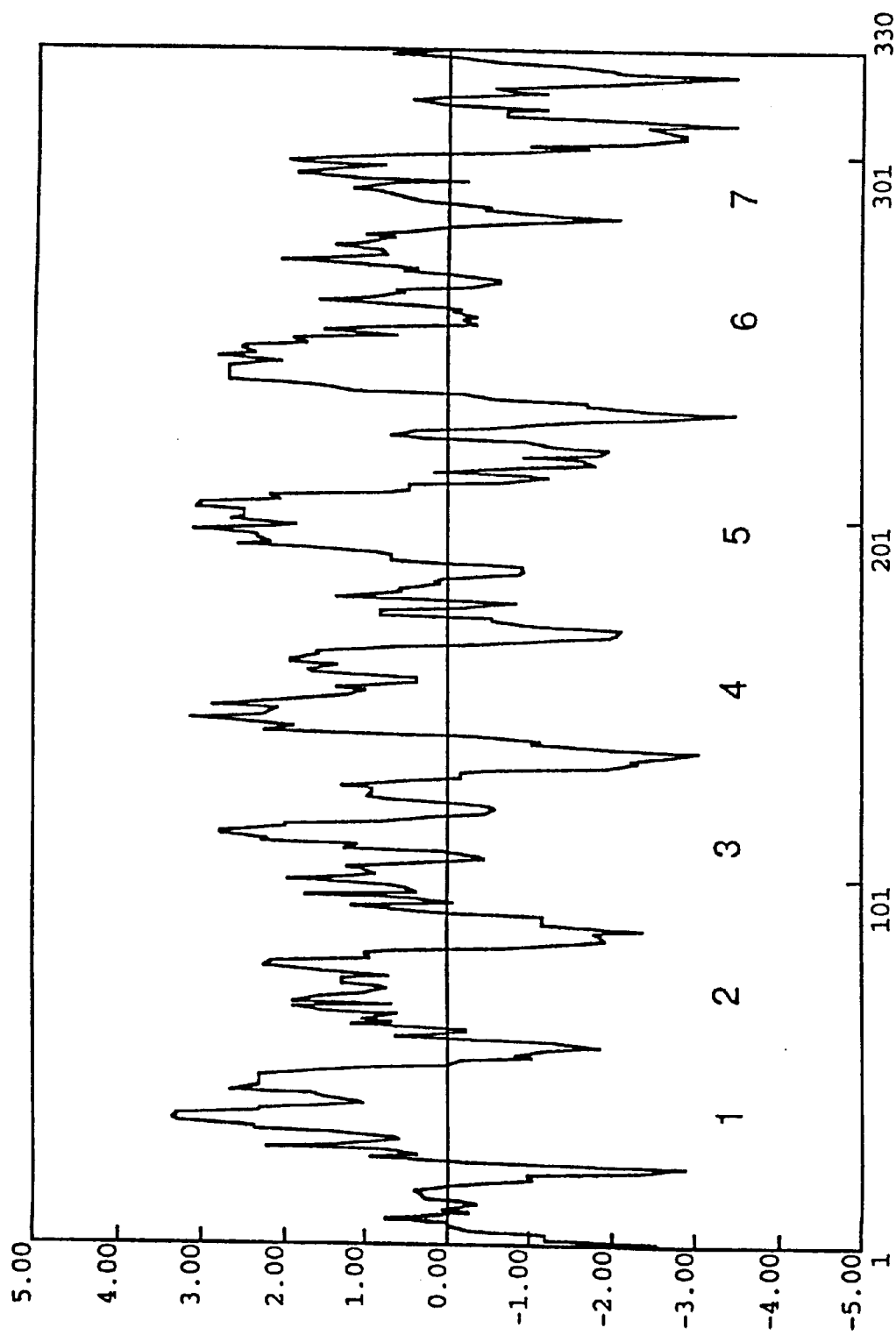

FIG. 70 is the hydrophobicity plotting profile of the protein encoded by the receptor protein cDNA included in pMAH2-17, prepared based upon the amino acid sequence shown in FIG. 69.

FIG. 71 is the amino acid sequence (75+13CODING) (SEQ ID NO: 372) of the protein encoded by the mouse-derived G protein coupled receptor protein cDNA fragment included in pMAH2-17, as shown in FIG. 69, relative to the known G protein coupled receptor proteins, mouse $P_{2U}$purinoceptor (P2UR MOUSE) (SEQ ID NO: 373) and chicken $P_{2Y}$purinoceptor (P2YR CHICK) (SEQ ID NO: 374), wherein reverse amino acid residues are in agreement.

FIG. 72 is the nucleotide sequence (SEQ ID NO: 375) (from 1st to 540th nucleotides) of the rabbit gastropyrolic part smooth muscle-derived G protein coupled receptor protein cDNA fragment included in the novel receptor protein cDNA clone, pMN128, obtained from rabbit gastropyrolic part smooth muscles by PCR amplification, and the amino acid sequence (SEQ ID NO: 376) encoded thereby, wherein the underlined 5' part corresponds to the synthetic primer used for the PCR amplification.

FIG. 73 is the nucleotide sequence (SEQ ID NO: 375) (from 541st to 843rd nucleotides) of the rabbit gastropyrolic part smooth muscle-derived G protein coupled receptor protein cDNA fragment included in the novel receptor protein cDNA clone, pMN128, obtained from rabbit gastropyrolic part smooth muscles by PCR amplification, and the amino acid sequence (SEQ ID NO: 376) encoded thereby, wherein the underlined 3' part corresponds to the synthetic primer used for the PCR amplification.

FIG. 74 is the hydrophobicity plotting profile of the protein encoded by the rabbit gastropyrolic part smooth muscle-derived G protein coupled receptor protein cDNA fragment included in pMN128, prepared based upon the amino acid sequences shown in FIGS. 72 and 73, suggesting the presence of hydrophobic domains.

FIG. 75 shows inward currents evoked by ATP in Xenopus oocytes injected with cDNA of pMAH2-17-encoded receptor.

FIG. 76 is the nucleotide sequence (SEQ ID NO: 377) of the human-derived G protein coupled receptor protein cDNA fragment included in ph3H2-17, relative to the nucleotide sequence (SEQ ID NO: 378) of the mouse-derived G protein coupled receptor protein cDNA fragment included in p3H2-17, wherein reverse base residues are in agreement.

FIGS. 77A and 77B are the nucleotide sequence (SEQ ID NO: 379) of the open reading frame and neighboring regions thereof of human-derived G protein coupled receptor protein cDNA included in phAH2-17 and the amino acid sequence (SEQ ID NO: 380) encoded thereby.

Figure 78:
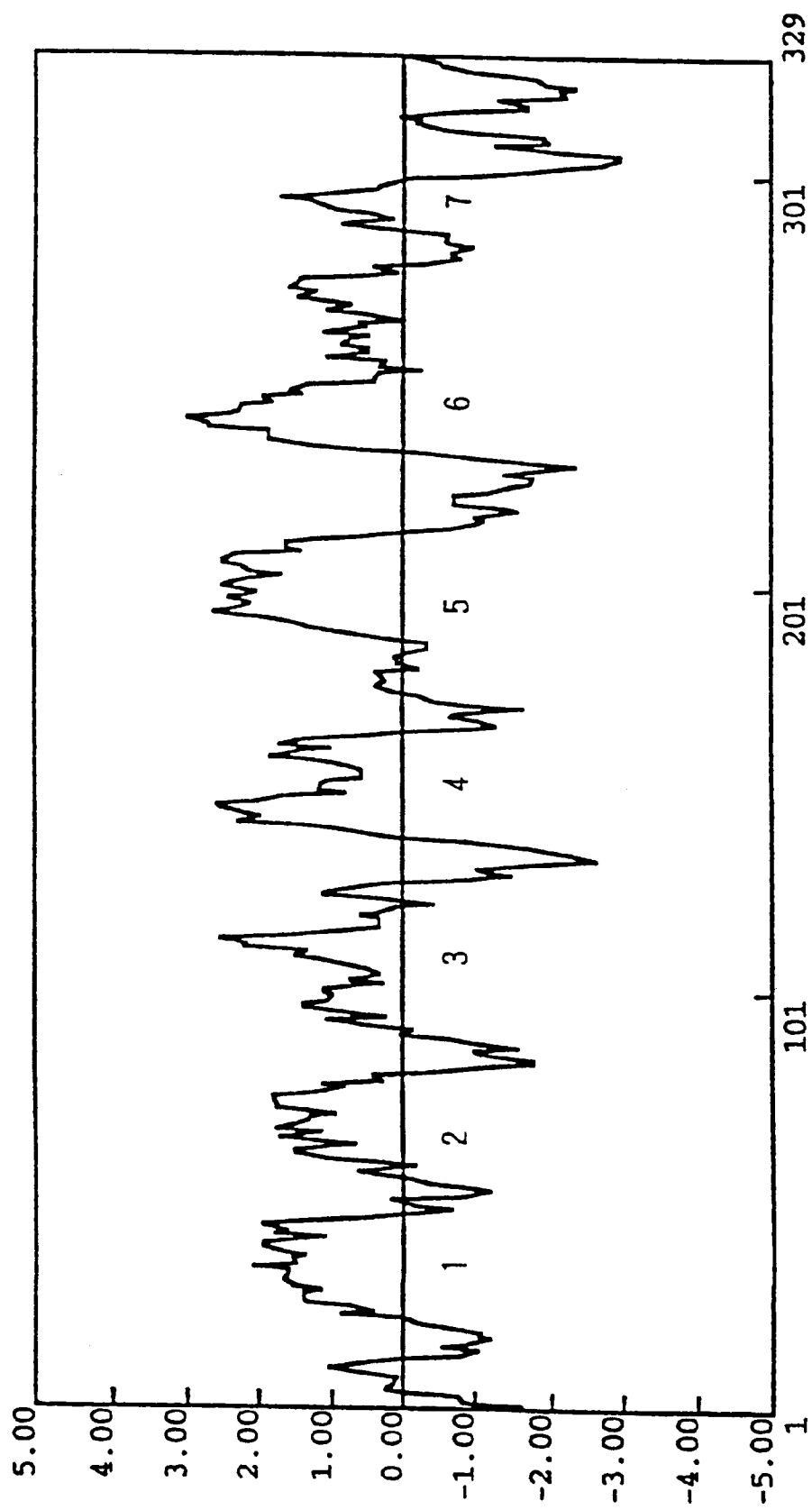

FIG. 78 is the hydrophobicity plotting profile of the protein encoded by the human-derived G protein coupled receptor protein cDNA included in phAH2-17.

FIG. 79 is the amino acid sequence (SEQ ID NO: 59) of human type purinoceptor encoded by phAH2-17, relative to the mouse purinoceptor (SEQ ID NO: 39) encoded by p3H2-17, wherein reverse amino acid residues are in agreement.

DETAILED DESCRIPTION OF THE PREFERRED EMBODIMENT

According to the present invention, DNA sequences comprising each a nucleotide sequence indicated by a SEQ ID NO selected from the group consisting of SEQ ID NO: 1 to SEQ ID NO: 19 have been synthesized and characterized. The DNA is a potent primer for polymerase chain reaction in order to amplify DNA sequences encoding part or all of the polypeptide sequence of G protein coupled receptor protein. PCR amplification methods of the DNA coding for part or all of the polypeptide sequence of G protein coupled receptor protein can be advantageously carried out with the said primer DNA. Screening of DNA libraries for the DNA encoding part or all of the polypeptide sequence of G protein coupled receptor protein can be successfully carried out through polymerase chain reaction techniques with the said primer DNA.

As a result, template DNAs coding for part or all of the polypeptide sequence of G protein coupled receptor protein, contained in the DNA library, can be selectively amplified and various DNA sequences encoding part or all of the polypeptide sequence of G protein coupled receptor protein may be isolated and characterized. Further, G protein coupled receptor proteins, peptide segments or fragments derived from the G protein coupled receptor protein, modified derivatives or analogues thereof, and salts thereof may be recognized, predicted, deduced, produced, expressed, isolated and characterized.

The primer DNA useful in PCR amplification of the DNA sequence encoding part or all of the polypeptide sequence of G protein coupled receptor protein is a degenerate deoxynucleotide which has an oligonucleotide sequence to which a SEQ ID NO selected from the group consisting of SEQ ID NO: 1 to SEQ ID NO: 19 is assigned.

The nucleotide sequence represented by SEQ ID NO: 1 is a base sequence having the following formula:

wherein S is G or C, M is A or C, $N_1$=A, G, C, or T, and Y is T or C (FIG. 1: HS-1).

The nucleotide sequence represented by SEQ ID NO: 2 (HS-2) is a base sequence having the following formula:

wherein $N_1$=A, G, C, or T, W is A or T, R is A or G, and K is G or T, which is complementary to a nucleotide sequence having the following formula:

wherein N=A, C, G, or T, M is A or C, Y is T or C, and W is A or T (FIG. 2).

The nucleotide sequence represented by SEQ :.D NO: 3 is a base sequence having the following formula:

wherein S is G or C, Y is C or T, M is A or C, R is A or G, and $N_2$=I (FIG. 4: 3D).

The nucleotide sequence represented by SEQ ID NO: 4 is a base sequence having the following formula:

5'-CATGTRGWAGGGAAN$_2$CCAGSAMAN$_2$RARRAA-3' wherein R is A or G, W is T or A, S is G or C, M is A or C, and $N_2$=I, which is complementary to a nucleotide sequence having the following formula:

wherein Y is C or T, $N_1$=A, G, C, or T, K is G or T. S is G or C, W is A or T (FIG. 6: 6C).

The nucleotide sequence represented by SEQ ID NO: 5 is a base sequence having the following formula:

wherein Y is C or T, R is A or G, S is G or C, M is A or C, and V is A, C or G, and $N_2$ is I (FIG. 3: 3A).

The nucleotide sequence represented by SEQ ID NO: 6 is a base sequence having the following formula:

5'-CTGACYGYTCTN$_2$RSN$_2$RYTGACMGVTAT-3' wherein Y is C or T, R is A or G, S is G or C, M is A or C, and V is A, C or G, and $N_2$ is I (FIG. 3: 3B).

The nucleotide sequence represented by SEQ ID NO: 7 is a base sequence having the following formula:

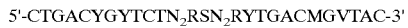

wherein S is G or C, Y is C or T, M is A or C, R is A or G, and $N_2$ is I (FIG. 4: 3C).

The nucleotide sequence represented by SEQ ID NO: 8 is a base sequence having the following formula:

wherein R is A or G, S is G or C, Y is C or T, and $N_2$ is I, which is complementary to a nucleotide sequence having the following formula:

wherein R is A or G, Y is C or T, S is G or C, and $N_1$ is A, T, G, or C (FIG. 5: 6A).

The nucleotide sequence represented by SEQ ID NO: 9 is a base sequence having the following formula:

wherein R is A or G, S is G or C, Y is C or T, and $N_2$ is I, which is complementary to a nucleotide sequence having the following formula:

wherein R is A or G, Y is C or T, S is G or C, and $N_1$ is A, T, G, or C (FIG. 5: 6B).

The nucleotide sequence represented by SEQ ID NO: 10 is a base sequence having the following formula:

wherein S is G or C, Y is C or T, W is A or T, H is A, C or T, and $N_2$ is I (FIG. 7: T2A).

The nucleotide sequence represented by SEQ ID NO: 11 (FIG. 8: T7A) is a base sequence having the following formula:

wherein R is A or G, S is G or C, and $N_2$ is I, which is complementary to a nucleotide sequence having the following formula:

wherein Y is C or T, $N_2$ is I, and S is G or C (FIG. 8).

The nucleotide sequence represented by SEQ ID NO: 12 is a base sequence having the following formula:

wherein S is G or C, K is G or T, M is A or C, and $N_2$ is I (FIG. 9: TM1-A2).

The nucleotide sequence represented by SEQ "D NO: 13 (FIG. 10: TM3-B2) is a base sequence having the following formula:

wherein Y is C or T, K is G or T, W is A or T, and $N_2$ is I, which is complementary to a nucleotide sequence having the following formula:

wherein M is A or C, W is A or T, R is A or G, and $N_2$ is I (FIG. 10).

The nucleotide sequence represented by SEQ ID NO: 14 is a base sequence having the following formula:

wherein K is G or T, S is G or C, Y is C or T, R is A or G, and $N_2$ is I (FIG. 11: TM3-C2).

The nucleotide sequence represented by SEQ ID NO: 15 (FIG. 12: TM6-E2) is a base sequence having the following formula:

5'-GWWGGGSAKCCAGCASAN₂GGCRAA-3' wherein W is A or T, S is G or C, K is G or T, R is A or G, and N₂ is I, which is complementary to a nucleotide sequence having the following formula:

5'-TTYGCCN₂TSTGCTGGMTSCCCWWC-3' wherein Y is C or T, S is G or C, M is A or C, W is A or T, and N₂ is I (FIG. 12).

The nucleotide sequence represented by SEQ ID NO: 16 is a base sequence having the following formula:

5'-ARYYTN₂GCN₂N₂TN₂GCN₁ GAY-3' wherein R is A or G, Y is C or T, N₁ is A, T, G, or C, and N₂ is I (FIG. 13: TM2F18).

The nucleotide sequence represented by SEQ —D NO: 17 (FIG. 14: TM6R21) is a base sequence having the following formula:

5'-N₂ GGN₂AN₂CCARCAN₁AN₁N₁RN₁RAA-3' wherein R is A or G, N is A, T, G, or C, and N₂ is I which is complementary to a nucleotide sequence having the following formula:

5'-TTYN₁YN₁N₁TN₁TGYTGGN₂TN₂CCN-3' wherein Y is C or T, N₁ is A, T, G, or C, and N₂ is I (FIG. 14).

The nucleotide sequence represented by SEQ ID NO: 18 is a base sequence having the following formula:

5'-GCCTSN₂TN₂ RN₂SATGWSTGTGGAN₂MGN₂T-3' wherein S is G or C, R is A or G, W is A or T, M is A or C, and N₂ is I (FIG. 15: S3A).

The nucleotide sequence represented by SEQ ED NO: 19 (FIG. 16: S6A) is a base sequence having the following formula:

5'-GAWSN₂TGMYN₂AN₂RTGGWAGGGN₂AN₂CCA-3' wherein W is A or T, S is G or C, M is A or C, Y is C or T, R is A or G, and N₂ is I, which is complementary to a nucleotide sequence having the following formula:

5'-TGGN₂TN₂CCCTWCCAYN₂TN₂RKCAN₂SWTC-3' wherein W is A or T, Y is C or T, R is A or G, K is G or T, and S is G or C (FIG. 16).

In a specific embodiment, symbols in the aforementioned SEQ ID NOs (R, Y, M, K, S, W, H, V and N) indicate the incorporation of plural bases, leading to multiple oligonucleotides in the primer preparation. In other words, SEQ ID NO: 1 to SEQ ID NO: 19 are degenerate nucleotide primers.

The nucleotide sequence represented by SEQ ID NO: 1 (FIG. 1: HS-1) is a nucleotide sequence highly homologous to the DNA sequence coding for the amino acid sequence corresponding to or near the first membrane-spanning (transmembrane) domain each of known G protein coupled receptor proteins such as human-derived TRH receptor protein (HTRHR), human-derived RANTES receptor protein (L10918, HUMRANTES), human Burkitt's lymphoma-derived receptor protein with an unknown ligand (X68149, HSBLR1A), human-derived somatostatin receptor protein (L14856, HUMSOMAT1), rat-derived μ-opioid receptor protein (U02083, RNU02083), rat-derived κ-opioid receptor protein (U00442, U00442), human-derived neuromedin B receptor protein (M73482, HUMNMBR), human-derived muscarinic acetylcholine receptor protein (X15266, HSHM4), rat-derived adrenaline α₁B receptor protein (L08609, RATAADRE01), human-derived somatostatin 3 receptor protein (M96738, HUMSSTR3X), human-derived C₅a receptor protein (HUMC5AAR), human-derived receptor protein with an unknown ligand (HUMRDC1A), human-derived receptor protein with an unknown ligand (M84605, HUMOPIODRE), rat-derived adrenaline α₂B receptor protein (M91466, RATA2BAR) and the like [FIG. 1].

The nucleotide sequence represented by SEQ ID NO: 2 (HS-2) is a nucleotide sequence which is complementary to the nucleotide sequence (FIG. 2) highly homologous to the DNA sequence coding for the amino acid sequence corresponding to or near the sixth membrane-spanning domain of known G protein coupled receptor proteins such as mouse-derived receptor protein with an unknown ligand (M80481, MUSGIR), human-derived bombesin receptor protein (L08893, HUMBOMB3S), human-derived adenosine A2 receptor protein (S46950, S46950), mouse-derived receptor protein with an unknown ligand (D21061, MUSGPCR), mouse-derived TRH receptor protein (S43387, S43387), rat-derived neuromedin K receptor protein (J05189, RATNEURA), rat-derived adenosine A1 receptor protein (M69045, RATA1ARA), human-derived neurokinin A receptor protein (M57414, HUMNEKAR), rat-derived adenosine A3 receptor protein (M94152, RATADENREC), human-derived somatostatin 1 receptor protein (M81829, HUMSTRI1A), human-derived neurokinin 3 receptor protein (S86390, S86371S4), rat-derived receptor protein with an unknown ligand (X61496, RNCGPCR), human-derived somatostatin 4 receptor protein (L07061, HUMSSTR4Z), rat-derived GnRH receptor protein (M31670, RATGNRHA) and the like [FIG. 2].

The nucleotide sequence represented by SEQ :ED NO: 5 (FIG. 3: 3A) or the nucleotide sequence represented by SEQ ID NO: 6 (FIG. 3: 3B) is a nucleotide sequence highly homologous to the DNA sequence coding for the amino acid sequence corresponding to or near the third membrane-spanning domain each of known G protein coupled receptors such as mouse-derived κ-opioid receptor protein (L11064), mouse-derived δ-opioid receptor protein (L11065), rat-derived μ-opioid receptor protein (D16349), mouse-derived bradykinin B2 receptor protein (X69676), rat-derived bradykinin B2 receptor protein (M59967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived receptor protein with an unknown ligand (L04672), rat-derived receptor protein with an unknown ligand (X61496), rat-derived receptor protein with an unknown ligand (X59249), rat-derived receptor protein with an unknown ligand (L09249), mouse-derived receptor protein with an unknown ligand (P30731), human-derived receptor protein with an unknown ligand (M31210), human-derived receptor protein with an unknown ligand (U03642) and the like [FIG. 3].

The nucleotide sequence represented by SEQ ID NO: 7 (FIG. 4: 3C) or the nucleotide sequence represented by SEQ ID NO: 3 (FIG. 4: 3D) is a nucleotide sequence highly homologous to the DNA sequence coding for the amino acid sequence corresponding to or near the third membrane-spanning domain each of known G protein coupled receptors such as mouse-derived angiotensin II receptor protein (L32840), rat-derived angiotensin Ib receptor protein (X64052), rat-derived angiotensin receptor protein subtype (M90065), human-derived angiotensin Ia receptor protein (M91464), rat-derived cholecystokinin a receptor protein (M88096), rat-derived cholecystokinin b receptor protein (M99418), human-derived cholecystokinin b receptor protein (L04473), mouse-derived low affinity interleukin 8 receptor protein (M73969), human-derived high affinity interleukin 8 receptor protein (X65858), mouse-derived C5a anaphylatoxin receptor protein (S46665), human-derived N-formylpeptide receptor protein (M60626) and the like [FIG. 4].

The nucleotide sequence represented by SEQ ED NO: 10 (FIG. 7: T2A) is a nucleotide sequence highly homologous to the DNA sequence coding for the amino acid sequence corresponding to or near the second membrane-spanning domain each of known G protein coupled receptors such as human galanin receptor (HUMGALAREC), rat α-1B-adrenergic receptor (RATADR1B), human β-1-adrenergic receptor (HUMADRB1), rabbit IL-8 receptor (RABIL8RSB), human opioid receptor (HUMOPIODRE), bovine substance K receptor (BTSKR), human somatostatin receptor-2 (HUMSRI2A), human somatostatin receptor-3 (HUMSSTR3Y), human gastrin receptor (HUMGARE), human cholecystokinin A receptor (HUMCCKAR), human dopamine receptor-D5 (HUMD1B), human serotonin receptor 5HT1E (HUM5HT1E), human dopamine receptor D4 (HUMD4C), mouse serotonin receptor-2 (MMSERO), rat α-1A-adrenergic receptor (RATADRA1A), rat histamine H2 receptor (S57565) and the like [FIG. 7].

The nucleotide sequence represented by SEQ ID NO: 8 (complementary to 6A of FIG. 5) or the nucleotide sequence represented by SEQ ID NO: 9 (complementary to 6B of FIG. 5) is a nucleotide sequence which is complementary to the nucleotide sequence (FIG. 5) highly homologous to the DNA sequence coding for the amino acid sequence corresponding to or near the sixth membrane-spanning domain of known G protein coupled receptors such as mouse-derived κ-opioid receptor protein (L11064), mouse-derived δ-opioid receptor protein (L11065), rat-derived μ-opioid receptor protein (D16349), mouse-derived bradykinin B2 receptor protein (X69676), rat-derived bradykinin B2 receptor protein (M59967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived receptor protein with an unknown ligand (L04672), rat-derived receptor protein with an unknown ligand (X61496), rat-derived receptor protein with an unknown ligand (X59249), rat-derived receptor protein with an unknown ligand (L09249), mouse-derived receptor protein with an unknown ligand (P30731), human-derived receptor protein with an unknown ligand (M31210) human-derived receptor protein with an unknown ligand (U03642) and the like [FIG. 5].

The nucleotide sequence represented by SEQ ID NO: 4 (complementary to 6C of FIG. 6) is a nucleotide sequence which is complementary to the nucleotide sequence (FIG. 6) highly homologous to the DNA sequence coding for the amino acid sequence corresponding to or near the sixth membrane-spanning domain of known G protein coupled receptors such as mouse-derived angiotensin II receptor protein (L32841), rat-derived angiotensin Ib receptor protein (X64052), rat-derived angiotensin receptor protein subtype (M90065), human-derived angiotensin Ia receptor protein (M91464), rat-derived cholecystokinin a receptor protein (M88096), rat-derived cholecystokinin b receptor protein (M99418), human-derived cholecystokinin 8 receptor protein (L04473), mouse-derived low affinity interleukin 8 receptor protein (M73969), human-derived high affinity interleukin 8 receptor protein (X65858), mouse-derived C5a anaphylatoxin receptor protein (S46665), human-derived N-formylpeptide receptor protein (M60626) and the like [FIG. 6].

The nucleotide sequence represented by SEQ ID NO: 11 (FIG. 8: T7A ) is a nucleotide sequence which is complementary to the nucleotide sequence (FIG. 8) highly homologous to the DNA sequence coding for the amino acid sequence corresponding to or near the seventh membrane-spanning domain each of known G protein coupled receptors such as human galanin receptor (HUMGALAREC), rat A1 adenosine receptor (RAT1DREC), porcine angiotensin receptor (PIGA2R), rat serotonin receptor (RAT5HTRTC), human dopamine receptor (S58541), human gastrin releasing peptide receptor (HUMGRPR), mouse GRP/bombesin receptor (MUSGRPBOM), rat vascular type 1 angiotensin receptor (RRVT1AIIR), human muscarinic acetylcholine receptor (HSHM4), human β-1 adrenergic receptor (HUMDRB1), human gastrin receptor (HUMGARE), rat cholecystokinin receptor (RATCCKAR), rat receptor with an unknown ligand (S59748), human somatostatin receptor (HUMSST28A), rat receptor with an unknown ligand (RNGPROCR), mouse somatostatin receptor-1 (MUSSRI1A), human α-A1-adrenergic receptor (HUMAIAADR), mouse delta-opioid receptor (S66181), human somatostatin receptor-3 (HUMSSTR3Y) and the like [FIG. 8].

The nucleotide sequence represented by SEQ ID NO: 12 (FIG. 9: TM1-A2) is a nucleotide sequence highly homologous to the DNA sequence coding for the amino acid sequence within the first membrane-spanning (transmembrane) domain each of known G protein coupled receptors such as mouse-derived bradykinin $B_2$ receptor (MUSBB2R), bovine-derived substance K receptor (BTSKR), bovine-derived endothelin $ET_B$ receptor (BOVEETBR), human-derived neuropeptide Y receptor (MMSUBKREC), human-derived prostaglandin E2 receptor (HUMPGE2R), human-derived prostacyclin receptor (HUMPIR), human-derived κ-opioid receptor (HSU11053), rat-derived melanocortin 3 receptor (RRMC3RA), human-derived melanocortin receptor (HUMMR), mouse-derived bombesin/GRP receptor (MUSGRPBOM), rat-derived cholecystokinin B receptor (RATCHOLREC), rat-derived cholecystokinin A receptor (RATCCKAR) and the like [FIG. 9].

The nucleotide sequence represented by SEQ ID NO: 13 (FIG. 10: TM3-B2) is a nucleotide sequence which is complementary to the nucleotide sequence (FIG. 10) highly homologous to the DNA sequence coding for the amino acid sequence corresponding to or near the end of the third membrane-spanning domain of known G protein coupled receptors such as human-derived cholecystokinin receptor (HUMCCKR), human-derived cholecystokinin B receptor (HUMCCKBGR), mouse-derived melanocortin 5 receptor (MMGMC5R), human-derived vasopressin receptor (HUMV2R), rat-derived neuromedin K receptor (RATNEURA), dog-derived gastrin receptor (DOGGSTRN), rat-derived serotonin receptor (RAT5HT5A), mouse-derived $\alpha_2$-adrenaline receptor (MUSALP2ADA), human-derived adenosine $A_1$ receptor (HUMADORA1X), human-derived opioid (presumed) receptor (HUMOPIODRE:, mouse-derived bombesin/GRP receptor (MUSGRPBOM), rat-derived cholecystokinin A receptor (RATCCKAR), human-derived TRH receptor (HSTRHREC) and the like [FIG. 10].

The nucleotide sequence represented by SEQ ID NO: 14 (FIG. 11: TM3-C2) is a nucleotide sequence highly homologous to the DNA sequence coding for the amino acid sequence corresponding to or near the end of the third membrane-spanning domain of known G protein coupled receptors such as human-derived neurokinin 3 receptor (HUMNK3R), human-derived oxytocin receptor (HSMRNAOXY), guinea pig-derived cholecystokinin A receptor (S68242), dog-derived cholecystokinin A receptor with an unknown ligand (CFCPCR4), mouse-derived substance P receptor (MMSUBPREC), human-derived receptor with an unknown ligand (HUMOPIODRE), human-derived galanin receptor (HUMGALAREC), human-derived serotonin receptor (HSS31G), human-derived 3-adrenaline receptor (HUMARB3A), human-derived prostacyclin receptor (HUMHPR), rat-derived cholecystokinin A receptor (RATCCKAR) and the like [FIG. 11].

The nucleotide sequence represented by SEQ ID NO: 15 (FIG. 12: TM6-E2) is a nucleotide sequence which is complementary to the nucleotide sequence (FIG. 12) highly homologous to the DNA sequence coding for the amino acid sequence within the sixth membrane-spanning domain of known G protein coupled receptors such as human-derived neurokinin A receptor (HUMNEKAR), human-derived substance P receptor (HUMSUBPRA), rat-derived substance K receptor (RATSKR), mouse-derived bombesin/GRP receptor (MUSGRPBOM), human-derived opioid (presumed) receptor (HUMOPIODRE), human-derived adenosine A2 receptor (HUMA2XXX), human-derived 2-adrenaline receptor (HUMADRBR), canine-derived receptor RDC5 with an unknown ligand (CFGPCR8), human-derived endothelin receptor (HUMETSR), mouse-derived neuropeptide Y1 receptor (MMNPY1CDS), human-derived oxytocin receptor (HSMRNAOXY), rat-derived cholecystokinin A receptor (RATCCKAR) and the like [FIG. 12].

The nucleotide sequence represented by SEQ ID NO: 16 (FIG. 13: TM2F18) is a nucleotide sequence highly homologous to the DNA sequence coding for the amino acid sequence corresponding to or near the second membrane-spanning domain of known G protein coupled receptors such as human-derived TSH receptor (HUMTSHX), human-derived neurokinin A receptor (HUMNEKAR), human-derived FMLP receptor (HUMFMLP), human-derived IL8 receptor B (HUMINTLEU8), human-derived $\alpha$-A1 adrenergic receptor (HUMA1AADR), human-derived IL8 receptor A (HUMIL8RA), human-derived dopamine D2 receptor (HSDD2), human-derived angiotensin type I receptor (HUMANTIR), human-derived somatostatin receptor (HUSOMAT), human-derived TRH receptor (HSTRHREC), human-derived delta-opioid receptor (HSUO7882) and the like [FIG. 13].

The nucleotide sequence represented by SEQ ID NO: 17 (FIG. 14: TM6R21) is a nucleotide sequence which is complementary to the nucleotide sequence (FIG. 14) highly homologous to the DNA sequence coding for the amino acid sequence corresponding to or near the sixth membrane-spanning domain of known G protein coupled receptors such as human-derived β-adrenergic receptor (HSBAR), human-derived neurokinin A receptor (HUMNEKAR), human-derived endothelin-1 receptor (HUMETN1R), human-derived histamine $H_2$ receptor (HUMHISH2R), human-derived $\alpha$-A1 adrenergic receptor (HUMA1AADR), human-derived IL8 receptor A (HUMIL8RA), human-derived neuromedin B receptor (HUMNMBR), human-derived neurokinin 1 receptor (HUMNKIRX), human-derived substance P receptor (HUMSUBPRA), human-derived 5-HT1D serotonin receptor (HUM5HT1DA), human-derived formylpeptide receptor (HUMPFPR2A), human-derived dopamine D2 receptor (HSDD2), human-derived neuropeptide Y receptor (HUMNEUYREC), human-derived adenosine A2 receptor (HUMA2XXX), human-derived bradykinin receptor BK-2 (HUMBK2A), human-derived FMLP-related receptor II (HUMFMLPX), human-derived somatostatin receptor subtype 3 (HUMSSTR3X), human-derived cholecystokinin receptor (HUMCCKR), human-derived neurotensin receptor (HSNEURA) and the like [FIG. 14].

The nucleotide sequence represented by SEQ ID NO: 18 (FIG. 15: S3A) is a nucleotide sequence highly homologous to the DNA sequence coding for the amino acid sequence corresponding to or near the third membrane-spanning domain of known G protein coupled receptors such as human-derived galanin receptor (HUMGALAREC), human-derived CCK-B receptor (S70057), human-derived $ET_A$ receptor (S67127), human-derived $ET_B$ receptor (S44866), human-derived C5A receptor (HUMC5AAR), human-derived angiotensin II receptor (HUMANTIR), human-derived bradykinin receptor (HUMBK2R), human-derived neurotensin receptor (HSNEURA), human-derived GRP receptor (HUMGRPR), human-derived somatostatin 5 receptor (HUMFSRS), human-derived IL-8 receptor (HUMIL8RA), human-derived neurokinin 2 (neurokinin A) receptor (HUMNEKAR) and the like [FIG. 15].

The nucleotide sequence represented by SEQ [D NO: 19 (FIG. 16: S6A) is a nucleotide sequence which is complementary to the nucleotide sequence (FIG. 16) highly homologous to the DNA sequence coding for the amino acid sequence corresponding to or near the sixth membrane-spanning domain of known G protein coupled receptors such as human-derived galanin receptor (HUMGLAREC), human-derived CCK-B receptor (S70057), human-derived $ET_A$ receptor (S67127), human-derived $ET_B$ receptor (S44866), human-derived C5A receptor (HUMC5AAR), human-derived angiotensin II receptor (HUMANTIR), human-derived bradykinin receptor (HUMBK2R), human-derived neurotensin receptor (HSNEURA), human-derived GRP receptor (HUMGRPR), human-derived somatostatin 5 receptor (HUMFSRS), human-derived IL-8 receptor (HUMIL8RA), human-derived neurokinin 2 (neurokinin A) receptor (HUMNEKAR) and the like [FIG. 16].

The above-mentioned abbreviations in the parentheses are the identifiers (or reference numbers) which are shown when GenBank/EMBL Data Bank is searched using a DNASIS Gene/Protein Sequence Data Base (CD019; Hitachi Software Engineering, Japan) and are usually called "Accession Numbers" or "Entry Names". HTRHR is, however, the sequence as described in Japanese Patent Application No. Hei 5-286986 (or No. 286986/1993) (EPA 638645).

The DNA (or nucleotides) of the present invention may be manufactured by DNA synthetic methods which are known per se or by methods similar thereto. The DNA (or nucleotides) of the present invention may be an oligonucleotide sequence having 8 to 60 base residues, preferably 12 to 50 base residues, more preferably 15 to 40 residues and most preferably 18 to 30 residues.

Among the DNAs of the present invention, the DNA having the nucleotide sequence represented by SEQ ID NO: 1 or SEQ ID NO: 12 is a nucleotide sequence which is commonly present in the nucleotide sequence of the DNA encoding the amino acid sequence corresponding to or near the first membrane-spanning domain of the above-mentioned known G protein coupled receptor protein. Therefore, it can be complementarily bonded (i.e. is hybridizable) with RNA or DNA (including genome DNA, cDNA) coding for the amino acid sequence corresponding to or near the first membrane-spanning domain of known or unknown G protein coupled receptor proteins and, furthermore, it can be complementarily bonded (i.e. is, hybridizable) with nucleotide sequences encoding other membrane-spanning domains as well.

The DNA having a nucleotide sequence represented by SEQ ID NO: 3, SEQ ID NO: 5, SEQ ID NO: 6, SEQ ID NO: 7, SEQ ID NO: 14 or SEQ ID NO: 18 is a nucleotide sequence which is commonly present in the nucleotide sequence of the DNA coding for the amino acid sequence corresponding to or near the third membrane-spanning domain of the above-mentioned known G protein coupled receptor protein. Therefore, it can be complimentarily bonded with RNA or DNA (including genome DNA, cDNA) coding for the part corresponding to or near the third membrane-spanning domain of known or unknown G protein coupled receptor proteins and, furthermore, it can be complementarily bonded with nucleotide sequences encoding other membrane-spanning domains as well.

The DNA having a nucleotide sequence represented by SEQ ID NO: 10 or SEQ ID NO: 16 is a nucleotide sequence which is commonly present in the nucleotide sequence of the DNA coding for the amino acid sequence corresponding to or near the second membrane-spanning domain of the above-mentioned known G protein coupled receptor protein. Therefore, it can be complementarily bonded with RNA or DNA (including genome DNA, cDNA) coding for the part corresponding to or near the second membrane-spanning domain of known or unknown G protein coupled receptor proteins and, furthermore, it can be complementarily bonded with nucleotide sequences encoding other membrane-spanning domains as well.

The DNA having a nucleotide sequence represented by SEQ ID NO: 2, SEQ ID NO: 4, SEQ ID NO: 8, SEQ ID NO: 9, SEQ ID NO: 15, SEQ ID NO: 17 or SEQ ID NO: 19 is a nucleotide sequence which is commonly present in the nucleotide sequence of the DNA coding for the amino acid sequence corresponding to or near the sixth membrane-spanning domain of the above-mentioned known G protein coupled receptor protein. Therefore, it can be complementarily bonded with RNA or DNA (including genome DNA, cDNA) coding for the part corresponding to or near the sixth membrane-spanning domain of known or unknown G protein coupled receptor proteins and, furthermore, it can be complementarily bonded with nucleotide sequences encoding other membrane-spanning domains as well.

The DNA having a nucleotide sequence represented by SEQ ID NO: 11 is a nucleotide sequence which is commonly present in the nucleotide sequence of the DNA coding for the amino acid sequence corresponding to or near the seventh membrane-spanning domain of the above-mentioned known G protein coupled receptor protein. Therefore, it can be complementarily bonded with RNA or DNA (including genome DNA, cDNA) coding for the part corresponding to or near the seventh membrane-spanning domain of known or unknown G protein coupled receptor proteins and, furthermore, it can be complementarily bonded with nucleotide sequences encoding other transmembrane domains as well.

The DNA having a nucleotide sequence represented by SEQ ID NO: 13 is a nucleotide sequence which is commonly present in the nucleotide sequence of the DNA coding for the amino acid sequence corresponding to or near the third membrane-spanning domain of the above-mentioned known G protein coupled receptor protein. Therefore, it can be complementarily bonded with RNA or DNA (including genome DNA, cDNA) coding for the part corresponding to or near the third membrane-spanning domain of known or unknown G protein coupled receptor proteins and, furthermore, it can be complementarily bonded with nucleotide sequences encoding other membrane-spanning domains as well.

Accordingly, the DNAs (or nucleotides) of tile present invention can be used as DNA primers for a polymerase chain reaction (hereinafter, sometimes referred to as PCR). For example:

(i) a polymerase chain reaction is carried out by mixing
  (1) a small amount of DNA (or DNA fragment(s)) which codes for G protein coupled receptor protein, said DNA (or DNA fragment(s)) acting as a template,
  (2) at least one DNA primer selected from the group consisting of DNA primers having a nucleotide sequence represented by SEQ ID NO: 1, DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 10, DNA primers having a nucleotide sequence represented by SEQ ID NO: 12, DNA primers having a nucleotide sequence represented by SEQ ID NO: 14, DNA primers having a nucleotide sequence represented by SEQ ID NO: 16 and DNA primers having a nucleotide sequence represented by SEQ ID NO: 18 and
  (3) at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 11, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19; or (ii) a polymerase chain reaction is carried out by mixing
  (1) a small amount of DNA (or DNA fragment(s)) coding for G protein coupled receptor protein, said DNA (or DNA fragment(s)) acting as a template,
  (2) at least one DNA primer selected from the group consisting of DNA primers having a nucleotide sequence represented by SEQ ID NO: 1 and DNA primers having a nucleotide sequence represented by SEQ ID NO: 12 and
  (3) at least one DNA primer selected from the group consisting of DNA primers having a nucleotide sequence represented by SEQ ID NO: 13 so that it is possible to amplify the target DNA (or DNA fragment(s)) coding for said receptor protein.

When the PCR is carried out using at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 11, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19, said DNA primer(s) is (are) bonded (hybridized) with the nucleotide sequence at the 3'-side of the +chain (plus chain) of template RNA or DNA (or fragment(s) thereof) coding for the sixth membrane-spanning domain or other membrane-spanning domains of G protein coupled receptor protein whereupon an elongation of the −chain (minus chain) proceeds in the 5'→3' direction.

When the PCR is carried out using at least one DNA primer selected from the group consisting of DNA primers having a nucleotide sequence represented by SEQ ID NO: 11, said DNA primer is bonded with the nucleotide sequence at the 3'-side of the +chain (plus chain) of template RNA or DNA (or fragment(s) thereof) coding for the seventh membrane-spanning domain or other membrane-spanning domains of the G protein coupled receptor protein whereupon an elongation of the −chain (minus chain) proceeds in the 5'→3' direction.

When the PCR is carried out using at least one DNA primer selected from the group consisting of DNA primers having a nucleotide sequence represented by SEQ ID NO: 1 and DNA primers having a nucleotide sequence represented by SEQ ID NO: 12, said DNA primer is bonded with the nucleotide sequence at the 3'-side of the −chain (minus chain) of template RNA or DNA (or fragment(s) thereof) coding for the first membrane-spanning domain or other membrane-spanning domains of G protein coupled receptor protein whereupon an elongation of the +chain (plus chain) proceeds in the 5'→3' direction.

When the PCR is carried out using at least one DNA primer selected from the group consisting of DNA primers having a nucleotide sequence represented by SEQ ID NO: 10 and DNA primers having a nucleotide sequence represented by SEQ ID NO: 16, said DNA primer is bonded with the nucleotide sequence at the 3'-side of the −chain (minus chain) of template RNA or DNA (or fragment(s) thereof) coding for the second membrane-spanning domain or other membrane-spanning domains of G protein coupled receptor protein whereupon an elongation of the +chain (plus chain) proceeds in the 5'→3' direction.

When the PCR is carried out using at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18, said DNA primer is bonded with the nucleotide sequence at the 3'-side of the −chain (minus chain) of template RNA or DNA (or fragment(s) thereof) coding for the third membrane-spanning domain or other membrane-spanning domains of G protein coupled receptor protein whereupon an elongation of the +chain (plus chain) proceeds in the 5'→3' direction.

Accordingly, when the DNA primers having nucleotide sequences represented by any of SEQ ID NO: 1 to SEQ ID NO: 19 of the present invention are used in combination each other, DNA (or DNA fragment(s)) coding for G protein coupled receptor protein can be successfully amplified.

One embodiment of the present invention provides:
(A) a method of amplifying DNA coding for the G protein coupled receptor protein (e.g., from the first to sixth membrane-spanning (transmembrane) domains or other segments of the G protein coupled receptor protein), characterized in that a polymerase chain reaction is carried out by mixing
① a DNA coding for the G protein coupled receptor protein, said DNA acting as a template,
② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19;

(B) a method of amplifying DNA coding for the G protein coupled receptor protein (e.g., from the first to seventh membrane-spanning (transmembrane) domains or other segments of the G protein coupled receptor protein), characterized in that a polymerase chain reaction is carried out by mixing
① a DNA coding for the G protein coupled receptor protein, said DNA acting as a template,
② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 11;

(C) a method of amplifying a DNA coding for the G protein coupled receptor protein (e.g., from the second to sixth membrane-spanning (transmembrane) domains or other segments of the G protein coupled receptor protein), characterized in that a polymerase chain reaction is carried out by mixing
① a DNA coding for the G protein coupled receptor protein, said DNA acting as a template,
② at least one DNA primer selected from the group consisting of DNA primers having a nucleotide sequence represented by SEQ ID NO: 10 and DNA primers having a nucleotide sequence represented by SEQ ID NO: 16 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19;

(D) a method of amplifying a DNA coding for the G protein coupled receptor protein (e.g., from the second to seventh membrane-spanning (transmembrane) domains or other segments of the G protein coupled receptor protein), characterized in that a polymerase chain reaction is carried out by mixing ① a DNA coding for the G protein coupled receptor protein, said DNA acting as a template, ② at least one DNA primer selected from the group consisting of DNA primers having a nucleotide sequence represented by SEQ ID NO: 10 and DNA primers having a nucleotide sequence represented by SEQ ID NO: 16 and ③ at least one DNA primer selected from the group consisting of DNA primers having a nucleotide sequence represented by SEQ ID NO: 11;

(E) a method of amplifying a DNA coding for the G protein coupled receptor protein (e.g., from the third to sixth membrane-spanning (transmembrane) domains or other segments of the G protein coupled receptor protein), characterized in that a polymerase chain reaction is carried out by mixing ① a DNA coding for the G protein coupled receptor protein, said DNA acting as a template, ② at least one DNA primer selected from the group consisting of DNA primers having a nucleotide sequence represented by SEQ ID NO: 3, DNA primers having a nucleotide sequence represented by SEE ID NO: 5, DNA primers having a nucleotide sequence represented by SEQ ID NO: 6, DNA primers having a nucleotide sequence represented by SEQ ID NO): 7, DNA primers having a nucleotide sequence represented by SEQ ID NO: 14 and DNA primers having a nucleotide sequence represented by SEQ ID NO: 18 and ③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19;

(F) a method of amplifying a DNA coding for the G protein coupled receptor protein (e.g., from the third to seventh membrane-spanning (transmembrane) domains or other segments of the G protein coupled receptor protein), characterized in that a polymerase chain reaction is carried out by mixing ① a DNA coding for the G protein coupled receptor protein, said DNA acting as a template, ② at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and ③ at least one DNA primer selected from the group consisting of DNA primers having a nucleotide sequence represented by SEQ ID NO: 11; and (G) a method of amplifying a DNA coding for the G protein coupled receptor protein (e.g., from the first to third membrane-spanning (transmembrane) domains or other segments of the G protein coupled receptor protein), characterized in that a polymerase chain reaction is carried out by mixing ① a DNA coding for the G protein coupled receptor protein, said DNA acting as a template, ② at least one DNA primer selected from the group consisting of DNA primers having a nucleotide sequence represented by SEQ ID NO: 1 and DNA primers having a nucleotide sequence represented by SEQ ID NO: 12 and ③ at least one DNA primer selected from the group consisting of DNA primers having a nucleotide sequence represented by SEQ ID NO: 13.

An example of more preferred combination of the DNA primers in the amplification according to the above-mentioned (A) includes a combination of a DNA primer having a nucleotide sequence represented by SEQ ID NO: 1 with a DNA primer having a nucleotide sequence represented by SEQ ID NO: 2 and the like.

An example of more preferred combination of the DNA primers in the amplification according to the above-mentioned (D) includes a combination of a DNA primer having a nucleotide sequence represented by SEQ ID NO: 10 with a DNA primer having a nucleotide sequence represented by SEQ ID NO: 11 and the like.

An example of more preferred combination of the DNA primers in the amplification according to the above-mentioned (E) includes:

(i) a combination of a DNA primer having a nucleotide sequence represented by SEQ ID NO: 5 or a DNA primer having a nucleotide sequence represented by SEQ ID NO: 6 with a DNA primer having a nucleotide sequence represented by SEQ ID NO: 8 or a DNA primer having a nucleotide sequence represented by SEQ ID NO: 9;

(ii) a combination of a DNA primer having a nucleotide sequence represented by SEQ ID NO: 3 or a DNA primer having a nucleotide sequence represented by SEQ ID NO: 7 with a DNA primer having a nucleotide sequence represented by SEQ ID NO: 4 and the like.

An example of more preferred combination of the DNA primers in the amplification according to the above-mentioned (G) includes a combination of a DNA primer having a nucleotide sequence represented by SEQ ID NO: 12 with a DNA primer having a nucleotide sequence represented by SEQ ID NO: 13 and the like.

The amplification may be carried out in accordance with known PCR techniques. For example, it may be carried out by the method described in Saiki, R. K. et al., Science, 239:487–491 (1988). Temperature, time, buffer, number of reaction cycles, enzyme such as DNA polymerase, addition of 2'-deoxy-7-deazaguanosine triphosphate or inosine, etc. in the PCR amplification may be suitably selected depending upon the type of target DNA and other factors. When RNA is used as a template, PCR amplification may be carried out, for example, by the method described in Saiki, R. K. et al., Science, 239:487–491(1988).

Moreover, the DNA having a nucleotide sequence represented by SEQ ID NO: 1 or SEQ ID NO: 12 of the present invention can be selectively and complementarily bonded (hybridized) with the nucleotide sequence at the 3'-side of the –chain of the DNA coding for the amino acid sequence corresponding to or near the first membrane-spanning domain of the G protein coupled receptor protein; the DNA having a nucleotide sequence represented by SEQ ID NO: 10 or SEQ ID NO: 16 of the present invention can be selectively and complementarily bonded (hybridized) with the nucleotide sequence at the 3'-side of the –chain of the DNA coding for the amino acid sequence corresponding to or near the second membrane-spanning domain of the G protein coupled receptor protein; the DNA having a nucleotide sequence represented by SEQ ID NO: 3, SEQ ID NO: 5, SEQ ID NO: 6, SEQ ID NO: 7, SEQ ID NO: 14 or SEQ ID NO: 18 of the present invention can be selectively and complementarily bonded (hybridized) with the nucleotide sequence at the 3'-side of the −chain of the DNA coding for the amino acid sequence corresponding to or near the third membrane-spanning domain of the G protein coupled receptor protein; the DNA having a nucleotide sequence represented by SEQ ID NO: 2, SEQ ID NO: 4, SEQ ID NO: 8, SEQ ID NO: 9, SEQ ID NO: 15, SEQ ID NO: 17 or SEQ ID NO: 19 of the present invention can be selectively and complementarily bonded (hybridized) with the nucleotide sequence at the 3'-side of the +chain of the DNA coding for the amino acid sequence corresponding to or near the sixth membrane-spanning domain of the G protein coupled receptor protein; the DNA having a nucleotide sequence represented by SEQ ID NO: 11 of the present invention can be selectively and complementarily bonded (hybridized) with the nucleotide sequence at the 3'-side of the +chain of the DNA coding for the amino acid sequence corresponding to or near the third membrane-spanning domain of the G protein coupled receptor protein; and the DNA having a nucleotide sequence represented by SEQ ID NO: 13 of the present invention can be selectively and complementarily bonded (hybridized) with the nucleotide sequence at the 3'-side of the +chain of the DNA coding for the amino, acid sequence corresponding to or near the third membrane-spanning domain of the G protein coupled receptor protein and, accordingly, said DNA is also advantageously useful as a probe for screening DNA libraries for DNA (or DNA fragment(s)) encoding part or all of the polypeptide sequence of G protein coupled receptor proteins.

These screening methods for DNA (or DNA fragment(s)) encoding part or all of the polypeptide sequence of G protein coupled receptor proteins from the DNA library by using as a reagent, because it can be used as a probe the DNA of the present invention may be carried out according to DNA cloning methods known per se by those of skill in the art or methods similar thereto. Especially when the DNA of the present invention is used as a DNA primer for the PCR, both amplification and screening of the DNA (or DNA fragment) coding for the G protein coupled receptor protein can be conducted in a single step.

Thus, when the DNAs of the present invention are suitably combined and used as the DNA primer for the PCR, said DNA primer(s) is(are) bonded (hybridized) with RNA or DNA (or fragment(s) thereof) encoding the amino acid sequence of the first membrane-spanning (transmembrane) domain, the second membrane-spanning domain, the third membrane-spanning domain, the sixth membrane-spanning domain, the seventh membrane-spanning domain or other membrane-spanning domains of G protein coupled receptor proteins to amplify, for example, ① RNA or DNA (or fragment(s) thereof) coding for the amino acid sequence of from the first membrane-spanning to the sixth membrane-spanning domains of G protein coupled receptor proteins, ② RNA or DNA (or fragment(s) thereof) coding for the amino acid sequence of from the first membrane-spanning to the seventh membrane-spanning domains of G protein coupled receptor proteins, ③ RNA or DNA (or fragment(s) thereof) coding for the amino acid sequence of from the third membrane-spanning to the sixth membrane-spanning domains of G protein coupled receptor proteins, ④ RNA or DNA (or fragment(s) thereof) coding for the amino acid sequence of from the third membrane-spanning to the seventh membrane-spanning domains of G protein coupled receptor proteins, ⑤ RNA or DNA (or fragment(s) thereof) coding for the amino acid sequence of from the second membrane-spanning to the sixth membrane-spanning domains of G protein coupled receptor proteins or RNA or DNA (or fragment(s) thereof) coding for the amino acid sequence of other domains thereof, ⑥ RNA or DNA (or fragment(s) thereof) coding for the amino acid sequence of from the second membrane-spanning to the seventh membrane-spanning domains of G protein coupled receptor proteins, ⑦ RNA or DNA (or fragment(s) thereof) coding for the amino acid sequence of from the first membrane-spanning to the third membrane-spanning domains of G protein coupled receptor proteins or ⑧ RNA or DNA (or fragment(s) thereof) coding for the amino acid sequence of other domains of G protein coupled receptor proteins.

Through using the DNA primer according to the present invention, therefore, selective amplifications of:

① RNA or DNA (or fragment(s) thereof) coding for the amino acid sequence covering from the first membrane-spanning domain to the sixth membrane-spanning domain of G protein coupled receptor proteins;

② RNA or DNA (or fragment(s) thereof) coding for the amino acid sequence covering from the first membrane-spanning domain to the seventh membrane-spanning domain of G protein coupled receptor proteins;

③ RNA or DNA (or fragment(s) thereof) coding for the amino acid sequence covering from the third membrane-spanning domain to the sixth membrane-spanning domain of G protein coupled receptor proteins;

④ RNA or DNA (or fragments) thereof) coding for the amino acid sequence covering from the third membrane-spanning domain to the seventh membrane-spanning domain of G protein coupled receptor proteins;

⑤ RNA or DNA (or fragment(s) thereof) coding for the amino acid sequence covering from the second membrane-spanning domain to the sixth membrane-spanning domain of G protein coupled receptor proteins or RNA or DNA (or fragment(s) thereof) coding for the amino acid sequence covering other areas thereof, ⑥ RNA or DNA (or fragment(s) thereof) coding for the amino acid sequence covering from the second membrane-spanning domain to the seventh membrane-spanning domain of G protein coupled receptor proteins;

⑦ RNA or DNA (or fragment(s) thereof) coding for the amino acid sequence covering from the first membrane-spanning domain to the third membrane-spanning domain of G protein coupled receptor proteins; and the like, from DNA libraries can be successfully achieved.

Among the DNA primers of the present invention, the combination of

① a DNA primer having a nucleotide sequence represented by SEQ ID NO: 1 or SEQ ID NO: 2; with ② at least one DNA primer selected from the group consisting of a DNA primer having a nucleotide sequence represented by SEQ ID NO: 2, a DNA primer having a nucleotide sequence represented by SEQ ID NO: 4, a DNA primer having a nucleotide sequence represented by SEQ ID NO: 8, a DNA primer having a nucleotide sequence represented by SEQ ID NO: 9, a DNA primer having a nucleotide sequence represented by SEQ ID NO: 15, a DNA primer having a nucleotide sequence represented by SEQ ID NO: 17 and a DNA primer having a nucleotide sequence represented by SEQ ID NO: 19;

is, unlike conventional primers, capable of selectively amplifying a broad area covering from the first membrane-spanning domain to the sixth membrane-spanning domain or other domains of G protein coupled receptor proteins.

Among the DNA primers of the present invention, the combination of
① a DNA primer having a nucleotide sequence represented by SEQ ID NO: 1 or SEQ ID NO: 12; with
② a DNA primer having a nucleotide sequence represented by SEQ ID NO: 11;
is, unlike conventional primers, capable of selectively amplifying a broad area covering from the first membrane-spanning domain to the seventh membrane-spanning domain or other domains of G protein coupled receptor proteins.

Among the DNA primers of the present invention, the combination of
① a DNA primer having a nucleotide sequence represented by SEQ ID NO: 10 or SEQ ID NO: 16; with
② at least one DNA primer selected from the group consisting of a DNA primer having a nucleotide sequence represented by SEQ ID NO: 2, a DNA primer having a nucleotide sequence represented by SEQ ID NO: 4, a DNA primer having a nucleotide sequence represented by SEQ ID NO: 8, a DNA primer having a nucleotide sequence represented by SEQ ID NO: 9, a DNA primer having a nucleotide sequence represented by SEQ ID NO: 15, a DNA primer having a nucleotide sequence represented by SEQ ID NO: 17 and a DNA primer having a nucleotide sequence represented by SEQ ID NO: 19;
is, unlike conventional primers, capable of selectively amplifying a broad area covering from the second membrane-spanning domain to the sixth membrane-spanning domain or other domains of G protein coupled receptor proteins.

Among the DNA primers of the present invention, the combination of
① a DNA primer having a nucleotide sequence represented by SEQ ID NO: 10 or SEQ ID NO: 16; with
② a DNA primer having a nucleotide sequence represented by SEQ ID NO: 11;
is, unlike conventional primers, capable of selectively amplifying a broad area covering from the second membrane-spanning domain to the seventh membrane-spanning domain or other domains of G protein coupled receptor proteins.

Among the DNA primers of the present invention, the combination of
① at least one DNA primer selected from the group consisting of a DNA primer having a nucleotide sequence represented by SEQ ID NO: 3, a DNA primer having a nucleotide sequence represented by SEQ ID NO: 5, a DNA primer having a nucleotide sequence represented by SEQ ID NO: 6, a DNA primer having a nucleotide sequence represented by SEQ ID NO: 7, a DNA primer having a nucleotide sequence represented by SEQ ID NO: 14 and a DNA primer having a nucleotide sequence represented by SEQ ID NO: 18; with
② a DNA primer having a nucleotide sequence represented by SEQ ID NO: 11;
is, unlike conventional primers, capable of selectively amplifying a broad area covering from the third membrane-spanning domain to the seventh membrane-spanning domain or other domains of G protein coupled receptor proteins.

Therefore, the protein hydrophobicity plotting of G protein coupled receptor proteins and the homology at the amino acid level or the nucleic acid level between G protein coupled receptor proteins and other similar receptor proteins; [said hydrophobicity plotting and homology both serve as standards for determining whether or not RNA or DNA (or fragment(s) thereof) obtained according to the present invention is (are) encoding part or all of the amino acid sequence of G protein coupled receptor protein] can now be more clearly calculated.

Among the DNA primers of the present invention, the combination of
① at least one DNA primer selected from the group consisting of a DNA primer having a nucleotide sequence represented by SEQ ID NO: 3, a DNA primer having a nucleotide sequence represented by SEQ ID NO: 5, a DNA primer having a nucleotide sequence represented by SEQ ID NO: 6, a DNA primer having a nucleotide sequence represented by SEQ ID NO: 7, a DNA primer having a nucleotide sequence represented by SEQ ID NO: 14 and a DNA primer having a nucleotide sequence represented by SEQ ID NO: 18; with
② at least one DNA primer selected from the group consisting of a DNA primer having a nucleotide sequence represented by SEQ ID NO: 2, a DNA primer having a nucleotide sequence represented by SEQ ID NO: 4, a DNA primer having a nucleotide sequence represented by SEQ ID NO: 8, a DNA primer having a nucleotide sequence represented by SEQ ID NO: 9, a DNA primer having a nucleotide sequence represented by SEQ ID NO: 15, a DNA primer having a nucleotide sequence represented by SEQ IS NO: 17 and a DNA primer having a nucleotide sequence represented by SEQ ID NO: 19;
is capable of amplifying the areas covering from the third membrane-spanning domain to the sixth membrane-spanning domain thereof at once like the conventional DNA primers and, moreover, it is capable of more selectively and efficiently amplifying DNA coding for G protein coupled receptor proteins though it has not been obtained through the conventional DNA primers.

Moreover, among the DNA primers of the present invention, the combination of
① at least one DNA primer selected from DNA primers; having a nucleotide sequence of SEQ ID NO: 1 and DNA primers; having a nucleotide sequence of SEQ ID NO: 12; with
② a DNA primer having a nucleotide sequence represented by SEQ ID NO: 13;
is capable of amplifying the areas covering from the first membrane-spanning domain to the third membrane-spanning domain thereof at once.

Then (a) the amplified DNA (or fragment(s) thereof) coding for the amino acid sequence of from the first membrane-spanning domain to the sixth membrane-spanning domain of G protein coupled receptor protein, (b) the amplified DNA (or fragment(s) thereof) coding for the amino acid sequence of from the first membrane-spanning domain to the seventh membrane-spanning domain of G protein coupled receptor protein, (c) the amplified DNA (or fragment(s) thereof) coding for the amino acid sequence of from the third membrane-spanning domain to the sixth membrane-spanning domain of G protein coupled receptor protein, (d) the amplified DNA (or fragment(s) thereof) coding for the amino acid sequence of from the third membrane-spanning domain to the seventh membrane-spanning domain of G protein coupled receptor protein, (e) the amplified DNA (or fragment(s) thereof) coding for the amino acid sequence of from the second membrane-spanning domain to the sixth membrane-spanning domain of G protein coupled receptor protein, (f) the amplified DNA (or fragment(s) thereof) coding for the amino acid sequence of from the second membrane-spanning domain to the seventh membrane-spanning domain of G protein coupled receptor protein, (g) the amplified DNA (or fragments) thereof) coding for the amino acid sequence of from the first membrane-spanning domain to the third membrane-spanning domain of G protein coupled receptor protein or (h) the amplified DNA (or fragment(s) thereof) coding for the amino acid sequence of other domains of G protein coupled receptor protein may be used as a probe(s) to screen for full-length DNA which completely encodes G protein coupled receptor proteins from DNA libraries according to methods known per se by those of skill in the art or methods similar thereto.

The DNA libraries used in the present invention include any of genome DNA libraries, cDNA libraries and RNA libraries. The term "DNA library" or "DNA libraries" as used herein refers to a DNA library or DNA libraries including all of those libraries.

The present invention further provides screening methods for target DNA (or fragment(s) thereof) coding for G protein coupled receptor protein from the DNA library containing DNA (or fragment(s) thereof) coding for receptor proteins, which comprise employing the DNA of the present invention as a DNA primer for the PCR.

One preferred embodiment of the present invention is a method for cloning full-length DNA which completely encodes an amino acid sequence of G protein coupled receptor protein from DNA libraries which comprises the steps of (i) using the DNA of the present invention as a DNA primer for PCR;

(ii) carrying out PCR in the presence of a mixture of said DNA primer with the DNA library to amplify and select. (i.e. screen for) a DNA fragment coding for the amino acid sequence of from the first membrane-spanning domain to the sixth membrane-spanning domain of G protein coupled receptor protein, a DNA fragment coding for the amino acid sequence of from the first membrane-spanning domain to the seventh membrane-spanning domain of G protein coupled receptor protein, a DNA fragment coding for the amino acid sequence of from the third membrane-spanning domain to the sixth membrane-spanning domain of G protein coupled receptor protein, a DNA fragment coding for the amino acid sequence of from the third membrane-spanning domain to the seventh membrane-spanning domain of G protein coupled receptor protein, a DNA fragment coding for the amino acid sequence of from the second membrane-spanning domain to the sixth membrane-spanning domain of G protein coupled receptor protein, a DNA fragment coding for the amino acid sequence of from the second membrane-spanning domain to the seventh membrane-spanning domain of G protein coupled receptor protein, a DNA fragment coding for the amino acid sequence of from the first membrane-spanning domain to the third membrane-spanning domain of G protein coupled receptor protein or a DNA fragment coding for other domains of G protein coupled receptor protein; and (iii) cloning said full-length DNA from the DNA library according to cloning methods known per se by those of skill in the art or methods similar thereto by using, as a probe, the DNA fragment obtained in the above step (ii).

Preferably, an embodiment of the present intention is a screening method of DNA coding for G protein coupled receptor proteins from DNA libraries, which comprises carrying out a polymerase chain reaction in the presence of a mixture of ① the DNA library,
② at least one DNA primer selected from the group consisting of DNA primers having a nucleotide sequence represented by SEQ ID NO: 1, DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 10, DNA primers having a nucleotide sequence represented by SEQ ID NO: 14, DNA primers having a nucleotide sequence represented by SEQ ID NO: 16 and DNA primers having a nucleotide sequence represented by SEQ ID NO: 18 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 11, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19 to selectively amplify template DNA coding for G protein coupled receptor protein contained in the DNA library.

More preferably, embodiments of the present invention include:

(1) a screening method of DNA coding for the amino acid sequence of G protein coupled receptor protein and the like (e.g. the regions spanning from the first transmembrane domain to the sixth transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19 to selectively amplify the DNA coding for the amino acid sequence of G protein coupled receptor protein and the like (e.g. the regions spanning from the first transmembrane domain to the sixth transmembrane domain of G protein coupled receptor protein or other domains thereof) contained in the DNA library;

(2) a screening method of DNA coding for the amino acid sequence of G protein coupled receptor protein and the like (e.g. the regions spanning from the first transmembrane domain to the seventh transmembrane domain of G protein coupled receptor protein or other domains thereof) from a DNA library, which comprises carrying out a polymerase chain reaction in the presence of a mixture of ① the DNA library,
② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 11 to selectively amplify the DNA coding for the amino acid sequence of G protein coupled receptor protein and the like (e.g. the regions spanning from the first transmembrane domain to the seventh transmembrane domain of G protein coupled receptor protein or other domains thereof) contained in the DNA library;

(3) a screening method of DNA coding for the amino acid sequence of G protein coupled receptor protein and the like (e.g. the regions spanning from the second transmembrane domain to the sixth transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 10 and DNA primers having a nucleotide sequence represented by SEQ ID NO: 16 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19
to selectively amplify the DNA coding for the amino acid sequence of G protein coupled receptor protein and the like (e.g. the regions spanning from the second transmembrane domain to the sixth transmembrane domain of G protein coupled receptor protein or other domains thereof) contained in the DNA library;

(4) a screening method of DNA coding for the amino acid sequence of G protein coupled receptor protein and the like (e.g. the regions spanning from the second transmembrane domain to the seventh transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 10 and DNA primers having a nucleotide sequence represented by SEQ ID NO: 16 and
③ at least one DNA primer selected from the group consisting of DNA primers having a nucleotide sequence represented by SEQ ID NO: 11
to selectively amplify the DNA coding for the amino acid sequence of G protein coupled receptor protein and the like (e.g. the regions spanning from the second transmembrane domain to the seventh transmembrane domain of G protein coupled receptor protein or other domains thereof) contained in the DNA library;

(5) a screening method of DNA coding for the amino acid sequence of G protein coupled receptor protein and the like (e.g. the regions spanning from the third transmembrane domain to the sixth transmembrane domain of G protein coupled receptor protein or other domains thereof) from a DNA, library, which comprises carrying out a polymerase chain reaction in the presence of a mixture of
① the DNA library,
② at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and
③ at least one DNA primer selected from the group consisting of DNA primers having a nucleotide sequence represented by SEQ ID NO: 2, DNA primers having a nucleotide sequence represented by SEQ ID NO: 4, DNA primers having a nucleotide sequence represented by SEQ ID NO: 8, DNA primers having a nucleotide sequence represented by SEQ ID NO: 9, DNA primers having a nucleotide sequence represented by SEQ ID NO: 15, DNA primers having a nucleotide sequence represented by SEQ ID NO: 17 and DNA primers having a nucleotide sequence represented by SEQ ID NO: 19
to selectively amplify the DNA coding for the amino acid sequence of G protein coupled receptor protein and the like (e.g. the regions spanning from the third transmembrane domain to the sixth transmembrane domain of G protein coupled receptor protein or other domains thereof) contained in the DNA library;

(6) a screening method of DNA coding for the amino acid sequence of G protein coupled receptor protein and the like (e.g. the regions spanning from the third transmembrane domain to the seventh transmembrane domain of G protein coupled receptor protein or other domains thereof) from a DNA library, which comprises carrying out a polymerase chain reaction in the presence of a mixture of
① the DNA library,
② at least one DNA primer selected from the group consisting of DNA primers having a nucleotide sequence represented by SEQ ID NO: 3, DNA primers having a nucleotide sequence represented by SEQ ID NO: 5, DNA primers having a nucleotide sequence represented by SEQ ID NO: 6, DNA primers having a nucleotide sequence represented by SEQ ID NO: 7, DNA primers having a nucleotide sequence represented by SEQ ID NO: 14 and DNA primers having a nucleotide sequence represented by SEQ ID NO: 18 and
③ at least one DNA primer selected from the group consisting of DNA primers having a nucleotide sequence represented by SEQ ID NO: 11
to selectively amplify the DNA coding for the amino acid sequence of G protein coupled receptor protein and the like (e.g. the regions spanning from the third transmembrane domain to the seventh transmembrane domain of G protein coupled receptor protein or other domains thereof) contained in the DNA library; and (7) a screening method of DNA coding for the amino acid sequence of G protein coupled receptor protein and the like (e.g. the regions spanning from the first transmembrane domain to the third transmembrane domain of G protein coupled receptor protein or other domains thereof) from a DNA library, which comprises carrying out a polymerase chain reaction in the presence of a mixture of
① the DNA library, ② at least one DNA primer selected from the group consisting of DNA primers having a nucleotide sequence represented by SEQ ID NO: 1 and DNA primers having a nucleotide sequence represented by SEQ ID NO: 12 and
③ at least one DNA primer selected from the group consisting of DNA primers having a nucleotide sequence represented by SEQ ID NO: 13 to selectively amplify the DNA coding for the amino acid sequence of G protein coupled receptor protein and the like (e.g. the regions spanning from the first transmembrane domain to the third transmembrane domain of G protein coupled receptor protein or other domains thereof) contained in the DNA library.

Particularly preferably, embodiments of the present invention include:

(8) a screening method of DNA coding for the amino acid sequence of G protein coupled receptor protein from a DNA library, which comprises carrying out a polymerase chain reaction in the presence of a mixture of
① the DNA library,
② a DNA primer having a nucleotide sequence represented by SEQ ID NO: 1 and
③ a DNA primer having a nucleotide sequence represented by SEQ ID NO: 2
to selectively amplify the DNA coding for the amino acid sequence of G protein coupled receptor protein contained in the DNA library;

(9) a screening method of DNA coding for the amino acid sequence of G protein coupled receptor protein from a DNA library, which comprises carrying out a polymerase chain reaction in the presence of a mixture of
① the DNA library,
② a DNA primer having a nucleotide sequence represented by SEQ ID NO: 3 and
③ a DNA primer having a nucleotide sequence represented by SEQ ID NO: 4
to selectively amplify the DNA coding for the amino acid sequence of G protein coupled receptor protein contained in the DNA library;

(10) a screening method of DNA coding for the amino acid sequence of G protein coupled receptor protein from a DNA library, which comprises carrying out a polymerase chain reaction in the presence of a mixture of
① the DNA library,
② a DNA primer having a nucleotide sequence represented by SEQ ID NO: 6 and
③ a DNA primer having a nucleotide sequence represented by SEQ ID NO: 8
to selectively amplify the DNA coding for the amino acid sequence of G protein coupled receptor protein contained in the DNA library; and

(11) a screening method of DNA coding for the amino acid sequence of G protein coupled receptor protein from a DNA library, which comprises carrying out a polymerase chain reaction in the presence of a mixture of
① the DNA library,
② a DNA primer having a nucleotide sequence represented by SEQ ID NO: 10 and
③ a DNA primer having a nucleotide sequence represented by SEQ ID NO: 11
to selectively amplify the DNA coding for the amino acid sequence of G protein coupled receptor protein contained in the DNA library.

The cloned DNAs can be analyzed, usually by restriction enzyme analysis and/or sequencing.

Target RNA or DNA (or fragment(s) thereof) coding for G protein coupled receptor protein in the amplification and the screening by the PCR techniques wherein the DNA of the present invention is employed may include RNA, DNA or fragments thereof coding for known (or prior art) G protein coupled receptor proteins and RNA, DNA or fragments thereof coding for unknown (novel) G protein coupled receptor proteins.

These target RNA or DNA (or fragment(s) thereof) may include novel nucleotide sequences and even known nucleotide sequences.

Examples of such nucleotide sequences are RNA or DNA (or fragment(s)) coding for a G protein coupled receptor protein, said RNA or DNA (or fragment(s)) being derived from all cells and tissues (e.g. pituitary gland, brain, pancreas, lung, adrenal gland, etc.) of vertebrate animals (e.g. mice, rats, cats, dogs, swines, cattle, horses, monkeys, human beings, etc.), insects or other invertebrate animals (e.g. *drosophilae*, silkworms, *Barathra brassicae*, etc.), plants (e.g. rice plant, wheat, tomato, etc.) and cultured cell lines derived therefrom, etc.

Specific examples of the nucleotide sequences are RNA or DNA (or fragment(s)) coding for G protein coupled receptor proteins such as receptor proteins to angiotensin, bombesin, canavinoid, cholecystokinin, glutamine, serotonin, melatonin, neuropeptide Y, opioid, purine, vasopressin, oxytocin, VIP (vasoactive intestinal and related peptide), somatostatin, dopamine, motilin, amylin, bradykinin, CGRP (calcitonin gene related peptide), adrenomedullin, leukotriene, pancreastatin, prostaglandin, thromboxane, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, family members thereof, etc.

In the PCR amplification using the DNA of the present invention, the DNA (or DNA fragment) acting as a template may include any DNA so far as it is derived from the above-mentioned tissues and cells. More specifically, the template DNA (or DNA fragment) includes any of genome DNA, genome DNA libraries, cDNA derived from the tissues and cells and cDNA libraries derived from the tissues and cells. cDNA libraries derived from human tissues and cells are particularly suitable. Vectors to be used in the DNA library may include any of bacteriophages, plasmids, cosmids, phagimids, etc. It is also possible to directly amplify the template DNA (or DNA fragment) by reverse transcriptase polymerase chain reaction (RT-PCR) techniques using mRNA fr act ions p reared from the tissues and cells. The DNA which is to be a template may be either DNA completely coding for G protein coupled receptor proteins or DNA fragments (or segments) thereof.

Preferably, the RNA or DNA (or fragment(s) thereof) obtained via the instant screening method for G protein coupled receptor protein coding DNA wherein said method uses the DNA according to the present invention is a G protein coupled receptor protein-encoding RNA or DNA (or fragment(s) thereof) contained in the used DNA library. More specifically, it is an RNA or DNA (or RNA fragment(s) or DNA fragment(s) (hereinafter, may be often abbreviated as just "DNA") coding for G protein coupled receptor proteins such as angiotensin receptor, bombesin receptor, canavinoid receptor, cholecystokinin receptor, glutamine receptor, serotonin receptor, melatonin receptor, neuropeptide Y receptor, opioid receptor, purine receptor, vasopressin receptor, oxytocin receptor, VIP receptor (vasoactive intestinal and related peptide receptor), somatostatin receptor, dopamine receptor, motilin receptor, amylin receptor, bradykinin receptor, CGRP receptor (calcitonin gene related peptide receptor), adrenomedullin receptor, leukotriene receptor, pancreastatin receptor, prostaglandin receptor, thromboxane receptor, adenosine receptor, adrenaline receptor, α- and β-chemokine receptor (receptors to IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin receptor, enterogastrin receptor, histamine receptor, neurotensin receptor, TRH receptor, pancreatic polypeptide receptor, galanin receptor, their family member receptors, etc.

When the DNA obtained by the screening method of the present invention is the DNA fragment which partially codes for a G protein coupled receptor protein, it is possible to isolate DNA completely encoding said G protein coupled receptor protein from a suitable DNA library according to cloning techniques known per se by using said DNA fragment as a probe.

Means for cloning the DNA completely encoding G protein coupled receptor proteins may include a PCR amplification employing a synthetic DNA primer having the partial nucleotide sequence of the DNA fragment partially coding for the G protein coupled receptor protein and a selection of the target DNA via a hybridization with DNA or synthetic DNA having part or all of the region of said DNA fragments. The hybridization may be conducted, for example, by the methods described in Molecular Cloning, 2nd ed.; J. Sambrook et al., Cold Spring Harbor Lab. Press, 1989. When the commercially available library is used, it may be conducted according to the manners described in the protocols attached thereto.

The DNA completely encoding G protein coupled receptor protein (full-length G protein coupled receptor protein DNA) may be used, depending upon its object, either as it is or after digesting with a restriction enzyme or after ligating with a linker if desired. Said DNA may have ATG at the 5'-terminal as the translation initiation codon and TAA, TGA or TAG at the 3' terminal as the translation termination codon. These translation initiation codons and translation termination codons may be added using a suitable synthetic DNA adaptor. In addition, it is possible to determine said receptor protein-expressing tissues/cells by northern blottings using said DNA as a probe. It is also possible to express target receptor proteins by introducing DNA having the entire coding region of the receptor protein into animal cells after binding with a suitable promoter.

The G protein coupled receptor protein according to the present invention is a G protein coupled receptor protein encoded by the G protein coupled receptor protein-encoding DNA obtained by the screening method of the present invention. More specifically, the G protein coupled receptor protein according to the present invention includes C protein coupled receptor proteins such as angiotensin receptor protein, bombesin receptor protein, canavinoid receptor protein, cholecystokinin receptor protein, glutamine receptor protein, serotonin receptor protein, melatonin receptor protein, neuropeptide Y receptor protein, opioid receptor protein, purine receptor protein, vasopressin receptor protein, oxytocin receptor protein, VIP receptor protein (vasoactive intestinal and related peptide receptor protein), somatostatin receptor protein, dopamine receptor protein, motilin receptor protein, amylin receptor protein, bradykinin receptor protein, CGRP receptor protein (calcitonin gene related peptide receptor protein), adrenomedullin receptor protein, leukotriene receptor protein, pancreastatin receptor protein, prostaglandin receptor protein, thromboxane receptor protein, adenosine receptor protein, adrenaline receptor protein, α- and β-chemokine receptor protein (receptor protein responsive to IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin receptor protein, enterogastrin receptor protein, histamine receptor protein, neurotensin receptor protein, TRH receptor protein, pancreatic polypeptide receptor protein, galanin receptor protein, family members thereof, etc.

According to the present invention, novel G protein coupled receptors proteins, peptide segments or fragments derived from the G protein coupled receptor protein, modified derivatives or analogues thereof, and salts thereof may be recognized, cloned, produced, isolated or characterized.

These G protein coupled receptor proteins are those derived from all cells and tissues (e.g. pituitary gland, pancreas, brain, kidney, liver, gonad, thyroid gland, cholecyst, bone marrow, adrenal, skin, muscle, lung, digestive duct, blood vessel, heart, etc.) of warm-blooded animals (e.g. guinea pig, rat, mouse, swine, sheep, cattle, monkey, human beings, rabbit, cat, dog, horse, etc.), and any of proteins as long as they comprise an amino acid sequence selected from the group consisting of an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27, an amino acid sequence represented by SEQ ID NO: 28, an amino acid sequence represented by SEQ ID NO: 34, an amino acid sequence represented by SEQ ID NO: 35, an amino acid sequence represented by SEQ ID NO: 38, an amino acid sequence represented by SEQ ID NO: 39, an amino acid sequence represented by SEQ ID NO: 56, and substantial equivalents to the amino acid sequence represented by SEQ ID NO: 24, SEQ ID NO: 25, SEQ ID NO: 26, SEQ ID NO: 27, SEQ ID NO: 28, SEQ ID NO: 34, SEQ ID NO: 35, SEQ ID NO: 38, SEQ ID NO: 39, and/or SEQ ID NO: 56.

In one embodiment of the present invention, G protein coupled receptor proteins are those derived from all cells and tissues (e.g. pituitary gland, pancreas, brain, kidney, liver, gonad, thyroid gland, cholecyst, bone marrow, adrenal, skin, muscle, lung, digestive duct, blood vessel, heart, etc.) of warm-blooded animals (e.g. guinea pig, rat, mouse, swine, sheep, cattle, monkey, human beings, cat, dog, horse, etc.), and any of proteins as long as they comprise an amino acid sequence selected from the group consisting of an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27, an amino acid sequence represented by SEQ ID NO: 28, and substantial equivalents to the amino acid sequence represented by SEQ ID NO: 24, SEQ ID NO: 25, SEQ ID NO: 26, SEQ ID NO: 27, or SEQ ID NO: 28. These G protein coupled receptor proteins may include proteins having an amino acid sequence selected from the group consisting of an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27 and an amino acid sequence represented by SEQ ID NO: 28, proteins wherein the amino acid sequence thereof is about 90% to 99.9% homologous to an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27 or an amino acid sequence represented by SEQ ID NO: 28 and the activity thereof is substantially equivalent to the protein having an amino acid sequence represented by SEQ ID NO: 24, an amino acid sequence represented by SEQ ID NO: 25, an amino acid sequence represented by SEQ ID NO: 26, an amino acid sequence represented by SEQ ID NO: 27 or an amino acid sequence represented by SEQ ID NO: 28 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present.

In another embodiment of the present invention, G protein coupled receptor proteins include human pituitary gland-derived G protein coupled receptor proteins comprising an amino acid sequence selected from the group consisting of an amino acid sequence represented by SEQ ID NO: 24, and/or an amino acid sequence represented by SEQ ID NO: 25, mouse pancreas-derived G protein coupled receptor proteins comprising an amino acid sequence represented by SEQ ID NO: 27, mouse pancreas-derived G protein coupled receptor proteins comprising an amino acid sequence represented by SEQ ID NO: 28, etc. Examples of the human pituitary gland-derived G protein coupled receptor protein comprising an amino acid sequence selected from the group consisting of an amino acid sequence represented by SEQ ID NO: 24, and an amino acid sequence represented by SEQ ID NO: 25, are human pituitary gland-derived G protein coupled receptor proteins comprising an amino acid sequence represented by SEQ ID NO: 24, etc. These G protein coupled receptor proteins may include proteins wherein one or more amino acid residues (preferably from 2 to 30 amino acid residues, more preferably from 2 to 10 amino acid residues) are deleted from the amino acid sequence of SEQ ID NO: 24, SEQ ID NO: 25, SEQ ID NO: 26, SEQ ID NO: 27 or SEQ ID NO: 28, proteins wherein one or more amino acid residues (preferably from 2 to 30 amino acid residues, more preferably from 2 to 10 amino acid residues) are added to the amino acid sequence of SEQ ID NO: 24, SEQ ID NO: 25, SEQ ID NO: 26, SEQ ID NO: 27 or SEQ ID NO: 28, proteins wherein one or more amino acid residues (preferably from 2 to 30 amino acid residues, more preferably from 2 to 10 amino acid residues) in the amino acid sequence of SEQ ID NO: 24, SEQ ID NO: 25, SEQ ID NO: 26, SEQ ID NO: 27 or SEQ ID NO: 28, are substituted with one or more amino acid residues, etc.

In yet another embodiment of the present invention, G protein coupled receptor proteins include those derived from all cells and tissues (e.g. amygdaloid nucleus, pituitary gland, pancreas, brain, kidney, liver, gonad, thyroid gland, cholecyst, bone marrow, lung, digestive duct, blood vessel, heart, thymus, spleen, leukocyte, etc.) of warm-bloodied animals (e.g. guinea pig, rat, mouse, pig, sheep, cattle, monkey, human beings, etc.), and any of proteins as long as they comprise an amino acid sequence selected from the group consisting of an amino acid sequence represented by SEQ ID NO: 34 and/or an amino acid sequence represented by SEQ ID NO: 35. These G protein coupled receptor proteins may include proteins having an amino acid sequence selected from the group consisting of an amino acid sequence represented by SEQ ID NO: 34 or/and an amino acid sequence represented by SEQ ID NO: 35, proteins wherein the amino acid sequence thereof is about 90% to 99.9% homologous to an amino acid sequence represented by SEQ ID NO: 34 or/and an amino acid sequence represented by SEQ ID NO: 35 and the activity thereof is substantially equivalent to the protein having an amino acid sequence represented by SEQ ID NO: 34 and/or an amino acid sequence represented by SEQ ID NO: 35, and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present.

Examples of the G protein coupled receptor protein are human amygdaloid nucleus-derived G protein coupled receptor proteins having an amino acid sequence selected from the group consisting of an amino acid sequence represented by SEQ ID NO: 34 and/or an amino acid sequence represented by SEQ ID NO: 35, etc. These G protein coupled receptor proteins may include proteins wherein one or more amino acid residues (preferably from 2 to 30 amino acid residues, more preferably from 2 to 10 amino acid residues) are deleted from the amino acid sequence of SEQ ID NO: 34 or SEQ ID NO: 35, proteins wherein one or more amino acid residues (preferably from 2 to 30 amino acid residues, more preferably from 2 to 10 amino acid residues) are added to the amino acid sequence of SEQ ID NO: 34 or SEQ ID NO: 35, proteins wherein one or more amino acid residues (preferably from 2 to 30 amino acid residues, more preferably from 2 to 10 amino acid residues) in the amino acid sequence of SEQ ID NO: 34 or SEQ ID NO: 35, are substituted with one or more amino acid residues, etc.

In still another embodiment of the present invention, these G protein coupled receptor proteins are those derived from all cells and tissues (e.g. amygdaloid nucleus, pituitary body, pancreas, brain, kidney, liver, gonad, thyroid gland, cholecyst, bone marrow, lung, digestive duct, blood vessel, heart, thymus, leukocyte, etc.) of warm-blooded animals (e.g. guinea pig, rat, mouse, swine, sheep, cattle, monkey, human beings, etc.), and any of proteins as long as they comprise an amino acid sequence represented by SEQ ID NO: 38, or substantial equivalents to the amino acid sequence represented by SEQ ID NO: 38, preferably an amino acid sequence represented by SEQ ID NO: 39, or substantial equivalents to the amino acid sequence represented by SEQ ID NO: 39. These G protein coupled receptor proteins may include proteins having an amino acid sequence represented by SEQ ID NO: 38, proteins wherein the amino acid sequence thereof is a-bout 90% to 99.9% homologous to an amino acid sequence represented by SEQ ID NO: 38 and the activity thereof is substantially equivalent to the protein having an amino acid sequence represented by SEQ ID NO: 38 and the like. These G protein coupled receptor proteins are preferably proteins having an amino acid sequence represented by SEQ ID NO: 39, proteins wherein the amino acid sequence thereof is about 90% to 99.9% homologous to an amino acid sequence represented by SEQ ID NO: 39 and the activity thereof is substantially equivalent to the protein having an amino acid sequence represented by SEQ ID NO: 39, etc. The substantially equivalent activity may include ligand binding activity, signal information transmitting, etc. The term substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular sizes or weights of receptor proteins are present.

It is suggested by data that the mouse pancreatic β-cell strain, MIN6-derived receptor protein of the present invention (e.g., SEQ ID NO: 38 and SEQ ID NO: 39, or proteins encoded by pMAH2-17) is a novel purinoceptor subtype which is clearly distinct from prior art purinoceptors.

In another more specific embodiment of the present invention, G protein coupled receptor proteins include mouse pancreatic β-cell line, MIN6, derived G protein coupled receptor proteins comprising an amino acid sequence represented by SEQ ID NO: 38, mouse pancreatic β-cell line, MIN6, derived G protein coupled receptor proteins wherein one or more amino acid residues (preferably from 2 to 30 amino acid residues, more preferably from 2 to 10 amino acid residues) are deleted from the amino acid sequence of SEQ ID NO: 38, proteins wherein one or more amino acid residues (preferably from 2 to 30 amino acid residues, more preferably from 2 to 10 amino acid residues) are added to the amino acid sequence of SEQ ID NO: 38, proteins wherein one or more amino acid residues (preferably from 2 to 30 amino acid residues, more preferably from 2 to 10 amino acid residues) are substituted with other amino acid residues in the amino acid sequence of SEQ ID NO: 38, etc. Further preferably these G protein coupled receptor proteins include mouse pancreatic R -cell line, MIN6, derived G protein coupled receptor proteins comprising an amino acid sequence represented by SEQ ID NO: 39, mouse pancreatic β-cell line, MIN6, derived G protein coupled receptor proteins wherein one or more amino acid residues (preferably from 2 to 30 amino acid residues, more preferably from 2 to 10 amino acid residues) are deleted from the amino acid sequence of SEQ ID NO: 39, proteins wherein one or more amino acid residues (preferably from 2 to 30 amino acid residues, more preferably from 2 to 10 amino acid residues) are added to the amino acid sequence of SEQ ID NO: 39, proteins wherein one or more amino acid residues (preferably from 2 to 30 amino acid residues, more preferably from 2 to 10 amino acid residues) in the amino acid sequence of SEQ ID NO: 39 are substituted with other amino acid residues, etc.

In still another embodiment of the present invention, these G protein coupled receptor proteins are those derived from all cells and tissues (e.g. placenta, gonad, amygdaloid nucleus, pituitary body, pancreas, brain, kidney, liver, thyroid gland, cholecyst, bone marrow, lung, digestive duct, blood vessel, heart, thymus, leukocyte, etc.) of human beings, and any of proteins as long as they comprise an amino acid sequence represented by SEQ ID NO: 56, or substantial equivalents to the amino acid sequence represented by SEQ ID NO: 56. These G protein coupled receptor proteins may include proteins having an amino acid sequence represented by SEQ ID NO: 56, proteins wherein the amino acid sequence thereof is about 90% to 99.9% homologous to an amino acid sequence represented by SEQ ID NO: 56 and the activity thereof is substantially equivalent to the protein having an amino acid sequence represented by SEQ ID NO: 56 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular sizes or weights of receptor proteins are present.

In another more specific embodiment of the present invention, G protein coupled receptor proteins include G protein coupled receptor proteins comprising an amino acid sequence represented by SEQ ID NO: 56, G protein coupled receptor proteins wherein one or more amino acid residues (preferably from 2 to 30 amino acid residues, more preferably from 2 to 10 amino acid residues) are deleted from the amino acid sequence of SEQ ID NO: 56, proteins wherein one or more amino acid residues (preferably from 2 to 30 amino acid residues, more preferably from 2 to 10 amino acid residues) are added to the amino acid sequence of SEQ ID NO: 56, proteins wherein one or more amino acid residues (preferably from 2 to 30 amino acid residues, more preferably from 2 to 10 amino acid residues) in the amino acid sequence of SEQ ID NO: 56, are substituted with other amino acid residues, etc.

A portion of the amino acid sequence may be modified (e.g. addition, deletion, substitution with other amino acids, etc.) in the G protein coupled receptor proteins of the present invention.

Furthermore, the G protein coupled receptor proteins of the present invention includes those wherein N-terminal Met is protected with a protecting group (e.g., $C_{1-6}$ acyl group such as formyl, acetyl, etc.), those wherein the N-terminal side of Glu is cleaved in vivo to make said Glu pyroglutaminated, those wherein the intramolecular side chain of amino acids is protected with a suitable protecting group (e.g., $C_{1-6}$ acyl group such as formyl, acetyl, etc.), conjugated proteins such as so-called "glycoproteins" wherein saccharide chains are bonded, etc.

The salt of said G protein coupled receptor protein of the present invention includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), etc.

The G protein coupled receptor protein or its salt of the present invention may be manufactured from the tissues or cells of warm-blooded animals by purifying methods which are known per se by those skilled in the art or methods similar thereto or may be manufactured by culturing the transformant (or transfectant) (as described herein below) containing G protein coupled receptor protein encoding DNA. The protein or its salt of the present invention may be manufactured by the peptide synthesis as described herein below.

The G protein coupled receptor protein fragment (the partial peptide of said G protein coupled receptor protein) may include, for example, the site which is exposed outside cell membranes, among the G protein coupled receptor protein molecule. Examples of the fragment are peptides containing a region which is analyzed as an extracellular area (hydrophilic region or site) in a hydrophobic plotting analysis on the G protein coupled receptor protein represented by any of FIGS. 24, 25, 28, 31, 32, 36, 38, 41, 44, 47, 50, 53, 57, 58, 59, 64, 70, 74, and 78. A peptide which partly contains a hydrophobic region or site may be used as well. Further, a peptide which separately contains each domain may be used too although the partial peptide (peptide fragment) which contains plural domains at the same time will be used as well.

The salt of said G protein coupled receptor protein fragment (partial peptide thereof) includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, malefic acid, succinic acid, tartaric acid, citric acid, malic acid, oxalic acid, benzoic acid, methanesulfonic acid, benzenesulfonic acid, etc.), etc.

The G protein coupled receptor protein fragment (the partial peptide of the G protein coupled receptor protein) may be manufactured by synthesizing methods for peptides which are known per se by those skilled in the art or methods similar thereto or by cleaving (digesting) G protein coupled receptor proteins by a suitable peptidase. Methods of synthesizing peptide may be any of a solid phase synthesis and a liquid phase synthesis. Thus, a partial peptide (peptide fragment) or amino acids which can construct the protein of the present invention is condensed with the residual part thereof and, when the product has a protective group, said protective group is detached whereupon a desired peptide can be manufactured. Examples of the known methods for condensation and for detachment of protective groups include the following ① to ⑤:

① M. Bodanszky and M. A. Ondetti: Peptide Synthesis, Interscience Publishers, New York (1966).

② Schroeder and Luebke: The Peptide, Academic Press, New York, 1965.

③ Nobuo Izumiya et al.: Fundamentals and Experiments of the Peptide Synthesis, Maruzen KK, Japan (1975).

④ Haruaki Yajima and Shumpei Sakakibara: "Seikagaku Jikken Koza 1" (Experiments of Biochemistry, Part 1), "Tanpakusitu No Kagaku IV" (Chemistry of Protein, IV), p. 205 (1977), Japan.

⑤ Haruaki Yajima (ed): Development of Pharmaceuticals (Second Series), Vol. 14, Peptide Synthesis, Hirokawa Shoten, Japan.

After the reaction, conventional purifying techniques such as salting-out, extraction with solvents, distillation, column chromatography, liquid chromatography, electrophoresis, recrystallization, etc. are optionally combined so that the protein of the present invention can be purified and isolated. When the protein obtained as such is a free compound, it may be converted to a suitable salt by known methods while, when it is obtained as a salt, the salt may be converted to a free compound or other salt compounds by known methods.

Furthermore, the product may be manufactured by culturing the transformant (transfectant) containing the DNA coding for said partial peptide.

The G protein coupled receptor protein-encoding DNA obtained by the above-mentioned screening method using the DNA of the present invention and the G protein coupled receptor protein encoded by said DNA or the peptide fragment (partial peptide thereof) encoded by said DNA may, for example, be used for the determination of a ligand to said G protein coupled receptor protein or for the screening of a compound which inhibits the binding of said protein coupled receptor protein with a ligand.

In that case, an expression system for the G protein coupled receptor protein-encoding DNA is at first constructed. Hosts for said DNA may be any of animal cells, insect cells, yeasts, *Bacillus subtilis, Escherichia coli*, etc. Promoters used therefor may be anyone so far as it is suitable as a promoter for the host used for gene expression. Incidentally, the utilization of enhancers for expression is effective as well.

Then the expressing cells per se which constructed to express the G protein coupled receptor protein or the cell membrane fractions prepared therefrom by methods known per se by those skilled in the art or methods similar thereto may be subjected to a variety of receptor binding experiments. Ligands used therefor may include any of compounds labeled by a commercially available radioisotope, etc., culture supernatants and tissue extracts which are directly labeled by a chloramine T method or by a lactoperoxidase method. Separation of bonded or free ligands may be carried out by a direct washing when cells adhered to substrates are used, while, in the case of floating cells or cell membrane fractions thereof, it may be carried out by means of centrifugal separation or filtration. Nonspecific binding with container, etc. may be estimated by addition of unlabeled ligands which are about 100 times as much concentrated relatively to the poured labeled ligand.

The ligand which is obtained by such a receptor binding experiment may be subjected to a discrimination of agonist versus antagonist.

To be more specific, a natural substance or compound which is presumed to be a ligand with the G protein coupled receptor protein-expressing cell is cultured and, after that, the culture supernatant liquid is collected or the cell is extracted. A change in the components contained therein is measured by, for example, a commercially available measuring kit (e.g. kits for cAMP, diacylglycerol, cGMP, proteinkinase A, etc.). Alternatively, it is possible to measure physiological responses such as liberation of Fura-2, [$^3$H] arachidonic acid and [$^3$H]inositol phosphate metabolites by methods known per se by those skilled in the art or methods similar thereto. The compound or natural substance which is obtained by such a screening is an agonist for said G protein coupled receptor protein or an antagonist for said G protein coupled receptor protein and is presumed to act on the tissues and cells in which said receptor is distributed. Accordingly, it is possible to check the pharmaceutical response (pharmaceutical effect) more efficiently by referring to the distribution disclosed (clarified) by a northern blotting or the like. Moreover, a development of compounds having a novel pharmaceutical response (pharmaceutical effect) in, for example, central nervous tissues, circulatory system, kidney, pancreas, etc. is expected. An efficient development of pharmaceuticals can be proceeded by amplifying G protein coupled receptor protein-encoding DNA selectively from tissues.

The G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 24 and/or which has an activity substantially equivalent to the amino acid sequence having SEQ ID NO: 24, a G protein coupled receptor protein which contains an amino acid sequence substantially equivalent to the amino acid sequence having SEQ ID NO: 25 and/or which has an activity substantially equivalent to the amino acid sequence having SEQ ID NO: 25, a G protein coupled receptor protein which contains an amino acid sequence substantially equivalent to the amino acid sequence having SEQ ID NO: 26 and/or which has an activity substantially equivalent to the amino acid sequence having SEQ ID NO: 26, a G protein coupled receptor protein which contains an amino acid sequence substantially equivalent to the amino acid sequence having SEQ ID NO: 27 and/or which has an activity substantially equivalent to the amino acid sequence having SEQ ID NO: 27, or a G protein coupled receptor protein which contains an amino acid sequence substantially equivalent to the amino acid sequence having SEQ ID NO: 28 and/or which has an activity substantially equivalent to the amino acid sequence having SEQ ID NO: 28.

Still the G protein coupled receptor protein-encoding DNA of the present invention may be any coding DNA as;

long as it contains a nucleotide sequence coding for a G protein coupled receptor protein which contains an amino acid sequence substantially equivalent to the amino acid sequence having SEQ ID NO: 34 and/or which has an activity substantially equivalent to the amino acid sequence having SEQ ID NO: 34, or a G protein coupled receptor protein which contains an amino acid sequence substantially equivalent to the amino acid sequence having SEQ ID NO: 35 and/or which has an activity substantially equivalent to the amino acid sequence having SEQ ID NO: 35.

Yet the G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 38 and/or which has an activity substantially equivalent to the amino acid sequence having SEQ ID NO: 38, or preferably a G protein coupled receptor protein which contains an amino acid sequence substantially equivalent to the amino acid sequence having SEQ ID NO: 39 and/or which has an activity substantially equivalent to the amino acid sequence having SEQ ID NO: 39.

Yet the G protein coupled receptor protein-encoding DNA of the present invention may be any coding DNA as long as it contains a nucleotide sequence coding for a G protein coupled receptor protein which contains an amino acid sequence substantially equivalent to the amino acid sequence having SEQ ID NO: 56 and/or which has an activity substantially equivalent to the amino acid sequence having SEQ ID NO: 56, or preferably a G protein coupled receptor protein which contains an amino acid sequence substantially equivalent to the amino acid sequence having SEQ ID NO: 56 and/or which has an activity substantially equivalent to the amino acid sequence having SEQ ID NO: 56.

The DNA of the present invention may be any one of a human genome DNA, a human genome DNA library, a human tissue and cell-derived cDNA, a human tissue and cell-derived cDNA library and a synthetic DNA. The vector used for the library may include bacteriophage, plasmid, cosmid, phagemid, etc. The DNA can be further amplified directly by the reverse transcriptase polymerase chain reaction (hereinafter briefly referred to as "RT-PCR") using mRNA fractions prepared from tissues and cells.

In an embodiment, the DNA coding for the human pituitary gland-derived G protein coupled receptor protein comprising the amino acid sequence of SEQ ID NO: 24 includes DNA having a nucleotide sequence represented by SEQ ID NO: 29, etc. The DNA coding for the human pituitary gland-derived G protein coupled receptor protein comprising the amino acid sequence of SEQ ID NO: 25 includes DNA having a nucleotide sequence represented by SEQ ID NO: 30, etc. The DNA coding for the human pituitary gland-derived G protein coupled receptor protein comprising the amino acid sequence of SEQ ID NO: 26 includes DNA having a nucleotide sequence represented by SEQ ID NO: 31, etc. The DNA coding for the mouse pancreas-derived G protein coupled receptor protein comprising the amino acid sequence of SEQ ID NO: 27 includes DNA having a nucleotide sequence represented by SEQ ID NO: 32, etc. The DNA coding for the mouse pancreas-derived G protein coupled receptor protein comprising the amino acid sequence of SEQ ID NO: 28 includes DNA having a nucleotide sequence represented by SEQ ID NO: 33, etc.

In another embodiment, the DNA coding for the human amygdaloid nucleus-derived G protein coupled receptor protein comprising the amino acid sequence of SEQ ID NO: 34 includes DNA having a nucleotide sequence represented by SEQ ID NO: 36, etc. The DNA coding for the human amygdaloid nucleus-derived G protein coupled receptor protein comprising the amino acid sequence of SEQ ID NO: 35 includes DNA having a nucleotide sequence represented by SEQ ID NO: 37, etc. The DNA coding for the human amygdaloid nucleus-derived G protein coupled receptor protein comprising the amino acid sequence of SEQ ID NO: 34 or the amino acid sequence of SEQ ID NO: 35 includes DNA having a nucleotide sequence represented by SEQ ID NO: 36, DNA having a nucleotide sequence represented by SEQ ID NO: 37, etc. Still in another embodiment, the DNA coding for the mouse pancreatic β-cell line, MIN6-derived G protein coupled receptor protein comprising the amino acid sequence of SEQ ID NO: 38 includes DNA having a nucleotide sequence represented by SEQ ID NO: 40, etc. The DNA coding for the mouse pancreatic β-cell line, MIN6-derived G protein coupled receptor protein comprising the amino acid sequence of SEQ ID NO: 39 includes DNA having a nucleotide sequence represented by SEQ ID NO: 41, etc. Yet in another embodiment, the DNA coding for the human-derived G protein coupled receptor protein comprising the amino acid sequence of SEQ ID NO: 56 includes DNA having a nucleotide sequence represented by SEQ ID NO: 57, etc.

The DNA completely coding for the G protein coupled receptor protein of the present invention can be cloned by (1) carrying out the PCR amplification using a synthetic DNA primer having a partial nucleotide sequence (nucleotide fragment) of the G protein coupled receptor protein; or (2) effecting the selection of a DNA constructed in a suitable vector, based on the hybridization with a labeled DNA fragment having part or all of the region encoding a human G protein coupled receptor protein or a labeled synthetic DNA having part or all of the coding region thereof. The hybridization is carried out according to methods as disclosed in, for example, Molecular Cloning, 2nd Ed., J. Sambrook et al., Cold Spring Harbor Lab. Press, 1989. When a DNA library commercially available in the market is used, the hybridization is carried out according to protocols manuals attached thereto.

The cloned G protein coupled receptor protein-encoding DNA of the present invention can be used as it is, or can be used, as desired, after modifications including digestion with a restriction enzyme or addition of a linker or adapter, etc. depending upon objects. The DNA may have an initiation codon, ATG, on the 5' terminal side and a termination codon, TAA, TGA or TAG, on the 3' terminal side. These initiation and termination codons can be ligated by using a suitable synthetic DNA adapter.

An expression vector for G protein coupled receptor proteins can be produced by, for example, (a) cutting out a target DNA fragment from the G protein coupled receptor protein-encoding DNA of the present invention and (b) ligating the target DNA fragment with the downstream site of a promoter in a suitable expression vector.

The vector may include plasmids derived from *Escherichia coli* (e.g., pBR322, pBR325, pUC12, pUC13, etc.), plasmids derived from *Bacillus subtilis* (e.g., pUB110, pTP5, pC194, etc.), plasmids derived from yeasts (e.g., pSH19, pSH15, etc.), bacteriophages such as λ-phage, and animal virus such as retrovirus, vaccinia virus and baculovirus.

According to the present invention, any promoter can be used as long as it is compatible with a host which is used for expressing a gene. When the host for the transformation is

*E. coli*, the promoters are preferably trp promoters, lac promoters, recA promoters, $\lambda_{PL}$ promoters, lpp promoters, etc. When the host for the transformation is the Bacillus, the promoters are preferably SPO1 promoters, SPO2 promoters, penP promoters, etc. When the host is an yeast, the promoters are preferably PHO5 promoters, PGK promoters, GAP promoters, ADH promoters, etc. When the host is an animal cell, the promoters include SV40-derived promoters, retrovirus promoters, metallothionein promoters, heat shock promoters, cytomegalovirus promoters, SRa promoters, etc. An enhancer can be effectively utilized for the expression.

As required, furthermore, a host-compatible signal sequence is added to the N-terminal side of the G protein coupled receptor protein. When the host is *E. coli*, the utilizable signal sequences may include alkaline phosphatase signal sequences, OmpA signal sequences, etc. When the host is the Bacillus, they may include α-amylase signal sequences, subtilisin signal sequences, etc. When the host is an yeast, they may include mating factor a signal sequences, invertase signal sequences, etc. When the host is an animal cell, they may include insulin signal sequences, α-interferon signal sequences, antibody molecule signal sequences, etc.

A transformant or transfectant is produced by using the vector thus constructed, which carries the G protein coupled receptor protein-encoding DNA of the present invention. The host may be, for example, Escherichia microorganisms, Bacillus microorganisms, yeasts, insect cells, animal cells, etc. Examples of the Escherichia and Bacillus microorganisms include *Escherichia coli* K12-DH1 [Proc. Natl. Acad. .3ci. USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)], C600 [Genetics, Vol. 39, 440 (1954)], etc. Examples of the Bacillus microorganism are, for example, *Bacillus subtilis* MI114 [Gene, Vol. 24, 255 (1983)], 207–21 [Journal of Biochemistry, Vol. 95, 87 (1984)], etc. The yeast may be, for example, *Saccharomyces cerevisiae* AH22, AH22R⁻, NA87-11A, DKD-5D, 20B-12, etc. The insect may include a silkworm (*Bombyx mori* larva), [Maeda et al, Nature, Vol. 315, 592 (1985)] etc. The host animal cell may be, for example, monkey-derived cell line, COS-7, Vero, Chinese hamster ovary cell line (CHO cell), DHFR gene-deficient Chinese hamster cell line (dhfr CHO cell), mouse L cell, murine myeloma cell, human FL cell, etc.

Depending on the host cell used, transformation is done using standard techniques appropriate to such cells. Transformation of Escherichia microorganisms can be carried out in accordance with methods as disclosed in, for example, Proc. Natl. Acad. Sci. USA, Vol. 69, 2110 (1972), Gene, Vol. 17, 107 (1982), etc. Transformation of Bacillus microorganisms can be carried out in accordance with methods as disclosed in, for example, Molecular & General Genetics, Vol. 168, 111 (1979), etc. Transformation of the yeast can be carried out in accordance with methods as disclosed in, for example, Proc. Natl. Acad. Sci. USA, Vol. 75, 1929 (1978), etc. The insect cells can be transformed in accordance with methods as disclosed in, for example, Bio/Technology, 6, 47–55, 1988. The animal cells can be transformed by methods as disclosed in, for example, Virology, Vol. 52, 456, 1973, etc. The transformants or transfectants which are transformed with expression vectors containing a G protein coupled receptor protein-encoding DNA are produced according to the aforementioned techniques.

Cultivation of the transformant (transfectant) in which the host is Escherichia or Bacillus microorganism can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeasts, vitamines, growth-promoting factors, etc. It is desired that the culture medium is pH from about 5 to about 8.

The Escherichia microorganism culture medium is preferably an M9 medium containing, for example, glucose and casamino acid (Miller, Journal of Experiments in Molecular Genetics), 431–433, Cold Spring Harbor Laboratory, New York, 1972. Depending on necessity, the medium may be supplemented with drugs such as 3β-indolyl acrylic acid in order to improve efficiency of the promoter. In the case of the Escherichia host, the cultivation is carried out usually at about 15 to 43° C. for about 3 to 24 hours. As required, aeration and stirring may be applied. In the case of the Bacillus host, the cultivation is carried out usually at about 30 to 40° C. for about 6 to 24 hours. As required, aeration and stirring may be also applied. In the case of the transformant in which the host is an yeast, the culture medium used may include, for example, a Burkholder minimum medium [Bostian, K. L. et al., Proc. Natl. Acad. Sci. USA, Vol. 77, 4505 (1980)], an SD medium containing 0.5% casamino acid [Bitter, G. A. et al., Proc. Natl. Acad. Sci. USA, Vol. 81, 5330 (1984)], etc. It is preferable that pH of the culture medium is adjusted to be from about 5 to about 8. The cultivation is carried out usually at about 20 to 35° C. for about 24 to 72 hours. As required, aeration and stirring may be applied. In the case of the transformant in which the host is an insect, the culture medium used may include those obtained by suitably adding additives such as passivated (or immobilized) 10% bovine serum and the like to the Grace's insect medium (Grace, T. C. C., Nature, 195, 788 (1962)). It is preferable that pH of the culture medium is adjusted to be about 6.2 to 6.4. The cultivation is usually carried out at about 27° C. for about 3 to 5 days. As desired, aeration and stirring may be applied. In the case of the transformant in which the host is an animal cell, the culture medium used may include MEM medium [Science, Vol. 122, 501 (1952)], DMEM medium [Virology, Vol. 8, 396 (1959)], RPMI 1640 medium [Journal of the American Medical Association, Vol. 199, 519 (1967)], 199 medium [Proceedings of the Society of the Biological Medicine, Vol. 73, 1 (.L950)], etc. which are containing, for example, about 5 to 23% of fetal calf serum. It is preferable that the pH is from about 6 to about 8. The cultivation is usually carried out at about 30 to 40° C. for about 15 to 60 hours. As required, aeration and stirring may be applied.

Separation and purification of the G protein coupled receptor protein from the above-mentioned cultures can be carried out according to methods described herein below.

To extract G protein coupled receptor proteins from the cultured microorganisms or cells, the microorganisms or cells are collected by known methods after the cultivation, suspended in a suitable buffer solution, disrupted by ultrasonic waves, lysozyme and/or freezing and thawing, etc. and, then, a crude extract of the G protein coupled receptor protein is obtained by centrifugation or filtration. Other conventional extracting or isolating methods can be applied. The buffer solution may contain a protein-denaturing agent such as urea or guanidine hydrochloride or a surfactant such as Triton X-100 (registered trademark, hereinafter often referred to as "TM").

In case where G protein coupled receptor proteins are secreted into culture media, supernatant liquids are separated from the microorganisms or cells after the cultivation is finished and the resulting supernatant liquid is collected by widely known methods. The culture supernatant liquid and extract containing G protein coupled receptor proteins can be purified by suitable combinations of widely known methods for separation, isolation and purification. The widely known methods of separation, isolation and purification may include methods which utilizes solubility, such as salting out or sedimentation with solvents methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as inverse-phase high-performance liquid chromatography, and methods utilizing a difference in the isoelectric point such as isoelectric electrophoresis, etc.

In case where the G protein coupled receptor protein thus obtained is in a free form, the free protein can be converted into a salt thereof by known methods or method analogous thereto. In case where the G protein coupled receptor protein thus obtained is in a salt form vice versa, the protein salt can be converted into a free form or into any other salt thereof by known methods or method analogous thereto.

The G protein coupled receptor protein produced by the transformant can be arbitrarily modified or a polypeptide can be partly removed therefrom, by the action of a suitable protein-modifying enzyme before or after the purification. The protein-modifying enzyme may include trypsin, chymotrypsin, arginyl endopeptidase, protein kinase, glycosidase, etc. The activity of the G protein coupled receptor protein thus formed can be measured by experimenting the coupling (or binding) with a ligand or by enzyme immunoassays (enzyme linked immunoassays) using specific antibodies.

The G protein coupled receptor protein-encoding DNA and the G protein coupled receptor protein of the present invention can be used for:
① methods of determining ligands for the G protein coupled receptor protein of the present invention,
② obtaining an antibody and an antiserum,
③ constructing a system for expressing a recombinant receptor protein,
④ developing a receptor-binding assay system using the above developing system and screening pharmaceutical candidate compounds,
⑤ designing drugs based upon the comparison with ligands and receptors which have a similar or analogous structure,
⑥ preparing a probe in the analysis of genes and preparing a PCR primer, and
⑦ gene manipulating therapy.

In particular, it is allowable to screen a G protein coupled receptor agonist or antagonist specific to a warm-blooded animal such as human being by a receptor-binding assay system which uses a system for expressing a recombinant G protein coupled receptor protein of the present invention. The agonist or antagonist thus screened or characterized permits various applications including prevention and/or therapy of a variety of diseases.

Concretely described below are uses of G protein coupled receptor proteins, partial peptide thereof (peptide fragment thereof), G protein coupled receptor protein-encoding DNAs and antibodies against the G protein coupled receptor protein according to the present invention.

As hereunder, more detailed description will be made on the usefulness of the G protein coupled receptor protein-encoding DNA obtained by the screening method for G protein coupled receptor protein-encoding DNAs according to the present invention, the G protein coupled receptor proteins encoded by said DNA, peptide fragments or segments thereof (including partial peptides thereof) or salts thereof (hereinafter, those including their salts, will be referred to as the "G protein coupled receptor protein or a peptide fragment thereof"), cells or cell membrane fractions thereof each containing the recombinant type G protein coupled receptor protein, etc. Their various applications are also disclosed herein below.

(1) Method for Determining Ligands to the G Protein Coupled Receptor Protein

The G protein coupled receptor protein (or the peptide segment thereof) is useful as a reagent for investigating or determining a ligand to said G protein coupled receptor protein.

According to the present invention, methods for determining a ligand to the G protein coupled receptor protein which comprises contacting the G protein coupled receptor protein or the peptide segment or fragment thereof with the compound to be tested are provided.

The compound to be tested may include not only known ligands such as angiotensins, bombesins, canavinoids, cholecystokinins, glutamine, serotonin, melatonins, neuropeptides Y, opioids, purine, vasopressins, oxytocins, VIP (vasoactive intestinal and related peptides), somatostatins, dopamine, motilins, amylins, bradykinins, CGRP (calcitonin gene related peptides), adrenomedullins, leukotrienes, pancreastatins, prostaglandins, thromboxanes, adenosine, adrenaline, α- and β-chemokines (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelins, enterogastrins, histamine, neurotensins, TRH, pancreatic polypeptides, galanin, modified derivatives thereof, analogues thereof, family members thereof and the like but also tissue extracts, cell culture supernatants, etc. of warm-blooded animals (such as mice, rats, swines, cattle, sheep, monkeys and human being), etc. For example, said tissue extract, said cell culture supernatant, etc. is added to the G protein coupled receptor protein for measurement of the cell stimulating activity, etc. and fractionated by relying on the measurements whereupon a single ligand can be finally obtained.

In one specific embodiment of the present invention, said method for determining the ligand includes a method for determining a compound or a salt thereof capable of stimulating a target cell which comprises binding said compound with the G protein coupled receptor protein either in the presence of the G protein coupled receptor protein or the peptide segment thereof or in a receptor binding assay system in which the expression system for the recombinant type receptor protein is constructed and used; and measuring the receptor-mediated cell stimulating activity, etc. Examples of said cell stimulating activities include promoting activity or inhibiting activity on biological responses, e.g. liberation of arachidonic acid, liberation of acetylcholine, liberation of endocellular $Ca^{2+}$, production of endocellular CAMP, production of endocellular cGMP, production of inositol phosphate, changes in the cell membrane potential, phosphorylation of endocellular protein, activation of c-fos, lowering in pH, activation of G protein, cell promulgation, etc. Examples of said compound or salt capable of stimulating the cell via binding with the G protein coupled receptor protein include peptides, proteins, nonpeptidic compounds, synthetic compounds, fermented products, etc.

In said method for determining the ligand, the characteristic feature is that when the G protein coupled receptor protein or the peptide segment thereof is contacted with the test compound, for example, the binding amount, the cell stimulating activity, etc. of the test compound to the G protein coupled receptor protein or the peptide segment thereof is measured.

In more specific embodiments of the present: invention, said methods for determining the ligand includes:

① a method of determining a ligand to a G protein coupled receptor protein, which comprises contacting a labeled test compound with a G protein coupled receptor protein or a peptide segment thereof, and measuring the amount of the labeled test compound binding with said protein or salt thereof or with said peptide fragment or salt thereof;

② a method of determining a ligand to a G protein coupled receptor protein, which comprises contacting a labeled test compound with cells containing the G protein coupled receptor protein or the membrane fraction of said cell, and measuring the amount of the labeled test compound binding with said cells or said cell fraction;

③ a method of determining a ligand to a G protein coupled receptor protein, which comprises contacting a labeled test compound with the G protein coupled receptor protein expressed on cell membranes by culturing transformants containing the DNA coding for the G protein coupled receptor protein, and measuring the amount of the labeled test compound binding with said G protein coupled receptor protein;

④ a method of determining a ligand to a G protein coupled receptor protein, which comprises contacting a test compound with cells containing the G protein coupled receptor protein, and measuring the cell stimulating activity (e.g. promoting or inhibiting activity on biological responses such as liberation of arachidonic acid, liberation of acetylcholine, liberation of endocellular $Ca^{2+}$, production of endocellular cAMP, production of endocellular cGMP, production of inositol phosphate, changes in the cell membrane potential, phosphorylation of endocellular protein, activation of c-fos, lowering in pH, activation of G protein, cell promulgation, etc.) via the G protein coupled receptor protein; and ⑤ a method of determining a ligand to the G protein coupled receptor protein, which comprises contacting a test compound with the G protein coupled receptor protein expressed on the cell membrane by culturing transformants containing the DNA coding for the G protein coupled receptor protein, and measuring the cell stimulating activity (activity for promoting or inhibiting physiological responses such as liberation of arachidonic acid, liberation of acetylcholine, liberation of endocellular $Ca^{2+}$, production of endocellular cAMP, production of endocellular cGMP, production of inositol phosphate, changes in the cell membrane potential, phosphorylation of endocellular protein, activation of c-fos, lowering in pH, activation of G protein, cell promulgation, etc.) via the G protein coupled receptor protein.

Described below are specific explanations on the determining method of ligands according to the present invention which are provided only for illustrative purposes.

First, the G protein coupled receptor protein used for the method for determining the ligand may include any material so far as it contains a G protein coupled receptor protein or a peptide fragment or segment thereof (including a partial peptide thereof) or a salt thereof although it is preferable to express a large amount of G protein coupled receptor proteins in animal cells.

In the manufacture of the G protein coupled receptor protein, the above-mentioned method can be used and it may be carried out by expressing said protein encoding DNA in mammalian cells or in insect cells. With respect to the DNA fragment coding for the aimed region, complementary DNA may be used although it is not limited thereto. For example, gene fragments or synthetic DNA may be used as well.

In order to introduce the G protein coupled receptor protein-encoding DNA fragment into host animal cells and to express it efficiently, it is preferred that said DNA fragment is incorporated into the downstream site of polyhedron promoters derived from nuclear polyhedrosis virus belonging to baculovirus, promoters derived from SV4C, promoters derived from retrovirus, metallothionein promoters, human heat shock promoters, cytomegalovirus promoters, SRα promoters, etc. Examinations of the quantity and the quality of the expressed receptor can be carried out by methods per se known to those of skill in the art or methods similar thereto. For example, they may be conducted by methods described in publications such as Nambi, P. et al: The Journal of Biochemical Society, vol.267, pages 19555-19559 (1992).

Accordingly, with respect to the determination of the ligand, the material containing a G protein coupled receptor protein or peptide segment thereof may include products containing G protein coupled receptor proteins which are purified by methods per se known to those of skill in the art or methods similar thereto, peptide fragments of said G protein coupled receptor protein, cells containing said G protein coupled receptor protein, membrane fractions of the cell containing said protein, etc.

When the G protein coupled receptor protein-containing cell is used in the determining method of the ligand, said cell may be immobilized with binding agents including glutaraldehyde, formalin, etc. The immobilization may be carried out by methods per se known to those of skill in the art or methods similar thereto.

The G protein coupled receptor protein-containing cells are host cells expressing the G protein coupled receptor protein. Examples of said host cells are microorganisms such as *Escherichia coli, Bacillus subtilis*, yeasts, insect cells, animal cells, etc.

The cell membrane fraction is a cell membrane-rich fraction which is prepared by methods per se known to those of skill in the art or methods similar thereto after disruption of cells. Examples of cell disruption may include a method for squeezing cells using a Potter-Elvejem homogenizer, a disruption by a Waring blender or a Polytron (manufactured by Kinematica), a disruption by ultrasonic waves, a disruption via blowing out cells from small nozzles together with applying a pressure using a French press or the like, etc. In the fractionation of the cell membrane, a fractionation method by means of centrifugal force such as a fractional centrifugal separation and a density gradient centrifugal separation is mainly used. For example, disrupted cellular liquid is centrifuged at a low speed (500 rpm to 3,000 rpm) for a short period (usually, from about one to ten minutes), the supernatant liquid is further centrifuged at a high speed (1,500 rpm to 3,000 rpm) usually for 30 minutes to two hours and the resulting precipitate is used as a membrane fraction. Said membrane fraction contains a lot of the expressed G protein coupled receptor protein and a lot of membrane components such as phospholipids and membrane proteins derived from the cells.

The amount of the G protein coupled receptor protein in the membrane fraction cell containing said G protein coupled receptor protein is preferably $10^3$–$10^8$ molecules per cell or, suitably, $10^5$ to $10^7$ molecules per cell. Incidentally, the more the expressed amount, the higher the ligand binding activity (specific activity) per membrane fraction whereby the construction of a highly sensitive screening system becomes possible and, moreover, it may enable us to measure the large amount of samples within the same lot.

In conducting the above-mentioned methods ① to ② wherein ligands capable of binding with the G protein coupled receptor protein are determined, a suitable G protein coupled receptor fraction and a labeled test compound are necessary. The G protein coupled receptor fraction is preferably a naturally occurring (natural type) G protein coupled receptor, a recombinant type G protein coupled receptor having the activity equivalent to that of the natural type. Here, the term "activity equivalent to" means the equivalent ligand binding activity, etc.

Suitable examples of the labeled test compound are angiotensin, bombesin, canavinoid, cholecystokinin, glutamine, serotonin, melatonin, neuropeptide Y, opioid, purine, vasopressin, oxytocin, VIP (vasoactive intestinal and related peptides), somatostatin, dopamine, motilin, amylin, bradykinin, CGRP (calcitonin gene related peptides), adrenomedullin, leukotriene, pancreastatin, prostaglandin, thromboxane, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptides, galanin, an analogue derivative thereof, etc. which are labeled with [$^3$H], [$^{125}$I], C], [$^{14}$C], [$^{35}$S], etc.

Specifically, the determination of ligands capable of binding with G protein coupled receptor proteins is carried out as follows:

First, cells or cell membrane fractions containing the G protein coupled receptor protein are suspended in a buffer suitable for the determining method to prepare the receptor sample in conducting the method of determining the ligand binding with the G protein coupled receptor protein. The buffer may include any buffer such as Tris-HCl buffer or phosphate buffer with pH 4–10 (preferably, pH 6–8), etc., as long as it does not inhibit the binding of the ligand with the receptor. In addition, surface-active agents such as CHAPS, Tween 80 (Kao-Atlas, Japan), digitonin, deoxycholate, etc. and various proteins such as bovine serum albumin (BSA), gelatin, milk derivatives, etc. may be added to the buffer with an object of decreasing the non-specific binding. Further, a protease inhibitor such as PMSF, leupeptin, E-64 (manufactured by Peptide Laboratory), pepstatin, etc. may be added with an object of inhibiting the decomposition of the receptor and the ligand by protease. A test compound labeled with a predetermined (or certain) amount (5,000 cpm to 500,000 cpm) of [$^3$H], [$^{125}$I], [$^{14}$C], [$^{35}$], etc. is made copresent in 0.01 ml to 10 ml of said receptor solution. In order to know the non-specific binding amount (NSB), a reaction tube to which a great excessive amount of the unlabeled test compound is added is prepared as well. The reaction is carried out at 0–50° C. (preferably at 4–37° C.) for 20 minutes to 24 hours (preferably 30 minutes to three hours). After the reaction, it is filtered through a glass fiber filter or the like, washed with a suitable amount of the same buffer and the radioactivity remaining in the glass fiber filter is measured by means of a liquid scintillation counter or a gamma-counter. The test compound in which the count (B−NSB) obtained by subtracting the non-specific binding amount (NSB) from the total binding amount (B) is more than 0 cpm can be selected as a ligand to the G protein coupled receptor protein of the present invention.

In conducting the above-mentioned methods ④ to ⑤ wherein ligands capable of binding with the G protein coupled receptor protein are determined, the cell stimulating activity (e.g. the liberation of arachidonic acid, the liberation of acetylcholine, endocellular Ca 2+ liberation, endocellular cAMP production, the production of insitol phosphate, changes in the cell membrane potential, the phosphorylation of endocellular protein, the activation of c-fos, lowering of pH, the activation of G protein, cell promulgation, etc.) mediated by the G protein coupled receptor protein may be measured by known methods or by the use of commercially available measuring kits. To be more specific, G protein coupled receptor protein-containing cells are at first cultured in a multi-well plate or the like.

In conducting the determination of ligand, it is substituted with a fresh medium or a suitable buffer which does not show toxicity to the cells in advance of the experiment, and incubated for certain period after adding a test compound, etc. thereto. Then, the cells are extracted or the supernatant liquid is recovered and the resulting product is determined by each of the methods. When it is difficult to identify the production of the substance (e.g. arachdonic acid) which is to be an index for the cell stimulating activity due to the decomposing enzyme contained in the cell, an assay may be carried out by adding an inhibitor against said decomposing enzyme. With respect to the activity such as an inhibitory action against cAMP production, it may be detected as an inhibitory action against the production of the cells whose fundamental production is increased by forskolin or the like.

The kit used for the method of determining the ligand binding with the G protein coupled receptor protein includes a G protein coupled receptor protein or a peptide fragment thereof, cells containing the G protein coupled receptor protein, a membrane fraction from the cells containing the G protein coupled receptor protein, etc.

Examples of the kit for determining the ligand are as follows:

1. Reagent for Determining the Ligand.

① Buffer for Measurement and Buffer for Washing.

The buffering product wherein 0.05% of bovine serum albumin (manufactured by Sigma) is added to Hanks' Balanced Salt Solution (manufactured by Gibco).

This product may be sterilized by filtration through a membrane filter with a 0.45 μm pore size, and stored at 4° C. or may be formulated upon use.

② G Protein Coupled Receptor Protein Sample.

CHO cells in which G protein coupled receptor proteins are expressed are subcultured at the rate of $5 \times 10^5$ cells/well in a 12-well plate and cultured at 37° C. in a humidified 5% $CO_2$/95% air atmosphere for two days to prepare the sample.

③ Labeled Test Compound.

The compound which is labeled with commercially available [$^3$H], [$^{125}$I], [$^{14}$C], [$^{35}$S], etc. or labeled with a suitable method.

The product in a state of an aqueous solution is stored at 4° C. or at −20° C. and, upon use, diluted to 1 μM with a buffer for the measurement. In the case of the test compound which is hardly soluble in water, it is dissolved in dimethylformamide, DMSO, methanol, etc.

④ Unlabeled Test Compound.

The same compound for the labeled one is prepared in a concentration of 100 to 1,000-fold concentrated state.

2. Method of Measurement.

① G protein coupled receptor protein-expressing CHO cells cultured in a 12-well tissue culture plate are washed twice with 1 ml of buffer for the measurement and then 490 μl of buffer for the measurement is added to each well.

② Five μl of the labeled test compound is added and the mixture is made to react at room temperature for one hour. For measuring the nonspecific binding amount, 5 μl of the unlabeled test compound is added.

③ The reaction solution is removed from each well, which is washed with 1 ml of a buffer for the measurement three times. The labeled test compound which is binding with the cells is dissolved in 0.2N NaOH-1% SDS and mixed with 4 ml of a liquid scintillator A (manufactured by Wako Pure Chemical, Japan).

④ Radioactivity is measured using a liquid scintillation counter (manufactured by Beckmann).

The ligand which can bind with the G protein coupled receptor protein include substances occurring or existing, for example, in brain, pituitary gland, pancreas, etc. Examples of the ligand are angiotensin, bombesin, canavinoid, cholecystokinin, glutamine, serotonin, melatonin, neuropeptide Y, opioid, purine, vasopressin, oxytocin, VIP (vasoactive intestinal and related peptide), somatostatin, dopamine, motilin, amylin, bradykinin, CGRP (calcitonin gene related peptide), adrenomedullin, leukotriene, pancreastatin, prostaglandin, thromboxane, thromboxatin, adenosine, adrenaline, α- and β-chemokine (IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, modified derivatives thereof, analogues thereof, etc.

Since the receptor protein encoded by pMAH2-17 is highly homologous to prinoceptors, it is considered that there are strong possibility of a subtype within prinoceptor families. All data including electrophysiological measurements are supporting that the mouse pancreatic β-cell strain, MIN6-derived receptor protein of the present invention (e.g., SEQ ID NO: 38 and SEQ ID NO: 39, or proteins encoded by pMAH2-17) is a novel purinoceptor subtype. In other words, it is suggested that the ligand capable of binding with the mouse pancreatic B -cell strain, MIN6-derived receptor protein of the present invention (e.g., SEQ ID NO: 38 and SEQ ID NO: 39, or proteins encoded by pMAH2-17) is a purine compound such as ATP. Further, the receptor protein :e.g., SEQ ID NO: 56, or proteins encoded by phAH2-17) is considered to be a novel human type purinoceptor. It is presumed that it is advantageously useful in efficiently screening for agonists or antagonists to receptor proteins which control or regulate functions in the central nervous system or immune system, related to purine compounds, and in developing pharmaceuticals.

(2) Preventive and Therapeutic Agent for of G Protein Conjugated Receptor Protein Deficiency Diseases If a ligand to the G protein coupled receptor protein is disclosed via the aforementioned method (1), the G protein coupled receptor protein-encoding DNA can be used a preventive and/or therapeutic agent for treating said G protein coupled receptor protein deficiency diseases depending upon the action that said ligand exerts.

For example, when there is a patient for whom the physiological action of the ligand cannot be expected because of a decrease in the G protein coupled receptor protein in vivo, the amount of the G protein coupled receptor protein in the brain cells of said patient can be increased whereby the action of the ligand can be fully achieved by:

(a) administering the G protein coupled receptor protein-encoding DNA to the patient to express it; or (b) inserting the G protein coupled receptor protein-encoding DNA into brain cells or the like to express it, followed by transplanting said brain cells or the like to said patient. Accordingly, the G protein coupled receptor protein-encoding DNA can be used as a safe and less toxic preventive and therapeutic agent for the G protein coupled receptor protein deficiency diseases. In an embodiment, it is suggested that the ligands capable of binding with the mouse pancreatic β-cell strain, MIN6-derived receptor protein of the present invention (e.g., SEQ ID NO: 38 and SEQ ID NO: 39, or proteins encoded by pMAH2-17) and further with the human-derived receptor protein of the present invention (e.g., SEQ ID NO: 56, or proteins encoded by phAH2-17) are purine compounds such as ATP. Therefore, the disease to be treated may include diseases or syndromes in connection with purine ligand compounds. Examples of such diseases may include cancer, immunodeficiency, autoimmune disease, rheumatoid arthritis, rejection or internal organ transplant, hypertension, diabetes, cystic fibrosis, hypotension, incontinence of urine, pain, etc.

(3) Preventive and Therapeutic Pharmaceutical Composition for Human-Derived G Protein Conjugated Receptor Protein Deficiency Diseases If the human-derived G protein coupled receptor protein-encoding DNA is screened and a ligand for said human-derived G protein coupled receptor protein can be clarified using the above-mentioned method (1), the human-derived G protein coupled receptor protein-encoding DNA can be used as an agent for the prevention or therapy of the deficiency diseases of said human-derived G protein coupled receptor protein depending upon the action that said ligand exhibits.

For example, when there is a patient for whom the physiological action of the ligand cannot be expected because of a decrease in the G protein coupled receptor protein in vivo, the amount of the G protein coupled receptor protein in the brain cells of said patient can be increased whereby the action of the ligand can be fully achieved by:

(a) administering the G protein coupled receptor protein-encoding DNA to the patient to express it; or (b) inserting the G protein coupled receptor protein-encoding DNA into brain cells or the like to express it, followed by transplanting said brain cells or the like to said patient. Accordingly, the G protein coupled receptor protein-encoding DNA can be used as a safe and less toxic preventive and therapeutic agent for the G protein coupled receptor protein deficiency diseases.

When the G protein coupled receptor protein-encoding DNA is used as the above-mentioned agent, said DNA may be used alone or after inserting it into a suitable vector such as retrovirus vector, adenovirus vector, adenovirus-associated virus vector, etc. followed by subjecting the product vector to a conventional means. Thus, it may be administered orally parenterally, by inhalation spray, rectally, or topically as pharmaceutical compositions or formulations. Oral formulations include tablets (sugar-coated if necessary), capsules, elixirs, microcapsules, etc. Parenteral formulations include injections such as an aseptic solution or a suspension in water or in other pharmaceutically acceptable liquid. For example, the DNA of the present invention is admixed in a unit dose form which is required for preparing generally approved pharmaceutical preparations together with a physiologically acceptable carriers, flavoring agents, adjuvants, excipients, diluents, fillers, vehicles, antiseptics, stabilizers, binders, etc. whereupon the preparation can be manufactured. The amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricating agents such as magnesium stearate; sweetening agents such as sucrose, lactose and saccharine; and flavoring agents such as pepper mint, akamono oil and cherry. When the unit dose form of the preparation is a capsule, a liquid carrier such as fat/oil may be further added in addition of the above-mentioned types of materials. The aseptic composition for injection may be formulated by conventional practices for the preparations such as that the active substance in a vehicle such as water for injection is dissolved or suspended in naturally occurring plant oil such as sesame oil and palm oil.

Examples of an aqueous liquid for injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), poly-alcohol (e.g. propylene glycol polyethylene glycol, etc.), nonionic surface-active agent (e.g. Polysorbate 80#, HCO-50, etc.), etc. may be jointly used. Examples of an oily liquid include sesame oil, soybean oil, etc. wherein benzyl benzoate, benzyl alcohol, etc. may be jointly used as auxiliary solubilizers. In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol phenol, etc.), antioxidants, etc. may be admixed therewith too. The prepared injection solution is filled in suitable ampoules. The preparation prepared as such is safe and less toxic and, therefore, it can be administered to warm-blooded animals (e.g., rat, rabbit, sheep, swine, cattle, cat, dog, monkey, human beings, etc.).

Specific dose levels of said DNA may vary depending upon a variety of factors including the activity of drugs employed, the age, body weight, general health, sex, diet, time of administration, route of administration, drug combination, and the severity of the symptom. In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object (patient) to be administered, organs to be administered, symptoms, administering methods, etc. but, in the case of injections, it is usually convenient to give by an intravenous route in an amount of about 0.01–30 mg, preferably about 0.1–20 mg or, more preferably, about 0.1–10 mg per day to adults (as 60 kg). In the case of other animals, the dose calculated for 60 kg may be administered as well.

(4) Quantitative Determination of Ligand to the G Protein Conjugated Receptor Protein of the Present Invention.

The G protein coupled receptor protein or a peptide fragment thereof has a binding property to ligand and, therefore, it is capable of determining quantitatively an amount of ligands in vivo with good sensitivity.

This quantitative determination may be carried out by, for example, combining with a competitive method. Thus, samples to be determined is contacted with G protein coupled receptor proteins or peptide fragments thereof so that the ligand concentration in said sample can be determined. In one embodiment of the quantitative determination, the protocols described in the following ① and ② or the methods similar thereto may be used:

① Hiroshi Irie (ed): "Radioimmunoassay" (Kodansha, Japan, 1974); and

② Hiroshi Irie (ed): "Radioimmunoassay, Second Series" (Kodansha, Japan, 1979).

(5) Screening of Compound Inhibiting the Binding of Ligand with the G Protein Conjugated Receptor Protein of the Present Invention.

G Protein coupled receptor proteins or peptide fragments thereof are used. Alternatively, expression systems for recombinant type G Protein coupled receptor proteins or peptide fragments thereof are constructed and receptor binding assay systems using said expression system are used. In these assay systems, it is possible to screen compounds (e.g. peptides, proteins, nonpeptidic compounds, synthetic compounds, fermented products, cell extracts, plant extracts, animal tissue extracts, etc.) or salts thereof which inhibits the binding of a ligand with the G protein coupled receptor protein. Such a compound includes a compound exhibiting a G protein coupled receptor-mediated cell stimulating activity (e.g. activity of promoting or activity of inhibiting physiological reactions including liberation of arachcionic acid, liberation of acetylcholine, endocellular $Ca^{2+}$ Liberation, endocellular cAMP production, endocellular cGMP production, production of inositol phosphate, changes in cell membrane potential, phosphorylation of endocellular proteins, activation of c-fos, lowering of pH, activation of G protein, cell promulgation, etc.) (so-called "G protein coupled receptor-agonist"), a compound free of such a cell stimulating activity (so-called "G protein coupled receptor-antagonist"), etc.

Thus, the present invention provides a method of screening a compound which inhibits the binding of a ligand with a G protein coupled receptor protein or a salt thereof, characterized in comparing the following two cases:

(i) the case wherein the ligand is contacted with the G protein coupled receptor protein or salt thereof, or a peptide fragment thereof or a salt thereof; and (ii) the case wherein the ligand is contacted with a fixture of the G protein coupled receptor protein or salt thereof or the peptide fragment or salt thereof and said test compound.

In said screening method, one characteristic feature of the present invention resides in that the amount of the ligand bonded with said G protein coupled receptor protein or the peptide fragment thereof, the cell stimulating activity of the ligand, etc. are measured in the case where (i) the ligand is contacted with G protein coupled receptor proteins or peptide fragments thereof and in the case where (ii) the ligand and the test compound are contacted with the G protein coupled receptor protein or the peptide fragment thereof, respectively and then compared therebetween.

In one more specific embodiment of the present invention, the following is provided:

① a method of screening a compound or a salt thereof which inhibits the binding of a ligand with a G protein coupled receptor protein, characterized in that, when a labeled ligand is contacted with a G protein coupled receptor protein or a peptide fragment thereof and when a labeled ligand and a test compound are contacted with a G protein coupled receptor protein or a peptide fragment thereof, the amounts of the labeled ligand bonded with said protein or peptide fragment thereof or salt thereof are measured and compared;

② a method of screening a compound or a salt thereof which inhibits the binding of a ligand with a G protein coupled receptor protein, characterized in that, when a labeled ligand is contacted with cells containing G protein coupled receptor proteins or a membrane fraction of said cells and when a labeled ligand and a test compound are contacted with cells containing G protein coupled receptor proteins or a membrane fraction of said cells, the amounts of the labeled ligand binding with said protein or peptide fragment thereof or salt thereof are measured and compared;

③ a method of screening a compound or a salt thereof which inhibits the binding of a ligand with a G protein coupled receptor protein, characterized in that, when a labeled ligand is contacted with G protein coupled receptor proteins expressed on the cell membrane by culturing a transformant containing a G protein coupled receptor protein encoding DNA and when a labeled ligand and a test compound are contacted with G protein coupled receptor proteins expressed on the cell membrane by culturing a transformant containing a G protein coupled receptor protein encoding DNA, the amounts of the labeled ligand binding with said G protein coupled receptor protein are measured and compared;

④ a method of screening a compound or a salt thereof which inhibits the binding of a ligand with a G protein coupled receptor protein, characterized in that, when a G protein coupled receptor protein-activating compound (e.g. a ligand to the G protein coupled receptor protein) is contacted with cells containing G protein coupled receptor proteins and when the G protein coupled receptor protein-activating compound and a test compound are contacted with cells containing G protein coupled receptor proteins, the resulting G protein coupled receptor protein-mediated cell stimulating activities (e.g. activities of promoting or activities of inhibiting physiological responses including liberation of arachdonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of G protein, cell promulgation, etc.) are measured and compared; and ⑤ a method of screening a compound or a salt thereof which inhibits the binding of a ligand with a G protein coupled receptor protein, characterized in that, when a G protein coupled receptor protein-activating compound (e.g. a ligand to the G protein coupled receptor protein) is contacted smith G protein coupled receptor proteins expressed on cell membranes by culturing transformants containing G protein coupled receptor protein-encoding DNA and when a G protein coupled receptor protein-activating compound and a test compound are contacted with the G protein coupled receptor protein expressed on the cell membrane by culturing the transformant containing the G protein coupled receptor protein-encoding DNA, the resulting G protein coupled receptor protein-mediated cell stimulating activities (activities of promoting or activities of inhibiting physiological responses such as liberation of arachdonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of CG protein, and cell promulgation) are measured and compared.

Before the G protein coupled receptor protein of the present invention was obtained, the G protein coupled receptor agonist or antagonist had to be screened by, first, obtaining a candidate compound by using G protein coupled receptor protein-containing cells, tissues or cell membrane fractions derived from rat or the like (primary screening) and, then, making sure whether the candidate compound really inhibits the binding between human G protein coupled receptor proteins and ligands (secondary screening). Other receptor proteins inevitably exist when the cells, the tissues or the cell membrane fractions are used as they are, whereby they intrinsically make it difficult to screen agonists or antagonists to the desired receptor proteins. By using the human-derived G protein coupled receptor protein, however, there is no need of effecting the primary screening, whereby it is allowable to efficiently screen a compound that inhibits the binding between a ligand and a G protein coupled receptor. Besides, it is allowable to evaluate whether the compound that is screened is a G protein coupled receptor agonist or a G protein coupled receptor antagonist.

Specific explanations of the screening method will be given as hereunder.

First, with respect to the G protein coupled receptor protein used for the screening method of the present invention, any product may be used so far as it contains G protein coupled receptor proteins or peptide fragment thereof although the use of a membrane fraction of mammalian organs is suitable. However, human organs is extremely hardly available and, accordingly, G protein coupled receptor proteins which are expressed in a large amount using a recombinant are suitable for the screening.

In the manufacture of the G protein coupled receptor protein, the above-mentioned method can be used and it may be carried out by expressing the DNA coding for said protein in mammalian cells or in insect cells. With respect to the DNA fragment coding for the target region, complementary DNA may be used although it is not limited thereto. Thus, for example, gene fragments or synthetic DNA may be used as well.

In order to introduce the G protein coupled receptor protein-encoding DNA fragment into host animal cells and to express it efficiently, it is preferred that said DNA fragment is incorporated into the downstream of polyhedron promoter of nuclear polyhedrosis virus belonging to baculovirus, promoter derived from SV40, promoter of retrovirus, metallothionein promoter, human heat shock promoter, cytomegalovirus promoter, SRα promoter, etc. Examinations of the quantity and the quality of expressed receptors can be carried out by known methods per se or modified methods substantially analogous thereto. For example, they may be conducted by the method described in publications such as Nambi, P. et al.: The Journal of Biochemical Society, vol.267, pages 19555–19559 (1992).

Accordingly, in the screening method, the substance containing a G protein coupled receptor protein or a peptide fragment thereof may be a G protein coupled receptor protein which is purified by known methods per se or a G protein coupled receptor protein fragment which is purified by known methods per se, or a cell containing said protein or a cell membrane fraction of the cell containing said protein, etc.

When the G protein coupled receptor protein-containing cells are used in the screening method, said cells may be immobilized with glutaraldehyde, formalin, etc. The immobilization may be carried out by known methods per se or modified methods substantially analogous thereto.

The G protein coupled receptor protein-containing cells are host cells expressing the G protein coupled receptor protein. Examples of said host cells may include *Escherichia coli*, *Bacillus subtilis*, yeasts, insect cells, animal cells such as CHO cell and COS cell, etc.

Cell membrane fractions are fractions which contain a lot of cell membranes prepared by known methods per se or modified methods substantially analogous thereto after disrupting or crushing the cells. Examples of disruptions of the cell may include methods by squeezing the cells with a Potter-Elvejem homogenizer, disrupting or crushing by a Waring blender or a Polytron (manufactured by Kinematica), disrupting or crushing by means of ultrasonic wave, disrupting by blowing out the cells from small nozzles together with apply ng a pressure with a French press or the like, etc. Fractionation of the cell membrane is carried out mainly by fractionation techniques by means of centrifugal force such as a fractional centrifugal separation and a density gradient centrifugal separation. For example, disrupted liquid of cells is centrifuged at a low speed (500 rpm to 3,000 rpm) for a short period (usually, from about one to ten minutes), the supernatant liquid is further centrifuged at a high speed (1,500 rpm to 3,000 rpm) usually for 30 minutes to two hours and the resulting precipitate is used as a membrane fraction. Said membrane fraction contains a lot of expressed G protein coupled receptor proteins and membrane components such as phospholipids and membrane proteins derived from the cells.

The amount of the G protein coupled receptor protein in the G protein coupled receptor protein-containing cell and in the cell membrane fraction obtained from the cell is preferably $10^3$–$10^8$ molecules per cell or, suitably, $10^5$ to $10^7$ molecules per cell. Incidentally, the more the expressed amount, the higher the ligand binding activity (specific activity) per membrane fraction whereby the construction of a highly sensitive screening system is possible and, moreover, it is possible to measure the large amount of samples in the same lot.

In conducting the above-mentioned methods ① to ③ for screening the compound capable of inhibiting the binding of the ligand with the G protein coupled receptor protein, a suitable G protein coupled receptor fraction and a labeled ligand are necessary. With respect to the G protein coupled receptor fraction, it is preferred to use naturally occurring G protein coupled receptors (natural type G protein coupled receptors) or recombinant type G protein coupled receptor fractions with the activity equivalent to that of the natural type G protein coupled. Here the term "activity equivalent to" means the same ligand binding activity, or the substantially equivalent ligand binding activity.

With respect to the labeled ligand, it is possible to use labeled ligands, labeled ligand analogized compounds, etc. For example, ligands labeled with [$^3$H], [$^{125}$I], [$^{14}$C], [$^{35}$S], etc. and other labeled substances may be utilized.

Specifically, G protein coupled receptor protein-containing cells or cell membrane fractions are first suspended in a buffer which is suitable for the determining method to prepare the receptor sample in conducting the screening for a compound which inhibits the binding of the ligand with the G protein coupled receptor protein. With respect to the buffer, any buffer such as Tris-HCl buffer or phosphate buffer of pH 4–10 (preferably, pH 6–8) which does not inhibit the binding of the ligand with the receptor may be used.

In addition, a surface-active agent such as CHAPS, Tween 80™ (Kao-Atlas, Japan), digitonin, deoxycholate, etc. and/or various proteins such as bovine serum albumin (BSA), gelatine, etc. may be added to the buffer with an object of decreasing the nonspecific binding. Further, a protease inhibitor such as PMSF, leupeptin, E-64 (manufactured by Peptide Laboratory, Japan), pepstatin, etc. may be added with an object of inhibiting the decomposition of the receptor and the ligand by protease. A labeled ligand in a certain amount (5,000 cpm to 500,000 cpm) is added to 0.01 ml to 10 ml of said receptor solution and, at the same time, $10^{-4}$ M to $10^{-10}$ M of a test compound is made copresent. In order to determine the nonspecific binding amount (NSB), a reaction tube to which a great excessive amount of unlabeled test compounds is added is prepared as well.

The reaction is carried out at 0–50° C. (preferably at 4–37° C.) for 20 minutes to 24 hours (preferably 30 minutes to three hours). After the reaction, it is filtered through a glass fiber filter, a filter paper, or the like, washed with a suitable amount of the same buffer and the radioactivity retained in the glass fiber filter, etc. is measured by means of a liquid scintillation counter or a gamma-counter. Supposing that the count ($B_0$–NSB) obtained by subtracting the nonspecific binding amount (NSB) from the total binding amount ($B_0$) wherein an antagonizing substance is not present is set at 100%, the test compound in which the specific binding amount (B–NSB) obtained by subtracting the nonspecific binding amount (NSB) from the total binding amount (B) is, for example, less than 50% may be selected as a candidate ligand to the G protein coupled receptor protein of the present invention.

In conducting the above-mentioned methods ④ to ⑤ for screening the compound which inhibits the binding of the ligand with the G protein coupled receptor protein, tie G protein coupled receptor protein-mediated cell stimulating activity (e.g. activities of promoting or activities of inhibiting physiological responses such as liberation of arachidonic acid, liberation of acetylcholine, endocellular $Ca^{2+}$ liberation, endocellular cAMP production, production of insitol phosphate, changes in the cell membrane potential, phosphorylation of endocellular proteins, activation of c-fos, lowering of pH, activation of G protein and cell promulgation, etc.) may be measured by known methods or by the use of commercially available measuring kits. To be more specific, G protein coupled receptor protein-containing cells are at first cultured in a multiwell plate or the like.

In conducting the screening, it is substituted with a suitable buffer which does not show toxicity to fresh media or cells in advance, incubated for a certain period after adding a test compound, etc. thereto. The resultant cells are extracted or the supernatant liquid is recovered and the resulting product is determined, preferably quantitatively, by each of the methods. When it is difficult to identify the production of the index substance (e.g. arachidonic acid, etc.) which is to be an index for the cell stimulating activity due to the presence of decomposing enzymes contained in the cell, an assay may be carried out by adding an inhibitor against said decomposing enzyme. With respect to the activities such as an inhibitory action against cAMP production, it may be detected as an inhibitory action against the cAMP production in the cells whose fundamental production has been increased by forskolin or the like.

In conducting a screening by measuring the sell stimulating activity, cells in which a suitable G protein coupled receptor protein is expressed are necessary. Preferred G protein coupled receptor protein-expressing cells are naturally occurring G protein coupled receptor protein (natural type G protein coupled receptor protein)-containing cell lines or strains (e.g. mouse pancreatic B cell line, MIN6, etc.), the above-mentioned recombinant type G protein coupled receptor protein-expressing cell lines or strains, etc.

Examples of the test compound includes peptides, proteins, non-peptidic compounds, synthesized compounds, fermented products, cell extracts, plant extracts, animal tissue extracts, serum, blood, body fluid, etc. Those compounds may be novel or known.

A kit for screening the compound which inhibits the binding of the ligand with the G protein coupled receptor protein or a salt thereof of the present invention comprises a G protein coupled receptor protein or a peptide fragment thereof, or G protein coupled receptor protein-containing cells or cell membrane fraction thereof.

Examples of the screening kit include as follows:

1. Reagent for Determining Ligand.

① Buffer for Measurement and Buffer for Washing.

The product wherein 0.05% of bovine serum albumin (manufactured by Sigma) is added to Hanks' Balanced Salt Solution (manufactured by Gibco).

This may be sterilized by filtration through a membrane filter with a 0.45 μm pore size, and stored at 4° C. or may be prepared upon use.

② Sample of G Protein Conjugated Receptor Protein.

CHO cells in which a G protein coupled receptor protein is expressed are subcultured at the rate of $5 \times 10^5$ cells/well in a 12-well plate and cultured at 37° C. with a 5% $CO_2$ and 95% air atomosphere for two days to prepare the sample.

③ Labeled Ligand.

The ligand which is labeled with commercially available [$^3$H], [$^{125}$I], [$^{14}$C], [$^{35}$S], etc.

The product in a state of an aqueous solution is stored at 4° C. or at −20° C. and, upon use, diluted to 1 μM with a buffer for the measurement.

④ Standard Ligand Solution.

Ligand is dissolved in PBS containing 0.1% of bovine serum albumin (manufactured by Sigma) to make 1 mM and stored at −20° C.

2. Method of the Measurement.

① CHO cells are cultured in a 12-well tissue culture plate to express G protein coupled receptor proteins. The G protein coupled receptor protein-expressing CHO cells are washed with 1 ml of buffer for the measurement twice. Then 490 μl of buffer for the measurement is added to each well.

② Five a 1 of a test compound solution of $10^{-3}$ to $10^{-10}$ M is added, then 5 μl of a labeled ligand is added and is made to react at room temperature for one hour. For knowing the non-specific binding amount, 5 μl of the ligand of $10^{-3}$ M is added instead of the test compound.

③ The reaction solution is removed from the well, which is washed with 1 ml of buffer for the measurement three times. The labeled ligand binding with the cells is dissolved in 0.2N NaOH-1% SDS and mixed with 4 ml of a liquid scintillator A (manufactured by Wako Pure Chemical, Japan).

④ Radioactivity is measured using a liquid scintillation counter (manufactured by Beckmann) and PMB (percent of maximum binding) is calculated by the following expression:

$$PMB=[(B-NSB)/(B_0-NSB)] \times 100$$

PMB: Percent of maximum binding
B: Value when a sample is added
NSB: Nonspecific binding
$B_0$ : Maximum binding The compound or a salt thereof obtained by the screening method or by the screening kit is a compound which inhibits the binding of a ligand with a G protein coupled receptor protein and, more particularly, it is a compound having a cell stimulating activity mediated via a G protein coupled receptor or a salt thereof (so-called "G protein coupled receptor agonist") or a compound having no said stimulating activity (so-called "G protein coupled receptor antagonist"). Examples of said compound are peptides;, proteins, non-peptidic compounds, synthesized compounds, fermented products, etc. and the compound may be novel or known.

Said G protein coupled receptor agonist ha, the same physiological action as the ligand to the G protein coupled receptor protein has and, therefore, it is useful as a safe and less toxic pharmaceutical composition depending upon said ligand activity.

On the other hand, said G protein coupled receptor antagonist is capable of inhibiting the physiological activity of the ligand to the G protein coupled receptor protein and, there fore, it is useful as a safe and less toxic pharmaceutical composition for inhibiting said ligand activity.

It is also strongly suggested that agonists and/or antagonists related to the receptor encoded by pMAH2-17 obtained in Example 19 and/or the receptor encoded by phAH2-17 obtained in Example 21 would be useful in therapeutic or prophylactic treatment of diseases or syndromes in connection with purine ligand compounds or related analogues. It is expected that the agonists of the receptor encoded by pMAH2-17 and/or of the receptor encoded by phAH2-17 are useful as an immunomodulator or an antitumor agent, in addition they are useful in therapeutically or prophylactically treating hypertension, diabetes, cystic fibrosis, etc. It is still expected that the antagonists of the receptor encoded by pMAH2-17 and/or of the receptor encoded by phAH2-17 are useful as hypotensive agents, analgesics, agents for therapeutically or prophylactically treating incontinence of urine, etc. With regard to purinoceptors, the mutation of conserved basic amino acid residues in the 6th or 7th putative transmembrane domain of purinoceptors introduces alteration into the receptor's responses to ATP (J. Biol. Chem., Vol. 270(9), pp. 4185–4188 (1995)). It is suggested that ATP is related to blood pressure control and circular systems via receptors (Circulation Research, Vol. 58(3), pp. 319–330 (1986)) and that ATP and purinoceptors are closely related (Am. Phys. Soc., pp. C577–C606 (1993).

When the compound or the salt thereof obtained by the screening method or by the screening kit is used as the above-mentioned pharmaceutical composition, a conventional means may be applied therefor. The compound or the salt thereof may be orally, parenterally, by inhalation spray, rectally, or topically administered as pharmaceutical compositions or formulations (e.g. powders, granules, tablets, pills, capsules, injections, syrups, emulsions, elixirs, suspensions, solutions, etc.). For example, it may be used by an oral route as tablets (sugar-coated if necessary), capsules, elixiers, microcapsules, etc. or by a parenteral route as injections such as an aseptic solution or a suspension in water or in other pharmaceutically acceptable liquid. The pharmaceutical compositions or formulations may comprise at least one such compound alone or in admixture with pharmaceutically acceptable carriers, adjuvants, vehicles, excipients and/or diluents. The pharmaceutical compositions cam be formulated in accordance with conventional methods. For example, said compound or the salt thereof is mixed in a unit dose form which is required for preparing a generally approved pharmaceutical preparations together with a physiologically acceptable carriers, flavoring and/or perfuming agents (fragrances), fillers, vehicles, antiseptics, stabilizers, binders, etc. whereupon the preparation can be manufactured. An amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricants such as magnesium stearate; sweetening agents such as sucrose, lactose and saccharine; preservatives such as parabens and sorbic acid; antioxidants such as ascorbic acid, α-tocopherol and cysteine; fragrances such as peppermint, akamono oil and cherry; disintegrants; buffering agents; etc. Other additives may include mannitol, maltitol, dextran, agar, chitin, chitosan, pectin, collagen, casein, albumin, synthetic or semi-s;ynthetic polymers, glyceride, lactide, etc. When the unit form of the preparation is a capsule, a liquid carrier such as fat/oil may be further added besides the above-mentioned types of materials. The aseptic composition for injection may be formulated by a conventional technique or practice for the preparations such as that the active substance in a vehicle such as water for injection is dissolved or suspended in a naturally occurring plant oil such as sesame oil and palm oil.

Examples of an aqueous liquid for the injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), polyalcohol (e.g. propylene glycol, polyethylene glycol, etc.), nonionic surface-active agent (e.g. Polysorbate 80™, HCO-50, etc.), etc. may be jointly used. In the case of the oily liquid, sesame oil, soybean oil, etc. may be exemplified wherein benzyl benzoate, benzyl alcohol, etc. may be jointly used as auxiliary solubilizers.

In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol, phenol, etc.), antioxidants, etc. may be compounded therewith too. The prepared injection solution is filled in suitable ampoules. The formulation prepared as such is safe and less toxic and, therefore, it can be administered to warm-blooded mammals such as rats, rabbits, sheep, swines, cattle, cats, dogs, monkeys, human being, etc.

Dose levels of said compound or the salt thereof may vary depending upon the symptom. Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object to be administered, organs to be administered, symptoms, administering methods, etc. The term "parenteral" as used herein includes subcutaneous injections, intravenous, intramuscular, intraperitoneal injections, or infusion techniques. In the case of injections, it is usually convenient to give by an intravenous route in an amount of about 0.01–30 mg, preferably about 0.1–20 mg or, more preferably, about 0.1–10 mg per day to adults (as 60 kg). In the case of other animals, the dose calculated for 60 kg may be administered as well.

(6) Manufacture of Antibody or Antiserum against the G Protein Coupled Receptor Protein of the Present Invention, Its Peptide Fragment or Its Salt.

Antibodies (e.g. polyclonal antibody and monoclonal antibody) and antisera against the G protein coupled receptor protein or salt thereof of the present invention or against the peptide fragment of the G protein coupled receptor protein or salt thereof of the present invention may be manufactured by antibody or antiserum-manufacturing methods per se known to those of skill in the art or methods similar thereto, using the G protein coupled receptor protein or its salt of the present invention or the peptide fragment of the G protein coupled receptor protein or its salt of the present invention. For example, monoclonal antibodies can be manufactured by the method as given below.

[Preparation of Monoclonal Antibody]

(a) Preparation of Monoclonal Antibody-Producing Cells.

The G protein coupled receptor protein of the present invention or its salt or the peptide fragment of the C; protein coupled receptor protein of the present invention or its salt (hereinafter, may be abbreviated as the "G protein coupled receptor protein") is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens and the use of mice and rats is preferred.

In the preparation of the cells which produce monoclonal antibodies, an animal wherein the antibody titer is noted is selected from warm-blooded animals (e.g. mice) immunized with antigens, then spleen or lymph node is collected after two to five days from the final immunization and antibody-producing cells contained therein are fused with myeloma cells to give monoclonal antibody-producing hybridomas. Measurement of the antibody titer in antisera may, for example, be carried out by reacting a labeled G protein coupled receptor protein (which will be mentioned later) with the antiserum followed by measuring the binding activity of the labeling agent with the antibody. The operation for fusing may be carried out, for example, by a method of Koehler and Milstein (Nature, 256, 495, 1975). Examples of the fusion accelerator are polyethylene glycol (PEG), Sendai virus, etc. and the use of PEG is preferred.

Examples of the myeloma cells are NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10–80% followed by incubating at 20–40° C. (preferably, at 30–37° C.) for one to ten minutes, an efficient cell fusion can he carried out.

Various methods may be applied for screening a hybridoma which produces anti-G protein coupled receptor antibody. For example, a supernatant liquid of hybridoma culture is added to a solid phase (e.g. microplate) to which the G protein coupled receptor protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then anti-G protein coupled receptor monoclonal antibodies bound on the solid phase are detected; or a supernatant liquid of the hybridoma culture is added to the solid phase to which anti-immunoglobulin or protein A is adsorbed, then the G protein coupled receptor labeled with a radioactive substance or an enzyme is added and anti-G protein coupled receptor monoclonal antibodies bonded with the solid phase is detected.

Selection and cloning of the anti-G protein coupled receptor monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1–20% (preferably 10–20%) of fetal calf serum (FCS), a GIT medium (Wako Pure Chemical, Japan) containing 1–20% of fetal calf serum and a serum-free medium for hybridoma culturing (SFM-101; Nissui Seiyaku, Japan). The culturing temperature is usually 20–40° C. and, preferably, about 37° C. The culturing time is usually from five days to three weeks and, preferably, one to two weeks. The culturing is usually carried out in 5% carbon dioxide gas. The antibody titer of the supernatant liquid of the hybridoma culture may be measured by the same manner as in the above-mentioned measurement of the antibody titer of the anti-G protein coupled receptor in the antiserum.

The cloning can be usually carried out by methods known per se such as techniques in semi-solid agar and limiting dilution. The cloned hybridoma is preferably cultured in modern serum-free culture media to obtain optimal amounts of antibody in supernatants. The target monoclonal antibody is also preferably obtained from ascitic fluid derived from a mouse, etc. injected intraperitoneally with live hybridoma cells.

(b) Purification of the Monoclonal Antibody.

Like in the separation/purification of conventional polyclonal antibodies, the separation/purification of the anti-G protein coupled receptor monoclonal antibody may be carried out by methods for separating/purifying imminoglobulin (such as salting-out, precipitation with an alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent (such as an antigen-binding solid phase, protein A or protein G) and the bond is dissociated whereupon the antibody is obtained.

The G protein coupled receptor antibody of the present invention which is manufactured by the aforementioned method (a) or (b) is capable of specifically recognizing G protein coupled receptors and, accordingly, it can be used for a quantitative determination of the G protein coupled receptor in test liquid samples and particularly for a quantitative determination by sandwich immunoassays.

Thus, the present invention provides, for example, the following methods:

(i) a quantitative determination of a G protein coupled receptor in a test liquid sample, which comprises
(a) competitively reacting the test liquid sample and a labeled G protein coupled receptor with an antibody which reacts with the G protein coupled receptor of the present invention, and
(b) measuring the ratio of the labeled G protein coupled receptor binding with said antibody; and (ii) a quantitative determination of a G protein coupled receptor in a test liquid sample, which comprises
(a) reacting the test liquid sample with an antibody immobilized on an insoluble carrier and a labeled antibody simultaneously or continuously, and
(b) measuring the activity of the labeling agent on the insoluble carrier wherein one antibody is capable of recognizing the i-terminal region of the G protein coupled receptor while another antibody is capable of recognizing the C-terminal region of the G protein coupled receptor.

When the monoclonal antibody of the present invention recognizing a G protein coupled receptor (hereinafter, may be referred to as "anti-G protein coupled receptor antibody") is used, G protein coupled receptors can be measured and, moreover, can be detected by means of a tissue staining, etc. as well. For such an object, antibody molecules per se may be used or $F(ab')_2$, Fab' or Fab fractions of the antibody molecule may be used too. There is no particular limitation for the measuring method using the antibody of the present invention and any measuring method may be used so far as it relates to a method in which the amount of antibody, artigen or antibody-antigen complex, depending on or corresponding to the amount of antigen (e.g. the amount of G protein coupled receptor, etc.) in the liquid sample to be measured, is detected by a chemical or a physical means and then calculated using a standard curve prepared by a standard solution containing the known amount of antigen. For example, nephrometry, competitive method, immunometric method and sandwich method are suitably used and, in terms of sensitivity and specificity, the sandwich method which will be described herein later is particularly preferred.

Examples of the labeling agent used in the Measuring method using the labeling substance are radioisotopes, enzymes, fluorescent substances, luminescent substances, colloids, magnetic substances, etc. Examples of the radioisotope are $[^{125}I]$, $[^{131}I]$, $[^{3}H]$ and $[^{14}C]$; preferred examples of the enzyme are those which are stable and with big specific activity, such as β-galactosidase, β-glucosidase, alkali phosphatase, peroxidase and malate dehydrogenase; examples of the fluorescent substance are fluorescamine, fluorescein isothiocyanate, etc.; and examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well.

Examples of the carrier are insoluble polysaccharides such as agarose, dextran and cellulose; synthetic resins such as polystyrene, polyacrylamide and silicone; glass; etc.

In a sandwich (or two-site) method, the test liquid is made to react with an insolubilized anti-G protein coupled receptor antibody (the first reaction), then it is made to react with a labeled anti-G protein coupled receptor antibody (the second reaction) and the activity of the labeling agent on the insoluble carrier is measured whereupon the amount of the G protein coupled receptor in the test liquid can be determined. The first reaction and the second reaction may be conducted reversely or simultaneously or they may be conducted with an interval. The type of the labeling agent and the method of insolubilization (immobilization) may be the same as those mentioned already herein. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used too.

In the method of measuring G protein coupled receptors by the sandwich method of the present invention, the preferred anti-G protein coupled receptor antibodies used for the first and the second reactions are antibodies wherein their sites binding to the G protein coupled receptors are different each other. Thus, the antibodies used in the first and the second reactions are those wherein, when the antibody used in the second reaction recognizes the C-terminal region of the G protein coupled receptor, then the antibody recognizing the site other than C-terminal regions, e.g. recognizing the N-terminal region, is preferably used in the first reaction.

The anti-G protein coupled receptor antibody of the present invention may be used in a measuring system other than the sandwich method such as a competitive method, an immunometric method and a nephrometry. In a competitive method, an antigen in the test solution and a labeled antigen are made to react with an antibody in a competitive manner, then an unreacted labeled antigen (F) and a labeled antigen binding with an antibody (B) are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In an immunometric method, an antigen in the test solution and an immobilized antigen are subjected to a. competitive reaction with a certain amount of a labeled antibody followed by separating into solid and liquid phases; or the antigen in the test solution and an excess amount of labeled antibody are made to react, then a immobilized antigen is added to bind an unreacted labeled antibody with the solid phase and separated into solid and liquid phases. After that, the labeled amount of any of the phases is measured to determine the antigen amount in the test solution.

In a nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for G protein coupled receptor may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikwa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immuochemical Techniques (Part A)); ibid. Vol. 73 (Immunochemical Techniques (Part B)); ibid. Vol. 74 (Immunochemical Techniques (Part C)); ibid. Vol. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Acacdemic Press); etc.

(7) Preparation of Animals Having the G Protein Coupled Receptor Protein-Encoding DNA of the Present Invention.

It is possible to prepare transgenic animals expressing G protein coupled receptors using G protein coupled receptor protein-encoding DNA. Examples of the animals are warm-blooded mammals such as rats, rabbit, sheep, swines, cattle, cats, dogs and monkeys.

In transferring the G protein coupled receptor protein-encoding DNA to the aimed animal, it is generally advantageous that said DAN is used by ligating with a site at the downstream of a promoter which is capable of expressing in animal cells. For example, when G protein coupled receptor protein DNA is to be transferred to a rabbit, a gene construct ligated with a site at the downstream of various promoters which are capable of expressing the G protein coupled receptor protein DNA derived from an animal compatible to the animal in animal host cells is subjected to a microinjection to the fertilized ovum (oosperm) of the aimed animal (e.g. fertilized ovum (embryo) of rabbit) whereupon the transgenic animal which produces the G protein coupled receptor protein in a high amount can be prepared.

Examples of the promoters used are promoters derived from virus and ubiquitous expression promoters such as metallothionein promoters may be used but, preferably, enolase gene promoters and NGF gene promoters capable of specifically expressing in brain are used.

Transfer of the G protein coupled receptor protein DNA at a fertilized ovum cell stage is secured in order that the DNA can be present in all of embryonal cells and body somatic cells of an aimed animal. The fact that the G protein coupled receptor protein is present in the fertilized ovum cells of the produced transgenic animal after the DNA transfer means that all progeny of the produced transgenic animal have the G protein coupled receptor protein in all of their embryonal cells and somatic cells. Descendants (offsprings) of the animal of this type which inherited the gene have the G protein coupled receptor protein in all of their embryonal cells and somatic cells.

The transgenic animal to which the G protein coupled receptor protein DNA is transferred can be subjected to a mating and a breeding for generations under a common breeding circumstance as the animal holding said DNA after confirming that the gene can be stably retained. Moreover, male and female animals having the desired DNA are mated to give a homozygote having the transduced gene in both homologous chromosomes and then those male and female animals are mated whereby it is possible to breed for generations so that all descendants have said DNA.

The animal to which the G protein coupled receptor protein DNA is transferred highly expresses the G protein coupled receptor protein and, accordingly, it is useful as the animal for screening for an agonist or an antagonist to said G protein coupled receptor protein.

The DNA-transferred animal can be used as a cell source for a tissue culture. For example, DNA or RNA in the tissue of the DNA-transferred mouse is directly analyzed or protein tissues expressed by gene are analyzed whereupon the G protein coupled receptor protein can be analyzed. Cells of the G protein coupled receptor protein-containing tissue are cultured by standard tissue culture techniques whereupon it is possible to study the function of the cells which are usually difficult to culture (e.g. those derived from brain and peripheral tissues) using the resulting culture. By using said cells, it is also possible to select the pharmaceuticals which can potentiate, for example, the functions of various tissues. Moreover, if a cell strain with a high expression is available, it is possible to separate and purify G protein coupled receptor proteins therefrom.

As such, the amount of G protein coupled receptor proteins can now be determined with a high precision using the anti-G protein coupled receptor antibody of the present invention.

(8) Antisense Oligonucleotides Capable of Inhibiting Replication of G Protein Coupled Receptor Protein Gene In another aspect of the present invention, antisense oligonucleotides (nucleic acids) capable of inhibiting the replication or expression of G protein coupled receptor protein gene may be designed and synthesized based on information on the nucleotide sequences of cloned and determined G protein coupled receptor protein-encoding DNAs. Such an antisense oligonucleotide (nucleic acid) is capable of hybridizing with RNA of G protein coupled receptor protein genes to inhibit the synthesis or function of said RNA or of modulating the expression of a G protein coupled receptor protein gene via interaction with G protein coupled receptor protein-related RNA. Oligonucleotides complementary to, and specifically hybridizable with, selected sequences of G protein coupled receptor protein-related RNA are useful in controlling or modulating the expression of a G protein coupled receptor protein gene in vitro and in vivo, and in treating or diagnosing disease states of suspected animals. The term "corresponding" means homologous to or complementary to a particular sequence of the nucleotide sequence or nucleic acid including the gene. As between nucleotides (nucleic acids) and peptides (proteins), "corresponding" usually refers to amino acids of a peptide (protein) in an order derived from the sequence of a nucleotides (nucleic acids) or its complement. The G protein coupled receptor protein gene 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop may be selected as preferred targets though any region may be a target among G protein coupled receptor protein genies. The relationship between the target and oligonucleotides complementary to at least a portion of the target, specifically hybridizable with the target, is denoted as "antisense". The antisense oligonucleotides may be polydeoxynucleotides containing 2-deoxy-D-ribose, polyribonucleotides containing D-ribose, any other type of polynucleotide which is an N-glycoside of a purine or pyrimidine base, or other polymers containing nonnucleotide backbones (e.g., protein nucleic acids and synthetic sequence-specific nucleic acid polymers commercially available) or nonstandard linkages, providing that the polymers contain nucleotides in a configuration which allows for base pairing and base stacking such as is found in DNA and RNA. They may include double- and single-stranded DNA, as well as double- and single-stranded RNA and DNA:RNA hybrids, and also include, as well as unmodified forms of the polynucleotide or oligonucleotide, known types of modifications, for example, labels which are known to those skilled in the art, "caps", methylation, substitution of one or more of the naturally occurring nucleotides with analogue, internucleotide modifications such as, for example, those with uncharged linkages (e.g., methyl phosphonates, phosphotriesters, phosphoramidates, carbamates, etc.) and with charged linkages or sulfur-containing linkages (e.g., phosphorothioates, phosphorodithioates, etc.), those containing pendant moieties, such as, for example, proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators; (e.g., metals, radioactive metals, boron, oxidative metals, etc.), those containing alkylators, those with modified linkages (e.g., alpha anomeric nucleic acids, etc.). The terms, "nucleoside", "nucleotide" and "nucleic acid" will include those moieties which contain not only the known purine and pyrimidine bases, but also other heterocyclic bases which have been modified. Such modifications include methylated purines and pyrimidines, acylated purines and pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The antisense nucleic acid of the present invention is RNA, DNA or a modified nucleic acid. Examples of modified nucleic acid are, but not limited to, degradation-resistant sulfurized and thiophosphate derivatives of nucleic acids, and poly- or oligonucleoside amides. Preferred design modifications of the antisense nucleic acids of the present invention are modifications that are designed to:

(1) increase the intracellular stability of the nucleic acid;
(2) increase the cellular permeability of the nucleic acid;
(3) increase the affinity of the nucleic acid for the target sense strand; or
(4) decrease the toxicity (if any) of the nucleic acid. Many such modifications are known to those skilled in the art, as described in J. Kawakami et al., Pharm Tech Japan, Vol. 8, pp.247, 1992; Vol. 8, pp.395, 1992; S. T. Crooke et al. ed., Antisense Research and Applications, CRC Press, 1993;etc. The nucleic acids may contain altered or modified sugars, bases or linkages, be delivered in specialized systems such as liposomes, microspheres or by gene therapy, or may have attached moieties. Such attached moieties include polycationic moieties such as polylysine that act as charge neutralizers of the phosphate backbone, or hydrophobic moieties such as lipids (e.g., phospholipids, cholesterols, etc.) that enhance interaction with cell membranes or increase uptake of the nucleic acid. Preferred lipids that may attached are cholesterols or derivatives thereof (e.g., cholesteryl chloroformate, cholic acid, etc.). The moieties may be attached at the 3' or 5' ends of the nucleic acids, and also may be attached through a base, sugar, or internucleoside linkage. Other moieties may be capping groups specifically placed at the 3' or 5' ends of the nucleic acids to prevent degradation by nuclease such as exonuclease, RNase, etc. Such capping groups include, but are not limited to, hydroxyl protecting groups known to those skilled in the art, including glycols such as polyethylene glycols, tetraethylene glycol and the like.

The inhibitory activity of antisense nucleic acids can be examined using the transformant (or transfectant) of the present invention, the in vitro and in vivo gene expression system of the present invention, or the in vitro and in vivo translation system of G protein coupled receptor proteins. The nucleic acid can be placed in the cell through any number of ways known per se.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA : Deoxyribonucleic acid
cDNA: Complementary deoxyribonucleic acid
A :Adenine
T :Thymine
G : Guanine
C :Cytosine
RNA : Ribonucleic acid
mRNA : Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP : Adenosine triphosphate
EDTA: Ethylenediamine tetraacetic acid
SDS : Sodium dodecyl sulfate
EIA: Enzyme Immunoassay G, Gly: Glycine (or Glycyl)
A, Ala: Alanine (or Alanyl)
V, Val: Valine (or Valyl)
L, Leu: Leucine (or Leucyl)
I, Ile: Isoleucine (or Isoleucyl)
S, Ser: Serine (or Seryl)
T, Thr: Threonine (or Threonyl)
C, Cys: Cysteine (or Cysteinyl)
M, Met: Methionine (or Methionyl)
E, Glu: Glutamic acid (or Glutamyl)
D, Asp: Aspartic acid (or Aspartyl)
K, Lys: Lysine (or Lysyl)
R, Arg: Arginine (or Arginyl)
H, His: Histidine (or Histidyl)
F, Phe: Pheylalanine (or Pheylalanyl)
Y, Tyr: Tyrossine (or Tyrosyl)
W, Trp: Tryptophan (or Tryptophanyl)
P, Pro: Proline (or Prolyl)
N, Asn: Asparagine (or Asparaginyl)
Q, Gln: Glutamine (or Glutaminyl)
NVal: Norvaline (or Norvalyl)
pGlu: Pyroglutamic acid (or Pyroglutamyl)
Blc: γ-Butyrolacton-γ-carbonyl
Kpc: 2-Ketopiperidinyl-6-carbonyl
Otc: 3-Oxoperhydro-1,4-thiazin-5-carbonyl
Me: Methyl
Et: Ethyl
Bu: Butyl
Ph: Phenyl
TC: Thiazolidinyl-4(R)-carboxamide The transformant *Escherichia coli*, designated INVα F'/p19P2, which is obtained in the Example 3 mentioned herein below, is on deposit under the terms of the Budapest Treaty from Aug. 9, 1994, with the National Institute of Bioscience and Human-Technology (NIBH), Agency of Industrial Science and Technology, Ministry of International Trade and Industry, Japan and has been assigned the Accession Number FERM BP-4776. It is also on deposit from Aug. 22, 1994 with the Institute for Fermentation, Osaka, Japan (IFO) and has been assigned the Accession Number IFO 15739.

The transformant *Escherichia coli*, designated INVα F'/pG3-2, which is obtained in the Example 4 mentioned herein below, is on deposit under the terms of the Budapest Treaty from Aug. 9, 1994, with NIBH and has been assigned the Accession Number FERM BP-4775. It is also on deposit from Aug. 22, 1994 with IFO and has been assigned the Accession Number IFO 15740.

The transformant *Escherichia coli*, designated INVα F'/p63A2, which is obtained in the Example 5 mentioned herein below, is on deposit under the terms of the Budapest Treaty from Aug. 9, 1994, with NIBH and has been assigned the Accession Number FERM BP-4777. It is also on deposit from Aug. 22, 1994 with IFO and has been assigned the Accession Number IFO 15738.

The transformant *Escherichia coli*, designated JM109/phGR3, which is obtained in the Example 6 mentioned herein below, is on deposit under the terms of the Budapest Treaty from Sep. 27, 1994, with NIBH and has been assigned the Accession Number FERM BP-4807. It is also on deposit from Sep. 22, 1994 with IFO and has been assigned the Accession Number IFO 15748.

The transformant *Escherichia coli*, designated JM109/p3H2-17, which is obtained in the Example 7 mentioned herein below, is on deposit under the terms of the Budapest Treaty from Sep. 27, 1994, with NIBH and has been assigned the Accession Number FERM BP-4806. It is also on deposit from Sep. 22, 1994 with IFO and has been assigned the Accession Number IFO 15747.

The transformant *Escherichia coli*, designated JM109/p3H2-34, which is obtained in the Example 8 mentioned herein below, is on deposit under the terms of the Budapest Treaty from Oct. 12, 1994, with NIBH and has been assigned the Accession Number FERM BP-4828. It is also on deposit from Oct. 12, 1994 with IFO and has been assigned the Accession Number IFO 15749.

The transformant *Escherichia coli*, designated JM109/pMD4, which is obtained in the Example 9 mentioned herein below, is on deposit under the terms of the Budapest Treaty from Nov. 11, 1994, with NIBH and has been assigned the Accession Number FERM BP-4888. It is also on deposit from Nov. 17, 1994 with IFO and has been assigned the Accession Number IFO 15765.

The transformant *Escherichia coli*, designated JM109/pMGR20, which is obtained in the Example 10 mentioned herein below, is on deposit under the terms of the Budapest Treaty from Dec. 15, 1994, with NIBH and has been assigned the Accession Number FERM BP-4937. It is also on deposit from Dec. 14, 1994 with IFO and has been assigned the Accession Number IFO 15773.

The transformant *Escherichia coli*, designated JM109/pMJ10, which is obtained in the Example 12 mentioned herein below, is on deposit under the terms of the Budapest Treaty from Dec. 15, 1994, with NIBH and has been assigned the Accession Number FERM BP-4936. It is also on deposit from Dec. 16, 1994 with IFO and has been assigned the Accession Number IFO 15784.

The transformant *Escherichia coli*, designated JM109/pMH28, which is obtained in the Example 14 mentioned herein below, is on deposit under the terms of the Budapest Treaty from Jan. 13, 1995, with NIBH and has been assigned the Accession Number FERM BP-4970. It is also on deposit from Jan. 20, 1995 with IFO and has been assigned the Accession Number IFO 15791.

The transformant *Escherichia coli*, designated JM109/pMN7, which is obtained in the Example 16 mentioned herein below, is on deposit under the terms of the Budapest Treaty from Feb. 22, 1995, with NIBH and has been assigned the Accession Number FERM BP-5011. It is also on deposit from Feb. 27, 1995 with IFO and has been assigned the Accession Number IFO 15803.

The transformant *Escherichia coli*, designated JM109/p5S38, which is obtained in the Example 17 mentioned herein below, is on deposit under the terms of the Budapest Treaty from Oct. 27, 1994, with NIBH and has been assigned the Accession Number FERM BP-4856. It is also on deposit from Oct. 25, 1994 with IFO and has been assigned the Accession Number IFO 15754.

The transformant *Escherichia coli*, designated JM109/PMAH2-17, which is obtained in the Example 19 mentioned herein below, is on deposit under the terms of the Budapest Treaty from Apr. 7, 1995, with NIBH and has been assigned the Accession Number FERM BP-5073. It is also on deposit from Mar. 31, 1995 with IFO and has been assigned the Accession Number IFO 15813.

The transformant *Escherichia coli*, designated JM109/pMN128, which is obtained in the Example 20 mentioned herein below, is on deposit under the terms of the Budapest Treaty from Mar. 17, 1995, with NIBH and has been assigned the Accession Number FERM BP-5039. It is also on deposit from Mar. 22, 1995 with IFO and has been assigned the Accession Number IFO 15810.

The transformant *Escherichia coli*, designated JM109/phAH2-17, which is obtained in the Example 21 mentioned herein below, is on deposit under the terms of the Budapest Treaty from Jul. 20, 1995, with NIBH and has been assigned the Accession Number FERM BP-5168. It is also on deposit from Jul. 14, 1995 with IFO and has been assigned the Accession Number IFO 15856.

Each SEQ ID NO set forth in the SEQUENCE LISTING of the specification refers to the following sequence:

[SEQ ID NO: 24] is a partial amino acid sequence of the human pituitary gland-derived G protein coupled receptor protein encoded by the human pituitary gland-derived G protein coupled receptor protein cDNA fragment included in p19P2,

[SEQ ID NO: 25] is a partial amino acid sequence of the human pituitary gland-derived G protein coupled receptor protein encoded by the human pituitary gland-derived G protein coupled receptor protein cDNA fragment included in p19P2,

[SEQ ID NO: 26] is an entire amino acid sequence of the human pituitary gland-derived G protein coupled receptor protein encoded by the human pituitary gland-derived G protein coupled receptor protein cDNA fragment included in phGR3,

[SEQ ID NO: 27] is a partial amino acid sequence of the mouse pancreatic β-cell line, MIN6-derived G protein coupled receptor protein encoded by the mouse pancreatic β-cell line, MIN6-derived G protein coupled receptor protein cDNA fragment having a nucleotide sequence (SEQ ID NO: 32), derives based upon the nucleotide sequences of the mouse pancreatic β-cell line, MIN6-derived G protein coupled receptor protein cDNA fragments each included in pG3-2 and pG1-10,

[SEQ ID NO: 28] is a partial amino acid sequence of the mouse pancreatic β-cell line, MIN6-derived G protein coupled receptor protein encoded by p5S38,

[SEQ ID NO: 29] is a nucleotide sequence of the human pituitary gland-derived G protein coupled receptor protein cDNA fragment included in p19P2,

[SEQ ID NO: 30] is a nucleotide sequence of the human pituitary gland-derived G protein coupled receptor protein cDNA fragment included in p19P2,

[SEQ ID NO: 31] is an entire nucleotide sequence of i-he human pituitary gland-derived G protein coupled receptor protein cDNA included in phGR3,

[SEQ ID NO: 32] is a nucleotide sequence of the mouse pancreatic β-cell line, MIN6-derived G protein coupled receptor protein cDNA, derived based upon the nucleotide sequences of the mouse pancreatic β-cell line, MIN6-derived G protein coupled receptor protein cDNA fragments each included in pG3-2 and pG1-10,

[SEQ ID NO: 33] is a nucleotide sequence of the mouse pancreatic β-cell line, MIN6-derived G protein cDNA included in p5S38,

[SEQ ID NO: 34] is a partial amino acid sequence of the human amygdaloid nucleus-derived G protein coupled receptor protein encoded by the cDNA fragment included in p63A2,

[SEQ ID NO: 35] is a partial amino acid sequence of the human amygdaloid nucleus-derived G protein coupled receptor protein encoded by the cDNA fragment included in p63A2,

[SEQ ID NO: 36] is a nucleotide sequence of the human amygdaloid nucleus-derived G protein coupled receptor protein cDNA fragment included in p63A2,

[SEQ ID NO: 37] is a nucleotide sequence of the human amygdaloid nucleus-derived G protein coupled receptor protein cDNA fragment included in p63A2,

[SEQ ID NO: 38] is a partial amino acid sequence enccded by the mouse pancreatic S -cell line, MIN6-derived G protein coupled receptor protein cDNA included in p3H2-17,

[SEQ ID NO: 39] is a full-length amino acid sequence encoded by the open reading frame of the mouse pancreatic β-cell line, MIN6-derived G protein coupled receptor protein cDNA included in pMAH2-17,

[SEQ ID NO: 40] is a nucleotide sequence of the mouse pancreatic β-cell line, MIN6-derived G protein coupled receptor protein cDNA included in p3H2-17,

[SEQ ID NO: 41] is a nucleotide sequence of the mouse pancreatic β-cell line, MIN6-derived G protein coupled receptor protein cDNA included in pMAH2-17,

[SEQ ID NO: 42] is a partial amino acid sequence encoded by the mouse pancreatic β-cell line, MIN6-derived G protein coupled receptor protein cDNA included in p3H2-34,

[SEQ ID NO: 43] is a nucleotide sequence of the mouse pancreatic β-cell line, MIN6-derived G protein coupled receptor protein cDNA fragment included in p3H2-34,

[SEQ ID NO: 44] is a partial amino acid sequence encoded by the rabbit gastropyrolic part smooth muscle-derived G protein coupled receptor protein cDNA included in pMD4,

[SEQ ID NO: 45] is a nucleotide sequence of the rabbit gastropyrolic part smooth muscle-derived G protein coupled receptor protein cDNA fragment included in pMD4,

[SEQ ID NO: 46] is an entire amino acid sequence encoded by the mouse pancreatic β-cell line, MIN6-derived G protein coupled receptor protein cDNA included in pMGR20,

[SEQ ID NO: 47] is a nucleotide sequence of the mouse pancreatic β-cell line, MIN6-derived G protein coupled receptor protein cDNA included in pMGR20,

[SEQ ID NO: 48] is a partial amino acid sequence encoded by the rabbit gastropyrolic part smooth muscle-derived G protein coupled receptor protein cDNA included in pMJ10,

[SEQ ID NO: 49] is a nucleotide sequence of the rabbit gastropyrolic part smooth muscle-derived G protein coupled receptor protein cDNA fragment included in pMJ10,

[SEQ ID NO: 50] is a partial amino acid sequence encoded by the rabbit gastropyrolic part smooth muscle-derived G protein coupled receptor protein cDNA included in pMH28,

[SEQ ID NO: 51] is a nucleotide sequence of the rabbit gastropyrolic part smooth muscle-derived G protein coupled receptor protein cDNA fragment included in pMH28,

[SEQ ID NO: 52] is a partial amino acid sequence encoded by the rabbit gastropyrolic part smooth muscle-derived G protein coupled receptor protein cDNA included in pMN7,

[SEQ ID NO: 53] is a nucleotide sequence of the rabbit gastropyrolic part smooth muscle-derived G protein coupled receptor protein cDNA fragment included in pMN7,

[SEQ ID NO: 54] is a partial amino acid sequence encoded by the rabbit gastropyrolic part smooth muscle-derived G protein coupled receptor protein cDNA included in pMN128,

[SEQ ID NO: 55] is a nucleotide sequence of the rabbit gastropyrolic part smooth muscle-derived G protein coupled receptor protein cDNA fragment included in pMN128,

[SEQ ID NO: 56] is a full-length amino acid sequence of the human-derived G protein coupled receptor protein encoded by the human-derived G protein coupled receptor protein cDNA included in phAH2-17, and

[SEQ ID NO: 57] is a nucleotide sequence of the human-derived G protein coupled receptor protein cDNA included in phAH2-17.

EXAMPLES

Described below are working examples of the present invention which are provided only for illustrative purposes, and not to limit the scope of the present invention. In light of the present disclosure, numerous embodiments within the scope of the claims will be apparent to those of ordinary skill in the art.

Example 1
Preparation of Synthetic DNA Primer for Amplifying DNA Coding for G Protein Coupled Receptor Protein A comparison of deoxyribonucleotide sequences coding for the known amino acid sequences corresponding to or near the first membrane-spanning domain each of human-derived TRH receptor protein (HTRHR), human-derived RANTES receptor protein (L10918, HUMRANTES), human Btrkitt's lymphoma-derived unknown ligand receptor protein (X68149, HSBLR1A), human-derived somatostatin receptor protein (L14856, HUMSOMAT), rat-derived μ-opioid receptor protein (U02083, RNU02083), rat-derived κ-opioid receptor protein (U00442, U00442), human-derived neuromedin B receptor protein (M73482, HUMNMBR), human-derived muscarinic acetylcholine receptor protein (X15266, HSHM4), rat-derived adrenaline $α_1B$ receptor protein (L08609, RATAADRE01), human-derived somatostatin 3 receptor protein (M96738, HUMSSTR3X), human-derived $C_5a$ receptor protein (HUMC5AAR), human-derived unknown ligand receptor protein (HUMRDC1A), human-derived unknown ligand receptor protein (M84605, HUMOPIODRE) and rat-derived adrenaline $α_2B$ receptor protein (M91466, RATA2BAR) was made. As a result, highly homologous regions or parts were found (FIG. 1).

Further, a comparison of deoxynucleotide sequences coding for the known amino acid sequences corresponding to or near the sixth membrane-spanning domain each of mouse-derived unknown ligand receptor protein (M80481, MUSGIR), human-derived bombesin receptor protein (L08893, HUMBOMB3S), human-derived adenosine A2 receptor protein (S46950, S46950), mouse-derived unknown ligand receptor protein (D21061, MUSGPCR), mouse-derived TRH receptor protein (S43387, S43387), rat-derived neuromedin K receptor protein (J05189, RATNEURA), rat-derived adenosine A1 receptor protein (M69045, RATA1ARA), human-derived neurokinin A receptor protein (M57414, HUMNEKAR), rat-derived adenosine A3 receptor protein (M94152, RATADENREC), human-derived somatostatin 1 receptor protein (M81829, HUMSR11A), human-derived neurokinin 3 receptor protein (S86390, S86371S4), rat-derived unknown ligand receptor protein (X61496, RNCGPCR), human-derived somatostatin 4 receptor protein (L07061, HUMSSTR4Z) and rat-derived GnRH receptor protein (M31670, RATGNRHA) was made. As a result, highly homologous regions or parts were found (FIG. 2).

The aforementioned abbreviations in the parentheses are identifiers (reference numbers) which are indicated when GenBank/EMBL Data Bank is retrieved by using DNASIS Gene/Protein Sequencing Data Base (CD019, Hitachi Software Engineering, Japan) and are usually called "Accession Numbers" or "Entry Names". HTRHR is, however, the sequence as disclosed in Japanese Unexamined Patent Publication No. 286986/1993 (EPA 638645).

Specifically, it was planned to incorporate mixed bases relying upon the base regions that were in agreement with cDNAs coding for a large number of receptor proteins in order to enhance base agreement of sequences with as many receptor cDNAs as possible even in other regions. Based upon these sequences, the degenerate synthetic DNA having a nucleotide sequence represented by SEQ ID NO: 1 which is complementary to the homologous nucleotide sequence of FIG. 1 and the degenerate synthetic DNA having a nucleotide sequence represented by SEQ ID NO: 2 which is complementary to the homologous nucleotide sequence of FIG. 2 were produced. Nucleotide synthesis was carried out by a DNA synthesizer.

[Synthetic DNAs]

5'-CGTGG (G or C) C (A or C) T (G or C) (G or C) TGGGCAAC (A, G, C or T) (C or T) CCTG-3'
(SEQ ID NO: 1)

5'-GT (A, G, C or T) G (A or T) (A or G) (A or G) GGCA (A, G, C or T) CCAGCAGA (G or T) GGCAAA-3'
(SEQ ID NO: 2)

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis.

Figure 17:
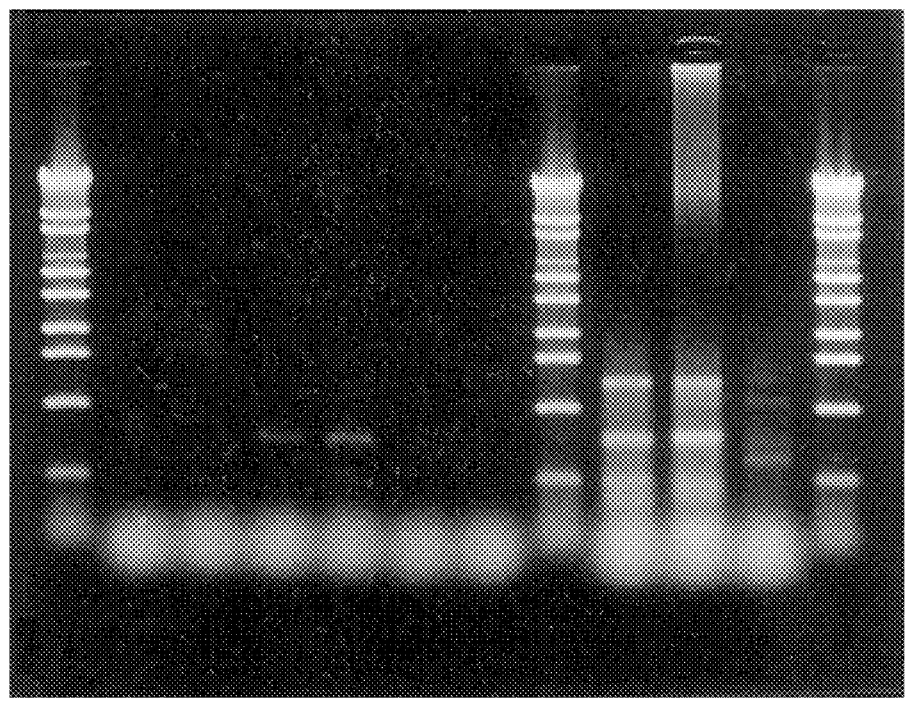
FIG. 17 is the 1.2% agarose gel electrophoresis profile of cDNA products each obtained from human brain amygdala (1, 2, 7), human pituitary body (3, 4, 8) and rat brain (5, 6, 9) by PCR amplification using the synthetic DNA primers having a nucleotide sequence represented by SEQ ID NO: 1 and the synthetic DNA primers having a nucleotide sequence represented by SEQ ID NO: 2, wherein lanes 1 to 6 show the results of when PCR is carried out under severe conditions as disclosed in Examples, lanes 7 to 9 show the results of when PCR is carried out under mild conditions, and M denotes a size marker which is obtained by cutting λ-phage DNA with restriction enzyme, EcoT14I.
Figure 24:
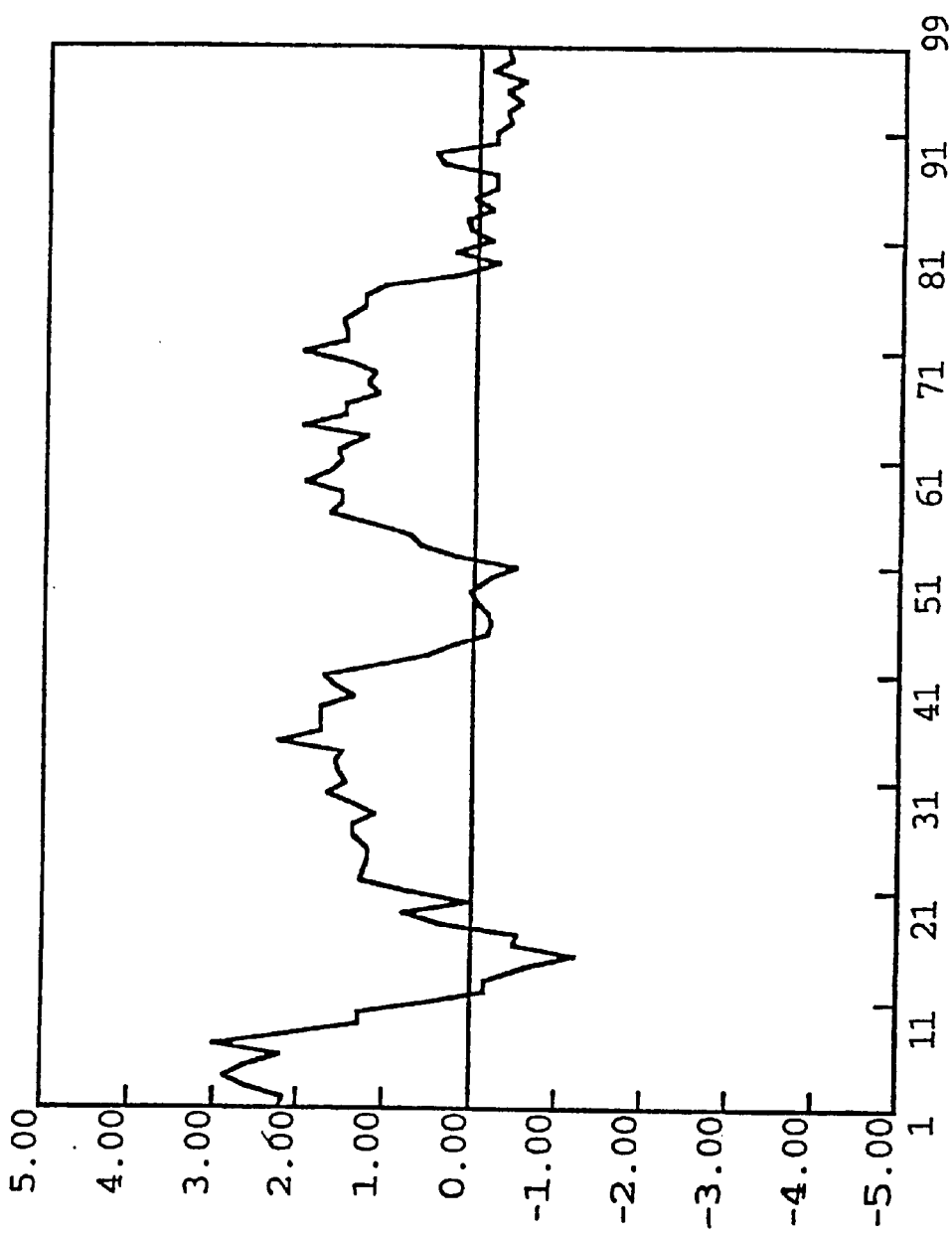
FIG. 24 is the partial hydrophobicity plotting profile of the protein encoded by the human pituitary gland-derived G protein coupled receptor protein cDNA fragment included in p19P2, prepared based upon the amino acid sequence shown in FIG. 22.
Figure 25:
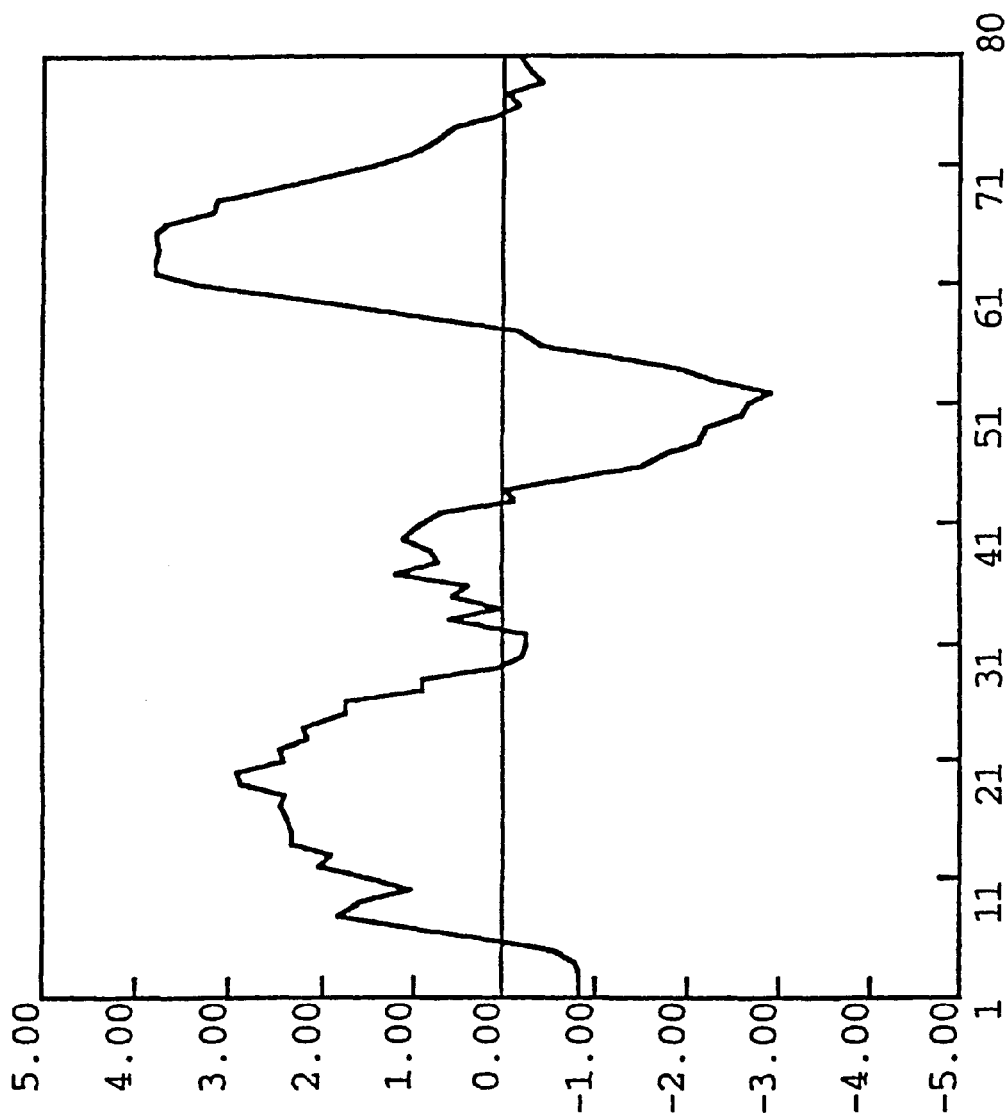
FIG. 25 is the partial hydrophobicity plotting profile of the protein encoded by the human pituitary gland-derived G protein coupled receptor protein cDNA fragment included in p19P2, prepared based upon the amino acid sequence shown in FIG. 23.
Figure 28:
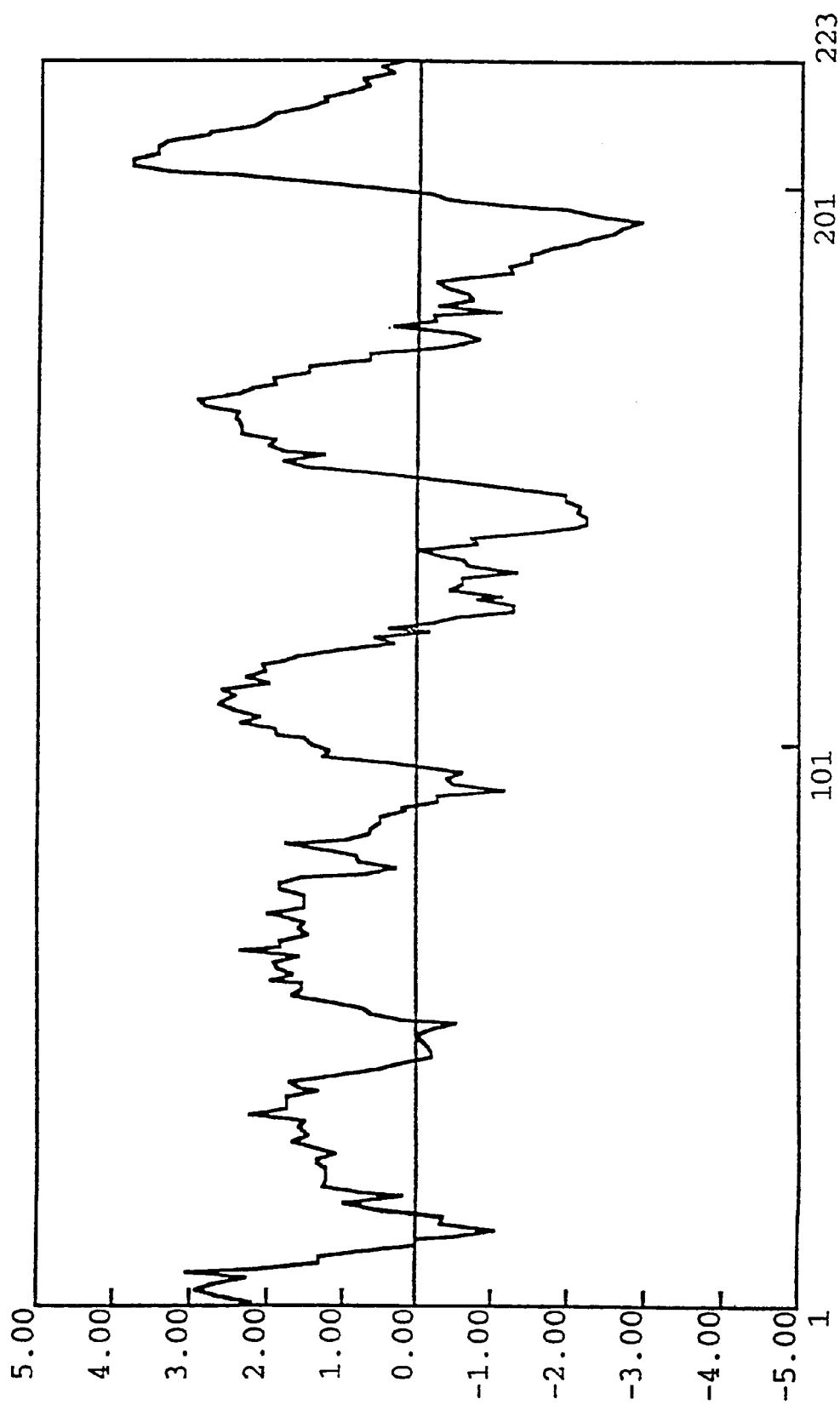
FIG. 28 is the partial hydrophobicity plotting profile of the MIN6-derived G protein coupled receptor protein, prepared based upon the partial amino acid sequence shown in FIG. 27.
Figure 31:
FIG. 31 is the hydrophobicity plotting profile, prepared based upon the amino acid sequence shown in FIG. 29, suggesting the presence of hydrophobic domains as designated by 1 to 3.
Figure 32:
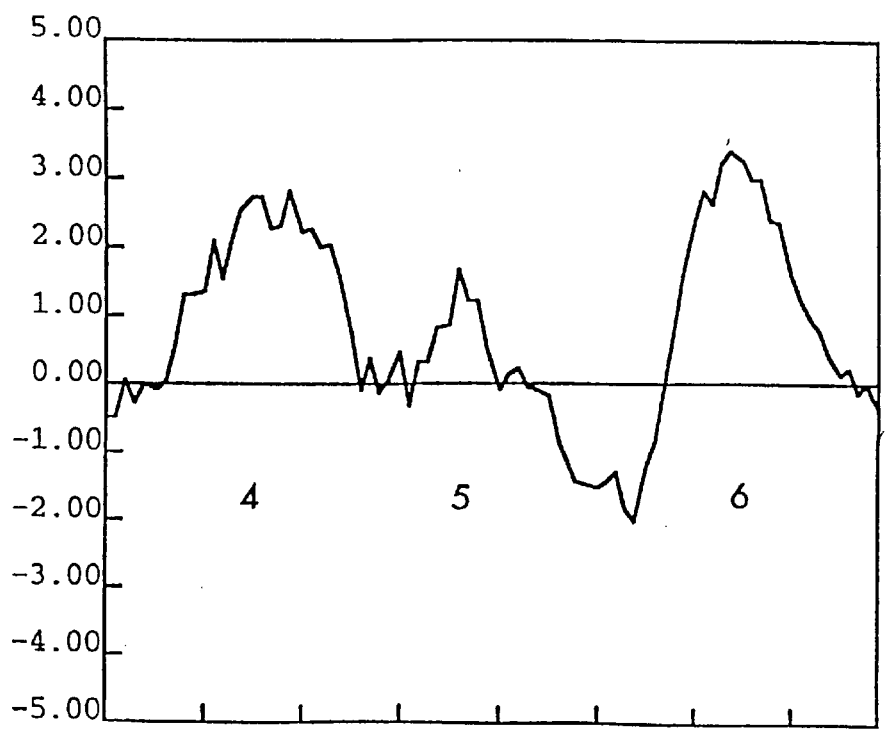
FIG. 32 is the hydrophobicity plotting profile, prepared based upon the amino acid sequence shown in FIG. 30, suggesting the presence of hydrophobic domains as designated by 4 to 6.

Example 2
Isolation of Human Somatostatin Receptor Protein-Encoding DNA, Human D5 Dopamine Receptor Protein-Encoding DNA, and Rat Somatostatin Receptor Protein-Encoding DNA (1) Amplification of DNA by Polymerase Chain Reaction (PCR)

cDNAs (QuickClone, CLONTECH Laboratories, Inc.) prepared from human brain amygdaloid nucleus, human pituitary gland and rat brain each in an amount of 1 ng as templates, the synthetic DNA primers prepared in Example 1 each in an amount of 1 μM, 2.5 mM dNTPs (deoxyribonucleoside triphosphates), and 2.5 units of Taq DNA polymerase (Takara Shuzo Co., Japan) were mixed together with a buffer attached to the enzyme kit such that the total amount was 100 μl. The polymerase chain reaction was carried out by using a Thermal Cycler manufactured by Perkin-Elmer Co. One cycle was set to include 96° C. for 30 sec., 45° C. for 1 min. and 60° C. for 3 min. Totally this one cycle was repeated 30 times to amplify DNAs. Amplification of DNAs was confirmed by 1.2% agarose electrophoresis [FIG. 17].

(2) Isolation of Amplified DNA and Analysis of DNA Sequence

By using a TA Cloning Kit (Invitrogen Co.), the DNA amplified by the PCR was inserted into a plasmid vector, pCR™II. The DNA was transfected into E. coli attached to the kit to form an amplified DNA library. Colonies formed by the transformants were selected under guidance based on the activity of R -galactosidase on X-gal (5-bromo-4-chloro-3-indolyl-β-D-galactoside)-added LB (Luria-Bertani) plates in order to separate only white colonies in which DNA fragments are inserted. They were cultured in an LB culture medium to which ampicillin was added and plasmid DNAs were prepared with an automatic plasmid extracting machine (Kurabo Co., Japan).

An aliquot of the DNA thus prepared was further digested with EcORI to confirm DNA fragments that were inserted, and a DNA yield each of clones was compared with a marker. An aliquot of the plasmid DNA thus prepared was treated with RNase, extracted with phenol/chloroform, precipitated in ethanol, and the resulting product was then reacted for sequencing by using a DyeDeoxy terminator cycle sequencing kit (Applied Biosystems Co.).

Sequencing was carried out by using a 370A fluorescent automatic sequencer manufactured by Applied Biosystems Co. The nucleotide sequences obtained were analyzed by using DNASIS (Hitachi Software Engineering, Japan). The nucleotide sequences obtained are shown in FIGS. 18, 19, 20 and 21. From these Figures and the results of homology retrieval, it was learned that the DNAs obtained were DNAs encoding human somatostatin receptor protein [FIGS. 18 and 19], human D5 dopamine receptor protein [FIG. 20] and rat somatostatin receptor protein [FIG. 21] that can be classified each into a group of G protein coupled receptor proteins.

In FIG. 18 as described herein, the nucleotide sequence of the DNA is in agreement with the nucleotide sequence encoding somatostatin receptor (HUMSOMAT) and the clone, A58, is a human somatostatin receptor cDNA. The underlined part represents the 5' side synthetic DNA primer used for the PCR. Thus, even when parts of the nucleotide sequence are mismatched, amplification is effected to a sufficient degree by the PCR.

It will be understood from FIG. 19 that the clone, A58 is in good agreement with the nucleotide sequence coding for the human somatostatin receptor (HUMSOMAT) even when the sequencing is carried out from the opposite side. The underlined part represents the 3' side synthetic DNA primer used for the PCR. In this figure, the nucleotide sequences are mismatched to some extent even in the portions other than the primer portion presumably due to base substitution at the time of PCR or due to partial deviation in the sequencing reaction. It can be confirmed via sequencing of chains complementary thereto as required.

In FIG. 20 as described herein, the nucleotide sequence of the DNA is in good agreement with a nucleotide sequence coding for the human D5 dopamine receptor (HUMDRD5A) except the primer portion (underlined). It was learned that the clone, 57-A-2, is a human D5 dopamine receptor cDNA.

In FIG. 21 as described herein, the DNA is in good agreement with a nucleotide sequence coding for the rat somatostatin receptor (RNU04738) except the primer portion (underlined). It was learned that the clone, B54, is a rat somatostatin receptor cDNA.

Example 3

Isolation of Human Pituitary Gland-Derived G Protein Coupled Receptor Protein-Encoding DNA (1) Amplification of Receptor cDNA by PCR Using Human Pituitary Gland-Derived cDNA By using human pituitary gland-derived cDNA (QuickClone, CLONTECH Laboratories, Inc.) as a template, PCR amplification using the DNA primers synthesized in Example 1 was carried out. The composition of the reaction solution consisted of the synthetic DNA primers (SEQ: 5' primer sequence and 3' primer sequence) each in an amount of 1 μM, 1 ng of the template cDNA, 0.25 mM dNTPs, 1 μl of Taq DNA polymerase and a buffer attached to the enzyme kit, and the total amount of the reaction solution was made to be 100 μl. The cycle for amplification including 95° C. for 1 min., 55° C. for 1 min. and 72° C. for 1 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(2) Subcloning of PCR Product into Plasmid Vector and Selection of Novel Receptor Candidate Clone via Decoding Nucleotide Sequence of Inserted cDNA Region The PCR products were separated by using a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned into the plasmid vector, pCR™II (TM represents registered trademark). The recombinant vectors were introduced into E. coli INVα F' competent cells (Invitrogen Co.) to produce transforriants. Then, transformant clones having a cDNA-inserted fragment were selected in an LB agar culture medium containing ampicillin and X-gal. Only transformant clones exhibiting white color were picked with a sterilized toothstick to obtain transformant Escherichia coli INVα F'/p19P2.

The individual clones were cultured overnight in an LB culture medium containing ampicillin and treated with an automatic plasmid extracting machine (Kurabo Co., Japan) to prepare plasmid DNAs. An aliquot of the DNA thus prepared was cut by EcORI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The underlined portions represent regions corresponding to the synthetic primers [FIGS. 22 and 23).

Homology retrieval was carried out based upon the determined nucleotide sequences [FIGS. 22 and 23]. As a result, it was learned that a novel G protein coupled receptor protein was encoded by the cDNA fragment insert in the plasmid, p19P2, possessed by the transformant Escherichia coli INVα F'/p19P2. To further confirm this fact, by using DNASIS (Hitachi System Engineering Co., Japan) the nucleotide sequences were converted into amino acid sequences [FIGS. 22 and 23], and homology retrieval was carried out in view of hydrophobicity plotting [FIGS. 24 and 25] and at the amino acid sequence level to find homology relative to neuropeptide Y receptor proteins [FIG. 26].

Example 4
Isolation of Mouse Pancreas-Derived G Protein Coupled Receptor Protein-Encoding DNA (1) Preparation of Poly(A)⁺RNA Fraction from Mouse Pancreatic βCell Strain, MIN6 and Synthesis of cDNA A total RNA was prepared from the mouse pancreatic βcell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)⁺RNA fractions were prepared with a mRNA purifying kit (Pharmacia Co.). Next, to 5 μg of the poly(A)⁺RNA fraction was added a random DNA hexamer (BRL Co.) as a primer, and the resulting mixture was subjected to reaction with mouse Moloney Leukemia virus (MMLV) reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE buffer (10 mM Tris-HCl at pH8.0, 1 mM EDTA at pH8.0).

(2) Amplification of Receptor cDNA by PCR Using MIN6-Derived cDNA and Sequencing By using, as a template, 5 μl of cDNA prepared from the mouse pancreatic β-cell strain, MIN6 in the above step (1), PCR amplification using the DNA primers synthesized in Example 1 was carried out under the same condition, as in Example 3(2). The resulting PCR product was subcloned into the plasmid vector, pCR™II, in the same manner as in Example 2 to obtain a plasmid, pG3-2. The plasinid pG3-2 was transfected into *E. coli* INVα F' to obtain transformed *Escherichia coli* INVα F'/pG3-2.

By using, as a template, 5 μl of the cDNA prepared from the mouse pancreatic β-cell strain, MIN6, PCR amplification using DNA primers as disclosed in Libert F. et al., "Science, 244:569–572, 1989", i.e., a degenerate synthetic primer represented by the following sequence:

5'-CTGTG (C or T) G (C or T) (G or C) AT (C or T) GCIIT
(G or T) GA (C or T) (A or C) G (G or C) TAC-3'
(SEQ ID NO: 60)

wherein I is inosine; and a degenerate synthetic primer represented by the following sequence:

5'-A (G or T) G (A or T) AG (A or T) AGGGCAGCCAGCAGAI
(G or C) (A or G) (C or T) GAA-3'
(SEQ ID NO: 61)

wherein I is inosine, was carried out under the same conditions as in Working Example 1. The resulting PCR product was subcloned into the plasmid vector, pCR™II, in the same manner as described in Example 3(2) to obtain a plasmid, pG1-10.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 27 shows a mouse pancreatic β-cell strain MIN6-derived G protein coupled receptor protein-encoding DNA and an amino acid sequence encoded by the isolated DNA based upon the nucleotide sequences of plasmids pG3-2 and p(;1-10 which are held by the transformant *Escherichia coli* INVα F'/pG3-2. The underlined portions represent regions corresponding to the synthetic primers.

Homology retrieval was carried out based upon the determined nucleotide sequence [FIG. 27]. As a result, it was learned that a novel G protein coupled receptor protein was encoded by the cDNA fragment obtained. To further confirm this fact, by using DNASIS (Hitachi System Engineering Co., Japan) the nucleotide sequence was converted into an amino acid sequence [FIG. 27], hydrophobicity plotting was carried out to confirm the presence of six hydrophobic regions [FIG. 28]. Upon comparing the amino acid sequence with that of p19P2 obtained in Example 3, furthermore, a high degree of homology was found as shown in [FIG. 61]. As a result, it is strongly suggested that the G protein coupled receptor proteins encoded by pG3-2 and pG1-10 recognize the same ligand as the G protein coupled receptor protein encoded by p19P2 does while the animal species from which the receptor proteins encoded by pG3-2 and pG1-10 are derived is different from that from which the receptor protein encoded by p19P2 is.

Example 5
Isolation of Human Amygdaloid Nucleus-Derived G Protein Coupled Receptor Protein-Encoding DNA (1) Amplification of Receptor cDNA by PCR Using Human Amygdaloid Nucleus-Derived cDNA By using an amplified human amygdala-derived cDNA (QuickClone, CLONTECH Laboratories, Inc.) as a template, PCR amplification using the DNA primers synthesized in Example 1 was carried out. The composition of the reaction solution consisted of the synthetic DNA primers (SEQ: 5' primer sequence and 3' primer sequence) each in an amount of 1 μM, 1 ng of the template cDNA, 0.25 mM dNTPs, 1 μl of Taq DNA polymerase and a buffer attached to the enzyme kit, and the total amount of the reaction solution was made to be 100 μl. The cycle for amplification including 95° C. for 1 min., 55° C. for 1 min. and 72° C. for 1 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(2) Subcloning of PCR Product into Plasmid Vector and Selection of Novel Receptor Candidate Clone via Decoding Nucleotide Sequence of Inserted cDNA Region The PCR products were separated by using a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* INVα F' competent cells (Invitrogen Co.) to produce transformants. Then, transformant clones having a cDNA-inserted fragment were selected in an LB agar culture medium containing ampicillin and X-gal. Only transformant clones exhibiting white color were picked with a sterilized toothstick to obtain transformant *Escherichia coli* INVα F'/p63A2.

The individual clones were cultured overnight in an LB culture medium containing ampicillin and treated with an automatic plasmid extracting machine (Kurabo Co., Japan) to prepare plasmid DNAs. An aliquot of the DNA thus prepared was cut by EcoRI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Homology retrieval was carried out based upon the determined nucleotide sequences [FIGS. 29 and 30]. As a result, it was learned that a novel G protein coupled receptor protein was encoded by the cDNA fragment insert in the plasmid, p63A2 possessed by the transformant *Escherichia coli* INVα F'/p63A2. To further confirm this fact, by using DNASIS (Hitachi System Engineering Co., Japan) the nucleotide sequences were converted into amino acid sequences [FIGS. 29 and 30], and homology retrieval was carried out in view of hydrophobicity plotting [FIGS. 31 and 32] and at the amino acid sequence level to find homology relative to mouse GIR [FIG. 33].

Example 6

Cloning of Human Pituitary Gland-Derived G Protein Coupled Receptor Protein cDNA (1) Cloning of cDNA Comprising Whole Coding Regions for Receptor Protein from Human Pituitary Gland-Derived cDNA Library The DNA library constructed by Clontech Co. wherein λ gt11 phage vector is used (CLONTECH Laboratories, Inc.; CLH L1139b) was employed as a human pituitary gland-derived cDNA library. The human pituitary gland cDNA library (2×10⁶ pfu (plaque forming units)) was mixed with *E. coli* Y1090 treated with magnesium sulfate, and incubated at 37° C. for 15 minutes followed by addition of 0.5% agarose (Pharmacia Co.) LB. The *E. coli* was plated onto a 1.5% agar (Wako-Junyaku Co.) LB plate (containing 50 μg/ml of ampicillin). A nitrocellulose filter was placed on the plate on which plaques were formed and the plaque was transferred onto the filter. The filter was denatured with an alkali and then heated at 80° C. for 3 hours to fix DNAs.

The filter was incubated overnight at 42° C. together with the probe mentioned herein below in a buffer containing 50% formamide, 5×SSPE (20×SSPE (pH 7.4) is 3 M NaCl, 0.2 M NaH₂PO₄ H₂O, 25 mM EDTA), 5×Denhardt's solution (Nippon Gene, Japan), 0.1% SDS and 100l g/ml of salmon sperm DNA for hybridization.

The probe used was obtained by cutting the DNA fragment inserted in the plasmid, p19P2, obtained in Working Example 3, with EcoRI, followed by recovery and labelling by incorporation of [³²P]dCTP (Dupont Co.) with a random prime DNA labelling kit (Amasham Co.).

It was washed with 2×SSC (20×SSC is 3 M NaCl, 0.3 M sodium citrate), 0.1% SDS at 55° C. for 1 hour and, then, subjected to an autoradiography at −80° C. to detect hybridized plaques.

In this screening, hybridization signals were recognized in three independent plaques. Each DNA was prepared from the three clones. The DNAs digested with EcoRI were subjected to an agarose electrophoresis and were analyzed by the southern blotting using the same probe as the one used in the screening. Hybridizing bands were identified at about 0.7 kb, 0.8 kb and 2.0 kb, respectively. Among them, the DNA fragment corresponding to the band at about 2.0 kb (λ nGR3) was selected. The λ hGR3-derived EcoRI fragment with a hybridizable size was subcloned to the EcoRI site of the plasmid, pUC18, and *E. coli* JM109 was transformed with the plasmid to obtain transformant *E. coli* JM109/phGR3. A restriction enzyme map of the plasmid, phGR3, was prepared relying upon a restriction enzyme map deduced from the nucleotide sequence as shown in Example 3.

As a result, it was learned that it carried a full-length receptor protein-encoding DNA which was predicted from the receptor protein-encoding DNA as shown in Example 3.

(2) Sequencing of Human Pituitary Gland-Derived Receptor Protein cDNA.

Among the EcoRI fragments inserted in the plasmid, phGR3, obtained in the above step (1), the from EcORI to NheI nucleotide sequence with about 1330 bp that is considered to be a receptor protein-coding region was sequenced. Concretely speaking, by utilizing restriction enzyme sites that exist in the EcoRI fragments, unnecessary parts were removed or necessary fragments were subcloned in order to prepared template plasmids for analyzing the nucleotide sequence.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with ENASIS (Hitachi System Engineering Co., Japan).

Figure 36:
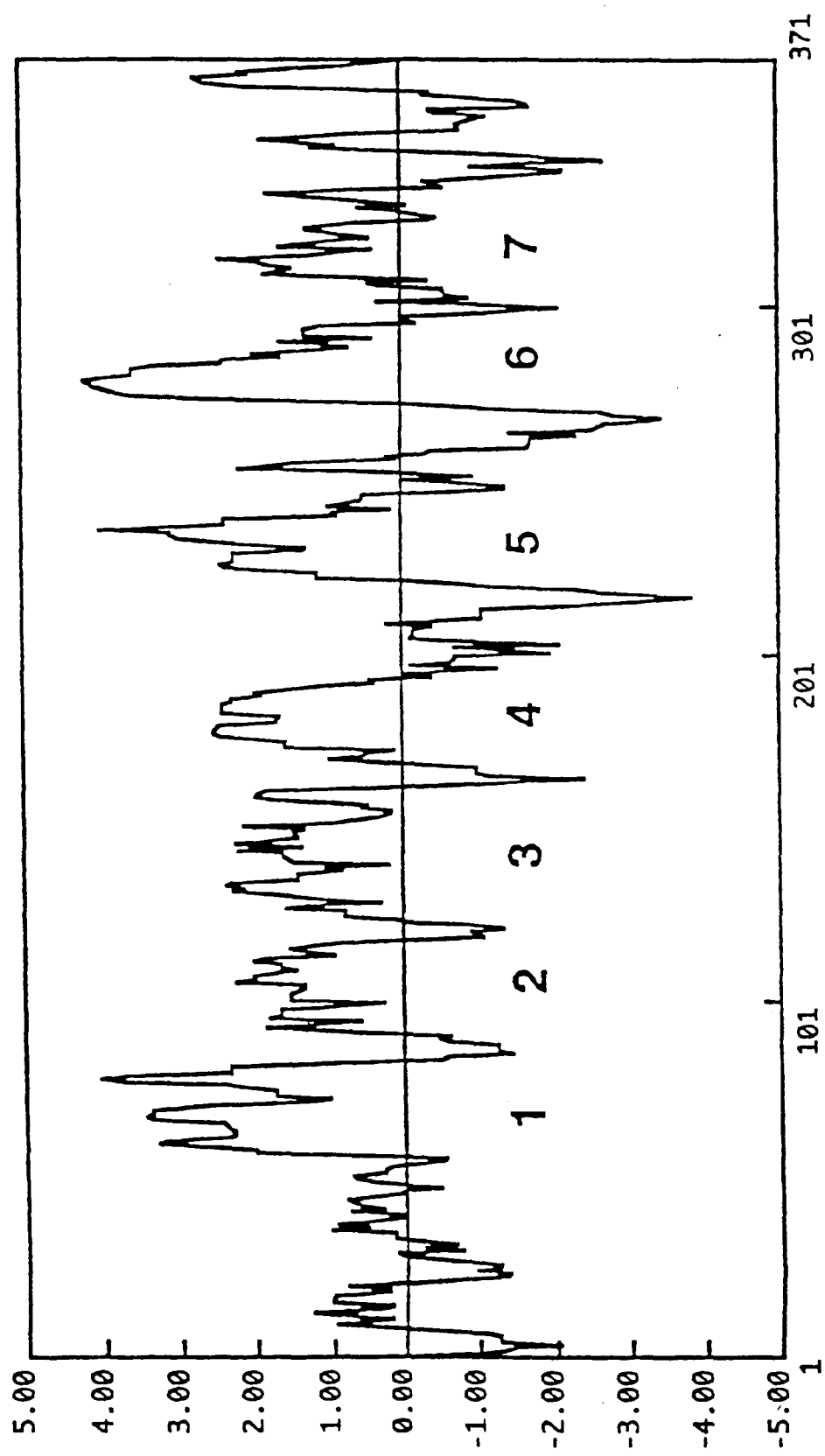
FIG. 36 is the hydrophobicity plotting profile of the protein encoded by the human pituitary gland-derived G protein coupled receptor protein cDNA included in phGR3, prepared based upon the amino acid sequence shown in FIG. 34.
Figure 38:
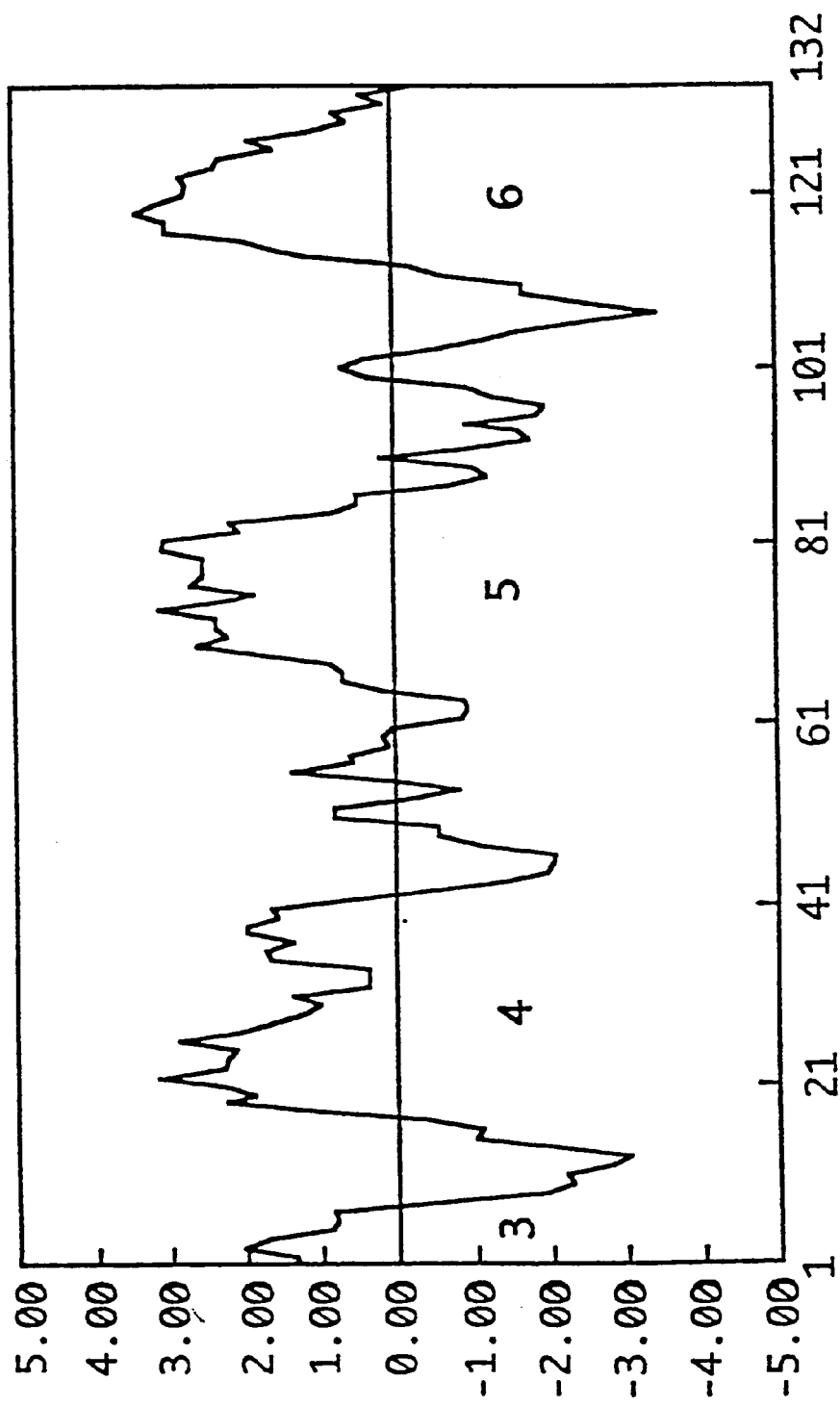
FIG. 38 is the hydrophobicity plotting profile, prepared based upon the amino acid sequence shown in FIG. 37, suggesting the presence of hydrophobic domains as designated by 3 to 6.
Figure 41:
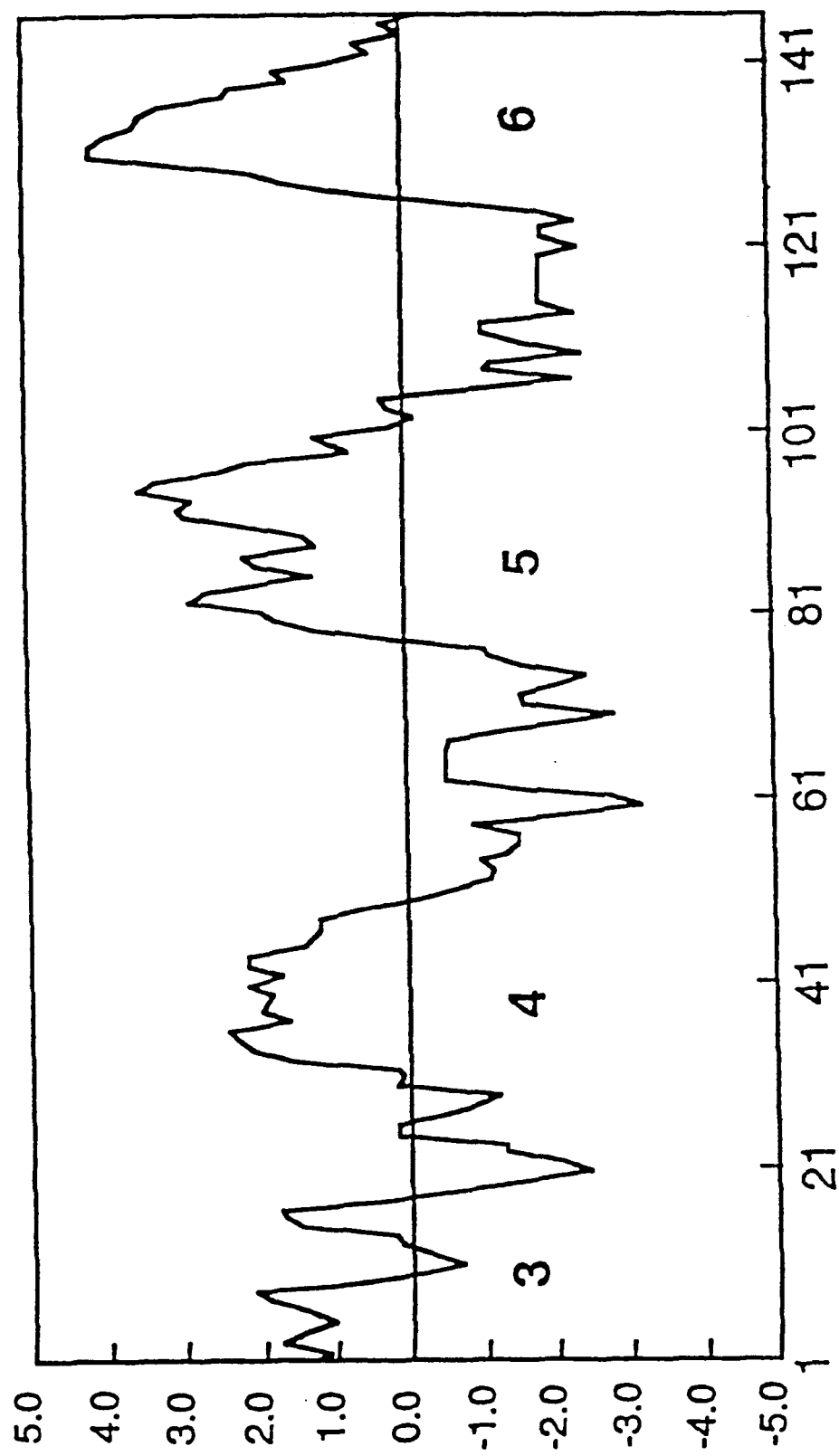
FIG. 41 is the hydrophobicity plotting profile, prepared based upon the amino acid sequence shown in FIG. 40, wherein the axis of ordinate represents an index of hydrophobicity, the axis of abscissa represents the number of amino acids and numerals 3 to 6 represent the presence of hydrophobic domains.
Figure 44:
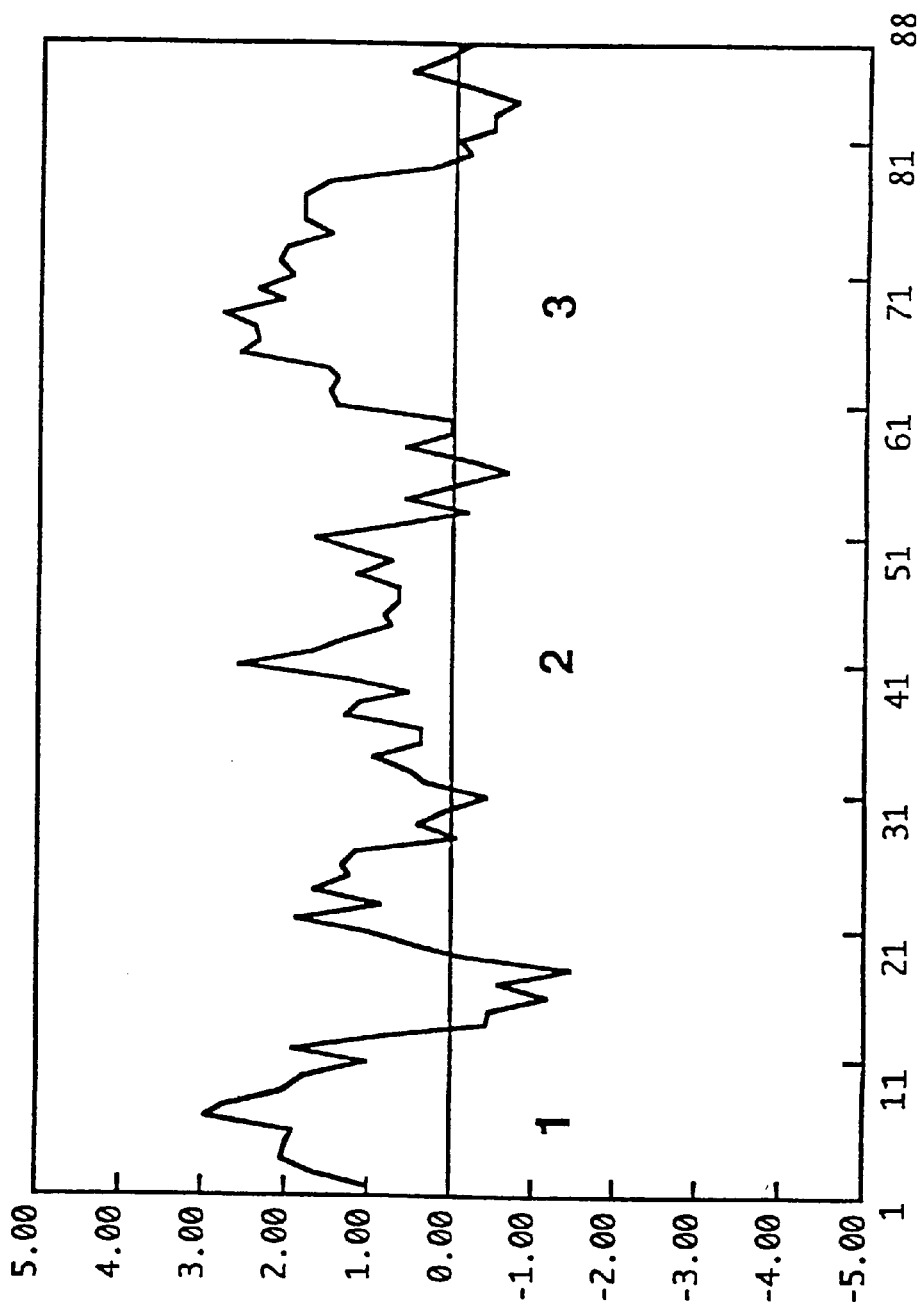
FIG. 44 is the hydrophobicity plotting profile of the protein encoded by the rabbit gastropyrolic part smooth muscle-derived G protein coupled receptor protein cDNA fragment included in pMD4, prepared based upon the amino acid sequence shown in FIG. 35, wherein numerals 1 to 3 suggest the presence of hydrophobic domains.
Figure 47:
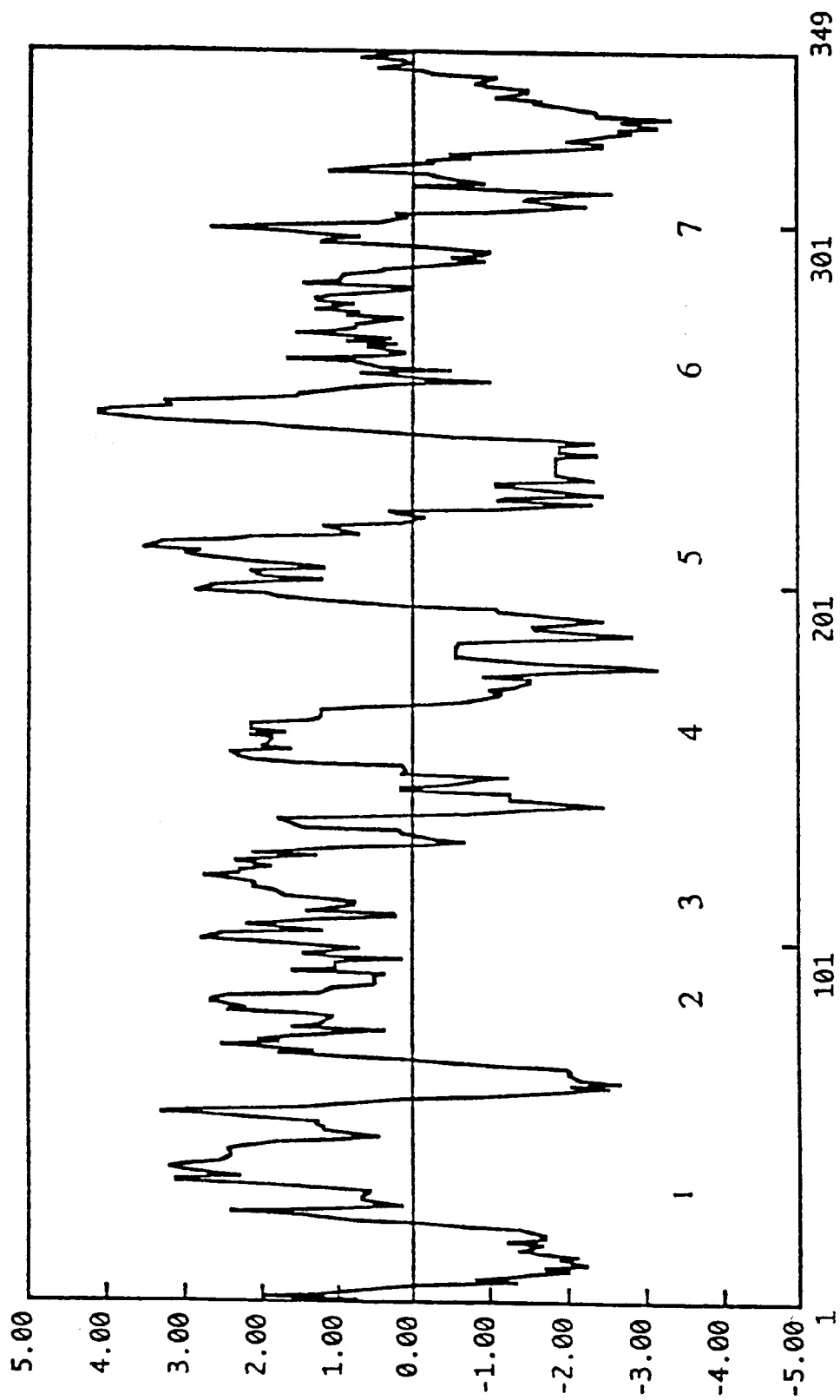
FIG. 47 is the hydrophobicity plotting profile, prepared based upon the amino acid sequence shown in FIG. 46, wherein the axis of ordinate represents an index of hydrophobic property, the axis of abscissa represents the number of amino acids, and numerals 1 to 7 represent the presence of hydrophobic domains.
Figure 50:
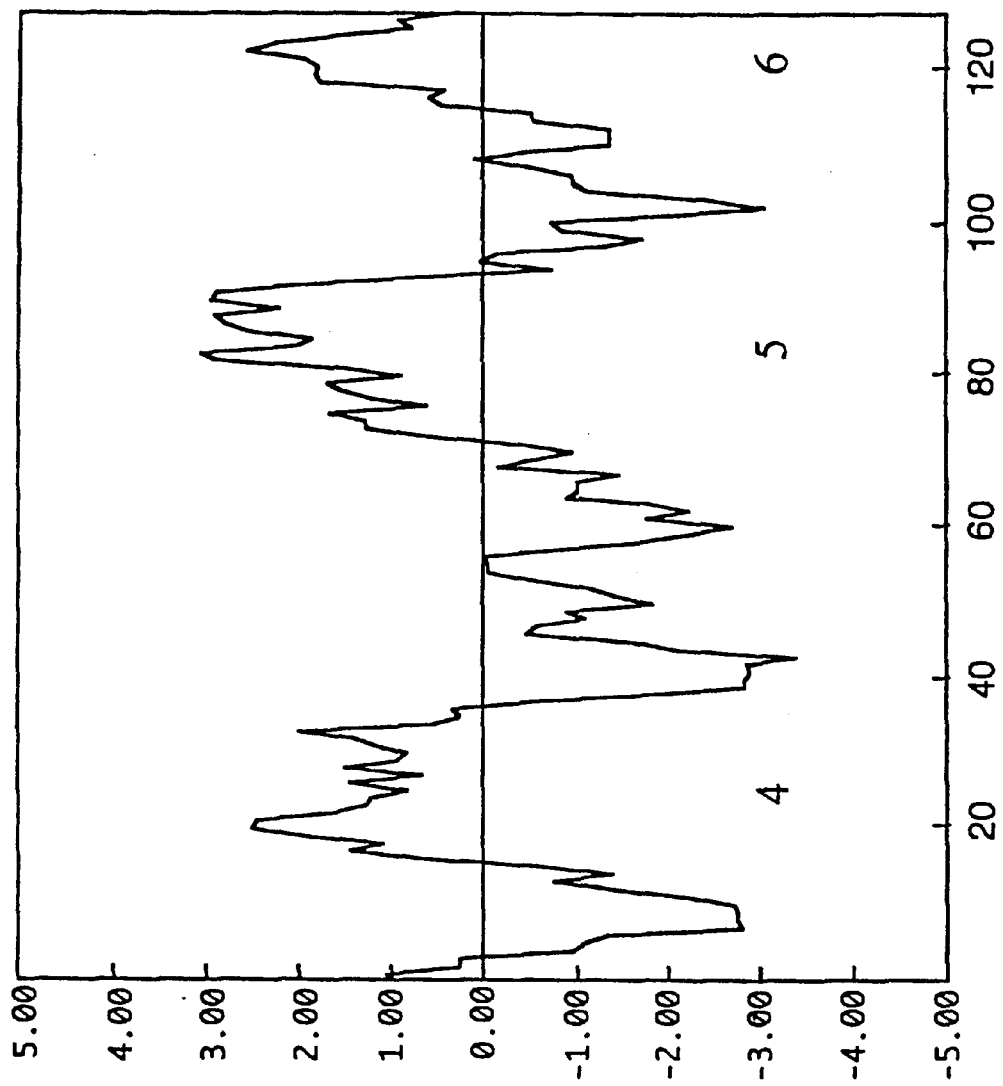
FIG. 50 is the hydrophobicity plotting profile of the protein encoded by the rabbit gastropyrolic part smooth muscle-derived G protein coupled receptor protein cDBA fragment included in pMJ10, prepared based upon the amino acid sequence shown in FIG. 49, wherein numerals 4 to 6 suggest the presence of hydrophobic domains.
Figure 53:
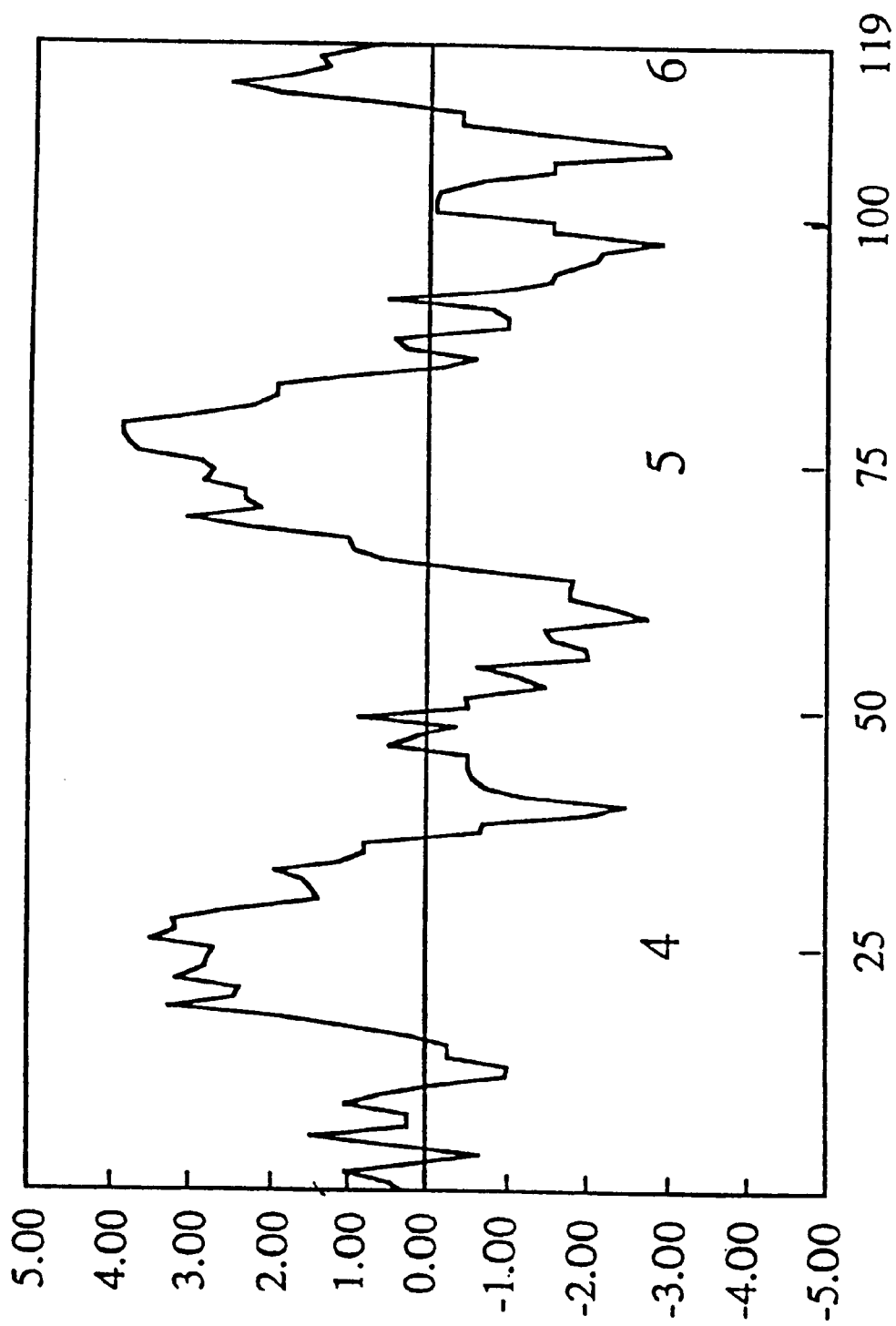
FIG. 53 is the hydrophobicity plotting profile of the protein encoded by the rabbit gastropyrolic part smooth muscle-derived G protein coupled receptor protein cDBA fragment included in pMH28, prepared based upon the amino acid sequence shown in FIG. 52, wherein numerals 4 to 6 suggest the presence of hydrophobic domains.
Figure 57:
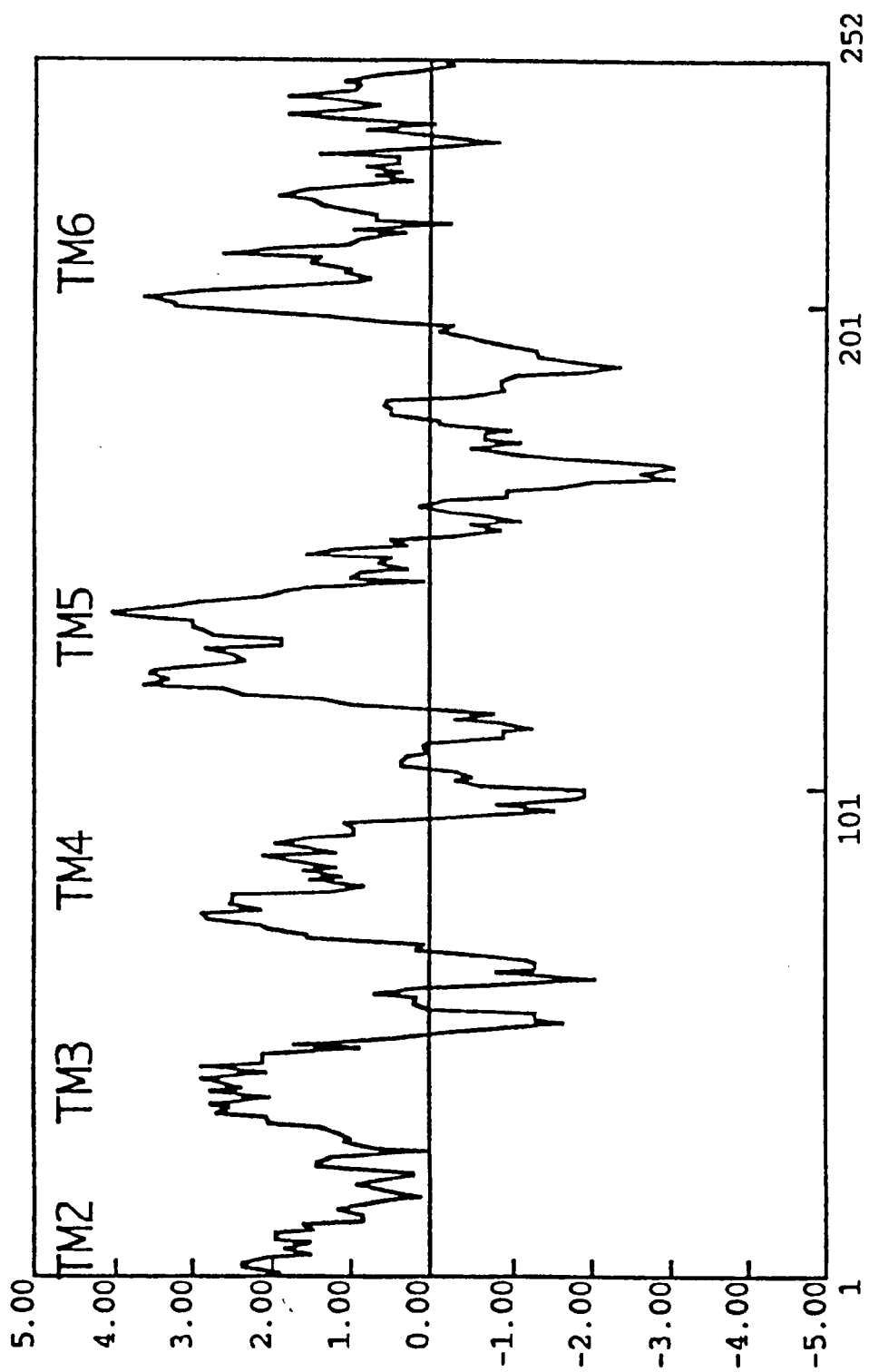
FIG. 57 is the hydrophobicity plotting profile of the protein encoded by the rabbit gastropyrolic part smooth muscle-derived G protein coupled receptor protein cDNA fragment included in pMN7, prepared based upon the amino acid sequences shown in FIGS. 55 and 56, wherein numerals TM2 to TM6 suggest the presence of hydrophobic domains.
Figure 58:
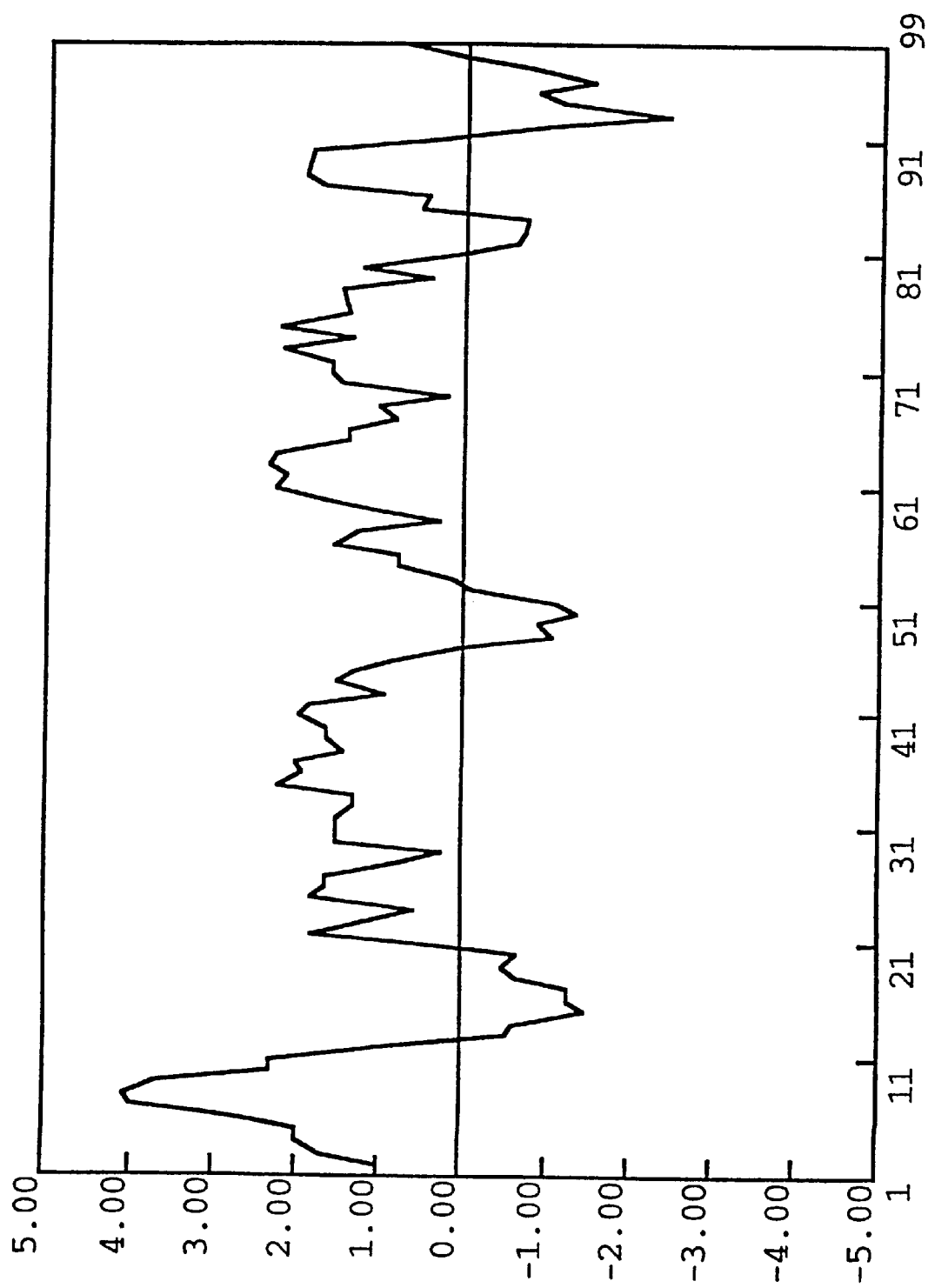
FIG. 58 is the partial hydrophobicity plotting profile of the protein encoded by the human pituitary gland-derived G protein coupled receptor protein cDNA fragment included in p19P2, prepared based upon the amino acid sequence shown in FIG. 22.
Figure 59:
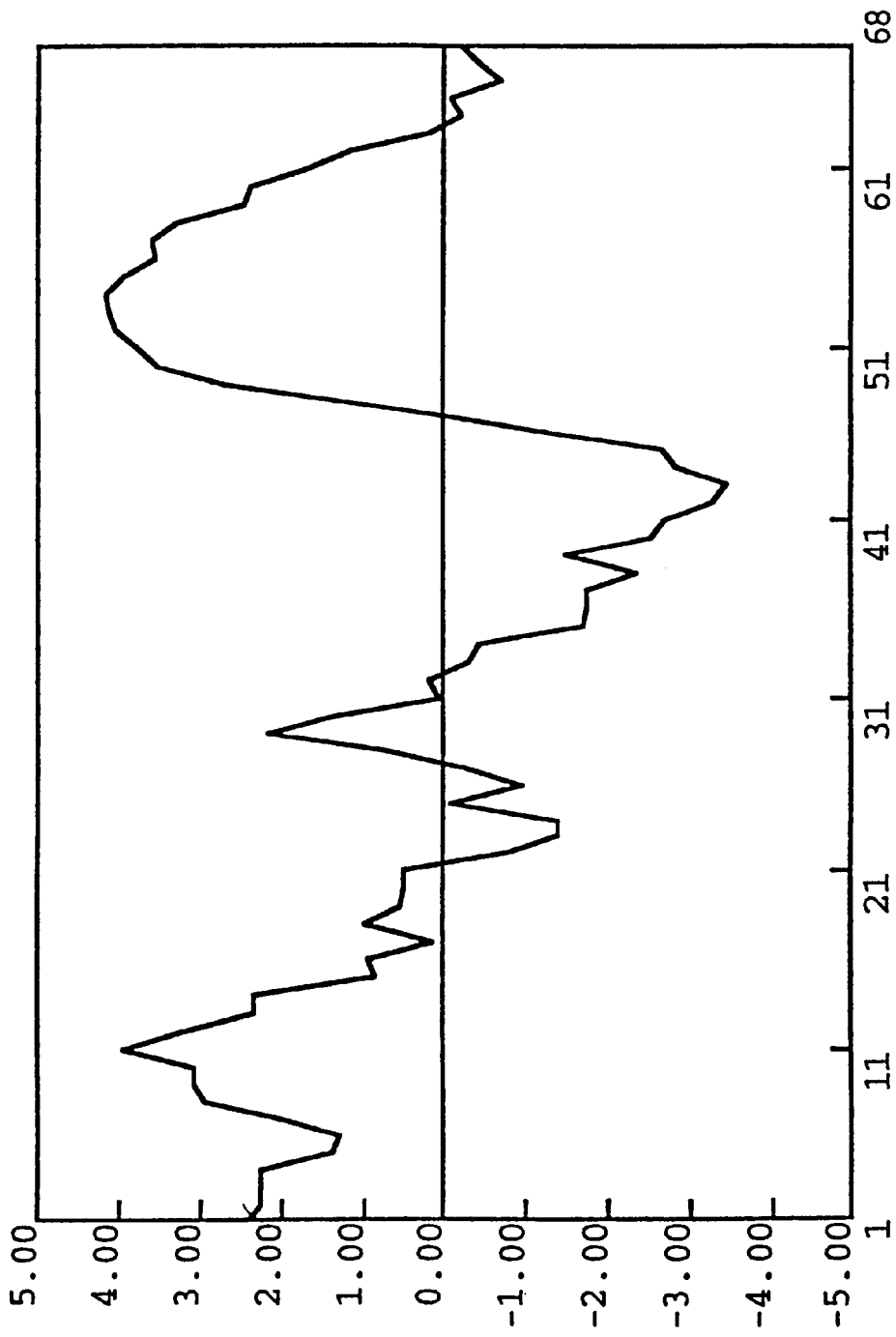
FIG. 59 is the partial hydrophobicity plotting profile of the protein encoded by the human pituitary gland-derived G protein coupled receptor protein cDNA fragment included in p19P2, prepared based upon the amino acid sequence shown in FIG. 23.

FIG. 34 shows a nucleotide sequence of from immediate after the EcoRI site up to the NheI site encoded by phGR3. The nucleotide sequence of the human pituitary gland-derived receptor protein-encoding DNA corresponds to the nucleotide sequence of from 118th to 123rd nucleotides [FIG. 34]. An amino acid sequence of the receptor protein that is encoded by the nucleotide sequence is shown in FIG. 34. FIG. 36 shows the results of hydrophobicity plotting based upon the amino acid sequence.

(3) Northern Hybridization with Human Pituitary Gland-Derived Receptor Protein-Encoding phGR3

Northern blotting was carried out in order to detect the expression of phGR3-encoded human pituitary gland-derived receptor proteins in the pituitary gland at a mRNA level. Human pituitary gland mRNA (2.5 a g, Clontech Co.) was used as a template mRNA and the same as the probe used in Working Example 5 was used as a probe. Nylon membrane (Pall Biodyne, U.S.A.) was used as a filter for northern blotting and migration of the mRNA and adsorption (sucking) thereof with the blotting filter was carried out according to the method as disclosed in Molecular Cloning, Cold Spring Harbor Laboratory Press, 1989.

Figure 35:
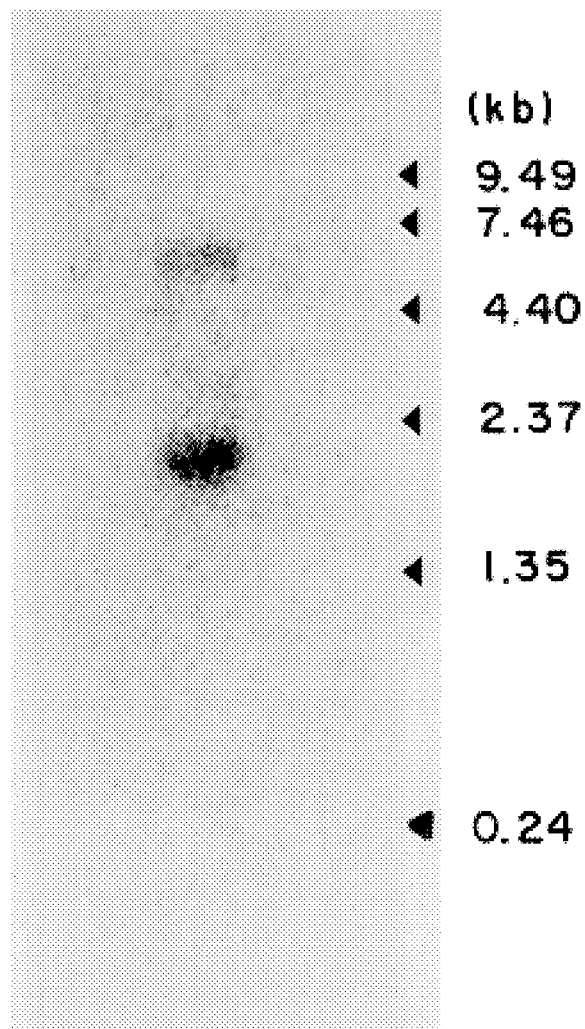
FIG. 35 is the northern blotting profile of the human pituitary gland mRNA of the receptor gene encoded by the human pituitary gland-derived cDNA clone, phGR3.

The hybridization was effected by incubating the above-mentioned filter and probe in a buffer containing 50% formamide, 5×SSPE, 5×Denhardt's solution, 0.1% SD3 and 100 μg/ml of salmon sperm DNA overnight at 42° C. The filter was washed with 0.1×SSC, 0.1% SDS at 50° C. and, after drying with an air, was exposed to an X-ray film (XAR5, Kodak) for three days at −80° C. The results were as shown in FIG. 35 from which it is considered that the receptor gene encoded by phGR3 is expressed in the human pituitary gland.

Example 7

Cloning of Mouse Pancreatic β-Cell Strain, MIN6-Derived G Protein Coupled Receptor Protein cDNA (1) Preparation of Poly(A)⁺RNA Fraction from Mouse pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)⁺RNA fractions were prepared with a mRNA purifying kit (Pharmacia Co.). Next, to 5 μg of the poly(A)⁺RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using MIN6-Derived cDNA and Sequencing By using, as a template, 5 μl of cDNA prepared from the mouse pancreatic β-cell strain, MIN6 in the above step (1), PCR amplification using the DNA primers synthesized in Example 1 was carried out. A reaction solution was composed of the synthetic DNA primers (SEQ: 5' primer sequence and 3' primer sequence) each in an amount of 100 pM, 0.25 mM dNTPs, 1 a 1 of Taq DNA polymerase and 10 μl of 10× buffer attached to the enzyme kit, and the total amount of the reaction solution was made to be 100 μl. The cycle for amplification including 96° C. for 30 sec., 45° C. for 1 min. and 60° C. for 3 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated by using a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co,), the recovered DNAs were subcloned to the plasmid vector, pCR II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG (isopropylthio-β-D-galactoside) and X-gal. Only transformant clones exhibiting white color were picked with a sterilized toothstick to obtain transformant *Escherichia coli* JM109/p3H2-17.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Homology retrieval was carried out based upon the determined nucleotide sequence [FIG. 37]. As a result, it was learned that a novel G protein coupled receptor protein was encoded by the cDNA fragment insert in the plasmid possessed by the transformant *Escherichia coli* JM109/p3H2-17. To further confirm this fact, by using DNASIS (Hitachi System Engineering Co., Japan) the nucleotide sequence were converted into an amino acid sequence [FIG. 37], and homology retrieval was carried out in view of hydrophobicity plotting [FIG. 38] and at the amino acid sequence level to find homology relative to chicken ATP receptor (P34996), human somatostatin receptor subtype 3 (A46226), human somatostatin receptor subtype 4 (JN0605) and bovine neuropeptide Y receptor (S28787) [FIG. 39]. Abbreviations in parentheses are reference numbers assigned when they are registered as data to NBRF-PIR/Swiss-PROT and are usually called "Accession Numbers".

Example 8

Cloning of Mouse Pancreatic β-Cell Strain, MIN6-Derived G Protein Coupled Receptor Protein cDNA (1) Preparation of Poly(A)+RNA Fraction from Mouse Pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)+RNA fractions were prepared with a mRNA purifying kit (Pharmacia Co.). Next, to 5 μg of the poly(A)+RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using MIN6-Derived cDNA and Sequencing By using, as a template, 5 μl of cDNA prepared from the mouse pancreatic β-cell strain, MIN6, in the above step (1), PCR amplification using the DNA primers synthesized in Example 1 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of 10× buffer attached to the enzyme kit, and the total amount of the reaction solution was made to be 100 μl. The cycle for amplification including 96° C. for 30 sec., 45° C. for 1 min. and 60° C. for 3 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, PCR™II. The recombinant vectors were introduced into *E. coli* JM109 competent cells (Takara Shuzo Co., Japan) to produce transformants. Then, transformant clones having a cDNA-inserted fragment were selected in an LIE agar culture medium containing ampicillin, IPTG and X-gal. Only transformant clones exhibiting white color were picked with a sterilized toothstick to obtain transformant *Escherichia coli* JM109/p3H2-34.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Homology retrieval was carried out based upon the determined nucleotide sequence [FIG. 40]. As a result, it was learned that a novel G protein coupled receptor protein was encoded by the cDNA fragment insert in the plasmid possessed by the transformant Escherichia coli JM109/p3H2-34. To further confirm this fact, by using DNASIS (Hitachi System Engineering Co., Japan) the nucleotide sequence were converted into an amino acid sequence [FIG. 40], and homology retrieval was carried out in view of hydrophobicity plotting [FIG. 41] and at the amino acid sequence level to find homology relative to human somatostatin receptor subtype 2 (B41795) and rat-derived ligand unknown receptor (A39297) [FIG. 42]. Abbreviations in parentheses are reference numbers assigned when they are registered as data to NBRF-PIR/Swiss-PROT and are usually called "Accession Numbers" or "Entry Names".

Example 9

Cloning of Rabbit Gastropyrolic Part Smooth Muscle-Derived G Protein Coupled Receptor Protein cDNA (1) Preparation of Poly(A)$^+$RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)$^+$RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE (Tris-EDTA solution).

(2) Amplification of Receptor cDNA by PCR Using Rabbit Gastropyrolic Part Smooth Muscle-Derived cDNA ard Sequencing By using, as a template, 1 μl of cDNA prepared from the rabbit gastropyrolic part smooth muscle in the above step (1), PCR amplification using the DNA primers synthesized in Example 1 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 1.0% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into E. coli JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant Escherichia coli JM109/pMD4.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The determined nucleotide sequence was as shown in FIG. 43. It was learned from FIG. 43 that the cloned cDNA fragment was amplified from both sides with only the synthetic DNA primer having a nucleotide sequence represented by SEQ ID NO: 1 as synthesized in Example 1.

Homology retrieval was carried out based upon the determined nucleotide sequence [FIG. 43]. As a result, it was learned that a novel G protein coupled receptor protein was encoded by the cDNA fragment insert in the plasmid possessed by the transformant Escherichia coli JM109/pMD4. To further confirm this fact, by using DNASIS (Hitachi System Engineering Co., Japan) the nucleotide sequence were converted into an amino acid sequence [FIG. 43], and homology retrieval was carried out in view of hydrophobicity plotting [FIG. 44] and at the amino acid sequence level to find homology relative to rat ligand-unknown receptor protein (A35639) [FIG. 45]. Abbreviations in parentheses are reference numbers assigned when they are registered as data to NBRF-PIR/Swiss-PROT and are usually called "Accession Numbers".

Example 10

Cloning of cDNA Comprising Whole Coding Regions for Receptor Protein from Mouse Pancreatic β-Cell Strain, MIN6-Derived cDNA Library (1) Cloning of cDNA Comprising Whole Coding Regions for Receptor Protein from Mouse Pancreatic β-Cell Strain, MIN6-Derived cDNA Library Superscript™ Lambda System (BRL, Cat. 8256) distributed by BRL Co. and Glgapack II Gold (Stratagene, Cat. 200215) distributed by Stratagene Co. were used to construct MIN6-derived cDNA libraries. By using the above kits, a MIN6 cDNA library with 2.2×10$^6$ pfu (plaque forming units) was constructed from 10 μg of MIN6 poly(A)$^+$ RNA. The cDNA library was mixed with E. coli Y1090 treated with magnesium sulfate, and incubated at 37° C. for 15 minutes followed by addition of 0.5% agarose (Pharmacia Co.) LB. The E. coli was plated onto a 1.5% agar (Wako-Junyaku Co.) LB plate (containing 50 μg/ml of ampicillin). A nitrocellulose filter was placed on the plate on which plaques were formed and the plaque was transferred onto the filter. The filter was denatured with an alkali and then heated at 80° C. for 3 hours to fix DNAs.

The filter was incubated overnight at 42° C. together with the probe mentioned herein below in a buffer containing 50% formamide, 5×SSPE, 5×Denhardt's solution, 0.1% SDS and 100 μg/ml of salmon sperm DNA for hybridization.

The probe used was obtained by cutting the DNA fragment inserted in the plasmid, p3H2-34, obtained in Working Example 8, with EcoRI, followed by recovery and labeling by incorporation of [$^{32}$P]dCTP (Dupont Co.) with a random prime DNA labelling kit (Amasham Co.).

It was washed with 2×SSC (150 mM NaCl and 15 mM sodium citrate), 0.1% SDS at 55° C. for 1 hour and, then, subjected to an autoradiography at −80° C. to detect hybridized plaques.

In this screening, hybridization signals were recognized in two independent plaques. Each DNA was prepared from the two clones. The DNAs digested with SalI and NotI were subjected to an agarose electrophoresis and were analyzed. Inserted fragments were identified at about 2.0 kb and 3.0 kb, respectively. Between them, the DNA fragment corresponding to the band at about 3.0 kb (λ No.20) was selected. The λ No.20-derived NotI-SalI fragment with about 3.0 kb was subcloned into the NotI-SalI site of the plasmid, pBluescript™II SK(+), and E. coli JM109 was transformed with the plasmid to obtain a transformant E. coli JM109/pMGR20. A restriction enzyme map of the plasmid, pMGR20, was prepared relying upon a restriction enzyme map deduced from the nucleotide sequence as shown in Working Example 8. As a result, it was learned that it carried a full-length receptor protein-encoding DNA which was predicted from the receptor protein-encoding DNA as shown in Working Example 8.

(2) Sequencing of MIN6-Derived Receptor Protein Full-Length cDNA

Among the NotI-SalI fragments inserted in the plasmid, pMGR20, obtained in the above step (1), the nucleotide sequence with total 1607 bp, including not only a region that is considered to be a receptor protein-coding region (ORF) but also a neighboring region thereof was sequenced. Concretely speaking, by utilizing restriction enzyme sites that exist in the NotI-SalI fragments, unnecessary parts were removed or necessary fragments were subcloned in order to prepare template plasmids for analyzing the nucleotide sequence thereof. As for the nucleotide sequences of part of the regions, primers for sequencing were synthesized based upon the nucleotide sequences that were determined already and used to makes confirmation.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 46 shows a nucleotide sequence around an open reading frame (ORF) of a mouse galanin receptor protein encoded by the cDNA insert in pMGR20. The nucleotide sequence of mouse galanin receptor protein-encoding DNA corresponds to from the 481st to 1525th nucleotides of the nucleotide sequence in FIG. 46. The nucleotide sequence was converted into an amino acid sequence [FIG. 46] and hydrophobicity plotting was carried out [FIG. 47]. Since the amino acid sequence [FIG. 46] has 92% homology to the human-derived galanin receptor protein at the amino acid sequence level [FIG. 48], it was learned that the cDNA insert in the pMGR20 is a mouse-derived galanin receptor protein-encoding cDNA.

Example 11
Preparation of Synthetic DNA Primer for Amplifying G Protein Coupled Receptor Protein-Encoding DNA Highly homologous parts were found by comparing nucleotide sequences corresponding to or near the third membrane-spanning domain [3C and 3D in FIG. 4] and the sixth membrane-spanning domain [6C of FIG. 6] among known G protein coupled receptors, i.e., rat-derived angiotensin II receptor protein (L32840), rat-derived angiotensin Ib receptor protein (X64052), rat-derived angiotensin receptor protein subtype (M90065), human-derived angiotensin Ia receptor protein (M91464), rat-derived cholecystokinin$_A$ receptor protein (m88096), rat-derived cholecystokinin$_B$ receptor protein (M99418), human-derived cholecystokinin$_B$ receptor protein (L04473), mouse-derived low-affinity interleukin 8 receptor protein (M73969), human-derived high-affinity interleukin 8 receptor protein (X65858), mouse-derived C5a anaphylatoxin receptor protein (S46665), human-derived N-formyl peptide receptor protein (M60626), etc.

The aforementioned abbreviations in parentheses are reference numbers that are indicated when the GenBank/EMBL data base is retrieved, and are usually called "Accession Numbers".

It was planned to incorporate mixed bases relying upon the base regions that were in agreement with a large number of receptor protein cDNAs in order to enhance base agreement of sequences with as many receptor cDNAs as possible even in other regions. Based upon these sequences, the degenerate synthetic DNA (3D of FIG. 4) having a nucleotide sequence represented by SEQ ID NO: 3 which is complementary to the homologous nucleotide sequence of FIG. 4 and the degenerate synthetic DNA (nucleotide sequence complementary to 6C of FIG. 6) having a nucleotide sequence represented by SEQ ID NO: 4 were produced. Nucleotide synthesis was carried out by a DNA synthesizer.

[Synthetic DNAs]

5'-CTCGC (G or C) GC (C or T) (A or C) TI (A or G) G
(C or T) ATGGA (C or T) CGITAT-3'
(SEQ ID NO: 3)
5'-CATGT (A or G) G (T or A) AGGGAAICCAG (G or C) A
(A or C) AI (A or G) A (A or G) (A or G) AA-3'
(SEQ ID NO: 4)

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

Example 12
Cloning of Rabbit Gastropyrolic Part Smooth Muscle-Derived G Protein Coupled Receptor Protein cDNA (1) Preparation of Poly(A)$^+$RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)$^+$RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using Rabbit Gastropyrolic Part Smooth Muscle-Derived cDNA and Sequencing By using, as a template, 1 μl of cDNA prepared from the rabbit gastropyrolic part smooth muscle in the above step (1), PCR amplification using the DNA primer having a nucleotide sequence represented by SEQ ID NO: 3 and the DNA primer having a nucleotide sequence represented by SEQ ID NO: 4 synthesized in Example 11 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated with a 1.0% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant *Escherichia coli* JM109/pMJ10.

The individual clones were cultured overnicht in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The determined nucleotide sequence was as shown in FIG. 49.

Homology retrieval was carried out based upon the determined nucleotide sequence [FIG. 49]. As a result, it was learned that a novel G protein coupled receptor protein was encoded by the cDNA fragment insert in the plasmid possessed by the transformant *Escherichia coli* JM109/pMJ10. To further confirm this fact, by using DNASIS (Hitachi System Engineering Co., Japan) the nucleotidle sequence were converted into an amino acid sequence [FIG. 49], and homology retrieval was carried out in view of hydrophobicity plotting [FIG. 50] and at the amino acid sequence level to find homology relative to human ligand unknown receptor protein (B42009), human N-formyl peptide receptor protein (JC2014), rabbit N-formyl peptide receptor protein (A46520), mouse C5a anaphylatoxin receptor protein (A46525) and bovine neuropeptide Y receptor protein (S28787) [FIG. 51]. Abbreviations in parentheses are reference numbers assigned when they are registered as data to NBRF-PIR/Swiss-PROT and are usuailly called "Accession Numbers".

Example 13
Preparation of Synthetic DNA Primer for Amplifying G Protein Coupled Receptor Protein-Encoding DNA A comparison of nucleotide sequences coding for regions corresponding to or near the third membrane-spanning domain among known G protein coupled receptors, i.e., mouse-derived κ-opioid receptor protein (L11064), mouse-derived δ-opioid receptor protein (L11065), rat-derived μ-opioid receptor protein (D16349), mouse-derived bradykinin B2 receptor protein (X69676), rat-derived bradykinin B2 receptor protein (M599967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived ligand unknown receptor proteins (L04672), (X61496), (X59249) and (L09249), mouse-derived ligand unknown receptor protein (P30731), human-derived ligand unknown receptor proteins (M31210) and (U03642), etc. was made. In particular, the degenerate DNA primer having a nucleotide sequence (3B in FIG. 3; SEQ ID NO: 6) with highly common bases (highly homologous nucleotides) was synthesized to enhance base agreement of sequences with as many receptor cDNAs as possible even in other regions on the basis of nucleotide sequence regions that were in agreement with a large number of receptor cDNAs. Nucleotide synthesis was carried out by a DNA synthesizer.

The nucleotide sequence represented by SEQ ID NO: 6 is:

---

5'-CTGAC (C or T) G (C or T) TCTI (A or G) (G or C) I (A or G) (C or T) TGAC (A or C) G (A, C or G) TAT-3'

---

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

Furthermore, a comparison of nucleotide sequences coding for regions corresponding to or near the sixth membrane-spanning domain among known G protein coupled receptors, i.e., mouse-derived κ-opioid receptor protein (L11064), mouse-derived δ-opioid receptor protein (L11065), rat-derived μ-opioid receptor protein (D16349), mouse-derived bradykinin B2 receptor protein (X69676), rat-derived bradykinin B2 receptor protein (M59967), mouse-derived bombesin receptor protein (M35328), human-derived neuromedin B receptor protein (M73482), human-derived gastrin releasing peptide receptor protein (M73481), human-derived bombesin receptor protein subtype 3 (L08893), mouse-derived substance K receptor protein (X62933), mouse-derived substance P receptor protein (X62934), rat-derived neurokinin 3 receptor protein (J05189), rat-derived endothelin receptor protein (M60786), rat-derived ligand unknown receptor proteins (L04672), (X61496), (X59249) and (L09249), mouse-derived ligand unknown receptor protein (P30731), human-derived ligand unknown receptor proteins (M31210) and (U03642), etc. was made. In particular, the degenerate DNA primer having a nucleotide sequence (SEQ ID NO: 8) which is complementary to the nucleotide sequence (6A in FIG. 5) with highly common bases (highly homologous nucleotides) was synthesized to enhance base agreement of sequences with as many receptor cDNAs as possible even in other portions on the basis of base regions that are in agreement with a large number of receptor cDNAs.

The nucleotide sequence represented by SEQ ]:D NO: 8 is:

| 5'-GATGTG (A or G) TA (A or G) GG (G or C) (A or G) ICCAACAGAIG (A or G) (C or T) AAA-3' |
|---|

The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis, provided that I denotes inosine.

The aforementioned abbreviations in parentheses are reference numbers indicated when the GenBank/EMBL data base is retrieved and are usually called "Accession Numbers".

Example 14
Cloning of Rabbit Gastropyrolic Part Smooth Muscle-Derived G Protein Coupled Receptor Protein cDNA (1) Preparation of Poly(A)+RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)+RNA fractions were prepared with a mRNA purifying kit (Pharmacia Co.). Next, to 5 μg of the poly(A)+RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using Rabbit Gastropyrolic Part Smooth Muscle-Derived cDNA and Sequencing By using, as a template, 1 μl of cDNA prepared from the rabbit gastropyrolic part-smooth muscle in the above step (1), PCR amplification using the DNA primer having a nucleotide sequence represented by SEQ ID NO: 6 and the DNA primer having a nucleotide sequence represented by SEC, ID NO: 8 synthesized in Example 13 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated by using a 1.0% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain transformant *Escherichia coli* JM109/pMH28.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The determined nucleotide sequence was as shown in FIG. 52.

Homology retrieval was carried out based upon the determined nucleotide sequence [FIG. 52]. As a result, it was learned that a novel G protein coupled receptor protein was encoded by the cDNA fragment insert in the plasmid possessed by the transformant *Escherichia coli* JM109/pMH28. To further confirm this fact, by using DNASIS (Hitachi System Engineering Co., Japan) the nucleotide sequence were converted into an amino acid sequence [FIG. 52], and homology retrieval was carried out in view of hydrophobicity plotting [FIG. 53] and at the amino acid sequence level to find homology relative to mouse IL-8 receptor protein (P35343), human somatostatin receptor protein 1 (A41795) and human somatostatin receptor protein 4 (A47457) [FIG. 54]. The aforementioned abbreviations in parentheses are reference numbers assigned when they are registered as data to NBRF-PIR or SWISS-PROT and are usually called "Accession Numbers".

Example 15
Preparation of Synthetic DNA Primer for Amplifying G Protein Coupled Receptor Protein-Encoding DNA A comparison of nucleotide sequences coding for regions corresponding to or near the second membrane-spanning domain among known G protein coupled receptors, i.e., human-derived galanin receptor (HUMGALAREC), rat-derived α-1B-adrenergic receptor (RATADR1B), human-derived β-1-adrenergic receptor (HUMADRB1), rabbit-derived IL-8 receptor (RABIL8RSB), human-derived opioid receptor (HUMOPIODRE), bovine-derived substance K receptor (BTSKR), human-derived somatostatin receptor-2 (HUMSTRI2A), human-derived somatostatin receptor-3 (HUMSSTR3Y), human-derived gastrin receptor (HUMGARE), human-derived cholecystokinin A receptor (HUMCCKAR), human-derived dopamine receptor-D5 (HUMD1B), human-derived serotonin receptor 5HT1E (HUM5HT1E), human-derived dopamine receptor D4 (HUMD4C), mouse-derived serotonin receptor-2 (MMSERO), rat-derived α-1A-adrenergic receptor (RATADRA1A), rat-derived histamine H2 receptor (S57565), etc. was made. In particular, the degenerate DNA primer having a nucleotide sequence (T2A in FIG. 7, SEQ ID NO: 10) with highly common bases (highly homologous nucleotides) was synthesized to enhance base agreement of sequences with as many receptor cDNAs as possible even in other regions on the basis of nucleotide sequence regions that were in agreement with a large number of receptor cDNAs. Nucleotide synthesis was carried out by a DNA synthesizer.

The nucleotide sequence represented by SEQ ID NO: 10 is:

5'-GYCACCAACN$_2$WSTTCATCCTSWN$_2$HCTG-3' wherein S represents G or C; Y represents C or T; W represents A or T; H represents A, C or T and N$_2$ represents I.

The parentheses indicate the incorporation of a plurality of bases, leading to multiple oligonucleotides in the primer preparation. In other words, nucleotide resides in parentheses of the aforementioned DNAs were incorporated in the presence of a mixture of plural bases at the time of synthesis, provided that I denotes inosine.

Furthermore, a comparison of nucleotide sequences coding for regions corresponding to or near the seventh membrane-spanning domain among known G protein coupled receptors, i.e., human-derived galanin receptor (HUMGALAREC), rat-derived A1 adenosine receptor (RAT1ADREC), porcine-derived angiotensin receptor (PIGA2R), rat-derived serotonin receptor (RAT5HTRTC), human-derived dopamine receptor (S58541), human-derived gastrin releasing peptide receptor (HUMGRPR), mouse-derived GRP/bombesin receptor (MUSGRPBOM), rat-derived vascular type 1 angiotensin receptor (RRVT1AIIR), human-derived muscarinic acetylcholine receptor (HSHM4), human-derived β-1 adrenergic receptor (HUMDRB1), human-derived gastrin receptor (HUMGARE), rat-derived cholecystokinin receptor (RATCCKAR), rat-derived ligand unknown receptor (S59748), human-derived somatostatin receptor (HUMSST28A), rat-derived ligand unknown receptor (RNGPROCR), mouse-derived somatostatin receptor 1 (MUSSRI1A), human-derived α-A1-adrenergic receptor (HUMA1AADR), mouse-derived delta-opioid receptor (S66181), human-derived somatostatin receptor-3 (HUMSSTR3Y), etc. was made. In particular, the degenerate DNA primer having a nucleotide sequence (T7A in FIG. 8, SEQ ID NO: 11) with highly common bases (highly homologous nucleotides) was synthesized to enhance base agreement of sequences with as many receptor cDNAs as possible even in other regions on the basis of nucleotide sequence regions that were in agreement with a large number of receptor cDNAs. Nucleotide synthesis was carried out by a DNA synthesizer.

The nucleotide sequence represented by SEQ ID NO: 11 is:

5'-ASN$_2$ SAN$_2$RAAGSARTAGAN$_2$GAN$_2$RGGRTT-3' wherein R represents A or G; S represents G or C and N$_2$ represents I.

The parentheses indicate the incorporation of a plurality of bases, leading to multiple oligonucleotices in the primer preparation. In other words, nucleotide residues in parentheses of the aforementioned DNAs were incorporated in the presence of a mixture of plural bases at the time of synthesis, provided that I denotes inosine.

The aforementioned abbreviations in parentheses are reference numbers indicated when the GenBank/EMBL data base is retrieved and are usually called "Accession Numbers".

Example 16
Cloning of Rabbit Gastropyrolic Part Smooth Muscle-Derived G Protein Coupled Receptor Protein cDNA (1) Preparation of Poly(A)$^+$RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)$^+$RNA fractions were prepared with a mRNA purifying kit (Pharmacia Co.). Next, to 5 μg of the poly(A)$^+$ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE.

(2) Amplification of Receptor cDNA by PCR Using Rabbit Gastropyrolic Part Smooth Muscle-Derived cDNA and Sequencing By using, as a template, 1 μl of cDNA prepared from the rabbit gastropyrolic part smooth muscle in the above step (1), PCR amplification using the DNA primer having a nucleotide sequence represented by SEQ ID NO: 10 and the DNA primer having a nucleotide sequence represented by SEQ ID NO: 11 synthesized in Example 15 was carried out. A reaction solution was composed of the synthetic DNA primers (SEQ: 5' primer sequence and 3' primer sequence) each in an amount of 100 pM, 0.25 mM dNTPs, 1 μl of Taq DNA polymerase and 10 μl of buffer attached to the enzyme kit, and the total amount of the reaction solution was made to be 100 μl. The cycle for amplification including 96° C. for 30 sec., 45° C. for 1 min. and 60° C. for 3 min. was repeated 25 times with a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via, Decoding Nucleotide Sequence of Inserted cDNA Region The PCR products obtained in the above step (2) were separated with a 1.4% low-melting temperature agarose gel, the band parts were excised from the gel with a razor blade, and were eluted electrophoretically, extracted with phenol and precipitated in ethanol to recover DNAs. According to the protocol attached to a TA Cloning Kit (Invitrogen Co.), the recovered DNAs were subcloned to the plasmid vector, pCR™II. The recombinant vectors were introduced into *E. coli* JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked with a sterilized toothstick to obtain 100 transformant cloies.

The individual clones were cultured overnight in an LB culture medium containing ampicillin and treated with the automatic plasmid extracting machine PI-100 (Kurabo Co., Japan) to prepare plasmid DNAs. An aliquot of the DNA thus prepared was cut by EcoRI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer.

Homology retrieval was carried out based upon the determined nucleotide sequence by using DNASIS (Hitachi System Engineering Co., Japan). As a result, it was learned that a novel G protein coupled receptor protein was encoded by the cDNA fragment insert in the plasmid possessed by the transformant *Escherichia coli* JM109/pMN7. FIG. 56 and FIG. 56 show the nucleotide sequences of the cDNA fragments. To further confirm this fact, by using DNASIS (Hitachi System Engineering Co., Japan), the nucleotide sequences were converted into amino acid sequences [FIG. 55] and [FIG. 56], and hydrophobicity plotting was carried out [FIG. 57]. As a result, the presence of hydrophobic domains which prove that it is a G protein coupled receptor protein were confirmed. Furthermore, homology retrieval was carried out at the amino acid sequence level to find that the DNAs were novel receptor proteins having 27% homology relative to rat-derived 3-adrenaline receptor protein (A41679), 29% homology relative to rat-derived serotonin (5-HT6) receptor protein (JN,)591), 27% homology relative to dog-derived histamine $H_2$ receptor protein (A39008), 27% homology relative to human-derived somatostatin receptor (type 4) protein (JN0605), 24% homology relative to human-derived dopamine $D_1$ receptor protein (S11377), 23% homology relative to rat-derived neurotensin receptor protein (JH0164), 31% homology relative to human-derived cholecystokinin B receptor protein (JC1352), and 30% homology relative to rat-derived gastrin receptor protein (JQ1614). The aforementioned abbreviations in parentheses are reference numbers assigned when they are registered as data to NBRF-PIR and are usually called "Accession Numbers".

Example 17
Amplification of Receptor cDNA by PCR Using MIN6-Derived cDNA and Sequencing By using, as a template, 5 μl of cDNA prepared from the mouse pancreatic β-cell strain, MIN6 in Working Example 4 (1), PCR amplification using the DNA primers synthesized in Example 4 (2) as disclosed in Libert F. et al., "Science, 244:569–572, 1989", i.e., a synthetic primer represented by the following sequence:

5'-CTGTG (C or T) G (C or T) (G or C) AT (C or T) GCIIT
   (G or T) GA (C or T) (A or C) G (G or C) TAC-3'
                                    (SEQ ID NO: 60)

wherein I is inosine; and a synthetic primer represented by the following sequence:

5'-A (G or T) G (A or T) AG (A or T) AGGGCAGCCAGCAGAI
   (G or C) (A or G) (C or T) GAA-3'
                                    (SEQ ID NO: 61)

wherein I is inosine, was carried out under the same conditions as in Example 3 (1). The resulting PCR product was subcloned to the plasmid vector, pCR II, in the same manner as in Example 3 (2) to obtain a plasmid, p5S38. The plasmid p5S38 was transfected into *E. coli* JM109 to obtain transformant *Escherichia coli* JM109/p5S38.

The reaction for determining the nucleotide sequence (sequencing) was carried out with a DyeDeoxy terminator cycle sequencing kit (ABI Co.), the DNA was decoded with the fluorescent automatic sequencer (ABI Co.), and thE data of the nucleotide sequence obtained were read with DNASIS (Hitachi System Engineering Co., Japan).

FIG. 62 shows a mouse pancreatic β-cell strain MIN6-derived G protein coupled receptor protein-encoding DNA (SEQ ID NO: 33) and an amino acid sequence (SEQ ID NO: 28) encoded by the isolated DNA based upon the nucleotide sequence of plasmid, p5S38. The underlined portions represent regions corresponding to the synthetic primers.

Homology retrieval was carried out based upon the determined nucleotide sequence [FIG. 62]. As a result, it was learned that a novel G protein coupled receptor protein was encoded by the cDNA fragment obtained. To further confirm this fact, by using DNASIS (Hitachi System Engineering Co., Japan), the nucleotide sequence was converted into an amino acid sequence [FIG. 62], and hydrophobicity plotting was carried out to confirm the presence of four hydrophobic regions [FIG. 64]. Upon comparing the amino acid sequence with those encoded by p19P2 obtained in Example 3 (2) and encoded by pG3-2 obtained in Example 4 (2), furthermore, a high degree of homology was found as shown in FIG. 63. As a result, it is strongly suggested that the mouse pancreatic β-cell strain, MIN6-derived G protein coupled receptor protein encoded by p5S38 recognizes the same ligand as the human pituitary gland-derived G protein coupled receptor protein encoded by p19P2 does while the animal species from which the receptor protein encoded by p5S38 is derived is different from that from which the receptor protein encoded by p19P2 is. It is also strongly suggested that the mouse pancreatic β-cell strain, MIN6-derived G protein coupled receptor protein encoded by p5S38 recognizes the same ligand as the mouse pancreatic β-cell strain, MIN6-derived 3 protein coupled receptor proteins encoded by pG3-2 and pG1-10 do and they are analogous receptor proteins one another (so-called "subtype").

Example 18
Northern Hybridization with cDNA Fragment Included in MIN6-Derived Receptor Protein-Encoding p3H2-17

Mouse cell line, MIN6, Neuro-2a, poly(A)⁺RNA (2.5 μg) and mouse brain, spleen, thymus and pancreas poly(A)⁺ RNAs (2.5 μg) were used as poly(A)⁺RNAs. The DNA fragment inserted into the plasmid, p3H2-17, obtained in Example 7 (3) was recovered as a DNA fragment with about 400 bp by cutting the plasmid with EcoRI and the resulting DNA fragment was labeled by incorporation of [³²P]dCTP (Dupont Co.) with a random prime DNA labeling kit (Amasham Co.). The about 400 bp labeled DNA fragment was used as a probe for hybridization.

Nylon membrane (PaLL Biodyne, U.S.A.) was used as a filter for northern blotting and migration of the poly(A)⁺ RNA and adsorption (sucking) thereof with the blotting filter was carried out according to the method as disclosed in Molecular Cloning, Cold Spring Harbor Laboratory Press, 1989.

The hybridization was carried out by incubating the above-mentioned filter and probe in a buffer containing 50% formamide, 5×SSPE (20×SSPE (pH 7.4) is 3 M NaCl, 0.2 M NaH₂PO₄H₂O, 25 mM EDTA), 5×Denhardt's solution (Nippon Gene, Japan), 0.1% SDS and 100 μg/ml of salmon sperm DNA overnight at 42° C. The filter was washed with 0.1×SSC (20×SSC is 3 M NaCl, 0.3 M sodium citrate), 0.1% SDS at 50° C. and, after drying with an air, was exposed to an X-ray film (XAR5, Kodak) for 15 days at −80° C. The results were as shown in FIG. 65.

Figure 65:
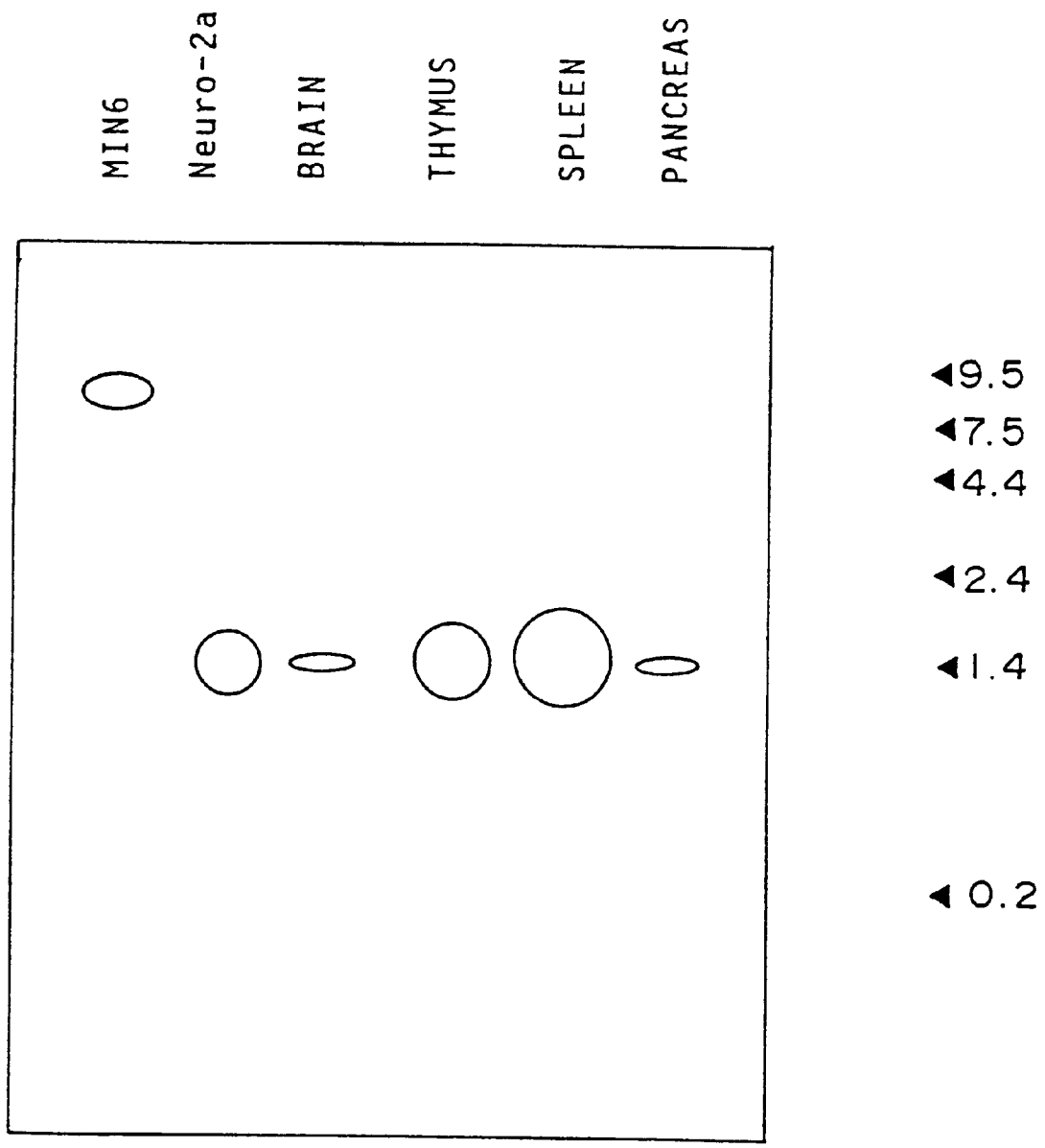
FIG. 65 shows the northern blot analysis profile of the receptor gene encoded by the cDNA included in the mouse pancreatic G -cell strain MIN6-derived novel receptor protein cDNA clone, p3H2-17, for mouse cell line, MIN6, Neuro-2a cell and mouse brain, thymus, spleen and pancreas poly(A)⁺RNA, wherein each arrow and number indicates the size marker position (unit of number: kb).

It is considered from FIG. 65 that mRNA for the the receptor gene encoded by the cDNA fragment included in p3H2-17 is expressed in the cell line, MIN6, Neuro-2a, and the mouse brain, pancreas, spleen and thymus and especially expressed in the mouse spleen and thymus intensely. The MIN6 signal position hybridizable in the northern hybridization plotting is different from those of other organ cells.

Example 19
PCR Cloning of cDNA Comprising Whole Coding Regions of Receptor Proteins from Mouse Spleen, Thymus-Derived Poly(A)⁺RNA and Sequencing (1) PCR Cloning of cDNA Comprising Whole Coding Region of Receptor Protein In order to obtain a full-length open reading frame (coding region) of the receptor protein encoded by the cDNA fragment included in p3H2-17, PCR amplification was carried out by 5'RACE and 3'RACE wherein poly(A)$^+$ RNA derived from mouse spleen and thymus was used.

Based on the nucleotide sequence of 3H2-17 which was disclosed, the following 4 primers were synthesized:

| (Nucleotide sequence of synthesized primer) | |
|---|---|
| ① 5'-TAGTGTGTGGAGTCGTGTGGCTGGCTG-3' | (SEQ ID NO: 20) |
| ② 5'-AGTCTTTGCTGCCACAGGCATCCAGCG-3' | (SEQ ID NO: 21) |
| ③ 5'-CAAGCCAGTAAGGCTATGAAGGGCAGCAAG-3' | (SEQ ID NO: 22) |
| ④ 5'-ACAGGACCTGCTGGGCCATCCTGGCGACACA-3' | (SEQ ID NO: 23) |

The 5'RACE was carried out according to the protocol of 5'Ampli Finder RACE kit from ClonTech Co. (ClonTech Co.).

Figure 66:
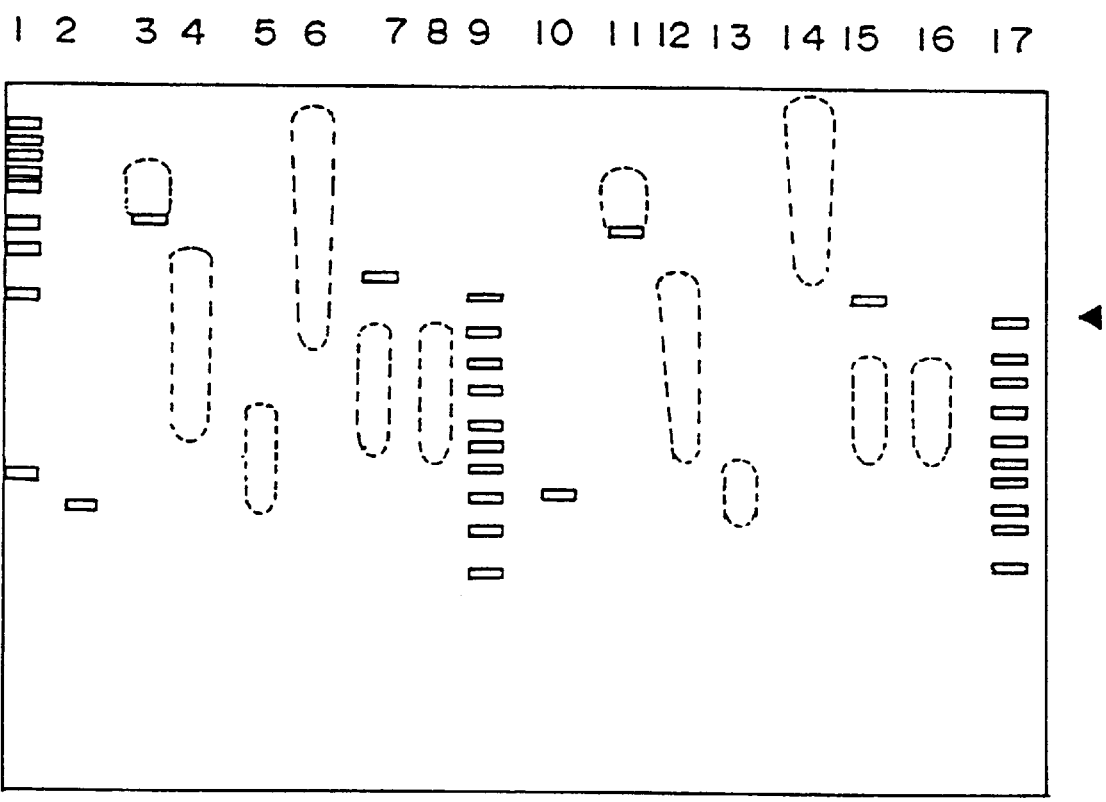
FIG. 66 shows the agarose gel electrophoresis analysis profile of the PCR products obtained by 5'RACE PCR of the receptor gene included in p3H2-17 using mouse thymus and spleen poly(A)⁺RNA.

In an embodiment, cDNA was prepared from 2 μg each of poly(A)$^+$RNAs derived from mouse spleen and thymus by using the aforementioned primer ④ and ligated with an anchor attached to the 5'RACE kit. A mixture of a 1/200 amount of the cDNA thus prepared, the anchor and the aforementioned primer ③ was subjected to PCR using 4 polymerases, Taq (Takara, Japan), Ex Taq (Takara, Japan), Vent (New England Biolabs) and Pfu (Stratagene) under the following conditions: 96° C. for 30 sec., 60° C. for 60 sec., 72° C. for 90 sec. and 35 cycles. A 1/5 amount of the PCR product was subjected to agarose electrophoresis and stained with ethidium bromide (EtBr). The results are shown in FIG. 66. The amplified DNA band appeared at an about 1 kbp position and the isolated about 1 kbp DNA band which was synthesized from poly(A)$^+$RNAs; derived from mouse spleen and thymus by the 5'RACE using Ex Taq polymerase was treated with SUPREC™-01 (Takara, Japan) to recover cDNA.

The isolated DNA was subcloned into pCR™II vector by using a TA Cloning Kit (Invitrogen Co.) and the vector was transfected into *E. coli* JM109 to obtain 3 transformant clones, N26, N64 and N75. The clone, N26, holds the thymus-derived cDNA which is amplified by the 5'RACE and the clone, N75, holds the spleen-derived cDNA which is amplified by the 5'RACE (FIG. 68).

The 3'RACE was carried out according to the protocol of 3' RACE kit (GIBCO BRL Co.).

In an embodiment, cDNA was prepared from 1 μg each of poly(A)$^+$RNAs derived from mouse spleen and thymus by using an adaptor primer attached to the 3' RACE kit. A mixture of the adaptor primer thus prepared and a 1/10 amount of cDNA which was prepared by using the aforementioned primer ① was subjected to 1st PCR using 4 polymerases, Taq (Takara, Japan), Ex Taq (Takara, Japan), Vent (NEB) and Pfu (Stratagene) under the following conditions: 96° C. for 30 sec., 55° C. for 60 sec., 72° C. for 120 sec. and 30 cycles. A mixture of a 1/50 amount of the 1st PCR product, the aforementioned primer ② and the adaptor primer was subjected to 2nd PCR using the aforementioned polymerases under the same conditions as aforementioned herein in the 5'RACE process. A 1/5 amount of the 2nd PCR product was subjected to agarose electrophoresis and stained with ethidium bromide. The results are shown in FIG. 67.

The amplified DNA band appeared at an about 1 kbp position (which was synthesized from poly(A)$^+$RNAs derived from mouse thymus by the 3'RACE using Vent polymerase) and the amplified DNA band appeared at an about 1 kbp position (which was synthesized from poly(A)$^+$ RNAs derived from mouse thymus by the 3'RACE using Pfu polymerase) were treated with SUPREC™-01 (Takara, Japan) to recover cDNA, respectively.

The isolated DNAs were treated with T4 polynucleotide kinase (Wako Pure Chemical Co., Japan) to add phosphate to the end thereof and the phosphorylated DNAs were ligated with pUC18 SmaI BAP (Pharmacia) by using DNA Ligation Kit (Takara, Japan) followed by transformation of *E. coli* JM109 to obtain 3 transformant clones, C2, C13 and C15. The clones, C13 and C15, hold the thymus-derived cDNA which is amplified by the 3'RACE and the clone, C2, holds the thymus-derived cDNA which is amplified by the 3'RACE (FIG. 68).

Based on the nucleotide sequences of clones, N26, N64 and N75, which are considered to hold the N-terminal region of the open reading frame (ORF) of the cDNA fragment included in p3H2-17 and the nucleotide sequences of clones, C2, C13 and C15, which are considered to hold the C-terminal region of the open reading flame (ORF) of the cDNA fragment included in p3H2-17, the entire nucleotide sequence coding for the open reading flame and neighboring region of the receptor protein encoded by the cDNA included in p3H2-17 was determined. To be more specific, sequencing was carried out with the primers used in the 5'RACE and 3'RACE or synthetic primers for sequencing by using a DyeDeoxy Terminator Cycle Sequencing Kit (ABI Co.), the nucleotide sequences were decoded by using a fluorescent automatic sequencer. The obtained data of the DNA were analyzed by DNASIS (Hitachi System Engineering Co., Japan).

PCR errors which presumably happen to occur upon PCR have been corrected by a way of thinking that, when nucleotides between two clones which are independently produced by PCR are identical (e.g. those between clones, N75 and N64, are identical) each other, the identical base is considered as correct. The determined nucleotide sequence is shown in FIG. 69. The amino acid sequence is deduced based on the determined nucleotide sequence (FIG. 69). Hydrophobicity plotting was carried out based on the deduced amino acid sequence (FIG. 70). As a result, it was learned that it was a seven transmembrane G protein coupled receptor, as it is suggested from the cDNA fragment included in p3H2-17.

Homology retrieval at the amino acid level indicates that it is homologous to mouse $P_{2U}$purinoceptor and chicken $P_{2Y}$purinoceptor.

Further, the clone which are free of an error in the open reading flame (ORF) was selected and used to construct plasmids carrying the full-length ORF of the receptor protein encoded by p3H2-17. In an embodiment, the cDNA fragment held by the clone, N75, was digested with restriction enzymes, DraIII and EcoRI, to obtain cDNA fragments which are the N-terminal region of the receptor protein held by p3H2-17. The C-terminal cDNA fragment encoded by C13 was digested with restriction enzymes, DraIII and EcoRI, to delete 5'-side regions from the DraIII site of the C-terminal and the long fragment was obtained by the digestion of C13 with restriction enzymes, DraIII and EcoRI. The N75-derived N-terminal cDNA DraIII-EcoRI fragment was ligated with the long C13-derived DraIII-EcoRI fragment by using a DNA Ligation Kit (Talara, Japan) and transfected into *Escherichia coli* JM109 to obtain transformant *Escherichia coli* JM109/pMAH2-17.

(2) Electrophysiological Measurement of Receptor Encoded by pMAH2-17

The receptor encoded by pMAH2-17 was examined electrophsiologically in Xenopus oocytes. The ORF of the receptor encoded by pMAH2-17 was inserted into the XhoI-XbaI sites of pBluescript™II SK(+) (Stratagene) with directing the sequence thereof downstream from T7 promoter. The resulting plasmid as a template was treated with a mCAP™mRNA Capping kit (Stratagene) to produce cRNA of this receptor gene.

The cRNA was injected into Xenopus oocytes (50 ng cRNA/50 nl/oocyte), previously prepared according to the method disclosed in Nathan Dascal et al., Proc. Natl. Acad. Sci. USA, Vol. 90, pp.6596–6600 (1993). The cRNA-injected oocytes were incubated at 20° C. for 2 to 3 days and subjected to electrophysiological measurements. The measurement was carried out with a microelectrode-applicable high input resistance amplifier (MEz-8300, Nippon Koden, Co., Japan), and a voltage clamping amplifier (CEz −/200, Nippon Koden, Co., Japan). The initial membrane potential of oocytes was set to −60 mV and responses (current changes of the membrane) evoked by addition of ligands were recorded with a recorder (Thermal Array recorder, Nippon Koden, Co., Japan) (Nathan Dascal et al., Proc. Natl. Acad. Sci. USA, Vol. 90, pp.6596–6600 (1993)).

Typical inward currents elicited upon activation of phospholipase C-coupled receptors were observed in oocytes injected with pMAH2-17 cRNA via stimulation by 10 $\mu$M ATP (FIG. 75). In contrast, such a current was not observed in oocytes injected with $H_2O$, instead of pMAH2-17 cRNA, by the ATP stimulation.

In conclusion, it is considered that the receptor encoded by pMAH2-17 cRNA is classified into a subtype within the ATP receptor, $P_2$ purinoceptor.

Example 20

Cloning of Rabbit Gastropyrolic Part Smooth Muscle-Derived G Protein Coupled Receptor Protein cDNA (1) Preparation of Poly(A)+RNA Fraction from Rabbit Gastropyrolic Part Smooth Muscle and Synthesis of cDNA A total RNA was prepared from rabbit gastropyrolic part smooth muscles by the guanidine thiocyanate method (Kaplan B. B. et al., Biochem. J. 183, 181–184 (1979)) and, then, poly(A)+RNA fractions were prepared with a mRNA purifying kit (Pharmacia Co.). Next, to 5 $\mu$g of the poly(A)+ RNA fraction was added a random DNA hexamer (BRL Co.) as a primer, and the resulting mixture was subjected to reaction with MMLV reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 $\mu$l of TE.

(2) Amplification of Receptor cDNA by PCR Using Rabbit Gastropyrolic Part Smooth Muscle-Derived cDNA and Sequencing By using, as a template, 1 $\mu$l of cDNA prepared from the rabbit gastropyrolic part smooth muscle in the above step (1), PCR amplification using the DNA primer having a nucleotide sequence represented by SEQ ID NO: 10 and the DNA primer having a nucleotide sequence represented by SEQ ID NO: 4 synthesized in Example 15 was carried out. A reaction solution was composed of the synthetic DNA primers (SEQ: 5' primer sequence and 3' primer sequence) each in an amount of 100 pM, 0.25 mM dNTPs, 1 $\mu$l of Taq DNA polymerase and 10 $\mu$l of buffer attached to the enzyme kit, and the total amount of the reaction solution was made to be 100 $\mu$l. The cycle for amplification including 96° C. for 30 sec., 45° C. for 1 min. and 60° C. for 3 min. was repeated 25 times by using a Thermal Cycler (Perkin-Elmer Co.). The amplified products were confirmed relying upon 1.2% agarose gel electrophoresis and ethidium bromide staining.

(3) Subcloning of PCR Product into Plasmid Vector and Selection of Novel Receptor Candidate Clone via Decoding Nucleotide Sequence of Inserted cDNA Region The PCR products obtained in the above step (2) were separated by using a 1.0% low-melting temperature agarose gel, the band parts were excised from the gel with a razor blade, and were electro-eluted, extracted with phenol and precipitated in ethanol to recover DNAs. According to the protocol attached to a TA Cloning Kit (Invitrogen Co.), the recovered DNAs were subcloned to the plasmid vector, pCR II. The recombinant vectors were introduced into E. coli JM109 competent cells (Takara Shuzo Co., Japan) to produce transformants. Then, transformant clones having a cDNA-inserted fragment were selected in an LB agar culture medium containing ampicillin, IPTG and X-gal. Only transformant clones exhibiting white color were picked. with a sterilized toothstick to obtain 100 transformant clones.

The individual clones were cultured overnight in an LB culture medium containing ampicillin and treated width the automatic plasmid extracting machine PI-100 (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer.

Homology retrieval was carried out based upon the determined nucleotide sequence. As a result, it was learned that a novel G protein coupled receptor protein was been encoded by the cDNA fragment insert in the plasmid possessed by the transformant Escherichia coli JM109/pMN128. The nucleotide sequences of the cDNA fragments are shown in FIGS. 71 and 72. To further confirm this fact, by using DNASIS (Hitachi System Engineering Co., Japan) the nucleotide sequences were converted into amino acid sequences [FIGS. 71 and FIG. 72], and homology retrieval was carried out in view of hydrophobicity plotting [FIG. 73] and at the amino acid sequence level to find a novel receptor protein which has 27% homology relative to hamster-derived 2-adrenaline receptor protein (A03159), 20% homology relative to rat-derived bradykinin receptor (type $B_2$) protein (A41283), 24% homology relative to human-derived dopamine $D_1$ receptor protein (S11377) and 23% homology relative to human-derived blue sensitive opsin receptor protein (A03156). The aforementioned abbreviations in parentheses are reference numbers assigned when they are registered as data to NBRF-PIR and are usually called "Accession Numbers".

Example 21

Cloning of cDNA Comprising Whole Coding Regions for Receptor Protein from Human-Derived DNA Library The DNA library constructed by Clontech wherein $\lambda$ gtll phage vector is used (CLONTECH Laboratories, Inc.; CLH L1008b) was employed as a human placenta-derived cDNA library. The human placenta cDNA library ($1\times10^5$ pfu (plaque forming units)) was thermally denatured. By using the human placenta-derived cDNA library, PCR amplification using the DNA primer having a nucleotide sequence represented by SEQ ID NO: 20 and the DNA primer having a nucleotide sequence represented by SEQ ID NO: 23 synthesized in Example 19 was carried out.

| (Nucleotide sequence of synthesized primer) | |
|---|---|
| ① 5'-TAGTGTGTGGAGTCGTGTGGCTGGCTG-3' | (SEQ ID NO: 20) |
| ② 5'-ACAGGACCTGCTGGGCCATCCTGGCGACACA-3' | (SEQ ID NO:23) |

The isolated DNA was subcloned using a TA Cloning Kit (Invitrogen Co.) and sequencing was carried out. FIG. 76 shows a nucleotide sequence of obtained cDNA fragment, ph3H2-17. As a result, it was learned that ph3H2-17 is highly homologous to the mouse purinoceptor cDNA fragment, p3H2-17. It is strongly suggested that the human-derived cDNA fragment is a partial nucleotide sequence of human purinoceptor.

Based on the nucleotide sequence of ph3H2-17 which was sequenced, the following 2 primers were synthesized:

| (Nucleotide sequence of synthesized primer) | |
|---|---|
| ③ 5'-ACAGCCATCTTCGCTGCCACAGGCAT-3' | (SEQ ID NO: 58) |
| ④ 5'-AGACAGTAGCAGGCCAGCAGGGCACAAA-3' | (SEQ ID NO: 59) |

The above synthetic 2 primers were each used in combination with λ gt 11 primers (Takara, Japan; catalogue 3864) for obtaining full-length human prinoceptor cDNA. Thus, using thermally denatured, human placenta-derived λ gt 11 cDNA libraries (CLONTECH; CLHL 1008b), first RCR amplification using a combination of the DNA primer having a nucleotide sequence represented by SEQ ID NO: 20 with λ gt 11 Forward primer, of the DNA primer having a nucleotide sequence represented by SEQ ID NO: 20 with λ gt 11 Reverse primer, of the DNA primer having a nucleotide sequence represented by SEQ ID NO: 23 with λ gt 11 Forward primer, and of the DNA primer having a nucleotide sequence represented by SEQ ID NO: 23 with λ gt 11 Reverse primer was carried out with Ex Taq polymerase (Takara. Japan) (30 cycles; 95° C./30 seconds, 55° C./60 seconds, and 72° C./60 seconds), respectively.

Next, by using a 1/50 of the 1st PCR product:, second RCR amplification was carried in the same manner as in the first PCR except for using the DNA primer having a nucleotide sequence represented by SEQ ID NO: 58 in place of SEQ ID NO: 20 and the DNA primer having a nucleotide sequence represented by SEQ ID NO: 59 in place of SEQ ID NO: 23 (30 cycles; 95° C./30 seconds, 65° C./60 seconds and 72° C./60 seconds). The amplified product DNA was subcloned using a TA Cloning Kit (Invitrogen Co.) and sequencing was carried out for three clones each of 5' and 3' sides (FIG. 77).

Based on the amino acid sequence (FIG. 77) deduced from the determined nucleotide sequence of human puriroceptor cDNA as shown in FIG. 77, hydrophobicity plotting was carried out (FIG. 78). As a result, it was learned that the human-derived receptor is a novel seven transmembrane G protein coupled receptor, similarly to the mouse type. It was also learned that the deduced amino acid sequence of human receptor has 87% homology relative to the amino acid sequence of mouse purinoceptor and its amino acid residues are well conserved (FIG. 79).

Clones free of PCR errors which often occur in a PCR amplification were selected and restriction enzyme regions comprising overlapping areas were obtained therefrom. The restriction enzyme regions thus obtained were subjected to construction of plasmid phAH2-17 having a full-length open reading frame of human purinoceptor cDNA. The plasmid phAH2-17 is possessed by transformant *Escherichia coli* JM109/phAH2-17.

The DNA primers of the present invention allow efficient amplification of DNAs that encode G protein coupled receptor proteins. This makes it possible to efficiently screen for the DNAs coding for G protein coupled receptor proteins and to accomplish the cloning.

The G protein coupled receptor protein of the present invention and their G protein coupled receptor protein-encoding DNA are advantageously useful in:

① determining ligands,
② obtaining antibodies and an antisera,
③ constructing systems for expressing recombinant receptor proteins,
④ investigating or developing receptor-binding assay systems and screening for pharmaceutical candidate compounds, by using the above expression system
⑤ designing drugs based upon comparisons with ligands and receptors having a structure similar or analogous thereto,
⑥ preparing probes and/or PCR primers in gene diagnosis, and
⑦ gene manipulating therapy.

In particular, discovering the structure and properties of the G protein coupled receptor will lead to the development of unique pharmaceuticals acting upon these systems.

The practice of the present invention will employ, otherwise indicated, conventional techniques of molecular biology, microbiology, recombinant DNA, pharmacology, immunology, bioscience, and medical technology, which are within the skill of the art. All patents, patent applications, and publications mentioned herein, both supra and infra, are hereby incorporated herein by reference.

SEQUENCE LISTING (1) GENERAL INFORMATION:

(iii) NUMBER OF SEQUENCES: 380

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:1:

CGTGGSCMTS STGGGCAACN YCCTG                                             25

(2) INFORMATION FOR SEQ ID NO:2:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:2:

GTNGWRRGGC ANCCAGCAGA KGGCAAA                                           27

(2) INFORMATION FOR SEQ ID NO:3:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:3:

CTCGCSGCYM TNRGYATGGA YCGNTAT                                           27

(2) INFORMATION FOR SEQ ID NO:4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:4:

CATGTRGWAG GGAANCCAGS AMANRARRAA                                        30

(2) INFORMATION FOR SEQ ID NO:5:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:5:

```
CTGACYGYTC TNRSNRYTGA CMGVTAC                                              27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:6:

CTGACYGYTC TNRSNRYTGA CMGVTAT                                              27

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:7:

CTCGCSGCYM TNRGYATGGA YCGNTAC                                              27

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:8:

GATGTGRTAR GGSRNCCAAC AGANGRYAAA                                           30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:9:

GATGTGRTAR GGSRNCCAAC AGANGRYGAA                                           30
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION:  N = inosine (xi) SEQUENCE DESCRIPTION: SEQ ID NO:10:

GYCACCAACN WSTTCATCCT SWNHCTG                                            27

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:11:

ASNSANRAAG SARTAGANGA NRGGRTT                                            27

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:12:

TGNTSSTKMT NGSNGTKGTN GGNAA                                              25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (ix) FEATURE:
        (D) OTHER INFORMATION: N = inosine (xi) SEQUENCE DESCRIPTION: SEQ ID NO:13:

AYCKGTAYCK GTCCANKGWN ATKGC                                              25

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:14:

CATKKCCSTG GASAGNTAYN TRGC                                              24

(2) INFORMATION FOR SEQ ID NO:15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:15:

GWWGGGSAKC CAGCASANGG CRAA                                              24

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N at position 6, 9, 10 & 12 = inosine;
                N at position 15 = A, T, C or G"

(xi) SEQUENCE DESCRIPTION: SEQ ID NO:16:

ARYYTNGCNN TNGCNGAY                                                     18

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N at position 1, 4 & 6 = inosine
                N at position 13, 15, 16 & 18 = A,T, C or G"

(xi) SEQUENCE DESCRIPTION: SEQ ID NO:17:

NGGNANCCAR CANANNRNRA A                                                 21

(2) INFORMATION FOR SEQ ID NO:18:

(i) SEQUENCE CHARACTERISTICS:

(A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:18:

GCCTSNTNRN SATGWSTGTG GANMGNT                                27

(2) INFORMATION FOR SEQ ID NO:19:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:19:

GAWSNTGMYN ANRTGGWAGG GNANCCA                                27

(2) INFORMATION FOR SEQ ID NO:20:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:20:

TAGTGTGTGG AGTCGTGTGG CTGGCTG                                27

(2) INFORMATION FOR SEQ ID NO:21:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:21:

AGTCTTTGCT GCCACAGGCA TCCAGCG                                27

(2) INFORMATION FOR SEQ ID NO:22:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:22:

```
CAAGCCAGTA AGGCTATGAA GGGCAGCAAG                                      30
```

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:23:

```
ACAGGACCTG CTGGGCCATC CTGGCGACAC A                                    31
```

(2) INFORMATION FOR SEQ ID NO:24:

(i) SEQUENCE CHARACTERISTICS:
        (A) LENGTH: 91 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

```
Leu Val Leu Val Ile Ala Arg Val Arg Arg Leu His Asn Val Thr Asn
1               5                   10                  15

Phe Leu Ile Gly Asn Leu Ala Leu Ser Asp Val Leu Met Cys Thr Ala
            20                  25                  30

Cys Val Pro Leu Thr Leu Ala Tyr Ala Phe Glu Pro Arg Gly Trp Val
        35                  40                  45

Phe Gly Gly Gly Leu Cys His Leu Val Phe Phe Leu Gln Pro Val Thr
    50                  55                  60

Val Tyr Val Ser Val Phe Thr Leu Thr Thr Ile Ala Val Asp Arg Tyr
65                  70                  75                  80

Val Val Leu Val His Pro Leu Arg Arg Arg Ile
                85                  90
```

(2) INFORMATION FOR SEQ ID NO:25:

(i) SEQUENCE CHARACTERISTICS:
        (A) LENGTH: 59 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

```
Gly Leu Leu Leu Val Thr Tyr Leu Leu Pro Leu Leu Val Ile Leu Leu
1               5                   10                  15

Ser Tyr Val Arg Val Ser Val Lys Leu Arg Asn Arg Val Val Pro Gly
            20                  25                  30

Cys Val Thr Gln Ser Gln Ala Asp Trp Asp Arg Ala Arg Arg Arg Arg
        35                  40                  45

Thr Phe Cys Leu Leu Val Val Val Val Val
    50                  55
```

(2) INFORMATION FOR SEQ ID NO:26:

(i) SEQUENCE CHARACTERISTICS:

(A) LENGTH: 370 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:26:

```
Met Ala Ser Ser Thr Thr Arg Gly Pro Arg Val Ser Asp Leu Phe Ser
1               5                   10                  15

Gly Leu Pro Pro Ala Val Thr Thr Pro Ala Asn Gln Ser Ala Glu Ala
            20                  25                  30

Ser Ala Gly Asn Gly Ser Val Ala Gly Ala Asp Ala Pro Ala Val Thr
        35                  40                  45

Pro Phe Gln Ser Leu Gln Leu Val His Gln Leu Lys Gly Leu Ile Val
    50                  55                  60

Leu Leu Tyr Ser Val Val Val Val Gly Leu Val Gly Asn Cys Leu
65                  70                  75                  80

Leu Val Leu Val Ile Ala Arg Val Arg Arg Leu His Asn Val Thr Asn
                85                  90                  95

Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Arg Ile Ser Leu Arg Leu Ser
                165                 170                 175

Ala Tyr Ala Val Leu Ala Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Leu
    210                 215                 220

Tyr Ala Trp Gly Leu Leu Leu Val Thr Tyr Leu Leu Pro Leu Leu Val
225                 230                 235                 240

Ile Leu Leu Ser Tyr Val Arg Val Ser Val Lys Leu Arg Asn Arg Val
                245                 250                 255

Val Pro Gly Cys Val Thr Gln Ser Gln Ala Asp Trp Asp Arg Ala Arg
            260                 265                 270

Arg Arg Arg Thr Phe Cys Leu Leu Val Val Val Val Val Phe Ala
        275                 280                 285

Val Cys Trp Leu Pro Leu His Val Phe Asn Leu Leu Arg Asp Leu Asp
    290                 295                 300

Pro His Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335

Trp Leu His Asp Ser Phe Arg Glu Glu Leu Arg Lys Leu Leu Val Ala
            340                 345                 350

Trp Pro Arg Lys Ile Ala Pro His Gly Gln Asn Met Thr Val Ser Val
        355                 360                 365

Val Ile
```

(2) INFORMATION FOR SEQ ID NO:27:

(i) SEQUENCE CHARACTERISTICS:
        (A) LENGTH: 206 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

```
Leu Val Leu Val Ile Ala Arg Val Arg Arg Leu Tyr Asn Val Thr Asn
 1               5                  10                  15
Phe Leu Ile Gly Asn Leu Ala Leu Ser Asp Val Leu Met Cys Thr Ala
             20                  25                  30
Cys Val Pro Leu Thr Leu Ala Tyr Ala Phe Glu Pro Arg Gly Trp Val
         35                  40                  45
Phe Gly Gly Gly Leu Cys His Leu Val Phe Phe Leu Gln Ala Val Thr
     50                  55                  60
Val Tyr Val Ser Val Phe Thr Leu Thr Thr Ile Ala Val Asp Arg Tyr
65                  70                  75                  80
Val Val Leu Val His Pro Leu Arg Arg Arg Ile Ser Leu Arg Leu Ser
                 85                  90                  95
Ala Tyr Ala Val Leu Ala Ile Trp Val Leu Ser Ala Val Leu Ala Leu
            100                 105                 110
Pro Ala Ala Val His Thr Tyr His Val Glu Leu Lys Pro His Asp Val
        115                 120                 125
Arg Leu Cys Glu Glu Phe Trp Gly Ser Gln Glu Arg Gln Arg Gln Leu
    130                 135                 140
Tyr Ala Trp Gly Leu Leu Leu Val Thr Tyr Leu Leu Pro Leu Leu Val
145                 150                 155                 160
Ile Leu Leu Ser Tyr Ala Arg Val Ser Val Lys Leu Arg Asn Arg Val
                165                 170                 175
Val Pro Gly Arg Val Thr Gln Ser Gln Ala Asp Trp Asp Arg Ala Arg
            180                 185                 190
Arg Arg Arg Thr Phe Cys Leu Leu Val Val Val Val Val
        195                 200                 205
```

(2) INFORMATION FOR SEQ ID NO:28:

(i) SEQUENCE CHARACTERISTICS:
        (A) LENGTH: 126 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Val Val Leu Val His Pro Leu Arg Arg Arg Ile Ser Leu Arg Leu Ser
 1               5                  10                  15
Ala Tyr Ala Val Leu Gly Ile Trp Ala Leu Ser Ala Val Leu Ala Leu
             20                  25                  30
Pro Ala Ala Val His Thr Tyr His Val Glu Leu Lys Pro His Asp Val
         35                  40                  45
Ser Leu Cys Glu Glu Phe Trp Gly Ser Gln Glu Arg Gln Arg Gln Ile
     50                  55                  60
```

```
Tyr Ala Trp Gly Leu Leu Leu Gly Thr Tyr Leu Pro Leu Leu Ala
 65                  70                  75                  80

Ile Leu Leu Ser Tyr Val Arg Val Ser Val Lys Leu Arg Asn Arg Val
                 85                  90                  95

Val Pro Gly Ser Val Thr Gln Ser Gln Ala Asp Trp Asp Arg Ala Arg
            100                 105                 110

Arg Arg Arg Thr Phe Cys Leu Leu Val Val Val Val Val
            115                 120                 125
```

(2) INFORMATION FOR SEQ ID NO:29:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:29:

```
CTGGTGCTGG TGATCGCGCG GGTGCGCCGG CTGCACAACG TGACGAACTT CCTCATCGGC    60

AACCTGGCCT TGTCCGACGT GCTCATGTGC ACCGCCTGCG TGCCGCTCAC GCTGGCCTAT   120

GCCTTCGAGC CACGCGGCTG GGTGTTCGGC GGCGGCCTGT GCCACCTGGT CTTCTTCCTG   180

CAGCCGGTCA CCGTCTATGT GTCGGTGTTC ACGCTCACCA CCATCGCAGT GGACCGGTAC   240

GTCGTGCTGG TGCACCCGCT GAGGCGGCGC ATC                                273
```

(2) INFORMATION FOR SEQ ID NO:30:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:30:

```
GGCCTGCTGC TGGTCACCTA CCTGCTCCCT CTGCTGGTCA TCCTCCTGTC TTACGTCCGG    60

GTGTCAGTGA AGCTCCGCAA CCGCGTGGTG CCGGGCTGCG TGACCCAGAG CCAGGCCGAC   120

TGGGACCGCG CTCGGCGCCG GCGCACCTTC TGCTTGCTGG TGGTGGTCGT GGTGGTG      177
```

(2) INFORMATION FOR SEQ ID NO:31:

(i) SEQUENCE CHARACTERISTICS:
        (A) LENGTH: 1110 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:31:

```
ATGGCCTCAT CGACCACTCG GGGCCCCAGG GTTTCTGACT TATTTTCTGG GCTGCCGCCG    60

GCGGTCACAA CTCCCGCCAA CCAGAGCGCA GAGGCCTCGG CGGGCAACGG GTCGGTGGCT   120

GGCGCGGACG CTCCAGCCGT CACGCCCTTC CAGAGCCTGC AGCTGGTGCA TCAGCTGAAG   180

GGGCTGATCG TGCTGCTCTA CAGCGTCGTG GTGGTCGTGG GCTGGTGGG CAACTGCCTG   240

CTGGTGCTGG TGATCGCGCG GGTGCGCCGG CTGCACAACG TGACGAACTT CCTCATCGGC   300

AACCTGGCCT TGTCCGACGT GCTCATGTGC ACCGCCTGCG TGCCGCTCAC GCTGGCCTAT   360
```

```
GCCTTCGAGC CACGCGGCTG GGTGTTCGGC GGCGGCCTGT GCCACCTGGT CTTCTTCCTG      420

CAGCCGGTCA CCGTCTATGT GTCGGTGTTC ACGCTCACCA CCATCGCAGT GGACCGCTAC      480

GTCGTGCTGG TGCACCCGCT GAGGCGGCGC ATCTCGCTGC GCCTCAGCGC CTACGCTGTG      540

CTGGCCATCT GGGCGCTGTC CGCGGTGCTG GCGCTGCCCG CCGCCGTGCA CACCTATCAC      600

GTGGAGCTCA AGCCGCACGA CGTGCGCCTC TGCGAGGAGT TCTGGGGCTC CCAGGAGCGC      660

CAGCGCCAGC TCTACGCCTG GGGGCTGCTG CTGGTCACCT ACCTGCTCCC TCTGCTGGTC      720

ATCCTCCTGT CTTACGTCCG GGTGTCAGTG AAGCTCCGCA ACCGCGTGGT GCCGGGCTGC      780

GTGACCCAGA GCCAGGCCGA CTGGGACCGC GCTCGGCGCC GGCGCACCTT CTGCTTGCTG      840

GTGGTGGTCG TGGTGGTGTT CGCCGTCTGC TGGCTGCCGC TGCACGTCTT CAACCTGCTG      900

CGGGACCTCG ACCCCACGC CATCGACCCT TACGCCTTTG GGCTGGTGCA GCTGCTCTGC      960

CACTGGCTCG CCATGAGTTC GGCCTGCTAC AACCCCTTCA TCTACGCCTG GCTGCACGAC     1020

AGCTTCCGCG AGGAGCTGCG CAAACTGTTG GTCGCTTGGC CCCGCAAGAT AGCCCCCCAT     1080

GGCCAGAATA TGACCGTCAG CGTGGTCATC                                     1110

(2) INFORMATION FOR SEQ ID NO:32:

(i) SEQUENCE CHARACTERISTICS:
        (A) LENGTH: 618 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:32:

CTGGTGCTGG TGATCGCGCG GGTGCGCCGG CTGTACAACG TGACGAATTT CCTCATCGGC       60

AACCTGGCCT TGTCCGACGT GCTCATGTGC ACCGCCTGCG TGCCGCTCAC GCTGGCCTAT      120

GCCTTCGAGC CACGCGGCTG GGTGTTCGGC GGCGGCCTGT GCCACCTGGT CTTCTTCCTG      180

CAGGCGGTCA CCGTCTATGT GTCGGTGTTC ACGCTCACCA CCATCGCAGT GGACCGCTAC      240

GTCGTGCTGG TGCACCCGCT GAGGCGGCGC ATCTCGCTGC GCCTCAGCGC CTACGCTGTG      300

CTGGCCATCT GGGTGCTGTC CGCGGTGCTG GCGCTGCCCG CCGCCGTGCA CACCTATCAC      360

GTGGAGCTCA AGCCGCACGA CGTGCGCCTC TGCGAGGAGT TCTGGGGCTC CCAGGAGCGC      420

CAGCGCCAGC TCTACGCCTG GGGGCTGCTG CTGGTCACCT ACCTGCTCCC TCTGCTGGTC      480

ATCCTCCTGT CTTACGCCCG GGTGTCAGTG AAGCTCCGCA ACCGCGTGGT GCCGGGCCGC      540

GTGACCCAGA GCCAGGCCGA CTGGGACCGC GCTCGGCGCC GGCGCACCTT CTGCTTGCTG      600

GTGGTGGTCG TGGTGGTG                                                   618

(2) INFORMATION FOR SEQ ID NO:33:

(i) SEQUENCE CHARACTERISTICS:
        (A) LENGTH: 378 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:33:

GTGGTTCTGG TGCACCCGCT ACGTCGGCGC ATTTCACTGA GGCTCAGCGC CTACGCGGTG       60

CTGGGCATCT GGGCTCTATC TGCAGTGCTG GCGCTGCCGG CCGCGGTGCA CACCTACCAT      120

GTGGAGCTCA AGCCCCACGA CGTGAGCCTC TGCGAGGAGT TCTGGGGCTC GCAGGAGCGC      180
```

```
CAACGCCAGA TCTACGCCTG GGGGCTGCTT CTGGGCACCT ATTTGCTCCC CCTGCTGGCC      240

ATCCTCCTGT CTTACGTACG GGTGTCAGTG AAGCTGAGGA ACCGCGTGGT GCCTGGCAGC      300

GTGACCCAGA GTCAAGCTGA CTGGGACCGA GCGCGTCGCC GCCGCACTTT CTGTCTGCTG      360

GTGGTGGTGG TGGTAGTG                                                    378
```

(2) INFORMATION FOR SEQ ID NO:34:

(i) SEQUENCE CHARACTERISTICS:
        (A) LENGTH: 70 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Val Cys His Val Ile Phe Lys Asn Gln Arg Met His Ser Ala Thr Ser
1               5                   10                  15

Leu Phe Ile Val Asn Leu Ala Val Ala Asp Ile Met Ile Thr Leu Ile
            20                  25                  30

Asn Thr Pro Phe Thr Leu Val Arg Phe Val Asn Ser Thr Trp Ile Phe
        35                  40                  45

Gly Lys Gly Met Cys His Val Ser Arg Phe Ala Gln Tyr Cys Ser Leu
    50                  55                  60

His Val Ser Ala Leu Thr
65                  70
```

(2) INFORMATION FOR SEQ ID NO:35:

(i) SEQUENCE CHARACTERISTICS:
        (A) LENGTH: 71 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Glu Pro Ala Asp Leu Phe Trp Lys Asn Leu Asp Leu Pro Thr Phe Ile
1               5                   10                  15

Leu Leu Asn Ile Leu Pro Leu Leu Ile Ile Ser Val Ala Tyr Val Arg
            20                  25                  30

Val Thr Lys Lys Leu Trp Leu Cys Asn Met Ile Val Asp Val Thr Thr
        35                  40                  45

Glu Gln Tyr Phe Ala Leu Arg Pro Lys Lys Lys Thr Ile Lys Met
    50                  55                  60

Leu Met Leu Val Val Val Leu
65                  70
```

(2) INFORMATION FOR SEQ ID NO:36:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:36:

```
GTCTGTCATG TCATCTTCAA GAACCAGCGA ATGCACTCGG CCACCAGCCT CTTCATCGTC       60
```

```
AACCTGGCAG TTGCCGACAT AATGATCACG CTGCTCAACA CCCCCTTCAC TTTGGTTCGC        120

TTTGTGAACA GCACATGGAT ATTTGGGAAG GGCATGTGCC ATGTCAGCCG CTTTGCCCAG        180

TACTGCTCAC TGCACGTCTC AGCACTGACA                                        210
```

(2) INFORMATION FOR SEQ ID NO:37:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:37:

```
GAGCCAGCTG ACCTCTTCTG GAAGAACCTG GACTTGCCCA CCTTCATCCT GCTCAACATC         60

CTGCCCCTCC TCATCATCTC TGTGGCCTAC GTTCGTGTGA CCAAGAAACT GTGGCTGTGT        120

AATATGATTG TCGATGTGAC CACAGAGCAG TACTTTGCCC TGCGGCCCAA AAAGAAGAAG        180

ACCATCAAGA TGTTGATGCT GGTGGTAGTC CTC                                    213
```

(2) INFORMATION FOR SEQ ID NO:38:

(i) SEQUENCE CHARACTERISTICS:
        (A) LENGTH: 115 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Ala Ser Trp His Lys Arg Gly Gly Arg Arg Ala Ala Trp Val Val Cys
1               5                   10                  15

Gly Val Val Trp Leu Ala Val Thr Ala Gln Cys Leu Pro Thr Ala Val
                20                  25                  30

Phe Ala Ala Thr Gly Ile Gln Arg Asn Arg Thr Val Cys Tyr Asp Leu
            35                  40                  45

Ser Pro Pro Ile Leu Ser Thr Arg Tyr Leu Pro Tyr Gly Met Ala Leu
    50                  55                  60

Thr Val Ile Gly Phe Leu Leu Pro Phe Ile Ala Leu Leu Ala Cys Tyr
65                  70                  75                  80

Cys Arg Met Ala Arg Arg Leu Cys Arg Gln Asp Gly Pro Ala Gly Pro
                85                  90                  95

Val Ala Gln Glu Arg Arg Ser Lys Ala Ala Arg Met Ala Val Val Val
                100                 105                 110

Ala Ala Val
        115
```

(2) INFORMATION FOR SEQ ID NO:39:

(i) SEQUENCE CHARACTERISTICS:
        (A) LENGTH: 328 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Met Glu Gln Asp Asn Gly Thr Ile Gln Ala Pro Gly Leu Pro Pro Thr

```
 1               5                    10                   15
Thr Cys Val Tyr Arg Glu Asp Phe Lys Arg Leu Leu Thr Pro Val
                20                  25                  30
Tyr Ser Val Val Leu Val Gly Leu Pro Leu Asn Ile Cys Val Ile
            35                  40                  45
Ala Gln Ile Cys Ala Ser Arg Arg Thr Leu Thr Arg Ser Ala Val Tyr
        50                  55                  60
Thr Leu Asn Leu Ala Leu Ala Asp Leu Met Tyr Ala Cys Ser Leu Pro
65                  70                  75                  80
Leu Leu Ile Tyr Asn Tyr Ala Arg Gly Asp His Trp Pro Phe Gly Asp
                85                  90                  95
Leu Ala Cys Arg Phe Val Arg Phe Leu Phe Tyr Ala Asn Leu His Gly
                100                 105                 110
Ser Ile Leu Phe Leu Thr Cys Ile Ser Phe Gln Arg Tyr Leu Gly Ile
            115                 120                 125
Cys His Pro Leu Ala Ser Trp His Lys Arg Gly Gly Arg Arg Ala Ala
            130                 135                 140
Trp Val Val Cys Gly Val Val Trp Leu Ala Val Thr Ala Gln Cys Leu
145                 150                 155                 160
Pro Thr Ala Val Phe Ala Ala Thr Gly Ile Gln Arg Asn Arg Thr Val
                165                 170                 175
Cys Tyr Asp Leu Ser Pro Pro Ile Leu Ser Thr Arg Tyr Leu Pro Tyr
            180                 185                 190
Gly Met Ala Leu Thr Val Ile Gly Phe Leu Leu Pro Phe Ile Ala Leu
            195                 200                 205
Leu Ala Cys Tyr Cys Arg Met Ala Arg Arg Leu Cys Arg Gln Asp Gly
            210                 215                 220
Pro Ala Gly Pro Val Ala Gln Glu Arg Arg Ser Lys Ala Ala Arg Met
225                 230                 235                 240
Ala Val Val Val Ala Ala Val Phe Ala Ile Ser Phe Leu Pro Phe His
                245                 250                 255
Ile Thr Lys Thr Ala Tyr Leu Ala Val Arg Ser Thr Pro Gly Val Ser
                260                 265                 270
Cys Pro Val Leu Glu Thr Phe Ala Ala Ala Tyr Lys Gly Thr Arg Pro
            275                 280                 285
Phe Ala Ser Val Asn Ser Val Leu Asp Pro Ile Leu Phe Tyr Phe Thr
            290                 295                 300
Gln Gln Lys Phe Arg Arg Gln Pro His Asp Leu Leu Gln Arg Leu Thr
305                 310                 315                 320
Ala Lys Trp Gln Arg Gln Arg Val
                325
```

(2) INFORMATION FOR SEQ ID NO:40:

(i) SEQUENCE CHARACTERISTICS:
        (A) LENGTH: 345 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:40:

```
GCTTCCTGGC ACAAGCGTGG AGGTCGCCGT GCTGCTTGGG TAGTGTGTGG AGTCGTGTGG      60

CTGGCTGTGA CAGCCCAGTG CCTGCCCACG GCAGTCTTTG CTGCCACAGG CATCCAGCGC     120
```

-continued

| | |
|---|---|
| AACCGCACTG TGTGCTACGA CCTGAGCCCA CCCATCCTGT CTACTCGCTA CCTGCCCTAT | 180 |
| GGTATGGCCC TCACGGTCAT CGGCTTCTTG CTGCCCTTCA TAGCCTTACT GGCTTGTTAT | 240 |
| TGTCGCATGG CCCGCCGCCT GTGTCGCCAG GATGGCCCAG CAGGTCCTGT GGCCCAAGAG | 300 |
| CGGCGCAGCA AGGCGGCTCG TATGGCTGTG GTGGTGGCAG CTGTC | 345 |

(2) INFORMATION FOR SEQ ID NO:41:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:41:

| | |
|---|---|
| ATGGAGCAGG ACAATGGCAC CATCCAGGCT CCAGGCTTGC CGCCCACCAC CTGCGTCTAC | 60 |
| CGTGAGGATT TCAAGCGACT GCTGCTAACC CCGGTATACT CGGTGGTGCT GGTGGTCGGC | 120 |
| CTGCCACTGA ACATCTGCGT CATTGCCCAG ATCTGCGCAT CCCGCCGGAC CCTGACCCGT | 180 |
| TCCGCTGTGT ACACCCTGAA CCTGGCACTG GCGGACCTGA TGTATGCCTG TTCACTACCC | 240 |
| CTACTTATCT ATAACTACGC CAGAGGGGAC CACTGGCCCT TCGAGACCT CGCCTGCCGC | 300 |
| TTTGTACGCT TCCTCTTCTA TGCCAATCTA CATGGCAGCA TCCTGTTCCT CACCTGCATT | 360 |
| AGCTTCCAGC GCTACCTGGG CATCTGCCAC CCCCTGGCTT CCTGGCACAA GCGTGGAGGT | 420 |
| CGCCGTGCTG CTTGGGTAGT GTGTGGAGTC GTGTGGCTGG CTGTGACAGC CCAGTGCCTG | 480 |
| CCCACGGCAG TCTTTGCTGC CACAGGCATC CAGCGCAACC GCACTGTGTG CTACGACCTG | 540 |
| AGCCCACCCA TCCTGTCTAC TCGCTACCTG CCCTATGGTA TGGCCCTCAC GGTCATCGGC | 600 |
| TTCTTGCTGC CCTTCATAGC CTTACTGGCT TGTTATTGTC GCATGGCCCG CCGCCTGTGT | 660 |
| CGCCAGGATG GCCCAGCAGG TCCTGTGGCC CAAGAGCGGC GCAGCAAGGC GGCTCGTATG | 720 |
| GCTGTGGTGG TGGCAGCTGT CTTTGCCATC AGCTTCCTGC CTTTCCACAT CACCAAGACA | 780 |
| GCCTACTTGG CTGTGCGCTC CACGCCCGGT GTCTCTTGCC CTGTGCTGGA GACCTTCGCT | 840 |
| GCTGCCTACA AAGGCACTCG GCCCTTCGCC AGTGTCAACA GTGTTCTGGA CCCCATTCTC | 900 |
| TTCTACTTCA CACAACAGAA GTTCCGGCGG CAACCCCACG ATCTCTTACA GAGGCTCACA | 960 |
| GCCAAGTGGC AGAGGCAGAG AGTC | 984 |

(2) INFORMATION FOR SEQ ID NO:42:

(i) SEQUENCE CHARACTERISTICS:
        (A) LENGTH: 128 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Ala Ala Met Ser Val Asp Arg Tyr Val Ala Ile Val His Ser Arg Arg
1               5                   10                  15

Ser Ser Ser Leu Arg Val Ser Arg Asn Ala Leu Leu Gly Val Gly Phe
            20                  25                  30

Ile Trp Ala Leu Ser Ile Ala Met Ala Ser Pro Val Ala Tyr His Gln
        35                  40                  45

Arg Leu Phe His Arg Asp Ser Asn Gln Thr Phe Cys Trp Glu Gln Trp
    50                  55                  60
```

Pro Asn Lys Leu His Lys Lys Ala Tyr Val Val Cys Thr Phe Val Phe
65                  70                  75                  80

Gly Tyr Leu Leu Pro Leu Leu Leu Ile Cys Phe Cys Tyr Ala Lys Val
                85                  90                  95

Leu Asn His Leu His Lys Lys Leu Lys Asn Met Ser Lys Lys Ser Glu
            100                 105                 110

Ala Ser Lys Lys Lys Thr Ala Gln Thr Val Leu Val Val Val Val Val
            115                 120                 125

(2) INFORMATION FOR SEQ ID NO:43:

(i) SEQUENCE CHARACTERISTICS:
        (A) LENGTH: 384 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:43:

GCCGCGATGT CTGTGGATCG CTACGTGGCC ATTGTGCACT CGCGGCGCTC CTCCTCCCTC      60

AGGGTGTCCC GCAACGCACT GCTGGGCGTG GGCTTCATCT GGGCGCTGTC CATCGCCATG     120

GCCTCGCCGG TGGCCTACCA CCAGCGTCTT TTCCATCGGG ACAGCAACCA GACCTTCTGC     180

TGGGAGCAGT GGCCCAACAA GCTCCACAAG AAGGCTTACG TGGTGTGCAC TTTCGTCTTT     240

GGGTACCTTC TGCCCTTACT GCTCATCTGC TTTTGCTATG CCAAGGTCCT TAATCATCTG     300

CATAAAAAGC TGAAAAACAT GTCAAAAAAG TCTGAAGCAT CCAAGAAAAA GACTGCACAG     360

ACCGTCCTGG TGGTCGTTGT AGTA                                           384

(2) INFORMATION FOR SEQ ID NO:44:

(i) SEQUENCE CHARACTERISTICS:
        (A) LENGTH: 71 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Val Leu Trp Phe Phe Gly Phe Ser Ile Lys Arg Thr Pro Phe Ser Val
1               5                   10                  15

Tyr Phe Leu His Leu Ala Ser Ala Asp Gly Ala Tyr Leu Phe Ser Lys
                20                  25                  30

Ala Val Phe Ser Leu Leu Asn Ala Gly Gly Phe Leu Gly Thr Phe Ala
            35                  40                  45

His Tyr Val Arg Ser Val Ala Arg Val Leu Gly Leu Cys Ala Phe Val
        50                  55                  60

Ala Gly Val Ser Leu Leu Pro
65                  70

(2) INFORMATION FOR SEQ ID NO:45:

(i) SEQUENCE CHARACTERISTICS:
        (A) LENGTH: 215 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:45:

```
GTGCTCTGGT TCTTCGGCTT CTCCATCAAG AGGACCCCCT TCTCCGTCTA CTTCCTGCAC      60

CTGGCCAGCG CCGACGGCGC CTACCTCTTC AGCAAGGCCG TGTTCTCCCT GCTGAACGCC     120

GGCGGCTTCC TGGGCACCTT CGCCCACTAT GTGCGCAGCG TGGCCCGGGT GCTGGGGCTC     180

TGCGCCTTCG TGGCGGGCGT GAGCCTCCTG CCGGC                                215
```

(2) INFORMATION FOR SEQ ID NO:46:

(i) SEQUENCE CHARACTERISTICS:
      (A) LENGTH: 348 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:46:

```
Met Glu Leu Ala Met Val Asn Leu Ser Glu Gly Asn Gly Ser Asp Pro
1               5                   10                  15

Glu Pro Pro Ala Pro Glu Ser Arg Pro Leu Phe Gly Ile Gly Val Glu
            20                  25                  30

Asn Phe Ile Thr Leu Val Val Phe Gly Leu Ile Phe Ala Met Gly Val
        35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Phe Ile Trp
145                 150                 155                 160

Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
            180                 185                 190

Lys Leu His Lys Lys Ala Tyr Val Val Cys Thr Phe Val Phe Gly Tyr
        195                 200                 205

Leu Leu Pro Leu Leu Leu Ile Cys Phe Cys Tyr Ala Lys Val Leu Asn
    210                 215                 220

His Leu His Lys Lys Leu Lys Asn Met Ser Lys Lys Ser Glu Ala Ser
225                 230                 235                 240

Lys Lys Lys Thr Ala Gln Thr Val Leu Val Val Val Val Val Phe Gly
                245                 250                 255

Ile Ser Trp Leu Pro His His Val Val His Leu Trp Ala Glu Phe Gly
            260                 265                 270

Ala Phe Pro Leu Thr Pro Ala Ser Phe Phe Phe Arg Ile Thr Ala His
        275                 280                 285

Cys Leu Ala Tyr Ser Asn Ser Ser Val Asn Pro Ile Ile Tyr Ala Phe
    290                 295                 300
```

```
Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
                325                 330                 335

Met Asp Thr Pro Pro Ser Thr Asn Cys Thr His Val
                340                 345
```

(2) INFORMATION FOR SEQ ID NO:47:

(i) SEQUENCE CHARACTERISTICS:
        (A) LENGTH: 1044 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:47:

```
ATGGAACTGG CTATGGTGAA CCTCAGTGAA GGGAATGGGA GCGACCCAGA GCCGCCAGCC      60
CCGGAGTCCA GGCCGCTCTT CGGCATTGGC GTGGAGAACT TCATTACGCT GGTAGTGTTT     120
GGCCTGATTT TCGCGATGGG CGTGCTGGGC AACAGCCTGG TGATCACCGT GCTGGCGCGC     180
AGCAAACCAG GCAACCCCCG CAGCACCACC AACCTGTTTA TCCTCAATCT GAGCATCGCA     240
GACCTGGCCT ACCTGCTCTT CTGCATCCCT TTTCAGGCCA CCGTGTATGC ACTGCCCACC     300
TGGGTGCTGG GCGCCTTCAT CTGCAAGTTT ATACACTACT TCTTCACCGT GTCCATGCTG     360
GTGAGCATCT TCACCCTGGC CGCGATGTCT GTGGATCGCT ACGTGGCCAT TGTGCACTCG     420
CGGCGCTCCT CCTCCCTCAG GGTGTCCCGC AACGCACTGC TGGGCGTGGG CTTCATCTGG     480
GCGCTGTCCA TCGCCATGGC CTCGCCGGTG CCTACCACC AGCGTCTTTT CCATCGGGAC      540
AGCAACCAGA CCTTCTGCTG GGAGCAGTGG CCCAACAAGC TCCACAAGAA GGCTTACGTG     600
GTGTGCACTT TCGTCTTTGG GTACCTTCTG CCCTTACTGC TCATCTGCTT TTGCTATGCC     660
AAGGTCCTTA ATCATCTGCA TAAAAAGCTG AAAAACATGT CAAAAAAGTC TGAAGCATCC     720
AAGAAAAAGA CTGCACAGAC CGTCCTGGTG GTCGTTGTAG TATTTGGCAT ATCCTGGCTG     780
CCCCATCATG TCGTCCACCT CTGGGCTGAG TTTGGAGCCT TCCCACTGAC GCCAGCTTCC     840
TTCTTCTTCA GAATCACCGC CCATTGCCTG GCATACAGCA ACTCCTCAGT GAACCCCATC     900
ATATATGCCT TTCTCTCAGA AAACTTCCGG AAGGCGTACA AGCAAGTGTT CAAGTGTCAT     960
GTTTGCGATG AATCTCCACG CAGTGAAACT AAGGAAAACA AGAGCCGGAT GGACACCCCG    1020
CCATCCACCA ACTGCACCCA CGTG                                           1044
```

(2) INFORMATION FOR SEQ ID NO:48:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

```
Leu Leu Thr Leu His Pro Val Trp Ser Gln Lys His Arg Thr Ser His
1               5                   10                  15

Trp Ala Ser Arg Val Val Leu Gly Val Trp Leu Ser Ala Thr Ala Phe
                20                  25                  30

Ser Val Pro Tyr Leu Val Phe Arg Glu Thr Tyr Asp Asp Arg Lys Gly
```

```
              35                  40                  45
Arg Val Thr Cys Arg Asn Asn Tyr Ala Val Ser Thr Asp Trp Glu Ser
             50                  55                  60

Lys Glu Met Gln Thr Val Arg Gln Trp Ile His Ala Thr Cys Phe Ile
 65                  70                  75                  80

Ser Arg Phe Ile Leu Gly Phe Leu Leu Pro Phe Leu Val Ile Gly Phe
                 85                  90                  95

Cys Tyr Glu Arg Val Ala Arg Lys Met Lys Glu Arg Gly Leu Phe Lys
                100                 105                 110

Ser Ser Lys Pro Phe Lys Val Thr Met Thr Ala Val Ile
                115                 120                 125

(2) INFORMATION FOR SEQ ID NO:49:

(i) SEQUENCE CHARACTERISTICS:
        (A) LENGTH: 377 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:49:

CTTCTCACCC TTCACCCAGT GTGGTCCCAA AAGCACCGAA CCTCACACTG GGCTTCCAGA      60

GTCGTTCTGG GAGTCTGGCT CTCTGCCACT GCCTTCAGCG TGCCCTATTT GGTTTTCAGG     120

GAGACATATG ATGACCGTAA AGGAAGAGTG ACCTGCAGAA ATAACTACGC TGTGTCCACT     180

GACTGGGAAA GCAAAGAGAT GCAAACAGTA AGACAATGGA TTCATGCCAC CTGTTTCATC     240

AGCCGCTTCA TACTGGGCTT CCTTCTGCCT TTCTTAGTCA TTGGCTTTTG TTATGAAAGA     300

GTAGCCCGCA AGATGAAAGA GAGGGGCCTC TTTAAATCCA GCAAACCCTT CAAAGTCACG     360

ATGACTGCTG TTATCTC                                                   377

(2) INFORMATION FOR SEQ ID NO:50:

(i) SEQUENCE CHARACTERISTICS:
        (A) LENGTH: 119 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

Phe Lys Ile Val Lys Pro Leu Ser Thr Ser Phe Ile Gln Ser Val Asn
  1               5                  10                  15

Tyr Ser Lys Leu Val Ser Leu Val Val Trp Leu Leu Met Leu Leu Leu
                 20                  25                  30

Ala Val Pro Asn Val Ile Leu Thr Asn Gln Arg Val Lys Asp Val Thr
                 35                  40                  45

Gln Ile Lys Cys Met Glu Leu Lys Asn Glu Leu Gly Arg Gln Trp His
             50                  55                  60

Lys Ala Ser Asn Tyr Ile Phe Val Gly Ile Phe Trp Leu Val Phe Leu
 65                  70                  75                  80

Leu Leu Ile Ile Phe Tyr Thr Ala Ile Thr Arg Lys Ile Phe Lys Ser
                 85                  90                  95

His Leu Lys Ser Arg Lys Asn Ser Ile Ser Val Lys Lys Ser Ser
                100                 105                 110

Arg Asn Ile Phe Ser Ile Val
```

-continued

115

(2) INFORMATION FOR SEQ ID NO:51:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:51:

```
TTCAAGATTG TGAAGCCCCT TTCCACGTCC TTCATCCAGT CTGTGAACTA CAGCAAACTC    60

GTCTCGCTGG TGGTCTGGTT GCTCATGCTC CTCCTCGCCG TCCCCAACGT CATTCTCACC   120

AACCAGAGAG TTAAGGACGT GACGCAGATA AAATGCATGG AACTTAAAAA CGAACTGGGC   180

CGCCAGTGGC ACAAGGCGTC AAACTACATC TTTGTGGGCA TTTTCTGGCT TGTGTTCCTT   240

TTGCTAATCA TTTTCTACAC TGCTATCACC AGGAAAATCT TTAAGTCCCA CCTGAAATCC   300

AGAAAGAATT CCATCTCGGT CAAAAAGAAA TCTAGCCGCA ACATCTTCAG CATCGTG      357
```

(2) INFORMATION FOR SEQ ID NO:52:

(i) SEQUENCE CHARACTERISTICS:
        (A) LENGTH: 252 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

```
Val Asp Leu Leu Ala Ala Leu Thr Leu Met Pro Leu Ala Met Leu Ser
1               5                  10                  15

Ser Ser Ala Leu Phe Asp His Ala Leu Phe Gly Glu Val Ala Cys Arg
            20                  25                  30

Leu Tyr Leu Phe Leu Ser Val Cys Phe Val Ser Leu Ala Ile Leu Ser
        35                  40                  45

Val Ser Ala Ile Asn Val Glu Arg Tyr Tyr Val His Pro Met
50                  55                  60

Arg Tyr Glu Val Arg Met Lys Leu Gly Leu Val Ala Ser Val Leu Val
65                  70                  75                  80

Gly Val Trp Val Lys Ala Leu Ala Met Ala Ser Val Pro Val Leu Gly
                85                  90                  95

Arg Val Ser Trp Glu Glu Gly Pro Pro Ser Val Pro Pro Gly Cys Ser
            100                 105                 110

Leu Gln Trp Ser His Ser Ala Tyr Cys Gln Leu Phe Val Val Phe
        115                 120                 125

Ala Val Leu Tyr Phe Leu Leu Pro Leu Leu Leu Ile Leu Val Val Tyr
    130                 135                 140

Cys Ser Met Phe Arg Val Ala Arg Val Ala Ala Met Gln His Gly Pro
145                 150                 155                 160

Leu Pro Thr Trp Met Glu Thr Pro Arg Gln Arg Ser Glu Ser Leu Ser
                165                 170                 175

Ser Arg Ser Thr Met Val Thr Ser Ser Gly Ala Pro Gln Thr Thr Pro
            180                 185                 190

His Arg Thr Phe Gly Gly Gly Lys Ala Ala Val Val Leu Leu Ala Val
        195                 200                 205
```

```
Gly Gly Gln Phe Leu Leu Cys Trp Leu Pro Tyr Phe Ser Phe His Leu
    210                 215                 220

Tyr Val Ala Leu Ser Ala Gln Pro Ile Ala Ala Gly Gln Val Glu Asn
225                 230                 235                 240

Val Val Thr Trp Ile Gly Tyr Phe Cys Phe Thr Ser
                245                 250
```

(2) INFORMATION FOR SEQ ID NO:53:

(i) SEQUENCE CHARACTERISTICS:
        (A) LENGTH: 756 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:53:

```
GTGGACCTGC TGGCTGCCCT GACCCTCATG CCTCTGGCCA TGCTCTCCAG CTCCGCCCTC      60

TTTGACCACG CCCTCTTTGG GGAGGTGGCC TGCCGCCTCT ACTTGTTCCT GAGCGTCTGC     120

TTTGTCAGCC TGGCCATCCT CTCGGTGTCC GCCATCAATG TGGAGCGCTA CTATTATGTG     180

GTCCACCCCA TGCGCTATGA GGTGCGCATG AAACTGGGGC TGGTGGCCTC TGTGCTGGTG     240

GGCGTGTGGG TGAAGGCCCT GGCCATGGCT TCTGTGCCAG TGTTGGGAAG GGTGTCCTGG     300

GAGGAAGGCC CTCCCAGTGT CCCCCCAGGC TGTTCACTCC AATGGAGCCA CAGTGCCTAC     360

TGCCAGCTTT TCGTGGTGGT CTTCGCCGTC CTCTACTTCC TGCTGCCCCT GCTCCTCATC     420

CTTGTGGTCT ACTGCAGCAT GTTCCGGGTG GCTCGTGTGG CTGCCATGCA GCACGGGCCG     480

CTGCCCACGT GGATGGAGAC GCCCCGGCAA CGCTCCGAGT CTCTCAGCAG CCGCTCCACT     540

ATGGTCACCA GCTCGGGGGC CCCGCAGACC ACCCCTCACC GGACGTTTGG CGGAGGGAAG     600

GCAGCAGTGG TCCTCCTGGC TGTGGGAGGA CAGTTCCTGC TCTGTTGGTT GCCCTACTTC     660

TCCTTCCACC TCTATGTGGC CCTGAGCGCT CAGCCCATTG CAGCGGGGCA GGTGGAGAAC     720

GTGGTGACCT GGATTGGCTA CTTCTGCTTC ACCTCC                               756
```

(2) INFORMATION FOR SEQ ID NO:54:

(i) SEQUENCE CHARACTERISTICS:
        (A) LENGTH: 263 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

```
Ala Asp Val Leu Val Thr Ala Ile Cys Leu Pro Ala Ser Leu Leu Val
1                   5                   10                  15

Asp Ile Thr Glu Ser Trp Leu Phe Gly His Ala Leu Cys Lys Val Ile
                20                  25                  30

Pro Tyr Leu Gln Ala Val Ser Val Ser Val Val Leu Thr Leu Ser
            35                  40                  45

Ser Ile Ala Leu Asp Arg Trp Tyr Ala Ile Cys His Pro Leu Leu Phe
        50                  55                  60

Lys Ser Thr Ala Arg Arg Ala Arg Gly Ser Ile Leu Gly Ile Trp Ala
65                  70                  75                  80

Val Ser Leu Ala Val Met Val Pro Gln Ala Ala Val Met Glu Cys Ser
                85                  90                  95
```

```
Ser Val Leu Pro Glu Leu Ala Asn Arg Thr Arg Leu Leu Ser Val Cys
            100                 105                 110

Asp Glu Arg Trp Ala Asp Asp Leu Tyr Pro Lys Ile Tyr His Ser Cys
        115                 120                 125

Phe Phe Ile Val Thr Tyr Leu Ala Pro Leu Gly Leu Met Ala Met Ala
    130                 135                 140

Tyr Phe Gln Ile Phe Arg Lys Leu Trp Gly Arg Gln Ile Pro Gly Thr
145                 150                 155                 160

Thr Ser Ala Leu Val Arg Asn Trp Lys Arg Pro Ser Asp Gln Leu Asp
                165                 170                 175

Asp Gln Gly Gln Gly Leu Ser Ser Glu Pro Gln Pro Arg Ala Arg Ala
            180                 185                 190

Phe Leu Ala Glu Val Lys Gln Met Arg Ala Arg Arg Lys Thr Ala Lys
        195                 200                 205

Met Leu Met Val Val Leu Leu Val Phe Ala Leu Cys Tyr Leu Pro Ile
    210                 215                 220

Ser Val Leu Asn Val Leu Lys Arg Val Phe Gly Met Phe Arg Gln Ala
225                 230                 235                 240

Ser Asp Arg Glu Ala Ile Tyr Ala Cys Phe Thr Phe Ser His Trp Leu
                245                 250                 255

Val Tyr Ala Asn Ser Ala Ala
            260

(2) INFORMATION FOR SEQ ID NO:55:

(i) SEQUENCE CHARACTERISTICS:
        (A) LENGTH: 789 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:55:

GCCGATGTGC TGGTGACAGC CATCTGCCTG CCGGCCAGTC TGCTGGTAGA CATCACGGAA      60

TCCTGGCTCT TTGGCCATGC CCTCTGCAAG GTCATCCCCT ATCTACAGGC CGTGTCCGTG     120

TCAGTGGTCG TGCTGACTCT CAGCTCCATC GCCCTGGACC GCTGGTACGC CATCTGCCAC     180

CCGCTGTTGT TCAAGAGCAC TGCCCGGCGC GCCCGCGGCT CCATCCTCGG CATCTGGGCG     240

GTGTCGCTGG CTGTCATGGT GCCTCAGGCT GCTGTCATGG AGTGTAGCAG CGTGCTGCCC     300

GAGCTGGCCA ACCGCACCCG CCTCCTGTCT GTCTGTGATG AGCGCTGGGC AGACGACCTG     360

TACCCCAAGA TCTACCACAG CTGCTTCTTC ATTGTCACCT ACCTGGCCCC ACTGGGCCTC     420

ATGGCCATGG CCTATTTCCA GATCTTCCGC AAGCTCTGGG GCCGCCAGAT CCCCGGCACC     480

ACCTCGGCCC TGGTGCGCAA CTGGAAGCGG CCCTCAGACC AGCTGGACGA CCAGGGCCAG     540

GGCCTGAGCT CAGAGCCCCA GCCCCGGGCC CGCGCCTTCC TGGCCGAGGT GAAACAGATG     600

CGAGCCCGGA GGAAGACGGC CAAGATGCTG ATGGTGGTGC TGCTGGTCTT CGCCCTCTGC     660

TACCTGCCCA TCAGTGTCCT CAACGTCCTC AAGAGGGTCT TCGGGATGTT CCGCCAAGCC     720

AGCGACCGAG AGGCCATCTA CGCCTGCTTC ACCTTCTCCC ACTGGCTGGT GTACGCCAAC     780

AGCGCCGCC                                                             789

(2) INFORMATION FOR SEQ ID NO:56:

(i) SEQUENCE CHARACTERISTICS:
        (A) LENGTH: 328 amino acids
```

(B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

Met Glu Trp Asp Asn Gly Thr Gly Gln Ala Leu Gly Leu Pro Pro Thr
1               5                   10                  15

Thr Cys Val Tyr Arg Glu Asn Phe Lys Gln Leu Leu Leu Pro Pro Val
            20                  25                  30

Tyr Ser Ala Val Leu Ala Ala Gly Leu Pro Leu Asn Ile Cys Val Ile
        35                  40                  45

Thr Gln Ile Cys Thr Ser Arg Arg Ala Leu Thr Arg Thr Ala Val Tyr
    50                  55                  60

Thr Leu Asn Leu Ala Leu Ala Asp Leu Leu Tyr Ala Cys Ser Leu Pro
65                  70                  75                  80

Leu Leu Ile Tyr Asn Tyr Ala Gln Gly Asp His Trp Pro Phe Gly Asp
                85                  90                  95

Phe Ala Cys Arg Leu Val Arg Phe Leu Phe Tyr Ala Asn Leu His Gly
            100                 105                 110

Ser Ile Leu Phe Leu Thr Cys Ile Ser Phe Gln Arg Tyr Leu Gly Ile
        115                 120                 125

Cys His Pro Leu Ala Pro Trp His Lys Arg Gly Gly Arg Ala Ala
    130                 135                 140

Trp Leu Val Cys Val Thr Val Trp Leu Ala Val Thr Thr Gln Cys Leu
145                 150                 155                 160

Pro Thr Ala Ile Phe Ala Ala Thr Gly Ile Gln Arg Asn Arg Thr Val
                165                 170                 175

Cys Tyr Asp Leu Ser Pro Pro Ala Leu Ala Thr His Tyr Met Pro Tyr
            180                 185                 190

Gly Met Ala Leu Thr Val Ile Gly Phe Leu Leu Pro Phe Ala Ala Leu
            195                 200                 205

Leu Ala Cys Tyr Cys Leu Leu Ala Cys Arg Leu Cys Arg Gln Asp Gly
    210                 215                 220

Pro Ala Glu Pro Val Ala Gln Glu Arg Arg Gly Lys Ala Ala Arg Met
225                 230                 235                 240

Ala Val Val Val Ala Ala Phe Ala Ile Ser Phe Leu Pro Phe His
            245                 250                 255

Ile Thr Lys Thr Ala Tyr Leu Ala Val Gly Ser Thr Pro Gly Val Pro
                260                 265                 270

Cys Thr Val Leu Glu Ala Phe Ala Ala Tyr Lys Gly Thr Arg Pro
            275                 280                 285

Phe Ala Ser Ala Asn Ser Val Leu Asp Pro Ile Leu Phe Tyr Phe Thr
    290                 295                 300

Gln Lys Lys Phe Arg Arg Arg Pro His Glu Leu Leu Gln Lys Leu Thr
305                 310                 315                 320

Ala Lys Trp Gln Arg Gln Gly Arg
                325

(2) INFORMATION FOR SEQ ID NO:57:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:57:

| | | | | | |
|---|---|---|---|---|---|
| ATGGAATGGG | ACAATGGCAC | AGGCCAGGCT | CTGGGCTTGC | CACCCACCAC | CTGTGTCTAC | 60 |
| CGCGAGAACT | TCAAGCAACT | GCTGCTGCCA | CCTGTGTATT | CGGCGGTGCT | GGCGGCTGGC | 120 |
| CTGCCGCTGA | ACATCTGTGT | CATTACCCAG | ATCTGCACGT | CCCGCCGGGC | CCTGACCCGC | 180 |
| ACGGCCGTGT | ACACCCTAAA | CCTTGCTCTG | GCTGACCTGC | TATATGCCTG | CTCCCTGCCC | 240 |
| CTGCTCATCT | ACAACTATGC | CCAAGGTGAT | CACTGGCCCT | TTGGCGACTT | CGCCTGCCGC | 300 |
| CTGGTCCGCT | TCCTCTTCTA | TGCCAACCTG | CACGGCAGCA | TCCTCTTCCT | CACCTGCATC | 360 |
| AGCTTCCAGC | GCTACCTGGG | CATCTGCCAC | CCGCTGGCCC | CCTGGCACAA | ACGTGGGGGC | 420 |
| CGCCGGGCTG | CCTGGCTAGT | GTGTGTAACC | GTGTGGCTGG | CCGTGACAAC | CCAGTGCCTG | 480 |
| CCCACAGCCA | TCTTCGCTGC | CACAGGCATC | CAGCGTAACC | GCACTGTCTG | CTATGACCTC | 540 |
| AGCCCGCCTG | CCCTGGCCAC | CCACTATATG | CCCTATGGCA | TGGCTCTCAC | TGTCATCGGC | 600 |
| TTCCTGCTGC | CCTTTGCTGC | CCTGCTGGCC | TGCTACTGTC | TCCTGGCCTG | CCGCCTGTGC | 660 |
| CGCCAGGATG | GCCCGGCAGA | GCCTGTGGCC | CAGGAGCGGC | GTGGCAAGGC | GGCCCGCATG | 720 |
| GCCGTGGTGG | TGGCTGCTGC | CTTTGCCATC | AGCTTCCTGC | CTTTTCACAT | CACCAAGACA | 780 |
| GCCTACCTGG | CAGTGGGCTC | GACGCCGGGC | GTCCCCTGCA | CTGTATTGGA | GGCCTTTGCA | 840 |
| GCGGCCTACA | AAGGCACGCG | GCCGTTTGCC | AGTGCCAACA | GCGTGCTGGA | CCCCATCCTC | 900 |
| TTCTACTTCA | CCCAGAAGAA | GTTCCGCCGG | CGACCACATG | AGCTCCTACA | GAAACTCACA | 960 |
| GCCAAATGGC | AGAGGCAGGG | TCGC | | | | 984 |

(2) INFORMATION FOR SEQ ID NO:58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:58:

ACAGCCATCT TCGCTGCCAC AGGCAT                                           26

(2) INFORMATION FOR SEQ ID NO:59:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:59:

AGACAGTAGC AGGCCAGCAG GGCAGCAAA                                      29

(2) INFORMATION FOR SEQ ID NO:60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:60:

CTGTGYGYSA TYGCNNTKGA YMGSTAC                                              27

(2) INFORMATION FOR SEQ ID NO:61:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (ix) FEATURE:
            (D) OTHER INFORMATION: N = inosine (xi) SEQUENCE DESCRIPTION: SEQ ID NO:61:

AKGWAGWAGG GCAGCCAGCA GANSRYGAA                                            29

(2) INFORMATION FOR SEQ ID NO:62:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:62:

CCTGGGCATT GTAGGCAACA TCATGGT                                              27

(2) INFORMATION FOR SEQ ID NO:63:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:63:

CATTGGCCTG GTTGGAAACA TCCTGGT                                              27

(2) INFORMATION FOR SEQ ID NO:64:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:64:

CCTGGGCGTG ATCGGCAACG TCCTGGT                                              27

(2) INFORMATION FOR SEQ ID NO:65:

(i) SEQUENCE CHARACTERISTICS:

(A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:65:

GGTGGGGCTG GTGGGCAACG CCCTGGT				27

(2) INFORMATION FOR SEQ ID NO:66:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:66:

AGTGGGCCTC TTCGGAAACT TCCTGGT				27

(2) INFORMATION FOR SEQ ID NO:67:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:67:

GGTGGGCTTA GTGGGCAATT CCCTGGT				27

(2) INFORMATION FOR SEQ ID NO:68:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:68:

CGTGGGCTTG CTGGGCAACA TCATGCT				27

(2) INFORMATION FOR SEQ ID NO:69:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:69:

GGTGACCATC ATCGGCAACA TCCTGGT				27

(2) INFORMATION FOR SEQ ID NO:70:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:70:

CTTTGCCATC GTGGGCAACA TCTTGGT                                          27

(2) INFORMATION FOR SEQ ID NO:71:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:71:

GGTGGGCCTG CTGGGTAACT CGCTGGT                                          27

(2) INFORMATION FOR SEQ ID NO:72:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:72:

GGTGGGAGTG CTGGGCAATG CCCTGGT                                          27

(2) INFORMATION FOR SEQ ID NO:73:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:73:

CATCGGCATG ATTGCCAACT CCGTGGT                                          27

(2) INFORMATION FOR SEQ ID NO:74:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:74:

CGTGGCGGTG CTCGGCAACC TCGTGGT                                          27

(2) INFORMATION FOR SEQ ID NO:75:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:75:

GCTGGCAGTG GCGGGCAACG TGCTGGT                27

(2) INFORMATION FOR SEQ ID NO:76:

(i) SEQUENCE CHARACTERISTICS:
        (A) LENGTH: 27 base pairs
        (B) TYPE: nucleic acid
        (C) STRANDEDNESS: unknown
        (D) TOPOLOGY: linear (ii) MOLECULE TYPE: other nucleic acid (xi) SEQUENCE DESCRIPTION: SEQ ID NO:76:

TTTGCCMTCT GCTGGNTGCC YYWCNAC                27

(2) INFORMATION FOR SEQ ID NO:77:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:77:

TTTGCCCTCT GCTGGTTCCC TCTCAAC                27

(2) INFORMATION FOR SEQ ID NO:78:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:78:

TTTGCCCTCT GCTGGTTGCC AAATCAC                27

(2) INFORMATION FOR SEQ ID NO:79:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:79:

TTTGCCCTCT GCTGGCTGCC CCTACAC                27

(2) INFORMATION FOR SEQ ID NO:80:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:80:

TTTGCCCTCG TCTGGTGCCC TCTCAAC                27

(2) INFORMATION FOR SEQ ID NO:81:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:81:

TTTGCCCTTT TATGGATGCC CTACAGG                        27

(2) INFORMATION FOR SEQ ID NO:82:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:82:

TTTGCCATCT GCTGGCTGCC CTATCAC                        27

(2) INFORMATION FOR SEQ ID NO:83:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:83:

TTTGCCCTCA GCTGGCTGCC GCTGCAT                        27

(2) INFORMATION FOR SEQ ID NO:84:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:84:

TTTGCCATCT GCTGGCTGCC CTATCAC                        27

(2) INFORMATION FOR SEQ ID NO:85:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:85:

TTTGCCATCT GCTGGCTGCC CTACCAC                        27

(2) INFORMATION FOR SEQ ID NO:86:

(i) SEQUENCE CHARACTERISTICS:
        (A) LENGTH: 27 base pairs (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:86:

TTTGCCTTGT GCTGGCTGCC TTTGTCC                                27

(2) INFORMATION FOR SEQ ID NO:87:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:87:

TTTGTCATCT GCTGGATGCC TTTCTAC                                27

(2) INFORMATION FOR SEQ ID NO:88:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:88:

TTTGCTATCT GCTGGCTGCC CTATCAT                                27

(2) INFORMATION FOR SEQ ID NO:89:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:89:

TTTGCCGCCT GCTGGATGCC TTTTACC                                27

(2) INFORMATION FOR SEQ ID NO:90:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:90:

TTTGTGCTCT GCTGGATGCC TTTCTAC                                27

(2) INFORMATION FOR SEQ ID NO:91:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:91:

TTTGCACACT GGTCGAAGCC AGACAAA                                                        27

(2) INFORMATION FOR SEQ ID NO:92:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:92:

CTCACCATGA TGAGCGTGGA CCGCTAC                                                        27

(2) INFORMATION FOR SEQ ID NO:93:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:93:

TTGACCATGA TGGAGTGTGA CCGCTAC                                                        27

(2) INFORMATION FOR SEQ ID NO:94:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:94:

CTCTGCACCA TGAGCGTGGA CCGCTAC                                                        27

(2) INFORMATION FOR SEQ ID NO:95:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:95:

CTGATGCTCG TGAGTATCGA CCGCTAC                                                        27

(2) INFORMATION FOR SEQ ID NO:96:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:96:

```
CTTACGGCAC TGTCAGCTGA CAGGTAC                                              27

(2) INFORMATION FOR SEQ ID NO:97:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:97:

CTCACTGCCC TCAGCGCCGA CAGGTAC                                              27

(2) INFORMATION FOR SEQ ID NO:98:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:98:

CTCACGGCGC TCTCGGCAGA CAGATAC                                              27

(2) INFORMATION FOR SEQ ID NO:99:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:99:

TTAACAATTC TCAGCGCTGA CAGATAC                                              27

(2) INFORMATION FOR SEQ ID NO:100:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:100:

ATGACCGCCA TCGCCGCTGA CAGGTAC                                              27

(2) INFORMATION FOR SEQ ID NO:101:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:101:

ATGACAACTG TGGCCTTTGA CAGATAC                                              27

(2) INFORMATION FOR SEQ ID NO:102:
```

(i) SEQUENCE CHARACTERISTICS:
    (A) LENGTH: 27 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:102:

ATGACAGCCA TTGCAGTGGA CAGGTAT            27

(2) INFORMATION FOR SEQ ID NO:103:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:103:

CTCTGCGCTC TCAGTGTGGA CAGGTAC            27

(2) INFORMATION FOR SEQ ID NO:104:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:104:

CTCACCTGCC TCAGCATTGA CCGCTAC            27

(2) INFORMATION FOR SEQ ID NO:105:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:105:

TTGCTGGCTA TCACTGTGGA CCGCTAC            27

(2) INFORMATION FOR SEQ ID NO:106:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:106:

TTGCTGGCCA TTGCTGTAGA CCGATAC            27

(2) INFORMATION FOR SEQ ID NO:107:

(i) SEQUENCE CHARACTERISTICS:
        (A) LENGTH: 27 base pairs
        (B) TYPE: nucleic acid

```
        (C) STRANDEDNESS: double
        (D) TOPOLOGY: linear (ii) MOLECULE TYPE: cDNA (xi) SEQUENCE DESCRIPTION: SEQ ID NO:107:

CTCACCTGCC TCAGCATTGA CCGCTAC                                            27

(2) INFORMATION FOR SEQ ID NO:108:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:108:

CTGACAGCTA TCGCAGTGGA CCGCCAC                                            27

(2) INFORMATION FOR SEQ ID NO:109:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:109:

CTCCTCGCCA TCGCCATTGA GCGCTAT                                            27

(2) INFORMATION FOR SEQ ID NO:110:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:110:

CTCACCGGCC TCAGCTTCGA CCGCTAC                                            27

(2) INFORMATION FOR SEQ ID NO:111:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:111:

ATTACCTGCA TGAGTGTCGA TAGGTAC                                            27

(2) INFORMATION FOR SEQ ID NO:112:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA
```

(xi) SEQUENCE DESCRIPTION: SEQ ID NO:112:

CTCACGTGTC TCAGCATCGA TCGCTAC                                          27

(2) INFORMATION FOR SEQ ID NO:113:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:113:

CTCACGTGTC TCAGCATCGA TCGCTAC                                          27

(2) INFORMATION FOR SEQ ID NO:114:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:114:

CTCACGTGTC TCAGCATTGA TCGATAC                                          27

(2) INFORMATION FOR SEQ ID NO:115:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:115:

CTGGTAGCCA TCTCTCTGGA GAGATAT                                          27

(2) INFORMATION FOR SEQ ID NO:116:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:116:

CTCGTGGCCA TAGCCCTGGA GCGATAC                                          27

(2) INFORMATION FOR SEQ ID NO:117:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:117:

CTCGTGGCCA TCGCACTGGA GCGGTAC                                          27

(2) INFORMATION FOR SEQ ID NO:118:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:118:

CTGGCCTGCA TCAGTGTGGA CCGTTAC                                27

(2) INFORMATION FOR SEQ ID NO:119:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:119:

TTGGCCTGCA TCAGTGTGGA CCGTTAC                                27

(2) INFORMATION FOR SEQ ID NO:120:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:120:

CTGGCTACCA TTAGTGCCGA CCGTTTC                                27

(2) INFORMATION FOR SEQ ID NO:121:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:121:

ATCGCCCTCA TTGCTCTGGA CCGCTGT                                27

(2) INFORMATION FOR SEQ ID NO:122:

(i) SEQUENCE CHARACTERISTICS:
        (A) LENGTH: 30 base pairs
        (B) TYPE: nucleic acid
        (C) STRANDEDNESS: unknown
        (D) TOPOLOGY: linear (ii) MOLECULE TYPE: other nucleic acid (xi) SEQUENCE DESCRIPTION: SEQ ID NO:122:

TTTRYCNTCT GTTGGNYSCC YTAYCACATC                             30

(2) INFORMATION FOR SEQ ID NO:123:

```
    (i) SEQUENCE CHARACTERISTICS:
        (A) LENGTH: 30 base pairs
        (B) TYPE: nucleic acid
        (C) STRANDEDNESS: unknown
        (D) TOPOLOGY: linear (ii) MOLECULE TYPE: other nucleic acid (xi) SEQUENCE DESCRIPTION: SEQ ID NO:123:

TTCRYCNTCT GTTGGNYSCC YTAYCACATC                                          30

(2) INFORMATION FOR SEQ ID NO:124:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:124:

TTCGTGGTGT GCTGGGCGCC CATCCACATC                                          30

(2) INFORMATION FOR SEQ ID NO:125:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:125:

TTCATCATCT GTTGGACCCC CATTCACATC                                          30

(2) INFORMATION FOR SEQ ID NO:126:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:126:

TTTATCGTCT GCTGGACCCC CATCCACATC                                          30

(2) INFORMATION FOR SEQ ID NO:127:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:127:

TTTGTGCTGT GTTGGGTGCC TTTCCAGATC                                          30

(2) INFORMATION FOR SEQ ID NO:128:

(i) SEQUENCE CHARACTERISTICS:
        (A) LENGTH: 30 base pairs
        (B) TYPE: nucleic acid
        (C) STRANDEDNESS: double
```

(D) TOPOLOGY: linear (ii) MOLECULE TYPE: cDNA (xi) SEQUENCE DESCRIPTION: SEQ ID NO:128:

TTTGCCTTCT GCTGGCTCCC CAACCATGTC                                              30

(2) INFORMATION FOR SEQ ID NO:129:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:129:

TTCATCTTCT GTTGGTTTCC AAACCACATC                                              30

(2) INFORMATION FOR SEQ ID NO:130:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:130:

TTCGCCTTCT GCTGGCTCCC CAATCATGTC                                              30

(2) INFORMATION FOR SEQ ID NO:131:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:131:

TTTGCCCTCT GCTGGTTGCC AAATCACCTC                                              30

(2) INFORMATION FOR SEQ ID NO:132:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:132:

TTTGCCATCT GCTGGCTGCC CTACCACCTC                                              30

(2) INFORMATION FOR SEQ ID NO:133:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:133:

TTCGCCATCT GCTGGCTGCC CTTCCACATC                                                    30

(2) INFORMATION FOR SEQ ID NO:134:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:134:

TTTGCCATCT GCTGGCTGCC CTATCACGTG                                                    30

(2) INFORMATION FOR SEQ ID NO:135:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:135:

TTCGCCCTGT GCTGGTTCCC TCTTCACTTA                                                    30

(2) INFORMATION FOR SEQ ID NO:136:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:136:

TTTGTCATCT GCTGGCTGCC CTACCACGTG                                                    30

(2) INFORMATION FOR SEQ ID NO:137:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:137:

TTTGCCGCCT GCTGGATGCC TTTTACCCTC                                                    30

(2) INFORMATION FOR SEQ ID NO:138:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:138:

TTTGCCTTGT GCTGGCTGCC TTTGTCCATC                                                    30

(2) INFORMATION FOR SEQ ID NO:139:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:139:

TTTGCCATCT GCTGGCTGCC CTACCACGTG                            30

(2) INFORMATION FOR SEQ ID NO:140:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:140:

TTTGCCCTCT GCTGGTTCCC TCTCAACTGC                            30

(2) INFORMATION FOR SEQ ID NO:141:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:141:

TTCATCGCCT GCTGGGCACC GCTCTTCATC                            30

(2) INFORMATION FOR SEQ ID NO:142:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:142:

TTTGCCCTGT GCTGGATGCC CTACCACCTG                            30

(2) INFORMATION FOR SEQ ID NO:143:

(i) SEQUENCE CHARACTERISTICS:
        (A) LENGTH: 30 base pairs
        (B) TYPE: nucleic acid
        (C) STRANDEDNESS: unknown
        (D) TOPOLOGY: linear (ii) MOLECULE TYPE: other nucleic acid (xi) SEQUENCE DESCRIPTION: SEQ ID NO:143:

TTYYTYNTKT SCTGGNTTCC CTWCYACATG                            30

(2) INFORMATION FOR SEQ ID NO:144:

(i) SEQUENCE CHARACTERISTICS:

(A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:144:

TTCATCATTT GCTGGCTTCC CTTCCATGTT                                            30

(2) INFORMATION FOR SEQ ID NO:145:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:145:

TTCTTCTTTT CCTGGGTTCC CCACCAAATA                                            30

(2) INFORMATION FOR SEQ ID NO:146:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:146:

TTCTTCTTTT CCTGGGTTCC CCACCAAATA                                            30

(2) INFORMATION FOR SEQ ID NO:147:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:147:

TTTTTCTTTT CCTGGATTCC CCACCAAATA                                            30

(2) INFORMATION FOR SEQ ID NO:148:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:148:

TTCTTCCTGT GCTGGATGCC CATCTTCAGC                                            30

(2) INFORMATION FOR SEQ ID NO:149:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:149:

TTCTTCCTGT GTTGGCTGCC AGTGTACAGC                                                30

(2) INFORMATION FOR SEQ ID NO:150:

(i) SEQUENCE CHARACTERISTICS:
          (A) LENGTH: 30 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:150:

TTTTTTCTGT GTTGGTTGCC AGTTTATAGT                                                30

(2) INFORMATION FOR SEQ ID NO:151:

(i) SEQUENCE CHARACTERISTICS:
          (A) LENGTH: 30 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:151:

TTCCTGCTTT GCTGGCTGCC CTACAACCTG                                                30

(2) INFORMATION FOR SEQ ID NO:152:

(i) SEQUENCE CHARACTERISTICS:
          (A) LENGTH: 30 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:152:

TTCCTGCTTT GCTGGCTGCC CTACAACCTG                                                30

(2) INFORMATION FOR SEQ ID NO:153:

(i) SEQUENCE CHARACTERISTICS:
          (A) LENGTH: 30 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:153:

TTCTTTATCT TCTGGCTGCC CTATCAGGTG                                                30

(2) INFORMATION FOR SEQ ID NO:154:

(i) SEQUENCE CHARACTERISTICS:
          (A) LENGTH: 30 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:154:

TTTTTTCTCT GCTGGTCCCC ATATCAGGTG                                30

(2) INFORMATION FOR SEQ ID NO:155:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:155:

ACCACCAACC TGTTCATCCT CAACCTG                                    27

(2) INFORMATION FOR SEQ ID NO:156:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:156:

CCCACCAACT ACTTTATCGT CAACCTG                                    27

(2) INFORMATION FOR SEQ ID NO:157:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:157:

ACCACCAACC TGTTCATCCT CAACCTG                                    27

(2) INFORMATION FOR SEQ ID NO:158:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:158:

GTCACCGACG TCTACCTGCT GAACCTG                                    27

(2) INFORMATION FOR SEQ ID NO:159:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:159:

GTCACCAACT CCTTCCTCGT GAACCTG                                    27

(2) INFORMATION FOR SEQ ID NO:160:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:160:

GTGACCAACT ACTTCATCGT CAACCTG                          27

(2) INFORMATION FOR SEQ ID NO:161:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:161:

ATCACCAACA TTTACATCCT CAACCTG                          27

(2) INFORMATION FOR SEQ ID NO:162:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:162:

GTCACCAACG TCTACATCCT CAACCTG                          27

(2) INFORMATION FOR SEQ ID NO:163:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:163:

GTCACCAACG CCTTCCTCCT CTCACTG                          27

(2) INFORMATION FOR SEQ ID NO:164:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:164:

GTCACCAACA TCTTCCTCCT CTCCCTG                          27

(2) INFORMATION FOR SEQ ID NO:165:

(i) SEQUENCE CHARACTERISTICS:
        (A) LENGTH: 27 base pairs (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:165:

CCCTCCAACT ACCTGATCGT GTCCCTG                                              27

(2) INFORMATION FOR SEQ ID NO:166:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:166:

ATGACCAACG TCTTCATCGT GTCTCTG                                              27

(2) INFORMATION FOR SEQ ID NO:167:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:167:

CCTGCCAACT ACCTAATCTG TTCTCTG                                              27

(2) INFORMATION FOR SEQ ID NO:168:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:168:

CCCACCAACT CCTTCATCGT GAGCCTG                                              27

(2) INFORMATION FOR SEQ ID NO:169:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:169:

GCCACCAACT ATTTCCTGAT GTCACTT                                              27

(2) INFORMATION FOR SEQ ID NO:170:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:170:

GTCACCAACT ATTTCATCGT GAACCTG                                              27

(2) INFORMATION FOR SEQ ID NO:171:

(i) SEQUENCE CHARACTERISTICS:
              (A) LENGTH: 27 base pairs
              (B) TYPE: nucleic acid
              (C) STRANDEDNESS: double
              (D) TOPOLOGY: linear (ii) MOLECULE TYPE: cDNA (xi) SEQUENCE DESCRIPTION: SEQ ID NO:171:

CTGACCAATT GCTTCATTGT GTCCCTG                                              27

(2) INFORMATION FOR SEQ ID NO:172:

(i) SEQUENCE CHARACTERISTICS:
              (A) LENGTH: 27 base pairs
              (B) TYPE: nucleic acid
              (C) STRANDEDNESS: unknown
              (D) TOPOLOGY: linear (ii) MOLECULE TYPE: other nucleic acid (xi) SEQUENCE DESCRIPTION: SEQ ID NO:172:

AAYCCYNTCN TCTAYTSCTT YNTSNCT                                              27

(2) INFORMATION FOR SEQ ID NO:173:

(i) SEQUENCE CHARACTERISTICS:
              (A) LENGTH: 27 base pairs
              (B) TYPE: nucleic acid
              (C) STRANDEDNESS: double
              (D) TOPOLOGY: linear (ii) MOLECULE TYPE: cDNA (xi) SEQUENCE DESCRIPTION: SEQ ID NO:173:

AATCCTATCA TTTATGCATT TCTCTCT                                              27

(2) INFORMATION FOR SEQ ID NO:174:

(i) SEQUENCE CHARACTERISTICS:
              (A) LENGTH: 27 base pairs
              (B) TYPE: nucleic acid
              (C) STRANDEDNESS: double
              (D) TOPOLOGY: linear (ii) MOLECULE TYPE: cDNA (xi) SEQUENCE DESCRIPTION: SEQ ID NO:174:

AACCCCATCG TCTATGCCTT CCGGATC                                              27

(2) INFORMATION FOR SEQ ID NO:175:

(i) SEQUENCE CHARACTERISTICS:
              (A) LENGTH: 27 base pairs
              (B) TYPE: nucleic acid
              (C) STRANDEDNESS: double
              (D) TOPOLOGY: linear (ii) MOLECULE TYPE: cDNA (xi) SEQUENCE DESCRIPTION: SEQ ID NO:175:

```
AATCCTCTCT TTTATGGCTT TCTGGGG                                              27
```

(2) INFORMATION FOR SEQ ID NO:176:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:176:

```
AACCCTATCA TCTACCCGCT CTTTATG                                              27
```

(2) INFORMATION FOR SEQ ID NO:177:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:177:

```
AACCCCATCA TTTATGCCTT TAATGCT                                              27
```

(2) INFORMATION FOR SEQ ID NO:178:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:178:

```
AACCCCTTTG CCCTCTACCT GCTGAGC                                              27
```

(2) INFORMATION FOR SEQ ID NO:179:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:179:

```
AACCCCTTTG CTCTTTATCT GCTGAGC                                              27
```

(2) INFORMATION FOR SEQ ID NO:180:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:180:

```
AACCCTCTGT TCTACGGCTT TCTGGGG                                              27
```

(2) INFORMATION FOR SEQ ID NO:181:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:181:

AACCCCATCA TCTACTGCCG CAGCCCC                                              27

(2) INFORMATION FOR SEQ ID NO:182:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:182:

AACCCCGTGT GCTATGCTCT GTGCAAC                                              27

(2) INFORMATION FOR SEQ ID NO:183:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:183:

AACCCCCTGG TCTACTGCTT CATGCAC                                              27

(2) INFORMATION FOR SEQ ID NO:184:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:184:

AACCCCATCA TCTATTGCTT CATGAAC                                              27

(2) INFORMATION FOR SEQ ID NO:185:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:185:

AATCCCATGC TCTACACCTT CGCTGGC                                              27

(2) INFORMATION FOR SEQ ID NO:186:

(i) SEQUENCE CHARACTERISTICS:
        (A) LENGTH: 27 base pairs
        (B) TYPE: nucleic acid (C) STRANDEDNESS: double
            (D) TOPOLOGY: linear (ii) MOLECULE TYPE: cDNA (xi) SEQUENCE DESCRIPTION: SEQ ID NO:186:

AACCCCGTCC TCTACGGCTT CCTCTCG                                              27

(2) INFORMATION FOR SEQ ID NO:187:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:187:

AACCCCATCC TCTACGGCTT CCTCTCC                                              27

(2) INFORMATION FOR SEQ ID NO:188:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:188:

AACCCCATAC TCTACGGCTT CCTGTCG                                              27

(2) INFORMATION FOR SEQ ID NO:189:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:189:

AACCCGCTCA TCTACCCCTG TTCCAGC                                              27

(2) INFORMATION FOR SEQ ID NO:190:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:190:

AACCCGGTTC TCTACGCCTT CCTGGAC                                              27

(2) INFORMATION FOR SEQ ID NO:191:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:191:

AACCCCATCC TTTATGGCTT CCTCTCC                                             27

(2) INFORMATION FOR SEQ ID NO:192:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:192:

TGGTGGTGGT GGTGGTGGTG GGCAA                                               25

(2) INFORMATION FOR SEQ ID NO:193:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:193:

TGGTGCTGGT GGCTGTGATG GGCAA                                               25

(2) INFORMATION FOR SEQ ID NO:194:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:194:

TGTTCGTGCT GGGCATCATC GGAAA                                               25

(2) INFORMATION FOR SEQ ID NO:195:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:195:

TGATCATTCT TGGTGTCTCT GGAAA                                               25

(2) INFORMATION FOR SEQ ID NO:196:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:196:

TGGTGCTGGT GGCTGTAACA GGCAA                                               25

(2) INFORMATION FOR SEQ ID NO:197:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:197:

TGTTCATCTT CGGGGTGGTG GGCAA                                      25

(2) INFORMATION FOR SEQ ID NO:198:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:198:

TGTTCGTGGC CGGTGTGGTG GGCAA                                      25

(2) INFORMATION FOR SEQ ID NO:199:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:199:

TGTTCGTCGT GGGCTTGGTG GGCAA                                      25

(2) INFORMATION FOR SEQ ID NO:200:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:200:

TGGTGATCCT GGCTGTGGTG AGGAA                                      25

(2) INFORMATION FOR SEQ ID NO:201:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:201:

TGGTTATCCT GGCCGTGGTC AGGAA                                      25

(2) INFORMATION FOR SEQ ID NO:202:

```
    (i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:202:

TCATCGTGAT AGGTCTTATT GGCAA                                              25

(2) INFORMATION FOR SEQ ID NO:203:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:203:

TCTTTCTGAT GAGTGTTGGC GGAAA                                              25

(2) INFORMATION FOR SEQ ID NO:204:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:204:

TATTCCTTCT CAGTGTGCGG GGGAA                                              25

(2) INFORMATION FOR SEQ ID NO:205:

(i) SEQUENCE CHARACTERISTICS:
        (A) LENGTH: 25 base pairs
        (B) TYPE: nucleic acid
        (C) STRANDEDNESS: unknown
        (D) TOPOLOGY: linear (ii) MOLECULE TYPE: other nucleic acid (xi) SEQUENCE DESCRIPTION: SEQ ID NO:205:

GCMATNWCMN TGGACMGRTA CMGRT                                              25

(2) INFORMATION FOR SEQ ID NO:206:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:206:

GCCATCGCAC TGGAGCGGTA CAG                                                23

(2) INFORMATION FOR SEQ ID NO:207:

(i) SEQUENCE CHARACTERISTICS:
        (A) LENGTH: 23 base pairs
        (B) TYPE: nucleic acid
        (C) STRANDEDNESS: double
```

(D) TOPOLOGY: linear (ii) MOLECULE TYPE: cDNA (xi) SEQUENCE DESCRIPTION: SEQ ID NO:207:

GCCATCGCAC TGGAGCGGTA CAG                                              23

(2) INFORMATION FOR SEQ ID NO:208:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:208:

GCCATTGCGG TGGACAGGTA CA                                               22

(2) INFORMATION FOR SEQ ID NO:209:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:209:

GCCATGACGC TGGACCGCCA CCG                                              23

(2) INFORMATION FOR SEQ ID NO:210:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:210:

GCCATTGCAG TGGACAGGTA                                                  20

(2) INFORMATION FOR SEQ ID NO:211:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:211:

GCCATCGCCC TGGAGCGATA CAG                                              23

(2) INFORMATION FOR SEQ ID NO:212:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:212:

GCAATAGCTT TGGACCGCTA CTGGT                                                   25

(2) INFORMATION FOR SEQ ID NO:213:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:213:

GCCATTAGTC TGGACCGCTA CTGGT                                                   25

(2) INFORMATION FOR SEQ ID NO:214:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:214:

GCAATTGCTG TGGACCGCTA CC                                                      22

(2) INFORMATION FOR SEQ ID NO:215:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:215:

GCCATCGCGG TGGACAGATA CA                                                      22

(2) INFORMATION FOR SEQ ID NO:216:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:216:

GCACTGTCAG CTGACAGGTA CAAA                                                    24

(2) INFORMATION FOR SEQ ID NO:217:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:217:

GCCATCTCTC TGGAGAGATA TGG                                                     23

(2) INFORMATION FOR SEQ ID NO:218:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:218:

GCCTTTACCA TTGAGAGGTA CATA                                        24

(2) INFORMATION FOR SEQ ID NO:219:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:219:

CATTGCGGTG GACAGGTATA TGGC                                        24

(2) INFORMATION FOR SEQ ID NO:220:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:220:

CATGTCCCTG GACCGCTGCC TGGC                                        24

(2) INFORMATION FOR SEQ ID NO:221:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:221:

CATATCGCTG GAGAGATACG GAGC                                        24

(2) INFORMATION FOR SEQ ID NO:222:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:222:

CATCGCTCTG GACAGGTACT GGGC                                        24

(2) INFORMATION FOR SEQ ID NO:223:

(i) SEQUENCE CHARACTERISTICS:

(A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:223:

TGGCCTTTGA CAGATACATG GC                                                22

(2) INFORMATION FOR SEQ ID NO:224:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:224:

CATCGCGGTG GACAGATACA TGGC                                              24

(2) INFORMATION FOR SEQ ID NO:225:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:225:

ATGTCCGTGG ACCGCTACGT GGC                                               23

(2) INFORMATION FOR SEQ ID NO:226:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:226:

CATTGCCCTG GACAGGTACT GGGC                                              24

(2) INFORMATION FOR SEQ ID NO:227:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:227:

CCTGGCCGTG GACCGCTACC TGGC                                              24

(2) INFORMATION FOR SEQ ID NO:228:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:228:

CATGGCCGTG GAGCGCTGCC TGGC                                              24

(2) INFORMATION FOR SEQ ID NO:229:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:229:

CATCTCTCTG GAGAGATATG GCGC                                              24

(2) INFORMATION FOR SEQ ID NO:230:

(i) SEQUENCE CHARACTERISTICS:
            (A) LENGTH: 24 base pairs
            (B) TYPE: nucleic acid
            (C) STRANDEDNESS: unknown
            (D) TOPOLOGY: linear (ii) MOLECULE TYPE: other nucleic acid (xi) SEQUENCE DESCRIPTION: SEQ ID NO:230:

TTYGCCNTST GCTGGMTSCC CWWC                                              24

(2) INFORMATION FOR SEQ ID NO:231:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:231:

TTTGCCATCT GCTGGCTGCC CTAC                                              24

(2) INFORMATION FOR SEQ ID NO:232:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:232:

TTCGCCATCT GCTGGCTGCC CTTC                                              24

(2) INFORMATION FOR SEQ ID NO:233:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:233:

```
TTTGCCATCT GCTGGCTGCC CTAC                                               24

(2) INFORMATION FOR SEQ ID NO:234:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:234:

TTTGCCTTCT GCTGGCTCCC CAAC                                               24

(2) INFORMATION FOR SEQ ID NO:235:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:235:

TTTGCCATCT GCTGGCTGCC CTA                                                23

(2) INFORMATION FOR SEQ ID NO:236:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:236:

TTTGCCCTCT GCTGGCTGCC CCT                                                23

(2) INFORMATION FOR SEQ ID NO:237:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:237:

TTCACCCTCT GCTGGCTGCC CTTC                                               24

(2) INFORMATION FOR SEQ ID NO:238:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:238:

TTCGCCCCTC TGTGGCTGCC CCT                                                23
```

(2) INFORMATION FOR SEQ ID NO:239:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:239:

TTTGCCCTCT GCTGGCTTCC CCT          23

(2) INFORMATION FOR SEQ ID NO:240:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:240:

TTCGCCGTCT GCTGGCTGCC CCT          23

(2) INFORMATION FOR SEQ ID NO:241:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:241:

TTCATCGTGT GCTGGACGCC TTTC          24

(2) INFORMATION FOR SEQ ID NO:242:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:242:

TTCTTCCTGT GCTGGATGCC CATC          24

(2) INFORMATION FOR SEQ ID NO:243:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:243:

AACCTGGCCT TTGCGGAT          18

(2) INFORMATION FOR SEQ ID NO:244:

(i) SEQUENCE CHARACTERISTICS:
        (A) LENGTH: 18 base pairs

-continued

```
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:244:

AATCTGGCGC TGGCTGAC                                                    18

(2) INFORMATION FOR SEQ ID NO:245:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:245:

AACCTGGCCG TGGCTGAC                                                    18

(2) INFORMATION FOR SEQ ID NO:246:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:246:

AACCTAGCCT TGGCCGAC                                                    18

(2) INFORMATION FOR SEQ ID NO:247:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:247:

AACCTGGCCG TGGCCGAC                                                    18

(2) INFORMATION FOR SEQ ID NO:248:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:248:

AACCTGGCCT TGGCCGAC                                                    18

(2) INFORMATION FOR SEQ ID NO:249:

(i) SEQUENCE CHARACTERISTICS:
            (A) LENGTH: 18 base pairs
            (B) TYPE: nucleic acid
            (C) STRANDEDNESS: double
            (D) TOPOLOGY: linear
```

(ii) MOLECULE TYPE: cDNA (xi) SEQUENCE DESCRIPTION: SEQ ID NO:249:

AGCCTCGCAG TGGCCGAC                                                              18

(2) INFORMATION FOR SEQ ID NO:250:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:250:

AATTTAGCAC TGGCTGAC                                                              18

(2) INFORMATION FOR SEQ ID NO:251:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:251:

AACCTGGCCG TAGCCGAC                                                              18

(2) INFORMATION FOR SEQ ID NO:252:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:252:

AGCTTGGCTG TGGCTGAT                                                              18

(2) INFORMATION FOR SEQ ID NO:253:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:253:

AGCCTGGCAG TAGCTGAT                                                              18

(2) INFORMATION FOR SEQ ID NO:254:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:254:

AACCTGGCCT TAGCCGAT                                         18

(2) INFORMATION FOR SEQ ID NO:255:

(i) SEQUENCE CHARACTERISTICS:
        (A) LENGTH: 21 base pairs
        (B) TYPE: nucleic acid
        (C) STRANDEDNESS: unknown
        (D) TOPOLOGY: linear (ii) MOLECULE TYPE: other nucleic acid (ix) FEATURE:
        (D) OTHER INFORMATION: "N at position 16, 18 & 21 =  inosine"

(xi) SEQUENCE DESCRIPTION: SEQ ID NO:255:

TTYNYNNTNT GYTGGNTNCC N                                     21

(2) INFORMATION FOR SEQ ID NO:256:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:256:

TTCACCCTCT GCTGGCTGCC C                                     21

(2) INFORMATION FOR SEQ ID NO:257:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:257:

TTTGCCATCT GCTGGCTGCC C                                     21

(2) INFORMATION FOR SEQ ID NO:258:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:258:

TTTGCTCTTT GCTGGTTCCC T                                     21

(2) INFORMATION FOR SEQ ID NO:259:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:259:

TTCATCATCT GCTGGTTTCC C                                     21

(2) INFORMATION FOR SEQ ID NO:260:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:260:

TTCGTGCTCT GCTGGTTCCC T                                          21

(2) INFORMATION FOR SEQ ID NO:261:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:261:

TTCCTGCTTT GCTGGCTGCC C                                          21

(2) INFORMATION FOR SEQ ID NO:262:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:262:

TTCATCTTCT GTTGGTTTCC T                                          21

(2) INFORMATION FOR SEQ ID NO:263:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:263:

TTCGCCATCT GCTGGCTGCC C                                          21

(2) INFORMATION FOR SEQ ID NO:264:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:264:

TTCGCCATCT GCTGGCTGCC C                                          21

(2) INFORMATION FOR SEQ ID NO:265:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:265:

TTTATCATCT GCTGGCTGCC C                                                  21

(2) INFORMATION FOR SEQ ID NO:266:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:266:

TTCTTCATCT GTTGGTTTCC C                                                  21

(2) INFORMATION FOR SEQ ID NO:267:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:267:

TTCATCATCT GCTGGCTGCC C                                                  21

(2) INFORMATION FOR SEQ ID NO:268:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:268:

TTTGCAGTCT GCTGGCTCCC T                                                  21

(2) INFORMATION FOR SEQ ID NO:269:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:269:

TTTGCCCTCT GCTGGCTGCC C                                                  21

(2) INFORMATION FOR SEQ ID NO:270:

(i) SEQUENCE CHARACTERISTICS:
            (A) LENGTH: 21 base pairs
            (B) TYPE: nucleic acid
            (C) STRANDEDNESS: double (D) TOPOLOGY: linear (ii) MOLECULE TYPE: cDNA (xi) SEQUENCE DESCRIPTION: SEQ ID NO:270:

TTCATCATCT GCTGGCTGCC C                                              21

(2) INFORMATION FOR SEQ ID NO:271:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:271:

TTCTTCATCT GTTGGTTTCC C                                              21

(2) INFORMATION FOR SEQ ID NO:272:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:272:

TTCGTGCTCT GCTGGATGCC C                                              21

(2) INFORMATION FOR SEQ ID NO:273:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:273:

TTTTTTCTGT GTTGGTTGCC A                                              21

(2) INFORMATION FOR SEQ ID NO:274:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:274:

TTTGTGGTCT GCTGGCTGCC C                                              21

(2) INFORMATION FOR SEQ ID NO:275:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:275:

CCCTGGCCGC GATGTCCGTG GACCGCT									27

(2) INFORMATION FOR SEQ ID NO:276:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:276:

GCCTCGTGGC CATCGCACTG GAGCGGT									27

(2) INFORMATION FOR SEQ ID NO:277:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:277:

ACCTCTGCGC TCTTAGTGTT GACAGGT									27

(2) INFORMATION FOR SEQ ID NO:278:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:278:

GTCTATGTGC TCTGAGTATT GACAGAT									27

(2) INFORMATION FOR SEQ ID NO:279:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:279:

TCCTGGCCAC CATCAGCGCC GACCGCT									27

(2) INFORMATION FOR SEQ ID NO:280:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:280:

TACTCACGTG TCTCAGCATT GATCGAT									27

(2) INFORMATION FOR SEQ ID NO:281:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:281:

TCCTGATGCT GGTGAGCATC GACCGCT                                    27

(2) INFORMATION FOR SEQ ID NO:282:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:282:

ACGTGGCCAG CCTGAGTGTG GAGCGCT                                    27

(2) INFORMATION FOR SEQ ID NO:283:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:283:

CACTCACGGC GCTCTCGGCA GACAGAT                                    27

(2) INFORMATION FOR SEQ ID NO:284:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:284:

GCCTGACAGT CATGAGCGTG GACCGCT                                    27

(2) INFORMATION FOR SEQ ID NO:285:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:285:

TGTTGGCCTG CATCAGTGTG GACCGTT                                    27

(2) INFORMATION FOR SEQ ID NO:286:

(i) SEQUENCE CHARACTERISTICS:

(A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:286:

CCATGACCGC CATTGCTGCC GACAGGT                                27

(2) INFORMATION FOR SEQ ID NO:287:

(i) SEQUENCE CHARACTERISTICS:
        (A) LENGTH: 27 base pairs
        (B) TYPE: nucleic acid
        (C) STRANDEDNESS: unknown
        (D) TOPOLOGY: linear (ii) MOLECULE TYPE: other nucleic acid (xi) SEQUENCE DESCRIPTION: SEQ ID NO:287:

TGGNTNCCCT WCCAYNTNRK CANSWTC                                27

(2) INFORMATION FOR SEQ ID NO:288:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:288:

TGGCTGCCGC ACCACATCAT CCATCTC                                27

(2) INFORMATION FOR SEQ ID NO:289:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:289:

TGGTTGCCAG TTTATAGTGC CAACACG                                27

(2) INFORMATION FOR SEQ ID NO:290:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:290:

TGGTTCCCTC TTCATTTAAG CCGTATA                                27

(2) INFORMATION FOR SEQ ID NO:291:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:291:

TGGCTTCCCC TTCACCTCAG CAGGATT                                              27

(2) INFORMATION FOR SEQ ID NO:292:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:292:

TGGTTGCCCT ACCAGGTGAC GGGGATA                                              27

(2) INFORMATION FOR SEQ ID NO:293:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:293:

TGGATTCCCC ACCAAATATT CACTTTT                                              27

(2) INFORMATION FOR SEQ ID NO:294:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:294:

TGGCTGCCCT TCCAGATCAG CACCTTC                                              27

(2) INFORMATION FOR SEQ ID NO:295:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:295:

TGGACTCCGT TCCTCTATGA CTTCTAC                                              27

(2) INFORMATION FOR SEQ ID NO:296:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:296:

TGGCTCCCCA ATCATGTCAT CTACCTG                                               27

(2) INFORMATION FOR SEQ ID NO:297:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:297:

TGGCTGCCCT TCTTCACCGT CAACATC                                               27

(2) INFORMATION FOR SEQ ID NO:298:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:298:

TGGCTGCCCT ACAACCTGGT CCTGCTG                                               27

(2) INFORMATION FOR SEQ ID NO:299:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:299:

TGGCTGCCCT ACCACCTCTA CTTCATC                                               27

(2) INFORMATION FOR SEQ ID NO:300:

(i) SEQUENCE CHARACTERISTICS:
        (A) LENGTH: 248 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:300:

GTGGGCATGG TGGGCAACCC CCTGGTCATC TTCGTGATCC TTCGCTACGC CAAGATGAAG    60

ACGGCTACCA ACATCTACCT GCTCAACCTG GCCGTAGCCG ACGAGCTCTT CATGCTGAGC   120

GTGCCCTTCG TGGCCTCGTC GGCCGCCCTG CGCCACTGGC CCTTCGGCTC CGTGCTGTGC   180

CGCGCGGTGC TCAGCGTCGA CGGCCTCAAC ATGTTCACCA GCGTCTTCTG TCTCACCGTG   240

CTCAGCGT                                                           248

(2) INFORMATION FOR SEQ ID NO:301:

(i) SEQUENCE CHARACTERISTICS:
        (A) LENGTH: 248 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:301:

```
GTGGGGCTGG TGGGCAACGC CCTGGTCATC TTCGTGATCC TTCGCTACGC CAAGATGAAG      60

ACGGCTACCA ACATCTACCT GCTCAACCTG GCCGTAGCCG ACGAGCTCTT CATGCTGAGC     120

GTGCCCTTCG TGGCCTCGTC GGCCGCCCTG CGCCACTGGC CCTTCGGCTC CGTGCTGTGC     180

CGCGCGGTGC TCAGCGTCGA CGGCCTCAAC ATGTTCACCA GCGTCTTCTG TCTCACCGTG     240

CTCAGCGT                                                              248
```

(2) INFORMATION FOR SEQ ID NO:302:

(i) SEQUENCE CHARACTERISTICS:
        (A) LENGTH: 228 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:302:

```
CAGTGTCCAC ACCCGGCCTG GTCGGCAGTC TTCGTGGTCT ACACTTTCCT GCTGGGCTTC      60

CTGCTGTCCG TGCTGTCCAT GGCCTGTGC TACCTGCTCA TCGTGGGCAA GATGCGCGCC     120

GTGTCCCTGC GCGCTGGCTG GCAGCAGCGC AGGCGCTCGG AGAAGAAAAT CACCAGGCTG     180

GTGCTGATGG TCGTGGTCGT CTTTGCCCTC TGCTGGTTGC CTCTCCAC                 228
```

(2) INFORMATION FOR SEQ ID NO:303:

(i) SEQUENCE CHARACTERISTICS:
        (A) LENGTH: 228 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:303:

```
CAGTGGCCAC ACCCGGCCTG GTCGGCAGTC TTCGTGGTCT ACACTTTCCT GCTGGGCTTC      60

CTGCTGCCCG TGCTGGCCAT GGCCTGTGC TACCTGCTCA TCGTGGGCAA GATGCGCGCC     120

GTGGCCCTGC GCGCTGGCTG GCAGCAGCGC AGGCGCTCGG AGAAGAAAAT CACCAGGCTG     180

GTGCTGATGG TCGTGGTCGT CTTTGTGCTC TGCTGGATGC CTTTCTAC                 228
```

(2) INFORMATION FOR SEQ ID NO:304:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:304:

```
GTGGGCATGC TGGGCAACCT CCTGGAAGGC AGTCGCCGAG GTGGCCGGTT ACTGGCCCTT      60

TGGAGCGTTC TGCGACGTCT GGGTGGCCTT CGACATCATG TGCTCCACTG CCTCCATCCT     120

GAACCTGTGC GTCATCAGCG TGGACCGCTA CTGGGCCATC TCCAGGCCCT TCCGCTACAA     180

GCGCAAGATG ACTCAGCGCA TGGCCTTGGT CATGGTCGGC CTGGCATGGA CCTTGTCCAT     240

CCTCATCTCC TTCATTCCGG TCCAGCTCAA CTGGGACAGG GACCAGGCGG GCTCTTGGGG     300
```

GGGGCTGGAC CTGCCAAA                                                        318

(2) INFORMATION FOR SEQ ID NO:305:

(i) SEQUENCE CHARACTERISTICS:
        (A) LENGTH: 317 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:305:

GTGGCGCTGC TGGTCATGCC CTGGAAGGCA GTCGCCGAGG TGGCCGGTTA CTGGCCCTTT           60

GGAGCGTTCT GCGACGTCTG GGTGGCCTTC GACATCATGT GCTCCACTGC CTCCATCCTG          120

AACCTGTGCG TCATCAGCGT GGACCGCTAC TGGGCCATCT CCAGGCCCTT CCGCTACAAG          180

CGCAAGATGA CTCAGCGCAT GGCCTTGGTC ATGGTCGGCC TGGCATGGAC CTTGTCCATC          240

CTCATCTCCT TCATTCCGGT CCAGCTCAAC TGGCACAGGG ACCAGGCGGC CTCTTGGGGC          300

GGGCTGGACC TGCCAAA                                                        317

(2) INFORMATION FOR SEQ ID NO:306:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:306:

GTGGGCATCG TGGGCAACAT CCTGGTCATA TTCGTGATCC TACGCTATGC CAAAATGAAG           60

ACAGCCACCA ACATCTACCT GCTCAACCTG GCCGTCGCTG ATGAGCTCTT CATGCTCAGT          120

GTGCCATTTG TGGCCTCGGC GGCTGCCCTG CGCCACTGGC CGTTCGGGGC GGTGCTGTGC          180

CGC                                                                      183

(2) INFORMATION FOR SEQ ID NO:307:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:307:

GTGGGCCTGG TAGGAAACGC CCTGGTCATA TTCGTGATCC TACGCTATGC CAAAATGAAG           60

ACAGCCACCA ACATCTACCT GCTCAACCTG GCCGTCGCTG ATGAGCTCTT CATGCTCAGT          120

GTGCCATTTG TGGCCTCGGC GGCTGCCCTG CGCCACTGGC CGTTCGGGGC GGTGCTGTGC          180

CGC                                                                      183

(2) INFORMATION FOR SEQ ID NO:308:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: cDNA (ix) FEATURE:
    (A) NAME/KEY: CDS
    (B) LOCATION: 1..297

(xi) SEQUENCE DESCRIPTION: SEQ ID NO:308:

| | | | | | | | | | | | | | | | | |
|---|---|---|---|---|---|---|---|---|---|---|---|---|---|---|---|---|
| GTG | GGC | ATG | GTG | GGC | AAC | GTC | CTG | CTG | GTG | CTG | GTG | ATC | GCG | CGG | GTG | 48 |
| Val | Gly | Met | Val | Gly | Asn | Val | Leu | Leu | Val | Leu | Val | Ile | Ala | Arg | Val | |
| 1 | | | | 5 | | | | | 10 | | | | | 15 | | |
| CGC | CGG | CTG | CAC | AAC | GTG | ACG | AAC | TTC | CTC | ATC | GGC | AAC | CTG | GCC | TTG | 96 |
| Arg | Arg | Leu | His | Asn | Val | Thr | Asn | Phe | Leu | Ile | Gly | Asn | Leu | Ala | Leu | |
| | | | | 20 | | | | | 25 | | | | | 30 | | |
| TCC | GAC | GTG | CTC | ATG | TGC | ACC | GCC | TGC | GTG | CCG | CTC | ACG | CTG | GCC | TAT | 144 |
| Ser | Asp | Val | Leu | Met | Cys | Thr | Ala | Cys | Val | Pro | Leu | Thr | Leu | Ala | Tyr | |
| | | | 35 | | | | | 40 | | | | | 45 | | | |
| GCC | TTC | GAG | CCA | CGC | GGC | TGG | GTG | TTC | GGC | GGC | GGC | CTG | TGC | CAC | CTG | 192 |
| Ala | Phe | Glu | Pro | Arg | Gly | Trp | Val | Phe | Gly | Gly | Gly | Leu | Cys | His | Leu | |
| | | 50 | | | | | 55 | | | | | 60 | | | | |
| GTC | TTC | TTC | CTG | CAG | CCG | GTC | ACC | GTC | TAT | GTG | TCG | GTG | TTC | ACG | CTC | 240 |
| Val | Phe | Phe | Leu | Gln | Pro | Val | Thr | Val | Tyr | Val | Ser | Val | Phe | Thr | Leu | |
| 65 | | | | | 70 | | | | | 75 | | | | | 80 | |
| ACC | ACC | ATC | GAA | GTG | GAC | CGG | TAC | GTC | GGT | GCT | GGT | GCA | CCC | GCT | GAG | 288 |
| Thr | Thr | Ile | Glu | Val | Asp | Arg | Tyr | Val | Gly | Ala | Gly | Ala | Pro | Ala | Glu | |
| | | | | 85 | | | | | 90 | | | | | 95 | | |
| GCG | GGG | CAT | | | | | | | | | | | | | | 297 |
| Ala | Gly | His | | | | | | | | | | | | | | |

(2) INFORMATION FOR SEQ ID NO:309:

(i) SEQUENCE CHARACTERISTICS:
      (A) LENGTH: 99 amino acids
      (B) TYPE: amino acid
      (D) TOPOLOGY: linear (ii) MOLECULE TYPE: protein (xi) SEQUENCE DESCRIPTION: SEQ ID NO:309:

Val Gly Met Val Gly Asn Val Leu Leu Val Leu Val Ile Ala Arg Val
 1               5                  10                  15

Arg Arg Leu His Asn Val Thr Asn Phe Leu Ile Gly Asn Leu Ala Leu
             20                  25                  30

Ser Asp Val Leu Met Cys Thr Ala Cys Val Pro Leu Thr Leu Ala Tyr
         35                  40                  45

Ala Phe Glu Pro Arg Gly Trp Val Phe Gly Gly Gly Leu Cys His Leu
     50                  55                  60

Val Phe Phe Leu Gln Pro Val Thr Val Tyr Val Ser Val Phe Thr Leu
65                  70                  75                  80

Thr Thr Ile Glu Val Asp Arg Tyr Val Gly Ala Gly Ala Pro Ala Glu
                 85                  90                  95

Ala Gly His (2) INFORMATION FOR SEQ ID NO:310:

(i) SEQUENCE CHARACTERISTICS:
      (A) LENGTH: 204 base pairs
      (B) TYPE: nucleic acid
      (C) STRANDEDNESS: double
      (D) TOPOLOGY: linear (ii) MOLECULE TYPE: cDNA (ix) FEATURE:

```
            (A) NAME/KEY: CDS
            (B) LOCATION: 1..204

(xi) SEQUENCE DESCRIPTION: SEQ ID NO:310:

GGC CTG CTG CTG GTC ACC TAC CTG CTC CCT CTG CTG GTC ATC CTC CTG        48
Gly Leu Leu Leu Val Thr Tyr Leu Leu Pro Leu Leu Val Ile Leu Leu
 1               5                  10                  15

TCT TAC GTC CGG GTG TCA GTG AAG CTC CGC AAC CCG GTG GTG CCG GTC        96
Ser Tyr Val Arg Val Ser Val Lys Leu Arg Asn Pro Val Val Pro Val
             20                  25                  30

TGC GTG ACC CAG AGC CAG GCC GAC TGG GAC CGC GCT CGG CGC CGG CGC       144
Cys Val Thr Gln Ser Gln Ala Asp Trp Asp Arg Ala Arg Arg Arg Arg
         35                  40                  45

ACC TTC TGC TTG CTG GTG GTG GTC GTG GTG GTG TTT GCC ATC TGC TGG       192
Thr Phe Cys Leu Leu Val Val Val Val Val Val Phe Ala Ile Cys Trp
     50                  55                  60

TTG CCT TAC TAC                                                       204
Leu Pro Tyr Tyr
 65

(2) INFORMATION FOR SEQ ID NO:311:

(i) SEQUENCE CHARACTERISTICS:
            (A) LENGTH: 68 amino acids
            (B) TYPE: amino acid
            (D) TOPOLOGY: linear (ii) MOLECULE TYPE: protein (xi) SEQUENCE DESCRIPTION: SEQ ID NO:311:

Gly Leu Leu Leu Val Thr Tyr Leu Leu Pro Leu Leu Val Ile Leu Leu
 1               5                  10                  15

Ser Tyr Val Arg Val Ser Val Lys Leu Arg Asn Pro Val Val Pro Val
             20                  25                  30

Cys Val Thr Gln Ser Gln Ala Asp Trp Asp Arg Ala Arg Arg Arg Arg
         35                  40                  45

Thr Phe Cys Leu Leu Val Val Val Val Val Val Phe Ala Ile Cys Trp
     50                  55                  60

Leu Pro Tyr Tyr
 65

(2) INFORMATION FOR SEQ ID NO:312:

(i) SEQUENCE CHARACTERISTICS:
            (A) LENGTH: 166 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:312:

Val Gly Met Val Gly Asn Val Leu Leu Val Leu Val Ile Ala Arg Val
 1               5                  10                  15

Arg Arg Leu His Asn Val Thr Asn Phe Leu Ile Gly Asn Leu Ala Leu
             20                  25                  30

Ser Asp Val Leu Met Cys Thr Ala Cys Val Pro Leu Thr Leu Ala Tyr
         35                  40                  45

Ala Phe Glu Pro Arg Gly Trp Val Phe Gly Gly Leu Cys His Leu
     50                  55                  60

Val Phe Phe Leu Gln Pro Val Thr Val Tyr Val Ser Val Phe Thr Leu
 65                  70                  75                  80
```

```
Thr Thr Ile Glu Val Asp Arg Tyr Val Gly Ala Gly Ala Pro Ala Glu
             85                  90                  95

Ala Gly His Gly Leu Leu Leu Val Thr Tyr Leu Leu Pro Leu Leu Val
            100                 105                 110

Ile Leu Leu Ser Tyr Val Arg Ser Val Lys Leu Arg Asn Pro Val Val
            115                 120                 125

Pro Val Cys Val Thr Gln Ser Gln Ala Asp Trp Asp Arg Ala Arg Arg
            130                 135                 140

Arg Arg Thr Phe Cys Leu Leu Val Val Val Val Val Phe Ala Ile
145                 150                 155                 160

Cys Trp Leu Pro Tyr Tyr
                165
```

(2) INFORMATION FOR SEQ ID NO:313:

(i) SEQUENCE CHARACTERISTICS:
        (A) LENGTH: 228 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:313:

```
Leu Gly Val Ser Gly Asn Leu Ala Leu Ile Ile Ile Leu Lys Gln
1                5                  10                  15

Lys Glu Met Arg Asn Val Thr Asn Ile Leu Ile Val Asn Leu Ser Phe
            20                  25                  30

Ser Asp Leu Leu Val Ala Val Met Cys Leu Pro Phe Thr Phe Val Tyr
            35                  40                  45

Thr Leu Met Asp His Trp Val Phe Gly Glu Thr Met Cys Lys Leu Asn
50                  55                  60

Pro Phe Val Gln Cys Val Ser Ile Thr Val Ser Ile Phe Ser Leu Val
65                  70                  75                  80

Leu Ile Ala Val Glu Arg His Gln Leu Ile Ile Asn Pro Arg Gly Trp
            85                  90                  95

Arg Pro Asn Asn Arg His Ala Tyr Ile Gly Ile Thr Val Ile Trp Val
            100                 105                 110

Leu Ala Val Ala Ser Ser Leu Pro Phe Val Ile Tyr Gln Ile Leu Thr
            115                 120                 125

Asp Glu Pro Phe Gln Asn Val Ser Leu Ala Ala Phe Lys Asp Lys Tyr
            130                 135                 140

Val Cys Phe Asp Lys Phe Pro Ser Asp Ser His Arg Leu Ser Tyr Thr
145                 150                 155                 160

Thr Leu Leu Leu Val Leu Gln Tyr Phe Gly Pro Leu Cys Phe Ile Phe
            165                 170                 175

Ile Cys Tyr Phe Lys Ile Tyr Ile Arg Leu Lys Arg Arg Asn Asn Met
            180                 185                 190

Met Asp Lys Ile Arg Asp Ser Lys Tyr Arg Ser Ser Glu Thr Lys Arg
            195                 200                 205

Ile Asn Val Met Leu Leu Ser Ile Val Val Ala Phe Ala Val Cys Trp
            210                 215                 220

Leu Pro Leu Thr
225
```

(2) INFORMATION FOR SEQ ID NO:314:

(i) SEQUENCE CHARACTERISTICS:
    (A) LENGTH: 669 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 1..669

(xi) SEQUENCE DESCRIPTION: SEQ ID NO:314:

```
GTG GGC ATG GTG GGC AAC ATC CTG CTG GTG CTG GTG ATC GCG CGG GTG          48
Val Gly Met Val Gly Asn Ile Leu Leu Val Leu Val Ile Ala Arg Val
 1               5                  10                  15

CGC CGG CTG TAC AAC GTG ACG AAT TTC CTC ATC GGC AAC CTG GCC TTG          96
Arg Arg Leu Tyr Asn Val Thr Asn Phe Leu Ile Gly Asn Leu Ala Leu
                20                  25                  30

TCC GAC GTG CTC ATG TGC ACC GCC TGC GTG CCG CTC ACG CTG GCC TAT         144
Ser Asp Val Leu Met Cys Thr Ala Cys Val Pro Leu Thr Leu Ala Tyr
        35                  40                  45

GCC TTC GAG CCA CGC GGC TGG GTG TTC GGC GGC GGC CTG TGC CAC CTG         192
Ala Phe Glu Pro Arg Gly Trp Val Phe Gly Gly Gly Leu Cys His Leu
    50                  55                  60

GTC TTC TTC CTG CAG GCG GTC ACC GTC TAT GTG TCG GTG TTC ACG CTC         240
Val Phe Phe Leu Gln Ala Val Thr Val Tyr Val Ser Val Phe Thr Leu
65                  70                  75                  80

ACC ACC ATC GCA GTG GAC CGC TAC GTC GTG CTG GTG CAC CCG CTG AGG         288
Thr Thr Ile Ala Val Asp Arg Tyr Val Val Leu Val His Pro Leu Arg
                85                  90                  95

CGG CGC ATC TCG CTG CGC CTC AGC GCC TAC GCT GTG CTG GCC ATC TGG         336
Arg Arg Ile Ser Leu Arg Leu Ser Ala Tyr Ala Val Leu Ala Ile Trp
                100                 105                 110

GTG CTG TCC GCG GTG CTG GCG CTG CCC GCC GCC GTG CAC ACC TAT CAC         384
Val Leu Ser Ala Val Leu Ala Leu Pro Ala Ala Val His Thr Tyr His
            115                 120                 125

GTG GAG CTC AAG CCG CAC GAC GTG CGC CTC TGC GAG GAG TTC TGG GGC         432
Val Glu Leu Lys Pro His Asp Val Arg Leu Cys Glu Glu Phe Trp Gly
        130                 135                 140

TCC CAG GAG CGC CAG CGC CAG CTC TAC GCC TGG GGG CTG CTG CTG GTC         480
Ser Gln Glu Arg Gln Arg Gln Leu Tyr Ala Trp Gly Leu Leu Leu Val
145                 150                 155                 160

ACC TAC CTG CTC CCT CTG CTG GTC ATC CTC CTG TCT TAC GCC CGG GTG         528
Thr Tyr Leu Leu Pro Leu Leu Val Ile Leu Leu Ser Tyr Ala Arg Val
                165                 170                 175

TCA GTG AAG CTC CGC AAC CGC GTG GTG CCG GGC CGC GTG ACC CAG AGC         576
Ser Val Lys Leu Arg Asn Arg Val Val Pro Gly Arg Val Thr Gln Ser
                180                 185                 190

CAG GCC GAC TGG GAC CGC GCT CGG CGC CGG CGC ACC TTC TGC TTG CTG         624
Gln Ala Asp Trp Asp Arg Ala Arg Arg Arg Arg Thr Phe Cys Leu Leu
            195                 200                 205

GTG GTG GTC GTG GTG GTG TTC ACC CTC TGC TGG CTG CCC TTC TTC             669
Val Val Val Val Val Val Phe Thr Leu Cys Trp Leu Pro Phe Phe
        210                 215                 220
```

(2) INFORMATION FOR SEQ ID NO:315:

(i) SEQUENCE CHARACTERISTICS:
    (A) LENGTH: 223 amino acids
    (B) TYPE: amino acid
    (D) TOPOLOGY: linear (ii) MOLECULE TYPE: protein (xi) SEQUENCE DESCRIPTION: SEQ ID NO:315:

| Val | Gly | Met | Val | Gly | Asn | Ile | Leu | Leu | Val | Leu | Val | Ile | Ala | Arg | Val |
|---|---|---|---|---|---|---|---|---|---|---|---|---|---|---|---|
| 1 | | | | 5 | | | | | 10 | | | | | 15 | |

| Arg | Arg | Leu | Tyr | Asn | Val | Thr | Asn | Phe | Leu | Ile | Gly | Asn | Leu | Ala | Leu |
|---|---|---|---|---|---|---|---|---|---|---|---|---|---|---|---|
| | | | 20 | | | | | 25 | | | | | 30 | | |

| Ser | Asp | Val | Leu | Met | Cys | Thr | Ala | Cys | Val | Pro | Leu | Thr | Leu | Ala | Tyr |
|---|---|---|---|---|---|---|---|---|---|---|---|---|---|---|---|
| | | 35 | | | | | 40 | | | | | 45 | | | |

| Ala | Phe | Glu | Pro | Arg | Gly | Trp | Val | Phe | Gly | Gly | Leu | Cys | His | Leu |
|---|---|---|---|---|---|---|---|---|---|---|---|---|---|---|
| | 50 | | | | | 55 | | | | | 60 | | | |

| Val | Phe | Phe | Leu | Gln | Ala | Val | Thr | Val | Tyr | Val | Ser | Val | Phe | Thr | Leu |
|---|---|---|---|---|---|---|---|---|---|---|---|---|---|---|---|
| 65 | | | | | 70 | | | | | 75 | | | | | 80 |

| Thr | Thr | Ile | Ala | Val | Asp | Arg | Tyr | Val | Leu | Val | His | Pro | Leu | Arg |
|---|---|---|---|---|---|---|---|---|---|---|---|---|---|---|
| | | | | 85 | | | | | 90 | | | | | 95 |

| Arg | Arg | Ile | Ser | Leu | Arg | Leu | Ser | Ala | Tyr | Ala | Val | Leu | Ala | Ile | Trp |
|---|---|---|---|---|---|---|---|---|---|---|---|---|---|---|---|
| | | | | 100 | | | | | 105 | | | | | 110 | |

| Val | Leu | Ser | Ala | Val | Leu | Ala | Leu | Pro | Ala | Ala | Val | His | Thr | Tyr | His |
|---|---|---|---|---|---|---|---|---|---|---|---|---|---|---|---|
| | | | 115 | | | | | 120 | | | | | 125 | | |

| Val | Glu | Leu | Lys | Pro | His | Asp | Val | Arg | Leu | Cys | Glu | Glu | Phe | Trp | Gly |
|---|---|---|---|---|---|---|---|---|---|---|---|---|---|---|---|
| | 130 | | | | | 135 | | | | | 140 | | | | |

| Ser | Gln | Glu | Arg | Gln | Arg | Gln | Leu | Tyr | Ala | Trp | Gly | Leu | Leu | Leu | Val |
|---|---|---|---|---|---|---|---|---|---|---|---|---|---|---|---|
| 145 | | | | | 150 | | | | | 155 | | | | | 160 |

| Thr | Tyr | Leu | Leu | Pro | Leu | Leu | Val | Ile | Leu | Leu | Ser | Tyr | Ala | Arg | Val |
|---|---|---|---|---|---|---|---|---|---|---|---|---|---|---|---|
| | | | | 165 | | | | | 170 | | | | | 175 | |

| Ser | Val | Lys | Leu | Arg | Asn | Arg | Val | Val | Pro | Gly | Arg | Val | Thr | Gln | Ser |
|---|---|---|---|---|---|---|---|---|---|---|---|---|---|---|---|
| | | | 180 | | | | | 185 | | | | | 190 | | |

| Gln | Ala | Asp | Trp | Asp | Arg | Ala | Arg | Arg | Arg | Arg | Thr | Phe | Cys | Leu | Leu |
|---|---|---|---|---|---|---|---|---|---|---|---|---|---|---|---|
| | | | 195 | | | | | 200 | | | | | 205 | | |

| Val | Val | Val | Val | Val | Val | Phe | Thr | Leu | Cys | Trp | Leu | Pro | Phe | Phe |
|---|---|---|---|---|---|---|---|---|---|---|---|---|---|---|
| | 210 | | | | | 215 | | | | | 220 | | | |

(2) INFORMATION FOR SEQ ID NO:316:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 25..234

(xi) SEQUENCE DESCRIPTION: SEQ ID NO:316:

```
GTGGGCATGC TGGGCAACGC CCTG GTC TGT CAT GTC ATC TTC AAG AAC CAG        51
                          Val Cys His Val Ile Phe Lys Asn Gln
                           1               5

CGA ATG CAC TCG GCC ACC AGC CTC TTC ATC GTC AAC CTG GCA GTT GCC       99
Arg Met His Ser Ala Thr Ser Leu Phe Ile Val Asn Leu Ala Val Ala
 10              15                  20                  25

GAC ATA ATG ATC ACG CTG CTC AAC ACC CCC TTC ACT TTG GTT CGC TTT      147
Asp Ile Met Ile Thr Leu Leu Asn Thr Pro Phe Thr Leu Val Arg Phe
                 30                  35                  40

GTG AAC AGC ACA TGG ATA TTT GGG AAG GGC ATG TGC CAT GTC AGC CGC      195
Val Asn Ser Thr Trp Ile Phe Gly Lys Gly Met Cys His Val Ser Arg
                 45                  50                  55
```

```
TTT GCC CAG TAC TGC TCA CTG CAC GTC TCA GCA CTG ACA                              234
Phe Ala Gln Tyr Cys Ser Leu His Val Ser Ala Leu Thr
         60                  65                  70
```

(2) INFORMATION FOR SEQ ID NO:317:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:317:

```
Val Cys His Val Ile Phe Lys Asn Gln Arg Met His Ser Ala Thr Ser
 1               5                  10                  15

Leu Phe Ile Val Asn Leu Ala Val Ala Asp Ile Met Ile Thr Leu Leu
             20                  25                  30

Asn Thr Pro Phe Thr Leu Val Arg Phe Val Asn Ser Thr Trp Ile Phe
             35                  40                  45

Gly Lys Gly Met Cys His Val Ser Arg Phe Ala Gln Tyr Cys Ser Leu
         50                  55                  60

His Val Ser Ala Leu Thr
 65              70
```

(2) INFORMATION FOR SEQ ID NO:318:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..240

(xi) SEQUENCE DESCRIPTION: SEQ ID NO:318:

```
GAG CCA GCT GAC CTC TTC TGG AAG AAC CTG GAC TTG CCC ACC TTC ATC    48
Glu Pro Ala Asp Leu Phe Trp Lys Asn Leu Asp Leu Pro Thr Phe Ile
 1               5                  10                  15

CTG CTC AAC ATC CTG CCC CTC CTC ATC ATC TCT GTG GCC TAC GTT CGT    96
Leu Leu Asn Ile Leu Pro Leu Leu Ile Ile Ser Val Ala Tyr Val Arg
             20                  25                  30

GTG ACC AAG AAA CTG TGG CTG TGT AAT ATG ATT GTC GAT GTG ACC ACA   144
Val Thr Lys Lys Leu Trp Leu Cys Asn Met Ile Val Asp Val Thr Thr
         35                  40                  45

GAG CAG TAC TTT GCC CTG CGG CCC AAA AAG AAG AAG ACC ATC AAG ATG   192
Glu Gln Tyr Phe Ala Leu Arg Pro Lys Lys Lys Lys Thr Ile Lys Met
     50                  55                  60

TTG ATG CTG GTG GTA GTC CTC TTT GCC CTC TGC TGG TTG CCT CTC GAC   240
Leu Met Leu Val Val Val Leu Phe Ala Leu Cys Trp Leu Pro Leu Asp
 65              70                  75                  80
```

(2) INFORMATION FOR SEQ ID NO:319:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:319:

```
Glu Pro Ala Asp Leu Phe Trp Lys Asn Leu Asp Leu Pro Thr Phe Ile
 1               5                  10                  15

Leu Leu Asn Ile Leu Pro Leu Leu Ile Ile Ser Val Ala Tyr Val Arg
            20                  25                  30

Val Thr Lys Lys Leu Trp Leu Cys Asn Met Ile Val Asp Val Thr Thr
        35                  40                  45

Glu Gln Tyr Phe Ala Leu Arg Pro Lys Lys Lys Thr Ile Lys Met
    50                  55                  60

Leu Met Leu Val Val Leu Phe Ala Leu Cys Trp Leu Pro Leu Asp
65              70                  75                  80
```

(2) INFORMATION FOR SEQ ID NO:320:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:320:

```
Val Cys His Val Ile Phe Lys Asn Gln Arg Met His Ser Ala Thr Ser
 1               5                  10                  15

Leu Phe Ile Val Asn Leu Ala Val Ala Asp Ile Met Ile Thr Leu Leu
            20                  25                  30

Asn Thr Pro Phe Thr Leu Val Arg Phe Val Asn Ser Thr Trp Ile Phe
        35                  40                  45

Gly Lys Gly Met Cys His Val Ser Arg Phe Ala Gln Tyr Cys Ser Leu
    50                  55                  60

His Val Ser Ala Leu Thr Glu Pro Ala Asp Leu Phe Trp Lys Asn Leu
65              70                  75                  80

Asp Leu Pro Thr Phe Ile Leu Leu Asn Ile Leu Pro Leu Leu Ile Ile
                85                  90                  95

Ser Val Ala Tyr Val Arg Val Thr Lys Lys Leu Trp Leu Cys Asn Met
                100                 105                 110

Thr Val Asp Val Thr Thr Glu Gln Tyr Phe Ala Leu Arg Pro Lys Lys
            115                 120                 125

Lys Lys Thr Ile Lys Met Leu Met Leu Val Val Val Leu
    130                 135                 140
```

(2) INFORMATION FOR SEQ ID NO:321:

(i) SEQUENCE CHARACTERISTICS:
        (A) LENGTH: 209 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:321:

```
Val Cys His Val Ile Phe Lys Asn Gln Arg Met His Ser Ala Thr Ser
 1               5                  10                  15

Leu Phe Ile Val Asn Leu Ala Val Ala Asp Ile Met Ile Thr Leu Leu
            20                  25                  30

Asn Thr Pro Phe Thr Leu Val Arg Phe Val Asn Ser Thr Trp Val Phe
        35                  40                  45

Gly Lys Gly Met Cys His Val Ser Arg Phe Ala Gln Tyr Cys Ser Leu
```

```
                50                    55                    60
His Val Ser Ala Leu Thr Leu Thr Ala Ile Ala Val Asp Arg His Gln
 65                  70                  75                  80

Val Ile Met His Pro Leu Lys Pro Arg Ile Ser Ile Thr Lys Gly Val
                 85                  90                  95

Ile Tyr Ile Ala Val Ile Trp Val Met Ala Thr Phe Phe Ser Leu Pro
            100                 105                 110

His Ala Ile Cys Gln Lys Leu Phe Thr Phe Lys Tyr Ser Glu Asp Ile
            115                 120                 125

Val Arg Ser Leu Cys Leu Pro Asp Phe Pro Glu Pro Ala Asp Leu Phe
        130                 135                 140

Trp Lys Tyr Leu Asp Leu Ala Thr Phe Ile Leu Leu Tyr Leu Leu Pro
145                 150                 155                 160

Leu Phe Ile Ile Ser Val Ala Tyr Ala Arg Val Ala Lys Lys Leu Trp
                165                 170                 175

Leu Cys Asn Thr Ile Gly Asp Val Thr Thr Glu Gln Tyr Leu Ala Leu
            180                 185                 190

Arg Arg Lys Lys Lys Thr Thr Val Lys Met Leu Val Leu Val Val Val
        195                 200                 205

Leu (2) INFORMATION FOR SEQ ID NO:322:

(i) SEQUENCE CHARACTERISTICS:
        (A) LENGTH: 1331 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 118..1227

(xi) SEQUENCE DESCRIPTION: SEQ ID NO:322:

CATCGTCAAG CAGATGAAGA TCATCCACGA GGATGGCTAC TCCGAGGGCC AGCAGAAATT    60

CTGCCCCTTC TTCCCGCGAG TGCTTTCCCG CTCTCCAAAC CCCACTCCCA GGTGGCC      117

ATG GCC TCA TCG ACC ACT CGG GGC CCC AGG GTT TCT GAC TTA TTT TCT    165
Met Ala Ser Ser Thr Thr Arg Gly Pro Arg Val Ser Asp Leu Phe Ser
  1               5                  10                  15

GGG CTG CCG CCG GCG GTC ACA ACT CCC GCC AAC CAG AGC GCA GAG GCC    213
Gly Leu Pro Pro Ala Val Thr Thr Pro Ala Asn Gln Ser Ala Glu Ala
                 20                  25                  30

TCG GCG GGC AAC GGG TCG GTG GCT GGC GCG GAC GCT CCA GCC GTC ACG    261
Ser Ala Gly Asn Gly Ser Val Ala Gly Ala Asp Ala Pro Ala Val Thr
             35                  40                  45

CCC TTC CAG AGC CTG CAG CTG GTG CAT CAG CTG AAG GGG CTG ATC GTG    309
Pro Phe Gln Ser Leu Gln Leu Val His Gln Leu Lys Gly Leu Ile Val
         50                  55                  60

CTG CTC TAC AGC GTC GTG GTG GTC GTG GGG CTG GTG GGC AAC TGC CTG    357
Leu Leu Tyr Ser Val Val Val Val Val Gly Leu Val Gly Asn Cys Leu
 65                  70                  75                  80

CTG GTG CTG GTG ATC GCG CGG GTG CGC CGG CTG CAC AAC GTG ACG AAC    405
Leu Val Leu Val Ile Ala Arg Val Arg Arg Leu His Asn Val Thr Asn
                 85                  90                  95

TTC CTC ATC GGC AAC CTG GCC TTG TCC GAC GTG CTC ATG TGC ACC GCC    453
Phe Leu Ile Gly Asn Leu Ala Leu Ser Asp Val Leu Met Cys Thr Ala
            100                 105                 110
```

```
TGC GTG CCG CTC ACG CTG GCC TAT GCC TTC GAG CCA CGC GGC TGG GTG      501
Cys Val Pro Leu Thr Leu Ala Tyr Ala Phe Glu Pro Arg Gly Trp Val
        115                 120                 125

TTC GGC GGC GGC CTG TGC CAC CTG GTC TTC TTC CTG CAG CCG GTC ACC      549
Phe Gly Gly Gly Leu Cys His Leu Val Phe Phe Leu Gln Pro Val Thr
    130                 135                 140

GTC TAT GTG TCG GTG TTC ACG CTC ACC ACC ATC GCA GTG GAC CGC TAC      597
Val Tyr Val Ser Val Phe Thr Leu Thr Thr Ile Ala Val Asp Arg Tyr
145                 150                 155                 160

GTC GTG CTG GTG CAC CCG CTG AGG CGG CGC ATC TCG CTG CGC CTC AGC      645
Val Val Leu Val His Pro Leu Arg Arg Arg Ile Ser Leu Arg Leu Ser
                165                 170                 175

GCC TAC GCT GTG CTG GCC ATC TGG GCG CTG TCC GCG GTG CTG GCG CTG      693
Ala Tyr Ala Val Leu Ala Ile Trp Ala Leu Ser Ala Val Leu Ala Leu
            180                 185                 190

CCC GCC GCC GTG CAC ACC TAT CAC GTG GAG CTC AAG CCG CAC GAC GTG      741
Pro Ala Ala Val His Thr Tyr His Val Glu Leu Lys Pro His Asp Val
        195                 200                 205

CGC CTC TGC GAG GAG TTC TGG GGC TCC CAG GAG CGC CAG CGC CAG CTC      789
Arg Leu Cys Glu Glu Phe Trp Gly Ser Gln Glu Arg Gln Arg Gln Leu
    210                 215                 220

TAC GCC TGG GGG CTG CTG CTG GTC ACC TAC CTG CTC CCT CTG CTG GTC      837
Tyr Ala Trp Gly Leu Leu Leu Val Thr Tyr Leu Leu Pro Leu Leu Val
225                 230                 235                 240

ATC CTC CTG TCT TAC GTC CGG GTG TCA GTG AAG CTC CGC AAC CGC GTG      885
Ile Leu Leu Ser Tyr Val Arg Val Ser Val Lys Leu Arg Asn Arg Val
                245                 250                 255

GTG CCG GGC TGC GTG ACC CAG AGC CAG GCC GAC TGG GAC CGC GCT CGG      933
Val Pro Gly Cys Val Thr Gln Ser Gln Ala Asp Trp Asp Arg Ala Arg
            260                 265                 270

CGC CGG CGC ACC TTC TGC TTG CTG GTG GTG GTC GTG GTG GTG TTC GCC      981
Arg Arg Arg Thr Phe Cys Leu Leu Val Val Val Val Val Val Phe Ala
        275                 280                 285

GTC TGC TGG CTG CCG CTG CAC GTC TTC AAC CTG CTG CGG GAC CTC GAC     1029
Val Cys Trp Leu Pro Leu His Val Phe Asn Leu Leu Arg Asp Leu Asp
    290                 295                 300

CCC CAC GCC ATC GAC CCT TAC GCC TTT GGG CTG GTG CAG CTG CTC TGC     1077
Pro His Ala Ile Asp Pro Tyr Ala Phe Gly Leu Val Gln Leu Leu Cys
305                 310                 315                 320

CAC TGG CTC GCC ATG AGT TCG GCC TGC TAC AAC CCC TTC ATC TAC GCC     1125
His Trp Leu Ala Met Ser Ser Ala Cys Tyr Asn Pro Phe Ile Tyr Ala
                325                 330                 335

TGG CTG CAC GAC AGC TTC CGC GAG GAG CTG CGC AAA CTG TTG GTC GCT     1173
Trp Leu His Asp Ser Phe Arg Glu Glu Leu Arg Lys Leu Leu Val Ala
            340                 345                 350

TGG CCC CGC AAG ATA GCC CCC CAT GGC CAG AAT ATG ACC GTC AGC GTG     1221
Trp Pro Arg Lys Ile Ala Pro His Gly Gln Asn Met Thr Val Ser Val
        355                 360                 365

GTC ATC TGATGCCACT TAGCCAGGCC TTGGTCAAGG AGCTCCACTT CAACTGGCCT      1277
Val Ile
    370

CCTAGGGCAC CACTCGAGGT CAATCTGGTG CTTATTCTCA GCACCAGAGC TAGC         1331

(2) INFORMATION FOR SEQ ID NO:323:

(i) SEQUENCE CHARACTERISTICS:
        (A) LENGTH: 370 amino acids
        (B) TYPE: amino acid
        (D) TOPOLOGY: linear
```

(ii) MOLECULE TYPE: protein (xi) SEQUENCE DESCRIPTION: SEQ ID NO:323:

| | | | | | | | | | | | | | | |
|---|---|---|---|---|---|---|---|---|---|---|---|---|---|---|
| Met | Ala | Ser | Ser | Thr | Thr | Arg | Gly | Pro | Arg | Val | Ser | Asp | Leu | Phe | Ser |
| 1 | | | | 5 | | | | | 10 | | | | | 15 | |
| Gly | Leu | Pro | Pro | Ala | Val | Thr | Thr | Pro | Ala | Asn | Gln | Ser | Ala | Glu | Ala |
| | | | 20 | | | | | 25 | | | | | 30 | | |
| Ser | Ala | Gly | Asn | Gly | Ser | Val | Ala | Gly | Ala | Asp | Ala | Pro | Ala | Val | Thr |
| | | 35 | | | | | 40 | | | | | 45 | | | |
| Pro | Phe | Gln | Ser | Leu | Gln | Leu | Val | His | Gln | Leu | Lys | Gly | Leu | Ile | Val |
| | 50 | | | | | 55 | | | | | 60 | | | | |
| Leu | Leu | Tyr | Ser | Val | Val | Val | Val | Gly | Leu | Val | Gly | Asn | Cys | Leu |
| 65 | | | | 70 | | | | | 75 | | | | | 80 |
| Leu | Val | Leu | Val | Ile | Ala | Arg | Val | Arg | Arg | Leu | His | Asn | Val | Thr | Asn |
| | | | | 85 | | | | | 90 | | | | | 95 | |
| Phe | Leu | Ile | Gly | Asn | Leu | Ala | Leu | Ser | Asp | Val | Leu | Met | Cys | Thr | Ala |
| | | | 100 | | | | | 105 | | | | | 110 | | |
| Cys | Val | Pro | Leu | Thr | Leu | Ala | Tyr | Ala | Phe | Glu | Pro | Arg | Gly | Trp | Val |
| | | 115 | | | | | 120 | | | | | 125 | | | |
| Phe | Gly | Gly | Gly | Leu | Cys | His | Leu | Val | Phe | Phe | Leu | Gln | Pro | Val | Thr |
| | 130 | | | | | 135 | | | | | 140 | | | | |
| Val | Tyr | Val | Ser | Val | Phe | Thr | Leu | Thr | Thr | Ile | Ala | Val | Asp | Arg | Tyr |
| 145 | | | | 150 | | | | | 155 | | | | | 160 |
| Val | Val | Leu | Val | His | Pro | Leu | Arg | Arg | Arg | Ile | Ser | Leu | Arg | Leu | Ser |
| | | | | 165 | | | | | 170 | | | | | 175 | |
| Ala | Tyr | Ala | Val | Leu | Ala | Ile | Trp | Ala | Leu | Ser | Ala | Val | Leu | Ala | Leu |
| | | | 180 | | | | | 185 | | | | | 190 | | |
| Pro | Ala | Ala | Val | His | Thr | Tyr | His | Val | Glu | Leu | Lys | Pro | His | Asp | Val |
| | | 195 | | | | | 200 | | | | | 205 | | | |
| Arg | Leu | Cys | Glu | Glu | Phe | Trp | Gly | Ser | Gln | Glu | Arg | Gln | Arg | Gln | Leu |
| | 210 | | | | | 215 | | | | | 220 | | | | |
| Tyr | Ala | Trp | Gly | Leu | Leu | Leu | Val | Thr | Tyr | Leu | Leu | Pro | Leu | Leu | Val |
| 225 | | | | 230 | | | | | 235 | | | | | 240 |
| Ile | Leu | Leu | Ser | Tyr | Val | Arg | Val | Ser | Val | Lys | Leu | Arg | Asn | Arg | Val |
| | | | | 245 | | | | | 250 | | | | | 255 | |
| Val | Pro | Gly | Cys | Val | Thr | Gln | Ser | Gln | Ala | Asp | Trp | Asp | Arg | Ala | Arg |
| | | | 260 | | | | | 265 | | | | | 270 | | |
| Arg | Arg | Arg | Thr | Phe | Cys | Leu | Leu | Val | Val | Val | Val | Val | Phe | Ala |
| | | 275 | | | | | 280 | | | | | 285 | | |
| Val | Cys | Trp | Leu | Pro | Leu | His | Val | Phe | Asn | Leu | Leu | Arg | Asp | Leu | Asp |
| | 290 | | | | | 295 | | | | | 300 | | | | |
| Pro | His | Ala | Ile | Asp | Pro | Tyr | Ala | Phe | Gly | Leu | Val | Gln | Leu | Leu | Cys |
| 305 | | | | 310 | | | | | 315 | | | | | 320 |
| His | Trp | Leu | Ala | Met | Ser | Ser | Ala | Cys | Tyr | Asn | Pro | Phe | Ile | Tyr | Ala |
| | | | | 325 | | | | | 330 | | | | | 335 | |
| Trp | Leu | His | Asp | Ser | Phe | Arg | Glu | Glu | Leu | Arg | Lys | Leu | Leu | Val | Ala |
| | | | 340 | | | | | 345 | | | | | 350 | | |
| Trp | Pro | Arg | Lys | Ile | Ala | Pro | His | Gly | Gln | Asn | Met | Thr | Val | Ser | Val |
| | | 355 | | | | | 360 | | | | | 365 | | | |
| Val | Ile |
| | 370 |

(2) INFORMATION FOR SEQ ID NO:324:

(i) SEQUENCE CHARACTERISTICS:
    (A) LENGTH: 396 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 1..396

(xi) SEQUENCE DESCRIPTION: SEQ ID NO:324:

```
GTG GGC CTG GTG GGC AAC ATC CTG GCT TCC TGG CAC AAG CGT GGA GGT        48
Val Gly Leu Val Gly Asn Ile Leu Ala Ser Trp His Lys Arg Gly Gly
 1               5                  10                  15

CGC CGT GCT GCT TGG GTA GTG TGT GGA GTC GTG TGG CTG GCT GTG ACA        96
Arg Arg Ala Ala Trp Val Val Cys Gly Val Val Trp Leu Ala Val Thr
                20                  25                  30

GCC CAG TGC CTG CCC ACG GCA GTC TTT GCT GCC ACA GGC ATC CAG CGC       144
Ala Gln Cys Leu Pro Thr Ala Val Phe Ala Ala Thr Gly Ile Gln Arg
         35                  40                  45

AAC CGC ACT GTG TGC TAC GAC CTG AGC CCA CCC ATC CTG TCT ACT CGC       192
Asn Arg Thr Val Cys Tyr Asp Leu Ser Pro Pro Ile Leu Ser Thr Arg
     50                  55                  60

TAC CTG CCC TAT GGT ATG GCC CTC ACG GTC ATC GGC TTC TTG CTG CCC       240
Tyr Leu Pro Tyr Gly Met Ala Leu Thr Val Ile Gly Phe Leu Leu Pro
 65                  70                  75                  80

TTC ATA GCC TTA CTG GCT TGT TAT TGT CGC ATG GCC CGC CGC CTG TGT       288
Phe Ile Ala Leu Leu Ala Cys Tyr Cys Arg Met Ala Arg Arg Leu Cys
                 85                  90                  95

CGC CAG GAT GGC CCA GCA GGT CCT GTG GCC CAA GAG CGG CGC AGC AAG       336
Arg Gln Asp Gly Pro Ala Gly Pro Val Ala Gln Glu Arg Arg Ser Lys
            100                 105                 110

GCG GCT CGT ATG GCT GTG GTG GTG GCA GCT GTC TTT GCC CTC TGC TGG       384
Ala Ala Arg Met Ala Val Val Val Ala Ala Val Phe Ala Leu Cys Trp
        115                 120                 125

CTG CCT CTC TAC                                                       396
Leu Pro Leu Tyr
    130
```

(2) INFORMATION FOR SEQ ID NO:325:

(i) SEQUENCE CHARACTERISTICS:
    (A) LENGTH: 132 amino acids
    (B) TYPE: amino acid
    (D) TOPOLOGY: linear (ii) MOLECULE TYPE: protein (xi) SEQUENCE DESCRIPTION: SEQ ID NO:325:

```
Val Gly Leu Val Gly Asn Ile Leu Ala Ser Trp His Lys Arg Gly Gly
 1               5                  10                  15

Arg Arg Ala Ala Trp Val Val Cys Gly Val Val Trp Leu Ala Val Thr
                20                  25                  30

Ala Gln Cys Leu Pro Thr Ala Val Phe Ala Ala Thr Gly Ile Gln Arg
         35                  40                  45

Asn Arg Thr Val Cys Tyr Asp Leu Ser Pro Pro Ile Leu Ser Thr Arg
     50                  55                  60

Tyr Leu Pro Tyr Gly Met Ala Leu Thr Val Ile Gly Phe Leu Leu Pro
 65                  70                  75                  80

Phe Ile Ala Leu Leu Ala Cys Tyr Cys Arg Met Ala Arg Arg Leu Cys
                 85                  90                  95
```

Arg Gln Asp Gly Pro Ala Gly Pro Val Ala Gln Glu Arg Arg Ser Lys
            100                 105                 110

Ala Ala Arg Met Ala Val Val Ala Ala Val Phe Ala Leu Cys Trp
            115                 120                 125

Leu Pro Leu Tyr
    130

(2) INFORMATION FOR SEQ ID NO:326:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:326:

Val Gly Leu Val Gly Asn Ile Leu Ala Ser Trp His Lys Arg Gly Gly
1               5                   10                  15

Arg Arg Ala Ala Trp Val Val Cys Gly Val Val Trp Leu Ala Val Thr
            20                  25                  30

Ala Gln Cys Leu Pro Thr Ala Val Phe Ala Ala Thr Gly Ile Gln Arg
            35                  40                  45

Asn Arg Thr Val Cys Tyr Asp Leu Ser Pro Pro Ile Leu Ser Thr Arg
    50                  55                  60

Tyr Leu Pro Tyr Gly Met Ala Leu Thr Val Ile Gly Phe Leu Leu Pro
65                  70                  75                  80

Phe Ile Ala Leu Leu Ala Cys Tyr Cys Arg Met Ala Arg Arg Leu Cys
                85                  90                  95

Arg Gln Asp Gly Pro Ala Gly Pro Val Ala Gln Glu Arg Arg Ser Lys
            100                 105                 110

Ala Ala Arg Met Ala Val Val Ala Ala Val Phe Ala Leu Cys Trp
            115                 120                 125

Leu Pro Leu Tyr
    130

(2) INFORMATION FOR SEQ ID NO:327:

(i) SEQUENCE CHARACTERISTICS:
        (A) LENGTH: 129 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:327:

Arg Tyr Thr Gly Val Val His Pro Leu Lys Ser Leu Gly Arg Leu Lys
1               5                   10                  15

Lys Lys Asn Ala Val Tyr Val Ser Ser Leu Val Trp Ala Leu Val Val
            20                  25                  30

Ala Val Ile Ala Pro Ile Leu Phe Tyr Ser Gly Thr Gly Val Arg Arg
            35                  40                  45

Asn Lys Thr Ile Thr Cys Tyr Asp Thr Thr Ala Asp Glu Tyr Leu Arg
    50                  55                  60

Ser Tyr Phe Val Tyr Ser Met Cys Thr Thr Val Phe Met Phe Cys Ile
65                  70                  75                  80

Pro Phe Ile Val Ile Leu Gly Cys Tyr Gly Leu Ile Val Lys Ala Leu

```
                          85                  90                  95
Ile Tyr Lys Asp Leu Asp Asn Ser Pro Leu Arg Arg Lys Ser Ile Tyr
            100                 105                 110
Leu Val Ile Ile Val Leu Thr Val Phe Ala Val Ser Tyr Leu Pro Phe
        115                 120                 125
His (2) INFORMATION FOR SEQ ID NO:328:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:328:

Arg Tyr Leu Ala Val Val His Pro Thr Arg Ser Ala Arg Trp Arg Thr
1               5                   10                  15
Ala Pro Val Ala Arg Thr Val Ser Ala Ala Val Trp Val Ala Ser Ala
            20                  25                  30
Val Val Val Leu Pro Val Val Phe Ser Gly Val Pro Arg Gly Met
        35                  40                  45
Ser Thr Cys His Met Gln Trp Pro Glu Pro Ala Ala Ala Trp Arg Ala
    50                  55                  60
Gly Phe Ile Ile Tyr Thr Ala Ala Leu Gly Phe Phe Gly Pro Leu Leu
65                  70                  75                  80
Val Ile Cys Leu Cys Tyr Leu Leu Ile Val Lys Val Arg Ser Ala
            85                  90                  95
Gly Arg Arg Val Trp Ala Pro Ser Cys Gln Arg Arg Arg Ser Glu
            100                 105                 110
Arg Arg Val Thr Arg Val Val Ala Val Ala Leu Phe Val Leu
        115                 120                 125
Cys Trp Met Pro Phe Tyr
        130

(2) INFORMATION FOR SEQ ID NO:329:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:329:

Arg Tyr Val Ala Val Val His Pro Leu Arg Ala Ala Thr Tyr Arg Arg
1               5                   10                  15
Pro Ser Val Ala Lys Leu Ile Asn Leu Gly Val Trp Leu Ala Ser Leu
            20                  25                  30
Leu Val Thr Leu Pro Ile Ala Ile Phe Ala Asp Thr Arg Pro Ala Arg
        35                  40                  45
Gly Gly Gln Ala Val Ala Cys Asn Leu Gln Trp Pro His Pro Ala Trp
    50                  55                  60
Ser Ala Val Phe Val Val Tyr Thr Phe Leu Leu Gly Phe Leu Leu Pro
65                  70                  75                  80
Val Leu Ala Ile Gly Leu Cys Tyr Leu Leu Ile Val Gly Lys Met Arg
```

-continued

```
                    85                  90                  95
Ala Val Ala Leu Arg Ala Gly Trp Gln Gln Arg Arg Ser Glu Lys
                   100                 105                 110
Lys Ile Thr Arg Leu Val Leu Met Val Val Val Phe Val Leu Cys
               115                 120                 125
Trp Met Pro Phe Tyr
        130
```

(2) INFORMATION FOR SEQ ID NO:330:

(i) SEQUENCE CHARACTERISTICS:
        (A) LENGTH: 123 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:330:

```
Arg Tyr Leu Ala Ile Val His Ala Thr Asn Ser Gln Lys Pro Arg Lys
  1               5                  10                  15
Leu Leu Ala Glu Lys Val Val Tyr Val Gly Val Trp Leu Pro Ala Val
                 20                  25                  30
Leu Leu Thr Ile Pro Asp Leu Ile Phe Ala Asp Ile Lys Glu Val Asp
             35                  40                  45
Glu Arg Tyr Ile Cys Asp Arg Phe Tyr Pro Ser Asp Leu Trp Leu Val
 50                  55                  60
Val Phe Gln Phe Gln His Ile Val Val Gly Leu Leu Leu Pro Gly Ile
 65                  70                  75                  80
Val Ile Leu Ser Cys Tyr Cys Ile Ile Ile Ser Lys Leu Ser His Ser
                 85                  90                  95
Lys Gly Tyr Gln Lys Arg Lys Ala Leu Lys Thr Thr Val Ile Leu Ile
                100                 105                 110
Leu Thr Phe Phe Ala Cys Trp Leu Pro Tyr Tyr
             115                 120
```

(2) INFORMATION FOR SEQ ID NO:331:

(i) SEQUENCE CHARACTERISTICS:
        (A) LENGTH: 435 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..435

(xi) SEQUENCE DESCRIPTION: SEQ ID NO:331:

```
GTG GGC CTG GTG GGC AAC TTC CTG GCC GCG ATG TCT GTG GAT CGC TAC      48
Val Gly Leu Val Gly Asn Phe Leu Ala Ala Met Ser Val Asp Arg Tyr
  1               5                  10                  15

GTG GCC ATT GTG CAC TCG CGG CGC TCC TCC TCC CTC AGG GTG TCC CGC      96
Val Ala Ile Val His Ser Arg Arg Ser Ser Ser Leu Arg Val Ser Arg
                 20                  25                  30

AAC GCA CTG CTG GGC GTG GGC TTC ATC TGG GCG CTG TCC ATC GCC ATG     144
Asn Ala Leu Leu Gly Val Gly Phe Ile Trp Ala Leu Ser Ile Ala Met
             35                  40                  45

GCC TCG CCG GTG GCC TAC CAC CAG CGT CTT TTC CAT CGG GAC AGC AAC     192
Ala Ser Pro Val Ala Tyr His Gln Arg Leu Phe His Arg Asp Ser Asn
```

```
                50                      55                      60
CAG ACC TTC TGC TGG GAG CAG TGG CCC AAC AAG CTC CAC AAG AAG GCT        240
Gln Thr Phe Cys Trp Glu Gln Trp Pro Asn Lys Leu His Lys Lys Ala
 65                  70                      75                  80

TAC GTG GTG TGC ACT TTC GTC TTT GGG TAC CTT CTG CCC TTA CTG CTC        288
Tyr Val Val Cys Thr Phe Val Phe Gly Tyr Leu Leu Pro Leu Leu Leu
                         85                      90                  95

ATC TGC TTT TGC TAT GCC AAG GTC CTT AAT CAT CTG CAT AAA AAG CTG        336
Ile Cys Phe Cys Tyr Ala Lys Val Leu Asn His Leu His Lys Lys Leu
                    100                     105                 110

AAA AAC ATG TCA AAA AAG TCT GAA GCA TCC AAG AAA AAG ACT GCA CAG        384
Lys Asn Met Ser Lys Lys Ser Glu Ala Ser Lys Lys Lys Thr Ala Gln
            115                     120                 125

ACC GTC CTG GTG GTC GTT GTA GTA TTT GCC CTC TGC TGG CTG CCT TTC        432
Thr Val Leu Val Val Val Val Val Phe Ala Leu Cys Trp Leu Pro Phe
    130                     135                 140

TAC                                                                    435
Tyr
145

(2) INFORMATION FOR SEQ ID NO:332:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:332:

Val Gly Leu Val Gly Asn Phe Leu Ala Ala Met Ser Val Asp Arg Tyr
 1               5                  10                  15

Val Ala Ile Val His Ser Arg Ser Ser Ser Leu Arg Val Ser Arg
            20                  25                  30

Asn Ala Leu Leu Gly Val Gly Phe Ile Trp Ala Leu Ser Ile Ala Met
            35                  40                  45

Ala Ser Pro Val Ala Tyr His Gln Arg Leu Phe His Arg Asp Ser Asn
 50                  55                      60

Gln Thr Phe Cys Trp Glu Gln Trp Pro Asn Lys Leu His Lys Lys Ala
 65                  70                      75                  80

Tyr Val Val Cys Thr Phe Val Phe Gly Tyr Leu Leu Pro Leu Leu Leu
                    85                      90                  95

Ile Cys Phe Cys Tyr Ala Lys Val Leu Asn His Leu His Lys Lys Leu
                100                     105                 110

Lys Asn Met Ser Lys Lys Ser Glu Ala Ser Lys Lys Lys Thr Ala Gln
            115                     120                 125

Thr Val Leu Val Val Val Val Val Phe Ala Leu Cys Trp Leu Pro Phe
    130                     135                 140

Tyr
145

(2) INFORMATION FOR SEQ ID NO:333:

(i) SEQUENCE CHARACTERISTICS:
        (A) LENGTH: 145 amino acids
        (B) TYPE: amino acid
        (C) STRANDEDNESS:
        (D) TOPOLOGY: linear (ii) MOLECULE TYPE: peptide
```

(xi) SEQUENCE DESCRIPTION: SEQ ID NO:333:

```
Val Gly Leu Val Gly Asn Phe Leu Ala Ala Met Ser Val Asp Arg Tyr
1               5                   10                  15

Val Ala Ile Val His Ser Arg Arg Ser Ser Leu Arg Val Ser Arg
            20                  25                  30

Asn Ala Leu Leu Gly Val Gly Phe Ile Trp Ala Leu Ser Ile Ala Met
            35                  40                  45

Ala Ser Pro Val Ala Tyr His Gln Arg Leu Phe His Arg Asp Ser Asn
        50                  55                  60

Gln Thr Phe Cys Trp Glu Gln Trp Pro Asn Lys Leu His Lys Lys Ala
65              70                  75                  80

Tyr Val Val Cys Thr Phe Val Phe Gly Tyr Leu Leu Pro Leu Leu Leu
                85                  90                  95

Ile Cys Phe Cys Tyr Ala Lys Val Leu Asn His Leu His Lys Lys Leu
            100                 105                 110

Lys Asn Met Ser Lys Lys Ser Glu Ala Ser Lys Lys Lys Thr Ala Gln
            115                 120                 125

Thr Val Leu Val Val Val Val Phe Ala Leu Cys Trp Leu Pro Phe
    130                 135                 140

Tyr
145
```

(2) INFORMATION FOR SEQ ID NO:334:

(i) SEQUENCE CHARACTERISTICS:
        (A) LENGTH: 147 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:334:

```
Met Phe Thr Ser Val Phe Cys Leu Thr Val Leu Ser Val Asp Arg Tyr
1               5                   10                  15

Val Ala Val Val His Pro Leu Arg Ala Ala Thr Tyr Arg Arg Pro Ser
            20                  25                  30

Val Ala Lys Leu Ile Asn Leu Gly Val Trp Leu Ala Ser Leu Leu Val
            35                  40                  45

Thr Leu Pro Ile Ala Ile Phe Ala Asp Thr Arg Pro Ala Arg Gly Gly
        50                  55                  60

Gln Ala Val Ala Cys Asn Leu Gln Trp Pro His Pro Ala Trp Ser Ala
65              70                  75                  80

Val Phe Val Val Tyr Thr Phe Leu Leu Gly Phe Leu Leu Pro Val Leu
                85                  90                  95

Ala Ile Gly Leu Cys Tyr Leu Leu Ile Val Gly Lys Met Arg Ala Val
            100                 105                 110

Ala Leu Arg Ala Gly Trp Gln Gln Arg Arg Arg Ser Glu Lys Lys Ile
            115                 120                 125

Thr Arg Leu Val Leu Met Val Val Val Phe Val Leu Cys Trp Met
    130                 135                 140

Pro Phe Tyr
145
```

(2) INFORMATION FOR SEQ ID NO:335:

(i) SEQUENCE CHARACTERISTICS:

(A) LENGTH: 148 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:335:

Gln Phe Thr Ser Ile Phe Cys Leu Thr Val Met Ser Ile Asp Arg Tyr
1               5                   10                  15

Leu Ala Val Val His Pro Ile Lys Ser Ala Lys Trp Arg Arg Pro Arg
            20                  25                  30

Thr Ala Lys Met Ile Thr Met Ala Val Trp Gly Val Ser Leu Leu Val
            35                  40                  45

Ile Leu Pro Ile Met Ile Tyr Ala Gly Leu Arg Ser Asn Gln Trp Gly
        50                  55                  60

Arg Ser Ser Cys Thr Ile Asn Trp Pro Gly Glu Ser Gly Ala Trp Tyr
65                  70                  75                  80

Thr Gly Phe Ile Ile Tyr Thr Phe Ile Leu Gly Phe Leu Val Pro Leu
                85                  90                  95

Thr Ile Ile Cys Leu Cys Tyr Leu Phe Ile Ile Lys Val Lys Ser
            100                 105                 110

Ser Gly Ile Arg Val Gly Ser Ser Lys Arg Lys Lys Ser Glu Lys Lys
            115                 120                 125

Val Thr Arg Met Val Ser Ile Val Val Ala Val Phe Ile Phe Cys Trp
    130                 135                 140

Leu Pro Phe Tyr
145

(2) INFORMATION FOR SEQ ID NO:336:

(i) SEQUENCE CHARACTERISTICS:
        (A) LENGTH: 148 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:336:

Met Phe Thr Ser Ile Tyr Cys Leu Thr Val Leu Ser Val Asp Arg Tyr
1               5                   10                  15

Val Ala Val Val His Pro Ile Lys Ala Ala Arg Tyr Arg Arg Pro Thr
            20                  25                  30

Val Ala Lys Val Val Asn Leu Gly Val Trp Val Leu Ser Leu Leu Val
            35                  40                  45

Ile Leu Pro Ile Val Val Phe Ser Arg Thr Ala Ala Asn Ser Asp Gly
        50                  55                  60

Thr Val Ala Cys Asn Met Leu Met Pro Glu Pro Ala Gln Arg Trp Leu
65                  70                  75                  80

Val Gly Phe Val Leu Tyr Thr Phe Leu Met Gly Phe Leu Leu Pro Val
                85                  90                  95

Gly Ala Ile Cys Leu Cys Tyr Val Leu Ile Ile Ala Lys Met Arg Met
            100                 105                 110

Val Ala Leu Lys Ala Gly Trp Gln Gln Arg Lys Arg Ser Glu Arg Lys
            115                 120                 125

Ile Thr Leu Met Val Met Met Val Val Met Val Phe Val Ile Cys Trp
    130                 135                 140

```
Met Pro Phe Tyr
145
```

(2) INFORMATION FOR SEQ ID NO:337:

(i) SEQUENCE CHARACTERISTICS:
        (A) LENGTH: 265 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..264

(xi) SEQUENCE DESCRIPTION: SEQ ID NO:337:

```
GTG GGC ATG GTG GGC AAC GTG CTG GTG CTC TGG TTC TTC GGC TTC TCC      48
Val Gly Met Val Gly Asn Val Leu Val Leu Trp Phe Phe Gly Phe Ser
 1               5                  10                  15

ATC AAG AGG ACC CCC TTC TCC GTC TAC TTC CTG CAC CTG GCC AGC GCC      96
Ile Lys Arg Thr Pro Phe Ser Val Tyr Phe Leu His Leu Ala Ser Ala
             20                  25                  30

GAC GGC GCC TAC CTC TTC AGC AAG GCC GTG TTC TCC CTG CTG AAC GCC     144
Asp Gly Ala Tyr Leu Phe Ser Lys Ala Val Phe Ser Leu Leu Asn Ala
         35                  40                  45

GGC GGC TTC CTG GGC ACC TTC GCC CAC TAT GTG CGC AGC GTG GCC CGG     192
Gly Gly Phe Leu Gly Thr Phe Ala His Tyr Val Arg Ser Val Ala Arg
     50                  55                  60

GTG CTG GGG CTC TGC GCC TTC GTG GCG GGC GTG AGC CTC CTG CCG GCC     240
Val Leu Gly Leu Cys Ala Phe Val Ala Gly Val Ser Leu Leu Pro Ala
 65                  70                  75                  80

GTG AGC ATG GAG CGC TGC GCG TCT G                                    265
Val Ser Met Glu Arg Cys Ala Ser
                 85
```

(2) INFORMATION FOR SEQ ID NO:338:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO:338:

```
Val Gly Met Val Gly Asn Val Leu Val Leu Trp Phe Phe Gly Phe Ser
 1               5                  10                  15

Ile Lys Arg Thr Pro Phe Ser Val Tyr Phe Leu His Leu Ala Ser Ala
             20                  25                  30

Asp Gly Ala Tyr Leu Phe Ser Lys Ala Val Phe Ser Leu Leu Asn Ala
         35                  40                  45

Gly Gly Phe Leu Gly Thr Phe Ala His Tyr Val Arg Ser Val Ala Arg
     50                  55                  60

Val Leu Gly Leu Cys Ala Phe Val Ala Gly Val Ser Leu Leu Pro Ala
 65                  70                  75                  80

Val Ser Met Glu Arg Cys Ala Ser
                 85
```

(2) INFORMATION FOR SEQ ID NO:339:

(i) SEQUENCE CHARACTERISTICS:
        (A) LENGTH: 88 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:339:

Val Gly Met Val Gly Asn Val Leu Val Leu Trp Phe Phe Gly Phe Ser
1               5                   10                  15

Ile Lys Arg Thr Pro Phe Ser Val Tyr Phe Leu His Leu Ala Ser Ala
            20                  25                  30

Asp Gly Ala Tyr Leu Phe Ser Lys Ala Val Phe Ser Leu Leu Asn Ala
        35                  40                  45

Gly Gly Phe Leu Gly Thr Phe Ala His Tyr Val Arg Ser Val Ala Arg
    50                  55                  60

Val Leu Gly Leu Cys Ala Phe Val Ala Gly Val Ser Leu Leu Pro Ala
65                  70                  75                  80

Val Ser Met Glu Arg Cys Ala Ser
                85

(2) INFORMATION FOR SEQ ID NO:340:

(i) SEQUENCE CHARACTERISTICS:
        (A) LENGTH: 88 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:340:

Cys Gly Leu Val Gly Asn Gly Leu Val Leu Trp Phe Phe Gly Phe Ser
1               5                   10                  15

Ile Lys Arg Thr Pro Phe Ser Ile Tyr Phe Leu His Leu Ala Ser Ala
            20                  25                  30

Asp Gly Ile Tyr Leu Phe Ser Lys Ala Val Ile Ala Leu Leu Asn Met
        35                  40                  45

Gly Thr Phe Leu Gly Ser Phe Pro Asp Tyr Val Arg Arg Val Ser Arg
    50                  55                  60

Ile Val Gly Leu Cys Thr Phe Phe Ala Gly Val Ser Leu Leu Pro Ala
65                  70                  75                  80

Ile Ser Ile Glu Arg Cys Val Ser
                85

(2) INFORMATION FOR SEQ ID NO:341:

(i) SEQUENCE CHARACTERISTICS:
        (A) LENGTH: 1607 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 481..1524

(xi) SEQUENCE DESCRIPTION: SEQ ID NO:341:

CAAAGCAACA GGTGCAACCT CAAGGCACTG AAAGCAAGGG GACGCAGCTC ACAAGGGCCA       60

AGGGATTGAA CCCATAACCG CTCAGAAGAT TCTCCGCCTG CCGAGAGCTG CGGAGGAGTC      120

CCACCCGTCC AGCTTGCTGA CTGCGAGCAG TGAGAGTCGC CTAGACCCGT ACCTCTGTGT      180

```
TCTGGAGCCT GCCGCCCCG CACGGGAAAG GCTTAGCTCG GACTTGCAG CACCGCCTCC        240

TCTTTAGCCA GGCCAGGCAC GAGGATAGTG TGATCGGGCA CAGCCAGGGT CGCTCTTCCA        300

GGCTTTCTTG CGGGTTGCGG GAGGTACTAG TTGGAGACGC GCGCGCTCGC TCTCGCCGCT        360

CTGTCCTGGG CCACTCCGTG ATCCTAAGGC TACCTCCAGA GCCAGTTTTC CCTGGCTGGC        420

ACAACTCTCC AGGGCGCTCC GGTCCGTTGC ACAGCGCCCC AAGGGGGTAC CCAGTAAGTG        480

ATG GAA CTG GCT ATG GTG AAC CTC AGT GAA GGG AAT GGG AGC GAC CCA         528
Met Glu Leu Ala Met Val Asn Leu Ser Glu Gly Asn Gly Ser Asp Pro
  1               5                  10                  15

GAG CCG CCA GCC CCG GAG TCC AGG CCG CTC TTC GGC ATT GGC GTG GAG         576
Glu Pro Pro Ala Pro Glu Ser Arg Pro Leu Phe Gly Ile Gly Val Glu
                 20                  25                  30

AAC TTC ATT ACG CTG GTA GTG TTT GGC CTG ATT TTC GCG ATG GGC GTG         624
Asn Phe Ile Thr Leu Val Val Phe Gly Leu Ile Phe Ala Met Gly Val
             35                  40                  45

CTG GGC AAC AGC CTG GTG ATC ACC GTG CTG GCG CGC AGC AAA CCA GGC         672
Leu Gly Asn Ser Leu Val Ile Thr Val Leu Ala Arg Ser Lys Pro Gly
 50                  55                  60

AAC CCC CGC AGC ACC ACC AAC CTG TTT ATC CTC AAT CTG AGC ATC GCA         720
Asn Pro Arg Ser Thr Thr Asn Leu Phe Ile Leu Asn Leu Ser Ile Ala
 65                  70                  75                  80

GAC CTG GCC TAC CTG CTC TTC TGC ATC CCT TTT CAG GCC ACC GTG TAT         768
Asp Leu Ala Tyr Leu Leu Phe Cys Ile Pro Phe Gln Ala Thr Val Tyr
                 85                  90                  95

GCA CTG CCC ACC TGG GTG CTG GGC GCC TTC ATC TGC AAG TTT ATA CAC         816
Ala Leu Pro Thr Trp Val Leu Gly Ala Phe Ile Cys Lys Phe Ile His
                100                 105                 110

TAC TTC TTC ACC GTG TCC ATG CTG GTG AGC ATC TTC ACC CTG GCC GCG         864
Tyr Phe Phe Thr Val Ser Met Leu Val Ser Ile Phe Thr Leu Ala Ala
            115                 120                 125

ATG TCT GTG GAT CGC TAC GTG GCC ATT GTG CAC TCG CGG CGC TCC TCC         912
Met Ser Val Asp Arg Tyr Val Ala Ile Val His Ser Arg Arg Ser Ser
130                 135                 140

TCC CTC AGG GTG TCC CGC AAC GCA CTG CTG GGC GTG GGC TTC ATC TGG         960
Ser Leu Arg Val Ser Arg Asn Ala Leu Leu Gly Val Gly Phe Ile Trp
145                 150                 155                 160

GCG CTG TCC ATC GCC ATG GCC TCG CCG GTG GCC TAC CAC CAG CGT CTT        1008
Ala Leu Ser Ile Ala Met Ala Ser Pro Val Ala Tyr His Gln Arg Leu
                165                 170                 175

TTC CAT CGG GAC AGC AAC CAG ACC TTC TGC TGG GAG CAG TGG CCC AAC        1056
Phe His Arg Asp Ser Asn Gln Thr Phe Cys Trp Glu Gln Trp Pro Asn
                180                 185                 190

AAG CTC CAC AAG AAG GCT TAC GTG GTG TGC ACT TTC GTC TTT GGG TAC        1104
Lys Leu His Lys Lys Ala Tyr Val Val Cys Thr Phe Val Phe Gly Tyr
            195                 200                 205

CTT CTG CCC TTA CTG CTC ATC TGC TTT TGC TAT GCC AAG GTC CTT AAT        1152
Leu Leu Pro Leu Leu Leu Ile Cys Phe Cys Tyr Ala Lys Val Leu Asn
210                 215                 220

CAT CTG CAT AAA AAG CTG AAA AAC ATG TCA AAA AAG TCT GAA GCA TCC        1200
His Leu His Lys Lys Leu Lys Asn Met Ser Lys Lys Ser Glu Ala Ser
225                 230                 235                 240

AAG AAA AAG ACT GCA CAG ACC GTC CTG GTG GTC GTT GTA GTA TTT GGC        1248
Lys Lys Lys Thr Ala Gln Thr Val Leu Val Val Val Val Val Phe Gly
                245                 250                 255

ATA TCC TGG CTG CCC CAT CAT GTC GTC CAC CTC TGG GCT GAG TTT GGA        1296
Ile Ser Trp Leu Pro His His Val Val His Leu Trp Ala Glu Phe Gly
                260                 265                 270
```

```
GCC TTC CCA CTG ACG CCA GCT TCC TTC TTC TTC AGA ATC ACC GCC CAT      1344
Ala Phe Pro Leu Thr Pro Ala Ser Phe Phe Phe Arg Ile Thr Ala His
        275                 280                 285

TGC CTG GCA TAC AGC AAC TCC TCA GTG AAC CCC ATC ATA TAT GCC TTT      1392
Cys Leu Ala Tyr Ser Asn Ser Ser Val Asn Pro Ile Ile Tyr Ala Phe
    290                 295                 300

CTC TCA GAA AAC TTC CGG AAG GCG TAC AAG CAA GTG TTC AAG TGT CAT      1440
Leu Ser Glu Asn Phe Arg Lys Ala Tyr Lys Gln Val Phe Lys Cys His
305                 310                 315                 320

GTT TGC GAT GAA TCT CCA CGC AGT GAA ACT AAG GAA AAC AAG AGC CGG      1488
Val Cys Asp Glu Ser Pro Arg Ser Glu Thr Lys Glu Asn Lys Ser Arg
                325                 330                 335

ATG GAC ACC CCG CCA TCC ACC AAC TGC ACC CAC GTG TGAAGGTTTG           1534
Met Asp Thr Pro Pro Ser Thr Asn Cys Thr His Val
                340                 345

CGGGAGCCTC CCGACTTCCA GCTCCCATGT GTGTTAGAGA GAGGAGGGCG GAGCGAATTA    1594

TCAAGTAACA TGG                                                       1607

(2) INFORMATION FOR SEQ ID NO:342:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:342:

Met Glu Leu Ala Met Val Asn Leu Ser Glu Gly Asn Gly Ser Asp Pro
1               5                   10                  15

Glu Pro Pro Ala Pro Glu Ser Arg Pro Leu Phe Gly Ile Gly Val Glu
            20                  25                  30

Asn Phe Ile Thr Leu Val Val Phe Gly Leu Ile Phe Ala Met Gly Val
        35                  40                  45

Leu Gly Asn Ser Leu Val Ile Thr Val Leu Ala Arg Ser Lys Pro Gly
    50                  55                  60

Asn Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Phe Ile Trp
145                 150                 155                 160

Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
            180                 185                 190

Lys Leu His Lys Lys Ala Tyr Val Val Cys Thr Phe Val Phe Gly Tyr
        195                 200                 205

Leu Leu Pro Leu Leu Leu Ile Cys Phe Cys Tyr Ala Lys Val Leu Asn
    210                 215                 220

His Leu His Lys Lys Leu Lys Asn Met Ser Lys Lys Ser Glu Ala Ser
```

| | | 225 | | | 230 | | | 235 | | | 240 |

Lys Lys Lys Thr Ala Gln Thr Val Leu Val Val Val Phe Gly
                245                 250                 255

Ile Ser Trp Leu Pro His His Val Val His Leu Trp Ala Glu Phe Gly
                260                 265                 270

Ala Phe Pro Leu Thr Pro Ala Ser Phe Phe Arg Ile Thr Ala His
                275                 280                 285

Cys Leu Ala Tyr Ser Asn Ser Ser Val Asn Pro Ile Ile Tyr Ala Phe
                290                 295                 300

Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
                325                 330                 335

Met Asp Thr Pro Pro Ser Thr Asn Cys Thr His Val
                340                 345

(2) INFORMATION FOR SEQ ID NO:343:

(i) SEQUENCE CHARACTERISTICS:
        (A) LENGTH: 349 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:343:

Met Glu Leu Ala Met Val Asn Leu Ser Glu Gly Asn Gly Ser Asp Pro
1               5                   10                  15

Glu Pro Pro Ala Pro Glu Ser Arg Pro Leu Phe Gly Ile Gly Val Glu
                20                  25                  30

Asn Phe Ile Thr Leu Val Val Phe Gly Leu Ile Phe Ala Met Gly Val
                35                  40                  45

Leu Gly Asn Ser Leu Val Ile Thr Val Leu Ala Arg Ser Lys Pro Gly
50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Thr Pro Trp Val Leu Gly Ala Phe Ile Cys Lys Phe Ile His
                100                 105                 110

Tyr Phe Phe Thr Val Ser Met Leu Val Ser Ile Phe Thr Leu Ala Ala
                115                 120                 125

Met Ser Val Asp Arg Tyr Val Ala Ile Val His Ser Arg Arg Ser Ser
                130                 135                 140

Ser Leu Arg Val Ser Arg Asn Ala Leu Leu Gly Val Gly Phe Ile Trp
145                 150                 155                 160

Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
                180                 185                 190

Lys Leu His Lys Lys Ala Tyr Val Val Cys Thr Phe Val Phe Gly Tyr
                195                 200                 205

Leu Leu Pro Leu Leu Leu Ile Cys Phe Cys Tyr Ala Lys Val Leu Asn
                210                 215                 220

His Leu His Lys Lys Leu Lys Asn Met Ser Lys Lys Ser Glu Ala Ser

```
225                 230                 235                 240

Lys Lys Lys Thr Ala Gln Thr Val Leu Val Val Val Phe Gly
            245                 250                 255

Ile Ser Trp Leu Pro His His Val Val His Leu Trp Ala Glu Phe Gly
            260                 265                 270

Ala Phe Pro Leu Thr Pro Ala Ser Phe Phe Arg Ile Thr Ala His
            275                 280                 285

Cys Leu Ala Tyr Ser Asn Ser Ser Val Asn Pro Ile Ile Tyr Ala Phe
290                 295                 300

Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
            325                 330                 335

Met Asp Thr Pro Pro Ser Thr Asn Cys Thr His Val Xaa
            340                 345
```

(2) INFORMATION FOR SEQ ID NO:344:

(i) SEQUENCE CHARACTERISTICS:
        (A) LENGTH: 351 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:344:

```
Met Glu Leu Ala Val Gly Asn Leu Ser Glu Gly Asn Ala Ser Cys Pro
1               5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
            35                  40                  45

Leu Gly Asn Ser Leu Val Ile Thr Val Leu Ala Arg Ser Lys Pro Gly
50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
            85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
            115                 120                 125

Met Ser Val Asp Arg Tyr Val Ala Ile Val His Ser Arg Arg Ser Ser
            130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
            165                 170                 175

Phe His Pro Arg Ala Ser Asn Gln Thr Phe Cys Trp Glu Gln Trp Pro
            180                 185                 190

Asp Pro Arg His His Lys Lys Ala Tyr Val Val Cys Thr Phe Val Phe Gly
            195                 200                 205

Tyr Leu Leu Pro Leu Leu Leu Ile Cys Phe Cys Tyr Ala Lys Val Leu
            210                 215                 220

Asn His Leu His Lys Lys Leu Lys Asn Met Ser Lys Lys Ser Glu Ala
```

```
                        225                 230                 235                 240
   Ser Lys Lys Lys Thr Ala Gln Thr Val Leu Val Val Val Val Phe
                        245                 250                 255

Gly Ile Ser Trp Leu Pro His His Ile Ile His Leu Trp Ala Glu Phe
                    260                 265                 270

Gly Val Phe Pro Leu Thr Pro Ala Ser Phe Leu Phe Arg Ile Thr Ala
                    275                 280                 285

His Cys Leu Ala Tyr Ser Asn Ser Ser Val Asn Pro Ile Ile Tyr Ala
                290                 295                 300

Phe Leu Ser Glu Asn Phe Arg Lys Ala Tyr Lys Gln Val Phe Lys Cys
   305                 310                 315                 320

His Ile Arg Lys Asp Ser His Leu Ser Asp Thr Lys Glu Asn Lys Ser
                    325                 330                 335

Arg Ile Asp Thr Pro Pro Ser Thr Asn Cys Thr His Val Xaa Xaa
                340                 345                 350

(2) INFORMATION FOR SEQ ID NO:345:

(i) SEQUENCE CHARACTERISTICS:
         (A) LENGTH: 434 base pairs
         (B) TYPE: nucleic acid
         (C) STRANDEDNESS: double
         (D) TOPOLOGY: linear (ii) MOLECULE TYPE: cDNA (ix) FEATURE:
         (A) NAME/KEY: CDS
         (B) LOCATION: 28..402

(xi) SEQUENCE DESCRIPTION: SEQ ID NO:345:

CTCGCGGCTC TGGGTATGGA TCGGTAT CTT CTC ACC CTT CAC CCA GTG TGG           51
                              Leu Leu Thr Leu His Pro Val Trp
                                1               5

TCC CAA AAG CAC CGA ACC TCA CAC TGG GCT TCC AGA GTC GTT CTG GGA         99
Ser Gln Lys His Arg Thr Ser His Trp Ala Ser Arg Val Val Leu Gly
     10                  15                  20

GTC TGG CTC TCT GCC ACT GCC TTC AGC GTG CCC TAT TTG GTT TTC AGG        147
Val Trp Leu Ser Ala Thr Ala Phe Ser Val Pro Tyr Leu Val Phe Arg
 25                  30                  35                  40

GAG ACA TAT GAT GAC CGT AAA GGA AGA GTG ACC TGC AGA AAT AAC TAC        195
Glu Thr Tyr Asp Asp Arg Lys Gly Arg Val Thr Cys Arg Asn Asn Tyr
                 45                  50                  55

GCT GTG TCC ACT GAC TGG GAA AGC AAA GAG ATG CAA ACA GTA AGA CAA        243
Ala Val Ser Thr Asp Trp Glu Ser Lys Glu Met Gln Thr Val Arg Gln
             60                  65                  70

TGG ATT CAT GCC ACC TGT TTC ATC AGC CGC TTC ATA CTG GGC TTC CTT        291
Trp Ile His Ala Thr Cys Phe Ile Ser Arg Phe Ile Leu Gly Phe Leu
         75                  80                  85

CTG CCT TTC TTA GTC ATT GGC TTT TGT TAT GAA AGA GTA GCC CGC AAG        339
Leu Pro Phe Leu Val Ile Gly Phe Cys Tyr Glu Arg Val Ala Arg Lys
     90                  95                 100

ATG AAA GAG AGG GGC CTC TTT AAA TCC AGC AAA CCC TTC AAA GTC ACG        387
Met Lys Glu Arg Gly Leu Phe Lys Ser Ser Lys Pro Phe Lys Val Thr
105                 110                 115                 120

ATG ACT GCT GTT ATC TCTTTTTTCT GTCCTGGCTT CCCTACCACA TG                434
Met Thr Ala Val Ile
                125

(2) INFORMATION FOR SEQ ID NO:346:
```

(i) SEQUENCE CHARACTERISTICS:
    (A) LENGTH: 125 amino acids
    (B) TYPE: amino acid
    (D) TOPOLOGY: linear (ii) MOLECULE TYPE: protein (xi) SEQUENCE DESCRIPTION: SEQ ID NO:346:

Leu Leu Thr Leu His Pro Val Trp Ser Gln Lys His Arg Thr Ser His
 1               5                  10                  15

Trp Ala Ser Arg Val Val Leu Gly Val Trp Leu Ser Ala Thr Ala Phe
            20                  25                  30

Ser Val Pro Tyr Leu Val Phe Arg Glu Thr Tyr Asp Asp Arg Lys Gly
        35                  40                  45

Arg Val Thr Cys Arg Asn Asn Tyr Ala Val Ser Thr Asp Trp Glu Ser
    50                  55                  60

Lys Glu Met Gln Thr Val Arg Gln Trp Ile His Ala Thr Cys Phe Ile
65                  70                  75                  80

Ser Arg Phe Ile Leu Gly Phe Leu Leu Pro Phe Leu Val Ile Gly Phe
                85                  90                  95

Cys Tyr Glu Arg Val Ala Arg Lys Met Lys Glu Arg Gly Leu Phe Lys
            100                 105                 110

Ser Ser Lys Pro Phe Lys Val Thr Met Thr Ala Val Ile
            115                 120                 125

(2) INFORMATION FOR SEQ ID NO:347:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:347:

Leu Leu Thr Leu His Pro Val Trp Ser Gln Lys His Arg Thr Ser His
 1               5                  10                  15

Trp Ala Ser Arg Val Val Leu Gly Val Trp Leu Ser Ala Thr Ala Phe
            20                  25                  30

Ser Val Pro Tyr Leu Val Phe Arg Glu Thr Tyr Asp Asp Arg Lys Gly
        35                  40                  45

Arg Val Thr Cys Arg Asn Asn Tyr Ala Val Ser Thr Asp Trp Glu Ser
    50                  55                  60

Lys Glu Met Gln Thr Val Arg Gln Trp Ile His Ala Thr Cys Phe Ile
65                  70                  75                  80

Ser Arg Phe Ile Leu Gly Phe Leu Leu Pro Phe Leu Val Ile Gly Phe
                85                  90                  95

Cys Tyr Glu Arg Val Ala Arg Lys Met Lys Glu Arg Gly Leu Phe Lys
            100                 105                 110

Ser Ser Lys Pro Phe Lys Val Thr Met Thr Ala Val Ile
            115                 120                 125

(2) INFORMATION FOR SEQ ID NO:348:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:348:

Ile Cys Val Leu His Pro Val Trp Ala Gln Asn His Arg Thr Val Ser
1               5                   10                  15

Leu Ala Met Lys Val Ile Val Gly Pro Trp Ile Leu Ala Leu Val Leu
            20                  25                  30

Thr Leu Pro Val Phe Leu Phe Leu Thr Thr Val Thr Ile Pro Asn Gly
            35                  40                  45

Asp Thr Tyr Cys Thr Phe Asn Phe Ala Ser Trp Gly Thr Pro Glu
    50                  55                  60

Glu Arg Leu Lys Val Ala Ile Thr Ile Met Leu Thr Ala Arg Gly Ile
65              70                  75                  80

Ile Arg Phe Val Ile Gly Phe Ser Leu Pro Met Ser Ile Val Ala Ile
                85                  90                  95

Cys Tyr Gly Leu Ile Ala Ala Lys Ile His Lys Lys Gly Met Ile Lys
            100                 105                 110

Ser Ser Arg Pro Leu Arg Val Leu Thr Ala Val Val Ala
            115                 120                 125

(2) INFORMATION FOR SEQ ID NO:349:

(i) SEQUENCE CHARACTERISTICS:
        (A) LENGTH: 124 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:349:

Val Cys Val Leu His Pro Val Trp Thr Gln Asn His Arg Thr Val Ser
1               5                   10                  15

Leu Ala Lys Lys Val Ile Ile Gly Pro Trp Val Met Ala Leu Leu Leu
            20                  25                  30

Thr Leu Pro Val Ile Ile Arg Val Thr Thr Val Pro Gly Lys Thr Gly
            35                  40                  45

Thr Val Ala Cys Thr Phe Asn Phe Ser Pro Trp Thr Asn Asp Pro Lys
        50                  55                  60

Glu Arg Ile Lys Val Ala Val Ala Met Leu Thr Val Arg Gly Ile Ile
65              70                  75                  80

Arg Phe Ile Ile Gly Phe Ser Ala Pro Met Ser Ile Val Ala Val Ser
                85                  90                  95

Tyr Gly Leu Ile Ala Thr Lys Ile His Lys Gln Gly Leu Ile Lys Ser
            100                 105                 110

Ser Arg Pro Leu Arg Val Leu Ser Phe Val Ala Ala
            115                 120

(2) INFORMATION FOR SEQ ID NO:350:

(i) SEQUENCE CHARACTERISTICS:
        (A) LENGTH: 126 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:350:

Ile Cys Val Leu His Pro Val Trp Ala Gln Asn His Arg Asn Val Ser

```
 1               5                  10                 15
Leu Ala Lys Lys Val Ile Val Gly Pro Trp Ile Cys Ala Leu Leu Leu
                20                 25              30

Thr Leu Pro Val Ile Ile Arg Val Thr Thr Leu Ser His Pro Arg Ala
             35              40              45

Pro Gly Lys Met Ala Cys Thr Phe Asp Trp Ser Pro Trp Thr Glu Asp
 50              55              60

Pro Ala Glu Lys Leu Lys Val Ala Ile Ser Met Phe Met Val Arg Gly
 65              70              75                       80

Ile Ile Arg Phe Ile Ile Gly Phe Ser Thr Pro Met Ser Ile Val Ala
             85              90              95

Val Cys Tyr Gly Leu Ile Ala Thr Lys Ile His Arg Gln Gly Leu Ile
            100             105             110

Lys Ser Ser Arg Pro Leu Arg Val Leu Ser Phe Val Val Ala
        115             120             125
```

(2) INFORMATION FOR SEQ ID NO:351:

(i) SEQUENCE CHARACTERISTICS:
        (A) LENGTH: 115 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:351:

```
Leu Leu Val Phe Lys Pro Ile Trp Cys Gln Lys Val Arg Gly Thr Gly
 1               5                  10                 15

Leu Ala Trp Met Ala Cys Gly Val Ala Trp Val Leu Ala Leu Leu Leu
                20                 25              30

Thr Ile Pro Ser Phe Val Tyr Arg Glu Ala Tyr Lys Asp Phe Tyr Ser
             35              40              45

Glu His Thr Val Cys Gly Ile Asn Tyr Gly Gly Ser Phe Pro Lys
 50              55              60

Glu Lys Ala Val Ala Ile Leu Arg Leu Met Val Gly Phe Val Leu Pro
 65              70              75                       80

Leu Leu Thr Leu Asn Ile Cys Tyr Thr Phe Leu Leu Leu Arg Thr Trp
             85              90              95

Ser Arg Lys Ala Thr Arg Ser Thr Lys Thr Leu Lys Val Val Met Ala
            100             105             110

Val Val Ile
        115
```

(2) INFORMATION FOR SEQ ID NO:352:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:352:

```
Leu Ala Ile Val His Ala Thr Asn Ser Gln Lys Pro Arg Lys Leu Leu
 1               5                  10                 15

Ala Glu Lys Val Val Tyr Val Gly Val Trp Leu Pro Ala Val Leu Leu
                20                 25              30
```

```
Thr Ile Pro Asp Leu Ile Phe Ala Asp Ile Lys Glu Val Asp Glu Arg
         35                  40                  45

Tyr Ile Cys Asp Arg Phe Tyr Pro Ser Asp Leu Trp Leu Val Val Phe
     50                  55                  60

Gln Phe Gln His Ile Val Val Gly Leu Leu Leu Pro Gly Ile Val Ile
 65                  70                  75                  80

Leu Ser Cys Tyr Cys Ile Ile Ile Ser Lys Leu Ser His Ser Lys Gly
                 85                  90                  95

Tyr Gln Lys Arg Lys Ala Leu Lys Thr Thr Val Ile Leu Ile Leu
             100                 105                 110
```

(2) INFORMATION FOR SEQ ID NO:353:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 28..384

(xi) SEQUENCE DESCRIPTION: SEQ ID NO:353:

```
CTGACTGCTC TGGGGACTGA CCGGTAT TTC AAG ATT GTG AAG CCC CTT TCC        51
                               Phe Lys Ile Val Lys Pro Leu Ser
                                1               5

ACG TCC TTC ATC CAG TCT GTG AAC TAC AGC AAA CTC GTC TCG CTG GTG      99
Thr Ser Phe Ile Gln Ser Val Asn Tyr Ser Lys Leu Val Ser Leu Val
     10                  15                  20

GTC TGG TTG CTC ATG CTC CTC CTC GCC GTC CCC AAC GTC ATT CTC ACC     147
Val Trp Leu Leu Met Leu Leu Leu Ala Val Pro Asn Val Ile Leu Thr
 25                  30                  35                  40

AAC CAG AGA GTT AAG GAC GTG ACG CAG ATA AAA TGC ATG GAA CTT AAA     195
Asn Gln Arg Val Lys Asp Val Thr Gln Ile Lys Cys Met Glu Leu Lys
                 45                  50                  55

AAC GAA CTG GGC CGC CAG TGG CAC AAG GCG TCA AAC TAC ATC TTT GTG     243
Asn Glu Leu Gly Arg Gln Trp His Lys Ala Ser Asn Tyr Ile Phe Val
             60                  65                  70

GGC ATT TTC TGG CTT GTG TTC CTT TTG CTA ATC ATT TTC TAC ACT GCT     291
Gly Ile Phe Trp Leu Val Phe Leu Leu Leu Ile Ile Phe Tyr Thr Ala
         75                  80                  85

ATC ACC AGG AAA ATC TTT AAG TCC CAC CTG AAA TCC AGA AAG AAT TCC     339
Ile Thr Arg Lys Ile Phe Lys Ser His Leu Lys Ser Arg Lys Asn Ser
 90                  95                 100

ATC TCG GTC AAA AAG AAA TCT AGC CGC AAC ATC TTC AGC ATC GTG         384
Ile Ser Val Lys Lys Lys Ser Ser Arg Asn Ile Phe Ser Ile Val
105                 110                 115

TTTATCCTCT GTTGGCCCCC CTACCACATC                                    414
```

(2) INFORMATION FOR SEQ ID NO:354:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:354:

Phe Lys Ile Val Lys Pro Leu Ser Thr Ser Phe Ile Gln Ser Val Asn

```
            1               5                   10                  15
Tyr Ser Lys Leu Val Ser Leu Val Val Trp Leu Leu Met Leu Leu Leu
                20                  25                  30

Ala Val Pro Asn Val Ile Leu Thr Asn Gln Arg Val Lys Asp Val Thr
            35                  40                  45

Gln Ile Lys Cys Met Glu Leu Lys Asn Glu Leu Gly Arg Gln Trp His
        50                  55                  60

Lys Ala Ser Asn Tyr Ile Phe Val Gly Ile Phe Trp Leu Val Phe Leu
65                  70                  75                      80

Leu Leu Ile Ile Phe Tyr Thr Ala Ile Thr Arg Lys Ile Phe Lys Ser
                85                  90                  95

His Leu Lys Ser Arg Lys Asn Ser Ile Ser Val Lys Lys Lys Ser Ser
            100                 105                 110

Arg Asn Ile Phe Ser Ile Val
        115
```

(2) INFORMATION FOR SEQ ID NO:355:

(i) SEQUENCE CHARACTERISTICS:
        (A) LENGTH: 119 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:355:

```
Phe Lys Ile Val Lys Pro Leu Ser Thr Ser Phe Ile Gln Ser Val Asn
1               5                   10                  15

Tyr Ser Lys Leu Val Ser Leu Val Val Trp Leu Leu Met Leu Leu Leu
                20                  25                  30

Ala Val Pro Asn Val Ile Leu Thr Asn Gln Arg Val Lys Asp Val Thr
            35                  40                  45

Gln Ile Lys Cys Met Glu Leu Lys Asn Glu Leu Gly Arg Gln Trp His
        50                  55                  60

Lys Ala Ser Asn Tyr Ile Phe Val Gly Ile Phe Trp Leu Val Phe Leu
65                  70                  75                      80

Leu Leu Ile Ile Phe Tyr Thr Ala Ile Thr Arg Lys Ile Phe Lys Ser
                85                  90                  95

His Leu Lys Ser Arg Lys Asn Ser Ile Ser Val Lys Lys Lys Ser Ser
            100                 105                 110

Arg Asn Ile Phe Ser Ile Val
        115
```

(2) INFORMATION FOR SEQ ID NO:356:

(i) SEQUENCE CHARACTERISTICS:
        (A) LENGTH: 115 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:356:

```
Leu Ala Ile Val His Ala Thr Ser Thr Leu Ile Phe Gln Lys Arg His
1               5                   10                  15

Leu Val Lys Phe Val Cys Ile Ala Met Trp Leu Leu Ser Val Ile Leu
                20                  25                  30
```

-continued

```
Ala Leu Pro Ile Leu Ile Leu Arg Asn Pro Val Lys Val Asn Leu Ser
        35                  40                  45

Thr Leu Val Cys Tyr Glu Asp Val Gly Asn Asn Thr Ser Arg Leu Arg
 50                  55                  60

Val Val Leu Arg Ile Leu Pro Gln Thr Phe Gly Phe Leu Val Pro Leu
 65                  70                  75                  80

Leu Ile Met Leu Phe Cys Tyr Gly Phe Thr Leu Arg Thr Leu Phe Lys
            85                  90                  95

Ala His Met Gly Gln Lys His Arg Ala Met Arg Val Ile Phe Ala Val
                100                 105                 110

Val Leu Val
        115

(2) INFORMATION FOR SEQ ID NO:357:

(i) SEQUENCE CHARACTERISTICS:
        (A) LENGTH: 123 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:357:

Val Ala Val Val His Pro Ile Lys Ala Ala Arg Tyr Arg Arg Pro Thr
  1               5                  10                  15

Val Ala Lys Val Val Asn Leu Gly Val Trp Val Leu Ser Leu Leu Val
                20                  25                  30

Ile Leu Pro Ile Val Val Phe Ser Arg Thr Ala Ala Asn Ser Asp Gly
        35                  40                  45

Thr Val Ala Cys Asn Met Leu Met Pro Glu Pro Ala Gln Arg Trp Leu
 50                  55                  60

Val Gly Phe Val Leu Tyr Thr Phe Leu Met Gly Phe Leu Leu Pro Val
 65                  70                  75                  80

Gly Ala Ile Cys Leu Cys Tyr Val Leu Ile Ile Ala Lys Met Arg Met
            85                  90                  95

Val Ala Leu Lys Ala Gly Trp Gln Gln Arg Lys Arg Ser Glu Arg Lys
                100                 105                 110

Ile Thr Leu Met Val Met Met Val Val Met Val
        115                 120

(2) INFORMATION FOR SEQ ID NO:358:

(i) SEQUENCE CHARACTERISTICS:
        (A) LENGTH: 122 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:358:

Val Ala Val Val His Pro Leu Arg Ala Ala Thr Tyr Arg Arg Pro Ser
  1               5                  10                  15

Val Ala Lys Leu Ile Asn Leu Gly Val Trp Leu Ala Ser Leu Leu Val
                20                  25                  30

Thr Leu Pro Ile Ala Ile Phe Ala Asp Thr Arg Pro Ala Arg Gly Gly
        35                  40                  45

Gln Ala Val Ala Cys Asn Leu Gln Trp Pro His Pro Ala Trp Ser Ala
 50                  55                  60
```

```
Val Phe Val Val Tyr Thr Phe Leu Leu Gly Phe Leu Leu Pro Val Leu
 65                  70                  75                  80

Ala Ile Gly Leu Cys Tyr Leu Leu Ile Val Gly Lys Met Arg Ala Val
                 85                  90                  95

Ala Leu Arg Ala Gly Trp Gln Gln Arg Arg Arg Ser Glu Lys Lys Ile
            100                 105                 110

Thr Arg Leu Val Leu Met Val Val Val
            115                 120
```

(2) INFORMATION FOR SEQ ID NO:359:

(i) SEQUENCE CHARACTERISTICS:
        (A) LENGTH: 810 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 28..783

(xi) SEQUENCE DESCRIPTION: SEQ ID NO:359:

```
GCCACCAACG TGTTCATCCT GTGTCTG GTG GAC CTG CTG GCT GCC CTG ACC           51
                              Val Asp Leu Leu Ala Ala Leu Thr
                                1               5

CTC ATG CCT CTG GCC ATG CTC TCC AGC TCC GCC CTC TTT GAC CAC GCC         99
Leu Met Pro Leu Ala Met Leu Ser Ser Ser Ala Leu Phe Asp His Ala
         10                  15                  20

CTC TTT GGG GAG GTG GCC TGC CGC CTC TAC TTG TTC CTG AGC GTC TGC         147
Leu Phe Gly Glu Val Ala Cys Arg Leu Tyr Leu Phe Leu Ser Val Cys
 25                  30                  35                  40

TTT GTC AGC CTG GCC ATC CTC TCG GTG TCC GCC ATC AAT GTG GAG CGC         195
Phe Val Ser Leu Ala Ile Leu Ser Val Ser Ala Ile Asn Val Glu Arg
                 45                  50                  55

TAC TAT TAT GTG GTC CAC CCC ATG CGC TAT GAG GTG CGC ATG AAA CTG         243
Tyr Tyr Tyr Val Val His Pro Met Arg Tyr Glu Val Arg Met Lys Leu
             60                  65                  70

GGG CTG GTG GCC TCT GTG CTG GTG GGC GTG TGG GTG AAG GCC CTG GCC         291
Gly Leu Val Ala Ser Val Leu Val Gly Val Trp Val Lys Ala Leu Ala
         75                  80                  85

ATG GCT TCT GTG CCA GTG TTG GGA AGG GTG TCC TGG GAG GAA GGC CCT         339
Met Ala Ser Val Pro Val Leu Gly Arg Val Ser Trp Glu Glu Gly Pro
 90                  95                 100

CCC AGT GTC CCC CCA GGC TGT TCA CTC CAA TGG AGC CAC AGT GCC TAC         387
Pro Ser Val Pro Pro Gly Cys Ser Leu Gln Trp Ser His Ser Ala Tyr
105                 110                 115                 120

TGC CAG CTT TTC GTG GTG GTC TTC GCC GTC CTC TAC TTC CTG CTG CCC         435
Cys Gln Leu Phe Val Val Val Phe Ala Val Leu Tyr Phe Leu Leu Pro
                125                 130                 135

CTG CTC CTC ATC CTT GTG GTC TAC TGC AGC ATG TTC CGG GTG GCT CGT         483
Leu Leu Leu Ile Leu Val Val Tyr Cys Ser Met Phe Arg Val Ala Arg
            140                 145                 150

GTG GCT GCC ATG CAG CAC GGG CCG CTG CCC ACG TGG ATG GAG ACG CCC         531
Val Ala Ala Met Gln His Gly Pro Leu Pro Thr Trp Met Glu Thr Pro
        155                 160                 165

CGG CAA CGC TCC GAG TCT CTC AGC AGC CGC TCC ACT ATG GTC ACC AGC         579
Arg Gln Arg Ser Glu Ser Leu Ser Ser Arg Ser Thr Met Val Thr Ser
170                 175                 180

TCG GGG GCC CCG CAG ACC ACC CCT CAC CGG ACG TTT GGC GGA GGG AAG         627
```

```
Ser Gly Ala Pro Gln Thr Thr Pro His Arg Thr Phe Gly Gly Gly Lys
185                 190                 195                 200

GCA GCA GTG GTC CTC CTG GCT GTG GGA GGA CAG TTC CTG CTC TGT TGG      675
Ala Ala Val Val Leu Leu Ala Val Gly Gly Gln Phe Leu Leu Cys Trp
                    205                 210                 215

TTG CCC TAC TTC TCC TTC CAC CTC TAT GTG GCC CTG AGC GCT CAG CCC      723
Leu Pro Tyr Phe Ser Phe His Leu Tyr Val Ala Leu Ser Ala Gln Pro
            220                 225                 230

ATT GCA GCG GGG CAG GTG GAG AAC GTG GTG ACC TGG ATT GGC TAC TTC      771
Ile Ala Ala Gly Gln Val Glu Asn Val Val Thr Trp Ile Gly Tyr Phe
        235                 240                 245

TGC TTC ACC TCC AACCCTCTCC TCTATTCCTT CCTCCCT                        810
Cys Phe Thr Ser
    250
```

(2) INFORMATION FOR SEQ ID NO:360:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO:360:

```
Val Asp Leu Leu Ala Ala Leu Thr Leu Met Pro Leu Ala Met Leu Ser
1               5                   10                  15

Ser Ser Ala Leu Phe Asp His Ala Leu Phe Gly Glu Val Ala Cys Arg
            20                  25                  30

Leu Tyr Leu Phe Leu Ser Val Cys Phe Val Ser Leu Ala Ile Leu Ser
        35                  40                  45

Val Ser Ala Ile Asn Val Glu Arg Tyr Tyr Val His Pro Met
    50                  55                  60

Arg Tyr Glu Val Arg Met Lys Leu Gly Leu Val Ala Ser Val Leu Val
65                  70                  75                  80

Gly Val Trp Val Lys Ala Leu Ala Met Ala Ser Val Pro Val Leu Gly
                85                  90                  95

Arg Val Ser Trp Glu Glu Gly Pro Pro Ser Val Pro Pro Gly Cys Ser
                100                 105                 110

Leu Gln Trp Ser His Ser Ala Tyr Cys Gln Leu Phe Val Val Val Phe
            115                 120                 125

Ala Val Leu Tyr Phe Leu Leu Pro Leu Leu Leu Ile Leu Val Val Tyr
        130                 135                 140

Cys Ser Met Phe Arg Val Ala Arg Val Ala Ala Met Gln His Gly Pro
145                 150                 155                 160

Leu Pro Thr Trp Met Glu Thr Pro Arg Gln Arg Ser Glu Ser Leu Ser
                165                 170                 175

Ser Arg Ser Thr Met Val Thr Ser Ser Gly Ala Pro Gln Thr Thr Pro
            180                 185                 190

His Arg Thr Phe Gly Gly Gly Lys Ala Ala Val Val Leu Leu Ala Val
        195                 200                 205

Gly Gly Gln Phe Leu Leu Cys Trp Leu Pro Tyr Phe Ser Phe His Leu
210                 215                 220

Tyr Val Ala Leu Ser Ala Gln Pro Ile Ala Ala Gly Gln Val Glu Asn
225                 230                 235                 240

Val Val Thr Trp Ile Gly Tyr Phe Cys Phe Thr Ser
                245                 250
```

(2) INFORMATION FOR SEQ ID NO:361:

(i) SEQUENCE CHARACTERISTICS:
        (A) LENGTH: 167 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:361:

```
Val Gly Met Val Gly Asn Val Leu Leu Val Leu Val Ile Ala Arg Val
1               5                   10                  15

Arg Arg Leu His Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
            35                  40                  45

Ala Phe Glu Pro Arg Gly Trp Val Phe Gly Gly Leu Cys His Leu
50                  55                  60

Val Phe Phe Leu Gln Pro Val Thr Val Tyr Val Ser Val Phe Thr Leu
65                  70                  75                  80

Thr Thr Ile Ala Val Asp Arg Tyr Val Val Leu Val His Pro Leu Arg
                85                  90                  95

Arg Arg Ile Gly Leu Leu Leu Val Thr Tyr Leu Leu Pro Leu Leu Val
                100                 105                 110

Ile Leu Leu Ser Tyr Val Arg Val Ser Val Lys Leu Arg Asn Arg Val
            115                 120                 125

Val Pro Gly Cys Val Thr Gln Ser Gln Ala Asp Trp Asp Arg Ala Arg
130                 135                 140

Arg Arg Arg Thr Phe Cys Leu Leu Val Val Val Val Val Phe Ala
145                 150                 155                 160

Ile Cys Trp Leu Pro Tyr Tyr
                165
```

(2) INFORMATION FOR SEQ ID NO:362:

(i) SEQUENCE CHARACTERISTICS:
        (A) LENGTH: 228 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:362:

```
Leu Gly Val Ser Gly Asn Leu Ala Leu Ile Ile Ile Leu Lys Gln
1               5                   10                  15

Lys Glu Met Arg Asn Val Thr Asn Ile Leu Ile Val Asn Leu Ser Phe
                20                  25                  30

Ser Asp Leu Leu Val Ala Val Met Cys Leu Pro Phe Thr Phe Val Tyr
            35                  40                  45

Thr Leu Met Asp His Trp Val Phe Gly Glu Thr Met Cys Lys Leu Asn
50                  55                  60

Pro Phe Val Gln Cys Val Ser Ile Thr Val Ser Ile Phe Ser Leu Val
65                  70                  75                  80

Leu Ile Ala Val Glu Arg His Gln Leu Ile Ile Asn Pro Arg Gly Trp
                85                  90                  95

Arg Pro Asn Asn Arg His Ala Tyr Ile Gly Ile Thr Val Ile Trp Val
                100                 105                 110
```

```
Leu Ala Val Ala Ser Ser Leu Pro Phe Val Ile Tyr Gln Ile Leu Thr
            115                 120                 125

Asp Glu Pro Phe Gln Asn Val Ser Leu Ala Ala Phe Lys Asp Lys Tyr
130                 135                 140

Val Cys Phe Asp Lys Phe Pro Ser Asp Ser His Arg Leu Ser Tyr Thr
145                 150                 155                 160

Thr Leu Leu Leu Val Leu Gln Tyr Phe Gly Pro Leu Cys Phe Ile Phe
                165                 170                 175

Ile Cys Tyr Phe Lys Ile Tyr Ile Arg Leu Lys Arg Arg Asn Asn Met
            180                 185                 190

Met Asp Lys Ile Arg Asp Ser Lys Tyr Arg Ser Ser Glu Thr Lys Arg
            195                 200                 205

Ile Asn Val Met Leu Leu Ser Ile Val Val Ala Phe Ala Val Cys Trp
210                 215                 220

Leu Pro Leu Thr
225

(2) INFORMATION FOR SEQ ID NO:363:

(i) SEQUENCE CHARACTERISTICS:
        (A) LENGTH: 167 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:363:

Val Gly Met Val Gly Asn Val Leu Leu Val Leu Val Ile Ala Arg Val
1               5                   10                  15

Arg Arg Leu His Asn Val Thr Asn Phe Leu Ile Gly Asn Leu Ala Leu
            20                  25                  30

Ser Asp Val Leu Met Cys Thr Ala Cys Val Pro Leu Thr Leu Ala Tyr
            35                  40                  45

Ala Phe Glu Pro Arg Gly Trp Val Phe Gly Gly Leu Cys His Leu
50                  55                  60

Val Phe Phe Leu Gln Pro Val Thr Val Tyr Val Ser Val Phe Thr Leu
65                  70                  75                  80

Thr Thr Ile Ala Val Asp Arg Tyr Val Val Leu Val His Pro Leu Arg
            85                  90                  95

Arg Arg Ile Gly Leu Leu Val Thr Tyr Leu Leu Pro Leu Leu Val
            100                 105                 110

Ile Leu Leu Ser Tyr Val Arg Val Ser Val Lys Leu Arg Asn Arg Val
            115                 120                 125

Val Pro Gly Cys Val Thr Gln Ser Gln Ala Asp Trp Asp Arg Ala Arg
130                 135                 140

Arg Arg Arg Thr Phe Cys Leu Leu Val Val Val Val Val Phe Ala
145                 150                 155                 160

Ile Cys Trp Leu Pro Tyr Tyr
            165

(2) INFORMATION FOR SEQ ID NO:364:

(i) SEQUENCE CHARACTERISTICS:
        (A) LENGTH: 223 amino acids
        (B) TYPE: amino acid
        (C) STRANDEDNESS:
        (D) TOPOLOGY: linear
```

(ii) MOLECULE TYPE: peptide (xi) SEQUENCE DESCRIPTION: SEQ ID NO:364:

```
Val Gly Met Val Gly Asn Ile Leu Leu Val Leu Val Ile Ala Arg Val
1               5                   10                  15

Arg Arg Leu Tyr Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
            35                  40                  45

Ala Phe Glu Pro Arg Gly Trp Val Phe Gly Gly Leu Cys His Leu
        50                  55                  60

Val Phe Phe Leu Gln Ala Val Thr Val Tyr Val Ser Val Phe Thr Leu
65                  70                  75                  80

Thr Thr Ile Ala Val Asp Arg Tyr Val Leu Val His Pro Leu Arg
                85                  90                  95

Arg Arg Ile Ser Leu Arg Leu Ser Ala Tyr Ala Val Leu Ala Ile Trp
                100                 105                 110

Val Leu Ser Ala Val Leu Ala Leu Pro Ala Ala Val His Thr Tyr His
                115                 120                 125

Val Glu Leu Lys Pro His Asp Val Arg Leu Cys Glu Glu Phe Trp Gly
130                 135                 140

Ser Gln Glu Arg Gln Arg Gln Leu Tyr Ala Trp Gly Leu Leu Leu Val
145                 150                 155                 160

Thr Tyr Leu Leu Pro Leu Leu Val Ile Leu Leu Ser Tyr Ala Arg Val
                165                 170                 175

Ser Val Lys Leu Arg Asn Arg Val Val Pro Gly Arg Val Thr Gln Ser
                180                 185                 190

Gln Ala Asp Trp Asp Arg Ala Arg Arg Arg Thr Phe Cys Leu Leu
                195                 200                 205

Val Val Val Val Val Phe Ile Leu Cys Trp Leu Pro Phe Phe
210                 215                 220
```

(2) INFORMATION FOR SEQ ID NO:365:

(i) SEQUENCE CHARACTERISTICS:
        (A) LENGTH: 434 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..432

(xi) SEQUENCE DESCRIPTION: SEQ ID NO:365:

```
CTG TGT GTC ATC GCG GTG GAT AGG TAC GTG GTT CTG GTG CAC CCG CTA       48
Leu Cys Val Ile Ala Val Asp Arg Tyr Val Val Leu Val His Pro Leu
1               5                   10                  15

CGT CGG CGC ATT TCA CTG AGG CTC AGC GCC TAC GCG GTG CTG GGC ATC       96
Arg Arg Arg Ile Ser Leu Arg Leu Ser Ala Tyr Ala Val Leu Gly Ile
                20                  25                  30

TGG GCT CTA TCT GCA GTG CTG GCG CTG CCG GCC GCG GTG CAC ACC TAC      144
Trp Ala Leu Ser Ala Val Leu Ala Leu Pro Ala Ala Val His Thr Tyr
            35                  40                  45

CAT GTG GAG CTC AAG CCC CAC GAC GTG AGC CTC TGC GAG GAG TTC TGG      192
His Val Glu Leu Lys Pro His Asp Val Ser Leu Cys Glu Glu Phe Trp
        50                  55                  60
```

```
GGC TCG CAG GAG CGC CAA CGC CAG ATC TAC GCC TGG GGG CTG CTT CTG    240
Gly Ser Gln Glu Arg Gln Arg Gln Ile Tyr Ala Trp Gly Leu Leu Leu
 65              70                  75                  80

GGC ACC TAT TTG CTC CCC CTG CTG GCC ATC CTC CTG TCT TAC GTA CGG    288
Gly Thr Tyr Leu Leu Pro Leu Leu Ala Ile Leu Leu Ser Tyr Val Arg
                 85                  90                  95

GTG TCA GTG AAG CTG AGG AAC CGC GTG GTG CCT GGC AGC GTG ACC CAG    336
Val Ser Val Lys Leu Arg Asn Arg Val Val Pro Gly Ser Val Thr Gln
                100                 105                 110

AGT CAA GCT GAC TGG GAC CGA GCG CGT CGC CGC ACT TTC TGT CTG        384
Ser Gln Ala Asp Trp Asp Arg Ala Arg Arg Arg Thr Phe Cys Leu
            115                 120                 125

CTG GTG GTG GTG GTG GTA GTG TTC ACG CTC TGC TGG CTG CCC TTC TAC    432
Leu Val Val Val Val Val Phe Thr Leu Cys Trp Leu Pro Phe Tyr
        130                 135                 140

CT                                                                 434

(2) INFORMATION FOR SEQ ID NO:366:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:366:

Leu Cys Val Ile Ala Val Asp Arg Tyr Val Leu Val His Pro Leu
 1               5                  10                  15

Arg Arg Arg Ile Ser Leu Arg Leu Ser Ala Tyr Ala Val Leu Gly Ile
            20                  25                  30

Trp Ala Leu Ser Ala Val Leu Ala Leu Pro Ala Ala Val His Thr Tyr
                35                  40                  45

His Val Glu Leu Lys Pro His Asp Val Ser Leu Cys Glu Glu Phe Trp
     50                  55                  60

Gly Ser Gln Glu Arg Gln Arg Gln Ile Tyr Ala Trp Gly Leu Leu Leu
 65              70                  75                  80

Gly Thr Tyr Leu Leu Pro Leu Leu Ala Ile Leu Leu Ser Tyr Val Arg
                 85                  90                  95

Val Ser Val Lys Leu Arg Asn Arg Val Val Pro Gly Ser Val Thr Gln
                100                 105                 110

Ser Gln Ala Asp Trp Asp Arg Ala Arg Arg Arg Thr Phe Cys Leu
            115                 120                 125

Leu Val Val Val Val Val Phe Thr Leu Cys Trp Leu Pro Phe Tyr
        130                 135                 140

(2) INFORMATION FOR SEQ ID NO:367:

(i) SEQUENCE CHARACTERISTICS:
        (A) LENGTH: 167 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:367:

Val Gly Met Val Gly Asn Val Leu Leu Val Leu Val Ile Ala Arg Val
 1               5                  10                  15

Arg Arg Leu His Asn Val Thr Asn Phe Leu Ile Gly Asn Leu Ala Leu
```

```
            20                  25                  30
Ser Asp Val Leu Met Cys Thr Ala Cys Val Pro Leu Thr Leu Ala Tyr
        35                  40                  45

Ala Phe Glu Pro Arg Gly Trp Val Phe Gly Gly Leu Cys His Leu
 50                  55                  60

Val Phe Phe Leu Gln Pro Val Thr Val Tyr Val Ser Val Phe Thr Leu
 65                  70                  75                  80

Thr Thr Ile Ala Val Asp Arg Tyr Val Leu Val His Pro Leu Arg
                 85                  90                  95

Arg Arg Ile Gly Leu Leu Leu Val Thr Tyr Leu Leu Pro Leu Leu Val
                100                 105                 110

Ile Leu Leu Ser Tyr Val Arg Val Ser Val Lys Leu Arg Asn Arg Val
                115                 120                 125

Val Pro Gly Cys Val Thr Gln Ser Gln Ala Asp Trp Asp Arg Ala Arg
130                 135                 140

Arg Arg Arg Thr Phe Cys Leu Leu Val Val Val Val Phe Ala
145                 150                 155                 160

Ile Cys Trp Leu Pro Tyr Tyr
                165

(2) INFORMATION FOR SEQ ID NO:368:

(i) SEQUENCE CHARACTERISTICS:
        (A) LENGTH: 223 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:368:

Val Gly Met Val Gly Asn Ile Leu Leu Val Leu Val Ile Ala Arg Val
 1               5                  10                  15

Arg Arg Leu Tyr Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
        35                  40                  45

Ala Phe Glu Pro Arg Gly Trp Val Phe Gly Gly Leu Cys His Leu
 50                  55                  60

Val Phe Phe Leu Gln Ala Val Thr Val Tyr Val Ser Val Phe Thr Leu
 65                  70                  75                  80

Thr Thr Ile Ala Val Asp Arg Tyr Val Leu Val His Pro Leu Arg
                 85                  90                  95

Arg Arg Ile Ser Leu Arg Leu Ser Ala Tyr Ala Val Leu Ala Ile Trp
                100                 105                 110

Val Leu Ser Ala Val Leu Ala Leu Pro Ala Ala Val His Thr Tyr His
                115                 120                 125

Val Glu Leu Lys Pro His Asp Val Arg Leu Cys Glu Glu Phe Trp Gly
130                 135                 140

Ser Gln Glu Arg Gln Arg Gln Leu Tyr Ala Trp Gly Leu Leu Leu Val
145                 150                 155                 160

Thr Tyr Leu Leu Pro Leu Leu Val Ile Leu Leu Ser Tyr Ala Arg Val
                165                 170                 175

Ser Val Lys Leu Arg Asn Arg Val Pro Gly Arg Val Thr Gln Ser
                180                 185                 190

Gln Ala Asp Trp Asp Arg Ala Arg Arg Arg Thr Phe Cys Leu Leu
```

```
                        195                 200                 205
Val Val Val Val Val Val Phe Thr Leu Cys Trp Leu Pro Phe Phe
        210                 215                 220

(2) INFORMATION FOR SEQ ID NO:369:

(i) SEQUENCE CHARACTERISTICS:
        (A) LENGTH: 144 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:369:

Leu Cys Val Ile Ala Val Asp Arg Tyr Val Val Leu Val His Pro Leu
1               5                   10                  15

Arg Arg Arg Ile Ser Leu Arg Leu Ser Ala Tyr Ala Val Leu Gly Ile
            20                  25                  30

Trp Ala Leu Ser Ala Val Leu Ala Leu Pro Ala Ala Val His Thr Tyr
        35                  40                  45

His Val Glu Leu Lys Pro His Asp Val Ser Leu Cys Glu Glu Phe Trp
    50                  55                  60

Gly Ser Gln Glu Arg Gln Arg Gln Ile Tyr Ala Trp Gly Leu Leu Leu
65                  70                  75                  80

Gly Thr Tyr Leu Leu Pro Leu Leu Ala Ile Leu Leu Ser Tyr Val Arg
                85                  90                  95

Val Ser Val Lys Leu Arg Asn Arg Val Val Pro Gly Ser Val Thr Gln
            100                 105                 110

Ser Gln Ala Asp Trp Asp Arg Ala Arg Arg Arg Thr Phe Cys Leu
        115                 120                 125

Leu Val Val Val Val Val Phe Thr Leu Cys Trp Leu Pro Phe Tyr
    130                 135                 140

(2) INFORMATION FOR SEQ ID NO:370:

(i) SEQUENCE CHARACTERISTICS:
        (A) LENGTH: 1020 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 28..1011

(xi) SEQUENCE DESCRIPTION: SEQ ID NO:370:

GAGCATAGGA AAGGCTGACA GGCAGTT ATG GAG CAG GAC AAT GGC ACC ATC          51
                            Met Glu Gln Asp Asn Gly Thr Ile
                              1               5

CAG GCT CCA GGC TTG CCG CCC ACC ACC TGC GTC TAC CGT GAG GAT TTC        99
Gln Ala Pro Gly Leu Pro Pro Thr Thr Cys Val Tyr Arg Glu Asp Phe
         10                  15                  20

AAG CGA CTG CTG CTA ACC CCG GTA TAC TCG GTG GTG CTG GTG GTC GGC       147
Lys Arg Leu Leu Leu Thr Pro Val Tyr Ser Val Val Leu Val Val Gly
 25                  30                  35                  40

CTG CCA CTG AAC ATC TGC GTC ATT GCC CAG ATC TGC GCA TCC CGC CGG       195
Leu Pro Leu Asn Ile Cys Val Ile Ala Gln Ile Cys Ala Ser Arg Arg
             45                  50                  55

ACC CTG ACC CGT TCC GCT GTG TAC ACC CTG AAC CTG GCA CTG GCG GAC       243
```

```
Thr Leu Thr Arg Ser Ala Val Tyr Thr Leu Asn Leu Ala Leu Ala Asp
            60                  65                  70

CTG ATG TAT GCC TGT TCA CTA CCC CTA CTT ATC TAT AAC TAC GCC AGA         291
Leu Met Tyr Ala Cys Ser Leu Pro Leu Leu Ile Tyr Asn Tyr Ala Arg
            75                  80                  85

GGG GAC CAC TGG CCC TTC GGA GAC CTC GCC TGC CGC TTT GTA CGC TTC         339
Gly Asp His Trp Pro Phe Gly Asp Leu Ala Cys Arg Phe Val Arg Phe
        90                  95                 100

CTC TTC TAT GCC AAT CTA CAT GGC AGC ATC CTG TTC CTC ACC TGC ATT         387
Leu Phe Tyr Ala Asn Leu His Gly Ser Ile Leu Phe Leu Thr Cys Ile
105                 110                 115                 120

AGC TTC CAG CGC TAC CTG GGC ATC TGC CAC CCC CTG GCT TCC TGG CAC         435
Ser Phe Gln Arg Tyr Leu Gly Ile Cys His Pro Leu Ala Ser Trp His
                125                 130                 135

AAG CGT GGA GGT CGC CGT GCT GCT TGG GTA GTG TGT GGA GTC GTG TGG         483
Lys Arg Gly Gly Arg Arg Ala Ala Trp Val Val Cys Gly Val Val Trp
            140                 145                 150

CTG GCT GTG ACA GCC CAG TGC CTG CCC ACG GCA GTC TTT GCT GCC ACA         531
Leu Ala Val Thr Ala Gln Cys Leu Pro Thr Ala Val Phe Ala Ala Thr
            155                 160                 165

GGC ATC CAG CGC AAC CGC ACT GTG TGC TAC GAC CTG AGC CCA CCC ATC         579
Gly Ile Gln Arg Asn Arg Thr Val Cys Tyr Asp Leu Ser Pro Pro Ile
170                 175                 180

CTG TCT ACT CGC TAC CTG CCC TAT GGT ATG GCC CTC ACG GTC ATC GGC         627
Leu Ser Thr Arg Tyr Leu Pro Tyr Gly Met Ala Leu Thr Val Ile Gly
185                 190                 195                 200

TTC TTG CTG CCC TTC ATA GCC TTA CTG GCT TGT TAT TGT CGC ATG GCC         675
Phe Leu Leu Pro Phe Ile Ala Leu Leu Ala Cys Tyr Cys Arg Met Ala
                205                 210                 215

CGC CGC CTG TGT CGC CAG GAT GGC CCA GCA GGT CCT GTG GCC CAA GAG         723
Arg Arg Leu Cys Arg Gln Asp Gly Pro Ala Gly Pro Val Ala Gln Glu
                220                 225                 230

CGG CGC AGC AAG GCG GCT CGT ATG GCT GTG GTG GTG GCA GCT GTC TTT         771
Arg Arg Ser Lys Ala Ala Arg Met Ala Val Val Val Ala Ala Val Phe
            235                 240                 245

GCC ATC AGC TTC CTG CCT TTC CAC ATC ACC AAG ACA GCC TAC TTG GCT         819
Ala Ile Ser Phe Leu Pro Phe His Ile Thr Lys Thr Ala Tyr Leu Ala
250                 255                 260

GTG CGC TCC ACG CCC GGT GTC TCT TGC CCT GTG CTG GAG ACC TTC GCT         867
Val Arg Ser Thr Pro Gly Val Ser Cys Pro Val Leu Glu Thr Phe Ala
265                 270                 275                 280

GCT GCC TAC AAA GGC ACT CGG CCC TTC GCC AGT GTC AAC AGT GTT CTG         915
Ala Ala Tyr Lys Gly Thr Arg Pro Phe Ala Ser Val Asn Ser Val Leu
                285                 290                 295

GAC CCC ATT CTC TTC TAC TTC ACA CAA CAG AAG TTC CGG CGG CAA CCC         963
Asp Pro Ile Leu Phe Tyr Phe Thr Gln Gln Lys Phe Arg Arg Gln Pro
                300                 305                 310

CAC GAT CTC TTA CAG AGG CTC ACA GCC AAG TGG CAG AGG CAG AGA GTC        1011
His Asp Leu Leu Gln Arg Leu Thr Ala Lys Trp Gln Arg Gln Arg Val
            315                 320                 325

TGAGGCCCC                                                               1020

(2) INFORMATION FOR SEQ ID NO:371:

(i) SEQUENCE CHARACTERISTICS:
        (A) LENGTH: 328 amino acids
        (B) TYPE: amino acid
        (D) TOPOLOGY: linear (ii) MOLECULE TYPE: protein
```

-continued (xi) SEQUENCE DESCRIPTION: SEQ ID NO:371:

| Met | Glu | Gln | Asp | Asn | Gly | Thr | Ile | Gln | Ala | Pro | Gly | Leu | Pro | Pro | Thr |
| 1 | | | | 5 | | | | | 10 | | | | | 15 | |

| Thr | Cys | Val | Tyr | Arg | Glu | Asp | Phe | Lys | Arg | Leu | Leu | Leu | Thr | Pro | Val |
| | | | 20 | | | | | 25 | | | | | 30 | | |

| Tyr | Ser | Val | Val | Leu | Val | Val | Gly | Leu | Pro | Leu | Asn | Ile | Cys | Val | Ile |
| | | 35 | | | | | 40 | | | | | 45 | | | |

| Ala | Gln | Ile | Cys | Ala | Ser | Arg | Arg | Thr | Leu | Thr | Arg | Ser | Ala | Val | Tyr |
| | 50 | | | | | 55 | | | | | 60 | | | | |

| Thr | Leu | Asn | Leu | Ala | Leu | Ala | Asp | Leu | Met | Tyr | Ala | Cys | Ser | Leu | Pro |
| 65 | | | | | 70 | | | | | 75 | | | | | 80 |

| Leu | Leu | Ile | Tyr | Asn | Tyr | Ala | Arg | Gly | Asp | His | Trp | Pro | Phe | Gly | Asp |
| | | | | 85 | | | | | 90 | | | | | 95 | |

| Leu | Ala | Cys | Arg | Phe | Val | Arg | Phe | Leu | Phe | Tyr | Ala | Asn | Leu | His | Gly |
| | | | 100 | | | | | 105 | | | | | 110 | | |

| Ser | Ile | Leu | Phe | Leu | Thr | Cys | Ile | Ser | Phe | Gln | Arg | Tyr | Leu | Gly | Ile |
| | | 115 | | | | | 120 | | | | | 125 | | | |

| Cys | His | Pro | Leu | Ala | Ser | Trp | His | Lys | Arg | Gly | Gly | Arg | Arg | Ala | Ala |
| | 130 | | | | | 135 | | | | | 140 | | | | |

| Trp | Val | Val | Cys | Gly | Val | Val | Trp | Leu | Ala | Val | Thr | Ala | Gln | Cys | Leu |
| 145 | | | | | 150 | | | | | 155 | | | | | 160 |

| Pro | Thr | Ala | Val | Phe | Ala | Ala | Thr | Gly | Ile | Gln | Arg | Asn | Arg | Thr | Val |
| | | | | 165 | | | | | 170 | | | | | 175 | |

| Cys | Tyr | Asp | Leu | Ser | Pro | Pro | Ile | Leu | Ser | Thr | Arg | Tyr | Leu | Pro | Tyr |
| | | | 180 | | | | | 185 | | | | | 190 | | |

| Gly | Met | Ala | Leu | Thr | Val | Ile | Gly | Phe | Leu | Leu | Pro | Phe | Ile | Ala | Leu |
| | | 195 | | | | | 200 | | | | | 205 | | | |

| Leu | Ala | Cys | Tyr | Cys | Arg | Met | Ala | Arg | Arg | Leu | Cys | Arg | Gln | Asp | Gly |
| | 210 | | | | | 215 | | | | | 220 | | | | |

| Pro | Ala | Gly | Pro | Val | Ala | Gln | Glu | Arg | Arg | Ser | Lys | Ala | Ala | Arg | Met |
| 225 | | | | | 230 | | | | | 235 | | | | | 240 |

| Ala | Val | Val | Val | Ala | Ala | Val | Phe | Ala | Ile | Ser | Phe | Leu | Pro | Phe | His |
| | | | | 245 | | | | | 250 | | | | | 255 | |

| Ile | Thr | Lys | Thr | Ala | Tyr | Leu | Ala | Val | Arg | Ser | Thr | Pro | Gly | Val | Ser |
| | | | 260 | | | | | 265 | | | | | 270 | | |

| Cys | Pro | Val | Leu | Glu | Thr | Phe | Ala | Ala | Tyr | Lys | Gly | Thr | Arg | Pro |
| | | 275 | | | | | 280 | | | | | 285 | | |

| Phe | Ala | Ser | Val | Asn | Ser | Val | Leu | Asp | Pro | Ile | Leu | Phe | Tyr | Phe | Thr |
| | | 290 | | | | | 295 | | | | | 300 | | | |

| Gln | Gln | Lys | Phe | Arg | Arg | Gln | Pro | His | Asp | Leu | Leu | Gln | Arg | Leu | Thr |
| 305 | | | | | 310 | | | | | 315 | | | | | 320 |

| Ala | Lys | Trp | Gln | Arg | Gln | Arg | Val |
| | | | | 325 | | | |

(2) INFORMATION FOR SEQ ID NO:372:

(i) SEQUENCE CHARACTERISTICS:
        (A) LENGTH: 327 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:372:

Met Glu Gln Asp Asn Gly Thr Ile Gln Ala Pro Gly Leu Pro Pro Thr

```
1               5                   10                  15
Thr Cys Val Tyr Arg Glu Asp Phe Lys Arg Leu Leu Thr Pro Val
                20                  25                  30
Tyr Ser Val Val Leu Val Gly Leu Pro Leu Asn Ile Cys Val Ile
        35                  40                  45
Ala Gln Ile Cys Ala Ser Arg Arg Thr Leu Thr Arg Ser Ala Val Tyr
50                  55                  60
Thr Leu Asn Leu Ala Leu Ala Asp Leu Met Tyr Ala Cys Ser Leu Pro
65                  70                  75                  80
Leu Leu Ile Tyr Asn Tyr Ala Arg Cys Asp His Trp Pro Phe Gly Asp
                85                  90                  95
Leu Ala Cys Arg Phe Val Arg Phe Leu Phe Tyr Ala Asn Leu His Gly
                100                 105                 110
Ser Ile Leu Phe Leu Thr Cys Ile Ser Phe Gln Arg Tyr Leu Gly Ile
                115                 120                 125
Cys His Pro Leu Ala Ser Trp His Lys Arg Gly Gly Arg Arg Ala Ala
                130                 135                 140
Trp Val Val Cys Gly Val Val Trp Leu Ala Val Thr Ala Gln Cys Leu
145                 150                 155                 160
Arg Thr Ala Val Phe Ala Ala Thr Gly Ile Gln Arg Asn Arg Thr Val
                165                 170                 175
Cys Tyr Asp Leu Ser Pro Pro Ile Leu Ser Thr Arg Tyr Leu Pro Tyr
                180                 185                 190
Gly Met Ala Leu Thr Val Ile Gly Phe Leu Leu Pro Phe Ile Ala Leu
                195                 200                 205
Leu Ala Cys Tyr Cys Arg Met Ala Arg Arg Leu Cys Arg Asp Gly Pro
210                 215                 220
Ala Gly Pro Val Ala Gln Glu Arg Arg Ser Lys Ala Ala Arg Met Ala
225                 230                 235                 240
Val Val Val Ala Ala Val Phe Ala Ile Ser Phe Leu Pro Phe His Ile
                245                 250                 255
Thr Lys Thr Ala Tyr Leu Ala Val Arg Ser Thr Pro Gly Val Ser Cys
                260                 265                 270
Pro Val Leu Glu Thr Phe Ala Ala Tyr Lys Gly Thr Arg Pro Phe
                275                 280                 285
Ala Ser Val Asn Ser Val Leu Asp Pro Ile Leu Phe Tyr Phe Thr Gln
290                 295                 300
Gln Lys Phe Arg Arg Gln Pro His Asp Leu Leu Gln Arg Leu Thr Ala
305                 310                 315                 320
Lys Trp Gln Arg Gln Arg Val
                325

(2) INFORMATION FOR SEQ ID NO:373:

(i) SEQUENCE CHARACTERISTICS:
        (A) LENGTH: 373 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:373:

Met Ala Ala Asp Leu Glu Pro Trp Asn Ser Thr Ile Asn Gly Thr Trp
1               5                   10                  15

Glu Gly Asp Glu Leu Gly Tyr Lys Cys Arg Phe Asn Glu Asp Phe Lys
```

-continued

```
                    20                  25                  30
Tyr Val Leu Leu Pro Val Ser Tyr Gly Val Val Cys Val Leu Gly Leu
                35                  40                  45
Cys Leu Asn Val Val Ala Leu Tyr Ile Phe Leu Cys Arg Leu Lys Ile
 50                  55                  60
Trp Asn Ala Ser Thr Thr Tyr Met Phe His Leu Ala Val Ser Asp Ser
 65                  70                  75                  80
Leu Tyr Ala Ala Ser Leu Pro Leu Leu Val Tyr Tyr Ala Arg Gly
                85                  90                  95
Asp His Trp Pro Phe Ser Thr Val Leu Cys Lys Leu Val Arg Phe Leu
                100                 105                 110
Phe Tyr Thr Asn Leu Tyr Cys Ser Ile Leu Phe Leu Thr Cys Ile Ser
                115                 120                 125
Val His Arg Cys Leu Gly Val Leu Arg Pro Leu His Ser Leu Arg Trp
130                 135                 140
Gly Arg Ala Arg Tyr Ala Arg Arg Val Ala Ala Val Val Trp Val Leu
145                 150                 155                 160
Val Leu Ala Cys Gln Ala Pro Val Leu Tyr Phe Val Thr Thr Ser Val
                165                 170                 175
Arg Gly Thr Arg Ile Thr Cys His Asp Thr Ser Ala Arg Glu Leu Phe
                180                 185                 190
Ser His Phe Val Ala Tyr Ser Ser Val Met Leu Gly Leu Leu Phe Ala
                195                 200                 205
Val Pro Phe Ser Val Ile Leu Val Cys Tyr Val Leu Met Ala Arg Arg
                210                 215                 220
Leu Leu Lys Pro Ala Tyr Gly Thr Thr Gly Gly Leu Pro Arg Ala Lys
225                 230                 235                 240
Arg Lys Ser Val Arg Thr Ile Ala Leu Val Leu Ala Val Phe Ala Leu
                245                 250                 255
Cys Phe Leu Pro Phe His Val Thr Arg Thr Leu Tyr Tyr Ser Phe Arg
                260                 265                 270
Ser Leu Asp Leu Ser Cys His Thr Leu Asn Ala Ile Asn Met Ala Tyr
                275                 280                 285
Lys Ile Thr Arg Pro Leu Ala Ser Ala Asn Ser Cys Leu Asp Pro Val
290                 295                 300
Leu Tyr Phe Leu Ala Gly Gln Arg Leu Val Arg Phe Ala Arg Asp Ala
305                 310                 315                 320
Lys Pro Pro Thr Glu Pro Thr Pro Ser Pro Gln Ala Arg Arg Lys Leu
                325                 330                 335
Gly Leu His Arg Pro Asn Arg Thr Val Arg Lys Asp Leu Ser Val Ser
                340                 345                 350
Ser Asp Asp Ser Arg Arg Thr Glu Ser Thr Pro Ala Gly Ser Glu Thr
                355                 360                 365
Lys Asp Ile Arg Leu
370
```

(2) INFORMATION FOR SEQ ID NO:374:

(i) SEQUENCE CHARACTERISTICS:
        (A) LENGTH: 362 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:374:

| Met | Thr | Glu | Ala | Leu | Ile | Ser | Ala | Ala | Leu | Asn | Gly | Thr | Gln | Pro | Glu |
|---|---|---|---|---|---|---|---|---|---|---|---|---|---|---|---|
| 1 | | | | 5 | | | | | 10 | | | | | 15 | |

| Leu | Leu | Ala | Gly | Gly | Trp | Ala | Ala | Gly | Asn | Ala | Thr | Thr | Lys | Cys | Ser |
|---|---|---|---|---|---|---|---|---|---|---|---|---|---|---|---|
| | | | | 20 | | | | | 25 | | | | | 30 | |

| Leu | Thr | Lys | Thr | Gly | Phe | Gln | Phe | Tyr | Tyr | Leu | Pro | Thr | Val | Tyr | Ile |
|---|---|---|---|---|---|---|---|---|---|---|---|---|---|---|---|
| | | | 35 | | | | | 40 | | | | | 45 | | |

| Leu | Val | Phe | Ile | Thr | Gly | Phe | Leu | Gly | Asn | Ser | Val | Ala | Ile | Trp | Met |
|---|---|---|---|---|---|---|---|---|---|---|---|---|---|---|---|
| | 50 | | | | | 55 | | | | | 60 | | | | |

| Phe | Val | Phe | His | Met | Arg | Pro | Trp | Ser | Gly | Ile | Ser | Val | Tyr | Met | Phe |
|---|---|---|---|---|---|---|---|---|---|---|---|---|---|---|---|
| 65 | | | | | 70 | | | | | 75 | | | | | 80 |

| Asn | Leu | Ala | Leu | Ala | Asp | Phe | Leu | Tyr | Val | Leu | Thr | Leu | Pro | Ala | Leu |
|---|---|---|---|---|---|---|---|---|---|---|---|---|---|---|---|
| | | | | 85 | | | | | 90 | | | | | 95 | |

| Ile | Phe | Tyr | Tyr | Phe | Asn | Lys | Thr | Asp | Trp | Ile | Phe | Gly | Asp | Val | Met |
|---|---|---|---|---|---|---|---|---|---|---|---|---|---|---|---|
| | | | | 100 | | | | | 105 | | | | | 110 | |

| Cys | Lys | Leu | Gln | Arg | Phe | Ile | Phe | His | Val | Asn | Leu | Tyr | Gly | Ser | Ile |
|---|---|---|---|---|---|---|---|---|---|---|---|---|---|---|---|
| | | | 115 | | | | | 120 | | | | | 125 | | |

| Leu | Phe | Leu | Thr | Cys | Ile | Ser | Val | His | Arg | Tyr | Thr | Gly | Val | Val | His |
|---|---|---|---|---|---|---|---|---|---|---|---|---|---|---|---|
| | 130 | | | | | 135 | | | | | 140 | | | | |

| Pro | Leu | Lys | Ser | Leu | Gly | Arg | Leu | Lys | Lys | Asn | Ala | Val | Tyr | Val |
|---|---|---|---|---|---|---|---|---|---|---|---|---|---|---|
| 145 | | | | | 150 | | | | | 155 | | | | 160 |

| Ser | Ser | Leu | Val | Trp | Ala | Leu | Val | Val | Ala | Val | Ile | Ala | Pro | Ile | Leu |
|---|---|---|---|---|---|---|---|---|---|---|---|---|---|---|---|
| | | | | 165 | | | | | 170 | | | | | 175 | |

| Phe | Tyr | Ser | Gly | Ile | Gly | Val | Arg | Arg | Asn | Lys | Thr | Ile | Thr | Cys | Tyr |
|---|---|---|---|---|---|---|---|---|---|---|---|---|---|---|---|
| | | | 180 | | | | | 185 | | | | | 190 | | |

| Asp | Thr | Thr | Ala | Asp | Glu | Tyr | Leu | Arg | Ser | Tyr | Phe | Val | Tyr | Ser | Met |
|---|---|---|---|---|---|---|---|---|---|---|---|---|---|---|---|
| | 195 | | | | | 200 | | | | | 205 | | | | |

| Cys | Thr | Thr | Val | Phe | Met | Phe | Cys | Ile | Pro | Phe | Ile | Val | Ile | Leu | Gly |
|---|---|---|---|---|---|---|---|---|---|---|---|---|---|---|---|
| 210 | | | | | 215 | | | | | 220 | | | | | |

| Cys | Tyr | Gly | Leu | Ile | Val | Lys | Ala | Leu | Ile | Tyr | Lys | Asp | Leu | Asp | Asn |
|---|---|---|---|---|---|---|---|---|---|---|---|---|---|---|---|
| 225 | | | | | 230 | | | | | 235 | | | | | 240 |

| Ser | Pro | Leu | Arg | Arg | Lys | Ser | Thr | Tyr | Leu | Val | Ile | Ile | Val | Leu | Thr |
|---|---|---|---|---|---|---|---|---|---|---|---|---|---|---|---|
| | | | | 245 | | | | | 250 | | | | | 255 | |

| Val | Phe | Ala | Val | Ser | Tyr | Leu | Pro | Phe | His | Val | Met | Lys | Thr | Leu | Asn |
|---|---|---|---|---|---|---|---|---|---|---|---|---|---|---|---|
| | | | 260 | | | | | 265 | | | | | 270 | | |

| Leu | Arg | Ala | Arg | Leu | Asp | Phe | Gln | Thr | Pro | Gln | Met | Cys | Ala | Phe | Asn |
|---|---|---|---|---|---|---|---|---|---|---|---|---|---|---|---|
| | 275 | | | | | 280 | | | | | 285 | | | | |

| Asp | Lys | Val | Tyr | Ala | Thr | Tyr | Gln | Val | Thr | Arg | Gly | Leu | Ala | Ser | Leu |
|---|---|---|---|---|---|---|---|---|---|---|---|---|---|---|---|
| 290 | | | | | 295 | | | | | 300 | | | | | |

| Asn | Ser | Cys | Val | Asp | Pro | Ile | Leu | Tyr | Phe | Leu | Ala | Gly | Asp | Thr | Phe |
|---|---|---|---|---|---|---|---|---|---|---|---|---|---|---|---|
| 305 | | | | 310 | | | | | 315 | | | | | | 320 |

| Arg | Arg | Arg | Leu | Ser | Arg | Ala | Thr | Arg | Lys | Ser | Ser | Arg | Arg | Ser | Glu |
|---|---|---|---|---|---|---|---|---|---|---|---|---|---|---|---|
| | | | | 325 | | | | | 330 | | | | | 335 | |

| Pro | Asn | Val | Gln | Ser | Lys | Ser | Glu | Glu | Met | Thr | Leu | Asn | Ile | Leu | Thr |
|---|---|---|---|---|---|---|---|---|---|---|---|---|---|---|---|
| | | | 340 | | | | | 345 | | | | | 350 | | |

| Glu | Tyr | Lys | Gln | Asn | Gly | Asp | Thr | Ser | Leu |
|---|---|---|---|---|---|---|---|---|---|
| | 355 | | | | | 360 | | | |

(2) INFORMATION FOR SEQ ID NO:375:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (ii) MOLECULE TYPE: cDNA (ix) FEATURE:
 (A) NAME/KEY: CDS
 (B) LOCATION: 28..816

(xi) SEQUENCE DESCRIPTION: SEQ ID NO:375:

| | | | | | | | | | | | | | | |
|---|---|---|---|---|---|---|---|---|---|---|---|---|---|---|
| GCCACCAACG TGTTCATCCT GTCACTG GCC GAT GTG CTG GTG ACA GCC ATC | | | | | | | | | | | | | | 51 |
| | | | | Ala | Asp | Val | Leu | Val | Thr | Ala | Ile | | | |
| | | | | 1 | | | | 5 | | | | | | |

```
TGC CTG CCG GCC AGT CTG CTG GTA GAC ATC ACG GAA TCC TGG CTC TTT      99
Cys Leu Pro Ala Ser Leu Leu Val Asp Ile Thr Glu Ser Trp Leu Phe
 10              15                  20

GGC CAT GCC CTC TGC AAG GTC ATC CCC TAT CTA CAG GCC GTG TCC GTG     147
Gly His Ala Leu Cys Lys Val Ile Pro Tyr Leu Gln Ala Val Ser Val
 25              30                  35                  40

TCA GTG GTC GTG CTG ACT CTC AGC TCC ATC GCC CTG GAC CGC TGG TAC     195
Ser Val Val Val Leu Thr Leu Ser Ser Ile Ala Leu Asp Arg Trp Tyr
             45                  50                  55

GCC ATC TGC CAC CCG CTG TTG TTC AAG AGC ACT GCC CGG CGC GCC CGC     243
Ala Ile Cys His Pro Leu Leu Phe Lys Ser Thr Ala Arg Arg Ala Arg
             60                  65                  70

GGC TCC ATC CTC GGC ATC TGG GCG GTG TCG CTG GCT GTC ATG GTG CCT     291
Gly Ser Ile Leu Gly Ile Trp Ala Val Ser Leu Ala Val Met Val Pro
             75                  80                  85

CAG GCT GCT GTC ATG GAG TGT AGC AGC GTG CTG CCC GAG CTG GCC AAC     339
Gln Ala Ala Val Met Glu Cys Ser Ser Val Leu Pro Glu Leu Ala Asn
 90                  95                 100

CGC ACC CGC CTC CTG TCT GTC TGT GAT GAG CGC TGG GCA GAC GAC CTG     387
Arg Thr Arg Leu Leu Ser Val Cys Asp Glu Arg Trp Ala Asp Asp Leu
105             110                 115                 120

TAC CCC AAG ATC TAC CAC AGC TGC TTC TTC ATT GTC ACC TAC CTG GCC     435
Tyr Pro Lys Ile Tyr His Ser Cys Phe Phe Ile Val Thr Tyr Leu Ala
                125                 130                 135

CCA CTG GGC CTC ATG GCC ATG GCC TAT TTC CAG ATC TTC CGC AAG CTC     483
Pro Leu Gly Leu Met Ala Met Ala Tyr Phe Gln Ile Phe Arg Lys Leu
                140                 145                 150

TGG GGC CGC CAG ATC CCC GGC ACC ACC TCG GCC CTG GTG CGC AAC TGG     531
Trp Gly Arg Gln Ile Pro Gly Thr Thr Ser Ala Leu Val Arg Asn Trp
                155                 160                 165

AAG CGG CCC TCA GAC CAG CTG GAC GAC CAG GGC CAG GGC CTG AGC TCA     579
Lys Arg Pro Ser Asp Gln Leu Asp Asp Gln Gly Gln Gly Leu Ser Ser
170                 175                 180

GAG CCC CAG CCC CGG GCC CGC GCC TTC CTG GCC GAG GTG AAA CAG ATG     627
Glu Pro Gln Pro Arg Ala Arg Ala Phe Leu Ala Glu Val Lys Gln Met
185                 190                 195                 200

CGA GCC CGG AGG AAG ACG GCC AAG ATG CTG ATG GTG GTG CTG CTG GTC     675
Arg Ala Arg Arg Lys Thr Ala Lys Met Leu Met Val Val Leu Leu Val
                205                 210                 215

TTC GCC CTC TGC TAC CTG CCC ATC AGT GTC CTC AAC GTC CTC AAG AGG     723
Phe Ala Leu Cys Tyr Leu Pro Ile Ser Val Leu Asn Val Leu Lys Arg
                220                 225                 230

GTC TTC GGG ATG TTC CGC CAA GCC AGC GAC CGA GAG GCC ATC TAC GCC     771
Val Phe Gly Met Phe Arg Gln Ala Ser Asp Arg Glu Ala Ile Tyr Ala
                235                 240                 245

TGC TTC ACC TTC TCC CAC TGG CTG GTG TAC GCC AAC AGC GCC GCC         816
Cys Phe Thr Phe Ser His Trp Leu Val Tyr Ala Asn Ser Ala Ala
                250                 255                 260

AATCCCCTCC TCTACTCCTT CCTCCCT                                       843
```

(2) INFORMATION FOR SEQ ID NO:376:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:376:

```
Ala Asp Val Leu Val Thr Ala Ile Cys Leu Pro Ala Ser Leu Leu Val
  1               5                  10                  15
Asp Ile Thr Glu Ser Trp Leu Phe Gly His Ala Leu Cys Lys Val Ile
             20                  25                  30
Pro Tyr Leu Gln Ala Val Ser Val Ser Val Val Leu Thr Leu Ser
         35                  40                  45
Ser Ile Ala Leu Asp Arg Trp Tyr Ala Ile Cys His Pro Leu Leu Phe
     50                  55                  60
Lys Ser Thr Ala Arg Arg Ala Arg Gly Ser Ile Leu Gly Ile Trp Ala
 65                  70                  75                  80
Val Ser Leu Ala Val Met Val Pro Gln Ala Ala Val Met Glu Cys Ser
                 85                  90                  95
Ser Val Leu Pro Glu Leu Ala Asn Arg Thr Arg Leu Leu Ser Val Cys
            100                 105                 110
Asp Glu Arg Trp Ala Asp Asp Leu Tyr Pro Lys Ile Tyr His Ser Cys
            115                 120                 125
Phe Phe Ile Val Thr Tyr Leu Ala Pro Leu Gly Leu Met Ala Met Ala
        130                 135                 140
Tyr Phe Gln Ile Phe Arg Lys Leu Trp Gly Arg Gln Ile Pro Gly Thr
145                 150                 155                 160
Thr Ser Ala Leu Val Arg Asn Trp Lys Arg Pro Ser Asp Gln Leu Asp
                165                 170                 175
Asp Gln Gly Gln Gly Leu Ser Ser Glu Pro Gln Pro Arg Ala Arg Ala
            180                 185                 190
Phe Leu Ala Glu Val Lys Gln Met Arg Ala Arg Arg Lys Thr Ala Lys
        195                 200                 205
Met Leu Met Val Val Leu Leu Val Phe Ala Leu Cys Tyr Leu Pro Ile
    210                 215                 220
Ser Val Leu Asn Val Leu Lys Arg Val Phe Gly Met Phe Arg Gln Ala
225                 230                 235                 240
Ser Asp Arg Glu Ala Ile Tyr Ala Cys Phe Thr Phe Ser His Trp Leu
                245                 250                 255
Val Tyr Ala Asn Ser Ala Ala
            260
```

(2) INFORMATION FOR SEQ ID NO:377:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:377:

```
TGACAACCCA GTGCCTGCCC ACAGCCATCT TCGCTGCCAC AGGCATCCAG CGTAACCGCA    60

CTGTCTGCTA TGACCTCAGC CCGCCTGCCC TGGCCACCCA CTATATGCCC TATGGCATGG   120
```

```
CTCTCACTGT CATCGGCTTC CTGCTGCCCT TTGCTGCCCT GCTGGCCTGC TACTGTCTCC    180

TGGCCTGCCG CC                                                         192

(2) INFORMATION FOR SEQ ID NO:378:

(i) SEQUENCE CHARACTERISTICS:
        (A) LENGTH: 396 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:378:

GTGGGCCTGG TGGGCAACAT CCTGGCTTCC TGGCACAAGC GTGGAGGTCG CCGTGCTGCT     60

TGGGTAGTGT GTGGAGTCGT GTGGCTGGCT GTGACAGCCC AGTGCCTGCC CACGGCAGTC    120

TTTGCTGCCA CAGGCATCCA GCGCAACCGC ACTGTGTGCT ACGACCTGAG CCCACCCATC    180

CTGTCTACTC GCTACCTGCC CTATGGTATG GCCCTCACGG TCATCGGCTT CTTGCTGCCC    240

TTCATAGCCT TACTGGCTTG TTATTGTCGC ATGGCCCGCC GCCTGTGTCG CCAGGATGGC    300

CCAGCAGGTC CTGTGGCCCA AGAGCGGCGC AGCAAGGCGG CTCGTATGGC TGTGGTGGTG    360

GCAGCTGTCT TTGCCCTCTG CTGGCTGCCT CTCTAC                              396

(2) INFORMATION FOR SEQ ID NO:379:

(i) SEQUENCE CHARACTERISTICS:
        (A) LENGTH: 1023 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 37..1020

(xi) SEQUENCE DESCRIPTION: SEQ ID NO:379:

TGACTCCCTG AACATAGGAA ACCCACCTGG GCAGCC ATG GAA TGG GAC AAT GGC       54
                                        Met Glu Trp Asp Asn Gly
                                         1               5

ACA GGC CAG GCT CTG GGC TTG CCA CCC ACC ACC TGT GTC TAC CGC GAG      102
Thr Gly Gln Ala Leu Gly Leu Pro Pro Thr Thr Cys Val Tyr Arg Glu
             10                  15                  20

AAC TTC AAG CAA CTG CTG CTG CCA CCT GTG TAT TCG GCG GTG CTG GCG      150
Asn Phe Lys Gln Leu Leu Leu Pro Pro Val Tyr Ser Ala Val Leu Ala
         25                  30                  35

GCT GGC CTG CCG CTG AAC ATC TGT GTC ATT ACC CAG ATC TGC ACG TCC      198
Ala Gly Leu Pro Leu Asn Ile Cys Val Ile Thr Gln Ile Cys Thr Ser
     40                  45                  50

CGC CGG GCC CTG ACC CGC ACG GCC GTG TAC ACC CTA AAC CTT GCT CTG      246
Arg Arg Ala Leu Thr Arg Thr Ala Val Tyr Thr Leu Asn Leu Ala Leu
 55                  60                  65                  70

GCT GAC CTG CTA TAT GCC TGC TCC CTG CCC CTG CTC ATC TAC AAC TAT      294
Ala Asp Leu Leu Tyr Ala Cys Ser Leu Pro Leu Leu Ile Tyr Asn Tyr
                 75                  80                  85

GCC CAA GGT GAT CAC TGG CCC TTT GGC GAC TTC GCC TGC CGC CTG GTC      342
Ala Gln Gly Asp His Trp Pro Phe Gly Asp Phe Ala Cys Arg Leu Val
             90                  95                 100

CGC TTC CTC TTC TAT GCC AAC CTG CAC GGC AGC ATC CTC TTC CTC ACC      390
Arg Phe Leu Phe Tyr Ala Asn Leu His Gly Ser Ile Leu Phe Leu Thr
```

```
            105                 110                      115
TGC ATC AGC TTC CAG CGC TAC CTG GGC ATC TGC CAC CCG CTG GCC CCC      438
Cys Ile Ser Phe Gln Arg Tyr Leu Gly Ile Cys His Pro Leu Ala Pro
    120                 125                 130

TGG CAC AAA CGT GGG GGC CGC CGG GCT GCC TGG CTA GTG TGT GTA ACC      486
Trp His Lys Arg Gly Gly Arg Arg Ala Ala Trp Leu Val Cys Val Thr
135                 140                 145                 150

GTG TGG CTG GCC GTG ACA ACC CAG TGC CTG CCC ACA GCC ATC TTC GCT      534
Val Trp Leu Ala Val Thr Thr Gln Cys Leu Pro Thr Ala Ile Phe Ala
                155                 160                 165

GCC ACA GGC ATC CAG CGT AAC CGC ACT GTC TGC TAT GAC CTC AGC CCG      582
Ala Thr Gly Ile Gln Arg Asn Arg Thr Val Cys Tyr Asp Leu Ser Pro
            170                 175                 180

CCT GCC CTG GCC ACC CAC TAT ATG CCC TAT GGC ATG GCT CTC ACT GTC      630
Pro Ala Leu Ala Thr His Tyr Met Pro Tyr Gly Met Ala Leu Thr Val
            185                 190                 195

ATC GGC TTC CTG CTG CCC TTT GCT GCC CTG CTG GCC TGC TAC TGT CTC      678
Ile Gly Phe Leu Leu Pro Phe Ala Ala Leu Leu Ala Cys Tyr Cys Leu
    200                 205                 210

CTG GCC TGC CGC CTG TGC CGC CAG GAT GGC CCG GCA GAG CCT GTG GCC      726
Leu Ala Cys Arg Leu Cys Arg Gln Asp Gly Pro Ala Glu Pro Val Ala
215                 220                 225                 230

CAG GAG CGG CGT GGC AAG GCG GCC CGC ATG GCC GTG GTG GTG GCT GCT      774
Gln Glu Arg Arg Gly Lys Ala Ala Arg Met Ala Val Val Val Ala Ala
                235                 240                 245

GCC TTT GCC ATC AGC TTC CTG CCT TTT CAC ATC ACC AAG ACA GCC TAC      822
Ala Phe Ala Ile Ser Phe Leu Pro Phe His Ile Thr Lys Thr Ala Tyr
            250                 255                 260

CTG GCA GTG GGC TCG ACG CCG GGC GTC CCC TGC ACT GTA TTG GAG GCC      870
Leu Ala Val Gly Ser Thr Pro Gly Val Pro Cys Thr Val Leu Glu Ala
            265                 270                 275

TTT GCA GCG GCC TAC AAA GGC ACG CGG CCG TTT GCC AGT GCC AAC AGC      918
Phe Ala Ala Ala Tyr Lys Gly Thr Arg Pro Phe Ala Ser Ala Asn Ser
    280                 285                 290

GTG CTG GAC CCC ATC CTC TTC TAC TTC ACC CAG AAG AAG TTC CGC CGG      966
Val Leu Asp Pro Ile Leu Phe Tyr Phe Thr Gln Lys Lys Phe Arg Arg
295                 300                 305                 310

CGA CCA CAT GAG CTC CTA CAG AAA CTC ACA GCC AAA TGG CAG AGG CAG     1014
Arg Pro His Glu Leu Leu Gln Lys Leu Thr Ala Lys Trp Gln Arg Gln
                315                 320                 325

GGT CGC TGA                                                          1023
Gly Arg
```

(2) INFORMATION FOR SEQ ID NO:380:

(i) SEQUENCE CHARACTERISTICS:
        (A) LENGTH: 328 amino acids
        (B) TYPE: amino acid
        (D) TOPOLOGY: linear (ii) MOLECULE TYPE: protein (xi) SEQUENCE DESCRIPTION: SEQ ID NO:380:

```
Met Glu Trp Asp Asn Gly Thr Gly Gln Ala Leu Gly Leu Pro Pro Thr
1               5                   10                  15

Thr Cys Val Tyr Arg Glu Asn Phe Lys Gln Leu Leu Pro Pro Val
            20                  25                  30

Tyr Ser Ala Val Leu Ala Ala Gly Leu Pro Leu Asn Ile Cys Val Ile
            35                  40                  45

Thr Gln Ile Cys Thr Ser Arg Arg Ala Leu Thr Arg Thr Ala Val Tyr
```

-continued

```
                50                      55                      60
Thr Leu Asn Leu Ala Leu Ala Asp Leu Leu Tyr Ala Cys Ser Leu Pro
 65                      70                      75                      80
Leu Leu Ile Tyr Asn Tyr Ala Gln Gly Asp His Trp Pro Phe Gly Asp
                 85                      90                      95
Phe Ala Cys Arg Leu Val Arg Phe Leu Phe Tyr Ala Asn Leu His Gly
                100                     105                     110
Ser Ile Leu Phe Leu Thr Cys Ile Ser Phe Gln Arg Tyr Leu Gly Ile
                115                     120                     125
Cys His Pro Leu Ala Pro Trp His Lys Arg Gly Gly Arg Arg Ala Ala
                130                     135                     140
Trp Leu Val Cys Val Thr Val Trp Leu Ala Val Thr Thr Gln Cys Leu
145                     150                     155                     160
Pro Thr Ala Ile Phe Ala Ala Thr Gly Ile Gln Arg Asn Arg Thr Val
                165                     170                     175
Cys Tyr Asp Leu Ser Pro Pro Ala Leu Ala Thr His Tyr Met Pro Tyr
                180                     185                     190
Gly Met Ala Leu Thr Val Ile Gly Phe Leu Leu Pro Phe Ala Ala Leu
                195                     200                     205
Leu Ala Cys Tyr Cys Leu Leu Ala Cys Arg Leu Cys Arg Gln Asp Gly
                210                     215                     220
Pro Ala Glu Pro Val Ala Gln Glu Arg Arg Gly Lys Ala Ala Arg Met
225                     230                     235                     240
Ala Val Val Val Ala Ala Ala Phe Ala Ile Ser Phe Leu Pro Phe His
                245                     250                     255
Ile Thr Lys Thr Ala Tyr Leu Ala Val Gly Ser Thr Pro Gly Val Pro
                260                     265                     270
Cys Thr Val Leu Glu Ala Phe Ala Ala Ala Tyr Lys Gly Thr Arg Pro
                275                     280                     285
Phe Ala Ser Ala Asn Ser Val Leu Asp Pro Ile Leu Phe Tyr Phe Thr
                290                     295                     300
Gln Lys Lys Phe Arg Arg Arg Pro His Glu Leu Leu Gln Lys Leu Thr
305                     310                     315                     320
Ala Lys Trp Gln Arg Gln Gly Arg
                325
```

We claim:

1. An isolated G protein coupled receptor comprising the amino acid sequence of SEQ ID NO: 26.
2. An isolated DNA encoding the G protein coupled receptor of claim 1.
3. An isolated DNA comprising the nucleotide sequence of SEQ ID NO: 31.
4. A recombinant vector comprising a DNA encoding the G protein coupled receptor of claim 1.
5. A host cell transformed with the recombinant vector of claim 4.
6. A method for producing a G protein coupled receptor comprising cultivating the host cell of claim 5 under conditions sufficient to express the receptor.

* * * * *

UNITED STATES PATENT AND TRADEMARK OFFICE
CERTIFICATE OF CORRECTION

PATENT NO.  : 6,114,139
DATED       : September 5, 2000
INVENTOR(S) : Shuji Hinuma, Masaki Hosoya and Ryo Fuji It is certified that error appears in the above-identified patent and that said Letters Patent is hereby corrected as shown below:

<u>Title page,</u>
Item [75], Inventors, replace "Shuji Hinuma, Masaki Hosoya, Ryo Fujii, Tetsuya Ohtaki, Shoji Fukusumi, Kazuhiro Ohgi" with -- Shujima Hinuma, Masaki Hosoya, Ryo Fuji --.

Signed and Sealed this

Twelfth Day of February, 2002

Attest:

JAMES E. ROGAN
Attesting Officer — Director of the United States Patent and Trademark Office